(12) United States Patent
Iyer et al.

(10) Patent No.: US 11,701,419 B2
(45) Date of Patent: Jul. 18, 2023

(54) PORCINE CIRCOVIRUS TYPE 3 (PCV3) VACCINES, AND PRODUCTION AND USES THEREOF

(71) Applicants: Boehringer Ingelheim Animal Health USA Inc., Duluth, GA (US); Iowa State University Research Foundation, Inc., Ames, IA (US)

(72) Inventors: Arun Iyer, Ames, IA (US); Luis Alejandro Hernandez, Ames, IA (US); Abby Patterson, Story City, IA (US); Bailey Arruda, Ames, IA (US); Luis Gabriel Gimenez-Lirola, Ames, IA (US); Dave Michael Anstrom, Ames, IA (US); Eric M. Vaughn, Ames, IA (US); Pablo E. Pineyro Pineiro, Ames, IA (US); Troy James Kaiser, Dearborn, MO (US); Joseph Ralph Hermann, Waukee, IA (US)

(*) Notice: Subject to any disclaimer, the term of this patent is extended or adjusted under 35 U.S.C. 154(b) by 0 days.

(21) Appl. No.: 16/841,485

(22) Filed: Apr. 6, 2020

(65) Prior Publication Data
US 2021/0128712 A1 May 6, 2021

Related U.S. Application Data

(60) Provisional application No. 62/829,400, filed on Apr. 4, 2019.

(51) Int. Cl.
| | |
|---|---|
| A61K 39/12 | (2006.01) |
| A61K 39/23 | (2006.01) |
| A61P 31/20 | (2006.01) |
| A61P 37/04 | (2006.01) |
| A61K 39/00 | (2006.01) |

(52) U.S. Cl.
CPC .............. *A61K 39/12* (2013.01); *A61K 39/23* (2013.01); *A61P 31/20* (2018.01); *A61P 37/04* (2018.01); *A61K 2039/545* (2013.01); *A61K 2039/552* (2013.01); *A61K 2039/70* (2013.01); *C12N 2750/10034* (2013.01); *C12N 2750/10071* (2013.01); *C12N 2750/14034* (2013.01)

(58) Field of Classification Search
None
See application file for complete search history.

(56) References Cited

U.S. PATENT DOCUMENTS

2021/0128712 A1* 5/2021 Iyer ......................... A61P 37/04

FOREIGN PATENT DOCUMENTS

| CN | 108 159 409 A | 6/2018 |
| CN | 108 359 677 A | 8/2018 |
| CN | 108 823 231 A | 11/2018 |
| CN | 109 053 896 A | 12/2018 |
| CN | 109 125 720 A | 1/2019 |

(Continued)

OTHER PUBLICATIONS

Alignment of SEQ ID No. 1 with Geneseq db access No. BDV50326 by Hause on Apr. 2017 in WO2017066772.*

(Continued)

*Primary Examiner* — Shanon A. Foley

(57) ABSTRACT

The present invention relates to the use of an immunogenic composition that comprises a porcine *circovirus* type 3 (PCV3) antigen for treatment of several clinical manifestations (diseases). Preferably, the clinical manifestations are associated with a PCV3 infection.

7 Claims, 95 Drawing Sheets

Specification includes a Sequence Listing.

(56) References Cited

FOREIGN PATENT DOCUMENTS

| CN | 109 207 441 A | 1/2019 |
|----|---------------|--------|
| CN | 109 550 045 A | 4/2019 |
| WO | 2017/066 772 A1 | 4/2017 |
| WO | WO2017/066772 * | 4/2017 |
| WO | 2018/233 264 A1 | 12/2018 |
| WO | WO 2019/238611 * | 12/2019 |

OTHER PUBLICATIONS

Alignment of SEQ ID No. 4 with Geneseq db access No. BDV50327 by Hause on Apr. 2017 in WO2017066772.*
Zhiwen et al. ("Recombinant virus-like particles obtained with PPV VP2 and PCV2 ORF2 and their immunogenicity." Chinese High Technology Letters (2010): 12).*
Temeeyasen et al. (Journal of General Virology. 2021; 102:001502 DOI 10.1099/jgv.0.001502).*
Vargas-Bermudez et al. (BMC Veterinary Research. 2021; 17:150).*
Ailor et al. (Current Opinion in Biotechnology 1999, 10:142-145).*
Alignment of SEQ ID 4 with UniProt database access No. A0A1V0D7H5_9CIRC by Shen et al. 2017.*
Ruiz et al. (Pathogens. 2022; 11; 118).*
Blanchard et al. (Vaccine. 2003; 21: 4565-4575).*
Sujia Zhang et al. 2019. "Development and application of a baculovirus-expressed capsid protein-based indirect ELISA for detection of porcine circovirus 3 IgG antibodies". BMC Veterinary Res. 15:1.

\* cited by examiner

SEQ ID NO:1

```
LOCUS       PCV3                     645 bp    DNA     linear   11-MAR-2019
PCV3 ORF2 Sequence
FEATURES             Location/Qualifiers
     source          1..645
                     /dnas_title="PCV3 ORF2 from BaculoG PCV3 ORF2"
ORIGIN
        1 atgagacaca gagctatatt cagaagaaga cccgcccaa ggagacgacg acgccacaga
       61 aggcgctatg ccagaagacg actattcatt aggaggccca cagctggcac atactacaca
      121 aagaaatact ccacaatgaa cgtcatatcc gttggaaccc ctcagaataa caagccctgg
      181 cacgccaacc acttcattac ccgcctaaac gaatgggaaa ctgcaattac ctttgaatat
      241 tataagatac taaaaatgaa agttacactc agccctgtaa tttctccggc tcagcaaaca
      301 aaaactatgt tcgggcacac agccatagat ctagacggcg cctggaccac aaacacttgg
      361 ctccaagacg acccttatgc ggaaagttcc actcgtaaag ttatgacttc taaaaaaaaa
      421 cacagccgtt acttcacccc caaaccactt ctggcgggaa ctaccagcgc tcacccagga
      481 caaagcctct tcttttctc cagacccacc ccatggctca acacatatga cccaccgtt
      541 caatggggag cactgctttg gagcatttat gtcccggaaa aaactggaat gacagacttc
      601 tacggcacca agaagtttg gattcgttac aagtccgttc tctga
```

SEQ ID NO:2

```
LOCUS       BaculoG PCV3 ORF2              133894 bp    DNA     circular VRL
12-MAR-2019
FEATURES             Location/Qualifiers
     source          1..134448
                     /dnas_title="BaculoG PCV3 ORF2"
                     /organism="Autographa californica nucleopolyhedrovirus"
                     /mol_type="genomic DNA"
                     /db_xref="taxon:46015"
                     /clone="Lot 3375-021"
     vector          5214..5215
                     /source="pVL1393"
                     /type="Custom cloned vector"
                     /dnas_title="pVL1393"
ORIGIN
        1 gaattctacc cgtaaagcga gtttagtttt gaaaaacaaa tgacatcatt tgtataatga
       61 catcatcccc tgattgtgtt ttacaagtag aattctatcc gtaaagcgag ttcagttttg
      121 aaaacaaatg agtcatacct aaacacgtta ataatcttct gatatcagct tatgactcaa
      181 gttatgagcc gtgtgcaaaa catgagataa gtttatgaca tcatccactg atcgtgcgtt
      241 acaagtagaa ttctactcgt aaagccagtt cggttatgag ccgtgtgcaa aacatgacat
      301 cagcttatga ctcatacttg attgtgtttt acgcgtagaa ttctactcgt aaagcgagtt
      361 cggttatgag ccgtgtgcaa aacatgacat cagcttatga gtcataatta atcgtgcgtt
      421 acaagtagaa ttctactcgt aaagcgagtt gaaggatcat atttagttgc gtttatgaga
      481 taagattgaa agcacgtgta aatgtttcc cgcgcgttgg cacaactatt tacaatgcgg
      541 ccaagttata aagattcta atctgatatg ttttaaaaca cctttgcggc ccgagttgtt
      601 tgcgtacgtg actagcgaag aagatgtgtg gaccgcagaa cagatagtaa aacaaaaccc
      661 tagtattgga gcaataatcg atttaaccaa cacgtctaaa tattatgatg gtgtgcattt
      721 tttgcgggcg ggcctgttat acaaaaaaat tcaagtacct ggccagactt gccgcctga
      781 aagcatagtt caagaattta ttgacacggt aaaagaattt acagaaaagt gtcccggcat
      841 gttggtgggc gtgcactgca cacacggtat aatcgcacc ggttacatgg tgtgcagata
      901 tttaatgcac accctgggta ttgcgccgca ggaagccata gatagattcg aaaaagccag
      961 aggtcacaaa attgaaagac aaaattacgt tcaagattta ttaatttaat taatattatt
     1021 tgcattcttt aacaaatact ttatcctatt ttcaaattgt tgcgcttctt ccagcgaacc
     1081 aaaactatgc ttcgcttgct ccgtttagct tgtagccgat cagtggcgtt gttccaatcg
     1141 acggtaggat taggccggat attctccacc acaatgttgg caacgttgat gttacgttta
```

FIG. 2B-1

```
1201 tgcttttggt tttccacgta cgtcttttgg ccggtaatag ccgtaaacgt agtgccgtcg
1261 cgcgtcacgc acaacaccgg atgtttgcgc ttgtccgcgg ggtattgaac cgcgcgatcc
1321 gacaaatcca ccactttggc aactaaatcg gtgacctgcg cgtctttttt ctgcattatt
1381 tcgtctttct tttgcatggt ttcctggaag ccggtgtaca tgcggtttag atcagtcatg
1441 acgcgcgtga cctgcaaatc tttggcctcg atctgcttgt ccttgatggc aacgatgcgt
1501 tcaataaact cttgtttttt aacaagttcc tggttttttt gcgccaccac cgcttgcagc
1561 gcgtttgtgt gctcggtgaa tgtcgcaatc agcttagtca ccaactgttt gctctcctcc
1621 tcccgttgtt tgatcgcggg atcgtacttg ccggtgcaga gcacttgagg aattacttct
1681 tctaaaagcc attcttgtaa ttctatggcg taaggcaatt tggacttcat aatcagctga
1741 atcacgccgg atttagtaat gagcactgta tgcggctgca atacagcgg tcgcccctt
1801 ttcacgacgc tgttagaggt agggccccca ttttggatgg tctgctcaaa taacgatttg
1861 tatttattgt ctacatgaac acgtatagct ttatcacaaa ctgtatattt taaactgtta
1921 gcgacgtcct tggccacgaa ccggacctgt tggtcgcgct ctagcacgta ccgcaggttg
1981 aacgtatctt ctccaaattt aaattctcca attttaacgc gagccatttt gatacacgtg
2041 tgtcgatttt gcaacaacta ttgtttttta acgcaaacta aacttattgt ggtaagcaat
2101 aattaaatat ggggaacat gcgccgctac aacactcgtc gttatgaacg cagacggcgc
2161 cggtctcggc gcaagcggct aaaacgtgtt gcgcgttcaa cgcggcaaac atcgcaaaag
2221 ccaatagtac agttttgatt tgcatattaa cggcgatttt taaattatc ttatttaata
2281 aatagttatg acgcctacaa ctccccgccc gcgttgactc gctgcacctc gagcagttcg
2341 ttgacgcctt cctccgtgtg gccgaacacg tcgagcgggt ggtcgatgac cagcggcgtg
2401 ccgcacgcga cgcacaagta tctgtacacc gaatgatcgt cgggcgaagg cacgtcggcc
2461 tccaagtggc aatattggca aattcgaaaa tatatacagt gggttgttt gcgcatatct
2521 atcgtggcgt tgggcatgta cgtccgaacg ttgatttgca tgcaagccga aattaaatca
2581 ttgcgattag tgcgattaaa acgttgtaca tcctcgcttt taatcatgcc gtcgattaaa
2641 tcgcgcaatc gagtcaagtg atcaaagtgt ggaataatgt tttctttgta ttcccgagtc
2701 aagcgcagcg cgtatttaa caaactagcc atcttgtaag ttagtttcat ttaatgcaac
2761 tttatccaat aatatattat gtatcgcacg tcaagaatta acaatgcgcc cgttgtcgca
2821 tctcaacacg actatgatag agatcaaata aagcgcgaat taaatagctt gcgacgcaac
2881 gtgcacgatc tgtgcacgcg ttccggcacg agctttgatt gtaataagtt tttacgaagc
2941 gatgacatga cccccgtagt gacaacgatc acgcccaaaa gaactgccga ctacaaaatt
3001 accgagtatg tcggtgacgt taaaactatt aagccatcca atcgaccgtt agtcgaatca
3061 ggaccgctgg tgcgagaagc cgcgaagtat ggcgaatgca tcgtataacg tgtggagtcc
3121 gctcattaga gcgtcatgtt tagacaagaa agctacatat ttaattgatc ccgatgattt
3181 tattgataaa ttgaccctaa ctccatacac ggtattctac aatggcgggg ttttggtcaa
3241 aatttccgga ctgcgattgt acatgctgtt aacggctccg cccactatta atgaaattaa
3301 aaattccaat tttaaaaaac gcagcaagag aaacatttgt atgaaagaat gcgtagaagg
3361 aaagaaaaat gtcgtcgaca tgctgaacaa caagattaat atgcctccgt gtataaaaaa
3421 aatattgaac gatttgaaag aaaacaatgt accgcgcggc ggtatgtaca ggaagaggtt
```

FIG. 2C-1

```
3481 tatactaaac tgttacattg caaacgtggt ttcgtgtgcc aagtgtgaaa accgatgttt
3541 aatcaaggct ctgacgcatt tctacaacca cgactccaag tgtgtgggtg aagtcatgca
3601 tcttttaatc aaatcccaag atgtgtataa accaccaaac tgccaaaaaa tgaaaactgt
3661 cgacaagctc tgtccgtttg ctggcaactg caagggtctc aatcctattt gtaattattg
3721 aataataaaa caattataaa tgtcaaattt gttttttatt aacgatacaa accaaacgca
3781 acaagaacat ttgtagtatt atctataatt gaaaacgcgt agttataatc gctgaggtaa
3841 tatttaaaat cattttcaaa tgattcacag ttaatttgcg acaatataat tttattttca
3901 cataaactag acgccttgtc gtcttcttct tcgtattcct tctcttttc attttctcc
3961 tcaTAaaaat taacatagtt attatcgtat ccatatatgt atctatcgta tagagtaaat
4021 tttttgttgt cataaatata tatgtctttt ttaatggggt gtatagtacc gctgcgcata
4081 gttttctgt aatttacaac agtgctattt tctggtagtt cttcggagtg tgttgcttta
4141 attattaaat ttatataatc aatgaatttg ggatcgtcgg ttttgtacaa tatgttgccg
4201 gcatagtacg cagcttcttc tagttcaatt acaccatttt ttagcagcac cggattaaca
4261 taactttcca aaatgttgta cgaaccgtta aacaaaaaca gttcacctcc cttttctata
4321 ctattgtctg cgagcagttg tttgttgtta aaaataacag ccattgtaat gagacgcaca
4381 aactaatatc acaaactgga aatgtctatc aatatatagt tgctgatatc atggagataa
4441 ttaaaatgat aaccatctcg caaataaata agtattttac tgttttcgta acagttttgt
4501 aataaaaaaa cctataaata ttccggatta ttcataccgt cccaccatcg ggcgcgGATC
4561 CGCCACCATG AGACACAgag ctatattcag aagaagaccc cgccaagga gacgacgacg
4621 ccacagaagg cgctatgcca gaagacgact attcattagg aggcccacag ctggcacata
4681 ctacacaaag aaatactcca caatgaacgt catatccgtt ggaaccccta agaataacaa
4741 gccctggcac gccaaccact tcattacccg cctaaacgaa tgggaaactg caattacctt
4801 tgaatattat aagatactaa aaatgaaagt tacactcagc cctgtaattt ctccggctca
4861 gcaaacaaaa actatgttcg ggcacacagc catagatcta gacggcgcct ggaccacaaa
4921 cacttggctc caagacgacc cttatgcgga aagttccact cgtaaagtta tgacttctaa
4981 aaaaaaacac agccgttact tcaccccccaa accacttctg gcgggaacta ccagcgctca
5041 cccaggacaa agcctcttct ttttctccag acccacccca tggctcaaca catatgaccc
5101 caccgttcaa tggggagcac tgctttggag cattatgtc ccggaaaaaa ctggaatgac
5161 agacttctac ggcaccaaaG AAGTTTGGAT TCGTTACAAG TCCGTTCTCT GAGCggccgc
5221 tgcagatctg atcctttcct gggacccggc aagaaccaaa aactcactct cttcaaggaa
5281 atccgtaatg ttaaacccga cacgatgaag cttgtcgttg gatggaaagg aaaagagttc
5341 tacagggaaa cttggacccg cttcatggaa gacagcttcc ccattgttaa cgaccaagaa
5401 gtgatggatg ttttccttgt tgtcaacatg cgtcccacta gacccaaccg ttgttacaaa
5461 ttcctggccc aacacgctct gcgttgcgac cccgactatg tacctcatga cgtgattagg
5521 atcgtcgagc cttcatggt gggcagcaac aacgagtacc gcatcagcct ggctaagaag
5581 ggcggcggct gcccaataat gaaccttcac tctgagtaca ccaactcgtt cgaacagttc
5641 atcgatcgtg tcatctggga gaacttctac aagcccatcg tttacatcgg taccgactct
5701 gctgaagagg aggaaattct ccttgaagtt tccctggtgt tcaaagtaaa ggagtttgca
```

FIG. 2D-1

```
5761 ccagacgcac ctctgttcac tggtccggcg tattaaaaca cgatacattg ttattagtac
5821 atttattaag cgctagattc tgtgcgttgt tgatttacag acaattgttg tacgtatttt
5881 aataattcat taaatttata atcTttaggg tggtatgtta gagcgaaaat caaatgattt
5941 tcagcgtctt tatatctgaa tttaaatatt aaatcctcaa tagatttgta aataggttt
6001 cgattagttt caaacaaggg ttgttttttcc gaaccgatgg ctggactatc taatggattt
6061 tcgctcaacg ccacaaaact tgccaaatct tgtagcagca atctagcttt gtcgatattc
6121 gtttgtgttt tgttttgtaa taaggttcg acgtcgttca aatattatg cgcttttgta
6181 tttctttcat cactgtcgtt agtgtacaat tgactcgacg taaacacgtt aaataaagct
6241 tggacatatt taacatcggg cgtgttagct ttattaggcc gattatcgtc gtcgtcccaa
6301 ccctcgtcgt tagaagttgc ttccgaagac gatttttgcca tagccacacg acgcctatta
6361 attgtgtcgg ctaacacgtc cgcgatcaaa tttgtagttg agcttttgg aattatttct
6421 gattgcgggc gtttttgggc gggtttcaat ctaactgtgc ccgattttaa ttcagacaac
6481 acgttagaaa gcgatggtgc aggcggtggt aacatttcag acggcaaatc tactaatggc
6541 ggcggtggtg gagctgatga taaatctacc atcggtggag gcgcaggcgg ggctggcggc
6601 ggaggcggag gcggaggtgg tggcggtgat gcagacggcg gtttaggctc aaatgtctct
6661 ttaggcaaca cagtcggcac ctcaactatt gtactggttt cgggcgccgt ttttggtttg
6721 accggtctga gacgagtgcg attttttttcg tttctaatag cttccaacaa ttgttgtctg
6781 tcgtctaaag gtgcagcggg ttgaggttcc gtcggcattg gtggagcggg cggcaattca
6841 gacatcgatg gtggtggtgg tggtggaggc gctggaatgt taggcacggg agaaggtggt
6901 ggcggcggtg ccgccggtat aatttgttct ggtttagttt gttcgcgcac gattgtgggc
6961 accggcgcag gcgccgctgg ctgcacaacg gaaggtcgtc tgcttcgagg cagcgcttgg
7021 ggtggtggca attcaatatt ataattggaa tacaaatcgt aaaaatctgc tataagcatt
7081 gtaatttcgc tatcgtttac cgtgccgata tttaacaacc gctcaatgta agcaattgta
7141 ttgtaaagag attgtctcaa gctcggatcc cgcacgccga taacaagcct tttcattttt
7201 actacagcat tgtagtggcg agacacttcg ctgtcgtcga cgtacatgta tgctttgttg
7261 tcaaaaacgt cgttggcaag ctttaaaata tttaaagaa catctctgtt cagcaccact
7321 gtgttgtcgt aaatgttgtt tttgataatt tgcgcttccg cagtatcgac acgttcaaaa
7381 aattgatgcg catcaatttt gttgttccta ttattgaata aataagattg tacagattca
7441 tatctacgat tcgtcatggc caccacaaat gctacgctgc aaacgctggt acaatttac
7501 gaaaactgca aaaacgtcaa aactcggtat aaaataatca acgggcgctt tggcaaaata
7561 tctattttat cgcacaagcc cactagcaaa ttgtatttgc agaaaacaat ttcggcgcac
7621 aatttttaacg ctgacgaaat aaaagttcac cagttaatga cgaccaccc aaattttata
7681 aaaatctatt ttaatcacgg ttccatcaac aaccaagtga tcgtgatgga ctacattgac
7741 tgtcccgatt tatttgaaac actacaaatt aaaggcgagc tttcgtacca acttgttagc
7801 aaatattatta gacagctgtg tgaagcgctc aacgatttgc acaagcacaa tttcatacac
7861 aacgacataa aactcgaaaa tgtcttatat ttcgaagcac ttgatcgcgt gtatgtttgc
7921 gattacggat tgtgcaaaca cgaaaactca cttagcgtgc acgacggcac gttggagtat
7981 tttagtccgg aaaaaattcg acaccacaac tatgcacgtt cgtttgactg gtacgccgtc
```

FIG. 2E-1

```
 8041 ggcgtgttaa catacaagtt gctaaccggc ggccgacacc catttgaaaa aagcgaagac
 8101 gaaatgttgg acttgaatag catgaagcgt cgtcagcaat acaatgacat tggcgtttta
 8161 aaacacgttc gtaacgttaa cgctcgtgac tttgtgtact gcctaacaag atacaacata
 8221 gattgtagac tcacaaatta caaacaaatt ataaaacatg agttttgtc gtaaaaatgc
 8281 cacttgtttt acgagtagaa ttctacgtgt aacacacgat ctaaaagatg atgtcatttt
 8341 ttatcaatga ctcatttgtt ttaaaacaga cttgttttac gagtagaatt ctacgtgtaa
 8401 agcatgatcg tgagtggtgt taataaaatc ataaaaatta ttgtaaatgt ttattattta
 8461 aaaacgattc aaatatataa taaaaacaat ctacatctat ttcttcacaa tccataacac
 8521 acaacaggtc catcaatgag tttttgtctt tatccgacat actatgtgca tgtaacaaat
 8581 caaatacatc ttttaaattt ttatacacat ctttacattg tctaccaaaa tctttaataa
 8641 ccctataaca aggaaaagac ttttcttctt gcgtggtttt gccgcgcaga tattgaaata
 8701 aaatgtgcat gcacgacaac ttgtgtttac taaaatgctc cttgcctata ccgcaaaacc
 8761 ggccatacat ttcggcgatt acacgcggac aattgtacga ttcgtctacg tgtaaacgat
 8821 catcataatc actcttgcgc aaacgaataa attttttcac cgcttccgac aaacgaggca
 8881 ccaattcggc gggcacgctt cgatacatta ttctgtgcac ataagttacc acacaaaatt
 8941 tattgtacca ccatccgaca acgtcgttat tagggttgaa cacgttggcg atgcgcagca
 9001 gtttccgtt tctcatgaaa tattcaaagc ggcccaaaat aatttgcaag caatccaaca
 9061 tgtcttgaga aatttctcgt tcaaaattgt tcaaagagaa tatctgccat ccgttttgaa
 9121 cgcgcacgct gacgggaacc accgcatcga tttgctccaa cacttcacgg acgttatcgt
 9181 cgatgcccat cgtttcgctg gtgctgaacc aatgggaaag gctcttgatg gaatcgcccg
 9241 cgtctatcat cttgaccgct tcgtcaaagg tgcaactgcc gctcttcaaa cgccgcatag
 9301 cggtcacgtc ccgctctatg cacgacatac cgtttacgta cgattctgat aggtattcct
 9361 gaactatacg gtaatggtga tacgactcgc catacacgtc gtgcacctca ttgtatttag
 9421 cataataatt gtaaattatt aactttgcag cgagagacat gttgtcagta aagcggtgct
 9481 aggctcaata atactgatgt acaggcacgc gtgctattta tatataattt cgcaaggagg
 9541 ggagctgtta tcggttgcta ttattaaaga atggccgtct gttttatca caagcttggc
 9601 agcctcaacc atgaagcgtc gtcattgtaa attaaattct ctgcctcaag aattatttga
 9661 caagattgtc gagtatttat ctttatctga ttactgcaat ttggtgcttg tctgtaaaag
 9721 accttctagt aaatataacg tgatatttga tagtactaat caccaacatt tgaaaggcgt
 9781 gtacaaaaag acagacgtgc aaataacaag ctacaacgaa tacatcaact gtatttgcaa
 9841 cgaactgaga caagacgaat tctatgccaa atcatcatgg attgcgagta tttgcggtca
 9901 ccagagagcg acaattttta gtgtaacaaa taacaagta gaaatgaaat atcatttgta
 9961 taatatagca attgtggaaa gtgaagattg caacggattt tacccatttg agccaacgcg
10021 cgattgttta atatgcaaac aaaaaaacca atgtcctcgt aattcattta ttgtttcgtt
10081 gtgtaaatat ttagaaaaac aaaatgtaca atcaaacttt atatattatt tatacgaaat
10141 aaatacataa taataactat tatacatgtt tttatttac aatacttcct gtataacctc
10201 tctaactaca ttaggagtac aatccacgtc aattacacgt ttagctattt ttctaatttt
10261 gtaatgttta tcgtagagtt tttcgttaat acattgaata gccaacaagg gatttgggtg
```

FIG. 2F-1

```
10321 cacaccgtca tagagtactt ccatgtcgtc ttcaaagcgc attttttcgct tgcgaaaatg
10381 ccgctcttgg cccaaaacaa aagcgagttt gatgcggtcg tcgatgcgtt ccgaaaatac
10441 ggccaaatgc tggtgtttgg tgatgtcgcg cggaaacgtc accgtgccat ttttgctttc
10501 cgccacgacg gcggttttca atttttcggc cgactgcagc atgttaagtt tggcgtcgag
10561 ttcgtgcaaa cgcaattcaa actgctcaaa cctgttgccc acctcgttct tgaacgtctc
10621 gtgggtgacc ataaatttt cgctgtttgc attcagtttc tttacatgtt ttaaaacaga
10681 ttcaatcttg tcgcgcaaat catcacgctc gccttcagtt tgaatgtgca gcaacgcgtt
10741 gcttttgttg gcaaaattta accgcatcaa aatttccaac aaccgtgct tggtcgcgaa
10801 caatgcgccc aacgagttga gatcgcgttt ggatctctgt ttgtgaaaaa caatttcgtt
10861 taaatggtaa acttgatcgc cgtcccaatt gcaatcaagt atgtcgtcgt gcgcaatttc
10921 aagacctttg caaaaatcta tcacattgta gcatttgcg ttcgtgtcgc tgtgcacgta
10981 tctgtacttg aaactgtgcg tgttgcattt gaatgagtcc catttaacga tgtgcgacca
11041 ttgttgggcg tttatgtggt acttttgta gtcgtctgca ttgaaccgat cttcggcggc
11101 gatggcgtcg ttgtcgttgt caccggacca catccaccag ttccataacc aggatagcat
11161 tgctttagct tgtctagcaa ttcctttgtt atacaacgag aaaatttcgt tcccttataa
11221 ttatagctgt acggtgcgcg tatttgtttg ttaacgttac aaaaaatatc cctgtccacg
11281 tccggccaat actgcaacgt gagcgcgtcc aagtttgaat cttgcatatg cggaacgtac
11341 aaacgtacgg cctctctcac acaatgcgca aaactgcccg gctgaatgta atcactgtcc
11401 aactttgcag gtttctcgaa agccttgtac cgatgcacgc gaacatttg agcggacgtg
11461 attttaaact tgtcggtgaa ttttaaccac aaatgaaatc cacggttgcc ggtatacatg
11521 actcttgaca cgttctcttc cgtgtaaaac aacagaaacg ccgtggcgcc aatgtaaatt
11581 ttcagcatta aatcgtgttc gtcaacataa ttttgtaat cggcgtctac gacccattcc
11641 ctgccgccgc cgtcgtccaa cggtttgacg tgcacgtcgg acactttgtt ttgcacaata
11701 taactataca attgtgcgga ggtatcaaaa tatctgtcgg cgtgaatcca gcgcgcgttg
11761 accgtcatga acgcgtactt gcggctgtcg ttgtacgcaa tggcgtccca catcatgtcg
11821 acgcgcttct gcgtataatt gcacactaac atgttgccct ttgaacttga cctcgattgt
11881 gttaattttt ggctataaaa aggtcaccct ttaaaatttg ttacataatc aaattaccag
11941 tacagttatt cggtttgaag caaaatgact attctctgct ggcttgcact gctgtctacg
12001 cttactgctg taaatgcggc caatatattg gccgtgtttc ctacgccagc ttacagccac
12061 catatagtgt acaaagtgta tattgaagcc cttgccgaaa aatgtcacaa cgttacggtc
12121 gtcaagccca aactgtttgc gtattcaact aaaacttatt gcggtaatat cacggaaatt
12181 aatgccgaca tgtctgttga gcaatacaaa aaactagtgg cgaattcggc aatgtttaga
12241 aagcgcggag tggtgtccga tacagacacg gtaaccgccg ctaactacct aggcttgatt
12301 gaaatgttca aagaccagtt tgacaatatc aacgtgcgca atctcattgc caacaaccag
12361 acgttgatt tagtcgtcgt ggaagcgttt gccgattatg cgttggtgtt tggtcacttg
12421 tacgatccgg cgcccgtaat tcaaatcgcg cctggctacg gtttggcgga aaactttgac
12481 acggtcggcg ccgtggcgcg gcacccgtc caccatccta acatttggcg cagcaatttc
12541 gacgacacgg aggcaaacgt gatgacggaa atgcgtttgt ataaagaatt taaaattttg
```

FIG. 2G-1

```
12601 gccaacatgt ccaacgcgtt gctcaaacaa cagtttggac ccaacacacc gacaattgaa
12661 aaactacgca acaaggtgca attgcttttg ctaaacctgc atcccatatt tgacaacaac
12721 cgacccgtgc cgcccagcgt gcagtatctt ggcggaggaa tccatcttgt aaagagcgcg
12781 ccgttgacca aattaagtcc ggtcatcaac gcgcaaatga acaagtcaaa aagcggaacg
12841 atttacgtaa gttttgggtc gagcattgac accaaatcgt ttgcaaacga gtttctttac
12901 atgttaatca atacgttcaa aacgttggat aattacacca tattatggaa aattgacgac
12961 gaagtagtaa aaacataac gttgcccgcc aacgtaatca cgcaaaattg gtttaatcaa
13021 cgcgccgtgc tgcgtcataa aaaaatggcg gcgtttatta cgcaaggcgg actacaatcg
13081 agcgacgagg ccttggaagc cgggataccc atggtgtgtc tgcccatgat gggcgaccag
13141 ttttaccatg cgcacaaatt acagcaactc ggcgtagccc gcgccttgga cactgttacc
13201 gtttccagcg atcaactact agtggcgata acgacgtgt tgtttaacgc gcctacctac
13261 aaaaaacaca tggccgagtt atatgcgctc atcaatcatg ataaagcaac gtttccgcct
13321 ctagataaag ccatcaaatt cacagaacgc gtaattcgat atagacatga catcagtcgt
13381 caattgtatt cattaaaaac aacagctgcc aatgtaccgt attcaaatta ctacatgtat
13441 aaatctgtgt tttctattgt aatgaatcac ttaacacact tttaattacg tcaataaatg
13501 ttattcacca ttatttacct ggttttttg agagggcttt tgtgcgactg cgcacttcca
13561 gcctttataa acgctcacca accaaagcag gtcattattg tgccaggacg ttcaaaggcg
13621 aaacatcgaa atggagtctg ttcaaacgcg cttatgtgcc agtagcaatc aatttgctcc
13681 gttcaaaaag cgccagcttg ccgtgccggt cggttctgtg aacagtttga cacacaccat
13741 cacctccacc accgtcacca gcgtgattcc aaaaaattat caagaaaaac gtcagaaaat
13801 atgccacata atatcttcgt tgcgtaacac gcacttgaat ttcaataaga tacagtctgt
13861 acataaaaag aaactgcggc atttgcaaaa tttgctaaga aaaagaacg aaattattgc
13921 cgagttggtt agaaaacttg aaagtgcaca gaagaagaca acgcacagaa atattagtaa
13981 accagctcat tggaaatact ttggagtagt cagatgtgac aacacaattc gcacaattat
14041 tggcaacgaa aagtttgtaa ggagacgttt ggccgagctg tgcacattgt acaacgccga
14101 gtacgtgttt tgccaagcac gcgccgatgg agacaaagat cgacaggcac tagcgagtct
14161 gctgacggcg gcgtttggtt cgcgagtcat agtttatgaa atagtcgcc ggttcgagtt
14221 tataaatccg gacgagattg ctagtggtaa acgtttaata attaaacatt tgcaagatga
14281 atctcaaagt gatattaacg cctattaatt tgaaaggtga ggaagagccc aattgcgttg
14341 agcgcattac cataatgcca tgtattttaa tagatactga gatctgttta aatgtcagat
14401 gccgttctcc ttttgccaaa ttcaaagtat tgattattgt agatggcttt gatagcgctt
14461 atattcaggc tacctttgt agcattagcg atagtgtaac aattgttaac aaatctaacg
14521 aaaagcatgt aacgtttgac gggtttgtaa ggccggacga tgaaggtaca acaatgcctt
14581 atgtcattgg accattatat tctgtcgacg ctgctgtcgc cgaccgtaaa gtgaaggacg
14641 tggtggattc aattcaaaac caacagacaa tgttaaaagt atttattaac gaggctaatg
14701 tgtataacaa atggaatatg cttaaaggtt taatttataa taataacaat gaatctgttt
14761 tagtaaaata atgtagtaaa atttataaag gtagataaaa attataatat taataaaaaa
14821 aataatgtta ctaaatgggt tcctgcgtta aattattta cgggtagaca gctattaact
```

FIG. 2H-1

```
14881 attttattta ttttttaaatt taaataaatg tattgttaga aaattgtgtt gttttattag
14941 tataacgaaa aaatacatga cataaaccgc ttccaatttt ggtcacacaa actcttgtgt
15001 ggatagttta cgtaatgagt taaataggcg ggcagttgtc cgctaaacgt gtcggtggtc
15061 aagtagatgt gcattaattt acgacaaccc aaagcggggc cgcttatgtc aagtattttt
15121 ttcacaaaat tggtaatggt ttcgttttgt tccttgtaca acacatgtc ggtgtgatcg
15181 ttgacgcacg agttgtacga ttccgccggc aggttggcaa acaagcgctt gagatgcttg
15241 agtctgcgtt caatttata atcaaacttg ttggtgaaaa tgtctttcag caagcacatt
15301 aactggtcgt tcaaacgcg ctgcaacgac gacaccaaca catgatattc gtttccaaaa
15361 agcgaaaaat ttttgatgca gcggtccgcg ttgaagggtc gtttcataat gcgcacgttg
15421 acaaaaaaca cgttgaaaga cagcggggct gtggttattt taacgccgtt gtcggtatac
15481 tcgtcgacgc cgtctgcgct tgttatgtca atttgtagcg caaatctaac caaatcaaac
15541 tcatcgttgt actgtgtctt tatgcatttt atatggcggt ttaagtgcaa gttgatttgg
15601 ccgtttaatc tataggctcc gttttgataa catttcagca ctaccaacgg atccgacatg
15661 taaacttgac gcgttagcac gtccaattca gcgtaatgtt ggtcgacgca ttttgtaaa
15721 ttagtttgca ggttgcaaaa cattttgcg caaaagccgt aatagtcaaa atctatgcat
15781 tttaatgcgc ttctgtcgtc gtcaatatgg catgtcacgg ctgcgcctcc agttaacacg
15841 aataaaccgc cgttttcgca aactacggct tcgaaacaat ctttgataaa tgccaacttt
15901 gctttagcca caatttatc gcgcaggcga tcttcaatat cctttgtcgt aatataaggt
15961 aggacgccaa gatttagttg attcaacaaa cgttccataa tgaatagcgg cgacgcaaca
16021 cgactacact gttcaaatgc gcacgcaaaa caaaccttg caactttatt tgccaatcgt
16081 aatcacagta gtttttacga gtacgccatc gcgtttgtaa gcacattgct ttttaaaaat
16141 aatttaaatt taatgaccgc gtgcaatttg atcaactcgt tgatcaactt tgaactcaac
16201 atgtttggta aaagtttatt gctaaatgga tttgttaatt tctgcattgc taacagcgac
16261 ggggttacga ttcaacataa aatgttaacc aacgtgttaa gttttttgtt ggaaaaatat
16321 tattaaaaat aaataaataa acttgttcag ttctaattat tgttttattt tttataaaat
16381 aatacaattt tatttataca ttaatacttt ggtatttatt aatacaatta tttacaatac
16441 tttatttaca ctataatact ttatttacat tagtactaaa ttaatactaa attacgctaa
16501 tactaaatta atactttata taatcaaaaa taatacttta tataatactt tctaatcatc
16561 ataaacgggt aatagttttt tctcttgaaa tttacgctgc aactcttcgc taaaacacat
16621 gggcggtgga gtgggagcgg gtggagtagg agtccttacg ggtttgatgg gcgacagttc
16681 tctggacttg cggaacagct tgggcgaaag cgtcggcgtg cgccgactaa tgatttcttc
16741 atcCGgcaAc Ggaggctcgc acattgtgca cgcgtccggt gaggtacaca aaactttctt
16801 gggcacgctg tacaccggct tgggcacgct atatgtgttg ccaaaataga actcgttgtg
16861 gttgccgaac ggagacgatg ggtgtgaaga cggcgatggc tgtgaagaca agtccgaagg
16921 cgcgataaaa gatgaaagtg tttctgaaac cgaagtggtg gtagaagtgg tagaaggcgg
16981 gtgcgttacg gcaaccacgc tgctgctatt tctgccttcg gagaccactt ccagcaatct
17041 agagttactc tctcgttctt cgcggcgata gtcaatgtcg caataatgtt cataagatgc
17101 cttttcggct tcggcgcgcc ttttcatgta tatgttgtga cgcatctcct ttaactgcac
```

FIG. 2I-1

```
17161 gtacaaattc cagcattgca cagccagtat cgtaagcacg cccattatga ttacgggata
17221 attttgatta aacacggtcg gctcgtgatc gcttacaatc gctcggcaca tgatgcattt
17281 tttgtaaatg ttcacataca cacagttttg gctcaaggtt tcggtatttg cgtagtcaat
17341 ttccagatac acgatagagt tccagcacat tgattccaaa tcgtagtgac gatataaaac
17401 atctagcgcc ggtagatgac catttttgaa cacgtagatt tgaaacgcgg caaacagcat
17461 ccaacacagc ccagtgatca cgtttaccat aatacacgtg atagcgacgt aaaagttttc
17521 tttcgcattg aaatttacat ttgtgtttga agagctgctg cgattttcg tccacacgat
17581 aatcttccat ataaaataaa acatgtaaaa taatatccac atgccgaacg ccagcattat
17641 cggtatagat agattgataa ccgattgctt tccttcaatt tccagcaaaa acgcgtatct
17701 gctgtctatc actcccatta tagataacac aaacactatc agatatgcta ataataatga
17761 ggcattaagc ccgaattgta aaactgcagt gattttattt aacattttga atatttaatt
17821 caacaactaa gtaatggcaa tatgtatcga gtactgatcg tgttttcct gttcgtgttt
17881 ctttatatag tgtaccagcc cttttatcag gcatacttgc atatcggaca tgcccaacaa
17941 gattacaatg acacgttgga cgataggatg gattacattg aatccgtaat gcgtagaagg
18001 cactacgtgc cgattgaagc gttgcccgca atcaggtttg atactaatct cggcacgttg
18061 gccggtgaca cgattaaatg catgtcggtg cctttgtttg ttagtgacat tgacctgccg
18121 atgtttgatt gtagtcagat atgcgataac ccgtctgcgg cgtatttctt tgtcaacgaa
18181 acggatgtgt ttgtggtcaa cggccacaga ctgacggtgg gcggatactg ctccactaat
18241 agtttgcccc gcaactgtaa tcgcgagacg agcgtcattt taatgagtct caatcagtgg
18301 acgtgcatag ccgaggaccc gcgttactat gcggcacag ataacatgac gcaactcgca
18361 ggcagacaac actttgaccg cattatgccc ggacagagtg ataggaacgt cctgtttgac
18421 cgattactag gccgagaggt gaacgtgacc actaacacgt ttcgccgcag ctgggacgag
18481 ttgctggagg acggcactag gcggttcgaa atgcgctgca acgcccgaga taacaacaat
18541 aatctcatgt ttgttaatcc gcttaatccc ctcgagtgtc tcccgaacgt gtgcactaac
18601 gttagcaacg tgcacaccag tgttagaccc gtatttgaaa cgggagagtg tgactgcggc
18661 gacgaagcgg tcacgcgtgt tacgcacatt gtgccggggg acaggacctc tatgtgtgcc
18721 agcattatag atggcctgga taaaagtacg gcatcatata gatatcgcgt agagtgcgtt
18781 aatctgtaca cctctattct aaattattct aataacaaat tgttatgtcc cagtgacact
18841 tttgatagta acacggacgc agctttgcc tttgaagtgc ccggctccta cccttatcg
18901 cgcaacggca tcaacgagcc aactatcgc ttttatcttg ataccagatc tcgagttaat
18961 tacaatgacg tcagagggca gttatcttaa ttgtgataac acaaacaata agtcatttaa
19021 atgttacgtc agtagttagt atataagccg tacatgttgg cttgcaaatt cagtcaatat
19081 caggctttta tcatggacgg tgtaaagctg ctaggacgt cgcgctaat aatttgtta
19141 tcgacgacga gtacagttgt cgggcgtgac cgtatcacgt ttacgccgat agaagatagc
19201 gcaggcctca tgtttgaacg catgtacggc ttgcgacatc atacagacga cagatttgtg
19261 tttgtgaaaa aattcaattt tgtttcggtg ctgcaagagc tcaataatat caaatctaaa
19321 attgaattat atgaagcgca agtttcaact tgcacaaacg tcagacaaat aaaacagaac
19381 agatcgagta tcatcaaagc tcgcattgaa aatcagctgc agttttttgac gcaactaaac
```

FIG. 2J-1

```
19441 aaaaatctca tcacatactc tgtggaaagc agcattttaa gcaacgacgt gctggacaac
19501 atcgatctgg aatatgacga cagcggtgag tttgacgttt acgacgaata cgaacagcct
19561 tcgcattgga gcaacatgac tgtatccgac gcgcaagctt tgctccgaaa cccgcccaaa
19621 gacagagtaa tgttttgga catggttacc accagcgacg tgagcagcaa atacgaagaa
19681 tacataaact gcattgtgag caaccgtacc gttgaaaacg agtgcatgtt tttagccaac
19741 atgatgaacg tgctcaacga caaattggac gacgcagcag ctttggccaa gatgctggag
19801 cgaatagtaa acaaacgcg aagaacaaa ctcaacatct ccaacacggt tatagacgac
19861 gacacgctgc taacggaaat gaaaaaatta acacaaactt tatacaacca aaaccgcgtg
19921 tgggtagtgg attttaacaa ggacatgaat agttatttcg atttgtcgca agcgtataaa
19981 ttgcatttat atgttgattt aaacacggtc attatgttta ttaccatgcc attgttaaaa
20041 tccaccgccg tttcgtttaa tttgtatcgc gtcatgacgg tgccttttg cagggcaaa
20101 atgtgtctgc ttatcatttc gggcaatgaa tactttggga ttacagacag caaaaactat
20161 tatgtgcccg tatctgataa ctttagacaa gattgccaag agtttacggg ctacaatgag
20221 tttttgtgtc ccgaaactga gccgattgcc actatgaact cgaaagtgtg cgagattgaa
20281 atgtttatgg gtcgatatag cgacgacgtg gacaacatgt gcgacattag ggtggccaat
20341 tataatccca aaaagctta cgtgaacact taatagact accgaaaatg gttgtacatt
20401 tttccaaaca cgaccgtgtc cgtccactat tattgtcacg acgcgcttgt agaagttgat
20461 acaaaagttt cgcccggcgt tggtgttatg ttttcgacta tggcgcaaac gtgttcgatt
20521 agaataacgt atgatgtgac cataactgta gattcgcgat tttatgtcag ccattcaact
20581 acatactggc taaaaagaa atttaatttt aacaactaca tcgaccaaat gttgcttgaa
20641 aaagcgacca ccagttttat accgactgtt gacaattta cccggccgt tttattgcaa
20701 cttcctcata aatttcacat taaagattac acatcgacgc cccatcattt tttccatcag
20761 tctaaaattt acaccaacag cgcggcgccc gacgaagact cgcaagacga cagtaatacc
20821 accgtggtaa ttatcgctat tgtcgctgca atgatcctat tctgtggatt attgttattt
20881 ttgttttgct gtataaaaaa acggtgtcat caatcaaata acgtggttgt gcaatacaaa
20941 aataacaatg aatttgtcac aatttgcaat aatttagaag acaatcgagc atacattaat
21001 ttacctaatg aatacgatag cgatgatatg ccaaaaccat tgtaccctt acttggcttt
21061 aatgatgatt tgttaaaaga tgataaacct gtgttgtacc ctatgattat agaaagaata
21121 aaataaaaca tgtataattg aaataaatat attatttaat aaaatgtttt ttatttatat
21181 actatttct attacatatt ccaatgcaca caaatgttta atggctatca gttttaattt
21241 tactaattcg tctaaacaaa aattattcac ttgctgtttt tcatccattt gacatatggc
21301 gtttataaat aattcgctgt gttttatgaa cgaatcgtaa accgctgcct gggccttcag
21361 cacggtcggc gcattgtatt tttgggtaaa gtacgcaata tttttagtca aacacagaga
21421 ttttaaatct ttttcattta tatccaagtc ggaacaatcg tatacaaaat ctagcttttc
21481 actttcgggc gcgcccagat actggtttac gagttcgagc tgctccactt ggcctttgat
21541 atcggccgct atgcacaaca ttttgtcgat tgcagtttca ttgttttaa cataataatt
21601 tttaactttt ttattttgca atttaatcaa actatttaaa ttcgcttgac ctttcttaca
21661 aagcgcagtt aatatgcaag acattttgac ttataataaa aaacaaaact tttatatatt
```

FIG. 2K-1

```
21721 catttattgt tcaataataa caaatattcc aggcttaaaa gctaacgaat agggcttttc
21781 ggtaattttc ttattattca tgtccgtcat ctgcatctct ttgccgtact tgacgccgtc
21841 aatggtgccc atcatgtaca ttttaatctc ctccgaaggt ccgtctattt tgtccatttc
21901 gaacaatcta tcaaaatctt caacgctcat tctctgcata tcaagaggaa cgtttctgat
21961 ctttccggtg gcgtaaattg atccgttgtt gtcacggttg attatgtaaa accgacgaat
22021 caacatgtcg cgctcgctag ttttgttctt atccggcaaa tgaatgcaca cgtttggttc
22081 catcttcaaa ggaaaatcgc tttgcaagtg tttttgcaaa atgttgccaa atatattgtt
22141 gtgtttgtga atgtctccgt attgaatgct aaaaaactgg ccaaagttgc ttttggcacg
22201 ttttatggtt ccaaagtcgg aaaaccaaaa tccgcagggc ttgccctgca ctcttggacc
22261 gatggtgtac gtagtcttgc cgttggccgg ctccaacacc acgatatttt tatcgggctc
22321 gggatacaac ttgtcttccc attcgtgcaa actgttcaaa ttagacagtc gacaaaattc
22381 gttttttcaaa aatctgcctt cgaaacaact acaattcagt attgaaaagt tgcctcgttt
22441 cacattaatc gccatctgct cctgccacaa catcttcgtc aactcgtgtg gctccaattg
22501 aatggacgac ggcgtaaaat agcacattac gcccgtttcg tcgtgtttca cgttaaaagc
22561 gccgctgttg tacggcacca gctgctggtc ctcaccacct tccgatcttt ccgcttcgg
22621 ctggttgtcg tcgctgctcg aatatccatc gccaatcttg cgtttagttg ccatgctacc
22681 gacgtgcgct gtctgctgtg gttcaagtct aattgaagtg tttcacagaa tataagatat
22741 ataataaata tggacgactc tgttgccagc atgtgcgtag acaacgcgtt tgcgtacact
22801 actgacgatt tattgaaaaa tattcctttt agtcattcca aatgcgcccc tttcaagcta
22861 caaaattaca ccgttttgaa gcggttgagc aacgggttta tcgacaagta tgtggacgtg
22921 tgctctatca gcgagttgca aaagtttaat tttaagatag atcggctaac caactacata
22981 tcaaacattt tcgagtacga gtttgtagtt ttagaacacg atttgtccac agtgcacgtc
23041 attaacgccg aaacaaaaac caaactgggc catataaacg tgtcgctaaa ccaaaacgac
23101 gcaaacgtgc tcattttgac cgtaacttta acgagctaaa atgaacgagg acacgccccc
23161 gttttatttt atcagcgtgt gtgacaactt tcgcgacaac accgccgaac acgtattcga
23221 catgttaata gaaagacata gttcgtttga aaattatccc attgaaaaca cggcgtttat
23281 taacagcttg atcgttaacg ggtttaaata caatcaagtt gacgatcacg ttgtgtgcga
23341 gtattgcgaa gcagaaataa aaaattggtc cgaagacgag tgtattgaat atgcacacgt
23401 aaccttgtcg ccgtattgcg cgtatgctaa caagatcgcc gagcgtgaat cgtttggcga
23461 caacattacc atcaacgctg tactagtgaa agaaggcaaa cccaagtgtg tgtacagatg
23521 catgtccaat ttacagtcgc gtatggatac gtttgttaac ttttggcctg ccgcattgcg
23581 tgacatgatt acaaacattg cggaagcggg acttttttac acgggtcgcg gagacgaaac
23641 tgtgtgtttc ttttgcgact gttgcgtacg tgattggcat actaatgaag acacctggca
23701 gcgacacgcc gccgaaaacc cgcaatgtta ttttgtattg tcggtgaaag gtaaagaatt
23761 ttgtcaaaac tcaattactg tcactcacgt tgataaacgt gacgacgaca atttaaacga
23821 aaacgccgac gacattgagg aaaaatatga atgcaaagtc tgtctcgaac gccaacgcga
23881 cgccgtgctt atgccgtgtc ggcattttg cgtttgcgtt cagtgttatt ttggattaga
23941 tcaaaagtgt ccgacgtgtc gtcaggacgt caccgatttt ataaaaatat ttgtggtgta
```

FIG. 2L-1

```
24001 ataaaatggt gttcaacgtg tactacaacg gctattatgt ggaaaaaaaa ttctccaagg
24061 agtttttaat tcatattgcg cctgatttga aaaacagcgt cgactggaac ggcagcacgc
24121 gcaaacagct gcgcgttcta gacaagcgcg cctacaggca ggtgttgcac tgcaacggca
24181 gatactactg gcccgatggc acaaagtttg tctctcatcc gtacaacaaa tctattcgca
24241 cgcacagcgc aacagtcaaa cggaccgaca gctcgcatcg attaaaaagc cacgtggtcg
24301 acaaacgacc gcgccgctct ttagattctc ctcgcttgga cggatatgtt ttggcatcgt
24361 cgcccatacc acacagcgac tggaatgaag aactaaagct gtacgcccag agccacggct
24421 acgacgacta cgacgacaat ttagaagatg gcgaaatcga cgaacgtgac tctttaaaaa
24481 gtttaaataa tcatctagac gacttgaatg tattagaaaa acaataaaac atgtattaaa
24541 aataataata ataaaactat attttgtaat atataatgta ttttatttaa aaattgtcta
24601 ttccgtagtt gagaaagttt tgtcttgact tcataactct cttctccata ttctgcagct
24661 cgtttacgtt ttttgtgacg cttttaattt tctcaaaatg ctggctgtca atagttattt
24721 tttgcttttg tctattaatt tcttccaatt gagatttaa atctcgctga gattgagatg
24781 cgttgtaatt ccttgagaac atcttgagaa acatacaga tgaggtaaaa cagcatcttt
24841 tatccaaatt aggagttaat tattattcat ttgtatcgcg accatttgct cgtacacatc
24901 ttccataaaa tggttatttt tattgcgata agtgttggca ttgacatttt gcaaatgtcg
24961 taggttaaag gggcaaatgg gctgcgtggc cgataaaaga ttccagttca acaatccctc
25021 ttcgcccccg tttaacttga aaatggcgct acacgtttct acgctatcgt gttcctgttg
25081 agtggcgcac ggttcgacca gtatcatctt gtgatatgcg gttttgacat tcatgtgcaa
25141 cggaataact tgcgggtcat cgcattcgtc ggaattaagc tttaaatggc gtccgtatgc
25201 tttccaaagt ttttcgtcgt cgaaccgcgg cactgcttgc aagtcgacgc ggggaaacgg
25261 cgctctgtac aaaacgccta aattcaaaaa ctgattgcat tgttgcagct ctgtccaatc
25321 gacgcgattt ttgtaatttt gaaacagcat caggttgaac gccgcgctgg cgcgcacgtt
25381 tgtaatcact gtgtaattga tcagcttgtg ccaatactgg gcattgaaat ttcttcaaa
25441 ctcatttcta aactctggat gcgcaaacat gtgtctaatg tagtacgcgg gcggggcgtt
25501 gaacgcagtc catttgtcaa tacacttcca gtctgaatgt aacgtgttca ccaaaccggg
25561 atattcgtca aacacgagca tgtgatccga ccacggtatg ctgtgggcga tcaattttag
25621 ttcttgcacg cggccttcgc gtaagcaata caaaatgagc gcgtcgctga tcttgacaca
25681 gtcttgcatg tacgcggaca aattaacgtt ttccatacag ctcacattgt ttattagcgc
25741 cgtgttcaag tgtttgtatt tggacacata atcgtagttg atgtactgtt taatgggttc
25801 ttgaaaccat tcttttagta gtatgtgact ggccactatg cgtttccaat ttaatttgtg
25861 tgcgtatttt tgctgcaccg acaacgagag gttattgtaa ttttggata tttcttccat
25921 gtccaacaag tccccaaacg cgagtataaa atcttgcgtc aaaatttttt gctcagacac
25981 caacgaccag atcaaatgtg atttaaacct gttggcgatt gttatcgaca acggcgaaat
26041 tgaaataatt ttccaatcca acttgttgcg aaacacgtga ataaaatcga cgcgtccgta
26101 acattcgcgc gatatgcgct tccaaaacgt gtcatcttgc aaattaagca aatagacacg
26161 attgttggga gatttgacgg ccaattcaat tattttata tattcttttt gctttaaagc
26221 gcgttgtagc acttgggttg gagccatgtc gactgaagct ccacgctgtt tgaagcaagg
```

FIG. 2M-1

```
26281 tgaccgtttt ggtcggcatg ttcaaacgtc gattacatgt ttgctttgca tcaaaatggc
26341 gtaattaatt aagaaacaac atgaaagcca tctgcatcat tagcggcgat gttcatggaa
26401 aaatttattt tcaacaagaa tcagcgaatc aaccgcttaa aattagcggc tatttgttaa
26461 atttgcctcg aggtttgcac ggctttcacg tgcacgaata tggcgacacg agcaacggtt
26521 gcacgtcggc cggtgagcac tttaatccca ccaatgagga ccacggcgct cccgatgctg
26581 aaattaggca tgttggcgac ttgggcaaca taaaatcggc tggctacaat tcactgaccg
26641 aagtaaacat gatggacaac gttatgtctc tatatggccc gcataatatt atcggaagaa
26701 gtttggtcgt gcacacggac aaagacgatt tgggccttac cgatcatccg ttgagcaaaa
26761 caaccggcaa ttctggcggc cgtttgggat gcggaataat tgccatatgt aaatgatgtc
26821 atcgttctaa ctcgctttac gagtagaatt ctacgtgtaa aacataatca agagatgatg
26881 tcatttgttt ttcaaaactg aactcaagaa atgatgtcat tgtttttca aaactgaact
26941 ggctttacga gtagaattct acttgtaacg catgatcaag ggatgatgtc atttgttttt
27001 caaaaccgaa ctcgctttac gagtagaatt ctacttgtaa aacataatcg aaagatgatg
27061 tcatttgttt tttaaaattg aactggcttt acgagtagaa ttctacttgt aaaacacaat
27121 cgagagatga tgtcatattt tgcacacggc tctaattaaa ctcgctttac gagtaaaatt
27181 ctacttgtaa cgcatgatca agggatgatg tattggatga gtcatttgtt tttcaaaact
27241 aaactcgctt tacgagtaga attctacttg taacgcacga tcaagggatg atgtcattta
27301 tttgtgcaaa gctgatgtca tcttttgcac acgattataa acactaatca aataatgact
27361 catttgtttt caaaactgaa ctcgctttac gagtagaatt ctacttgtaa aacacaatca
27421 aggatgatg tcattataca atgatgtcat tgtttttca aaactaaact cgctttacga
27481 gtagaattct acgtgtaaaa cacaatcaag ggatgatgtc atttactaaa ataaaataat
27541 tatttaaata aaaatgtttt tattgtaaaa tacacattga ttacacgtga catttacgat
27601 ggcgaacaat aatttcactt tttatattag gacacgacgt gtatatagga aagcttaagc
27661 gtttcaataa agccatggcg tacacgctaa gcttgcccag cttgcggctc tttgaaatct
27721 gtagttttcg gggagtaccg tcgttcttca gtgccacata cgtcaacttg cgatcgtaca
27781 ctttataata cgtgttgtag ttatttttt ccagaaattc cctcataaag caatccttgg
27841 ataaagtttt tgatccgtac agttggccac accggtccat gcacaggtac acacacgtga
27901 tggcgttttg aatgacgatg cgatttctgt caacggcaac gcgcttgaat atggtgtcga
27961 cgttgtccga ttcaatggtt ccgtaaacag ctccgtctgg atttactgcc aaaaactgcc
28021 ggttaataaa cagctggccg ggaatagacg tgcccgtgat gtgtgtcagc agagctgagc
28081 agtcagccat agaggctaga gctacaagtg ccagcaagcg atacatgatg aactttaatt
28141 ccccacagca aactggcgct tttatataaa aatttgggcc attttggcg attagataat
28201 ttttgaagat tagataatat tgagattagt taataatttg tgtgattaga taactttta
28261 gggtattgcg cattataaat caaggtcgag ttgtataaac tgctctggcg tgtaaaactg
28321 cagacttaag ttttttgcaa acactcggtc tgaatcgcta aaatctttct gaccggtggt
28381 tagattaatt cggccagccg cgtcgcccac ataaaaagat tgttccttgt caatatgcgt
28441 aaactgtttg gccatctcgc gccacattcc cgtgtcgggc ttcgatgct catccttgtt
28501 gggcgacaca taaaacgata tgggcacgcc agtagctttt ttaatattct ctaatttata
```

FIG. 2N-1

```
28561 taataaatcg ctcgctttga ttttgccgga acctaaatgg gcttggttcg taaaaacaac
28621 taaatcgtag cctaattcgt acaaacgctt tagcttgtgt gcgcacggaa ggagctgcca
28681 gtcgtctggg tttttttggaa atttggaccg tgtctttgag ctaattagcg tgccgtccaa
28741 atcaaaagcc gcaattttgg ttcttttagc gccgtcatga accgcgtacg catacaaatc
28801 gggctgctgt aacgtccaca tggtgaatgc atcttactca aagtccatca attcgtacgc
28861 gtttgtgtcc aggtcgggcg ttgaaaaatt gtagcttgcc attagatcgg atagcgattc
28921 aaattttgta agcgtttgta gcgcacgttt ggcatcttgt ttaaaattac acgacgacag
28981 acagtaaaaa tattcctcga taagcatgac tacacccata tcactgttta agtgctcgac
29041 gtagttgttg catgttatgt cgcgtgtgcc gcgatacgcg tgatttcggt gaaaatcaca
29101 ccacaaccag tcggcgtgcg tgtaacaaag tcgacagcga aacaatttat cgttttccaa
29161 aaaatttaaa tactcgacag ttttgcagct tagattccgc gtttgattca ccttaaaatc
29221 gtcgtcagcc tctataatct cgggcaacag cttgccttgt tgccccatcg tatcgatcac
29281 ctcccccaag tggcccggtg ttatattaag tcgtttaaaa tcatttattg cttcctgcac
29341 gtcggcctgg taattttttga ccacgggcgt ggaaatcaat tgccgttgaa gggaaataat
29401 tcgtggtgtg ggtatcggcc gcctgttgca caattccacc agcggtggag gcaagggcgc
29461 attcacagca accgttgtca tttataagta atagtgtaaa aatgcaaata ttcatcaaaa
29521 cattgacggg caaaaccatt accgccgaaa cggaacccgc agagacggtg gccgatctta
29581 agcaaaaaat tgccgataaa gaaggtgtgc ccgtagatca acaaagactt atctttgcgg
29641 gcaaacaact ggaagattcc aaaactatgg ccgattacaa tattcagaag gaatctactc
29701 ttcacatggt gttacgatta cgaggagggt attaataata acaataataa aaaccattaa
29761 atatacataa aagttttttta tttaatctga catatttgta tcttgtgtat tatcgctaac
29821 cattaaaagt gctggagcca cagtgttgcg gcgagtcttt atagaagatc gttgtttggc
29881 tggaactgag cttttccttt tcctgctgcc gctaatggga gtgggcacgt actctgtagt
29941 agacggtgca acgggcaact tgagcgctac cgtcttaaat ttggccatac ttttagtgat
30001 gaaatcgcgc gttaacactt cgtcgtaaat gttacttagc agaggcgcaa cattgtgatt
30061 aaatgtctcg tttaacaagc tgtaaaactc cgaataaagc ttatcgcgca tttcgcagct
30121 ctccttcaat tctgccaaat ttgcgttggt aagcaccaca gtctgtcttt ttttgctcgc
30181 tggaattgct gcgttctcgc ttgaagacga cgatgtcgat cggtcggcca tttttttgcc
30241 cagcttttca gtgtgatcaa aaatgaacac aaaatctgcc aattcgggct tgtttttcac
30301 caaatcccac atggccgggc tactaggcca ctcgggctgc ttgatcttag tgtaccaact
30361 gttaaacaaa atgtatttat tgttgttaat cactttcttc ttgcgtttgg acatttgcg
30421 ttcgtcttgc atgacaggca ccacgttaag gatatagtta atgttctttc tttccaagaa
30481 atttacaata acggccagct ggtccatgtt ggatttgttg taagagctcg attccagttt
30541 attcaacagc ttttcatttt tgcacacggc cgcagtctcc ggagattgtt gctccggcac
30601 gttaccatg tttgcttctt gtaaaccttt gaacaaccc gtttgtattc ttgatgatat
30661 atttttttaa tgcccaacaa cctggcaatt cgtttgtgat gaagacacac cttacgcttc
30721 gaacatttgt cggtgattac tgtgaaatgg cctaaattag ctcttatata ttctttttata
30781 cgctcaaacg acacgatgtc caacatgtgc gcgcagacgt tttctgtgtt catcgtgtgc
```

FIG. 20-1

```
30841 ttgagcgtgt tgatggcttc cctgaacagc gcttgtattt cgctgcgagt caagcagtcc
30901 gaatcacacc cgcctaagtg cgtgcaattt tggggggca tcgttgtcta tctttttcag
30961 agtggcgtag aaaaagtcct gcaattgcct attatcaaaa cgcgccttga cgctgcgcac
31021 aaaatcaaaa aattcaatgt aattgctgta atcgtacgtg atcagttgtt tgtcgttcat
31081 ataattaaag tatttgttga gcggcacgat ggccaggctg cgcgctattt cgcaattgaa
31141 gcgtcgcgt tttaacatta tacggtagtc attgccaaac gtgcccggca acaacttcac
31201 ggtgtacgtg ttgggtttgg cgttcacgtt aatcaagttg ccgcgcacga cgcctacgta
31261 tatcaaatac ttgtaggtga cgccgtcatc tttccattgt aacgtaaatg caacttgta
31321 gatgaacgcg ctgtcaaaaa accggccagt ttcttccaca aactcgcgca cggctgtctc
31381 gtaaactttt gcgtcgcaac aatcgcgatg acctcgtggt atggaaattt tttctaaaaa
31441 agtgtcgttc atgtcggcgg cgggcgcgtt cgcgctccgg tacgcgcgac gggcacacag
31501 caggacagcc ttgtccggct cgattatcat aaacaatcct gcagcgtttc gcattttaca
31561 tatttgacac ttaaaaaatt gcgcacacga gcaccatcgt ttgatacctc attgcaacta
31621 tttacaattt atcagtttac gttgaacccg ttttaatttt ttagatccgt ccttgttcag
31681 ttgcaagttg actaaatgac aaaattttc ggttctgcaa aaccgcccctt gtctgttcca
31741 cccgttgtat ttgaaaaaac tttttttcac gcggcgacaa ctgcttgtat aatattgccc
31801 aatgtaaaca tgcaaaattt tgttactctc gtcaaaacag cggttggcgt tccattccat
31861 aatttttta ttatttatca acgatggcca ttgtaaattg tcgtcattta tacgcatcat
31921 atgatttaac aaaagctttt cgtatagcgg aacttcaatt cccttggaac attttcaaa
31981 cgataattta atttgtttct cggttggcag catttcatgc ttgattaaca atcgcctgac
32041 ttttatagcc acgtttatgt ctttgcacag caaatgtggg ttgtcgacaa tgtaatagtg
32101 caaagcattt gttacggcaa atgcgtagtt tgatttgacg acgcccttt tcttgacggg
32161 cattgcggct tttaaaatta cttgcaagca ttgtacgaat acctctttgt gtttaaacaa
32221 taatatggac aaacatcggc gaaacaattt gtaataatta tgaaatccca aattgcaggt
32281 tttaaacttc tttgttactt gttttataat aaataaaatt tgctgaccca tgtctgcgcc
32341 cacaacttta attaaccatt tgtgcgcata ttgattgtct cgttgttccc aaccggaaaa
32401 ttgattgatc tcgagccacc ggcattggtc gtttgatacc gtcgttaacg ccgacgctcc
32461 tgcctgtttg attacgggtt ctaaaagacg aaacagcagc gtaaatttgt ttttgcgtcg
32521 gtagtatttt ggcaggcaat aatcaaaaaa atccgtaagc aattctctgc atctattaat
32581 attcgttgcg tacgaatcga gttttcaaa aattactttg tttgtatgaa ataacgtttt
32641 gggcttctca caataataat cttcgttgta gaacagaaac ggtttgcgag aattggcacg
32701 tttgtccatg attggctcag tgtaacgatt gattcaaatc aaaattgaca acacgtttgc
32761 cgtaatgtgc accggttcgc acacgtttgc cgcgtatgta atccatgttt atttcgctgt
32821 cgcaattgat tacacgattg tgttgggcgg cgcgttttat tgaatttagg cgacgcgtcg
32881 acaactccaa aggattgtaa agcgcagatt tttccagagt aaacgagttt aagtggccac
32941 cgttgaacca ttccagagcc acgattgtgt acagcaaaaa gaatatttct ttgtcgacgt
33001 tttcaaacgc aaacttgttt ttaggcaat agtagtaaaa ttttaacgaa ttgtataaat
33061 aaaacataaa attgccattt ttaaagtaaa attctacatc cgtgacgaac aaaaggttta
```

FIG. 2P-1

```
33121 ctattttgtt ctccaacaag tgtgccaatt ttcttaagta caccattgaa tttttgtcgt
33181 cgtccatctc gatcaacaac acgtacggcg ttttggaatt taaaattatt ctaaaatttt
33241 cctgttgcaa cgattccaca gcgtccgacc aatatgacgc tgccacctct agacagatgt
33301 atttcttgga aaacacgtgt cgtttgataa cctcgctgat ggacgtgatc gattgtaaat
33361 acttttcaaa cgtcgcgtct tcccaaccac gcaccgacac gggcgctgtc gtgtcgggct
33421 gatgtttgaa atccaaacca ctctgaatta acttggttgt gattcgtatg ctcaactgtt
33481 gacccaacgt gtagtgatct tcgtaggcgc gctcccacat cacgttacac acaaatttga
33541 cgagatcatc aacgtctttc tgttgcaaaa ttcgccgcaa acgcgccaca tcgcccttgt
33601 accaccgatc tcggcacaca agctgtagca tttttaaatc gtgatcgctc aagctattaa
33661 ttctggttag atttatatag tcgtcaatat cctcgggcgt ggtttgcgtc atgtctgtaa
33721 aacgtgcaaa atcaaacatt tttatgttgt agtcgaatct aacaaatcca tcggcgttca
33781 cttgcacttc gcgctttaca aaacgaggta gcgtgtaatc gaaccgttt aaatagattg
33841 cgtacaaaac cagcacttca tcttccagtt tgcacgcttg cggcaaaaat tgtgtggtgt
33901 gctccaaccg ggtgacaaac atgactatgg aaaataacgc ggaattcaac agacgactag
33961 agtacgtggg cacgatcgcc acaatgatga acgaacatt gaacgttta cgacagcagg
34021 gctattgcac gcaacaggat gcggattctt tgtgcgtgtc agacgacacg gcggcctggt
34081 tatgcggccg tttgccgacc tgcaattttg tatcgttccg cgtgcacatc gaccagtttg
34141 agcatccaaa tccggcgttg gaatatttta aatttgaaga aagtctggcg caacgccaac
34201 acgtgggccc gcgttacacg tacatgaatt acacgctttt taaaaacgtc gtggccctca
34261 aattggtcgt gtacacgcgc acgctacaag ctaacatgta cgcggacggg ttgccgtatt
34321 ttgtgcaaaa ttttccagaa acaagctaca aacatgttcg tgtgtatgtt agaaaacttg
34381 gtgcgataca agtagcgaca ttatcagttt acgaacaaat tattgaagat acaataaatg
34441 aactcgtcgt caatcacgtt gattagataa tgtccgtgtt aaatgtgata tcttagatta
34501 cgagcgcgca ataaccatag tttaatcgaa gagaatagcc gtcgccacaa tggataatta
34561 caaattgcaa ttgcaagaat tttttgacca agcgcccgac aacgacgatc ccaactttga
34621 acatcaaacg cccaatctat tggcgcatca gaaaaaggc atacagtgga tgattaacag
34681 agaaaaaaac ggccggccca acggcggcgt gcttgccgac gacatgggac tcggcaaaac
34741 gctctctgtg ctaatgttaa tcgcaaaaaa caactctcta caattgaaaa ctctaatagt
34801 gtgtcctttg tctttaatca atcattgggt aaccgaaaac aagaagcata atttaaattt
34861 taacatttta aagtattaca aatctttgga tgccgacacg tttgagcatt accacattgt
34921 ggtgaccacg tacgacgttt tattggcaca tttcaaattg atcaaacaaa ataaacagtc
34981 aagtctgttt tcaacccgct ggcatcgagt tgttctagat gaagcgcata ttatcaaaaa
35041 ctgcaagacg ggcgtgcaca acgccgcgtg cgctttgacc gcaacaaacc gatggtgcat
35101 taccggcaca ccgatccaca caagcattg gacatgtac tcgatgatta atttttttgca
35161 atgtcgtcct tttaacaatc caagagtgtg gaaaatgtta aataaaaaca acgactctac
35221 aaatcgcata aaagtatta ttaaaaaaat tgtttttaaaa cgcgacaaat ctgaaatttc
35281 ttctaacatt cctaaacaca cggttgagta tgtacatgtt aattttaatg aagaagaaaa
35341 aacgttgtac gataaattaa agtgtgaatc ggaagaggcg tatgtgaagg ctgtggcagc
```

FIG. 2Q-1

```
35401 gcgtgaaaac gaaaacgcac taagccgatt gcagcaaatg cagcacgtgt tatggctaat
35461 actgaaattg aggcaaatct gctgccaccc gtatttggcc atgcacggta aaatatttt
35521 ggaaacaaac gactgtttta aaatggatta tatgagcagc aagtgcaaac gagtgctcga
35581 cttggtagac gacattttga acacaagcaa cgacaagata atattggttt cgcaatgggt
35641 ggaatattta aaatatttg aaactttt taaacaaaaa acattgcta cgttaatgta
35701 cacgggccaa ttaaaagtgg aagacaggat tttggccgag acgacattca atgatgctgc
35761 caatactcaa catcgaattt tgctgctttc cattaagtgc ggcggcgtcg ggttaaactt
35821 aataggcgga accacattg taatgttgga gcctcattgg aacccgcaaa ttgaattgca
35881 ggcgcaagac cgaatcagtc gtatgggaca acaaaaaac cgtacgtgt acaagatgct
35941 aaatgtggaa gacaacagca tcgaaaaata cattaaacaa cgccaagaca aaaagattgc
36001 gtttgtcaac acggtctttg aagagactct gctcaattac gaagacatta aaaattttt
36061 caacttgtag ctggtaagtc gtcatgaaca cccgatatgc tacttgctat gtttgcgacg
36121 agttggtgta cttgtttaag aaaacgttta gtaacatgtc cccttcggcc gctgcgtttt
36181 accaacggcg catggccatt gttaaaaacg gtatcgtgct gtgcccacgt tgttcgtcgg
36241 aactaaaaat tggcaacggc gtttcgattc caatttaccc ccaccgcgct caacaacatg
36301 cacgacggtc gcgttaagac gcaagcgctt cgagttttgg cccgctcgct acctccgctg
36361 tacgactcga ccgtcgatcg acacggctgc aaggtgttca cggtgcggcg ctacaacaga
36421 cgcgtaatcg actttgcggg cattcgcaac aaaacgctgg aaatcattaa acggataga
36481 aacttgccgc tcaacacaga atgcaatgtg aaagttgtcg acagtgcatg catgcgttgc
36541 agaaaaagtt tcgcagttta cccgccgtt acctatctgc attgcggaca ttcgtgtctg
36601 tgcaccgact gcgacgaaac ggtaaacgtg gacaacacgt gtcctaaatg taaaagcggc
36661 attagatata aattaaaata caaaactttg taacatgttg ccctacgaaa tggtgattgc
36721 cgtgttggtt tacttgtcgc cggcgcagat tctaaattta aaccttcctt ttgcatacca
36781 aaaagtgtg ctgtttgcca gcaactctgc aaaagttaac gaacgcatca ggcggcgagc
36841 gcgtgacgac aacgacgacg accctatt ttactacaaa cagttcataa agattaattt
36901 tttaactaaa aaaataataa atgtttataa taaaactgaa aagtgtatta gagcgacgtt
36961 tgatggtcgg tatgtggtta cacgcgacgt tttaatgtgc tttgtaaaca agagttatat
37021 gaagcaattg ctgcgcgagg ttgacactcg cattacacta cagcaacttg ttaaaatgta
37081 tagtccagaa tttggttttt atgtaaatag caaaattatg tttgtgttaa ctgaatcggt
37141 gttggcgtct atttgtttaa aacactcgtt cggcaaatgc gagtggttgg acaaaaatat
37201 aaaaactgtg tgtttacaat taagaaaaat ttgtattaat aataagcaac attcgacatg
37261 tctatcgtat tgattattgt catagttgta atatttttaa tatgtttttt gtacctatca
37321 aatagcaata ataaaaatga tgccaataaa aacaatgctt ttattgatct caatcccttg
37381 ccgctcaatg ctacaaccgc tactactacc actgccgttg ctaccaccac taccaacaac
37441 aacaacagca tagtggcctt tcggcaaaac aacattcaag aactacaaaa ctttgaacga
37501 tggttcaaaa ataatctctc atattcgttt agccaaaaag ctgaaaaggt ggtaaatccc
37561 aatagaaatt ggaacgacaa cacggtattt gacaatttga gtccgtggac aagcgttccg
37621 gactttggta ccgtgtgcca cacgctcata gggtattgcg tacgctacaa caacaccagc
```

FIG. 2R-1

```
37681 gacacgttat accagaaccc tgaattggct tacaatctca ttaacgggct gcgcatcatt
37741 tgcagcaaac tgcccgatcc gccgccgcac caacaagcgc cctggggccc ggtcgccgat
37801 tggtaccatt tcacaatcac aatgcccgag gtgtttatga acattaccat tgtgctaaac
37861 gaaacgcagc attacgacga agctgcgtcc ctcacgcgtt actggctcgg cttgtatctg
37921 cccacggccg tcaactcgat gggctggcac cggacggcag gcaactcaat gcgcatgggt
37981 gtgccctaca cgtacagtca aatgttgcgc ggatattcat tggcgcaaat taggcaagag
38041 cagggaatac aagaaatcct aaacacgatc gcgtttccgt acgtgactca aggcaacggc
38101 ttgcacgtcg attcgatata catcgatcac attgacgtgc gcgcttacgg ctatttgata
38161 aattcatact ttacgtttgc ctattacacg tactattttg gagacgaggt aatcaacacg
38221 gtgggtttga cgagagccat cgaaaacgtg ggcagtcccg agggagttgt ggtgccaggc
38281 gtcatgtctc gaaacggcac gttgtactcc aacgtgatag gcaactttat tacgtatccg
38341 ttggccgtcc attcggccga ttactccaaa gtgttgacca aactttcaaa aacatattac
38401 ggttcggttg tgggcgtaac gaataggttg gcttactacg aatccgatcc cacaaacaac
38461 attcaagcgc ccctgtggac catggcgcgg cgcatttgga atcggcgcgg cagaattatc
38521 aactataatg ccaacacggt gtcgtttgag tcgggtatta ttttgcaaag tttgaacgga
38581 atcatgcgca tccgtcggg caccacgtcc acgcagtcgt tcagaccgac cattggccaa
38641 acggctatag ccaaaacgga cacggccggc gccattttgg tgtacgccaa gtttgcggaa
38701 atgaacaatt tgcaatttaa atcgtgcacg ttgttctacg atcacggcat gttccagcta
38761 tattacaaca ttggcgtgga accaaactcg ctcaacaaca caaacgggcg ggtgattgtg
38821 ctaagcagag acacgtcggt caacaccaac gatttgtcat ttgaagcgca aagaattaac
38881 aacaacaact cgtcggaagg caccacgttc aacggtgtgg tctgtcatcg cgttcctatc
38941 acaaacatca acgtgccttc tctgaccgtt cgaagtccca attctagcgt cgaactagtc
39001 gagcagataa ttagttttca aacaatgtac acggccacgg cttcggcctg ttacaaatta
39061 aacgtcgaag gtcattcgga ttccctgaga gcttttagag ttaattccga cgaaaacatt
39121 tatgtaaacg tgggcaacgg cgttaaagcc ctgtttaatt atccctgggt aatggtcaaa
39181 gaaaataaca aagtgtcttt catgtcggct aacgaagaca ctactatacc atttagcgtt
39241 ataatgaatt ccttcacctc tatcggcgaa ccagctttgc aatactctcc atcaaattgc
39301 tttgtgtatg gaaacggttt caaattgaac aacagcacgt ttgatttaca atttattttt
39361 gaaattgtgt aattatattt agggagaatg tgatattcaa aagactgact gttaacacaa
39421 aagactgata ttgttgttgt tacaaaatag ataataaaac aaaaaataaa ttaaatatta
39481 tttatttatt aaactgttta attttaatgc taacgcgtac aaatcacgct gttccgacgt
39541 ggacatggaa ttgcgcagaa aagtcttgat agtgtcgatt tcttcgccgt catccacttc
39601 catatatttg atttcttcct cgatttgcat ttccaagttt gcgtattctt gcaaataata
39661 atctagtcgt tgggcgacct cgccaatttt aaataataca ttatccgaca ccaaatgcca
39721 gcgagtgact gtgcgctcca tcatcctggc acttttaat gtgaatatta aaaggttgtt
39781 gcatatatat cgttaaacgt ttatgtttac tttcacgtta gctcgtttca ttgatgtaaa
39841 catttagttt tataacagcg tcggtaattt tatttttaa agtaaacaga ccaaaatcaa
39901 aggtgtcttc gacaggtacg attattttcc cattgacact gttttcgtgc acagatataa
```

FIG. 2S-1

```
39961 ttttatcacc gtttattatt ttgcccaaac acacgtactc gtttcttctc aagccaacta
40021 tttctaaaca attcacttt ctattatcgt gtacgcaatt aaaagtaaac gaagcgctac
40081 aattgtcgta ttctattaca attctgcggc atttataaaa tttattaatg ttgacgcaaa
40141 ttccatgcag cgcatccatt tcgtactgca aatgcggcgc aattaaaaaa tttcctcgtc
40201 gttgttaaca atcttgggcg ctaaaaagca cgccaacacg cccacgtctt taatgcaata
40261 ttccaatttg aacggcagtt cctcggacat gtatattgtc acggtgggcg ccaaaggagc
40321 ggcttagca aatgacaca agtaatcgcc cgcaaaagtg tgcgttacgg tttgctttgc
40381 tttgagaacg gaaaagtttt cgttgtccgc gctcatctgc acgtccgccg agccaatgtc
40441 gccatttgct ctaaactgca gacccttctt ggaacacgac acaataatat cgtggtcgaa
40501 ttgcgtcatg tctttgcaca cctgcgcaaa ctcgacgctc gacatgtgga cgacgcaatc
40561 gtaatcgcta tccggaattc ccaaatgttc cacgtcgatg cacatcaact tgagcgtgta
40621 cgtgcagatt ctattgtcgt tgttgaacac gaacgccatc acatcgccct gatcttccgc
40681 tttcatcagt acagagctgc gctcgttaac gcatttgaca attttactta aactgtttat
40741 ggacacgttg agcggcacgt tgcggtcaca tctatatttt ttgaaaccct cggcgtgtag
40801 ttgcaacgac acgagcgcga catgcgaggt gtccataacc tgcatgctta cgcctcgatt
40861 atcacaatca aaagtagcgt gcggcagcag atccttaaaa gtttccacca gcctcttcaa
40921 aactgcgccg gttttaaatt ccgcttcgaa cattttagc agtgattcta attgcagctg
40981 ctctttgata caactaattt tacgacgacg atgcgagctt ttattcaacc gagcgtgcat
41041 gtttgcaatc gtgcaagcgt tatcaatttt tcattatcgt attgttgcac atcaacaggc
41101 tggacaccac gttgaactcg ccgcagtttt gcggcaagtt ggacccgccg cgcatccaat
41161 gcaaactttc cgacattctg ttgcctacga acgattgatt ctttgtccat tgatcgaagc
41221 gagtgccttc gacttttcg tgtccagtgt ggcttgtttt aataaattct ttgaaaatat
41281 tgtcgggtgt attattaaat agcatgtatg gtatgttgaa gatgggataa cgcttggcgt
41341 gcgggtcgtc atgatttcca ccgcgcacca catatttgcg ctcaattta tcaaaattgg
41401 actggcgaga caaaaacgag acgggcgaca ggcatatttg ggcgtgcgta ccatcttcgg
41461 ccatccactc ggtcaggtct tcgctgcggt taaacacacc tttctgaccg tgaatgccac
41521 atattttat tccttccaaa tcgttggtgg acgtgactat gactatttta agcataacgt
41581 tgtcgccgtt aaccaccatg ctggcgtcga gttttcaat ttttgattt taatttgtc
41641 taaagtaaac gtacactttg taaacgttaa aattgccgtt ggtgcacgtt tcaatttgt
41701 accgtcggcc gtcgtacacc caattaatct ttgcgttgct caccaacaca ccggccatgt
41761 acagcacaag tccgtcgtct agcgcaacgt aattttgtc gctactattc gtaaacttta
41821 ctaaacacga ctgcttgggg ccgaccacaa gcttgccctt caatttgttc actttgttgt
41881 tgtataaaca aatggcagc gcaatgtgcg gaatgtacgg atcttcggcg gtcatgagtt
41941 tattgtctcg caccaacgtc cacaatttaa acatttatt gttgagcaaa atggacttgt
42001 ttaccgccac agagtagcca tttggtaaac ccgatacgca attttcctct ttgtactcaa
42061 acacgggcat ggcattcttt agattggtta gggacacaat caatttgggt acgggcgtgg
42121 tatgaaataa atgtataaaa ttacgataat aatactgctc caacttggac atgagcgatt
42181 tgacgtcatc gttttctacg atcgtacact gaataatggg attatagtat atagaatgtt
```

FIG. 2T-1

```
42241 tatagtggta ttcgtagggt gtcaacaata cgttaatgtc ggcttcgttg ttcacccgca
42301 actttttttt gatgcatatc attccttcgt gatgattaac gtaaagtatt ctgtctgtaa
42361 tcttcaattc gatgggcgcc atgtttcttt tcatagtgta cacgataaac gacgtgtttg
42421 attttaaaca ttttaaattt gtgggtctat cattaaacgc gatcagcaac gagtcgtctt
42481 gaacgtcgtt gaggtcgtcc acgaacgcga ccagattgtg ttttagcaaa tattgaaatt
42541 tttgcgcaac catttcgtag tccacgttgg gcaaacatgc gttgcggcaa aggaaaaact
42601 ttttgcccgc cacggtcatt tcgccgtgaa aaaaactgcc aataaatttc acaaaatcct
42661 ttttttgctt caacattttc tggcgcatgc tgtcgttggt gattcgcgcc acctcgttgc
42721 cgacgcgata ttttaacacg ggcaacgaaa tttcaatatt gttattgctg ctgttgtcct
42781 gttgattggg aaagactttg cgttgcttgc taaaagtttt cgatacgcaa tatatgagac
42841 gcccgttgac tatacaatcg acaatctttt tcgactcttt gttgtacaag acgctttgaa
42901 ttttacgacg cttgttcgcc accgtgtacg cgtcgtcgtc ggccgtcttg tcgagaactc
42961 gttgatagtt ttgcaaaatt gtcgaagtta ataacagttc tatcaaatag gcgtgcttgt
43021 atacaatttt gttggccaaa ctgtctatag aatagtttat gtcgtgattc ataataattt
43081 ttatgtgttc cacgagttgt tgcttgtgaa gcgtgttgta ttcgaagaga aaatcgagcg
43141 gtttccattt gccgctgttg gccagatatg tttccagcac agaatttaaa tcttccgtca
43201 ctacgtaatc gctagcgtac acgtctcgag caaacaggac gtcgtcttgt ttgtcgtaaa
43261 ctagttggat tgcgcgattg atgtgcttct cttgatccac gttgccgtac aaaaacatgc
43321 gtttgcaatg tttggcgtat agcttgtcgt agaaattgtg caccaaaacg ttgttgttca
43381 tcattatgtt gggaaaactc aaaaatctgc cgtccagcat aaaagttccg ttaatattgt
43441 tgtttgcgtc gacatcgtcc gttctctaa attgcttgtc taagcgcgtg ccgaatataa
43501 cgggcacaca tttatgcatt acgcaactga gctgttcatt aagagcgcaa cacaaataag
43561 acttgcgttc ttgaatagcg caaaaaagca tacgttcatt gctgtttgta gcgcaatcaa
43621 aagtatattt taatttgtat ttattttcaa ttctatcgta caactcgttg aaatcttgaa
43681 ccacgtccgt catcgtgaag cgattactgc gcactaatta tgtctaaacg tgttcgtgaa
43741 cggtcggttg tttcggatga aacggccaaa cgcattcgac aaaacgaaca ctgtcatgcc
43801 aaaaatgaat cttttttggg gttttgcaac ttggaagaaa ttgattatta tcaatgttta
43861 aaaatgcaat acgttccgga ccaaaagttt gacaacgatt ttattttaac agtgtacaga
43921 atggccaacg tggtgacgaa acaagttaga ccgtataaca gtatcgacga aaagcaccat
43981 tacaacacgg tgcgtaacgt gttgatttta ataaaaaatg cgcgtttagt gcttagtaat
44041 agtgtcaaaa agcaatacta tgacgatgtg ttaaaattga aaaaaaatac agacttggaa
44101 tcgtacgatc cattgattac ggtcttttta caaattggcg aatctgtaaa tgaagaaata
44161 caaaaactca gaaaagcttt ggtcaatttt tttactaata acccgacaa gtcggatata
44221 aacaacccag atgtagtttc gtatcaattt attttggca gagtacaaaa attgtataac
44281 agggcaatta aacaaaaaac taaaactata attgtaaaac gtcctacaac tatgaacaga
44341 attcaaatag attggaaaac tctttccgaa gacgaacaaa aaatgactag acaagaaatt
44401 gccgaaaaaa ttgtaaagcc ttgttttgag caatttggca ctatattaca catatacgta
44461 tgtccttaa aacacaaccg aattattgtc gagtatgcaa actcagagtc ggtacaaaaa
```

FIG. 2U-1

```
44521 gccatgactg taaatgacga cactcgattt acagttacag agtttccgt ggttcagtac
44581 tacaacgtgg ccaaaacaga aatggtgaac cagcgaattg acataataag caaggacatt
44641 gaggatttaa gaaacgcttt aaaatcttac acataaatta aaatatcgaa caaaggaaaa
44701 aaacaattgt aacaaaata atttacatta aaatttacaa gttttttct agtgtcgtac
44761 tttttacaa tgcgtctgtt gtccgtcgag cattgcaaac atattgtgga cggcgcaaaa
44821 tagcaaacaa aaggcacgtc cgcgctctcc cacgctattc taaaacgatg aatccatatt
44881 aattttcat tgtcgccaaa cgtcgctccg ctggcctcct tccaataaca aatactcaga
44941 aacacaaaca tgtacaattg ctgtcgcggc gttaattgtc gctgttttc caaatagtct
45001 attatgggaa acaaacactt gtcacaacac aaatactcgt taattgtcac aaccgacaag
45061 cacatttggc aaaatgcgtc gcaattttg tacggacgag attctatgcg aagttcgttg
45121 tccatgacgt cttgggtcca cttttcaac aagcacttt tatatttgtg atttgtacaa
45181 ctttggtacg tgttagagtg tttttgataa gctttgataa gtttaaaact gttggagtaa
45241 ggccacgtca ttatgttctg cacctttgt ttaaaagaca gaaattacta tatgttcaaa
45301 ctatttaaag attattggcc aacgtgcacg acagaatgcc agatatgtct tgagaaaatt
45361 gacgataacg ggggcatagt ggcaatgccc gacactggca tgttaaactt ggaaaagatg
45421 tttcacgaac aatgtattca gcgttggcgt cgcgaacata ctcgagatcc ctttaatcgt
45481 gttataaaat attattttaa ctttccccca aaaacactag aggagtgcaa cgtgatgctt
45541 cgagaaacta aagggtTtat aggcgatcac gaaattgatc gcgtttacaa acgcgtttat
45601 caacgcgtta cacaggaaga cgccctggac attgaactcg attttaggca ttttttaaa
45661 atgcaatcat gacgaacgta tggttcgcga cggacgtcaa cctgatcaat tgtgtactga
45721 aagataattt atttttgata gataataatt acattatttt aaatgtgttc gaccaagaaa
45781 ccgatcaagt tagacctctg tgcctcggtg aaattaacgc ccttcaaacc gatgcggccg
45841 cccaagccga tgcaatgctg gatacatcct cgacgagcga attgcaaagt aacgcgtcca
45901 cgtaacaatt attcagatcc cgataacgaa aacgacatgt gcacatgac cgtgttaaac
45961 agcgtgtttt tgaacgagca cgcgaaattg tattatcggc acttgttgcg caacgatcaa
46021 gccgaggcga gaaaaacaat tctcaacgcc gacagcgtgt acgagtgcat gttaattaga
46081 ccaattcgta cggaacattt tagaagcgtc gacgaggctg gcgaacacaa catgagcgtt
46141 ttaaagatca tcatcgatgc ggtcatcaag tacattggca aactggccga cgacgagtac
46201 attttgatag cggaccgcat gtatgtcgat ttaatctatt ccgaatttag ggccattatt
46261 ttgcctcaaa gcgcgtacat tatcaaagga gattacgcag aaagcgatag tgaaagcggg
46321 caaagtgtcg acgtttgtaa tgaactcgaa tatccttgga aattaattac ggcgaacaat
46381 tgtattgttt ctacggacga gtcacgtcag tcgcaataca tttatcgcac ttttcttttg
46441 tacaatacag tcttgaccgc aattcttaaa caaaacaatc cattcgacgt aattgccgaa
46501 aatacttcta tttcaattat agtcaggaat ttgggcagct gtccaaacaa taaagatcgg
46561 gtaaagtgct gcgatcttaa ttacggcggc gtcccgccgg acatgtcat gtcccgccg
46621 cgtgagatca ccaaaaaagt ttttcattac gcaaagtggg ttcgaaatcc caacaagtac
46681 aaacgataca gcgagttaat cgcgcgccaa tcagaaaccg gcggcggatc tgcgagttta
46741 cgcgaaaacg taaacaacca gctacacgct cgagatgtgt ctcaattaca tttattggat
```

FIG. 2V-1

```
46801 tgggaaaact ttatgggtga attcagcagt tattttggtc tgcacgcaca caacgtgtag
46861 catcgccagt atttaacagc tgacctattt gttaaacaag cattcttatc tcaataattg
46921 gtccgacgtg gtgacaattg tatccacaat catgaaaaaa gtagcgcttg aaaaattat
46981 cgaaaacaca gtagaaagca aatataaaag caacagtgtg tcgtcgtcat tgtcaacggg
47041 cgccagtgca aaattgagtt taagcgaata ttacaaaact tttgaagcaa ataaagtggg
47101 ccagcacact acgtacgacg tggtcggcaa gcgagattac acgaaatttg acaaattggt
47161 gaaaaaatat tgacatgctg cgatcaatca tgcgacgttt caagagtaca acaatctca
47221 gcaaaaaacc ctccgattat tatgtagtgt tatgtccaaa gtgttatttt gtgacgtcgg
47281 ccgaagtgag cgtggctgaa tacatagaaa tgcataaaaa ttttaacacg aaattcgccg
47341 atcggtgccc taacgatttt attgtgacca actctaaaag ttggaataat catgaaaatt
47401 gttctgccct attttacect ctgtgttaat aaagtttgtt gtttgtattt tgtggttta
47461 tttatttacg ctagatattg ggtttaaggt tcttagaaat agagttgtat tttccctacc
47521 aaaagggatt tgagcttcat ataaatacaa ttttcgctcg acaagcggtt tatttcactc
47581 ggaggtatta tatcaggcag tcgaacgtgc gcgatgaaac atcccgttta cgctagatat
47641 ttggagtttg atgatgtagt gttagatttg actagtttaa tatttttaga gtttgataac
47701 gctcaaaatg aagagtacat tattttatg aatgtaaaaa aggcgtttta caaaaacttt
47761 cacattactt gtgatttgtc gcttgaaacg ctgaccgtgt tggtgtacga aaaagctcgc
47821 ctaattgtga aacaaatgga gtttgagcag ccgccaaact ttgttaattt tatcagtttc
47881 aacgcgaccg acaacgacaa ctccatgata atagacttgt gttccgacgc gcgcataatc
47941 gtggccaaga agctgacgcc cgacgaaacg tatcatcagc gcgtgtccgg attttggat
48001 tttcaaaaac gtaactgcat acctcggccc ccaatcgagt cggacccaaa agtgcgagac
48061 gccttggatc gtgaactaga aataaaacta tacaagtaga aaaaaattaa tttattaata
48121 gttgtaataa ttatcttcgt cctcatcttc gctggtgtca taatgcggtg gtgtgtttgt
48181 gttttgtttt aatcgtttgc gcgtcgacac cacttcgccg ataggaaatt ttttggattt
48241 cgcattaaat gcccgcttag cgacgcgccg tttacgacta ctaaacatgt tgacgcgctc
48301 gtcgtcttca gtgtcataat ccgtgctagt gttttcgttg ttattttcta tgagacgatc
48361 gtttgattta gttttcgtag aattgtccgc gttatcgtcg ctttcgtcga tgtcgtccct
48421 aactatctcg taggcggctt tgcgcggaat ccaagAattt tgcaatgtat ctattttaac
48481 gtactttct tcgagcgctt ttctagcttt atgcatagca atgtcttcgt cgccgccgtt
48541 catttatga tactttgtaa acgtctcgac gaataacttt ttggcgcgag gaggcatttt
48601 ttcattgtat aacatatcgg gaatttgata cattgtaatt agaattaagc aagttcgtct
48661 tcggttgtac tgtattcggt ttctgtatct gtagtggaat cctctgtact agtagtagtg
48721 tcgctattgt tggcgtcagg ccttggctgc catttaccgt ctatcaacat gtattttttc
48781 ctaacagcac aacatgctag cttggtagct atctgtgtcg acttatattt ttgtaaacta
48841 cgatcgtaga attttttcaaa tatcctctta ccgttatagg gaaggttttg ataatattta
48901 ggcaacatat caataaaaga caatataaaa actttgtgtt tgtgtttttat ttatcacata
48961 aaatggacgt ctggcaagaa tcacaaccaa tattagtgtt ttttttctta cattacgaga
49021 ttcaacttga tactaaaatt aattattaat taaattaaat taaattttga agcatttttt
```

FIG. 2W-1

```
49081 cgctatcgtt ttcagactca aaattatcga cgctatcgct atgaaaagcg taatatttgt
49141 tggctttgag atattctata ttttgctcat ttttaacaat aaacacgcga ctcttttcgt
49201 cgcgtctcac cataacaccg tttttacaaa tggaaatgta tttgtaaaac ggcaacagag
49261 cgtcgcgagt ttttttaagt aacagctttt gctccgctgt ggcggcaca aatattttta
49321 cgggcccgtc gtaattaatg tttaaattaa aatttttaag tcgacgctcg cgcgacttgg
49381 tttgccattc tttagcgcgc gtcgcgtcac acagcttggc cacaatgtgg tttttgtcaa
49441 acgaagattc tatgacgtgt ttaaagttta ggtcgagtaa agcgcaaatc ttttttaaat
49501 aatagtttct aattttttta ttattcagcc tgctgtcgtg aataccgtat atctcaacgc
49561 tgtctgtgag attgtcgtat tctagccttt ttagttttc gctcatcgac ttgatattgt
49621 ccgacacatt ttcgtcgatt tgcgttttga tcaacgactt gagcagagac acgttaatca
49681 actgttcaaa ttgatccata ttaactatat caacccgatg cgtatatggt gcgtaaaata
49741 tattttttaa ccctcttata ctttgcactc tgcgttaata cgcgttcgtg tacagacgta
49801 atcatgtttt cttttttgga taaaactcct actgagtttg acctcatatt agaccctcac
49861 aagttgcaaa acgtggcatt ttttaccaat gaagaattta agttatttt aaaaaatttc
49921 atcacagatt taagaagaa ccaaaaatta aattatttca acagtttaat cgaccaatta
49981 atcaacgtgt acacagacgc gtcggtgaaa aacacgcagc ccgacgtgtt ggctaaaatt
50041 atcaaatcaa cttgtgttat agtcacagat ttgccgtcca acgtgtttct caaaaagttg
50101 aagaccaaca agtttacaga cactattaat tatttaattt tgccccactt tattttgtgg
50161 gatcacaatt ttgttatatt tttaaacaaa gctttcaatt ctaaacatga aaacaatctg
50221 gttgacattt cgggcgctct gcagaaaatc aaacttacac acggtgtcat caaagatcag
50281 ttgcagagca aaaacgggta cgcggtccaa tacttgtact cgacgtttct caacacggcc
50341 tcgttctacg ccaacgtgca atgtttaaat ggtgtcaacg aaattatgcc gccgcggagc
50401 agcgtaaagc gctattatgg acgtgatgtg acaacgtgc gtgcatggac cacgcgtcat
50461 cccaacatta gccagctgag tacgcaagtc tcggacgtcc acattaacga gtcatctacc
50521 gactggaatg taaaagtggg tctgggaata tttcccggcg ctaacacaga ctgcgacggt
50581 gacaaaaaaa ttattacatt tttacccaaa cctaattccc taatcgactc ggaatgcctt
50641 ttgtacggcg accctcggtt taatttcatt tgctttgaca aaaaccgttt gtcgtttgtg
50701 tcacaacaaa tttattattt gtacaaaaat attgacgcaa tggaggcgtt gtttaaatct
50761 acaccattgg tttacgcgct gtggcaaaaa cataaacatg agcagtttgc acagaggcta
50821 gagatgttgt tgcgtgattt tgcttaatt gccagttcaa acgctagtta tttacttttt
50881 aaacagctta cacagctcat agctaacgaa gaaatggtgt gcggagatga agaaatattc
50941 aatttaggcg gccaatttgt agacatgatt aaaagcggtg ctaaggcag tcaaaatctg
51001 attaaaagca cgcaacaata ccgacagact ttaaatacag atattgaaac tgtgtcttca
51061 cgagccacca ccagtttaaa tagttacata tcttctcaca ataaggtaaa agtgtgtggc
51121 gccgacatat atcataacac ggttgtgtta cagagcgtgt ttattaaaaa taactatgtt
51181 tgttacaaaa acgacgaacg tacaatcatg aatatttgcg ctttgccctc tgagtttctg
51241 tttccagaac atttgctcga catgttcatt gaatgataat ataaatagag cgcatttgat
51301 tgcatgcaat cagtgttttta ttaattttag agcaacatgt acgataaatt tatgatctat
```

FIG. 2X-1

```
51361 cttcacttga atgggctgca cggagaagca aaatactaca aatatttaat gtctcaaatg
51421 gattttgaaa atcaagtagc cgatgaaatc aagcggtttt gtgaaactcg tctgaaaccg
51481 gcaatcagtt gcaacacttt aactgcggaa agtctcaata cgctcgtaga cagcgtagtc
51541 tgcaaaaatg gactgttaaa tccttacgcc aaagaagtac agtttgcttt gcaatatctt
51601 tttgacgatg acgaaatatc caaacgagat caagatggct ttaaactatt tttattacat
51661 aattatgaca ggtgtgaaaa tatggaagaa tatttttaa ttaacaattt tagcatagca
51721 gactacgaat ttgaagacat gtttgaaatt gttcgtattg attgtagaga tctgttatta
51781 cttcttgcta aatataatat gtaattaaaa ttttgtttgt tttattaaaa tcctggatta
51841 aaaaatgacg aataatttga tttgcgtgca cgccaacaag attcttcgtc attatgatca
51901 atgcgtgcat caagtttatg cttttgtaat tggcttctga ccactttagc catttgagcg
51961 tatctgcatt cgtcgtctag agtttcaaac accagatcgg cgcaattata aaatccttca
52021 cccacgggat ctatgcgctg ccaacgcaca tacattacaa attgatttga cctgtacggt
52081 attactacgg gtatagaata gactagactg ttgtcacata atgaatcgcc cggatttgga
52141 attaaatttg aatcgttacc acctatgtat tctaattcgt tccaagttat tggattgcga
52201 cgatcccagt ttgatttagt aataaacact tcaaaataac tgggctcgtg tatggctgtt
52261 ggacaaaaat gaacattcat ctgataaacc ggttgatagc gatttaaata tagcgtattt
52321 ggcctccagt tgttaaaagg ttcgtccatt ccgcttttat caccaaacac agaattgcga
52381 tcgtttgaac cggcaccgca aagtgtgtgc ggcacaaccc tttgttCgat taggtcaaaa
52441 tcgtcataat taggaccggc cacagccgcg tattccatat actgttgaaa catgtattgc
52501 gctgtggaag cggccgcccc ggattctaaa tcgagagctc gatatttata atagactgat
52561 ttgtaagcat tgcggcacgc ggcgtcggga atgttatcgc cattgtcggg ccaataaaag
52621 tttccatctt taaaacattt atattgacgg gccgtcggca cggacaaata gccgtgagag
52681 cgcactgccg gcgcgtgaat cgcagcaaac aatgcaatta ataatgcaat cattatgatt
52741 atacttatag aacactaatc ggaataataa ccgctgtcgt aatcttggtc aaaaacgtta
52801 tgttgaaaca taataacacc ttacagtaac atacaataaa acaacatagt atcgtatata
52861 attataaact ttattttttc attttataca aacaaaattt atacgtattg ttagcacatt
52921 gagtgtcatt ttcgctgtct gaactatcac aatcatcgtc atcatcatca tcattgtcat
52981 cgtcgtcgtc acgtttgcgt ttgacactgc atttttttg gttaatttc actaacactg
53041 gttcttttcg atcgtacaat tgattctgca tgtacttttg catgatcgcg gtaaaacact
53101 ttgcaatttt atcctttgt tcgtcgccaa atatttccag caactcgttc ataaatgtgc
53161 acaaaatgcc catgtgtttt atccagctga ttcgcatttt cactggatcg aacaaacgca
53221 aggggtacgc ttttctgtt accttgcctt cgatgtctat caaaaggtac gggatacgat
53281 ctccgttgcc gggcacaaaa tccgtgcctt tgttaaccaa aatttctcta caatgcctag
53341 ccaccgtaat cacgcgtctt ttgggtgacg gaccctcatt atcgtcagtt gatttgcgtt
53401 ttttgcccgg gttatcgtta taggtcatac taaagctgta gtcggtcaac gatttgatt
53461 tggcaaactc atcatagtat tcataaaaac tagtctgtaa actttgcaaa catttgtcca
53521 tgtccaaatg acgcaatatt tgttccactg ccgtcctaaa cgcgattctc ataaaaacgg
53581 gcatatcctt tttaactaac caaccccttgt atacgatttt attctcactg ttgagatagc
```

FIG. 2Y-1

```
53641 aatattttt  ctttttaat  agtattaaaa  ctttcattaa  attttcaaat  gccattttgt
53701 aaccgtccgt  gaatgagtta  ttaacgcgtg  tctcaacatg  tgtgcatatt  tgttttaatg
53761 tgtcggtttc  gttggatatt  tcgttatagt  taaatgtggg  caaaacaaat  gtagaatctg
53821 tgtcgccgta  cacaactta   aaagtgatgc  tcccagatt   gaattttct   aaaatctcag
53881 ggtcgttgct  caaaccttca  atcagagaaa  tggccagccg  caactgattg  cgaccaactc
53941 tagtgatgta  gtttgcaagc  actttgtaaa  aaatgccata  ataaccgtat  atgctattgg
54001 cggtgcgctt  cacggaattt  tgttttgat   cgtacagatc  gtacaagaat  gccgattcgc
54061 tttgattgtc  gcgattcttt  ttaaatttgc  acctttcgct  taacaatttt  aatagcaatt
54121 taacaactat  tgcacgcgaa  ttgtggttca  aatacacgtt  gccgtcttcg  cataaaatta
54181 aattggacaa  acaagcacaa  atggctatca  ttatagtcaa  gtacaagaa   ttaaaatcga
54241 gagaaaacgc  gttcttgtaa  atgcctgcac  gaggttttaa  cactttgccg  cctttgtact
54301 tgaccgtttg  attggcgggt  cccaaattga  tggcatcttt  aggtatgttt  tttagaggta
54361 tcaattttct  tttgagatta  gaaatacccg  ctgcggcttt  gtcggctttg  aattggcccg
54421 atattattga  cagatcgttt  ttgttaaaaa  aatacgggtc  aggctcctct  ttgccggtgc
54481 tctcgttaat  gcgcgtgttt  gtgatggctg  cgtaaaagca  cgccacgcta  atcaaatgcg
54541 aaatattaca  tatcacgtcg  tctgtacaca  aacgatgcaa  tatcattgc   gaatatacag
54601 aatcggccat  tttcaatttg  acaaacaatt  ttatcggcaa  catgcaatcc  tgcacgttgt
54661 acttggcaat  cacgtccagc  cgtcgagtgt  tgtacatctt  gaccatttcg  gtccaaggca
54721 aatcgatttt  gttttcaccc  aaatagtaac  tactgattgt  gttcaattga  aagttttcaa
54781 ctttatgctg  attagaatcg  ctgctgaaaa  atttatacaa  atcaatgtga  atgtaatagt
54841 taaaataata  cgtgtccact  ttgttgccca  acttgtttat  aaacagcttt  gtcgtcggcg
54901 ccgcagccgg  caaatcgtaa  cgctttaata  gcattttggt  tttattcaat  cgtccaagta
54961 tatagggcag  atcaaatacg  tctccgttaa  aatccaaaat  cacatcggga  tttgtaattt
55021 ttatcatgtc  aaaaaacgct  gtaatcatgt  cgatttcatt  ttgaaacatg  accacatacg
55081 tgtcatcgtc  ataggtctct  ggaatctggg  tcggcagctt  gtgatacata  aaacaaaatt
55141 ttgcatactc  gtcgtttttg  tacaccacaa  atcctataga  cattatgcaa  tcaaccgatg
55201 ctttcgacat  gttgtggccg  tccgaatgag  tctcaatgtc  atagcacgac  aaaacgggca
55261 tgatgccgct  ggttaaagtc  atttcatcga  ccaactcaaa  gtcttcatta  aaatgttgca
55321 aattaaacat  gcgcgtcgtc  gatccaccga  catagttatt  ttggcagcgt  tgtgtttct
55381 tgaatcgcat  ataggcgcct  tccacaaacg  gcgtttgcat  gtgtacgcga  ttaacgttgt
55441 gaagaaactt  gtccaaacac  gccgcgttgt  ccgatggcgc  tgctttgttt  ctttcgtatt
55501 taatcacgtt  tatcttgttc  aaataatttc  cttccacgcc  cggcgccaca  aacgtggtgt
55561 agctgatgca  cttgttgcgg  caagacggaa  atatgtgctt  gtcgtagcat  tgtttgtaag
55621 aatacaaatt  tagttttact  ttaaagtaaa  actgcagcac  tcgttctttg  atatttgtat
55681 tacaaaatgc  aaacaagcaa  ccttgttttt  catcgtaatg  caaacgaatg  atacgaaacg
55741 tatcggctga  agtaatattg  aattctcctg  gttttgcata  ttctgcaaag  cgcgtttttga
55801 gttcattgta  aggatatatt  ttcatttta   aatatgcagc  gatggcccaa  atatggaggc
55861 acagacgtca  acacgcgcac  tgtacacgat  tgttaaaca   ccataaacac  catgagtgct
```

FIG. 2Z-1

```
55921 cgaatcaaaa ctctggagcg gtatgagcac gctttgcgag agattcacaa agtcgttgta
55981 attttgaaac cgtccgcgaa cacacatagc tttgaacccg acgctctgcc ggcgttgatt
56041 atgcaatttt tatcggattt cgccggccga gatatcaaca cgttgacgca caacatcaac
56101 tacaagtacg attacaatta tccgccggcg cccgtgcccg cgatgcaacc accgccaccg
56161 cctcctcaac cccccgcgcc acctcaacca ccgtattaca acaattatcc gtattatccg
56221 ccgtatccgt tttcgacacc gccgccaaca cagccgccag aatcgaacgt cgcgggcgtc
56281 ggcggctcgc aaagtttgaa tcaaatcacg ttgactaacg aggaggagtc tgaactggcg
56341 gctttattta aaaacatgca aacgaacatg acttgggaac ttgttcaaaa tttcgttgaa
56401 gtgttaatca ggatcgtacg cgtgcacgta gtaaacaacg tgaccatgat taacgttata
56461 tcgtctataa cttccgttcg aacattaatt gattacaatt ttacagaatt tattagatgc
56521 gtataccaaa aaacaaacat cgttttgca atagatcagt atctgtgcac taacatagtt
56581 acgtttatag attttttac tagagtcttt tatttggtga tgcgaacaaa ttttcagttc
56641 accacttttg accaattgac ccaatactct aacgaacttt acacaagaat tcaaacgagc
56701 atacttcaaa gcgcggctcc tctttctcct ccgaccgtgg aaacggtcaa cagcgatatc
56761 gtcatttcaa atttgcaaga acaattaaaa agagaacgcg ctttgatgca acaaatcagc
56821 gagcaacata gaattgcaaa cgaaagagtg gaaactctgc aatcgcaata cgacgagttg
56881 gatttaaagt ataaagagat atttgaagac aaaagtgaat cgcacaaca aaaaagtgaa
56941 aacgtgcgaa aaattaaaca attagagaga tccaacaaag aactcaacga caccgtacag
57001 aaattgagag atgaaaatgc cgaaagattg tctgaaatac aattgcaaaa aggcgatttg
57061 gacgaatata aaaacatgaa tcgccagttg aacgaggaca tttataaact caaaagaaga
57121 atagaatcga catttgataa agattacgtc gaaaccttga acgataaaat tgaatcgttg
57181 gaaaagcaat tggatgataa acaaaattta accgggaac taagaagcag catttcaaaa
57241 atagacgaaa ctacacagag gtacaaactt gacgccaaag atattatgga actcaaacag
57301 tcggtatcga ttaaagatca agaaattgcc atgaaaaacg ctcaatattt agaattgagt
57361 gctatatatc aacaaactgt aaatgaatta actgcaacta aaaatgaatt gtctcaagtc
57421 gcgacaacca atcaaagttt atttgcagaa aatgaagaat ctaaagtgct tttagaaggc
57481 acgttggcgt ttatagatag cttttatcaa ataattatgc agattgaaaa acctgattac
57541 gtgccgattt ctaaaccaca gcttacagca caagaaagta tatcaaac ggattatatc
57601 aaagattggt tgcaaaaatt gaggtctaaa ctgtcaaacg ccgacgttgc caatttgcaa
57661 tcagtttccg aattgagtga tttaaaaagt caaataattt ctattgtacc acgaaatatt
57721 gtaaatcgaa ttttaaaaga aaattataaa gtaaagtag aaaatgtcaa tgcagaatta
57781 ctggaaagtg ttgctgtcac aagtgctgta agcgctttag tacagcaata tgaacgatca
57841 gaaaagcaaa acgttaaact tagacaagaa ttcgaaataa aattaaacga tttacaaaga
57901 ttattggagc aaaatcagac tgattttgag tcaatatcag agtttatctc acgagatccg
57961 gctttcaaca gaaatttaaa tgacgagcga ttccaaaact tgaggcaaca atacgacgaa
58021 atgtctagta aatattcagc cttggaaacg actaaaatta aagagatgga gtctattgca
58081 gatcaggctg tcaaatctga aatgagtaaa ttaaacacac aactagatga attaaactct
58141 ttatttgtta aatataatcg taaagctcaa gacatatttg agtggaaaac tagcatgctt
```

FIG. 2A-2

```
58201 aaaaggtacg aaacgttggc gcgaacaaca gcggccagcg ttcaaccaaa cgtcgaatag
58261 aattacaaaa atttatattc attttcatct tcgtcatact tcaacagtcc caacacgttc
58321 atgttgtgat tctcgccgtt Ttcgacagtt acgtaaatag ttactttgat taaattatct
58381 tccagcagca ttgagatttg attgaaatcc gcacatagct tttgtagcga atccgcttcT
58441 Ttttttttat ttgtgttgac gtagaaaaca gatttgttcc atttgcccaa gtcggaagag
58501 gtagaacagt catccgaatc ggcaatgttc aactcgtcgc ttttaaactg cacaataaac
58561 ttgttatcgc ccatgtcatt ttcttccaat tcgctttta acacatttac attgtacgaa
58621 gcaacgtgtt tgttcgatcg actaatgttg atctttgcgt ttgtcaatt ttgcaaattt
58681 gaatatgctt cgctttcttt agcctcgcac aattcgatgc gcgtagagtt gaccacgttc
58741 caattcatgt acacgtttga tccattaaaa atttgttgac actttatact gtaaatggta
58801 aagatttggt tttcattgtc ttttaaatat ttaaacacct cattgatgtc gtcagacccc
58861 tttatattgt tcttgaatag atttattagt gttttcgcat tgacagaaca ttccacttga
58921 accacgtcgg gatcgtcgtt gagattttg tacacaacct caaaaacaac tttgtacaaa
58981 ccgctgttga ttttcttgta gataaatttg tactttacaa taatattgac gccatcttca
59041 ttttcaaaat gtttgttagt caaatagtcg ctcatggggg ttgcagtttc aatttccatt
59101 tcacattctt tgtattcgtt gatctgaatc atttgactaa actttgtttt cacataattt
59161 aaactaatgt catagcactt gccttcttcc atgtctttga aagattgcga atcgccgtag
59221 tattcttgaa ttttgttgtc ggacattatt cgaaaagtgt aatggtattc attatcgata
59281 ctcaacgtca ttttgctcat caatttacca ctaatccttt tgtaattttc tctaatcttc
59341 ttggggctac tggccatagc catgcgtttt ataagcggct caccgctact ttctccagac
59401 aaagatcttt tggtcgccat attgctgttg tcgatatgtg ggaatctatc cgatggcaaa
59461 tactgaatgg cgacgaaatc gaagtgtcgc cagagcaccg ttcgttagcg tggagggagt
59521 tgattataaa cgtggccagc aacacgccgc tcgacaacac gttcagaaca atgtttcaaa
59581 aagccgattt tgaaaatttc gactacaaca cgccgattgt gtacaattta aaaacaaaaa
59641 ctttaacaat gtacaacgag agaataagag cggctctgaa cagacccgtc cgatttaacg
59701 atcaaacggt caatgttaat attgcgtacg tattttttgtt ctttatttgt atagttttgc
59761 tgagcgtgtt ggccgtcttt ttcgacacaa acattgcgac cgacacgaag agtaaaaatg
59821 ttgcagcaaa aattaaataa actcaaagat ggtttgaaca cgttcagcag caagtcggtg
59881 gtttgcgctc gctcaaaatt atttgacaaa cgcccaacgc gcagacctag atgttggcga
59941 aaactatcag agatcgacaa aaagtttcac gtttgccgac acgttgacac gttttggat
60001 ttgtgcggcg gacgggcga gtttgccaac tataccatgt cgttgaaccc gctttgcaaa
60061 gcgtatggcg tcacgttgac aaacaactcg gtgtgcgtgt acaaccgac agtgcgcaaa
60121 cgcaaaaatt tcacaaccat tacggggccc gacaagtcag gcgacgtgtt tgataaaaat
60181 gttgtatttg agattagcat caagtgtggc aacgcgtgcg atctggtgtt ggcagatggc
60241 tcggttgacg ttaatggacg cgaaaacgaa caagaacgtc tcaactttga tttgatcatg
60301 tgcgagacgc agctaatttt aatttgcctg cgtcccggcg gcaattgcgt tttaaagtt
60361 ttcgacgcgt ttgaacacga aacgatccaa atgctaaaca agtttgttaa ccatttcgaa
60421 aaatgggttt tatacaaacc gcctttctct cggcctgcca attccgaacg ctatttaatt
```

FIG. 2B-2

```
60481 tgtttcaata aattagttag accgtattgt aacaattatg tcaacgagtt ggaaaaacag
60541 tttgaaaaat attatcgcat acaattaaaa aacttaaaca agttgataaa cttgttgaaa
60601 atataacgtg tgtataaaaa gccagcggct tcaaatcagg catcattcaa catggattcg
60661 ctagccaatt tgtgcttgaa aaccctgcct tacaagtttg agccgcctaa gttttacga
60721 acaaatatt gcgacgcatg tcgctacaga tttttaccaa aatttctga tgaaaaattt
60781 tgtggacaat gcatatgcaa catatgcaac aatccaaaaa atatagattg tccatcatca
60841 tatatatcga aaattaaacc gaagaaagaa aacaagaaa tatatattac cagcaacaag
60901 tttaataaaa cgtgcaaaaa cgaatgtaat caacaatcaa accggagatg tttaatttcc
60961 tatttacaa atgaaagttg taaagagctc aattgttgtt ggtttaataa aaactgttac
61021 atgtgtttgg aatataaaaa gaatttatac aatgtaaatt tgtatacgat tgatggtcat
61081 tgtccttcgt ttaaagccgt tgttttca tgtataaaaa gaatcaaaac gtgccaagtt
61141 tgcaatcaac cttattgaa aatgtacaaa gagaagcaag aagagcgttt gaagatgcag
61201 tcgctgtacg caacgttggc cgatgtagat ttaaaaatat tagacattta cgatgtcgac
61261 aattattcta gaaaaatgat attgtgtgct caatgtcata tatttgcacg ctgttttgt
61321 accaatacca tgcaatgttt ttgtcctcga cagggttata agtgtgaatg tatatgccga
61381 cgatctaaat attttaaaaa taatgtattg tgtgttaaaa gtaaagcggc ttgttttaat
61441 aaaatgaaaa taaaacgtgt tccaaaatgg aagcatagtg tagattatac tttcaaaagt
61501 atatacaagt taataaatgt ttaatttta ggatattgtt atggaataaa ctataaaatg
61561 aatttgatgc aatttaattt tttgatactt tccacagacg gtagattcag aacgatggca
61621 aacatgtcgc tagacaatga gtacaaactt gaattggcca aaacgggct gttttctcac
61681 aataacctga ttaaatgtat aggctgtcgc acgatttgg acaagattaa cgccaagcaa
61741 attaaacgac acacgtattc gaattattgc atatcgtcaa ccaacgcgtt gatgttcaat
61801 gaatcgatga gaaaaaaatc atttacgagt tttaaaagct ctcggcgtca gtttgcatca
61861 caatccgtgg tcgttgacat gttggctcgt cgcggcttct attatttttgg caaagccggc
61921 catttgcgtt gttccggatg ccatatagtt tttaaatata aaagcgtaga cgacgcccaa
61981 cgccggcaca aacaaaattg caagtttctc aacgcaatag aagactattc cgtcaatgaa
62041 caatttggca aactcgatgt tgcggaaaaa gaatactgg ctgccgattt gattcctccg
62101 cggctaagcg ttaaaccttc ggcgccgccc gccgaaccgc taactcaaca ggtctccgaa
62161 tgcaaagttt gttttgatag agaaaatcg gtgtgtttca tgccgtgccg tcacctggct
62221 gtgtgcacgg aatgttcgcg tcggtgcaag cgttgttgtg tgtgcaacgc aaaaattatg
62281 cagcgcatcg aaacattacc tcagtaaaca ttgcaaacga ctacgacatt ctttaaaaat
62341 aagctatata taaatattgc attgtatgac aaaaaaatta ttaacctact gcaaagtaaa
62401 acttgtaaaa ggcttttcaa aaaaatttgc gagtttattt tgtcgctgcg tcgtgtcgca
62461 tctaagcgac gaagacgaca gcgacggtga tcgctattat cagtataata acaattgtaa
62521 tttcatatac ataaatattg taaaataaaa gacatattat tgtacataat gttttattgt
62581 aattaaatta atacaccaat ttaaacacat gttgatgttg ttgtgaataa ttttttaaatt
62641 tttacttttt tcgtcaaaca ctatggcgtt gcttcgatt agttttttcg ttagcatttc
62701 atctaaaaaa tcaaactgtt tgcccggcgc gtttagggat tctatggtgt agtcgggcgt
```

FIG. 2C-2

```
62761 gtcgctgttt agatattggt ccacttcgcg cattatgtcc aagacgttgt tctgcaaatg
62821 aatgagcttt gtcaccacgt ccacggacgt gttcatgttt cttttttgaa aactaaattg
62881 caacaattgt acgtgtccac tatacaattc ggcttaatat actcgtcggc gcaatcgtat
62941 ttgcaatcca atttcgtgtt caacaaattg gtgatgatat ctttgaacgt gcacgttttc
63001 aatttgtcct tatcggccaa cgcaagtttc aattcgctct gtaaagtttc taaaattttg
63061 tctttattgt tgtcaaattc gtgcgtgttg cgttccaacc acaatttgaa cggctcgtcg
63121 acaaaaatgc tgcgcaacac ctcgtacaac tgtctgccta acgtgtacac ttgctcgtat
63181 tctttcatgc tgacctcttt gctaacgtac attactaaaa aatctacaag tattttcaaa
63241 cattgtaat aggcgacgta ttttgattta agttttaaac cgtccaccgt gtattcgtcc
63301 acgttcgcat cgaccacttt tcgattatta tcgccgcttg ttgccggcgc gtcggcctgt
63361 tcggttttaa ctatatccgg ttcaatattt aagtttcaa aagatttaat ggcattcata
63421 aaatcatctt tttgctttgg cgtggtcaat ggtaaatcta tcgaggagtt gtcgtccgtg
63481 tgctcttcgg gcacgctgtt cagacgtaac gtaatctttt tgggatcgtc ttcatcgggt
63541 atcaaatcgg ctttaatttt attagaattg agcaacgaca tggtggtcgc ttgtaaattt
63601 aataaattaa ttaaagactg aaattgtata ttgcacaaat ttattttcat ttttattgat
63661 cttactatta atacgctggc agttggtatg cttcatccat ttttgtgact agaaaatttg
63721 ctaaaaaact gagctcgtcc tgtgttaaaa cgttgtcgtc cacgaatcta tgcaatgtaa
63781 atgttacact gacattgttt aacaatgcat gtattaaaaa atcaacctgt cgcctactga
63841 gtttattaga agagtcgacc gtttctacta gtttgtagat tttgttattt tcaatttcat
63901 tgtttaaaaa catgttaact actcgtttga gtttaagcga aaaatcctttg tccggataga
63961 cttgttcgca cagccaattg ctaagagtgg ttttgaccac ggacaccttg gtggtgaacg
64021 tcgtcgattt gaccagttcg gtgaaaaagt ttttcattaa attggacatt taacaaaca
64081 cttatcaatc tattgagctg gtatttttgt ttagaatcgc atcaagcgct tgctcgatct
64141 ccaattttt tcggacgctc ttagctttat gactcggtat gtcttctacg gtagactcgg
64201 tgttcttact tataatggcc gggctgacga taataaacac gagaaacaat atgagcagat
64261 acaaaaagat gctgttttcc ttttttgtcat acactaggct aaatatggcc agtgcgccca
64321 acaacaaata taaattcatt tttattccct tactctattc gttgcgatag tacaacaacg
64381 attctcccga cgaacggac gaattgcgat tatgctgcgc gtcgtcgtcg tcgttgttgt
64441 tctcctcttc gctgctcgtt tcgtctaaac ctatattgta tttgttcaag taatgtttgg
64501 tgcttgcgga ggattcgtgg ttcattaatt tggccacttt ttgtaaaggc acgccgctat
64561 tgtataggtt actgctcaaa taatgtctta tcatgttgct gcgcggccgt tccatctcga
64621 cgcccgactc ttcaaggagt cgcctgaaat ctttgaaggg cgtcgaggtg tttttagata
64681 tttgcaaaat ggtcgggttt cgtgaataaa tctcgcgtgc caattccaac ggtttcattt
64741 tgatgttgtt gagtgtgtta ttacgactgc gttttcgctt taaattaatc gtgtcgctgt
64801 gcagttttcc tcttttaatt agcacgttga gatcgtccac gctgagttgg cgcgcttcgt
64861 tgattcgcat acccgtccct aacatgatgc aaaacactat cgcgcccta attagaccgc
64921 ggtcgtgaac ataatcgctg ttgagcattt taattttatc attaataaaa tttaatatgg
64981 tatctattac gttttaagc attaaattct tttccttttc cctgatattt ttgagctcct
```

FIG. 2D-2

```
65041 tgtcgcgcgg cagcataacc atgcggggaa ttttgtattc gggcaagttc atcatgttgg
65101 tgtaaaagtt tatagtcaac tgtagtgttt ctttggtgac cgagcgaagt tcgagcatgc
65161 gcctgcacag ttcttgggga tcaatgagaa gtgtttggtt ttctatcgag tcaaactcct
65221 tgtccaacga gtacgacatg tcttccaggt gaacatcgtc taccgagcag tacacaattt
65281 taatgaatcg agacttgtaa cttttaaag tggtgggcgc aaacgtttg gggaacatgt
65341 acttgctcca cagactgttg tttttcacct cgtcgggcgt gcatcgttgc cgatcggtgg
65401 ccaaatcgaa cacggactcg aaccggggag cggattgaat ttttattttc caagaattaa
65461 aattgttttc gttgcgaaca ttaaaaccgt tcattgtggt taatcaaatt tattaaaaac
65521 aaaaggagaa tcggtgtcaa tactatccga atattgttgt tgttctctta atattacgaa
65581 ataatatatt acatacagca gtaagaataa agctataaaa gcgactacac taattaaaat
65641 tataattccc gccgacacgt tgctcgtcgt gttgtcatag cccaccatgt cgtttattgg
65701 cattttgtga acgggctcgc taaattgttg cggttcgctg gcagtatcgt cgttgagcgc
65761 caatttcaac gggatgtatt ccaccttttc gtggttgccc aaccgatagt agggcacgtc
65821 caaattcatg tttacaactt atttgctaac aggaatttat gcaacaaaag tggtttggct
65881 ttgatgagac gcaatttgaa atacttgctg catttacgct taagattgta ttccatgcgg
65941 gcggcggtct tgtagtcgta cgcgctcgcg ctgtgataca cgagccgtaa attggttgcg
66001 ttgcgcaaac acttggcgcc ttgtttgttc gaatgctgtt ttatgcgtct gttaagattg
66061 ctcgtgatgc ccgtgtacaa ttttccattg tcttgccgca gaatgtacac gcaccacacc
66121 ttgttggtgt acagagtcgt cgccatgatt atgcagtgcg cccttcgtg ttcggccgag
66181 tggcgttagg cgcagccgcg gcaataatcg cgttggcgtc cttgttgtaa tttatttgtt
66241 gaaaaataaa acgtcttaga gtttcgtttt ggaacgccaa ttcggtcaag ctctcctggc
66301 aagcgctttt ggtcaaatga gcggccggcg aattgaccgc gttggcggcc gacgttaaga
66361 aggtggcgtt ctggaacatg ctgggctgct tgccggctcg cgtcgccagc tcggccatgt
66421 aattgaatat gttggcagac gcagatagcg cgccaaaaa cgcaacgttc tcttttaaac
66481 tcatgactcg cgccctgttt ttttcgttca gcacgtagtg gtagtaatcg ccgccgcgg
66541 caaacagatc gtcaatcacg gcgttgatca gatcgttgat catgttgatg tgcggaaagc
66601 gacgcgactc gactgcgctc tgtatgtttg gcggcagagt ggcgtgcttg agcaacagag
66661 tcatgtaatt gttggccagc tgctgattga aaggtaacgg aatgggaatg ttgcacgtca
66721 ccgcttccgc caccatgtac tggacggcca gactgagttg tttggcggcc tcggccaaag
66781 cgtctttgcc caacatatca gcgccaccgt tgtaaaactt ttgcgcgtac gccggcagcg
66841 aatttagcac aaacgatggc tgaaatatat ttgaatcgct cgacagggac tcggccgcgt
66901 tgctctgtcc caactctttt tgcaaccgaa tcaggtggcg tatcatggtt tcctccgatt
66961 caaaccgctt taccacgttt acgctgattg ggttcgtgtc gatgcacatg tcacgaatag
67021 tgtttataaa aagaatcatg agaggactaa gttctgacat gtcattgcac ctgtaatatc
67081 taataatctt ttgaacaaaa tccacacatt tgttgtacca aatagattca ccggcgtcga
67141 gcgtcggttc tttgctcttg ttgtacggtg caatcgctac cgagtttgtg ctgttgctgc
67201 ggctcgtgta atccatcctg ttgtcgcgcg tggcgacggt cgtaggcacc gtgccggcg
67261 gcacgtaccc gggcgcgttg taagtttgcg cgctggtgaa tatggccgtt gccggattag
```

FIG. 2E-2

```
67321 agggatacct cagcggcgga ggggtgttgt aataaaaatt gccacgttca tctgtcatac
67381 tttttatttg tactcttatg attacaaaac tcaatatacg gattacttat aatatagttg
67441 ttgtgacaaa aaagcgataa taaaattaac aaaattatca acaagttaat catggaaaat
67501 ttttcaacgt tgaataacaa caacaaaatg gcgcaggtca acagcaccgt tgaaaactg
67561 acgcgccgac acaaatgct ttcgcaattt ctaaaagcca cattaaacga attttcacct
67621 ttgatataat cacgcagttc tttttacaa cattcgtcgc acaaaattaa caccttata
67681 atgaggccgt cggtgtgtat cgtttgaaat gtccgcggtt gactgcctgg atgaaattca
67741 aacgagtacc cagtggacac gtgtatctgt gcaaaataat gggctaatat cgaggcgccc
67801 gttttttaa cctttacttt tgatatttta ataacattaa tgttgttatt tgcgtaatca
67861 gagttttat tgtggtgatc atcgtacaaa taatgaagca acagttcact atcgtattta
67921 atcttgttta gcgttgtcaa gttttgttt cttaggcgtt ggagcgtctc cgtcgtcgat
67981 attttcttcg aaatcgagtc caacaacgtc ggcgtttcct tcttgctcat cgatagcggc
68041 ggcggaggcg gcctctccgt cgtcgtcatt ctcggtttct acagtgcgtt tgggcgacga
68101 cgtgtgtaca gcagcgtccg tcttactatt atcggaccgc caaattttg tttgaaataa
68161 catttggccc ttgttcaact ttatttcggc gcagttaaac attattgcat taagatcata
68221 ttcgccgttt tgcaccaaat tgcacaaaac accatagttg ccgcacgaca ctgtagaata
68281 ggcgttttg tacaacaatc tgagttgcgg cgagctagcc accttgataa tatgggcgcc
68341 aacgcccgt tttttaagt aatattcgtc ttcaattata aaatctagta cgttttcatc
68401 ttcactgttg atttgggcgt tcacgatgat gtctggcgta atgttgctca tgcttgccat
68461 ttttcttata atagcgttta ctttaatgta tttggcaatt tattttgaat ttgacgaaac
68521 gactttcacc aagcggctcc aagtgatgac tgaatatgtg aagcgcacca acgcagacga
68581 acccacaccc gacgtaatag gctacgtgtc ggatattatg caaaacactt atattgtaac
68641 gtggttcaac accgtcgacc tttccaccta tcacgaaagc gtgcatgatg accggattga
68701 aattttgat ttcttaaatc aaaaatttca acctgttgat cgaatcgtac acgatcgcgt
68761 tagagcaaat gatgaaaatc ccaacgagtt tatttgagc ggcgacaagg ccgacgtgac
68821 catgaaatgc ccgcatatt ttaactttga ttacgcacaa ctaaaatgtg ttcccgtgcc
68881 gccgtgcgac aacaagtctg ccggtcttta tccatggac gagcgtttgc tggacacgtt
68941 ggtgttgaac caacacttgg acaaagatta ttctaccaac gcgcacttgt atcatccac
69001 gttctatctt aggtgttttg caaacggagc gcacgcagtc gaagaatgtc cagataatta
69061 cacgtttgac gcggaaaccg gccagtgtaa agttaacgaa ttgtgtgaaa acaggccaga
69121 cggctatata ctatcatact ttccctccaa tttgctcgtc aaccagttta tgcagtgcgt
69181 aaatgggcgc cacgtggtgg gcgaatgccc cgcgaataaa atatttgatc gcaacttaat
69241 gtcgtgcgtg gaagcgcatc cgtgcgcgtt taacggcgcc ggacacacgt acataacggc
69301 cgatatcggc gacacgcaat atttcaaatg tttgaataat aacgagtcac aactgataac
69361 gtgcatcaac cggatcagaa actctgacaa ccagtacgag tgttccggcg actccagatg
69421 catagattta cccaacggta cgggccaaca tgtattcaaa cacgttgacg acgatatttc
69481 gtacaacagt ggccaattgg tgtgcgataa ttttgaagtt atttccgaca tcgaatgtga
69541 tcaatcaaac gtgtttgaaa acgcgttgtt tatggacaaa tttagattaa acatgcaatt
```

FIG. 2F-2

```
69601 cccaactgag gtgtttgacg gcaccgcgtg cgtgccagcc accgcggaca atgtcaactt
69661 tttacgttcc acgtttgcca ttgaaaatat tccaaaccat tatggcatcg acatgcaaac
69721 ctccatgttg ggcacgaccg aaatggttaa acagttggtt tccaaagatt tgtcgttaaa
69781 caacgacgcc atctttgctc aatggctttt gtatgcgaga gacaaagacg ccatcgggct
69841 taacccgttc accggcgagc ctatcgactg ttttggagac aacttgtacg atgtgtttga
69901 cgctagacgc gcaaacattt gtaacgattc gggaacgagc gttttaaaaa cgctcaattt
69961 tggcgatggc gagttttaa acgtattgag cagcacgctg accggaaaag atgaggatta
70021 tcgccaattt tgtgctatat cctacgaaaa cggccaaaaa atcgtagaaa cgaacattt
70081 tcagcgacgt atattgacaa atatactaca gtcggacgtt tgtgccgacc tatatactac
70141 actttaccaa aaatatacta cactaaactc taaatatact acaactccac ttcaatataa
70201 ccacactctc gtaaaacggc ccaaaaatat cgaaatatat gggcaaata cacgtttaaa
70261 aaacgctacg attccaaaaa acgctgcaac tattccgccc gtgtttaatc cctttgaaaa
70321 ccagccaaat aacaggcaaa acgattctat tctaccctg tttaacccctt ttcaaacgac
70381 cgacgccgta tggtacagcg aaccaggtgg cgacgacgac cattgggtag tggcgccgcc
70441 aaccgcacca cctccaccgc ccgagccaga accagagcca gaacccgagc cagaacccga
70501 gccagagtta ccgtcaccgc taatattaga caacaaagat ttatttatt catgccacta
70561 ctcggttccg ttttttcaagc taaccagttg tcatgcggaa aatgacgtca ttattgatgc
70621 tttaaacgag ttacgcaaca acgttaaagt ggacgctgat tgcgaattgg ccaaagacct
70681 atcgcacgtt ttgaacgcgt acgcttatgt gggcaatggg attggttgta gatccgcgta
70741 cgacggagat gcgatagtgg taaaaaaaga agccgtgcct agtcacgtgt acgccaacct
70801 gaacacgcaa tccaacgacg gcgtcaaata caaccgttgg ttgcacgtca aaaacggcca
70861 atacatggcg tgtcccgaag aattgtacga taacaacgaa tttaaatgta acatagaatc
70921 ggataaatta tactatttgg ataatttaca agaagattcc attgtataaa cattttatgt
70981 cgaaaacaaa tgacatcatt ccggatcatg atttacgcgt agaattctac ttgtaaagca
71041 agttaaaata agccgtgtgc aaaaatgaca tcagacaaat gacatcatct acctatcatg
71101 atcatgttaa taatcatgtt ttaaaatgac atcagcttat gactaataat tgatcgtgcg
71161 ttacaagtag aattctactc gtaaagcgag tttagttttg aaaaacaaat gagtcatcat
71221 taaacatgtt aataatcgtg tataaaggat gacatcatcc actaatcgtg cgttacaagt
71281 agaattctac tcgtaaagcg agttcggttt tgaaaaacaa atgacatcat ttcttgattg
71341 tgttttacac gtagaattct actcgtaaag tatgttcagt taaaaaaca aatgacatca
71401 ttttacagat gacatcattt cttgattatg ttttacaagt agaattctac tcgtaaagca
71461 agtttagttt taaaaaacaa atgacatcat ctcttgatta tgttttacaa gtagaattct
71521 actcgtaaag cgagtttagt tttgaaaaac aaatgacatc atctcttgat tatgttttac
71581 aagtagaatt ctactcgtaa agcgagttta gttttcaaaa acaaatgaca tcatcccttg
71641 atcatgcgtt acaagtagaa ttctactcgt aaagcgagtt gaatttgat tacaaatatt
71701 ttgtttatga tagcaagtat aaataaccga acaaagttaa attttttttca tttacttgtc
71761 accatgtttc gaatatacccc taataacaca actgtgcccg ttgtttagt gggtgacatt
71821 attcaagttc gttataaaga tgtatcacat attcgctttt tgtcagatta tttatctttg
```

FIG. 2G-2

```
71881 atgcctaacg ttgcgattgt aaacgaatat ggacctaaca accagttagt aataaaacgc
71941 aaaaacaaat cgctgaaaag cttgcaagat ttgtgtctgg acaaaatagc cgtttcgctc
72001 aagaaacctt ttcgtcagtt aaaatcgtta aatgctgttt gtttgatgcg agacattata
72061 ttttcgctgg gtttaccaat tatttttaat ccggctttgc tacaaagaaa agtgccgcag
72121 cgcagcgtgg gatatttcat gaattcaaaa ttggaaaggt ttgccaattg tgatcggggt
72181 catgtcgttg aagagaaaca attgcagagt aatttgtata tagattatt ttgtatgatt
72241 tgtggtttaa atgtttttaa aataaaagaa taacaattta cacattgttt tattacatgg
72301 ataatgttgt ttgtttgaca ttaaaggtta tcatggtgca atgattaata ataaaacaat
72361 attatgacat tatttcctg ttatttaca atataaaatc acccaattg tgcaaagttt
72421 tattatttgt ttgtcgacgg tcgaggggtc agcggcgtgt gcaacaataa aaaacatgaa
72481 gctgttaaca attttgattt tattttattc attttttatg aatttgcaag cgctaccaga
72541 ttaccatcaa gcaaataggt gtgtgttgct gggaactcgc attggatgga acgatgacaa
72601 tagccaagat cccaacgtat attggaaatg gtgttaaata aaagtgaata tattttttat
72661 aaaatttttt atttaaaatt ccaagtaatc cctgcaaaca ttaaacactg taggtatttt
72721 taaatcttgc cacatgcgaa caacgcacgg cctgtcgtcg aacaccgcta ttacattata
72781 ttttcctctg atatagttgt taaacaattt taattttaat aaataatctt tacaagtatc
72841 gtctgaaggc ctcataaaca atttatatga tttaatatca aaatactttt caatccagtt
72901 tcgagtgggc tgttcacaaa ttacgcttct cccgctcata aacacgataa ttgcgtcgtg
72961 gcaatttgcc aaatacttaa cgcaagtaat aacgtctaag cgggcttcat cttgagcaac
73021 tctattatca aaatcataaa acgatctatt tgtgggcaaa gctactgtac cgtctaaatc
73081 acataataca gcgcggggaa atttgtcgcc gacaggaacg taatattcga aattatttac
73141 ctttagaaac ttttatatt gcttttaat agtttctgga tttaatggaa atttatcaga
73201 gcgtttataa ttgcgttcaa gagccgtttc caaagaaacg tccatcaaac gcgttaaaaa
73261 atggtaatta tgcgttgcgg ccatttttg ccacatgtcc accgattgag tgttcaaatt
73321 agtgtcgctg acaaccacgt tggcaccaca ttttgcggct tttaaaaact gttcaatgca
73381 cattttggta atttgttctt ctttagtttg tctacatttc cgcgattggt tatagaaagc
73441 gttcagtttt gtataatcgc cgtttaaaaa caacttaacg cgcacgtcgt ctctgttgat
73501 ttctgtatag cctttaaaac ttttggcata cgtgctttg cccgaacccg aaatgcctat
73561 caacaccaac aattgttttg aagaaggcaa tttaattgtt ggagcaagtt tattatttaa
73621 tgcctgctta gtcgatacaa attttataat atttttgatc attttaattt tttcaggctc
73681 ggttaatttt aaaaattcgc tctccacatc gatcgtttgt gctttacgac atctgtacgc
73741 taaacatttc cacggcaaag tttgcaccag ttcgttgaaa cgctgttgat tcaaagtcaa
73801 acccgacacc ataatattta ttgtagactc gttggtgaac gtgtttctag catcaacgta
73861 cggtttaatg acacttttta aatgcgggaa aagagctaga aagtcatcgt gttcgccatt
73921 tataacaagc tgcgccaatt tagtaggatt ttcagcacgg ctctgatttt tgtgcatgtt
73981 caaatacacg tcgctttaa tcttgcatag tggcgcgttg ttttatcgt aaactacaaa
74041 tccttcttcc aaattttca actgggccgc gtgttcgaca cattcttgca cagacgtaaa
74101 ctcgtaacat ttggGgtatt tgcaaaacgg caaattggaa cagtaaaaat aatcgcccgt
```

FIG. 2H-2

```
74161 ttcgttgttt ctgcttgcca aataccacaa cgttggctgt tcatcgtaaa cggttacaat
74221 tctgttgtgt ttgcttgtta actcaaacat gtgagtcgac gcgcagtcta aatattcgtt
74281 acacaacgct tgaaattgat tgtgggcctc gtcaagttga agagcttgca aaactaaacg
74341 tttaaacgtc acgtctgaca cgcaaaggtt tctgcaaaa gcacttcctc gggtgctggc
74401 atgccattcg ccgttgtact tgtagatttt aattaaactt ccgtcgattt tttcgtaaaa
74461 cttaaaattc tccttcgatt ggaacagttt gtgatgagca tcttcgccgc cgatattttg
74521 tagcaattct tgaaaattaa agaaacgatc gaaagaacgc gacacaacgg cgtacgtgcg
74581 gctgttaaga attaaaccgc gacattccac gaccacagga tgatctcgat cgcgttcaaa
74641 cgattcgtaa ttaagaacca tcaaatcgtg ttcggtataa tttttaattt tgactttaaa
74701 cttgtcacaa agattttttca ctccgccgtt tgcaagtaga cgcgaaacgt gcaacatgat
74761 tgctgtttaa taatgcatac caatgctaaa ctgtctatta tataaagtgc agtgataact
74821 ttgttatcaa cgcgttcgat gccgacatat ataaacgcaa tgtaacagtt tttgctagta
74881 ccatcgcata caacattatg aatacaaggg gttgtgttaa taataataaa atgatattta
74941 tgaatgcttt gggcttgcaa cctcaaagta aattgaaaat tattgcacat aaaatactag
75001 aaaaatgtaa acgtgacgcg tacacgcgtt tcaagggcgt aaaggcgatc aagaatgaac
75061 taaaaacata caatcttacg ttgcaacaat acaacgaggc gctcaatcag tgcgctttaa
75121 acgatagccg atggcgcgac acaaataatt ggcatcacga tattgaagaa ggtgtgaaaa
75181 taaacaagag acatatatat agagttaatt ttaattctaa acccaagaa attgaagaat
75241 attattacat taaagtagaa tgttatgtaa acagttaatt aatctacatt tattgtaaca
75301 tttgtggtaa tagtggcgtt ggttatacat ttatatgatt gtaatgttgt gtactcgttt
75361 tgtaataaat ttttgtgttt aatcaattca atatttttat ttgataaaac cttatttttcg
75421 ctactcaatt tggcgttttt agacgcaagt tttgcgtaat cgtcattgag cgattttagc
75481 gccttttcag ttgtaattcg tttcagttgc aattctttaa aagatttatg catgttgttg
75541 tagtcgcttt taattttgtc taacttttct tgcatagaaa cgcttgtttg ttgtaatttg
75601 tctaaatcta attgttgttt aatgttgagc tgcgtttgtt cggcaatgtc tacctgtagt
75661 ttttttagta tcgcttgtgc ttcagacagc atagtgtcgt cggcatttgc gttgttgtct
75721 tctgcgtcgt ccaacagact tttttcaaac aacacactgg ccaaagaggc cgcatcaaaa
75781 ttagcgttta ttttattcca ttgtgcgaca ctcgacgcgc tgcatttaat cacatccaca
75841 acgtttcggt ttacgctgta acgttgaaa tgcaaacttt caaccctaca caagggacat
75901 ggtacttttt ttcgttttct aatcttgcgt atacacattg agcataattg atgtttgcac
75961 gtgtctagtt ctaatacggg tattatagtc aatctgtcta ttggttgcag aaaataattt
76021 ttaatttctg caaccgaaaa acaaatgttg cattgcaatt taacaaactc cattttaga
76081 cggctattcc tccacctgct tcgcctgcaa caccaggcgc aggacctgcc actgcgccgc
76141 cgcccagagt agcgttagga tttgctcttg gtataaagtc gttgcgcaaa aagttgtttt
76201 ctgaattgat tatttggtat cccaaaaaca gcggaacgta cgtcgggtat tcttcgtatc
76261 cgctaagcgt tctgtccagc tcacgtgtgt cgccttcaaa tttcaaaacg tttctaattt
76321 gcaaacgatt gggttgactt ctcataatgt cactgcttct tatcgggttg tacaactcgg
76381 ggccgtcggg cacagacgcg accagacccg tttcgtcaat tatacacgtg gcgcaatttc
```

FIG. 2I-2

```
76441 taaacctcaa ttcctccgtg tcgatttgca agtactcggg cgctactgcg cgtcgaatca
76501 aattttgcaa aaatccactg taattgttaa ataattgatc gccagcaccg cctcgaagcg
76561 ctcggcgtt ggtcacgtca agaaacgca attcgtctcg cgacacccgc gaacaaaacg
76621 tgttcgggtt tgtggtgtcc agaatgcttt ttgtagttgc gtaaacgctg tgtataacgc
76681 gttgcgtgtt gcttgtgaaa ccttcggtat attttagatt gtcgcatata gtgttaactg
76741 cgttttcgtt gttatatatc aaatgaaaga ttagctgttc ggcttgcatc atactgttta
76801 gattaaacac gtcttggtaa ttggttgcgc ttggaattaa aattcgcttg atacctcttt
76861 ctttatttcc aactaaatgc ctagcgatcg tcattttgaa ttgattgtcg tcttcgtcga
76921 aaatgggcaa aaccattttt gacattttaa aacgttttat gaggtggttg ttgcaaataa
76981 accatccatc gtcatgatac gcgtcgggcg aacacggcga tttgtatgtt atgcacgcgt
77041 cgaacgacac gatggacgcg aaaatgcagc gattaactct catttgtcgc ggcgccatac
77101 ccacgggcac tagcgccata ttgttgccgt tataaatatg gactacggcg attttgtgat
77161 tgagaaagaa atctcttatt caataaattt tagccaagat ttgttgtata aaattttaaa
77221 ttcttatatt gttcctaatt attcgctggc acaacaatat ttcgatttgt acgacgaaaa
77281 cggctttcgc actcgtatac ctattcagag cgcttgcaat aacataatat caagcgtgaa
77341 aaagactaat tccaaacaca aaaaatttgt ttattggcct aaagatacca acgcgttggt
77401 gccgttggtg tggagagaaa gcaaagaaat caaactgcct tacaagactc tttcgcacaa
77461 cttgagtaaa ataattaaag tgtacgttta ccaacacgat aaaattgaaa tcaaatttga
77521 acatgtatat ttttcgaaaa gtgacattga tctatttgat tccacgatgg cgaacaagat
77581 atccaaactg ctgactttgt tggaaaatgg ggacgcttca gagcgctgc aaaactcgca
77641 agtgggcagc gatgaaattt tggccgcat acgtctcgaa tatgaatttg acgacgacgc
77701 gcccgacgac gcgcagctaa acgtgatgtg caacataatt gcggacatgg aagcgttaac
77761 cgacgcgcaa aacatatcac cgttcgtgcc gttgaccacg ttgattgaca agatggcccc
77821 tcgaaaattt gaacgggaac aaaaatagt gtacggcgac gacgcgttcg acaacgcgtc
77881 cgtaaaaaaa tgggcgctca aattggacgg tatgcggggc agaggtctgt ttatgcgcaa
77941 tttttgcatt attcaaaccg acgatatgca attctacaaa accaaaatgg ccaatctgtt
78001 tgcgctaaac aacattgtgg cctttcaatg cgaggttatg gacaaacaaa agatttacat
78061 tacagatttg ctgcaagtgt ttaaatacaa atacaacaat cgaacacagt acgaatgcgg
78121 cgtgaacgcg tcatacgcta tagatccggt gacggccatc gaatgtataa actacatgaa
78181 caacaacgtg caaagcgtca cgttgaccga cacttgcccc gcaattgaat tAcggtttca
78241 gcaatttttt gatccaccgc tacagcagag caattacatg accgtgtccg tggacgggta
78301 tgtcgtgctc gacaccgagt tgagatacgt caaatataaa tggatgccaa caaccgagtt
78361 agagtatgac gccgtgaata agtcgtttaa cacactcaat gggccattga acggtctcat
78421 gatttaacc gacttgccgg agttactgca cgaaaacatt tacgaatgtg taatcacgga
78481 cacgacaata aacgtgttga acatcgtcg gaccgaatc gtgccaaatt aaagcacgtt
78541 aagcggatac aacggcagt ccgagctgtt aaagtcaata caaccatcgt taacaaacga
78601 atacgcattg ttgtgacagc tgaggatata aaaggaata gagaagtaat tgcaatgaaa
78661 tatcccgtta caattccacg gcacagcgta tgttgctcga gttctatcag ttgcacacaa
```

FIG. 2J-2

```
78721 cggcctaaga aaatttatta atgcttcatt tgtatctata ttagaaggat aatacatagg
78781 ttcgcccaaa ggactgggag aaggcggcgg cgaaggtgta ggtgtaggag gaataggaga
78841 aggcggcggc gaaggtgtag gtgttggagg aataggagaa ggcggcggcg aaggtgtagg
78901 tgtaggagga ataggagaag gtggaggtgt aggtgtaggt gttggaggta taggtgttgg
78961 aggaggtgta ggtgtaggtg ttggaggtat aggtgttgga ggaggtgtag gcgaaggtgg
79021 agaaggtgta ggagtaggtg gaggtgtagg taacggtaca attggtggag atgtaggtgg
79081 tggtacaatt ggtggatttg gatacaattc ctgaatgtcg tctaatattt ttaaagttaa
79141 taaaattatt ataaataaat ttaatattat tattattatt attatcacaa taatgtacca
79201 catgttgctt aaatataaaa attaaacaaa gaatgttgta ttattgcaaa tttaacaatt
79261 ttttgtattc tccccatgtc atgcgttcgt aatgagcggg cggttttta tttctttgta
79321 tccacttgta atcgttaatg tggttgtgaa aagtcatact gacgtaggcc attaaatttt
79381 tcatgagcat attatttgac acaactgcaa catctgcgcc tgccgttct tgctggtacg
79441 aatcgacaaa cgtaatgtct gtgccgtatt tttctttgtc aagtgcaatt tctataagct
79501 caatgtggta aatgatgaaa cctttgacgt tcatataatg atcgcggcac atggcgcact
79561 gtagtatgaa aaatacgttg taaaatagca ccttcattgt tttcaactgc tgcatgacaa
79621 aatctaaact gcttttgtct cgcgtataca ccatatcgtc gatgatgaga ctgagaaagt
79681 gcatggtgtc ccatatggta gtaaacgtgt aagtaaaact cttgggctgg cacgaacgca
79741 aattgagttc tgtggttttg tccataaatt ctatgcgaaa ctgttgcaag tccatgtcgg
79801 gggatgcgtt aatggcccat tcgatcaact gctgcacctc gtacttttga atgtctttgt
79861 atttcatcaa acacgcaaaa tggtataagt aagttgcttg cgaagacaac agtttggtga
79921 ggtgcgtcga tttagaggct cgcaaaaggt ctatgagacg aaacgaatac aacagatagc
79981 tgtctttgta acgagaaaaa agcggcgtca gcggtatcat ggcgactagc aaaacgatcg
80041 tgctgtactt gtgtcaggcg ccggccacag cgtcgttgta cgttagcgca gacacggacg
80101 ccgacgagcc tattatttat ttcgaaaata ttacagaatg tcttacggac gaccaatgcg
80161 acaagtttac ttattttgct gaactcaaac aggagcaagc cttatttatg aaaaaagtat
80221 acaaacactt ggtgcttaaa aacgagggtg cttttaacaa acaccacgta ttgttcgatg
80281 caatgattat gtataagaca tatgtgcatt tggtcgacga gtctgcgttc ggaagcaacg
80341 ttatcaacta ttgcgaacag tttatcacgg ccattttga aattttacg ctcagcagta
80401 aaatcgtcgt ggccgtgccc gtcaattggg aaaacgataa tttaagtgta cttttgaaac
80461 atttgcacaa cctaaatctc attggaattg aaattgtaaa ttaaaacaaa tcatgtgggg
80521 aatcgtgtta cttatcgttt tgctcatact gttttatctt tattggacga atgcattaaa
80581 tttcaattcc ttaaccgagt cgtcgcccag tttagggcag agcagcgact cggtggaatt
80641 agacgagaac aaacaattaa acgtaaagct gaataacggc cgggtggcca acttgcgcat
80701 cgcacacggc gataataaat tgagccaagt gtatattgcc gaaaaaccgc tatctataga
80761 cgacatagtc aaagagggct ccaacaaggt gggcactaac agcgttttc tgggcacgt
80821 atacgactat ggaatcaaat caccaaacgc ggccagcaca tctagtaatg taaccatgac
80881 gcgcggcgcc gcaaactttg atatcaagga attcaagtcc atgtttatcg tattcaaggg
80941 tgtgacgccc actaaaactg tagaggacaa tggcatgttt cgattcgaag tcgacaacat
```

FIG. 2K-2

```
81001 gattgtgtgt tgatcgacc ccaacacggc gccgctgtcc gaacgagagg tgcgcgaatt
81061 gcgcaaatct aattgcactt tggtgtacac aagaaacgcg gcagctcagc aagtttttatt
81121 ggaaaataac tttaccgtca ttaatgctga acaaacgcc tatctcaaaa actataaatc
81181 atacagagaa atgaattaat aaaacaaaaa gtctatttat ataatatatt atttattaac
81241 atacaaaatt tggtacacta gtgttcaaat cgttctgtt caacgccatt gtcatgttat
81301 aaaacacatt tgtagtttta ttgtaattat ttttaaattt atttttaatt tgctgtaata
81361 aaacttgttc attaaataca aaagactttg aactacttgc gtttatattc tttttataat
81421 tgtactgaac aaacgagggg tgcaaaaagt ttttcaaatg ctgcacggca ataccctatca
81481 tctcctccat tttgtcctct cctattgtaa tagtggcact gcgcaccgtt ttaatgttta
81541 gaatgtaaat gagcgcatac agcggactat tgttggtgct caagcacatt aggttgtgct
81601 tatgcatagg gtcgttgctc agcagcgttt tgtatactac aaagcccgtt ttggggtcgc
81661 gtctgtacat tagtacgtgc gacaaaaaca aacgcaccgg cgtcacaagc gactcgtaat
81721 acatgctttc tatcggaaac tgtttggact tgatgtgttc gtacacggag ccggcaaact
81781 tgacgctgtc tacaaactta tggttcgtgt aaacaatcaa aaatctgtct tgtacaccgt
81841 cgtcataatc gtccacgtac agcggcttgt tgttaacaat taacattttg tagttggctt
81901 catactttag cagcccttgg tattttctgc tcttggaatc gctcttgctc gaatcggcat
81961 gcttcttaaa gtacgactcg ctgcattgtt tcaactcgtt gatagtgtac aactgcgagt
82021 tgagtttgct cacttccttg tcgctcgttt ccttgttgga ctctccgctg tggttgtcat
82081 cgtcaaactt gtgcatcaac accaaatagt ccaacagctc aaaaaacgac gacttgcccg
82141 aacccggttc gccgggcatg taaatagcct tctttccgta atctacggga atggccaaac
82201 tagcggcgaa atgcatcaac ataatcgcgt tcgcgtgatt aaaattggtg aagcgtttaa
82261 agtacaaata gccttcgaca atcttttca aataattgta cgagtactcc ttcaagtcca
82321 ctttggacat gatgatgcgc atgtagaatc gagtcagcca gtgggcaaa tcgtccgtgc
82381 tgcgcgccaa tatgattttg tccaccaca cattgtactt cttcaagatc attaacgcgt
82441 cggcgtggtg cgtgtaaaat ttggaaatgt tatccgattc ttcaaactga acatcgggtt
82501 cacgtgcaac atcatcgcgc aattcggtta aaaacaaacg tttatcatta aacttgtcca
82561 tcaacatgtc gacatattcg attttgtgaa ttgttcgata caagtactga ataattttgt
82621 tgtgttcttt ggaaaaaaac tctccgtgtt ggttaacaaa ttcgctgttc gtgcgaatca
82681 acgtggtcga cacgtacgtt ttgttagtaa aaattagcat ccaaatcaat tcgctcaatt
82741 ctgcatcgtt accgaacatg tccgccatca agcagacttt tagcgctttt ctattgatct
82801 ttatttctt gtagcatttg cattttggtc gagatcccga taccgttgac cgacacggtt
82861 tgcattttag gttgtgcaac atgtcggaaa ccctgttctt gtttacgtac agagcgagcg
82921 taatcagatt ttcatcgtcc aaattccaca aatcgcgaaa caggttgttt aacgcgactc
82981 gcatatcggc ttggcatgtg ttgcaattgc ccatgtagtt aactatggcc gtgttagttt
83041 ttagcatttt tacatctcgg cacattttgg cgatgtgata agttctataa atgctgagct
83101 cgtcggcgct agtagatagc atgtaattaa acgcgtcctc gggcaaatac ttttcgtcgg
83161 tgggcttctt gaatgtctgc ggcaacgtgg tgcccaacaa aaatggacag ctcgaatgaa
83221 agctgttggt gaacacgttg tacacaccgt gcgttgtcaa gtacaagtat ttccaattgt
```

FIG. 2L-2

```
83281 taaattttat gttgctcaac ttgtaacaat tgcttttggt caatttgaat aggtcatcct
83341 ctttctttac aatttgataa tgtttgccgt tgaaaaccaa attgactccg gtcactacgt
83401 tttccaattt tctaaagaat cctttacaca caatgtcagg cggcaagttt agcgccatca
83461 cattctcgta cgtgtacgcc cacaattcat cgtgatccaa aatttcgttt ttagccgact
83521 gagtcaaata tatcatgtag tgtatgccaa aataatagcc caacgatacg cacaatttgg
83581 tatcgtcaaa gtcaaaccaa tgattgcagg ccctattaaa cactattttc tcttgttttt
83641 tgtaaggctc acatcgcttc aaagcttcat tcaaagcttc tttgtcgcag gcaaataatg
83701 attcacacaa aagttccaaa aacagtttga tgtcggtttc tctgtacgag aaattttcgt
83761 tcttggtcaa tatcttccac agtacataga ttaaaaaatc aaaatttta aatttgcttt
83821 tttcaaagta ttgttgtaga aggtttggat cgttggctcg ttcgtgggtc gccaaaactt
83881 taaccatgtt ctcgtgaatt gctataagcc ccaaattgat ttgcgtttga atgtagtctg
83941 cattttcgct gctcgccgat ataatgggta cgatgcgcgg ttttctggaa cgcgtgtcgc
84001 tcaagtccac gtcgtttttg tcaaaattgt tgttctcgaa cactctgagg cttttgaggt
84061 tgacgttgac gatatgcttg tacttgggca ccgtaatgca ttcctccaaa ttaatgtcgt
84121 ccctaatgta attgaaaaaa tttttatccg aattgaccag ctcgccatta actttgcacg
84181 tggccacagt gccgtcggcc attttgagta taaacaagtc ttcgtgagaa tcgtcaaact
84241 tggttttttcc atttacaaac agcgtttgcg gcggatcgtg attcgtgcgc aggctgagct
84301 cgacgttgag aaaacattta gggtcaaaca caaacaaatc cacaggcct agttttttgt
84361 tgtgtatgat tggtatcgtg ggttcgatga caattccaaa ttttatattt aaaaacagct
84421 gccatccgtt aaaagagaaa gcttgctttt tgggccagtt gggccaataa tagtaatcgc
84481 ccgcttgcac gcatttgtta atgtatccag ggtcggtgct cttgaaaaaa tcttcaaaat
84541 taatatactt ttgtatgatg tcatagtgct tcttcaaaat gaaaggtttt acaaaaatgc
84601 aaaaatcgtt actttccaac accagtcgt ggccgtctaa tgtttgagct gcgtgtttct
84661 ctgcaggttc ttcggtgtct tcgcaagatg cgcccatgtc gtgtttcgcg cacggaccgt
84721 taaagttgtt tctaattgtg tttaagaact gttgaaagtt gttgacgtac tcaaacaatc
84781 tacgtgttcc tgttcgcgtg tttctaatga ttaaatgatt tgcatcttgc aagttgttaa
84841 tctcgtacgt tttgtcttga ggcacgtttt tcaaaaaaaa ttgtaaaatg ttgtcaatca
84901 tgttggctat cgtgtttgta cttttcgtgt taatttattt aataatttcg atcaaaaatc
84961 accatccatt cttacataga atagaaacgc taatacaaga tttcaacaac acattgttgt
85021 ttggcgcgta tgtacagatt tacgatttaa gcacgcccgc cgcaccgaa cgattgttta
85081 ttattgcgcc cgaaaatgtg gtgttgtata attttaacaa aacgctctat tattacttgg
85141 actcggcgaa cgtgttttgt cccaacgagt ttagcgtgac cacgttcacg caatccacta
85201 ttaaaacgat caacgagacg ggaatatatg ccaccgcatg cacgccggtc agcagcttga
85261 cgctaattga acattttgca acattaaaaa ataacgtgcc cgatcacacg ctcgttctcg
85321 atgtggtcga ccaacagatt cagttttcaa tactcgacat tatcaattat ttgatttaca
85381 atggctacgt ggatttgttg gccgaataac gcgtatatag acgcttgtac gttcatcgta
85441 gtaatcattt taatacattt gattgaacta acatacatc tgcaatgggt gaaagagtca
85501 ctaaattttg caatggaaaa cggcgataaa gaagacagcg acaatgaata gagtttatat
```

FIG 2M-2

```
85561 ttttatttaa taaaatattg ttcgtaatcc ataatgtttt gtattatttc attgtgataa
85621 tgttcccaat cttgcacggg ggtggggcat cgtttgactt tgacgtagaa atcgtacgcg
85681 tagttattag ttggcagatc gtcgacaagt gtgatcgact tgaaaaagtt tacatttta
85741 tcgctcaaat atttaattac aattttttggc gatttgggta tattgttgtc ggatcgatga
85801 ttgtgaatgt caaaaacaaa tttattttca atgaaacgct tttttaaatt gtaatctaca
85861 atagcgttgt gtgaattttg aactaaatca gagcgttctt cttgaacggt ggaaccttcg
85921 ctgataatga tatcaaaata gccttccaaa tcgacgtctc gcatcgagtg tgctacatga
85981 tctctactgc catacgacca caagactaaa acgcaaccca tctcgtgcaa ctcctgcaag
86041 ctgtcataca caaacggatc tcgaatctca acttgctcct cttcggttat gagagtgctg
86101 tccaaatcaa acacgaccac gtgcggaaat ccccacgtca aagattcgct tttgagagag
86161 accactttgt agtgtggcaa tagaaaccat tctttaagaa acgaatacat tggcggtttg
86221 ttgctaagca cgcacatgtg gcccaacact ggcgttttga atgcgcgttt aatattgtgc
86281 ctgatgtcgc gcatgtcgtc ggcgggcgct ttgaatattt gcatacagta attgtaattg
86341 ttttctatga tcttgcacag ctgcgggtcg ttgcaaaatt gaaatattac atattcaaaa
86401 aatttatact tttcaaagcc aaggtatttg aggtcggcgt actcgcttaa aacgagaaca
86461 tgtcgtttga tgatggcgtc gttaaggcgc aaacagatcc atttgctttg aagcgaggag
86521 gccataatgt acaaaatgg accagttacg ccttatttaa actgtttaaa gagtttcgta
86581 taaacaaaaa ctactctaaa ctaatagatt cttaacaga aatttttccc aacaacgtca
86641 aaaacaaaac gttcaacttt tcgtctaccg gccatctgtt tcactcgttg cacgcgtacg
86701 tgcccagcgt cagtgatttg gtgaaagagc gcaaacaaat tcgattgcag acagaatatt
86761 tggcaaagct gttcaacaac acaataaacg atttcaaact gtacactgag ctgtacgagt
86821 ttatcgaacg gaccgaaggc gtcgattgct gttgtccgtg ccagctattg cacaagagtc
86881 tactcaacac caaaaattac gtggaaaact taaattgcaa actgtttgac ataaagccgc
86941 ccaaatttaa aaaAAaacct tttgacaaca ttctttacaa gtattcccta aattacaaaa
87001 gtttgttgtt gaaaaaTaag gaaaaacata ccagcactgg gtgtacacgc aaaagaaaa
87061 tcaaacacag gcaaatattg aatgataaag ttatttattt acaaaacagt aataaaaata
87121 aactatttga gcttagcggg cttagtttaa aatcttgcag acatgatttt gtaacagtcg
87181 aaagccaaac gagggcaggc gacgaaatcg cttcgttcat tcgctactgt cggctgtgtg
87241 gaatgtctgg ttgttaatag tagcgtgttc tgtaacttcg gcgacctgtc gatgaacggc
87301 tcctggatct tctgtatgtg cggggtctac ccgggcggcg tctgtaaccc gagcttctgc
87361 gcctgcgtgt cgaaccatat gtggtaccgg ttgaagaacg gcgacggcga cgataaacca
87421 tgtttaaatt gtgtaattta tgtagctgta attttaccct tattaatatt ttttacgctt
87481 tgcattcgac gactgaactc ccaaatatat gtttaactcg tcttggtcgt ttgaatttt
87541 gttgctgtgt ttcctaatat tttccatcac cttaaatatg ttattgtaat cctcaatgtt
87601 gaacttgcaa ttggacacgg catagttttc catagtcgtg taaaacatgg tattggctgc
87661 attgtaatac atccgactga gcgggtacgg atctatgtgt ttgagcagcc tgttcaaaaa
87721 ctctgcatcg tcgcaaaacg gaatttcggt accgctgttg atgtattgtt gcggctgcaa
87781 catttgtatc ttttcgccgc gctcgatcaa caattcttca agagtggtgc gtttgtcgcg
```

FIG. 2N-2

```
87841 ctgtaaagcc acgttttgta acagcactat tttcgcatat ctcataatcg gactgttgaa
87901 acagcgtgca aacgacgacc gcataatatc gacggtcgtc aagtcgattg tggtcgaagg
87961 catctccaac agagatcgca cggcgtccaa cagcgtgtcc gtttgaacct gcgtcatttg
88021 cggtctgcac gtgtagtcgt caaacgtggt ttcgagcagt ttgaacaacg aatgatactt
88081 ttccgatcgc agcaaaaata tcatggtcat gaccacgtcg ctgattttgt attctgtaga
88141 actggtgctg ttcaacgaat agtgatggat tagtttgcga gcagcatttc tgtatcggcg
88201 catgttgatc aactcttcgg aaggctgcgc gggcgcggcg gcgttggctc gcgcaaacaa
88261 atttattacg ggacgcggcg taggctgcgc ggacgctggc gcggcgacga cgtccgcgtt
88321 tcccgccgcg tactgagacg ctatggcagc gttgttattt aaaattgtgt tttgcgattt
88381 gcgagccacg tgcatcataa aatttatcaa cacgtcggtg ttcaactgca cgctttgatg
88441 ttcgtcgcag agcaaaggaa atagctgggg ccatatcgcc aattgcatag gctcgtctat
88501 ttttaaccgc aatttgttta tttccaaata caacgcgata gcgctcatcg tgaccgacga
88561 cgcacactta ctctgtaact atcacttgga tcgtgttgtc gtaaacgctt cccaaaaagt
88621 ctaacacgtt gaccgtttcg attctattca acttaattgt ggacgcgttg gcttgcatcg
88681 gttccaacag actgcgcgct ccgacagatt gagtagacaa aatttttaaa ctttccgtct
88741 tattgggcgt aatgtcgttg attaacaacg acgcagccgt ttgagaggcc gcagtgttga
88801 tggtttgcaa catgtcgacg gccgccattt gcgtttgcgc gaaggtcttt gctggcggcc
88861 tgttgcggcg gtttcttcgt gcttgcgaca tgttgtcgtc agtgtccata tcggtatcat
88921 ttattgaagc aatcatggtt gagttcgata agcagagata tttcgttgtc caattggtac
88981 ttggtaatga tgtgccttat aaatgtttcg ggcacaatca tttctgtcat tagcacgtta
89041 caaatatcta ttttgatcaa tttcaattta tgaattaaca gattaatgtt ttcgtccgag
89101 tacttgctca tgatgaaacg acaaacgttg cggagttcca actccgctac cggatacgct
89161 ttgttgggca aactctctaa atagtgtctc aaataaaagc cgatcaatac ggtggacgct
89221 attttgttaa cctttttcat tttagtattg cggcccattt ctatcatgaa gttttaaac
89281 ggtagcaaca gcctgtctcc gttagcaaca gtggagcagc cgttgcattg cgcgctcaaa
89341 atactcaaca cgcgctcgtg atcttcttgg cgcaatccga cggttgcttt tttgcattct
89401 ttgacaaatg gcacgcacat gtcgcgtttc gtgtacaaag aatacgcttt gtcgcaaatc
89461 aagttataga aaaattgcac aaatatctgc gtaatcaagt tgttttcgtt aataatgtca
89521 ctttcgtttt tgtaatcggt tcgaagcaac acgtacaaca tcagaggcat gccgaacatg
89581 ggtcttaaaa aaatgtccca accattttgc aagcccgcgt cgagggtgct cagcgaggac
89641 gccaagtatt tgcatttgca ctcaaaacat tgaattttgt ttgcgggctt gcacgactga
89701 cacatgatcg catccacgtc gggtgccggc gtcggattgt aatatttttg caagtattgc
89761 ataatggtcc taaaatgggg tacctgtttg ataaactcgt cgcgcaaaaa tatcgaaaaa
89821 atgttttta cattgtgtat gttgtctgtg ttgttggctt gattctcaaa actactcttt
89881 atggaaacaa tacatttgtt aaattctgtg aaaaagtaa gacctttact gtccacgatc
89941 aagctttggt tgaaatattt tgaaaataaa aaacacaacg aatcgatttc atcttgtaac
90001 aattgcgctt caaaacacac gttttcaaag cggtcgtaaa tgttaaacct taaactgtat
90061 tgtaatctgt aagcgcacat ggtgcattcg atataacctt ataatatgaa cgattccaat
```

FIG. 20-2

```
90121 tctctgttga ttacgcgttt ggcagcgcaa atactgtcca gaaacatgca aacggtggat
90181 gtgattgttg acgacaaaac gctcagtttg gaagaaaaaa tagacacgtt gaccagcatg
90241 gtgttggctg taaatagccc gccgcaatcg ccgccgcggg taacatccag cgacctggcc
90301 gcatcgatca ttaaaaataa cagcaaaatg gtgggcaacg attttgaaat gcgatacaac
90361 gtgttgcgta tggccgtcgt ttttgttaag cattatccca agtattacaa cgagacgacc
90421 gccggtttag ttgccgaaat agaaagtaat ctgttgcaat atcaaaatta tgtaaaccaa
90481 ggcaattatc agaacattga gggttacgat agtttattaa ataaggcgga agagtgttat
90541 gttaaaattg atagactatt taaagagagc attaaaaaaa tcatggacga cacggaagcg
90601 ttcgaaagag aacaggaagc ggagagattg agggccgaac aaactgccgc aaacgctctt
90661 ctggagaggc gagcgcagac gtccgcagac gatgtcgtta atcgtgccga cgccaatatt
90721 cccacggcat ttagcgatcc gcttccaggc cccagcgcgc cgcggtacat gtacgaaagt
90781 tcagagtcgg acacgtacat ggaaaccgcc cgacgtaccg ccgaacatta caccgatcag
90841 gacaaagact acaacgcggc gtacactgcc gacgagtaca attccctggt caagacggtt
90901 cttttgcgtt taatcgaaaa ggcgctggcc actctaaaaa atcggttgca cataacaact
90961 attgatcaat tgaaaaagtt tagagattat ctgaatagcg atgctgatgc tggagaattt
91021 caaatatttt taaaccagga agattgtgtg tatactgaaaa atttgtcaaa tttagcgtca
91081 aagtttttca acgttcgttg cgtggccgac acgttagagg taatgttgga agcgcttcgc
91141 aataatattg agttggtgca gcctgaaagc gatgccgtac ggcgaatagt cataaaaatg
91201 acgcaagaaa ttaaagattc gagcacgccg ctgtacaaca ttgccatgta caaaagcgat
91261 tatgacgcca taaaaaacaa aaacattaaa accttgttcg acttgtacaa cgacaggctg
91321 ccaatcaatt tcttggacac gtccgcaacc agtccagttc gcaaaacttc cggcaagaga
91381 tctgcggaag acgacttgtt gccgactcgc agcagcaaac gtgccaatag acccgaaatt
91441 aatgtaatat cgtcagaaga cgagcaggaa gatgatgacg ttgaagatgt cgactacgaa
91501 aaagaaagta aacgcagaaa attagaagac gaagattttc tcaaattaaa agcattagaa
91561 tttagcaagg acattgtcaa cgaaaagctt caaaaaatta ttgtggtcac cgacggtatg
91621 aaacggctgt acgaatactg caactgcaaa aattctttag agactttacc gagcgccgct
91681 aactatggca gcttgctcaa aaggctaaac ctgtacaatc tcgatcatat cgaaatgaat
91741 gtaaattttt acgagttgct gtttccattg acactgtaca atgacaatga taacagtgac
91801 aaaacgcttt ctcatcaatt ggtaaattac atattttgg ccagtaacta ttttcaaaac
91861 tgcgctaaaa acttcaacta tatgcgcgaa acttttaacg tgtttggccc gtttaaacaa
91921 atcgactttta tggtcatgtt tgttataaaa tttaactttt tatgcgacat gcgtaatttt
91981 gccaaattaa tcgacgagct ggtgcccaac aaacagccca acatgagaat tcacagcgtg
92041 ttggtcatgc gggataaaat tgttaaacta gcttttagta atttacaatt caaacctttt
92101 tcaaagaaag acaagtcgcg caacacaaaa catttgcaaa gactaataat gttgatgaac
92161 gcaaactaca atgttatata ataaaaaatt ataaatatt ttaattttt atttatattc
92221 agtacattta cacatattaa catattgttt atacaaattc ttataatcat tatgatttaa
92281 attgaattgt tgtctaaaca aattaaacac tttattaaac aataacttt cgttgtaatt
92341 ttttactttg cacatgttat aacaaaaaat taaaatttc atcatgtctg atttgtctat
```

FIG. 2P-2

```
92401  ggcgtcacag ttgcttttaa tgtaatcgca agttaaccac tcaaaaggac cctttcctat
92461  ttttaatttg tttaaatctt tataatcaga cttcagtttg taaattagat ttccacatcg
92521  aataataaat ccttccagcg ggctttgggg aaacattaaa gacttgaaat ttaaccttc
92581  tacaaaatcg ttgtacaaat atttgtgaca cggaatagta ttaaacccca cgttagtcaa
92641  caactcttgc gcctccacaa agggcacaaa ctccccgccg tataattgaa tttcgtaagc
92701  gtagtatttc aaactctctt tctggtccac gtagttaatt acgttaatgg gtgtcgtttt
92761  tgcgtcgtct ttccaaccca ttaattcgcc gtagacaata aaaccgtcat gaaccgcgc
92821  ctgaagcgat cgcatgcacg tttctaaatc ttttcgaatg cggtaataat tcataaaatt
92881  gccgtccggt ctgtaagtgt ttcttgaccc gtacgtaatt ttattttggt tgcaaatgat
92941  tctgaaatta caaccgtcca acttttcttg aacaataatt tctttgtcgg ccaacgtacc
93001  tttttacct tgatctagat gcgacacaga tggataaatt tgatacacaa ttttattctc
93061  atcttcgggc attacgggtc cgcgttcatt taacgcgtac atgacaatgt tgtggcgaat
93121  gtcggtgcgc tccggcggtt ctggcacgtg gtgcagtctg tcctgcaatt gttgcttcca
93181  ttgttgaaaa tattcggtcc attcttgttg atactcgccg cgttgcatga gttttacgta
93241  cagttttaaa agtttgacat tctttacaaa taacgttaga gtttcgtcga ttttgtatcc
93301  tccattattt ttgtttaaat ccaatacatt taaatcgttc actaccagtt gattgttttt
93361  atccatcgta attttatct catcgcccac gttgaacaac atgtttaaaa ttttggtgga
93421  tttcggcgca cgtttataat ctaaataata ttcaacgtac acgtaattga acatgagctg
93481  caacaatcct ttggcattgt tcaaaatttt gtatctcatc aaagtataaa taattttcac
93541  catcgacacc gtcatcaact tggttacaaa ctcgtacaat tgcaagtttt caataccgta
93601  tttgtcttta aaatcttcac gttactgaa catgcttaat tcgggagatt ttccagtcaa
93661  aatgccaatt aatcccgtgt acaagtcaac gtatttgaca tcgttgcccg attcatcttt
93721  tgcatgtcga tttttcaaaa gctcttatt gtcgataaat ttttcaaagg tctctcgatc
93781  acatttagtg taaatatggt agtcagtgtc gctgctttcg accgcgtatc ccttggcatg
93841  gctgcccgta tcaatgcaaa tgtacaccat gttagaatgt gctgcttact gtgcctgtat
93901  caagccttat atacctcaaa atatttcaca tttttgcatc atcgtaaaat atacatgcat
93961  ataattgtgt acaaatatg actcattaat cgatcgtgcg ttacaagtag aattctactg
94021  gtaaagcaag ttcggttgtg agccgtgtgc aaaacatgac atcataacta atcatgttta
94081  taatcatgtg caaaatatga catcatccga cgattgtgtt ttacaagtag aattctactc
94141  gtaaagcgag tttaaaaatt ttgtgacgtc aatgaaacaa cgtgtaatat ttttacaat
94201  atttaagtga aacattatga cttccaataa ttttgtggat gtggatacgt ttgcaagaca
94261  attgattaca gataaatgta gtgctctaat caaaagtgcg gatctgttgc cggcaaacat
94321  tttagagatt gtagagaagg ccagagacaa gtattttgag gagccaactc aaaaaaacta
94381  tgaatacatt aaaaaattat ttttacgaac aaaatatatg gacgattcga tagattataa
94441  agattttaac agacgcatcc tattgatagt ttttaaattc gctttaaaca agagcaccaa
94501  ctactttcca tcgtacaaag agatcatcga ggtggccatt aaacgtttaa acaaaattaa
94561  ccccgattta aagagttctc cgcgcgcaat gcttcagcat tacaatgaat gtttggaaaa
94621  tctagacaat ccagtcacgg acgaacatca tttgttaaca tttggaaaag aagttgctac
```

FIG. 2Q-2

```
94681 aaaatattt atcgaagcgt ttgaatacag ttacaccaac actaatgcca tcagcatgga
94741 caaaacagat gaatttgatt ttattaaacc ggcattgaaa cctttgccag atgcaagacc
94801 gccatcgctt ttggccaacg tgatgaacga acgtaaaaga aaattacaaa acaccaactc
94861 aacggcaaaa tgtttgctac cagcaccacc gccacaattg cgtaaacttg aaaaaagaa
94921 tcatttattg cctttgtttt ctttgtaatt atattgttgc atttctattt ctaatatcat
94981 agttttctaa taaagtagtt tcatatttt gttttgtac agtaattgtt tcttggttta
95041 acaagatcac aaccaataac ataagaata acacaatcat aacaaaatt aaaagccgc
95101 atactactag aacaaattct ttaattagcg atcggtttct atttacaaat tggccgagct
95161 gatcgccttc agtcggcgag ttgtgggctt ggatgatgtc gacgatattg ttgccggcgc
95221 gaccgcctgt cgctctcgat ataatgtcgg ccgccgtcgg tttcatgatg tgcttaacta
95281 caaataatag ttgtacttga cgggcgtcac cgtgatgccg ctgctaaaac ctccgtccgt
95341 taagacgcgt tgcgttacaa aattaatgtt tgtccgatta gcgtagtcgg aataatcaaa
95401 cgtgttgggc ggactaaaat cggcatgtt gatgggcaca atgccgctgg agctgatagc
95461 aatgctgtcg ttcttgcaaa acagccgaat tttttgtag ggctctgctt tattcggcgc
95521 agacgacacc atctggtcaa agttgttcaa ttttatgatt acgttgggta ccaattgata
95581 ggggaaaatt attttctgga acattttgac aaagtccaca accgtttggc tatagtcggg
95641 aatgccgagc aaagactgcg cctgtttaat gtatttgaga ctggagcggt ttactgtagc
95701 gcaattggat ggcacgtcgc ccttcataag ccggcgcgtt ctctcccaat tcaatttgtt
95761 gtacaaatta tcaatctcct cgtgcggcag attgattaca tagcgcgcgg gctgtttgcg
95821 atattgaaag atgcaaaaaa tgcgtttcaa cgacaatatc ttcaccatgg tggacgtttc
95881 cagattgaaa cataacaaaa agtcattgct ttccaccaat tctttaaaat gagacagcgg
95941 aatttcacaa gcgatcggtc gcaaattgct ttttattgga ggcggaacgc tttgaccgtt
96001 gcggttttt agtaacgcgc tgcacgcaga ttgcatgtcc gtttcgggat acgtaaactc
96061 gatgggacat ttggggtttt catggtgaac gatcatagtg ttgcaataaa acaagttgtt
96121 ggtcaggagc acgctaaaaa cacgcgtttc gcccgcaccg atttcggtga tgggtaccaa
96181 cgggttccag tagactatgg tggcggacgc tgttttttt ggcgatcgac tgtctatgtt
96241 aacatcatgc tcgtgcctgt cactagcac agaattgaat tttggaaatt gttttttgtc
96301 aatgtacaac cggtcgtcgt ctgtgggcac gtacacgatc aagttttcga ttaatttgtt
96361 gcctacgtcg ctttgcggtt ccaccaaatt gtgagggaac gcaaaaagc gatcgctaat
96421 acaaacttga atctgaaacg ggcactccat cgtgatgtat atgtcttact tcattagact
96481 ttagattatt ttaatttgtg aactcgtacc gtattcaata gggtgtcggg cacgtaattg
96541 taatggtaaa acagatcctg ttgaacacgt gcgttgttca ctacgattga aatgcaaaaa
96601 tacatcaagt acataaacac tatgattaga aaggtagcag acagaaaata tttcatcttt
96661 aaatcttatg ctagttgaat aaaatacata gtactttat acgtttattt atatttgttt
96721 tctttgttat aaccgtaatt gtaaaacttg tgatcgtgct cgccaggcat aatttctttg
96781 cacatcagct tgcgaatata tgtgacatct tcgtacaccg atttcttgat gttaccatcg
96841 tgaagcgttg tcggcttgag aggtttgcgg tcgttgttgt aaaaattttg caccgaataa
96901 ttatccatag tgcagcacag gcaatgtcac tgatgcatat gctttaattt tttattgcat
```

FIG. 2R-2

```
96961 tcagttatta tatgatttaa taaacgtaca caatagcacg tttatcggtt aaagataact
97021 ttcaatatat aaaagtgttt gaattgcgag accgtcaaca taacgtttat caacgcgatg
97081 actaaacgac aatttgcttt gctgtttgtg tggcaccacg acaaccaatt tgtttgcaac
97141 acggacgaat accgttttg gcacaacatt gaataccatg cacggcgcta taaatgcatc
97201 gttttgtact gtgtggaaaa cgacggatcg ctacaactgc ccgtttgcaa aacataaat
97261 ctcataaatt ataaaaagc gtatcctcat tattatggaa actgtgttga cagtatagtg
97321 aaacgtgctg gcaaaattga ttatatgaaa gtaactgcaa tgttaaaccc ccacctgttg
97381 gacgtcgcgt acaattattt gctgttgatg gacatggatt gtgtggtgca aagcgtgcaa
97441 tggaaacaat tgtcaaccga cacgtattgt tttgagccgt tttacgactc tcaaattaaa
97501 tggttgtacg cgcccaaaag cggacaaagt tttgatagtt atcttgaaaa ctatgcaact
97561 ctaattcgag tcaaacaagt gcagcaacat cgaaagaat taatactgca ttgtgtggat
97621 tttcttacaa tgaaagcaaa tgacaatttt atggtgttca aaaattatat taacatgatt
97681 ataaagtgt atttgcaatt ttacaattac agatttccca tcaattttga ggacaacacg
97741 atgaaacctt gtgtaaattt aacttttaga cgtggcggca gttggaaaac tcaactgcaa
97801 cccgtatgca attatgttta caaagtaaa aatatgccaa aatttattaa ataaaacaaa
97861 ttaatttaaa caagcgtttt tattgacaat actcacattt gatattattt ataatcaaga
97921 aatgatgtca tttgttttca aaattgaact ggctttacga gtagaatttt acttgtaaaa
97981 cacaatcaag aaatgatgtc atttttgtac gtgattataa acatgtttaa acatggtaca
98041 ttgaacttaa ttttgcaag ttgataaaca tgattaatgt acgactcatt tgtttgtgca
98101 agttgataaa cgtgattaat atatgactca tatgtttgtg caaaaatgat gtcatcgtac
98161 aaactcgctt tacgagtaga attctacttg taacgcatga tcaagggatg atgtcatttg
98221 tttttttaaa attcaactcg ctttacgagt agaattctac ttgtaaaaca caatcgaggg
98281 atgatgtcat ttgtagaatg atgtcatttg ttttcaaaa ccgaactcgc tttacgagta
98341 gaattctact tgtaacgcaa gatcggtgga tgatgtcatt taaaaatga tgtcatcgta
98401 caaactcgct tacgagtag aattctacgt gtaaaacacg attacagcac ttcgtagttg
98461 tatcgaaaat tgttcaatgg ctctttgtta atgtcgtaat tgattaatat gtcgtacaat
98521 ttggcggcgt tgtgtttgca cacgaccgtt tttagttctt gaaacatttt ttcgtgtatg
98581 tttagcatgt tgtatttcag agtgcgatgt gtaatgctgg tgacgagcat caaaatgata
98641 aaatctaaag cggctaattt gtaatcccgt tcatacgctc tgtaatcgcc aacaactctg
98701 tggccagatc ttttagatt tgacaggcg ttatggtacg aattgataat atttactata
98761 gttctcttg ttatcggttt gtcgattaaa ctgttaacaa acatcacgtt gcccaagcgc
98821 gacggtttag acaccgactt gtttttgtc tgttcaaatt tgtacaaatt aaaaacgctc
98881 atagactggt cgtcaggcag tgtgtcgtta tacaaacaaa atggtaaaac gtttaattcg
98941 acaaacgacg agcacattaa agtttgttgg ctgttaacgt cctggggatg taaactgtta
99001 ttcataacgt aacacacttc aatgtcggaa tgcttgtttt caaatttgtc cttgtctaca
99061 gttcaatgg tgattgagcg aggtttgagt ttatttgta aattcatttg gatattttca
99121 atatggtata ccaccgacac gttgtgagcc agcgatcctt gattggtttt aatcatattc
99181 aaaatattca tgatatggtt gaaaaaagag tctgtcaaaa cgtttgtgtc gttgttaaat
```

FIG. 2S-2

```
 99241 atcgctttcc agggtttact gttgcgtgac tcaacgacgg ccgtgtaaca taacaagcgc
 99301 gccagttgca tgtgcgacaa cttaatgtta tcaatgtcgg tgatgtttgg caccagattt
 99361 tcattgccgt cttccagtag cgtgctcagt tcggtcgagt agttattcaa cgatcgattg
 99421 tgcgattcaa acaagtttac tatcgcaggt tgtacatagt tttttatgtc gtcaaattga
 99481 attatatcga tcttgtcctt gttctccagc ataaacgaca aattttttag gtcgaattta
 99541 atatttggcg cgttttcgtt ggacttttg taatttaaca acatcgccaa cagtttgtgt
 99601 aactcgccgt tagcttgatc tttgctaaac agtttattgg tagcgtaatt cacgttgtcg
 99661 ttcaaaaaca gcaactcgtt gatgatcatt ttttgtaaaa gcgcgtactt gctcatgttg
 99721 acagaatctc ttacatttca gttgtaaacg cgtctgtaca aattggccat gcgattcgga
 99781 atgcacacgg ggatcgtgcg agccagtgcc gtttggcgaa atagcatttt ttcatagccg
 99841 ctcgaacaat cgcacgcgtc cggcgaaaat tgcaccgtgt tcaaattcat attcaaccgg
 99901 ccgtcgttgc atagataagg cctcggtgtt cccgtatcgt ccaccaagtc tctgtacgtg
 99961 ctcacgcatg tttgagacac gacaaaatct ccgccggcgg agaaacgtg aaccaagccc
100021 agtgcgggat cgcattctat caagtccgga gcctgcgcgt ttaccaaagc gtcggaggcg
100081 ttgcaaaagc catcctggca ggtcaactcg tttgcagcgc tggagatcac gcagttgtct
100141 ctacactgct gatccgtcac gcacggtaac cggttcaatg aacaatctac gcctcgattg
100201 cgctgaaacg taaaatttaa cggcggcgct tccaactcgt taatgtgcat gtatgcatct
100261 tgcaaaataa attttgaac aaatttaaac gtgtacatgt acacgattag tataattacc
100321 agtagaataa gtatttgcca aaagttcaac atgatcgtct taactgagtg tgaaaagcgt
100381 ggtgtgacgc acgaaatgac tggttgcgca aaaataaac cggggtctat ataactcggc
100441 gtcgacgcg ttcatttta ccgtcatgca tctgacggct aatgtattgc tcgttcctaa
100501 cgcgctcaaa aagcgggacg tgaaatacat ttataatacc tatttgaaaa attacagtgt
100561 aattgaaggt gtgatgtgtt gcaatggcga ttgtttggcc gtggtggtgt tggaccgaaa
100621 tcagctgcaa aacacggaca tggaagtgtt ggagagttta gaatacacta gtgacaacat
100681 tgaactgtta tgcgaaaaaa tatgtgtgat agttgataat tacgacaagt attaccaaaa
100741 aaattgtgta taataaaat accaaatttt attatatcat tttgttttat ttaataatta
100801 aagaatacaa cgccacatct attcctagta caacaaataa tttgattatt atttttgagt
100861 gcacattaaa aaataacaaa cagtgtaaaa atactacaga ataatacaat acataaatat
100921 tatagtaaat agctgcaatt ttgatagcgt aatttatact ttgatatttt tcaacgtaca
100981 acgttaaatg ttgatacgca ttattcacaa ataacaaaat ttttctaata tgccatttgt
101041 ccgcaattgt ttttgcgata tcaaagcctt tttcaaacaa ttgaaaaatt gcaaacaaaa
101101 ccacgtacat gacgttatac atagtgttaa agtttttaca taacaattct ataatgaaga
101161 aaattgctaa acacggcatg agcgcgcaca taatcgcgtt ggccgcaaat atctcgtacg
101221 tacaaaaata ctcggacatt ctccaataag taaaatgcat tttgctatta tactgttgtt
101281 tcttctagtg attattgcaa tagtgtacac gtatgtagac ttatagatg tgcaccatga
101341 agaggtgcgt tatcctatta cggttttga caacacgc gcgccgctta ttgaaccgcc
101401 gtccgaaata gtaatcgaag gcaatgcaca cgaatgtcac aaaactttga cgccgtgctt
101461 cacacacggc gattgcgatc tgtgccgcga aggattagcc aactgccagt tgtttgacga
```

FIG. 2T-2

```
101521  agatacaata gtcaagatgc gtggagatga cggccaagaa cacgagacgc ttattcgagc
101581  gggagaagcg tactgcttgg ctttggatcg agaacgcgcc cgatcgtgta accccaacac
101641  gggtgtgtgg ttgttggccg aaactgaaac tggtttcgct cttttgtgca actgcttacg
101701  gcccggactt gttacgcagc tcaacatgta cgaagactgc aacgtgcccg tgggctgcgc
101761  gcctcacggc cgtatcgaca atatcaacag cgcttcgatc cggtgcgtgt gcgacgacgg
101821  gtacgtgagc gactataacg ccgacaccga aactccgtat tgccgtccgc gcaccgtgcg
101881  cgacgtaatg tacgacgaga gttttttttcc gcgggcgcca tgcgcagacg gccaagttcg
101941  tctggatcat ccggcgctca atgatttta ccgcagacac tttagactcg aagacatttg
102001  cgtgatcgac ccttgctcgg tggacccgat tagcgggcaa cgcacatcgg gacgcttatt
102061  tcaccaacca accgtaaatg gtgtgggaat caacggatgc aattgtccgg ccgatgacgg
102121  gttactgccc gtgtttaatc gacacaccgc cgacacgggc atggttagac aaagcgaccg
102181  caccgtcgcg aacgcttgct tgcagccgtt taacgtgcac atgttatcgt tgcgtcatgt
102241  ggattacaaa ttttttctggg gccgcagcga ccacaccgag tttgccgacg cggacatggt
102301  gtttcaagcg aatgtcaacc aactcagtca cgaacggtat cgagcgattt tgtactcgtt
102361  gctcgagtcg cacccggacg taacagaaat cgtaacagtc aacatgggtg tcatgaaaat
102421  ttccgtgtca tacgatacca cattgaaaaa tatactatta ccatcttctg tttttaggct
102481  atttagattt aagaaagtg gcactgctca gccggtatgc ttctttccag gcgtaggacg
102541  gtgcataacc gtcaattccg attcgtgcat caggcgacac gctggtggtc aagtgtggac
102601  cgcagaaacg ttcaccaact cgtggtgtgt actgagtcgt gaaggtacgc atataaaagt
102661  ttggagtcgc gcgtcacgat atccacgcgg agacgcgcct gcagcgttaa gattgcgcgg
102721  cttctttctg aacaacgatc gcgaacgaaa cacaataaga gcggtcacta caggcgacat
102781  gacccaaggg caacaaatag acgcattaac ccaaatactt gaaacttacc ccaactactc
102841  tgtataacaa catgagcatt ttaaaagttg tagaagcgtg cgatttggca cacacttttt
102901  tgaaattggg ttatttattt agggccaaga cttgtttgga tatcgcttta gataatttgg
102961  aactattgcg tcgaaagact aacataaaag aagtggcagt catgttaaac aagaaaacta
103021  cagagtgttt gcaattgaaa cgaaaaatag ataaaaaaat tgcacaacgt gttttaataa
103081  aaatttacac tatcaaatga tgacatcata acgggttcaa tattctgtgt gcaaaaataa
103141  atgacatcat atttcaaact tgttttacgc gtaaaattct actggtaaaa caagtttgag
103201  atatgatgtc atcatcacaa ataatagtat gtaataaaat aaacatattt gtgtgtaaat
103261  ataattttatt acaaataaat tttacattga atcaatctgt cttcgtgttt gttgtaaggt
103321  cttcgaatct tgtgtttcag ccctcggga tggtcaaaat gcgccgtagt aattgttaat
103381  ggatctttca acgatttttt gcccatggcg agtgtgacaa acgcggccac gacaaacagc
103441  aggataatca gtttcatggt gttctatatt Tgacaatata tgggtcgctt ctaaatcacc
103501  ttgtccccaa aagcctcttt tatagttttt tagaacacgt tgtgtattcc aacagtaatt
103561  gttccatctc tttcaacagc cattcagcat ccggtcgttg actgtaatca tgctgaatta
103621  atttacaaac aatttcggtc aatttaggat ggccttggga taaacttgcc ggcatttgct
103681  gtacattgtt tctaaagtta gttagcgtag tttcgcgttc caaagcagtc ttgaagggca
103741  ttatcaattc gaataaaaca atgcccaaac tatacatgtc attttgggg gtgtacactt
```

FIG. 2U-2

```
103801 ttttgatttg ttctggtgca gcgtacaaag ttatattttg agggttgttt ttgataaacg
103861 ttttgtatag actgccaaac atgccgccca catacaaatc aaagtcgggc ccagtcatga
103921 aaatatcttc gggattaata ttgtggtgca cgatatttac ggaatgaatc gctttcacgg
103981 cgctcaccaa atcaacaaac ttgctaatat aaaagccaaa atccgccgga actttaatgt
104041 tggtctttgc aaaagtttgc aaattgcgtt gtttcaaata gtcgctcaac atgtactcgt
104101 ttagaggcga cgcaaaatat atgcggtgct gccgcggatt caaataaacc aattgttcgg
104161 gtttcatggt atacagttaa gtgttaacgc gtcactaaat tcagacacga gcgcacgccc
104221 tatatacata caatttatcg cacaagatgc ttaacgcgat ctgtttataa actaaaacgc
104281 actgcaataa attttagcaa gcatttgtat ttaatcaatc gaaccgtgca ctgatataag
104341 aattaaaaat gggtttgttt gcgtgttgca caaaatacac aaggctgtcg accgacacaa
104401 aaatgaagtt tccctatgtt gcgttgtcgt acatcaacgt gacgctgtgc acctacaccg
104461 ccatgttggt gggatacatg gtaacattca atgactccag cgaattgaaa tatttacaat
104521 actggttgct gttgtcgttt ttgatgtccg tggtgctaaa cgctccgact ctgtggacga
104581 tgctcaaaac cacagaagcc catgaagtaa tttacgaaat gaagctgttc cacgccatgt
104641 actttagtaa cgtgctgttg aattatgtgg tgttttttgga caatcaaatg ggtacaaatt
104701 ttgttttgt taacaattta attcactgtt gtgtactttt tatgatattt gttgaattgc
104761 ttatcctgtt gggccacaca atgggcacgt acacggatta tcaatatgtc aaatcgtgtt
104821 atatggttat attgtttgtt tcagttatga gtgttactat tgttatgggt ttagagtgtt
104881 tgaaaacgaa actaattgat aacagtttga tgtttaacgc gtttgtgtgc gctttgtaca
104941 ttgtgattgc aataatgtgg tctttaaaaa ataatttgac tagttattac gtttcaaatt
105001 tacaaagtat tcaagttgtt ccgttttcat acaacgatcc gccgccaccg ttctctaaca
105061 ttgtaatgga tgacataaaa aataaaaaat aatttataaa aatgtttttt attctttcac
105121 aattctgtaa attctaaaca aaaatataa atacaaactt attatgttgt cgtctaaata
105181 aacatcaatt tgtaaatctg gacacctatt catatcattg atattacagt ctactataca
105241 acaattaaaa ctaaccaaat tatctttaca acaattaaag caattaaaac aatttaaata
105301 atcttcattg tcgtcgtata agtttatttg cactgtagac ggtgttacac agcgatccat
105361 tcgacgttcg tgttcgatca acttctcgc caacttgtac cataaaaatt gtttggacaa
105421 aaagttttcc aacaatggta acggccaatt caacgtgacg atgcgcacgt cctcgggtat
105481 gcatttgtta aaaacacac agctcgcttt accaaacgaa agcaaggta ctaaatatgg
105541 cgccattggc tgatttgtta ttccaagata attacaaata aactgatccg tcgtgggtg
105601 ataactggca ggtgtcagct ttaaataatc ttcaacgttg ttgtcgcgca aaagtctgca
105661 ttttacacgc gttgttaatc ccacgacttt tgcatgtaaa atcggatcca aatactgcag
105721 aatcgtgtct ataatttcta atggtaaacg tatgcgtttt gctcgtgggc gctttgtaac
105781 gctcgacatc ctaataacaa ctaacacaaa actaaaatga tactcaatat attgctttta
105841 cagttcatct ttaggtttaa actgtgcgtt tatcgcgttg agcaagtcgc cgttatcggc
105901 atcaatctcc caagcaaaca ggccgcccaa tttatttcgg tcgacatatt taacttttcc
105961 taacacagag tcgacgctgt caaacgaaat caaatcacct ttactttat cgaaaacgta
106021 cgacgcttga gcggcgctgt caaacgtgta cacataattg ttgagatctt tttgaatttg
```

FIG. 2V-2

```
106081 acgataatct acaacaccgt cctcccacgt gcccgacacc ggcccgttgc cagtgccgga
106141 aaaatagttg tcattcgtat aatttgttac gccggtccag ccgcggccgt acatggcgac
106201 gcccacaatt attttgttgg gatcgacgcc ttgtttcagt aacgcatcga cagcgtagtg
106261 tgtagtgtat agctcttccg agttccaact tggcgcgtag actgttgttt ggtagcccaa
106321 atccgtgttt gaccaagccc ctttaaaatc gtaactcatg agaaatattt tgcctaatga
106381 cttttgcgct tcggcgtagt ttaccacggc aatcttgtcg taacccgcgc ttatagcgct
106441 tgttaattcg taaaccctgc cggtttgcgc ttcgaggtcg tctagcattg cgcgcagctc
106501 ctccaacaac aaaatgtatg ttttggcgtc acgctccgca tcgcccaacg acgggttagc
106561 ccctttgccg cccggaaact cccaatcgat gtctacaccg tcaaagaatt ccacacttg
106621 cagaaattcc ttaaccgaat ctacaaaaac gtttcttttt tcaacatcgt gcataaaata
106681 aaatgggtct gatagagtcc agcctcctat tgaaggaaga attttaaat gggggtttgc
106741 taatttgcc gccatcaact gtccaaaatt gcctttatac ggctcgttcc aagcggacac
106801 acctttttgg ggttttttgta cggcggccca cggatcgtga atggcaactt tgaaatcttc
106861 gcgtcccttg cacgatcttt gcaaagattc aaagcttccg ggtatcgttt tgagggcgtc
106921 gtttattcca tcgccgccgc agatgggtat gaaaccatac aacaagtgtg ataaatttgg
106981 caagggaact ttgtctacgg gaaagttgcg cccgtacaca ccccactcaa caaagtacgc
107041 agcgacaatt ttatcctctc tcctgccagg tttgttgttt tccagccatg tgtattcgag
107101 cggtgccaga tggccgccgt cggtgtctgc gactttgacc aacacgggat cgctcacgga
107161 acagccgtcc tcattgcaaa gtttgacacg catgttaaat tgcccgctca caagaacttt
107221 aatggtagcc cttttacttt cggcgtcgcc tttccatacc tgctgctcgt caaacaacac
107281 gtacgctatg tcgccaatgt cgccgttcca gacgttccaa ctgacttgaa cgtcgacttg
107341 ttctttaggc tttattaaat tttcgtaagc ggtggcctcg taatttattt ctacgagcgc
107401 ataattgcga tcgcccaat cgatcaccgg cgtgccggga atcgcgttag aaacggcgac
107461 caaccacaaa acgtttaaca atttgtacaa cattttaatt tatcttaatt ttaagttgta
107521 attattttat gtaaaaaaat gaacaaaatt ttgtttattt tgtttgtgta cggcgttgta
107581 aacagcgcgg cgtacgacct tttgaaagcg cctaattatt ttgaagaatt tgttcatcga
107641 ttcaacaaag attatggtag cgaagttgaa aaattgcgaa gattcaaaat tttccaacac
107701 aatttaaatg aaattattaa taaaaaccaa aacgattcgg ccaaatatga aataaacaaa
107761 ttctcggatt tgtccaaaga cgaaactatc gcaaaataca caggtttgtc tttgcctatt
107821 cagactcaaa attttgcaa agtaatagtc ctagaccagc caccgggcaa agggcccctt
107881 gaattcgact ggcgtcgtct caacaaagtc actagcgtaa aaaatcaggg catgtgtggc
107941 gcctgctggg cgtttgccac tctggctagt ttggaaagtc aatttgcaat caaacataac
108001 cagttgatta atctgtcgga gcagcaaatg atcgattgtg attttgtcga cgctggctgt
108061 aacggcggct tgttgcacac agcgttcgaa gccatcatta aatgggcgg cgtacagctg
108121 gaaagcgact atccatacga agcagacaat aacaattgcc Ttatgaactc caataagttt
108181 ctagttcaag taaaagattg ttatagatac attaccgtgt acgaggaaaa acttaaagat
108241 ttgttacgcc ttgtcggccc tattcctatg gccatagacg ctgccgacat tgttaactat
108301 aaacagggta ttataaaata ttgtttcaac agcggtctaa accatgcggt tctttttagtg
```

FIG. 2W-2

```
108361 ggttatggtg ttgaaaacaa cattccatat tggaccttta aaaacacttg gggcacggat
108421 tggggagagg acggattttt cagggtacaa caaaacataa acgcctgtgg tatgagaaac
108481 gaacttgcgt ctactgcagt catttattaa tctcaacaca ctcgctattt ggaacataat
108541 catatcgtct cagtagctca aggtagagcg tagcgctctg gatcgtatag atcttgctaa
108601 ggttgtgagt tcaagtctcg cctgagatat taaaaaactt tgtaatttta aaaattttat
108661 tttataatat acaattaaaa actatacaat tttttattat tacattaata atgatacaat
108721 ttttattatt acatttaata ttgtctatta cggtttctaa tcatacagta caaaaataaa
108781 atcacaatta atataattac aaagttaact acatgaccaa acatgaacga agtcaattta
108841 gcggccaatt cgccttcagc catggaagtg atgtcgctca gactggtgcc gacgccgcca
108901 aacttggtgt tctccatggt ggttatgagg ttgctttttt gttgggcaat aaacgaccag
108961 ccgctggcat ctttccaact gtcgtgatag gtcgtgttgc cgatggtcgg gatccaaaac
109021 tcgacgtcgt cgtcaattgc tagttccttg tagttgctaa atctatgca ttgcgacgag
109081 tccgtgttgg ccacccaacg cccttctttg tagatgctgt tgttgtagca attactggtg
109141 tgtgccggcg gattggtgca cggcatcagc aaaaacgtgt cgtccgacaa aatgttgaa
109201 gaaacagagt tgttcatgag attgccaatc aaacgctcgt ccaccttggc cacggagact
109261 atcaggtcgt gcagcatatt gtttagcttg ttgatgtgcg catgcatcag ctcaatgttc
109321 attttcagca aatcgttttc gtacatcagc tcctcttgaa tatgcatcag gtcgcctttg
109381 gtggcagtgt ctccctctgt gtacttggct ctaacgttgt ggcgccaagt gggcggccgc
109441 ttcttgactc ggtgctcgac tttgcgttta atgcatctgt taaacttgca gttccacgtg
109501 tttttagaaa gatcatatat atcattgtca atcaaacagt gttcgcgtgt caccgactcg
109561 gggttatttt tgtcatcttt aatgagcaga cacgcagctt ttatttggcg cgtggtgaac
109621 gtagactttt gtttgagaat catactcacg ccgtctcgat gaagcacagt gtccacggtc
109681 acgttgatgg ggttgccctc agcgtccaaa atgtatacct ggcactcgtc cgtgtcgtcc
109741 tggcactcga gcctgctgta cattttcgaa gtggaaatgc cgcatcgcca cgatttgttg
109801 cacgtgtggt gcgcaaagtg attgttattc tgccgcttca ccaactcttt gcctttgacc
109861 cactggccgc ggccctcgtt gtcgcgaaaa cagtcgtcgc tgtcactgcc ccaacggtcg
109921 atcagctctt cgcccacctc gcactgctgc ctgatgctcc acataagcaa atcctctttg
109981 cccacattca gcgttttcat ggtttcttcg acgcgtgtgt tgggatccag cgagccgccg
110041 ttgtacgcat acgcctggta gtaccccttg tagccgataa tcacgttttc gttgtagtcc
110101 gtctccacga tggtgatttc cacgtccttt tgcagcgttt ccttgggcgg ggtaatgtcc
110161 aagtttttaa tcttgtacgg acccgtcttc atttgcgcgt tgcagtgctc cgccgcaaag
110221 gcagaatgcg ccgccgccgc caaaagcaca tataaaacaa tagcgcttac catcttgctt
110281 gtgtgttcct tattgaagcc ttggtgtgac tgatttacta gtagcattga ggcatcttat
110341 atacccgacc gttatctggc ctacgtgaca caaggcacgt tgttagatta ataatcttat
110401 ctttttatct taattgataa gattattttt atctggctgt tataaaaacg ggatcatgaa
110461 cacggacgct cagtcgacat cgaacacgcg caacttcatg tactctcccg acagcagtct
110521 ggaggtggtc atcattacca attcggacgg cgatcacgat ggctatctgg aactaaccgc
110581 cgccgccaaa gtcatgtcac cttttcttag caacggcagt tcggccgtgt ggaccaacgc
```

FIG. 2X-2

```
110641 ggcgccctcg cacaaattga ttaaaaacaa taaaaattat attcatgtgt ttggtttatt
110701 taaatatctg tcaaattaca atttaaataa taaaaagcgt cctaaagagt attcaccct
110761 taaatcgatt attagcgact tgcttatggg cgctcaaggc aaagtatttg atccgctttg
110821 cgaagtaaaa acgcaactgt gtgcgattca ggagagtctc aacgaggcta tttcgatttt
110881 gaacgttcat agcaacgatg cggccgccaa cccgcctgcg ccagacatta acaagttgca
110941 agaactgata caagatttgc agtctgaata caataaaaaa attacctta ccactgatac
111001 aattttggag aatttaaaaa atataaagga tttaatgtgc ctgaataaat aataataagg
111061 gttttgtacg atttcaacaa tgaacttttg ggccacgttt agcatttgtc tggtgggtta
111121 tttggtgtac gcgggacact tgaataacga ctacaagaa ataaaatcaa tattagtggt
111181 catgtacgaa tctatggaaa agcattttc caatgtggta gacgaaattg attctcttaa
111241 aacggacacg ttatgatgt tgagcaactt gcaaaataac acgattcgaa cgtgggacgc
111301 agttgtaaaa aatggcaaaa aaatatccaa tctcgacgaa aaaattaacg tgttattaac
111361 aaaaaacggg gtagttaaca acgtgctaaa cgttcaataa acgcttatca ctaagttaat
111421 atactaaaaa tcacatagtc actacaatat ttcaaaatat gaagccgacg aataacgtta
111481 tgttcgacga cgcgtcggtc ctttggatcg acacggacta catttatcaa aatttaaaaa
111541 tgcctttgca ggcgtttcaa caacttttgt tcaccattcc atctaaacat agaaaaatga
111601 tcaacgatgc gggcggatcg tgtcataaca cggtcaaata catggtggac atttacggag
111661 cggccgttct ggttttgcga acgccttgct cgttcgccga ccagttgttg agcacattta
111721 ttgcaaacaa ttatttgtgc tacttttacc gtcgtcgccg atcacgatca cgctcacgat
111781 cacgctcgcg atcacgttct cctcattgca gacctcgttc gcgctctcct cattgcagac
111841 ctcgttcgcg atctcggtcc cggtctagat cgcggtcacg ttcatcgtct cccaggcgag
111901 ggcgtcgaca aatattcgac gcgctggaaa agattcgtca tcaaaacgac atgttgatga
111961 gcaacgtcaa ccaaataaat ctcaaccaaa ctaatcaatt tttagaattg ccaacatga
112021 tgacgggcgt gcgcaatcaa aacgtgcagc tcctcgcggc gttggaaacc gctaaagatg
112081 ttattttgac cagattaaac acattgcttg ccgagattac agactcgtta cccgacttga
112141 cgtccatgtt agataaatta gctgaacaat tgttggacgc catcaacacg gtgcagcaaa
112201 cgctgcgcaa cgagttgaac aacaccaact ctattttgac caatttagcg tcaagcgtca
112261 caaacatcaa cggtacgctc aacaatttgc tagccgctat cgaaaactta gtaggcggcg
112321 gcggcggtgg caattttaac gaagccgaca gacaaaaact ggacctcgtg tacactttgg
112381 ttaacgaaat caaaaatata ctcacgggaa cgctgacaaa aaaataagca tgtccgacaa
112441 aacaccaaca aaaagggtg gcagccatgc catgacgttg cgagagcgcg gcgtaacaaa
112501 acccccaaaa agtctgaaa agttgcagca atacaagaaa gccatcgctg ccgagcaaac
112561 gctgcgcacc acagcagatg tttcttcttt gcagaaccc ggggagagtg ccgttttca
112621 agagttggaa agattagaga atgcagttgt agtattagaa aatgaacaaa aacgattgta
112681 tccatatta gatacgcctc ttgataattt tattgtcgca ttcgtgaatc cgacgtatcc
112741 catggcctat tttgtcaata ccgattacaa attaaaacta gaatgtgcca gaatcagaag
112801 cgatttactt tacaaaaaca aaaacgaagt cgctatcaac aggcctaaga tatcgtcttt
112861 taaattgcaa ttgaacaacg taatttaga cactatagaa actattgaat acgatttaca
```

FIG. 2Y-2

```
112921 aaataaagtt ctcacaatta ctgcacctgt tcaagatcaa gaactaagaa aatccattat
112981 ttattttaat attttaaata gtgacagttg ggaagtacca aagtatatga aaaaattgtt
113041 tgatgaaatg caattggaac ctcccgtcat tttaccatta ggtctttaga tttggtaagg
113101 ctagcacgtc gacatcatgt ttgcgtcgtt gacctcagag caaaagctgt tattaaaaaa
113161 atataaattt aacaattatg tgaaaacgat cgagttgagt caagcgcagt tggctcattg
113221 gcgttcaaac aaagatattc agccaaaacc tttggatcgt gcagaaattt tacgtgtcga
113281 aaaggccacc aggggacaaa gcaaaaatga gctgtggacg ctattgcgtt tggatcgcaa
113341 cacagcgtct gcatcgtcca actcgtccgg caacatgtta caacgaccag cgcttttgtt
113401 tggaaacgcg caagaaagtc acgtcaaaga aaccaacggc atcatgttag accacatgcg
113461 cgaaatcata gaaagtaaaa ttatgagcgc ggtcgttgaa acggttttgg attgcggcat
113521 gttctttagc cccttgggtt tgcacgccgc ttcgcccgat gcgtattttt ctctcgccga
113581 cggaacgtgg atcccagtgg aaataaaatg tccgtacaat taccgagaca cgaccgtgga
113641 gcagatgcgt gtcgagttgg ggaacggcaa tcgcaagtat cgcgtgaaac acaccgcgct
113701 gttggttaac aagaaaggca cgccccagtt cgaaatggtc aaaacggatg cgcattacaa
113761 gcaaatgcaa cggcagatgt atgtgatgaa cgcgcctatg ggcttttacg tggtcaaatt
113821 caaacaaaat ttggtggtgg tttctgtgcc gcgcgacgaa acgttctgca caaagaact
113881 gtctacggaa acaacgcgt acgtggcgtt tgccgtggaa aactccaact gcgcgcgcta
113941 ccaatgcgcc gacaagcgac ggctttcatt caaaacgcac agctgcaatc acaactatag
114001 tggtcaagaa atcgatgcta tggtcgatcg cggaatatat ttagattatg gacatttaaa
114061 atgtgcgtac tgtgattta gctcagacag tcgggaaacg tgcgattctg ttttaaaacg
114121 cgagcacacc aactgcaaaa gttttaactt gaaacataaa aactttgaca atcctacata
114181 ctttgattat gttaaaagat tgcaaagttt gctaaagagt caccacttta gaaacgacgc
114241 taaaacactt gcctattttg gttactattt aactcataca ggaaccctga agacctttg
114301 ctgcggatcg caaaactcgt cgcccaccaa acacgatcat ttaaacgact gtgtatatta
114361 tttggaaata aaataaacct ttatattata tataattctt ttatttatac atttgtttat
114421 acaattttat ttacgacaaa tattgactcg tgttcagaa agtttaataa gcttgtcaat
114481 ttcttcggct tgcaaagggc tgccaacgcg ttcgtttga atgcgcgtaa tccggtttac
114541 ggtattgttg gcgcgaacaa taaactcctc aactggcaaa ttaacaattt tgtttgcgta
114601 ctcattgtgc actgcggcca ggttttgtag aatgttttcg ggaaaaatgg caattctatt
114661 aaatttgaca tgttttgat tgtatacata gttttgatat cttccagcg taggatattt
114721 gtttaaactc ttgacgcatt caatgtacaa tttgtgcagt gacaaaattc tgttaaaatc
114781 caaacgagaa catttctcaa aagttatttc ttgaccgttg aaatgtacac tttgcaattg
114841 tttcaataaa ctgtcgtaaa aagttttcc ttcttcaagc acaaacgcgg ggcgcatcgt
114901 gttatctaca acgcttatgt acttgtcaaa atcttcaatt atatgataga aatacaaata
114961 tctctccgcg tttatggacg tgtcgtttaa acatgttcg tcaacaactc cgttatgatt
115021 tactttcaaa aatttcaaat cttgcaaagc gtccgcgttg gtcaacttgt tgataataaa
115081 tttgtctttg cattcaaacg ctctgtttgc aatccactcc acagcgtcca aaacggacat
115141 gcgtttaaac atgttgatac gttttagaca atacgctcgt ttttttaccg cctcaacgtt
```

FIG. 2Z-2

```
115201 cacgtccgtg tagtcgcacc attgcaggat ttgcaacatg tcctcggcaa aatgcgcgaa
115261 ctgccgcagc ttttcctttc caaaatgttg attgtcgtgt ttaaaaagca cgttgaaat
115321 ttccgagaca taccacaaag ccgtgggcaa ttttactttg atcagcggct ccatagccag
115381 gttgctgaac ccgatcatgc attccgtgtt gttaatgcgg taaatgacat agcgtttaaa
115441 gtagtccttt acattatcgt caatgtattc tgcgtcgttt atgtgcttgt acagcaaata
115501 gtacataagg cccgcgttaa acgcgacctt tttagcgtca aaatacgtgc acgccaacac
115561 gtaatcgttg tattcgtcga attgctcgtt gggcactatg gcgcccgtaa aagggcgtct
115621 gctgcgcggt gacaaacgcg ttccatgctg aatcaactgc ttcaaacttt ccaaattata
115681 acaatattca attgaatttt taatctcttt attttggctc cataaaagag gaaactcgag
115741 tcggctttta aacttggtca aactgccctg aattgtttca acaagttgt aatgtgttaa
115801 caatatggcc ggcacaccgc tatcgttggc taaaatacaa tcggggaatc gaatattttc
115861 tacgttgctg taatcgtacg cttcgtcgtc gtcgttggca acaacatcgt cggtttcggc
115921 gtccacgctc gctaacttgt tctgatagtg taaattttc attacatcaa aagcgtatga
115981 cttgttgcga ttgtgcaaat aatttatggc cgtgctaatg gtgctgtcga taatttatc
116041 aaaattgaga acatcggcgt tatacaacgt tttataaat tctgttgact tgaacgtgtt
116101 tacaaactca ttttattt taatctggtc aaaattcata ctagaattgt tagtttgttt
116161 gatttcgctg aatagccgct ggcggagacg cttcagcttg tccacctcgt ttaacacgtt
116221 ggcgtccgtc ggcatggaat tgataaattt gaaccgaaca aagacagca gttcatcttt
116281 tttcgatata aatttttcgg ttgtaatgat atcgtagtta aattctttgg ttaaattgac
116341 ccattcgacc atttcatcgt tgcgataaat cttgcagtcc gagttgttga caaacgccga
116401 ggcaacggac aaatcaatct gttccgtgtt attattgatg gcataaaaca caatgcgttc
116461 gaaactaaac ggttttcgt ttagcaaatt tttgcaaacg tttgcctcat ttttggaaat
116521 ttggccgtcg gtcaccatgt acaaaagttt caacttgccg tcgagcaagt ttatattctt
116581 gtgaatccac tttatgaatt cgctgggcct ggtgtcagta ccctcgccat tgcggcgcaa
116641 ataacgactc ttgacgtctc cgatttcttt tggcggcaa taagcactcc aatgcaaata
116701 caaaactttg tcgcaactac tgatgttttc gatttcattc tgaaattgtt ctaaagtttg
116761 taacgcgttc ttgttaaagt aatagtccga gtttgtcgac aaggaatcgt cggtggcgta
116821 cacgtagtag ttaatcatct tgttgattga tatttaattt tggcgacgga tttttatata
116881 cacgagcgga gcggtcacgt tctgtaacat gagtgatcgt gtgtgtgtta tctctggcag
116941 cgcgatagtg gtcgcgaaaa ttacacgcgc gtcgtaacgt gaacgtttat attataaata
117001 ttcaacgttg cttgtattaa gtgagcattt gagctttacc attgcaaaat gtgtgtaatt
117061 tttccggtag aaatcgacgt gtcccagacg attattcgag attgtcaggt ggacaaacaa
117121 accagagagt tggtgtacat taacaagatt atgaacacgc aattgacaaa accgttctc
117181 atgatgttta acatttcggg tcctatacga agcgttacgc gcaagaacaa caatttgcgc
117241 gacagaataa aatcaaagt cgatgaacaa tttgatcaac tagaacgcga ttacagcgat
117301 caaatggatg gattccacga tagcatcaag tatttaaag atgaacacta ttcggtaagt
117361 tgccaaaatg gcagcgtgtt gaaaagcaag tttgctaaaa ttttaaagag tcatgattat
117421 accgataaaa agtctattga agcttacgag aaatactgtt tgcccaaatt ggtcgacgaa
```

FIG. 2A-3

```
117481 cgcaacgact actacgtggc ggtatgcgtg ttgaagccgg gatttgagaa cggcagcaac
117541 caagtgctat ctttcgagta caacccgatt ggtaacaaag ttattgtgcc gtttgctcac
117601 gaaattaacg acacgggact ttacgagtac gacgtcgtag cttacgtgga cagtgtgcag
117661 tttgatggcg aacaatttga agagtttgtg cagagtttaa tattgccgtc gtcgttcaaa
117721 aattcggaaa aggttttata ttacaacgaa gcgtcgaaaa acaaaagcat gatctacaag
117781 gctttagagt ttactacaga atcgagctgg ggcaaatccg aaaagtataa ttggaaaatt
117841 ttttgtaacg gttttattta tgataaaaaa tcaaaagtgt tgtatgttaa attgcacaat
117901 gtaactagtg cactcaacaa aaatgtaata ttaaacacaa ttaaataaat gttaaaattt
117961 attgcctaat attatttgt cattgcttgt catttattaa tttggatgat gtcatttgtt
118021 tttaaaattg aactggcttt acgagtagaa ttctacgcgt aaaacacaat caagtatgag
118081 tcataatctg atgtcatgtt ttgtacacgg ctcataaccg aactggcttt acgagtagaa
118141 ttctacttgt aatgcacgat cagtggatga tgtcatttgt ttttcaaatc gagatgatgt
118201 catgttttgc acacggctca taaactcgct ttacgagtag aattctacgt gtaacgcacg
118261 atcgattgat gagtcatttg ttttgcaata tgatatcata caatatgact catttgtttt
118321 tcaaaaccga acttgattta cgggtagaat tctacttgta aagcacaatc aaaagatga
118381 tgtcatttgt ttttcaaaac tgaactcgct ttacgagtag aattctacgt gtaaaacaca
118441 atcaagaaat gatgtcattt gttataaaaa taaagctga tgtcatgttt tgcacatggc
118501 tcataactaa actcgcttta cgggtagaat tctacgcgta aaacatgatt gataattaaa
118561 taattcattt gcaagctata cgttaaatca aacggacgtt atggaattgt ataatattaa
118621 atatgcaatt gatccaacaa ataaaattgt aatagagcaa gtcgacaatg tggacgcgtt
118681 tgtgcatatt ttagaaccgg gtcaagaagt gttcgacgaa acgctaagcc agtaccacca
118741 atttcctggc gtcgttagtt cgattatttt cccgcaactc gtgttaaaca caataattag
118801 cgttttgagc gaagacggca gtttgctcac gttgaaactc gaaaacactt gttttaattt
118861 tcacgtgtgc aataaacgct ttgtgtttgg caatttgcca gcggcggtcg tgaataatga
118921 aacgaagcaa aaactgcgca ttggagctcc aattttgcc ggcaaaaagc tggtttcggt
118981 cgtgacggcg tttcatcgtg ttggcgaaaa cgaatggctg ttaccggtga cgggaattcg
119041 agaggcgtcc cagctgtcgg gacatatgaa ggtgctgaac ggcgtccgtg ttgaaaaatg
119101 gcgacccaac atgtccgtct acgggactgt gcaattgccg tacgataaaa ttaaacagca
119161 tgcgctcgag caagaaaata aaacgccaaa cgcgttggag tcttgtgtgc tattttacaa
119221 agattcagaa atacgcatca cttacaacaa ggggactat gaaattatgc atttgaggat
119281 gccgggacct ttaattcaac ccaacacaat atattatagt taaataagaa ttattatcaa
119341 atcatttgta tattaattaa aatactatac tgtaaattac attttattta caatcatgtc
119401 aaagcctaac gttttgacgc aaattttaga cgccgttacg gaaactaaca caaaggttga
119461 cagtgttcaa actcagttaa acggctgga agaatcattc cagcttttgg acggtttgcc
119521 cgctcaattg accgatctta acactaagat ctcagaaatt caatccatat tgaccggcga
119581 cattgttccg gatcttccag actcactaaa gcctaagctg aaaagccaag cttttgaact
119641 cgattcagac gctcgtcgtg gtaaacgcag ttccaagtaa atgaatcgtt tttaaaataa
119701 caaatcaatt gttttataat attcgtacga ttctttgatt atgtaataaa atgtgatcat
```

FIG. 2B-3

```
119761 taggaagatt acgaaaaata taaaaaatat gagttctgtg tgtataacaa atgctgtaaa
119821 cgccacaatt gtgtttgttg caaataaacc catgattatt tgattaaaat tgttgttttc
119881 tttgttcata gacaatagtg tgttttgcct aaacgtAtac tgcataaact ccatgcgagt
119941 gtatagcgag ctagtggcta acgcttgccc caccaaagta gattcgtcaa aatcctcaat
120001 ttcatcaccc tcctccaagt ttaacatttg gccgtcggaa ttaacttcta aagatgccac
120061 ataatctaat aaatgaaata gagattcaaa cgtggcgtca tcgtccgttt cgaccatttc
120121 cgaaaagaac tcgggcataa actctatgat ttctctggac gtggtgttgt cgaaactctc
120181 aaagtacgca gtcaggaacg tgcgcgacat gtcgtcggga aactcgcgcg gaaacatgtt
120241 gttgtaaccg aacgggtccc atagcgccaa aaccaaatct gccagcgtca atagaatgag
120301 cacgatgccg acaatggagc tggcttggat agcgattcga gttaacgctt tggcagtcac
120361 ggtcagcgtt ttgatggcga tcacgttgag cgagtgcact aacgcggctt tgtaagtctc
120421 tcccaacatg cgcacggtca cgcgccgagt cgtgctaagc aacatgtgtt tcatggccgg
120481 aatgagagaa gtgttaattt ttttcaacat gcttttaaac ccggacatta gcatatcaaa
120541 gccaatgtcc gtagcaatac cgaaaacgag cgcgtaatct tccaaaaacg atgttataat
120601 tgactccaag tcttggtcgc tgattgaacg gtcgagcgcc tcgaaatgtt cgacacgtgc
120661 acgttcgtta ccgcggtaat tgtatgcgat cggagtttta gtaaagccgg tttcggccgt
120721 gtacgtgatc tggacgggcg acccgttgac gatcatgccc aaatcgttta gtgttggatt
120781 tttgttaaaa agtttttcaa attccaagtc tgtggcgtta tcgcgcacgc tgcgccattg
120841 cgctagtatt gcgttggagt ccacgttggg tcgtggcggt agtatgctgg aaggcgcttt
120901 gtaatcaaaa tcgcgcagtt cgctaaaaat gttgttggcc agcattttga aagtgacaaa
120961 gatcgtgtcg cccagcacga atccgatgag cgattcccac catctaaacg aacaaccgcc
121021 gttgaatagc tctctgccga aacgtcgaca gtaggcttcg ttgaattcgc ctttaaagcg
121081 ttcgggaaac aaggggtcgg gatcggccg aacgttaaaa gccggcacat cgtccacgcc
121141 catgatcgtg tgttcttcgg tgcgcaagta tgggctgtta aagtacattt tggacagcga
121201 gtccactaag atgcatttgt tgtcgagcgt gtatctaaac tcggcagact gaacttgggt
121261 ttcggcgcct tcacgcatgg ccgccgccct gtccaggtgg tagcacgcgg gctgcgcgta
121321 acccacgcta gtctcggagg tctgcgtgta catgaacggc gtcgtgttgg acacgacgcc
121381 ggtttcgtga aacggatagc agctcatgct ttcacacccg cgcttgctga aagccagttt
121441 gacggccagc gctttgtcgg ccaatttcgg cggcacataa taatcgtcgt cacttgacgc
121501 gggacgcagc gtgtagtcga ttagtatatg cggaaacctg gtgcgccatc tcgaaataaa
121561 ctcgagacga tgcatatgta tggcatacct actggcatta gttaaatcga cggctgttaa
121621 aaccgccatg ttatatagga cttaaaataa acaacaatat ataatgaaat atttattaga
121681 ttatattata gcaatacatt tacatttatt ataacaatac tttttattta atctgattat
121741 attataacga tacatttta tttagacatt gttatttaca atattaatta actttttata
121801 cattttaaa tcataatata taatcatttc gttgtgcatt tcaaagcttt tgatagcttc
121861 aaagtaatac atgaatttag agtattcagg aaaatgataa acgttggtaa acccgcattt
121921 ggtacaatat aacacgggat ttttataata cagtttagtt tttttacaca atttgcaata
121981 gttgttagtt gtaggttcca aaggaaacgt gattgcgccg tccaataccc gggtaaactt
```

FIG. 2C-3

```
122041 tttgacttta acagtggcaa acacggttcc tttgatacccc gaaaatcggt tgtcttgcag
122101 agcggccatc atttcgcttg gctcttgaag tataaaacag ttgacgtcat ccaccacgtc
122161 gggtctggtg cacatgcttc ggtagcgctg caacactata ttggtgtatg tttccctgag
122221 aacgagaccg ccggtggtgc taagatcgat tgtttgaatg cgctcgttgg gctctttgtg
122281 atttcgaatt atgcgccgaa ttatttcaaa cactttgcag ttgtgatcgt caattctcaa
122341 ttctttaact tccgtcgtgt gctctaaact tacagggaaa atgtattggt aaaaaaacct
122401 ctctctggct aaatagctga ggtcgaccaa attgatagaa ggatatattt cgtacgaggt
122461 ttttggaacg ttgtgatata gatagcattt ttgacagcag atgtctatgc ggtcaggatc
122521 gtccaacggc ttttcgatgt gaaccacaac atacaaaaac cattcgcgcg tgttgtcttt
122581 gaatctataa ttgcaagtgg tgcatcgcga atcgctcatg tgctccatag tcttcttgta
122641 tttcacaggc ctgcttgcaa atttgcccgt catgcgcata tctttgctgt ttatgtagcc
122701 cataatgtaa ttggtggaaa attttagcgt ggctttcatg atgtcgcgtt ctaaatcgct
122761 catgaaatgc atacgtagat cgcgctcttg tttgaaatcc agtttgtcgc tgtacgcggg
122821 caaaccttca aacttgttcc caaactcggg cggcacaaaa tatccatctt ttctgttgac
122881 gactggtttt ttacttacaa tgctgctgtg ctccaacggc ttggccggag aggtgcgcgt
122941 aggctgttta ggcggagaga tgcgcgtagg tggtttgatg ttagattttg gcggcggacg
123001 aacaggcgac ggcggcgagt tggcggcagg cgctggcaaa gatttggcac gaccccttgcc
123061 cccggtcctt ggcgcgtcaa aaatgttatt ctctcgaaaa aaacggttca ttgtaactgt
123121 tagttagcac tcagaaatca acacgatact gtgcacgttc agccatcgag aggctttata
123181 tatggaaacc ttatctatag agataagatt gtatatgcgt aggagagcct ggtcacgtag
123241 gcactttgcg cacggcacta gggctgtgga ggggacaggc tatataaagc ccgtttgccc
123301 aactcgtaaa tcagtatcaa ttgtgctccg gcgcacacgc tcgcttgcgc gccggatagt
123361 ataagtaatt gataacgggc aacgcaacat gataagaacc agcagtcacg tgctgaacgt
123421 ccaggaaaat ataatgacgt caaactgtgc gtcatcgcca tattcgtgcg aggcaacgtc
123481 cgcttgcgca gaagctcaac aggtaatgat cgataacttt gttttctttc acatgtacaa
123541 cgccgacata caaattgacg caaagctgca atgcggcgtg cgctcggccg cgtttgcaat
123601 gatcgacgat aaacatttgg aaatgtacaa gcatagaata gagaataaat tttttttatta
123661 ctatgatcaa tgtgccgaca ttgccaaacc cgaccgtctg cccgatgacg acggcgcgtg
123721 ctgtcaccat tttatttttg atgcccaacg tattattcaa tgtattaaag agattgaaag
123781 cgcgtacggc gtgcgtgatc gcggcaatgt aatagtgttt tatccgtact tgaaacagtt
123841 gcgagacgcg ttgaagctaa ttaaaaactc ttttgcgtgt tgttttaaaa ttataaattc
123901 tatgcaaatg tacgtgaacg agttaatatc aaattgcctg ttgtttattg aaaagctgga
123961 aactattaat aaaactgtta aagttatgaa tttgtttgta gacaatttgg ttttgtacga
124021 atgcaatgtt tgtaaagaaa tatctacgga tgaaagattt ttaaagccaa aagaatgttg
124081 cgaatacgct atatgcaacg cgtgctgcgt taacatgtgg aagacggcca ccacgcacgc
124141 aaaatgtcca gcgtgcagga catcgtataa ataagcacgc aacgcaaaat gagtggtggc
124201 ggcaacttgt tgactctgga aagagatcat tttaaatatt tatttttgac cagctatttt
124261 gatttaaaag ataatgaaca tgttccttca gagcctatgg catttattcg caattacttg
```

FIG. 2D-3

```
124321 aattgcacgt ttgatttgct agacgatgcc gtgctcatga actatttcaa ttacttgcaa
124381 agcatgcaat tgaaacattt ggtgggcagc acgtcgacaa acattttcaa gtttgtaaag
124441 ccacaattta gatttgtgtg cgatcgcaca actgtggaca ttttagaatt tgacacgcgc
124501 atgtacataa aaccggcac gcccgtgtac gccacgaacc tgttcacgtc caatccccgc
124561 aagatgatgg ctttcctgta cgctgaattt ggcaaggtgt ttaaaaataa aatattcgta
124621 aacatcaaca actacggctg cgtgttggcg ggcagtgccg gtttcttgtt cgacgatgcg
124681 tacgtggatt ggaatggtgt gcgaatgtgt gcggcgccgc gattagataa caacatgcat
124741 ccgttccgac tgtatctact gggcgaggac atggctaagc actttgtcga taataatata
124801 ctaccgccgc acccttctaa cgcaaagact cgcaaaatca acaattcaat gtttatgctg
124861 aaaaacttt acaaaggtct gccgctgttc aaatcaaagt acacggtggt gaacagcact
124921 aaaatcgtga cccgaaaacc caacgatata tttaatgaga tagataaaga attaaatggc
124981 aactgtccgt ttatcaagtt tattcagcgc gactacatat tcgacgccca gtttccgcca
125041 gatttgcttg atttgctaaa cgaatacatg accaaaagct cgatcatgaa aataattacc
125101 aagtttgtga ttgaagaaaa ccccgctatg agcggtgaaa tgtctcgcga gattattctt
125161 gatcgctact cagtagacaa ttatcgcaag ctgtacataa aaatggaaat aaccaaccag
125221 tttcctgtca tgtacgatca tgaatcgtcg tacattttg tgagcaaaga cttttgcaa
125281 ttgaaaggca ctatgaacgc gttctacgcg cccaagcagc gtatattaag tattttggcg
125341 gtgaatcgtt tgtttggcgc cacggaaacg atcgactttc atcccaacct gctcgtgtac
125401 cggcagagtt cgccgccggt ccgtttgacg ggcgacgtgt atgttgttga taagaacgaa
125461 aaagttttt tggtcaaaca cgtgttctca aacacggtgc ctgcatatct tttaataaga
125521 ggtgattacg aaagttcgtc tgacttgaaa tcccttcgcg atttgaatcc gtgggttcag
125581 aacacgcttc tcaaattatt aatccccgac tcggtacaat aatatgattt acactgatcc
125641 cactactggc gctacgacta gcacagacgc gccgtccaca aactatttaa acaggctaac
125701 tccaaacatg ttcttgacca tcttggctgt agtagtaatt attgctttaa taattatatt
125761 tgttcaatct agcagtaatg gaaacagctc gggggtaat gtacctccaa acgccctggg
125821 gggtttgta aatcctttaa acgctaccat gcgagctaat ccctttatga acacgcctca
125881 aaggcaaatg ttgtagataa gtgtataaaa aatgaaacgt atcaaatgca acaaagttcg
125941 aacggtcacc gagattgtaa acagcgatga aaaatccaa aagacctacg aattggctga
126001 atttgattta aaaaatctaa gcagtttaga aagctatgaa actctaaaaa ttaaattggc
126061 gctcagcaaa tacatggcta tgctcagcac cctggaaatg actcaaccgc tgttggaaat
126121 atttagaaac aaagcagaca ctcggcagat tgccgccgtg gtgtttagca cattagcttt
126181 tatacacaat agattccatc cccttgttac taatttttact aacaaaatgg agtttgtggt
126241 cactgaaacc aacgacacaa gcattcccgg agaacccatt ttgtttacgg aaaacgaagg
126301 tgtgctgctg tgttccgtgg acagaccgtc tatcgttaaa atgctaagcc gcgagtttga
126361 caccgaggct ttagtaaact ttgaaaacga caactgcaac gtgcggatag ccaagacgtt
126421 tggcgcctct aagcgcaaaa acacgacTcg cagcgatgat tacgagtcaa ataaacaacc
126481 caattacgat atggatttga gcgatttag cataactgag gttgaagcca ctcaatattt
126541 aactctgttg ctgaccgtcg aacatgccta tttacattat tatatttta aaaattacgg
```

FIG. 2E-3

```
126601 ggtgtttgaa tattgcaaat cgctaacgga ccattcgctt tttaccaaca aattgcgatc
126661 gacaatgagc acaaaaacgt ctaatttact gttaagcaaa ttcaaattta ccattgaaga
126721 ttttgacaaa ataaactcaa attctgtaac atcagggttt aatatatata attttaataa
126781 ataattaaat aatatacaat gttttatta attatatttt taatattaat taaagtatta
126841 atatttaaaa aaatgaatca aattcatcta aagtgtcaca gcgataaaat ttgtcctaaa
126901 gggtattttg gcctcaacgc cgatccctat gattgcacgg cgtattatct gtgtccgcat
126961 aaagtgcaaa tgttttgcga attaaatcac gaatttgact tggactccgc cagctgcaag
127021 cctatcgtgt acgatcacac gggcagcggg tgtacggctc gcatgtatag aaacttgtta
127081 ctatgaagag cgggtttcca gttgcacaac actattatcg atttgcagtt cggacataa
127141 atgtttaaat atatcgatgt ctttgtgatg cgcgcgacat ttttgtaggt tattgataaa
127201 atgaacggat acgttgcccg acattatcat taaatccttg gcgtagaatt tgtcgggtcc
127261 attgtccgtg tgcgctagca tgcccgtaac ggacctcgta cttttggctt caaaggtttt
127321 gcgcacagac aaaatgtgcc acacttgcag ctctgcatgt gtgcgcgtta ccacaaatcc
127381 caacggcgca gtgtacttgt tgtatgcaaa taaatctcga taaaggcgcg gcgcgcgaat
127441 gcagctgatc acgtacgctc ctcgtgttcc gttcaaggac ggtgttatcg acctcagatt
127501 aatgtttatc ggccgactgt tttcgtatcc gctcaccaaa cgcgtttttg cattaacatt
127561 gtatgtcggc ggatgttcta tatctaattt gaataaataa acgataaccg cgttggtttt
127621 agagggcata ataaagaaa tattgttatc gtgttcgcca ttagggcagt ataaattgac
127681 gttcatgttg gatattgttt cagttgcaag ttgacactgg cggcgacaag atcgtgaaca
127741 accaagtgac tatgacgcaa attaatttta acgcgtcgta caccagcgct tcgacgccgt
127801 cccgagcgtc gttcgacaac agctattcag agttttgtga taaacaaccc aacgactatt
127861 taagttatta taaccatccc accccggatg gagccgacac ggtgatatct gacagcgaga
127921 ctgcggcagc ttcaaacttt ttggcaagcg tcaactcgtt aactgataat gatttagtgg
127981 aatgtttgct caagaccact gataatctcg aagaagcagt tagttctgct tattattcgg
128041 aatcccttga gcagcctgtt gtggagcaac catcgcccag ttctgcttat catgcggaat
128101 cttttgagca ttctgctggt gtgaaccaac catcggcaac tggaactaaa cggaagctgg
128161 acgaatactt ggacaattca caaggtgtgg tgggccagtt taacaaaatt aaattgaggc
128221 ctaaatacaa gaaaagcaca attcaaagct gtgcaaccct tgaacagaca attaatcaca
128281 acacgaacat tgcacggtc gcttcaactc aagaaattac gcattatttt actaatgatt
128341 ttgcgccgta tttaatgcgt ttcgacgaca acgactacaa ttccaacagg ttctccgacc
128401 atatgtccga aactggttat tacatgtttg tggttaaaaa aagtgaagtg aagccgtttg
128461 aaattatatt tgccaagtac gtgagcaatg tggtttacga atatacaaac aattattaca
128521 tggtagataa tcgcgtgttt gtggtaactt ttgataaaat taggtttatg atttcgtaca
128581 atttggttaa agaaaccggc atagaaattc ctcattctca agatgtgtgc aacgacgaga
128641 cggctgcaca aaattgtaaa aaatgccatt tcgtcgatgt gcaccacacg tttaaagctg
128701 ctctgacttc atattttaat ttagatatgt attacgcgca aaccacattt gtgactttgt
128761 tacaatcgtt gggcgaaaga aaatgtgggt ttcttttgag caagttgtac gaaatgtatc
128821 aagataaaaa tttatttact ttgcctatta tgcttagtcg taaagagagt aatgaaattg
```

FIG. 2F-3

```
128881  agactgcatc taataatttc tttgtatcgc cgtatgtgag tcaaatatta aagtattcgg
128941  aaagtgtgca gtttccgac  aatcccccaa acaaatatgt ggtggacaat ttaaatttaa
129001  ttgttaacaa aaaaagtacg ctcacgtaca aatacagcag cgtcgctaat cttttgttta
129061  ataattataa atatcatgac aatattgcga gtaataataa cgcagaaaat ttaaaaaagg
129121  ttaagaagga ggacggcagc atgcacattg tcgaacagta tttgactcag aatgtagata
129181  atgtaaaggg tcacaatttt atagtattgt ctttcaaaaa cgaggagcga ttgactatag
129241  ctaagaaaaa caaagagttt tattggattt ctggcgaaat taaagatgta gacgttagtc
129301  aagtaattca aaaatataat agatttaagc atcacatgtt tgtaatcggt aaagtgaacc
129361  gaagagagag cactacattg cacaataatt tgttaaaatt gttagcttta atattacagg
129421  gtctggttcc gttgtccgac gctataacgt ttgcggaaca aaaactaaat tgtaaatata
129481  aaaaattcga atttaattaa ttatacatat attttgaatt taattaatta tacatatatt
129541  ttatattatt tttgtctttt attatcgagg ggccgttgtt ggtgtggggt tttgcataga
129601  aataacaatg ggagttggcg acgttgctgc gccaacacca cctcctcctc ctcctttcat
129661  catgtatctg tagataaaat aaaatattaa acctaaaaac aagacgcgc  ctatcaacaa
129721  aatgataggc attaacttgc cgctgacgct gtcactaacg ttggacgatt tgccgactaa
129781  accttcatcg cccagtaacc aatctagacc caagtcgcca actaaatcac caaacgagta
129841  aggttcgatg cacatgagtg tttggcccgc aggaagatcg ctaatatcta cgtattgagg
129901  cgaatctggg tcggcggacg gatcgctgcc gcgacaaact gttttttcta cttcatagtt
129961  gaatccttgg cacatgttgg ttagttcggg cggattgtta ggcaacaagg ggtcgaatgg
130021  gcaaatggta acatccgact gatttagatt ggggtcttga cgacaagtgc gctgcaataa
130081  caagcaggcc tcggcgattt ctccggcgtc tttaccttgc acataataac ttccgccggt
130141  gttattgatg gcgttgatta tatcttgtac tagtgtggcg gcgctaaaca agaaatagcc
130201  gccggtggcc aagagtatgc ccgttcctcc tacttttaag ctttgcatgt aactatgtag
130261  acggggttt  tgctgcagtg cgttttgaac accttcgggc gtgcgcacgt tggtttccgg
130321  gaagttttgt ttgactgcat tggatcgcgt ctgcttggtg tggtaattaa agtctggcac
130381  gttgtccacg cgccgcaatt ggctcaatga gtttatttga gggtctgaaa tgccctgaaa
130441  tactccgcgt atgttgggga catcattgtt acgagtaatt ctgttatgt  ctgaagtgct
130501  cacaaactgg ttgttagata gttgatagcc cggctgaaat ctgttgtttc caatgttgcg
130561  tacactgggc gcgttgagca cattgtgaa  accggcggga gtgcttgtta aagacgcgt
130621  attatcagta ataaactgg  cctgattagg atacaattta ttgactgcgc gaagatttga
130681  aaaaaactc  attttaaagc aaacttattt aataaatata tcacagtaaa ggttttgcaa
130741  aactgccgtc gtcaatacaa cacggcagcg gcgtcatgtt ggtaaaatct aatcttctcc
130801  ttgctttaga ttctggcga  gaaggcgcat tgttgtgta  agttatttcg acgtctgcat
130861  tatttgttgt gtaaggtatc tcgacgtatg aagcaacttt aacattgtta taatttttt
130921  taaatattga tgcgctccac ggcgcgcgtt gatacggatg atatctctcc attgtatgat
130981  cgctaaattt atataccgtt tcaataaata tgttaaaacc caacatgtta attataatat
131041  tcataatagt ttgtttgttt tcaataatta ttttactgt  tttgaaatct aaaagaggtg
131101  acgatgacga atcagacgac gggttcagtt gctataacaa accaattgga gtaaatttc
```

FIG. 2G-3

```
131161 cgcatcctac tagatgtgac gctttctaca tgtgtgtcgg tttaaatcaa aaattagagt
131221 taatctgccc tgaaggattt gaatttgatc cagatgttaa aaattgtgtt cctatatcag
131281 attatggatg taccgctaac caaaactaaa aataaaataa aatttatata gattaatgaa
131341 ataaaattta tatagattaa taaaataaaa tttatttaat atattatact atttatatta
131401 tttacaacac ttaacgtcta gacataacag tttgtaactt agaaactaaa tcagagttac
131461 tgcgctcaaa ctctgaaaat ttggcttgag actcggccac ctgcttacgc aattgttctt
131521 gcagattatt cacagtcgat tgcaactctt ctgatttctt ggtagattct tgcaagtcat
131581 agtttgcctt ttgtaaatct aattcggcga cagcatgctt gtgtttaagc ataatgtagt
131641 cgctgtttaa catggtcatt ttatgttcaa cttggctggt cttggctcgc agctcggaca
131701 gttcttttg caattgctcc acatagttca agtccgtggt gtgattgttg accgtgttat
131761 tttctaaaag ctcgcgccaa tgctgtttga tggaatcctg gttacgagtg acgttaatgg
131821 gcataaattc tacatacccg tgcttattgt acacgcgaca atctgatgaa gtagcgctgc
131881 aaaaacattt gtacacagaa ttgtccataa ttatcttgac ataacacttg aaacacacag
131941 catggttaca atgaatcgaa gtcacaaacg aggaatttac gttttagtg tctttaaaag
132001 tagtaaaaca aatattacac gaaacctcta cttcttcttc gggttctgat tgctgctgct
132061 gctgctgctg cggctgcgga gactgcggcg aggcaaacaa atctggcgac tgtggtatta
132121 cgtaattcgg cgaataagat ggactataag tgggagacct tggggcaatc tcattcatca
132181 gctgagcctc aagatctaaa cctcgttgca gagccctctg cgcagctgtc tccgacgcaa
132241 tgttatcctg gtactgctgg gcagtgatgt cgggaaaccg ttcacgatcc acattttcac
132301 tattaattag tatgacgtca tcctcttgac ttaatagcgg atcgtcattg ctaatgttaa
132361 cctgacgtg cacgtaatac gtgacaccct gacgatggta ggtgcgcgtc aacggctcgt
132421 tgacgttccc gataatctgc acgttttctt cgctgacacg ctgctcctga cgccgctcct
132481 gacggcgatg gctgcgactg cttgaagacg gctggctgcg actgcttgaa gacggctggg
132541 cttcgggaga tgttgtaaag ttgatgcggc gacggctgag agacagcctg tggcggcggc
132601 tgctgctggg agtggcggcg ttgatttggc gactcatggc tgggctggta ggatactgtt
132661 cactaggctg tgaggcttga actgtgctta cgagtagaac ggcagctgta tttatactgt
132721 ttatcagtac tgcacgactg ataagacaat agtggtgggg gaacttgcca ggcaaaaatg
132781 aacttttttg taatgcaaaa aagttgatag tgtagtagta tattgggagc gtatcgtaca
132841 gtgtagacta ttctaataaa atagtctacg atttgtagag attgtactgt atatggagtg
132901 tcaggcaaaa gtgaactttt ttgcattgca aaaaaattca ttttaaattt atcatatcac
132961 aggctgcagt ttctgttatc tgtcccccac tcaggcgtgc agctataaaa gcaggcactc
133021 accaactcgt aagcacagtt cgttgtgaag tgaacacgga gagcctgcca ataagcaaaa
133081 tgccaaggga caccaacaat cgccaccggt ctacgccata tgaacgtcct acgcttgaag
133141 atctccgcag acagttgcaa gacaatttgg acagcataaa ccCcgagac agaatgcaag
133201 aagaacaaga agaaaacctg cgctatcaag tgcgtagaag gcagcgtcaa aaccagctcc
133261 gctccataca aatggaacag cagcgaatga tggcggaatt aaacaacgag ccggtgatta
133321 attttaaatt tgagtgtagt gtgtgtttag aaacatattc ccaacaatct aacgatactt
133381 gtccttttt gattccgact acgtgcgacc acggttttg tttcaaatgc gtcatcaatc
```

FIG. 2H-3

```
133441 tgcaaagcaa cgcgatgaat attccgcatt ccactgtgtg ctgtccattg tgcaataccc
133501 aggtaaaaat gtggcgttcc ttaaagccta acgctgttgt gacgtgtaag ttttacaaga
133561 aaactcaaga aagagttccg cccgtgcagc agtataaaaa cattattaaa gtgctacaag
133621 aacggagcgt gattagtgtc gaagacaacg acaataattg tgacataaat atggagaatc
133681 aggcaaagat agctgctttg gaagctgaat tggaagaaga aaaaaatcac agtgatcaag
133741 tagcttctga aaaccgacag ctgatagaag aaaatactcg tctcaatgaa cagattcaag
133801 agttgcagca tcaggtgagg acattggtgc cgcaacgtgg cattacggtt aatcagcaaa
133861 ttggccgtga cgacagtgcg ccagccgagc tgaacgagcg ttttcgctca cttgtctatt
133921 cgactatttc agagctgttt attgaaaatc gcgttcatag tattcaaaat tatgtttatg
133981 ccggaacttc tgctgctagt tcatgtgatg taaatgttac tgttaatttt gggtttgaaa
134041 attaatgtga tatgaaatgt atatataaaa atgatggaat aaataataaa cattttata
134101 cttttatgt tttttttatt tcatgtgatt aagaaacttt taagatggat agtagtaatt
134161 gtattaaaat agatgtaaaa tacgatatgc cgttacatta tcaatgtgac aataacgcag
134221 ataaagacgt tgtaaatgcg tatgacacta tcgatgttga ccccaacaaa agatttataa
134281 ttaatcataa tcacgaacaa caacaagtca atgaaacaaa taacaagtt gtcgataaaa
134341 cattcataaa tgacacagca acatacaatt cttgcataat aaaaatttaa atgacatcat
134401 atttgagaat aacaaatgac attatccctc gattgtgttt tacaagta
```

FIG. 3

```
LOCUS     MiSeq_127 PCV3-ISU-2018052781-Tissue              2000 bp
DEFINITION  PCV3-ISU-2018052781-Tissue, DNA 2000 bases.
FEATURES          Location/Qualifiers
   Source     1..2000
              /isolate="PCV3-ISU-2018052781-Tissue "
   gene       223..1110
              /gene="ORF1"
   CDS        223..1110
              /gene="ORF1"
              /note="start codon not determined"
              /codon_start=1
              /product="replication-associated protein"
/translation="VRRESPKHRWCFTINNWTPTEWESIVECGGSIARYLIIGKEVGKGG
TPHLQGYVNFKNKRRLSSVKRLPGFGRAHLEPARGSHKEASEYCKKEGDYLEIGEDSSSG
TRSDLQAAARILTETSGNLTEVAEKMPAVFIRYGRGLRDFCGVMGLGKPRDFKTEVYVFI
GPPGCGKTREACADAAARELQLYFKPRGPWWDGYNGEGAVILDDFYGWVPFDELLRIGDR
YPLRVPVKGGFVNFVAKVLYITSNVVPEEWYSSENIRGKLEALFRRFTKVVCWGEGGIKK
DMETVYPINY"              SEQ ID NO 3
   gene       complement(1346..1987)
              /gene="ORF2"
   CDS        complement(1346..1987)
              /gene="ORF2"
/translation="MRHRAIFRRKPRPRRRRRHRRRYVRRKLFIRRPTAGTYYTKKYSTMNVISVGTPQN
NKPWHANHFITRLNEWETAISFEYYKILKMKVTLSPVISPAQQTKTMFGHTAIDLDGAWT
TNTWLQDDPYAESSTRKVMTSKKKHSRYFTPKPILAGTTSAHPGQSLFFFSRPTPWLNTY
DPTVQWGALLWSIYVPEKTGMTDFYGTKEVWIRYKSVL"      SEQ ID NO 4
```

FIG. 10A

ORIGIN
```
   1 TAGTATTACC CGGCACCTCG GAACCCGGAT CCACGGAGGT CTGTAGGGAG
  51 AAAAAGTGGT ATCCCATTAT GGATGCTCCG CACCGTGTGA GTGGATATAC
 101 CGGGCAGTGG ATGATGAAGC GGCCTCGTGT TTTGATGCCG CAGGACGGGG
 151 ACTGGATAAC TGAGTTTTTG TGGTGCTACG AGTGTCCTGA AGATAAGGAC
 201 TTTTATTGTC ATCCTATTCT AGGTCCGGAG GGAAAGCCCG AAACACAGGT
 251 GGTGTTTTAC GATAAACAAC TGGACCCCGA CCGAGTGGGA ATCTATTGTG
 301 GAGTGTGGAG GCAGTATAGC GAGATACCTT ATTATCGGCA AAGAGGTTGG
 351 AAAAGGCGGT ACCCACACT TGCAAGGGTA CGTGAATTTC AAGAACAAAA
 401 GGCGACTCAG CTCGGTGAAG CGCTTACCCG GATTTGGTCG GGCCCATCTG
 451 GAGCCGGCGA GGGGGAGCCA CAAAGAGGCC AGCGAGTATT GCAAGAAAGA
 501 GGGGGATTAC CTCGAGATTG GCGAAGATTC CTCTTCGGGT ACCAGATCGG
 551 ATCTTCAAGC AGCAGCTCGG ATTCTGACGG AGACGTCGGG AAATCTGACT
 601 GAAGTTGCGG AGAAGATGCC TGCAGTATTT ATACGCTATG GGCGGGGTTT
 651 GCGTGATTTT TGCGGGGTGA TGGGGTTGGG TAAACCGCGT GATTTTAAAA
 701 CTGAAGTTTA TGTTTTTATT GGTCCTCCAG GATGCGGGAA AACGCGGGAA
 751 GCTTGTGCGG ATGCGGCTGC GCGGGAATTG CAGTTGTATT TCAAGCCACG
 801 GGGGCCTTGG TGGGATGGTT ATAATGGGGA GGGTGCTGTT ATTCTGGATG
 851 ATTTTTATGG GTGGGTTCCA TTTGATGAAT TGCTGAGAAT TGGGGACAGG
 901 TACCCTCTGA GGGTTCCTGT TAAGGGTGGG TTTGTTAATT TTGTGGCTAA
 951 GGTATTATAT ATTACTAGTA ATGTTGTACC GGAGGAGTGG TATTCCTCGG
1001 AGAATATTCG TGGAAAGTTG GAGGCCTTGT TTAGGAGGTT CACTAAGGTT
```

FIG. 10B

```
1051 GTTTGTTGGG GGGAGGGGGG GATAAAGAAA GACATGGAGA CAGTGTATCC
1101 AATAAACTAT TGATTTTATT TGCACTTGTG TACAATTATT GCGTTGGGGT
1151 GGGGGTATTT ATTGGGTGGG TGGGTGGGCA GCCCCTAGC CACGGCTTGT
1201 CGCCCCCACC GAAGCATGTG GGGATGGGG TCCCCACATG CGAGGGCGTT
1251 TACCTGTGCC CGCACCCGAA GCGCAGCGGG AGCGCGCGCG AGGGGACACG
1301 GCTTGTCGCC ACCGGAGGGG TCAGATTTAT ATTTATTATC ACTTAGAGAA
1351 CGGACTTGTA ACGAATCCAA ACTTCTTTGG TGCCGTAGAA GTCTGTCATT
1401 CCAGTTTTTT CCGGGACATA AATGCTCCAA AGCAGTGCTC CCCATTGAAC
1451 GGTGGGGTCA TATGTGTTGA GCCATGGGGT GGGTCTGGAG AAAAAGAAGA
1501 GGCTTTGTCC TGGGTGAGCG CTGGTAGTTC CCGCCAGAAT TGGTTTGGGG
1551 GTGAAGTAAC GGCTGTGTTT TTTTTTAGAA GTCATAACTT TACGAGTGGA
1601 ACTTTCCGCA TAAGGGTCGT CTTGGAGCCA AGTGTTTGTG GTCCAGGCGC
1651 CGTCTAGATC TATGGCTGTG TGCCCGAACA TAGTTTTTGT TTGCTGAGCT
1701 GGAGAAATTA CAGGGCTGAG TGTAACTTTC ATCTTTAGTA TCTTATAATA
1751 TTCAAAGCTA ATTGCAGTTT CCCATTCGTT TAGGCGGGTA ATGAAGTGGT
1801 TGGCGTGCCA GGGCTTATTA TTCTGAGGGG TTCCAACGGA AATGACGTTC
1851 ATGGTGGAGT ATTTCTTTGT GTAGTATGTG CCAGCTGTGG GCCTCCTAAT
1901 GAATAGTTTT CTTCTGACAT AGCGCCTTCT GTGGCGTCGT CGTCTCCTTG
1951 GGCGGGGTTT TCTTCTGAAT ATAGCTCTGT GTCTCATTTT GGTGCCGGGC
```

FIG. 10C

History Plot
Pre-MSV+1 Production
BaculoG PCV3 ORF2 08FEB19 (Finished)
Selection: 2/8/2019 1:20:29 PM - 2/15/2019 2:06:01 PM

- - - - O2SP.Value;Db 1.0 %
- · - · PH.Value;Db 0.10 PH
——— PO2.Value;Db 1.0 %

FIG. 21

SF + Cell Count During Infection with BaculoG/PCV3 ORF2

- - ○ - - Viable Cells
——○—— Total Cells

FIG. 22A

SF + Cell Viability and Size During Infection with BaculoG/PCV3 ORF2

- - ○ - - Average Cell Diameter
——○—— Cell Viability

MegAlign - [Alignment Report of PCV3 and PCV2 ORF2 Alignment.meg ClustalW (Slow/Accurate, Gonnet)]
File Edit Align View Options Net Search Window Help
Majority Blue = PCV2 Structure 3R0R
Red = BFDV Structure 5J36

```
                                     10          20          30          40          50          60          70          80
Majority                      ----MWLTIRR-----RFRRRRRYXRR---RRRH-RRRLY---RRRRRYXRRR--XTNGI FNXRLXRTFGFTWK Baculovirus PCV3 ORF2.pro     ------------------------------MRHR---------AIFRRRPRPRR--RRRH-RRRY--ARRRLFIRR--PTAGTYYKKYSTMNVISV    51
Circoflex ORF2.pro            ------------------------------MTYPRR--------RYRRRRHRPRSHLGQIL-RRRPWLVHPRHRYRWR--RKNGIFNRLSRTFGYTVK    58
PCV2 BDH ORF2                 ------------------------------MTYPRR--------RFRRRRHRPRSHLGQIL-RRRPWLVHPRHRYRWR--RKNGIFNRLSRTIGYTVK    58
Beak and Feather virus Capsid.pro ------------------------MWGTSNCPCAIFQIRR-IARPRYRRHH-IRRYR--PRRTYFRRRRFSTNRIYTLRLTRQFKFELR    61
BFDV Capsid from 5J36.pro     ------------------------MWGTSNCACATFQIRRYARP-IRRYARP-YRRRH-IRRYR--RRRRHFRRRRFSTNRIYTLRLTRQFQFKIN    61
Bat Circovirus ASU92176.pro   MTAHAQGGARHASAMFLFLEMARWHTRRMRRATLHAVARSHRRRHAMGGRRRRHRRR--STYKFFHVRLTRYTVLMP    78
CCV ORF2.pro                  ------------------------------MRVRRHARAS----------RSYR-TRPLNRYRRRQNRFKLFHLRLRRTLTADWP    46
Canary Circovirus Capsid NP_573443.pro ------------------MWLTFN---QVARRRRPLAPR--RRRW--RRRYWXRRRRIPANRRGHRTNRVRFRVREFGQVLQ    59
Goose Circovirus Capsid NP_150370.pro ------------------MPLYRARPRSLYSRRRRATNR---------RRRY---RRRRLHIGRIRSKYTIENVKQTQNISFTFF    55
Bat Circovirus 3 Capsid YP_009551495.pro -----------------MRRKFR---RFRRKFKKFSRRFKRHFGGKRRK-TTRQVQFKFK-VQTVPYLNGSIAPSSSINWM    59
Bat associated circovirus 1 AGL09970.pro -----------------MPIRRRS---RYSRRRWRRNTR---------RRR---VARGAYRR--RKNGIINVRLSATKDWTMA    51

Majority                      KTTXX-----TLS-----WNADHLXFNLDDFLPXGPGS------XXXPFEYRIRKVVEXRPXN-PXTQ BC Loop            NKP  WHANHFITRLNEWET                          CD Loop 113       DE Loop 160

Baculovirus PCV3 ORF2.pro     GTPQN----NKP----WHANHFITRLNEWET---------------------------AITFEYYKILKMKVTLSPVTISPAQQ     99
Circoflex ORF2.pro            ATTVT----TPS----WNDMMRFNIDDFVPPGGGT---------------------NKISIPFEYYRIRKVKVEFWPCS-PITQ    113
PCV2 BDH ORF2                 KTTVR----TPS----WNDMMRFNINDFLPPGGGS---------------------NPLTVPFEYYRIRKVKVEFWPCS-PITQ    113
Beak and Feather virus Capsid.pro KQTTQPG--NLI----WNADYTFTLENFLTNTPNP------------------SALNFEDYRIKLARMEMKPTWGHYSI    117
BFDV Capsid from 5J36.pro     KQTTSVG--NLI----FNADYITFALDDFLQAVPNP------------------HTLNFEDYRIKLARMEMRPTGGHYTV    117
Bat Circovirus ASU92176.pro   KATTPSDDTETTYG--WNLDHVNEKLSDFLPMDSSG------------------RPSLPAFKDYNITKAVVRVKPINVPVSM    140
CCV ORF2.pro                  TAPVKPTNDPQTETPLLMNFDHLSFKLIDFLQASHGTG----------------DFQHLPPFRFYKFKKVIRARWINWPRTL    113
Canary Circovirus Capsid NP_573443.pro KGTGG-S------QLS----FGTDGINIILDDFLDWGTIN--------------------WRLPFEDYRIRLAKVEMRPLN-ESWE    113
Goose Circovirus Capsid NP_150370.pro GTGSP-D------KNK----WQAMSLEAVQSSGTSPKPGINLRFAVFGDRLPGTGNQYHYPFDYYMIRMVKVLRPAF-NPFQ    126
Bat Circovirus 3 Capsid YP_009551495.pro NTSNT------------------------ASHYTEAFTLGDIPHYSDLS----------------SVFDAAKLAAVKLKFVPRYTMGQL    108
Bat associated circovirus 1 AGL09970.pro STTAE------------G--YNVARLEVNLRQF MPAGPGSAI-----------------NTKSIPWAYYRIRKMKFEILPKM-IPAQ    106
```

CD Loop = Exposed
2-fold axis near c-
term projections

DE Loop = 5-fold interface loop

B-sheet C borders 3-
fold axis

EF Loop = 3-fold axis
partially exposed
partially buried

| Majority | XF NLXDPPX------- | |
|---|---|---|
| | 330 340 | |
| Baculovirus PCV3 ORF2.pro | SVL | 214 |
| Circoflex ORF2.pro | EFNLKDPPLEP. | 234 |
| PCV2 BDH ORF2 | EFNLKDPPLNPK. | 235 |
| Beak and Feather virus Capsid.pro | QFAPNNPST | 247 |
| BFDV Capsid from 5J36.pro | QFAPNNPST | 247 |
| Bat Circovirus ASU92176.pro | EFDLDFNPHA | 281 |
| CCV ORF2.pro | EFDYETGRQL. | 271 |
| Canary Circovirus Capsid NP_573443.pro | QMNLTHLATPK | 250 |
| Goose Circovirus Capsid NP_150370.pro | QWT GLSP | 250 |
| Bat Circovirus 3 Capsid YP_009551495.pr | QI RLL | 231 |
| Bat associated circovirus 1 AGL09970.pr | EF NLI DYPAQAPLLVDEEPSE | 238 |

Decoration 'Decoration #1': Shade (with bright yellow at 90% fill) residues that match Baculovirus PCV3 ORF2.pro exactly.

FIG. 31C

| | | | | | |
|---|---|---|---|---|---|
| PCV3 ORF2 FG 645 nt  SEQ ID NO:6 | ATGCGCCACC GAGACACCGC CCGCCGGTAC GTCGGCACCC TCGCCTGAAC TGAAGATGAA AAGACTATGT TAACACCTGG TCATGACCCA CTGGCTGGAA CCGCCCCACC CCCTGCTGTG TACGGCACCA | GTGCTATCTT CGTCGTTACG TTACTACACC CACAGAACAA GAGTGGGAAA GGTGACCCTG TCGGCCACAC CTGCAGGACG GCCATTCTCT CCACTTCCGC CCATGGCTGA GTCTATCTAC AGGAAGTGTG | CAGGCGTAGG CTAGACGCCG AAGAAGTACT CAAGCCTTGG CTGCCATCAC TCCCTGTCA TGCTATCGAC ACCCTACGC CACTCAAGAT CCACCCTGGA ACACTTACGA GTCCCGAGA GATCAGGTAC | CCTAGGCCCA TCTGTTCATC CCACTATGAA CACGCTAACC CTTCGAGTAC TCAGCCCGC CTGGACGGAG CGAATCCAGC ACTTCACTCC CAGTCTCTGT CCCTACCGTG AGACTGGTAT AAGTCAGTCC | GAAGGAGGAG AGGAGACCAA CGTGATCAGC ACTTCATCAC TACAAGATCC TCAGCAGACC CCTGGACCAC ACTAGGAAGG AAAGCCTCTG TCTTCTTCTC CAGTGGGGTG GACCGACTTC TGTGA |
| PCV3 ORF2 FG 214 aa  SEQ ID NO:7 | MRHRAIFRRR VGTPQNNKPW KTMFGHTAID LAGTTSAHPG YGTKEVWIRY | PRPRRRRHR HANHFITRLN LDGAWTTNTW QSLFFFSRPT KSVL | RRYARRRLFI EWETAITFEY LQDDPYAESS PWLNTYDPTV | RRPTAGTYYT YKILKMKVTL TRKVMTQPFS QWGALLWSIY | KKYSTMNVIS SPVISPAQQT HSRYFTPKPL VPEKTGMTDF |
| PCV3 ORF2 PC 735 nt  SEQ ID NO:8 | ATGCGCCACC GAGACACCGC CCGCCGGAAC GTCGGTACCC TCGCCTGAAC TGAAGATGAA AAGACTATGT TAACACCTGG TCATGACCTC CTGGCTGGCA CCGCCCTACC CCCTGCTGTG TACGGTACCA CAACATCAAC CTCTGCCACT | GTGCTATCTT CGTCGTTACG TTACTACACC CTCAGAACAA GAGTGGGAAA GGTGACCCTG TCGGTCACAC CTGCAGGACG CAAGAAGAAG CCACTTCTGC CCTGGCTGA GTCCATCTAC AGGAAGTCTG CTGACTCCTC GAGGTTCGGT | CCGCCGTAGG CTAGACGCCG AAGAAGTACT CAAGCCATGG CTGCCATCAC TCTCCAGTCA TGCTATCGAC ACCCCTACGC CACTCAAGAT CCACCCAGGA ACACTTACGA GTCCCTGAGA GATCAGGTAC CCGTGGCTAC TGCGGCCACC | CCAAGGCCTA TCTGTTCATC CTACTATGAA CACGCTAACC CTTCGAGTAC TCTCACCTGC CTGGACGGCG CGAATCCAGC ACTTCACTCC CAGTCCCTGT CCCTACTGTG AGACTGGAAT AAGAGCGTGC TTCTCGTGTG GTTGA | GACGCCGTAG AGGAGACCTA CGTGATCTCA ACTTCATCAC TACAAGATCC TCAGCAGACC CCTGGACCAC ACTAGGAAGG CAAGCCACTG TCTTCTTCTC CAGTGGGGCG GACCGACTTC TGGTCAAGAT CCAAGCAGAG |
| PCV3 ORF2 PC 244 aa  SEQ ID NO:9 | MRHRAIFRRR VGTPQNNKPW KTMFGHTAID LAGTTSAHPG YGTKEVWIRY | PRPRRRRHR HANHFITRLN LDGAWTTNTW QSLFFFSRPT KSVLVKININ | RRYARRRLFI EWETAITFEY LQDDPYAESS PWLNTYDPTV LTPPVATSRV | RRPTAGTYYT YKILKMKVTL TRKVMTSKKK QWGALLWSIY PSRALPLRFG | KKYSTMNVIS SPVISPAQQT HSRYFTPKPL VPEKTGMTDF CGHR |

FIG. 34

```
Met Arg His Arg Ala Ile Phe Arg Arg Arg Pro Arg Pro Arg Arg Arg
1               5                   10                  15
Arg Arg His Arg Arg Arg Tyr Ala Arg Arg Arg Leu Phe Ile Arg Arg
            20                  25                  30
Pro Thr Ala Gly Thr Tyr Tyr Thr Lys Lys Tyr Ser Thr Met Asn Val
            35                  40                  45
Ile Ser Val Gly Thr Pro Gln Asn Asn Lys Pro Trp His Ala Asn His
    50                  55                  60
Phe Ile Thr Arg Leu Asn Glu Trp Glu Thr Ala Ile Thr Phe Glu Tyr
65                  70                  75                  80
Tyr Lys Ile Leu Lys Met Lys Val Thr Leu Ser Pro Val Ile Ser Pro
                85                  90                  95
Ala Gln Gln Thr Lys Thr Met Phe Gly His Thr Ala Ile Asp Leu Asp
            100                 105                 110
Gly Ala Trp Thr Thr Asn Thr Trp Leu Gln Asp Asp Pro Tyr Ala Glu
            115                 120                 125
Ser Ser Thr Arg Lys Val Met Thr Gln Pro Phe Ser His Ser Arg Tyr
    130                 135                 140
Phe Thr Pro Lys Pro Leu Leu Ala Gly Thr Thr Ser Ala His Pro Gly
145                 150                 155                 160
Gln Ser Leu Phe Phe Phe Ser Arg Pro Thr Pro Trp Leu Asn Thr Tyr
                165                 170                 175
Asp Pro Thr Val Gln Trp Gly Ala Leu Leu Trp Ser Ile Tyr Val Pro
            180                 185                 190
Glu Lys Thr Gly Met Thr Asp Phe Tyr Gly Thr Lys Glu Val Trp Ile
            195                 200                 205
Arg Tyr Lys Ser Val Leu Val Lys Ile Asn Ile Asn Leu Thr Pro Pro
    210                 215                 220
Val Ala Thr Ser Arg Val Pro Ser Arg Ala Leu Pro Leu Arg Phe Gly
225                 230                 235                 240
Cys Gly His Arg
```

FIG. 35

PORCINE CIRCOVIRUS TYPE 3 (PCV3) VACCINES, AND PRODUCTION AND USES THEREOF

RELATED APPLICATIONS AND INCORPORATION BY REFERENCE

This application claims priority to U.S. provisional application 62/829,400 filed on Apr. 4, 2019, the entire contents of which are hereby incorporated by reference herein. Reference is also made to WO 2006/072065 and U.S. Pat. Nos. 6,103,526; 9,610,345; 9,669,087 and 10,450,351; the disclosures of which are hereby incorporated by reference in their entireties.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BI 19-AH009 (generic)_SL.txt. The text file is 218 KB; it was created on Nov. 10, 2021; and it is being submitted electronically via EFS-Web, concurrent with the filing of the specification.

FIELD OF THE INVENTION

Disclosed herein is a recombinant baculovirus vector containing a polynucleotide encoding Porcine *Circovirus* Type 3 (PCV3) ORF2. Also disclosed herein are compositions and vaccines produced from the baculovirus derived PCV3 ORF2 and BaculoG/PCV3 ORF2. Also disclosed is a recombinant baculovirus vector containing a mutated polynucleotide encoding Porcine *Circovirus* Type 3 (PCV3) ORF2. Also disclosed are compositions and vaccines produced from the baculovirus derived mutated PCV3 ORF2 and BaculoG/PCV3 ORF2.

BACKGROUND OF THE INVENTION

Porcine *circovirus* type 3 (PCV3) is a non-enveloped, icosahedral single-stranded DNA (ssDNA) virus belonging to the genus *Circovirus* in the family Circoviridae. The genome encodes for two major open reading frames (ORFs) where ORF1 encodes a replication-associated protein (rep) and ORF2 encodes the viral capsid (cap) protein, which determines the antigenic characteristics of the virus. PCV3 is genetically distinct from porcine *circovirus* type 2 (PCV2); specifically, there is only 48% amino acid identity in the rep gene and 26% amino acid identity in the cap gene between the two viruses.

PCV3 was originally reported in 2016 in the U.S., Palinski, Rachel, et al. "A Novel Porcine *Circovirus* Distantly Related to Known Circoviruses Is Associated with Porcine Dermatitis and Nephropathy Syndrome and Reproductive Failure." Journal of Virology, vol. 91, no. 1, 26 Oct. 2016. The virus has since been identified worldwide including Germany, Japan, Korea, Russia, China, Thailand, Italy, Spain, Denmark, South Korea, Poland, Brazil, Columbia, India, Serbia and Sweden. While testing is limited to date, the finding of PCV3 in retrospective samples indicates that the virus was likely circulating in swine populations worldwide decades prior to the initial 2017 reports. It is hypothesized that as testing increases, PCV3 will be identified in more countries and in older samples.

Additionally, Chinese patent application CN109207441A entitled, "3 type Cap protein of recombinant baculovirus expression pig circular ring virus and its construction method and primer," claims priority to CN201810912587.1A, filed Aug. 12, 2018. It describes the construction of Baculovirus expression of PCV3 ORF2 for the manufacturing of 3 type Cap proteins of pig circular ring virus.

CN109207441A entitled, "3 type Cap protein of recombinant baculovirus expression pig circular ring virus and its construction method and primer," claims priority to CN201810912587.1A, filed Aug. 12, 2018. It describes the administration of the Baculovirus expressed PCV3 ORF2 in mice and provides ELISA seroconversion data.

CN109207522A entitled, "It expresses 3 type of pig circular ring virus and truncates Cap protein of recombinant baculovirus and its construction method and primer," claims priority to CN201810912585.2A, filed Aug. 12, 2018. It describes Baculovirus-truncated CAP/ORF2, administration in mice, and provides ELISA seroconversion data.

Additionally, U.S. Pat. No. 10,450,351 (i.e., application Ser. No. 15/768,356) entitled, "Porcine *Circovirus* Type 3 Immunogenic Compositions and Methods of Making and Using the Same," was first published as US 2018/0305410 A1 on Oct. 25, 2018. It claims priority to provisional patent application 62/242,866, filed Oct. 16, 2015. (Inventor Ben Hause, assigned to Kansas State University Research Foundation. See also Palinski, Rachel, et al. Journal of Virology, vol. 91, no. 1, 26 Oct. 2016, doi:10.1128/jvi.01879-16. Published online Oct. 26, 2016. It relates to PCV3 from tissues "collected from four sows from a farm with chronic poor reproductive performance which died acutely with clinical symptoms consistent with PDNS." While the patent application does not say where the farm was located, it does describe that immunohistochemistry (IHC) and quantitative PCR (qPCR) were negative for PCV2, porcine reproductive and respiratory syndrome virus (PRRSV), and influenza A virus (IAV) on sows and mummified, stillborn and/or weak fetuses. This patent application describes isolation of the virus, but not of a propagating cell culture.

Examples in the '351 patent describe the qPCR detection of the PCV3 capsid gene, isolating the virus, cloning the PCV3 capsid protein, developing an anti-PCV3 capsid monoclonal antibody, PCV3 detection, and development of a recombinant PCV3 capsid ELISA. However, no vaccine studies or data are described.

Recently, an article was published describing intranasally inoculating 4- and 8-week-old specific-pathogen-free piglets with an infectious PCV3 DNA clone to evaluate PCV3 pathogenesis. However, no discussion of vaccines to prevent PCV3 infection was made. Jiang, Haijun, et al. "Induction of Porcine Dermatitis and Nephropathy Syndrome in Piglets by Infection with Porcine *Circovirus* Type 3." Journal of Virology, vol. 93, no. 4, 28 Nov. 2018, doi:10.1 128/jvi.02045-18.

Citation or identification of any document in this application is not an admission that such document is available as prior art to the present invention.

SUMMARY OF THE INVENTION

Disclosed are PCV3 ORF2 antigenic proteins and variants thereof that are useful in the vaccination of or treatment of animals, in particular swine.

Typically, the swine is a pig.

In some aspects of the present invention, the animal is a piglet. Typically, the piglet is not older than 15 weeks of age, or not older than 6 weeks of age, or not older than 3 weeks of age, or not older than 2 weeks of age, or not older than 1 week of age sow.

In some aspects of the present invention, swine is a sow or a gilt.

In some aspects of the present invention the swine is a sow or gilt (i.e. a sow that has not farrowed) that is less than 1 year in age, typically more than 4 months and less than 1 year in age, typically more than 5 months and less than 1 year in age, typically more than 6 months and less than 1 year in age, typically between 4 to 8 months in age, typically between 5 to 8 months in age, typically between 5 to 7 months in age, typically between 5 to 6 months in age.

In some aspects of the present invention the swine is a pregnant sow that is less than 1 year in age, typically more than 4 months and less than 1 year in age, typically more than 5 months and less than 1 year in age, typically more than 6 months and less than 1 year in age.

In some aspects of the present invention the swine is a pre-breeding gilt that is less than 1 year in age, typically more than 4 months and less than 1 year in age, typically more than 5 months and less than 1 year in age, typically more than 6 months and less than 1 year in age, typically between 4 to 8 months in age, typically between 5 to 8 months in age, typically between 5 to 7 months in age, typically between 5 to 6 months in age.

Disclosed is the development of baculovirus derived PCV3 ORF2, expressed from "BaculoG/PCV3 ORF2", compositions, and three vaccines: BaculoG/PCV3 ORF2, P9; live, adjuvanted with 50% ISA 207VG vaccine; BaculoG/PCV3 ORF2, P9; live, adjuvanted with 20% Carbopol® vaccine, and control BaculoG/no insert, P4; live, adjuvanted with 20% Carbopol® vaccine. Data showing efficacy of the vaccines to prevent PCV3 disease was provided.

Also disclosed is the development of baculovirus derived PCV3 ORF2 derived from killed virus.

Also disclosed is the development of baculovirus derived PCV3 ORF2 derived from mutated killed virus.

In a first aspect, the present invention thus relates to a composition comprising a PCV3 ORF2 protein, preferably an antigenic PCV3 ORF2 protein (a PCV3 ORF2 antigen). Said composition is also termed "the composition of the present invention" hereinafter. It also understood that the term "composition of the present invention", as described herein, is equivalent to "composition of the disclosure".

Preferably, the composition of the present invention further comprises a veterinary acceptable carrier selected from the group consisting of: a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, an immunomodulatory agent, and/or any combination thereof.

The present disclosure further relates to a porcine *circovirus* type 3 (PCV3) ORF2 protein; and a veterinary-acceptable carrier comprising a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral or expression vector, an immunomodulatory agent and/or any combination thereof.

In one embodiment, the veterinary-acceptable carrier comprises an adjuvant, immunomodulatory agent, cell culture supernatant, viral or expression vector or any combination thereof. In another embodiment, the veterinary-acceptable carrier comprises an adjuvant.

The PCV3 ORF2 can be from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4). Thus, the PCV3 as mentioned herein is any phylogenetic clade of PCV3 or combination of clades or preferably selected from the group consisting of PCV3a and PCV3b, and most preferably selected from the group consisting PCV3a1, PCV3b1, PCV3b2 and PCV3c. The composition of the present invention thus preferably comprises a PCV3 ORF2 protein selected from the group consisting of PCV3a ORF2 protein and PCV3b ORF2 protein, or most preferably comprises a PCV3 ORF2 protein is any phylogenetic clade of PCV3 or combination of clades or selected from the group consisting of PCV3a1 ORF2 protein, PCV3b1 ORF2 protein and PCV3b2 ORF2 protein. In another embodiment, the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity or sequence homology with SEQ ID NO:1. Preferably the PCV3 ORF2 protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 4. According to a particular preferred aspect, the PCV3 ORF2 protein is a recombinant protein, or most preferably a recombinant baculovirus expressed protein. Thus, the composition preferably comprises recombinant PCV3 ORF2 protein, or most preferably comprises baculovirus expressed PCV3 ORF2 protein.

In another embodiment, the PCV3 ORF2 protein is a recombinant PCV3 ORF2 protein from expression thereof by an expression vector, comprising a polynucleotide sequence that encodes the PCV3 ORF2 protein. Advantageously, the expression vector is a baculovirus.

In yet another embodiment, the composition further comprises a PCV2 ORF protein, which may be from expression by an expression vector, comprising a polynucleotide sequence that encodes the PCV2 ORF2 protein. Advantageously, the expression vector is a baculovirus.

Furthermore, the composition may further comprise at least one additional antigen of an additional porcine pathogen. The additional antigen or antigens of porcine pathogens comprises a PRRSV antigen, a *Mycoplasma hyopneumoniae* bacterin antigen, a *Mycoplasma hyopneumoniae* supernatant antigen, an Aujeszky's disease or pseudorabies virus antigen, a IAV antigen, a swine fever antigen (classical or African or combination thereof), an *Actinobacillus pleuropneumoniae* antigen, an *Escherichia coli* antigen, a porcine parvovirus (PPV) antigen, a *Pasteurella multocida* antigen, a *Erysipelothrix rhusiopathiae* antigen or a *Mycoplasma hyorhinis* antigen.

In another embodiment, PCV3 ORF2 protein is present in an amount of 0.2 to about 400 µg/ml, or 2 to about 400 µg/ml, or 4 to about 400 µg/ml, or 8 to about 400 µg/ml, or about 0.3 to about 200 µg/ml, or 2 to about 200 µg/ml, or 4 to about 200 µg/ml, or 8 to about 200 µg/ml, or about 0.35 to about 100 µg/ml, or 2 to about 100 µg/ml, or 4 to about 100 µg/ml, or 8 to about 100 µg/ml, or about 0.4 to about 50 µg/ml, or 2 to about 50 µg/ml, or 4 to about 50 µg/ml, or 8 to about 50 µg/ml, or about 0.45 to about 30 µg/ml, or about 0.6 to about 15 µg/ml, or about 0.75 to about 8 µg/ml, or about 1.0 to about 6 µg/ml, or about 1.3 to about 3.0 µg/ml, or about 1.4 to about 2.5 g/ml, or about 1.5 to about 2.0 µg/ml, or about 1.6 µg/ml. In a particular embodiment, the composition may have PCV3 ORF2 protein in an amount in a range from about 1.5 to about 2.0 g/ml of the composition. For example, in an embodiment a 1 ml dose of the composition may include about 1.6 ug of PCV3 ORF2 protein.

In another embodiment, PCV3 ORF2 protein or total PCV2 and PCV3 ORF2 proteins are present in an amount of about 0.2 to about 400 µg/dose, or 2 to about 400 µg/dose, or 4 to about 400 µg/dose, or 8 to about 400 µg/dose, or about 0.3 to about 200 µg/dose, or 2 to about 200 µg/dose, or 4 to about 200 µg/dose, or 8 to about 200 µg/dose, or about 0.35 to about 100 µg/dose, or 2 to about 100 µg/dose, or 4 to about 100 µg/dose, or 8 to about 100 µg/dose, or about 0.4 to about 50 µg/dose, or 2 to about 50 µg/dose, or 4 to about 50 µg/dose, or 8 to about 50 µg/dose, or about 0.45 to about 30 µg/dose, or about 0.6 to about 15 µg/dose, or about 0.75 to about 8 µg/dose, or about 1.0 to about 6 µg/dose, or about 1.3 to about 3.0 µg/dose, or about 1.4 to about 2.5 µg/dose, or about 1.5 to about 2.0 µg/dose, or about 1.6 µg/dose. In a particular embodiment, the composition may have a total PCV3 and PCV2 ORF2 protein in an amount in a range from about 1.5 to about 2.0 µg/ml of the composition. For example, in an embodiment a 1 ml dose of the composition may include about 1.6 ug of combined PCV3 and PCV2 ORF2 protein.

In another embodiment, the adjuvant comprises aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, a Carbopol®; Carbopol® 974P; Carbopol® 934P; Carbopol® 971P; a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer crosslinked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

In yet another embodiment, there may be about 50 µg to about 2000 µg of adjuvant; or wherein adjuvant present in an amount about 250 µg/ml dose of the composition, or wherein the adjuvant is present in an amount of about 100 µg to about 10 mg per dose; or wherein the adjuvant is present in an amount of about 500 µg to about 5 mg per dose; the adjuvant is present in an amount of about 750 µg to about 2.5 mg per dose; or the adjuvant is present in an amount of about 1 mg per dose. In a particular embodiment, the composition may include adjuvant in a range from about 750 ug to about 2.5 mg per dose of the composition. For example, in an embodiment a dose of the composition may include about 1 mg of adjuvant.

In one embodiment, the immunomodulatory agent comprises interleukin(s), interferon(s), or other cytokine(s).

The dosage of the antibiotic(s) may be from about 1 ug/ml to about 60 µg/ml of antibiotic(s), or less than about 30 µg/ml of antibiotic(s). For example, an embodiment of the composition may include less than about 30 µg/ml of antibiotic(s).

In one embodiment, the antibiotic(s) comprise Gentamicin.

A composition of the disclosure may comprise (i) PCV3 ORF2 protein, (ii) at least a portion of baculovirus that expressed said PCV3 ORF2 protein, (iii) a portion of cell culture of cells that were infected or transfected with recombinant baculovirus that expressed said PCV3 ORF2 protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration. In one embodiment, about 90% of the components (i) to (iii) may have a size smaller than 1 m and the pH of said composition is adjusted to about 6.5 to 7.5. In another embodiment, the BEI is from the cell culture having been treated with about 2 to 8 or about 5 mM BEI to inactivate the baculovirus. In another embodiment, the composition contains about 2 to 8 or about 5 mM BEI The composition may contain about 1 mg of the Carbopol® or Carbopol® 971. For example, an embodiment of the composition may include a cell culture that has been treated with BEI at a concentration of about 5 mM to inactivate the baculovirus. In some embodiments, a dose of the composition may include residual BEI and/or about 1 mg of Carbopol®, Carbopol® 971, or a combination thereof.

Any composition of the disclosure may be formulated and/or packaged for a single dose or one shot administration, as well as a multi-dose regimen. It is presumed that a single administration can overcome the presence of maternally derived antibodies.

In one embodiment, the composition may be a PCV3 and PPV (advantageously packaged in a VLP) and/or PRRSV advantageously for use in breeding age sows/gilts. In such an embodiment, one or more doses for administration is contemplated.

According to another aspect the composition of the present invention is an immunogenic composition.

The invention further provides the composition of the present invention for use as a medicament.

Further, the composition of the present invention is provided for use as a vaccine.

According to a particular preferred aspect, the composition of the present invention is for use in method for eliciting an immune response or an immunologic response or a protective immune or immunological response against (i) PCV3 and/or (ii) PCV2 and PCV3 and/or (iii) PCV3 and other porcine pathogens and/or (iv) PCV3, PCV2 and other porcine pathogens.

According to another preferred aspect, the composition of the present invention is for use in a method of reducing or preventing the clinical signs or disease caused by an infection with PCV3 in an animal or for use in a method of treating or preventing an infection with PCV3 in an animal, and wherein said animal is preferably a pig.

Further, the composition of the present invention is provided for use in a method for inducing an immune response against PCV3 in a pig, in particular in a preferably pregnant sow.

According to still another aspect, the composition of the present invention is provided for use in a method of reducing or preventing the clinical signs or disease caused by an infection with a PCV3 in a piglet, wherein the piglet is to be suckled by a sow to which the composition has been administered.

Thus, the present invention further provides the composition of the present invention for use in a method of reducing or preventing the clinical signs or disease caused by an infection with a PCV3 in a piglet, wherein the piglet is to be suckled by a sow to which the composition of the present invention has been administered, and wherein preferably said sow to which the composition has been administered is a sow to which the immunogenic composition has been administered while said sow has been pregnant, in particular with said piglet, or a pre-breeding gilt.

Preferably, the composition of the present invention for use in any one of the aforementioned methods is administered intramuscularly or intradermally, in particular to said sow.

The present disclosure also encompasses a method for eliciting an immune response or an immunological response or a protective immune or immunological response against (i) PCV3 and/or (ii) PCV2 and PCV3 and/or (iii) PCV3 and another porcine pathogen and/or (iv) PCV3, PCV2 and another porcine pathogen, comprising administering to an animal any of the herein disclosed compositions. The animal may be a porcine. Advantageously, the porcine may be a pig or a piglet or a sow. The pig or piglet may be not older than 15 weeks of age, or not older than 6 weeks of age, or not older than 3 weeks of age, or not older than 2 weeks of age, or not older than 1 week of age. The administration may occur within at least 1 or 2 or 3 weeks of exposure to virulent Porcine Circovirus. The administration may occur within at least 1 or 2 or 3 weeks of exposure to virulent Porcine Circovirus. For some aspects, the administration may comprise a single, one shot administration; or a single, one dose administration of the protein of the present invention or the composition of the present invention; and not a multi-shot or multi-dose regimen. For some aspects, the administration may comprise a multi-shot or multi-dose regimen of the protein of the present invention or the composition of the present invention.

Further, the present invention provides a method of immunizing a subject comprising administering to the subject the composition of the present invention.

Further, the present invention provides a method of immunizing swine against a clinical disease caused by at least one pathogen in said animal, said method comprising the step of administering to the animal the composition of the present invention, wherein said immunogenic composition fails to cause clinical signs of infection but is capable of inducing an immune response that immunizes the animal against pathogenic forms of said at least one pathogen, and wherein said at least one pathogen is preferably PCV3.

Further, the present invention provides a method for inducing the production of antibodies specific for PCV3 in a sow, wherein said method comprises administering the composition of the present invention. The sow can be a pregnant sow. Alternatively, the sow can be a gilt (i.e. a sow that has not farrowed)—preferably a pre-breeding gilt.

Further, the present invention provides a method of reducing or preventing the clinical signs or clinical symptoms caused by an infection with a PCV3 in a piglet, wherein said method comprises
  administering the composition of the present invention to a sow, and
  allowing said piglet to be suckled by said sow, and wherein said sow is preferably a sow being pregnant, in particular with said piglet.

Preferably, the latter above-mentioned methods comprise the steps of
  administering the composition of the present invention to a sow being pregnant with said piglet,
  allowing said sow to give birth to said piglet, and
  allowing said piglet to be suckled by said sow.

Further, the present invention provides a method of reducing the clinical signs and/or clinical symptoms caused by an infection with a porcine epidemic diarrhea virus (PEDV) in a piglet, wherein the piglet is to be suckled by a sow to which the composition of the present invention has been administered.

Preferably, in any one of the aforementioned methods, where applicable, the composition of the present is administered intramuscularly or intradermally, in particular to said sow.

According to another preferred aspect, the immunogenic composition of the present invention is administered twice, in particular intramuscularly or intradermally, to said sow.

In another preferred aspect, the clinical signs, as mentioned herein, are selected from the group consisting of reduction of average daily weight gain and mortality.

In a further preferred aspect, the clinical signs, as mentioned herein, are selected from the group consisting of expelling of mummified, stillborn and/or weak fetuses.

In yet another preferred aspect, the clinical symptoms, as mentioned herein, are selected from the group consisting of, gross lesions, histologic lesions, replication of PCV3 in a tissue, and PCV3 viremia.

In still a further preferred aspect, the clinical symptoms, as mentioned herein, are selected from the group consisting of development or production of a mummified, stillborn and/or weak fetus.

The present disclosure also encompasses use of any of the herein disclosed compositions in any of the herein disclosed methods; or use of a PCV3 ORF2 protein, alone or in combination, of any one of the herein disclosed compositions, for use in the preparation of a composition for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen, or for use in a method for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen.

In one embodiment, the composition may be a PCV3 and PPV (advantageously packaged in a VLP) and/or PRRSV advantageously for use in breeding age sows/gilts. In such an embodiment, one or more doses for administration is contemplated. This particular embodiment encompasses use of a PCV3 ORF2 protein in combination with a PPV protein and optionally a PRRSV protein for use in the preparation of a composition for inducing an immunological or immune response or a protective immune or immunological response PCV3 and PPV and optionally PSSRV, or for use in a method for inducing an immunological or immune response or a protective immune or immunological response against PCV3 and PPV and optionally PSSRV.

In this embodiment, a composition may comprise a (i) porcine *circovirus* type 3 (PCV3) ORF2 protein, a parvovirus (PPV) protein and optionally a PRRSV (porcine respiratory and reproductive syndrome virus) protein and (ii) a veterinary-acceptable carrier selected from the group consisting of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, an immunomodulatory agent, and/or any combination thereof. The veterinary-acceptable carrier may comprise an adjuvant, immunomodulatory agent, cell culture supernatant, viral or expression vector or any combination thereof. The veterinary-acceptable carrier may comprise an adjuvant. The composition may be utilized in a method for eliciting an immune response or an immunological response or a protective immune or immunological response against PCV3, PPV and/or PRRSV. In one embodiment, the composition may be utilized in a method for inducing an immune response against PCV3 in a pig, in particular in a preferably pregnant sow. In another embodiment, the composition may be utilized in a method of reducing or preventing the clinical signs or disease caused by an infection with a PCV3 in a piglet, wherein the piglet is to be suckled by a sow to which the composition has been administered. The composition may be administered intramuscularly or intradermally. The embodiment also relates to method for eliciting an immune response or an immunological response or a protective immune or immunological response against PCV3, PPV and/or PRRSV which may comprise administering to an animal any one of the above compositions. The embodiment also relates to method of immunizing swine against a clinical disease caused by at least one pathogen in said animal, said method comprising the step of administering to the animal any one of the above compositions, wherein said immunogenic composition fails to cause clinical signs of infection but is capable of inducing an immune response that immunizes the animal against pathogenic forms of said at least one pathogen.

PPV is an autonomous replicating virus of the Parvovirinae subfamily of the genus *Protoparvovirus* within the family Parvoviridae containing a single stranded DNA molecule of about 5100 nucleotides (Cotmore et al., 2014: Arch Virol.: 159(5): 1239-1247; *Molitor* et al., 1984: Virology: 137(2):241-54). Only the minus strand of the DNA is packaged into virions. The genome of the virus encodes three capsid proteins (VP1, VP2, VP3) and one non-structural protein (NS1). The capsid of parvovirus is about 22-25 nanometers in diameter and is comprised of VP1 and VP2 subunits. These proteins are derived from alternatively spliced versions of the same RNA molecule and thus overlap in sequence. Further, porcine parvovirus exhibits a high level of sequence similarity to feline panleukopenia virus, canine parvoviruses and rodent parvovirus (Ranz et al., 1989: J. gen. Virol: 70:2541-2553).

The PPV protein can be from an inactivated or killed whole cell or a subunit of PPV. Advantageously, the PPV protein is a recombinant PPV protein.

EP 0 551 449 A1 discloses a method for producing a VP2 subunit vaccine against porcine parvovirus. Cadar D et al. (Infection, Genetics and Evolution 2012, 12: 1163-1171) describe the phylogeny and evolutionary genetics of porcine parvovirus in wild boars. Streck A F et al. (Journal of General Virology 2011, 92: 2628-2636) describe the high rate of viral evolution in the capsid protein of porcine parvovirus. WO 88/02026 relates to empty viral capsid vaccines. Martinez C et al. (Vaccine 1992, 10(10): 684-690), discloses the production of porcine parvovirus empty capsids with high immunogenic activity. Xu F et al. (Applied and Environmental Microbiology 2007, 73(21): 7041-7047) describe the induction of immune responses in mice after intragastric administration of *Lactobacillus casei* producing porcine parvovirus VP2 protein. And U.S. Pat. No. 10,485,866 discloses immunogenic compositions comprising PPV viral protein 2 (VP2) advantageously a mutant PPV VP2 comprising one or more mutations.

The term "porcine parvovirus" or "PPV" is well known to the person skilled in the art. However, "Porcine parvovirus" is an autonomous replicating virus of the genus parvovirus within the family Parvoviridae containing a single stranded DNA molecule. The genome of the virus encodes three capsid proteins (VP1, VP2, VP3) and one non-structural protein (NS1). The disease caused by PPV in pigs is often referred to as a SMEDI (an acronym of stillbirth, mummification, embryonic death, and infertility). The term "porcine parvovirus" encompasses all possible strains, genotypes, phenotypes and serotypes of the porcine parvovirus. The term "viral protein 2" or "VP2" relates to the capsid protein VP2 of the porcine parvovirus. The term "viral protein 2" or "VP2" is well known to the person skilled in the art.

Porcine reproductive and respiratory syndrome (PRRS) is viewed by many as the most important disease currently affecting the pig industry worldwide. PRRS virus (PRRSV) is an enveloped single stranded RNA virus classified in the family Arteriviridae. There is large variability in the antigenic characteristics of the different isolates of PRRSV and effective measures to prevent infections are limited. There are three major groups of vaccines available for PRRS, attenuated modified live virus (MLV), killed virus vaccine or recombinant vaccines. The viral envelope proteins of PRRSV are generally categorized into major and minor proteins based on abundance of proteins in the virion. The major viral envelope proteins are gp5 (ORF 5) and M (ORF 6) and form a dimer. The minor envelope proteins are gp2 (ORF2), gp3 (ORF3), gp4 (ORF4) and E (ORF2b) and probably a newly identified viral protein gp5a (ORF 5a). The active antigenic component can include the ORF4, ORF5, ORF6, or ORF7 from PRRSV virus.

The recombinant PRRSV antigen may be expressed in a vectored PRRSV vaccine or composition that comprises one or more engineered, recombinant adenovirus vectors that harbor and express certain PRRSV antigens, and optionally a pharmaceutically or veterinarily acceptable carrier, adjuvant, excipient, or vehicle. Advantageous, the vector is an adenovirus vector although other vectors, such as a baculovirus, are also contemplated.

The PRRSV may be any strain, as the novel and inventive compositions and methods disclosed herein are universally applicable to all known and yet to be discovered PRRSV strains. PRRSV virus exists as two genotypes referred to as "US" and "EU" type which share about 50% sequence homology (Dea S et al. (2000). Arch Virol 145:659-88). These two genotypes can also be distinguished by their immunological properties. Most sequencing information on various isolates is based on the structural proteins, namely the envelope protein GP5 which accounts for only about 4% of the viral genome, while only little is known on the non-structural proteins (nsp). Isolation of PRRSV and manufacture of vaccines have been described in a number of publications (WO 92/21375, WO 93/06211, WO93/03760, WO 93/07898, WO 96/36356, EP 0 676 467, EP 0 732 340, EP 0 835 930, U.S. Pat. No. 10,039,821). The PRRSV antigen includes PRRSV minor proteins (e.g. gp2, gp3, gp4, gp5a, gp5 or E), in any combination, and optionally includes additional PRRSV major proteins (e.g. gp5 or M). For example, the PRRSV antigens could be displayed on the surface of virus-like particles (VLPs). In other embodiments, soluble versions of the antigens could be administered to the host animal, wherein oligomerization (including trimerization) of the proteins with each other, or additionally, with components of VSV-G, or other viral proteins or any oligomerization (including trimerization motifs) (e.g. motifs from bacterial GCN4, and the like). Moreover, the TM/CT domains of Type I viral surface glycoproteins are envisioned to accomplish the same purpose as, and are therefore interchangeable with, the corresponding domains from VSV-G.

In some embodiments, the one or more vectors comprise either: a nucleotide sequence encoding a PRRSV E antigen, polypeptide, ectodomain or variant thereof, or, a nucleotide sequence encoding a modified PRRSV gp2, gp3, gp4, gp5a, gp5 or M antigen, polypeptide, ectodomain, or variant thereof, wherein an existing cellular localization sequence of gp2, gp3, gp4, gp5a, gp5 or M has been replaced with a cell-surface expression determinant sequence from an heterologous gene. In some embodiments, the one or more vectors comprise a mixture of two vectors, a first vector expressing retargeted PRRSV minor proteins, and a second vector expressing re-targeted PRRSV major proteins In an advantageous embodiment, the immunogenic composition comprising PCV3, PPV and/or PRRSV is administered in two doses to a subject of need. However, the immunogenic composition comprising PCV3, PPV and/or PRRSV may be administered at two or more doses, with a first dose being administered prior to the administration of a second (booster) dose. Preferably, the second dose is administered at least 15 days after the first dose. More preferably, the second dose is administered between 15 days and 40 days after the first dose. Even more preferably, the second dose is administered at least 17 days after the first dose. Still more preferably, the second dose is administered between 17 days and 30 days after the first dose. Even more preferably, the second dose is administered at least 19 days after the first dose. Still more preferably, the second dose is administered between 19 days and 25 days after the first dose. Most preferably the second dose is administered at least 21 days after the first dose. Even more preferably, the second dose is administered at about 21 days after the first dose or at 21 days after the first dose. In a preferred aspect of the two-time administration regimen, both the first and second doses of the immunogenic composition comprising PCV3, PPV and/or or PRRSV are administered in the same amount. Preferably, each dose is in the preferred amounts specified above, with a dose of 1 ml or 2 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The dose volume per subject depends on the route of vaccination and the age of the subject. Preferably, the total volume is between about 0.2 ml and 5 ml, more preferably between about 0.5 ml and 3.0 ml, even more preferably between about 1.0 ml and 2.5 ml, even more preferably between about 1.0 ml and 2.0 ml. Most preferred the volume is 1 ml, 1.5 ml, 2 ml or 2.5 ml per dose.

The immunogenic composition comprising PCV3, PPV and/or PRRSV is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, more preferred the immunogenic composition comprising PCV3, PPV and/or PRRSV is administered subcutaneously or intramuscularly. Most preferred the immunogenic composition comprising PCV3, PPV and/or PRRSV is administered intramuscularly.

In one aspect, said immunogenic composition comprising PCV3, PPV and/or PRRSV is administered intramuscularly.

In one aspect, said immunogenic composition comprising PCV3, PPV and/or PRRSV is administered to gilts and/or sows.

Preferably, the immunogenic composition comprising PCV3, PPV and/or PRRSV is administered to gilts and/or sows being at least three 3 months of age, more preferably at least 4 months of age, most preferably at least 5 months of age.

In one aspect, the immunogenic composition is administered to gilts and/or sows being at least three 3 month of age.

In one aspect, said immunogenic composition comprising PCV3, PPV and/or PRRSV comprising PCV3, PPV and/or PRRSV is administered to gilts and/or sows before pregnancy.

In a two shot regime, the second dose of said immunogenic composition comprising PCV3, PPV and/or PRRSV is advantageously administered to gilts and/or sows 2, 3, 4 or 5 weeks before mating/insemination, most preferably about 3 weeks before mating/insemination. Preferably, the first dose of said immunogenic composition is administered to gilts and/or sows 2, 3, 4, 5 or 6 weeks before administering the second dose, most preferably about 3 weeks before administering the second dose. However, after the 2 shot regime has been applied, preferably, gilts and/or sows are revaccinated every 3, 4, 5, 6, 7 or 8 months, most preferably about every 6 months.

In one aspect of the present invention said immunogenic composition is administered to gilts and/or sows during pregnancy and lactation.

In one aspect of the present invention the immunogenic composition is safe for gilts and/or sows during pregnancy and lactation.

It is further claimed that, the vaccine is able to protect bred gilts and sows when challenged with PCV3 in all or two or at least one trimester during the 114 days of gestation.

It is also claimed that the vaccine is able to significantly reduce the incidence of mummies, stillborns and fetus in vaccinated gilts and sows vaccinated when challenged with PCV3 in all or two or at least one trimester during the 114 days of gestation.

In one aspect of the present invention the immunogenic composition is safe for gilts and/or sows from 30 days of gestation, preferably from 40 days of gestation.

Preferably, the immunogenic composition comprising PCV3, PPV and/or PRRSV comprises between 0.1 μg and 150 μg, preferably between 0.25 μg and 75 μg, more preferably between 0.5 μg and 37.5 μg, even more preferably between 0.5 μg and 15 μg, most preferably between 0.5 μg and 6 μg of the PCV3, PPV and/or PRRSV antigen. The immunogenic composition comprising PCV3, PPV and/or PRRSV can be in amounts of about 0.25 μg, 0.5 μg, 0.75 μg, 1 μg, 1.25 μg, 1.5 μg, 1.75 μg, 2 μg, 2.25 μg, 2.5 μg, 2.75 μg, 3 μg, 3.5 μg, 4 μg, 4.5 μg, 5 μg, 5.5 μg, 6 μg, 6.5 μg, 7 μg, 7.5 μg, 8 μg, 8.5 μg, 9 μg, 9.5 μg, 10 μg, 10.5 μg, 11 μg, 11.5 μg, 12 μg, 12.5 μg, 13 μg, 13.5 μg, 14 μg, 14.5 μg or 15 μg.

In one aspect of the present invention the immunogenic composition comprises between 0.1 μg and 150 μg of the PPV VP2 antigen, preferably between 0.5 μg and 30 μg of the immunogenic composition comprising PCV3, PPV and/or PRRSV antigens.

In one aspect, the immunogenic composition protects against a homologous and/or a heterologous challenge.

The PCV3 ORF2 protein may be produced by a baculovirus expression system in cultured insect cells. The method may include inactivating the baculovirus. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection. The inactivating may comprise heat treatment or use of a virus inactivating agent. The inactivating agent may comprise an aziridine compound, such as BEI.

The present disclosure also includes a recombinant vector comprising a polynucleotide sequence that encodes a polypeptide sequence that encodes a PCV3 ORF2 protein. The PCV3 ORF2 may be from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4). In another embodiment, the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity or sequence homology with SEQ ID NO: 4. The recombinant vector may be a baculovirus. In another embodiment, the recombinant vector may comprise at least 90% or at least 91%, or at least 92%, or at least 93%, or at least 94%, or at least 95%, or at least 96%, or at least 97%, or at least 98%, or at least 99%, or 100% sequence identity or sequence homology with SEQ ID NO:2.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the disclosure.

The porcine, pig or piglet to which there is administration can have antibodies against a PCV, such as PCV2 and/or PCV3, e.g., maternal antibodies.

These and other embodiments are disclosed or are obvious from and encompassed by, the following Detailed Description.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1 is the sequence of the PCV3 ORF2 nucleotide sequence in recombinant baculovirus BaculoG/PCV3 ORF2, SEQ ID NO:1.

FIG. 2A-1 to FIG. 2H-3 is the sequence of the recombinant baculovirus BaculoG/PCV3 ORF2, SEQ ID NO:2.

FIG. 3 shows the map of the recombinant baculovirus containing the PCV3 ORF2 gene under control of the baculovirus polyhedrin promoter (BaculoG/PCV3 ORF2 Clone 4B4-2E12 Pre-MSV p8).

FIG. 10A-C shows sequence information on the PCV3 PCR positive tissue homogenate used for challenge material (SEQ ID NOs: 3-5).

FIG. 21 shows a history plot of pre-MSV+1 production.

FIG. 22A shows cell count and FIG. 22B shows cell viability and size during infection with BaculoG/PCV3 ORF2.

Figure 23:
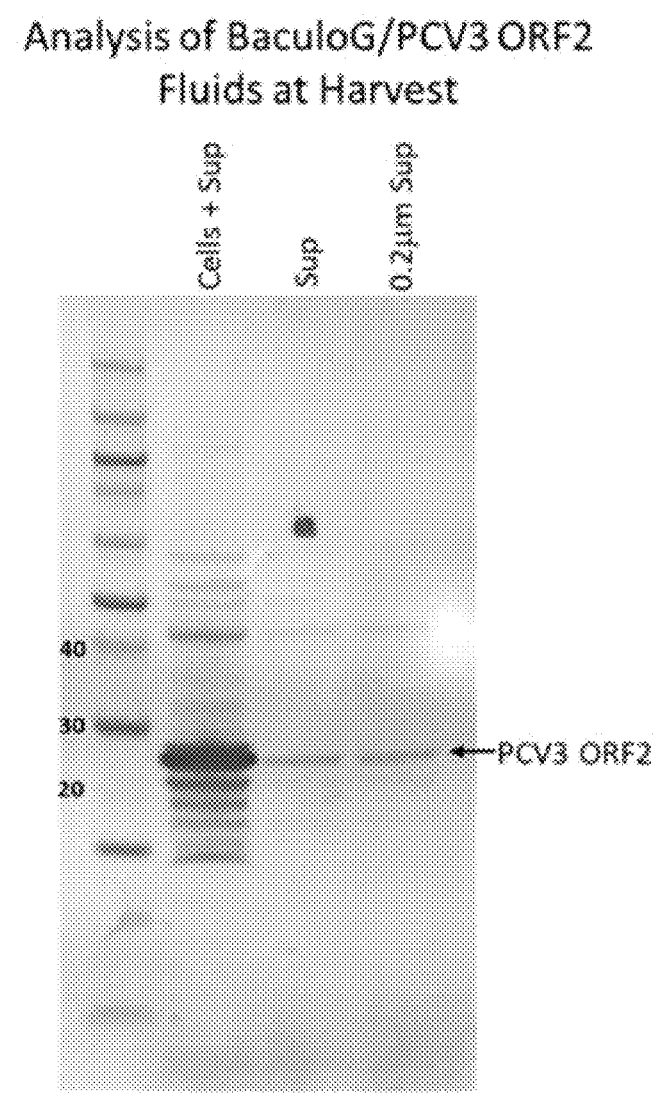

FIG. 23 shows an analysis of BaculoG/PCV3 ORF2 fluids at harvest.

FIG. 31A-C shows the alignment of the amino acid sequence of the PCV3 capsid with the capsid of porcine PCV2 and the capsid of beak and feather disease virus (BFDV). FIG. 31 discloses SEQ ID NOS 22-33, respectively, in order of appearance.

FIG. 32 discloses SEQ ID NOS 14 and 17-19, respectively, in order of appearance.

FIG. 33 discloses SEQ ID NOS 34-37, respectively, in order of appearance. FIG. 33 discloses SEQ ID NOS 14, 17-19, 11-12, and 34-37, respectively, in order of appearance.

FIG. 34 depicts the nucleotide and amino acid sequences of a PCV3 ORF2 mutant in the FG loop having mutations in the lysines and histidines and a PCV3 ORF2 mutant wherein the native stop codon for the PCV3 capsid protein was mutated and the C-terminus was extended to the next stop codon (SEQ ID NOs: 6-9).

FIG. 35 depicts the amino acid sequence of Mutated PCV3 ORF2 "FG-PC" (SEQ ID NO: 10).

DETAILED DESCRIPTION OF THE INVENTION

Figure 4:
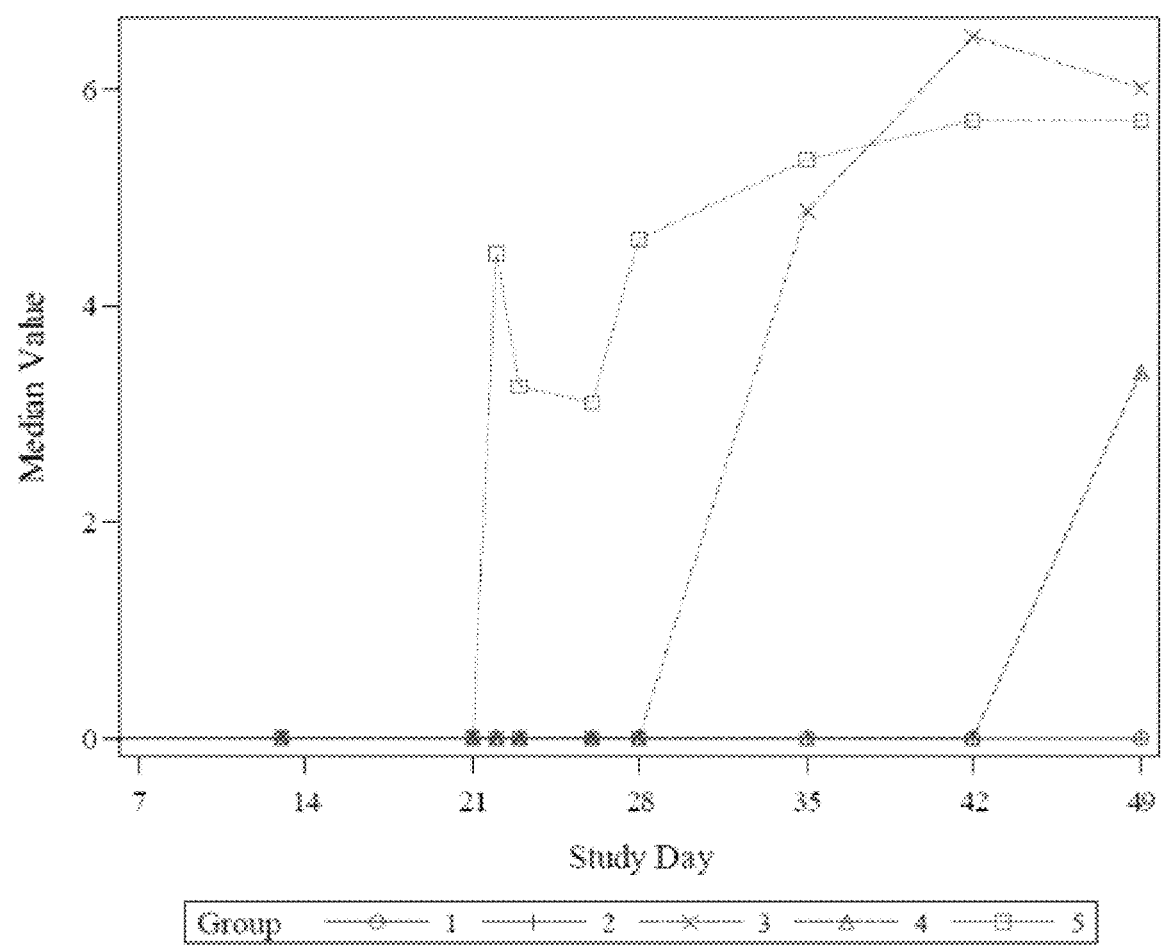
FIG. 4 shows group median log 10 PCV3 DNA genomic copies/mL in serum by study day; Groups 1-5.

The present disclosure relates to a PCV3 vaccine.

Any sequence of PCV3 is contemplated. See, eg., Phan, Tung Gia, et al. "Detection of a Novel *Circovirus* PCV3 in Pigs with Cardiac and Multi-Systemic Inflammation." *Virology Journal*, vol. 13, no. 1, 2016, p. 184, doi:10.1186/s12985-016-0642-z. Published Nov. 11, 2016 and Fux et al., "Full genome characterization of porcine *circovirus* type 3 isolates reveals the existence of two distinct groups of virus strains," Virology Journal (2018) 15:25, DOI 10.1186/s12985-018-0929-3 the disclosures of which are incorporated by reference.

The PCV3 ORF2 and the PCV3 genome sequences were derived from KT869077 (GenBank). Whole PCV3 genome in a plasmid was used and described in the Examples. ORF2 and whole genome were synthesized at Genscript.

Two additional constructs, re-circularized PCV3 genome derived by two different methods, were used in cell culture to rescue the virus.

The following sequences are presented in the sequence listing:

| SEQ ID NO: | Type | Description |
| --- | --- | --- |
| 1 | DNA | Polynucleotide encoding PCV3 ORF2 from baculovirus vector |
| 2 | DNA | Polynucleotide encoding PCV3 ORF2 in baculovirus vector |
| 3 | Protein | PCV3 ORF1 isolated from tissue |
| 4 | Protein | PCV3 ORF2 isolated from tissue |
| 5 | DNA | Polynucleotide encoding PCV3 ORF2 isolated from tissue |
| 6 | DNA | Polynucleotide encoding mutated PCV3 ORF2 "FG" |
| 7 | DNA | Polynucleotide encoding mutated PCV3 ORF2 "PC" |
| 8 | Protein | Mutated PCV3 ORF2 "FG" |

-continued

| SEQ ID NO: | Type | Description |
|---|---|---|
| 9 | Protein | Mutated PCV3 ORF2 "PC" |
| 10 | Protein | Mutated PCV3 ORF2 "FG-PC" |
| 11 | Protein | Portion of PCV3 ORF2 protein FG Loop |
| 12 | Protein | Replacement portion of PCV3 ORF2 protein FG Loop |
| 13 | Protein | PCV2 ORF2 (capsid) protein epitope |
| 14 | Protein | substitution in the FG loop of SEQ ID No. 1 |
| 15 | Protein | substitution in the FG loop of SEQ ID No. 1 |
| 16 | Protein | PCV2 ORF2 (capsid) protein epitope |
| 17 | Protein | Replacement portion of PCV3 ORF2 protein FG Loop |
| 18 | Protein | Replacement portion of PCV3 ORF2 protein FG Loop |
| 19 | Protein | Replacement portion of PCV3 ORF2 protein FG Loop |
| 20 | Protein | C-terminal extension of PCV3 ORF2 protein |
| 21 | Protein | C-terminal extension of PCV3 ORF2 protein |
| 22-33 | DNA | aa alignment of capsids of PCV3, PCV2 and BFVD |
| 34-37 | Protein | PCV3 ORF2 mutations in the lysines and histidines of the FG loop |

PCV3 ORF2 "FG" is an antigenic protein according to the present invention that comprises amino acid substitutions in the FG loop of the natural PCV3 ORF2 protein.

PCV3 ORF2 "PC" is an antigenic protein according to the present invention that comprises an amino acid extension at the C terminal end of the natural PCV3 ORF2 protein.

In a preferred aspect, the polypeptide of the present disclosure is a recombinant PCV3 ORF2 protein, such as a recombinant baculovirus expressed PCV3 ORF2 protein. The term "recombinant PCV3 ORF2 protein", as used herein, in particular refers to a protein molecule which is expressed from a recombinant DNA molecule, such as a polypeptide, which is produced by recombinant DNA techniques. An example of such techniques includes the case when DNA encoding the expressed protein is inserted into a suitable expression vector, preferably a baculovirus expression vector, which is in turn used to transfect, or in case of a baculovirus expression vector to infect, a host cell to produce the protein or polypeptide encoded by the DNA. The term "recombinant PCV3 ORF2 protein", as used herein, thus in particular refers to a protein molecule, which is expressed from a recombinant DNA molecule.

According to a particular example, the recombinant PCV3 ORF2 protein is produced by a method with the following steps: The gene for PCV3 ORF2 is cloned into a baculovirus transfer vector; the transfer vector is used to prepare recombinant baculovirus containing said gene by homologous recombination in insect cells; and the PCV3 ORF2 protein is then expressed in insect cells during infection with the recombinant baculovirus.

It is further understood that the term "recombinant PCV3 protein consisting of a sequence" in particular also concerns any cotranslational and/or posttranslational modification or modifications of the sequence affected by the cell in which the polypeptide is expressed. Thus, the term "recombinant PCV3 ORF2 protein consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

Preferably, the recombinant PCV3 ORF2 protein according to the disclosure is produced or obtainable by a baculovirus expression system, in particular in cultured insect cells.

In yet a further preferred aspect, the polypeptide of the present disclosure is a PCV3 ORF2 protein comprising or consisting of an amino acid sequence having at least 90%, preferably at least 92%, more preferably at least 94%, even more preferably at least 96%, still more preferably at least 98%, or in particular 100% sequence identity with the amino acid sequence of SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

The present invention also encompasses mutations of PCV3 proteins, such as but not limited to mutations of the PCV3 capsid protein. Despite the divergence of the capsid amino acid sequences between PCV2 and beak and feather disease virus (BFDV), the crystal structures are very similar despite their sequence divergence. Advantageously, the mutations of PCV3 are to stabilize virus-like particles (VLPs). The PCV3 capsid protein should self-assemble into a VLP, however, the level of expression of the PCV3 protein is significantly lower as compared to the PCV2 capsid protein. Specifically, only about 20% of the protein assembles into VLPs whereas the remaining 80% of the protein aggregates into an insoluble fraction.

In some embodiments, the variant protein of the present invention is capable of a higher yield of VLPs than the protein encoded by SEQ ID No. 1. It is understood that higher yield in particular—and for example—relates to higher molar yield. Alternatively expressed, the variant protein of the present invention is capable of a larger assembly of CAP (capsid (ORF2) protein) VLPs than the protein encoded by SEQ ID No. 1. Examples of higher yields include at least 5% higher yield, or at least 10% higher yield, or at least 15% higher yield, or at least 20% higher yield, or at least 25% higher yield, or at least 30% higher yield, or at least 35% higher yield, or at least 40% higher yield, or at least 50% higher yield. Thus, for example, if without a modification of the PCV3 ORF2 protein, by baculorvirus expression, there is 20% PCV3 soluble protein (VLP) and 80% PCV3 insoluble protein, e.g., by Western Blot, and by the modification there is, instead, 25%, or 30%, or 35%, or 40%, or 45%, or 50%, or 55%, or 60% or higher PCV3 soluble protein (VLP) (whereby there has been an increase of 5% or 10%, or 15%, or 20%, or 25%, or 30%, or 35%, or 40%, or 45%, etc of PCV3 soluble protein (VLP)), that represents a higher yield. Advantageously, from modifying the PCV3 ORF2 protein, the VLP yield (soluble PCV3 proteins) is at least 50% of the PCV3 proteins expressed by the recombinant baculovirus system.

Assays and techniques suitable for use in the present invention include those that have been used for the tracking or quantifying the assembly and disassembly of porcine *circovirus* capsid (ORF2) protein into virus-like particles (VLPs) and these include: enzyme-linked immunosorbent assay (ELISA), SDS/PAGE optionally with silver stain or coomassie stain, western blot or immunoblot, size exclusion chromatography (SEC), dynamic light scattering (DLS) or multi-angled light scattering (MALS), transmission electron microscopy (TEM), analytical ultracentrifugation, and fluorescence spectroscopic analysis (FSA) optionally coupled with high performance liquid chromatography (HPLC). Additional suitable techniques may also include: agarose gel retardation tests of protein-nucleic acid complexes, immune diffusion tests e.g. single radial immunodiffusion (SRID), nanoparticle tracking analysis (NTA), metabolic labelling and chemiluminescent enzyme-based assays. Each of these assays is well-known in the art and is described in, for example, Fang, Mingli et al. "Detection of the Assembly and Disassembly of PCV2b Virus-Like Particles Using Fluorescence Spectroscopy Analysis" *Intervirology* vol. 58, 2015, pp. 318-323; Thompson, Christine et al. "Analytical technologies for influenza virus-like particle candidate vaccines: challenges and emerging approaches" *Virology Journal* vol 10, 2013, p. 141; Steppert, Petra et al. "Quantification and characterization of virus-like particles by size-exclusion chromatography and nanoparticle tracking analysis" *Journal of Chromatography* A vol. 1487, 2017, pp. 89-99; Yadav, Shalini et al. "A facile quantitative assay for viral particle genesis reveals cooperativity in virion assembly and saturation of an antiviral protein" *Virology*, vol 429, No. 2, 2012, pp. 155-162; and Zeltins, Andris "Construction and Characterization of Virus-Like Particles: A Review" *Molecular Biotechnology* vol. 53, 2013, pp. 92-107, each of which is incorporated herein by reference in its entirety.

In one aspect, the variant protein of the present invention is capable of a higher yield of VLPs than the protein encoded by SEQ ID No. 1 as determinable by Western blot analysis. In other words, the variant protein of the present invention is capable of a larger assembly of CAP VLPs than the protein encoded by SEQ ID No. 1 as determinable by Western blot analysis.

In the various embodiments discussed herein wherein there is mutation or mutations of the PCV3 ORF2 capsid protein, e.g., to increase VLP yield. For example, in various embodiments there can be one, two, three, or four mutations in the FG loop. Exemplified and discussed herein are embodiments that may involve the SKKK (SEQ ID NO: 11) of the PCV3 ORF2 protein FG Loop replaced with QPFS (SEQ ID NO: 12) (e.g., a PCV2 ORF2 protein motif). In making the substitution(s), the skilled artisan can practice the invention by only replacing the S with Q or only replacing the first K with P or only replacing the second K with F or only replacing the third K with S, or any combinations of these replacements, e.g., S to Q and first K to P or S to Q and second K to F or S to Q and third K to S, or S to Q and first K to P and second K to F, or S to Q and first K to P and third K to S, etc. Likewise, in these embodiments, in addition to or as an alternative to the replacement(s) or mutation(s) in the FG loop, the skilled artisan can practice the invention by adding amino acids to the C-terminus of the PCV3 ORF2 protein. Without an extension or addition to the C-terminus, the PCV3 ORF2 protein may be, in the three dimensional structure, buried, versus exposed as are the C-terminus of other *circovirus* ORF2 or capsid proteins. In embodiments where there is extension or addition of the C-terminus of the PCV3 ORF2 protein, it may be advantageous to extend or add to the C-terminus of the PCV3 ORF2 protein with a motif from another *circovirus*, such as, for example, PCV2. Thus, for instance, one skilled in the art can extend or add to the C-terminus of the PCV3 ORF2 protein with amino acids found at the C-terminus of a PCV2 ORF2 protein or capsid protein, such as amino acids 215-234 or 215-233 of a PCV2 ORF2 protein or capsid protein. The skilled artisan can extend or add to the PCV3 ORF2 protein or capsid protein with epitope(s) of a PCV2 ORF2 protein or capsid protein. In this regard, mention is made of Trible et al., "Antibody Recognition of Porcine *Circovirus* Type 2 Capsid Protein Epitopes after Vaccination, Infection and Disease, Clinical and Vaccine Immunology 18(5): 749-757 (2011) doi:10.1128/CVI.00418-10 (incorporated herein by reference). In PCV2 ORF2 (capsid) protein immunoreactive regions are reported between residues 47 and 85, 165 and 200, and 200 and 233. Antibody reactive regions of PCV2 ORF2 (capsid) protein are reported as between amino acids 23 and 43, 71 and 85, 117 and 131, and 171 and 202. The PCV2 ORF2 (capsid) protein region of amino acids 117 to 131 is reported as a dominant antibody recognition region, and amino acids 156 to 162, 175 to 192, 195 to 202 and 228 to 223 are reported as associated with antibody recognition. Another PCV2 ORF2 (capsid) protein epitope is 169-STIDYFQPNNKR (SEQ ID NO: 13), e.g., amino acids 169-180 (wherein Y-173, F-174, Q-175, and K-179 amino acid residues may contribute to antibody recognition). Other PCV2 ORF2 (capsid) protein epitopes can be amino acids 43-233, 43-135, 43-160, 91-160, 43-180, 160-233, 135-233 and 91-233, as well as amino acids 169-188. Any of these, or any combination of these PCV2 ORF2 epitope(s) can be the C-terminus extension or addition to the PCV3 ORF2 (capsid) protein. In this regard, it is mentioned that the C-terminus extension of PCV3 ORF2 can be up to about 200 amino acids, or up to about 190 amino acids, or up to about 185 amino acids, or up to about 180 amino acids, or up to about 175 amino acids, or up to about 170 amino acids or up to about 165 amino acids, or up to about 160 amino acids or up to about 155 amino acids, or up to about 150 amino acids, or up to about 145 amino acids, or up to about 140 amino acids, or up to about 135 amino acids, or up to about 130 amino acids, or up to about 125 amino acids, or up to about 120 amino acids, or up to about 115 amino acids, or up to about 110 amino acids, or up to about 105 amino acids, or up to about 100 amino acids, up to about 90 amino acids, or up to about 80 amino acids or up to about 70 amino acids, or up to about 60 amino acids, or up to about 50 amino acids, or up to about 40 amino acids, or up to about 30 amino acids, in length; for instance, from 1-50 amino acids or 10-50 amino acids or 10-40 amino acids or 20 to 40 amino acids or about 30 amino acids in length.

In embodiments where a composition contains a PCV3 ORF2 (capsid) protein of the invention, e.g., such a protein that has been mutated, e.g., wherein the mutation includes addition or extension of the C-terminus, e.g., wherein the addition or extension of the C-terminus comprises epitope(s) of PCV2 ORF2 (capsid) protein, and the composition also includes a PCV2 ORF2 (capsid) protein (e.g., for a one-shot administration against both PCV2 and PCV3 or indications or symptoms or conditions thereof, e.g., each from baculovirus expression, e.g., alone or with one or more antigen of a porcine pathogen, such as those antigen(s) or porcine pathogen(s) disclosed throughout this disclosure), it may be advantageous that the PCV2 ORF2 (capsid) protein epitope(s) be of a clade that is the same as or different than that of the PCV2 ORF2 (capsid) protein included in the composition. For example, if the PCV2 ORF2 (capsid) protein component is from PCV2a strains (as Ingelvac CircoFlex may be based upon), it may be advantageous for the addition or extension on the PCV3 ORF2 capsid protein (C-terminus) to be from a different clade, e.g., a PCV2b, PCV2c, or PCVd-mPCV2b genotype. With respect to PCV2 genotypes or strains or clade, mention is made of Franzo et al., "Revisiting the taxonomical classification of Porcine *Circovirus* type w (PCV2): still a real challenge," Virol J 12: 131 (2015) doi: 10.1186/s12985-015-0361-x (incorporated herein by reference). It may be advantageous that the PCV3 ORF2 capsid protein C-terminus addition or extension be of the same clade, strain or genotype as that of the PCV2 ORF2 capsid protein component of the composition, or a different clade, strain or genotype, but is an eptipe of a PCV2 ORF2 capsid protein that provides an immunological response against one or more of the PCV2 clades, strains or genotypes. With respect to the foregoing, and more generally, the mutated PCV3 ORF2 capsid proteins of the invention discussed throughout this disclosure, the invention comprehends nucleic acid molecules encoding such mutated PCV3 ORF2 capsid proteins, vectors, such as baculovirus vectors (see EP 2 460 821 A2, incorporated herein by reference, along with the documents cited therein as the methods and materials therein for expressing PCV2 ORF2 capsid protein via a baculovirus expression system can be employed in the practice of the present invention to express PCV3 ORF2 capsid protein, including such mutated proteins as herein disclosed, as well as a PCV2 ORF2 capsid protein, if desired to include such in a composition of the invention), containing such nucleic acid molecules, and methods for producing or expressing such mutated PCV3 ORF2 capsid proteins of the invention, such as by infecting or transfecting relevant cells with the vector (e.g., if the vector be baculovirus, a relevant cell can be an insect or Sf cell or Sf+cell; see EP 2 460 821 A2, incorporated herein by reference, along with the documents cited therein). It is advantageous to recover or isolate the protein after expression or production, e.g., separating solids and retaining liquid or supernatant that contains soluble protein (e.g., VLPs). Compositions as discussed in this paragraph as well as throughout this disclosure can contain mutated PCV3 ORF2 capsid protein (and optionally additionally PCV2 ORF2 capsid protein and/or one or more additional antigen of a porcine pathogen), in amounts as discussed throughout this disclosure, and can be administered in regimen(s) as discussed throughout this disclosure, such as in a one-shot, or single dose, administration, and can be so administered to pigs or piglets as discussed throughout this disclosure.

In the context of the invention, the protein of the present invention as the antigen in the composition, such as the immunological composition, prevents or treats a PCV3 infection-associated disease or condition in a subject by for example inducing, stimulating or enhancing the immune response against PCV3.

Previous studies have shown that expressing the full-length PCV3 cap gene and NLS domains presenting within the N-terminal arginine rich motif (ARM) may cause misfolding of the protein and induce formation of circular virus complexes of 10-12 nm (Sarker et al. *Nat Commun.* 2016 Oct. 4; 70:13014). Wang et al. (*AMB Expr* 10, 3 (2020) https://doi.org/10.1186/s13568-019-0940-0) reported the ability of PCV3 VLPs to self-assemble which were successfully expressed in *E. coli* and applied in the development of an ELISA for testing the specific antibodies of clinical pig serum. Specifically, to achieve high-level expression of recombinant PCV3 Cap in *E. coli*, the gene of wild-type entire Cap (wt-eCap) was amplified from clinical samples, and three optimized entire Cap (opti-eCap) and one optimized Cap deleted nuclear location signal (NLS) (opti-dCap) gene fragments encoding the same amino acid sequence with wt-eCap were synthesized based on the codon bias of *E. coli*. Unlike the present invention, regions beside the NLS of the PCV3 capsid have not been targeted with respect to VLP assembly and/or stability. Furthermore, removal of the NLS does not necessarily result in improved VLP assembly. However, embodiments of the invention can include removal or alteration of the PCV3 ORF2 capsid protein NLS, e.g., in addition to one or more of the FG loop mutations and/or C-terminus extension(s) discussed herein.

In an advantageous embodiment, the present invention encompasses mutating regions encoding positively charged amino acids in PCV proteins, such as but not limited to a PCV3 capsid protein. In particular, PCV3 capsid contains large amounts of positive charge in the FG loop, which sits at the 5-fold interface of the PCV3 capsid. The large amount of positive charge in this region may result in repulsive forces without the presence of nucleic acid, as would be expected of VLPs. In one embodiment of the invention, the positively charged amino acids are mutated to neutral and/or negative charged amino acids. In an advantageous embodiment, the lysines and histidine in this loop are mutated to the amino acids from PCV2 capsid (SEQ ID NO: 6).

In an embodiment, the invention provides an engineered PCV3 ORF2 protein comprising reduced amounts of positive charged amino acids as compared to a non-engineered PCV3 ORF2 protein. The non-engineered protein can be a wild-type or naturally occurring PCV3 ORF2 protein or can be an ORF2 protein already modified for another purpose for which it is desired to improve capsid formation activity, such as improved self-assembly in the presence or absence of a packageable polynucleotide.

In an embodiment, one or more positively charged amino acids are substituted, such as one or more lysine, arginine, or histidine, or combination thereof. In an embodiment, two or more positively charged amino acids are substituted. In an embodiment, three or more positively charged amino acids are substituted. In certain embodiments, charge associated with a region of the ORF2 protein, such as but not limited to the FG loop, is made more negative by substituting in one or more negatively charged amino acids. In certain embodiments, positively charged amino acids are substituted by amino acids that are less positively charged, and/or non-positively charged amino acids are substituted by amino acids more negatively charged. That is, the charge of a region of ORF2 can be made by altered by removing positive charge, adding negative charge, or both.

In an advantageous embodiment, the present invention encompasses adding additional amino acids to PCV proteins, such as but not limited to a PCV3 capsid protein. The short hydrophobic nature of the PCV3 capsid C-terminus would lead to the C-terminus being buried in the capsid and could lead to VLP instability without the presence of nucleic acid. In contrast, the C-terminus of PCV2 and BFDV capsid proteins project out away from the capsid. In one embodiment, the C-terminus of the PCV3 capsid is extended by about 1 to 50 amino acids, about 10 to 40, amino acids, or about 20 to 30 amino acids. In another embodiment, the C-terminus of the PCV3 capsid is extended by about 20, about 21, about 22, about 23, about 24, about 25, about 26, about 27, about 28, about 29, about 30, about 31, about 32, about 33, about 34, about 35, about 36, about 37, about 38, about 39 or about 40 amino acids. In an advantageous embodiment, the C-terminus of the PCV3 capsid protein is extended by mutating the stop codon. In a particularly advantageous embodiment, the native stop codon for the PCV3 capsid protein is mutated and the C-terminus was extended to the next stop codon in the virus sequence (SEQ ID NO: 7). In another embodiment, the C-termimus of the PCV capsid may be extended and/or swapped out with the C-terminus of other porcine circoviruses. The C-termimus of the PCV3 capsid protein may be extended about 50 to about 200 amino acids, about 60 to about 190 amino acids, about 70 to about 180 amino acids, about 80 to about 170 amino acids, about 90 to about 160 amino acids or about 100 to about 150 amino acids.

In certain embodiments, C-terminal extension comprises addition of amino acids at the C-terminus of a PCV3 capsid, for example by mutation of a stop codon. A stop codon can be mutated by deletion, substitution or insertion. In certain embodiments, C-terminal extension comprise insertion of amino acids near the C-terminus, including but not limited to insertion of amino acids one residue from the C-terminus, or two residues from the C-terminus, or three residues, or four residues, or five residues, or six, or seven, or eight, or more residues upstream form the C-terminus. In one embodiment, the residues may be any set of negatively charged amin acids.

It should be understood that the proteins of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

In some embodiments, the substitution introduces a conservative change, which replaces the amino acid with another amino acid of similar chemical structure, similar chemical properties or similar side-chain volume. The amino acids introduced may have similar polarity, hydrophilicity or hydrophobicity to the amino acids they replace. Conservative amino acid changes are well known in the art. Where amino acids have similar polarity, this can also be determined by reference to the hydropathy scale for amino acid side chains.

Conservative amino acid changes may also be determined by reference to the Point Accepted Mutation (PAM) or BLOcks Substitution Matrix (BLOSUM) family of scoring matrices for conservation of amino acid sequence. Thus, conservative amino acid changes may be members of an equivalence group, being a set of amino acids having mutually positive scores in the similarity representation of the scoring matrix selected for use in an alignment of the reference and mutant polypeptide chains.

It is to be understood non-polar amino acids include amino acids with aliphatic side chains and amino acids with aromatic side chains. The amino acid proline is classified as non-polar but it also has the property of being rigid and can cause changes in secondary structure. For example prolines are often found at the end of helices. Also, depending on the specific context of the side chain of a given amino acid residue, for example the amino acid tyrosine, generally classed as non-polar due to its aromatic ring, may have analogous functional effects to a polar amino acid residue such as threonine via its hydroxyl group. Thus, tyrosine may be considered to be both a non-polar and a polar amino acid for the purposes of the invention. Furthermore, amino acids which are described as polar or hydrophilic may be uncharged or charged, and may also be basic or acidic. The amino acid histidine is well known to have a pKa value near 7, so that at neutral pH depending upon the protein environment, it may or not be protonated on its side chain, and thus may or not carry a charge. Thus, histidine may be considered to be both a polar charged or a polar uncharged amino acid residue for the purposes of the invention.

The mutations discussed herein are generally introduced into the protein by using methods known in the art, such as site directed mutagenesis of the protein, PCR and gene shuffling methods or by the use of multiple mutagenic oligonucleotides in cycles of site-directed mutagenesis. Thus, the mutations may be introduced in a directed or random manner. The mutagenesis method thus produces one or more polynucleotides encoding one or more different mutants.

The development of a recombinant baculovirus containing the Porcine *Circovirus* 3 ORF2 gene under control of the baculovirus polyhedrin promoter (BaculoG/PCV3 ORF2 Clone 4B4-2E12 Pre-MSV p8; lot no. 3624-039) is described in Example 1. In some embodiments, the use of such a recombinant baculovirus described in Example 1 in a vaccine may encompass killed and/or inactivated versions of the recombinant virus. Alternatively, in some vaccines, a recombinant virus, for example similar to that shown in Example 1, may be used as a live, modified virus.

Figure 3:
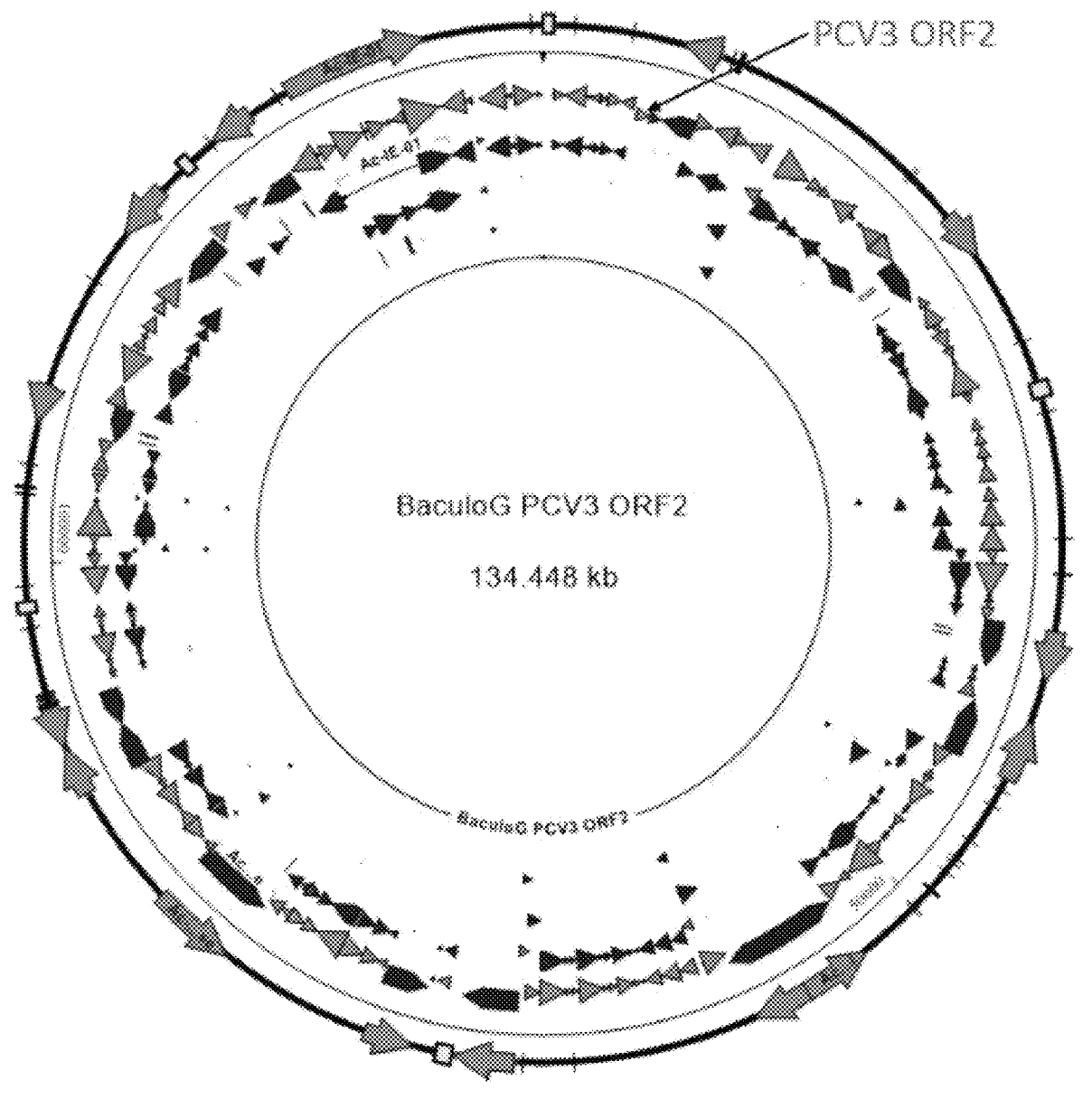

FIGS. 2A-1 to 2H-3 provides the sequence of the recombinant baculovirus BaculoG/PCV3 ORF2, SEQ ID NO:2. The backbone sequence annotations are from Genbank accession NC_001623. One of skill in the art will appreciate that minor mutations in the backbone from construct to construct is to be expected given the complexity of the DNA sequence. A map of the construct is shown in FIG. 3. The baculovirus expression vector, BaculoG/PCV3 ORF2, may be used to develop PCV3 vaccines and/or controls. Preferred adjuvants for a given vaccine and/or control may differ based on the type of expression vector used, for example, live, live modified, inactivated, or killed. Adjuvant effectiveness may vary based on the status of the vector (e.g., virus) used. An amount of adjuvant used in a vaccine may be predetermined, for example, a predetermined percentage may be selected to be within a given range (e.g., weight percentage and/or volume percentage in the vaccine) for a given adjuvant and/or combination of adjuvants. In some instances, for example, when using live vaccines multiple adjuvants may be used. For example, in some embodiments, a combination of adjuvants such as Carbopol® and Montanide ISA 207VG may be used. Alternatively, a vaccine that includes a live expression vector, such as BaculoG/PCV3 ORF2, may be adjuvanted with ISA 207VG and/or Carbopol®. For example, the adjuvant may be present in the vaccine at a predetermined concentration. For example, a vaccine may include a concentration of 50% ISA 207VG by weight of the vaccine. Alternatively, another vaccine including live BaculoG/PCV3 ORF2 may include an adjuvant, such as Carbopol® at 20% by volume of the vaccine.

Vaccines that include killed expression vectors, such as viruses, may include Carbopol® as an adjuvant. For example, a vaccine that includes killed BaculoG/PCV3 ORF2 may in some embodiments include Carbopol® as the effective adjuvant. For example, such a vaccine may include a predetermined amount of adjuvant, for example a predetermined weight or volume percentage of the vaccine. In particular, a vaccine that includes killed BaculoG/PCV3 ORF2 may include Carbopol® at 20% by volume of the vaccine. Alternately, a vaccine may include killed BaculoG/PCV3 ORF2 and adjuvant at about 50% of the weight of the vaccine solution. For example, a vaccine that includes killed BaculoG/PCV3 ORF2 may include ISA 207VG as an adjuvant at a predetermined weight percentage of the vaccine, such as fifty percent.

For example, the Baculovirus expression vector BaculoG/PCV3 ORF2, was used to develop two PCV3 vaccines and a control as outlined herein:

Development of BaculoG/PCV3 ORF2, P9; live, adjuvanted with 50% ISA 207VG vaccine (methods used to develop the vaccine are disclosed in Example 3.)

Development of BaculoG/PCV3 ORF2, P9; live, adjuvanted with 20% Carbopol® vaccine (methods used to develop the vaccine are disclosed in Example 4.)

Development of the control—BaculoG/no insert, P4; live, adjuvanted with 20% Carbopol® vaccine (methods used to develop the vaccine are disclosed in Example 5.)

Development of BaculoG/PCV3 ORF2, P9; killed, adjuvanted with 50% ISA 207VG vaccine (methods used to develop the vaccine are disclosed in Example 3.)

Development of BaculoG/PCV3 ORF2, P9; killed, adjuvanted with 20% Carbopol® vaccine (methods used to develop the vaccine are disclosed in Example 4.)

Development of the control—BaculoG/no insert, P4; killed, adjuvanted with 20% Carbopol® vaccine (methods used to develop the vaccine are disclosed in Example 5.)

Efficacy of the vaccines may be tested using PCV3 whole virus and PCR positive tissue (low count). Homogenates from the tissues may be generated and sequenced. The homogenates and/or the whole virus may be used to challenge vaccinated animals.

For example, in order to test the efficacy of the vaccines, PCV3 whole virus and PCR positive tissue (low count) were provided. Homogenates from the tissues were generated and sequenced. The homogenates and whole virus were used to challenge vaccinated animals.

The PCV3 recombinant ORF2 protein subunit vaccine and/or an immunogenic composition of the instant disclosure may be produced using a method of WO 2006/072065, Example 1, modified to express PCV3 ORF2 protein (rather than PCV2 ORF2 protein).

The PCV3 ORF2 coding sequence may be amplified by polymerase chain reaction (PCR) from PCV3 genomic DNA and/or a synthetically synthesized PCV3 ORF2. Restriction sites may be used to insert the desired coding sequence into a transfer vector. For example, in some embodiments, an amplified PCV3 ORF2 coding sequence may include a Kozak consensus sequence (see, e.g., Kozak M (October 1987) Nucleic Acids Res. 15 (20): 8125-8148) directly 5' of the start codon along with flanking restriction enzyme sites.

In some embodiments, the amplified PCV3 ORF2 coding sequence may be subcloned into a baculovirus transfer vector utilizing the flanking restriction sites to generate the desired transfer vector. For example, the amplified PCV3 ORF2 coding sequence may be subcloned into a baculovirus transfer vector utilizing the flanking restriction sites to generate transfer vectors such as pVL1392-PCV3 ORF2 or pVL1393-PCV3 ORF2. Other transfer vectors commonly known in the art may be used. Recombinant baculovirus may be generated by co-transfection of insect cells with a transfer vector and baculovirus DNA. Baculovirus DNA used may include linearized and/or circular baculovirus DNA. For example, in an embodiment, recombinant baculovirus may be generated by co-transfection of Sf9 (*Spodoptera frugiperda*) insect cells with a transfer vector (e.g., such as pVL1392-PCV3 ORF2 and/or pVL1393-PCV3) and linearized BaculoGold™ baculovirus DNA. The linearized baculovirus DNA may be derived from *Autographa californica* nuclear polyhedrosis virus (AcNPV) and may contain a lethal deletion in the polyhedrin locus, therefore, rescue of viable baculovirus may be generated upon co-transfection with a transfer vector, such as pVL1392-PCV3 ORF2 and/or pVL1393-PCV3 ORF2. The resulting recombinant baculovirus may include a PCV3 ORF2 coding sequence under control of the baculovirus polyhedrin promoter. The recombinant baculovirus may be amplified on Sf9 insect cells and subsequently purified by limiting dilution cloning on Sf9 insect cells. In some embodiments, a full length circular baculovirus DNA such as Bac-to-Bac may be used. For example, Bac-to-Bac may uses transposon-mediated recombination to insert a gene of interest into a polyhedron locus. Other methods known in the art may also be used. In some embodiments, a method may be chosen based on the potential stability of the method during commercialization. For example, baculoviruses that confer increased stability in the vaccine may be selected.

In some embodiments, after seeding flasks with of a master cell culture, the flasks may be incubated at a predetermined temperature and for a specific time frame. For example, a culture may be incubated at 27° C. for four hours. Each flask may then be seeded with a recombinant baculovirus containing the PCV3 ORF2 gene. For example, a pVL1392 plasmid containing a PCV3 ORF2 gene can be co-transfected with BaculoGold® (BD Biosciences Pharmingen) baculovirus DNA into Sf+insect cells (Protein Sciences, Meriden, Conn.) to generate a recombinant baculovirus containing a PCV3 ORF2 gene. The recombinant baculovirus containing the PCV3 ORF2 gene may be plaque-purified and Master Seed Virus (MSV) propagated on the SF+cell line, aliquotted, and stored at −70° C. The MSV may be positively identified as PCV3 ORF2 baculovirus by PCR-RFLP using baculovirus specific primers. Insect cells infected with PCV3 ORF2 baculovirus to generate MSV or Working Seed Virus may express PCV3 ORF2 antigen as detected by polyclonal serum or monoclonal antibodies in an indirect fluorescent antibody assay. Additionally, the identity of the PCV3 ORF2 baculovirus may be confirmed by N-terminal amino acid sequencing. The PCV3 ORF2 baculovirus MSV is also tested for purity in accordance with 9 C.F.R. Sections 113.27 (c), 113.28, and 113.55. Each recombinant baculovirus seeded into the spinner flasks may have varying multiplicities of infection (MOIs).

After being seeded with the baculovirus, the flasks may be incubated at 27±2° C. for 7 days and may also be agitated at 100 rpm during that time. The flasks may use ventilated caps to allow for air flow. Samples from each flask may be taken every 24 hours for the next 7 days. After extraction, each sample may be centrifuged, and both the pellet and the supernatant are separated and then microfiltered through a 0.45-1.0 m pore size membrane.

The amount of ORF3 in the resulting samples may then be quantified via an ELISA assay. The ELISA assay may be conducted with an anti-PCV3 antibody diluted to 1:6000 in 0.05M Carbonate buffer (pH 9.6). 100 µL of the antibody may then be placed in the wells of the microtiter plate, sealed, and incubated overnight at 37° C. The plate is then washed three times with a wash solution which comprised 0.5 mL of Tween 20 (Sigma, St. Louis, Mo.), 100 mL of 10×D-PBS (Gibco Invitrogen, Carlsbad, Calif.) and 899.5 mL of distilled water. Subsequently, 250 µL of a blocking solution (5g Carnation Non-fat dry milk (Nestle, Glendale, CALIF.) in 10 mL of D-PBS QS to 100 mL with distilled water) is added to each of the wells. The next step is to wash the test plate and then add pre-diluted antigen. The pre-diluted antigen is produced by adding 200 µL of diluent solution (0.5 mL Tween 20 in 999.5 mL D-PBS) to each of the wells on a dilution plate. The sample is then diluted at a 1:240 ratio and a 1:480 ratio, and 100 µL of each of these diluted samples is then added to one of the top wells on the dilution plate (i.e. one top well received 100 µL of the 1:240 dilution and the other received 100 µL of the 1:480 dilution). Serial dilutions may then be done for the remainder of the plate by removing 100 µL from each successive well and transferring it to the next well on the plate. Each well is mixed prior to doing the next transfer. The test plate washing includes washing the plate three times with the wash buffer. The plate is then sealed and incubated for an hour at 37° C. before being washed three more times with the wash buffer. The detection antibody used is an antibody to PCV ORF2. It is diluted to 1 to 300 in diluent solution, and 100 µL of the diluted detection antibody was then added to the wells. The plate is then sealed and incubated for an hour at 37° C. before being washed three times with the wash buffer. Conjugate diluent is then prepared by adding normal rabbit serum (Jackson Immunoresearch, West Grove, Pa.) to the diluent solution to 1% concentration.

Conjugate antibody Goat anti-mouse (H+1)-HRP (Jackson Immunoresearch) is diluted in the conjugate diluent to 1:10,000. 100 µL of the diluted conjugate antibody is then added to each of the wells. The plate is then sealed and incubated for 45 minutes at 37° C. before being washed three times with the wash buffer. 100 µL of substrate (TMB Peroxidase Substrate, Kirkgaard and Perry Laboratories (KPL), Gaithersburg, Md.), mixed with an equal volume of Peroxidase Substrate B (KPL) is added to each of the wells. The plate is incubated at room temperature for 15 minutes. 100 µL of IN HCL solution is then added to all of the wells to stop the reaction. The plate is then run through an ELISA reader.

Advantageous insect cells can be cultured, and the PCV3 ORF2 protein produced, under serum-free conditions; such as the serum-free insect cells of U.S. Pat. No. 6,103,526 (expresSF+cell line).

The adjuvants, cell culture supernatants, preservatives, stabilizing agents, viral vectors, immunomodulatory agents and dosages disclosed in U.S. Pat. Nos. 9,610,345 and 9,669,087 are contemplated, both incorporated herein by reference.

The immunogenic composition as used herein is effective for inducing an immune response against PCV3 and preventing, reducing and/or lessening the severity of the clinical symptoms associated with PCV3 infection. The composition generally comprises at least one PCV3 antigen.

PCV3 in pigs may exhibit a wide variety of symptoms and in many cases individual animals exhibit only a small subset of the potential symptoms. Symptoms associated with the presence of PCV3 include viremia, virus shedding, for example, the presence of viral nucleic acids in emissions from the body such as colostrum, milk, feces, saliva, and eye swabs. For example, Jiang et al., "Induction of porcine dermatitis and nephropathy syndrome in piglets by infection with porcine *circovirus* type 3", J. Virol. doi:10.1128/JVI.02045-18, the disclosure of which is incorporated by reference, relates to inoculating piglets with PCV3 and observing resultant clinical signs. The present disclosure relates to treating and/or reducing symptoms of porcine dermatitis and nephropathy syndrome (PDNS)—like disease, lymphocytic dysplasia and necrosis caused by PCV3 by administering a composition of the disclosure.

The mere presence of antibodies, especially in young pigs or piglets, e.g., pigs or piglets of less than 15 weeks of age, such as less than 10 weeks of age, for instance, less than 6 weeks of age, for instance, less than 3, 2 or 1 week of age or at birth, may not be indicative of exposure to PCV3 and/or disease. Pigs or piglets that have had exposure and/or have antibodies against PCV3 can still enjoy benefits of compositions of the disclosure, e.g., by reducing or preventing or lessening severity of symptoms.

Thus, the compositions of the disclosure can be used in methods for eliciting an immune response, which can be a protective immune response, as well as methods for reducing or preventing or lessening severity of symptoms and, the dosages, formulations and the like for reducing or preventing or lessening severity of symptoms are as for methods for eliciting an immune response. Thus, herein where methods are described as to eliciting an immune response, these methods can be practiced for reducing or preventing or lessening severity of symptoms; and compositions described herein, which are useful for eliciting an immune response, are likewise useful for and compositions for reducing or preventing or lessening severity of symptoms (as well as being compositions for eliciting an immune response).

Unless defined otherwise, all technical and scientific terms used herein have the same meanings as commonly understood by one of ordinary skill in the art to which this disclosure belongs. The term "immunogenic composition" as used herein refers to any pharmaceutical composition containing a PCV3 antigen, which composition can be used to prevent or treat a PCV3 infection-associated disease or condition in a subject. A preferred immunogenic composition can induce, stimulate or enhance the immune response against PCV3. The term thus encompasses both subunit immunogenic compositions, as described below, as well as compositions containing whole killed, or attenuated and/or inactivated PCV3.

The term "subunit immunogenic composition" as used herein refers to a composition containing at least one immunogenic polypeptide or antigen, but not all antigens, derived from or homologous to an antigen from PCV3. Such a composition is substantially free of intact PCV3. Thus, a "subunit immunogenic composition" is prepared from at least partially purified or fractionated (preferably substantially purified) immunogenic polypeptides from PCV3, or recombinant analogs thereof. A subunit immunogenic composition can comprise the subunit antigen or antigens of interest substantially free of other antigens or polypeptides from PCV3, or in fractionated form. A preferred immunogenic subunit composition comprises the PCV3 ORF2 protein as described below.

An "immunological or immune response" to a composition or vaccine is the development in the host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in number or severity of, or lack of one or more of the symptoms associated with PCV3 infections as described above.

The terms "immunogenic" protein or polypeptide or "antigen" as used herein refer to an amino acid sequence which elicits an immunological response as described above. An "immunogenic" protein or polypeptide, as used herein, includes the full-length sequence of any PCV3 proteins, analogs thereof, or immunogenic fragments thereof. The term "immunogenic fragment" refers to a fragment of a protein, which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

In a preferred embodiment of the present disclosure, an immunogenic composition that induces an immune response and, more preferably, confers protective immunity against the clinical signs of PCV3 infection, is provided. The composition most preferably comprises the polypeptide, or a fragment thereof, expressed by ORF2 of PCV3, as the antigenic component of the composition. PCV3 ORF2 DNA and protein, used herein for the preparation of the compositions and within the processes provided herein is a highly conserved domain within PCV3 isolates and thereby, any PCV3 ORF2 would be effective as the source of the PCV3 ORF2 DNA and/or polypeptide as used herein. A preferred PCV3 ORF2 protein translated from the nucleotide sequence of SEQ ID NO. 1. A preferred PCV3 ORF2 polypeptide is provided herein, but it is understood by those of skill in the art that this sequence could vary by as much as 6-10% in sequence homology and still retain the antigenic characteristics that render it useful in immunogenic compositions. Moreover, the antigenic characteristic of a modified antigen is still retained, when the modified antigen confers at least 30%, at least 40%, at least 50%, at least 60%, at least 70%, at least 80%, at least 90% or at least 100% of the protective immunity as compared to the PCV3 ORF2 protein, encoded by the polynucleotide sequence of SEQ ID NO: 1. An "immunogenic composition" as used herein, means a PCV3 ORF2 protein which elicits an "immunological response" in the host of a cellular and/or antibody-mediated immune response to PCV3 ORF2 protein. Preferably, this immunogenic composition is capable of eliciting or enhancing an immune response against PCV3 thereby conferring protective immunity against PCV3 infection and a reduction in the incidence of, severity of, or prevention of one or more, and preferably all of the clinical signs associated therewith.

In some forms, immunogenic portions of PCV3 ORF2 protein are used as the antigenic component in the composition. The term "immunogenic portion" as used herein refers to truncated and/or substituted forms, or fragments of PCV3 ORF2 protein and/or polynucleotide, respectively. Preferably, such truncated and/or substituted forms, or fragments will comprise at least 6 contiguous amino acids from the full-length ORF2 polypeptide. More preferably, the truncated or substituted forms, or fragments will have at least 10, more preferably at least 15, and still more preferably at least 19 contiguous amino acids from the full-length ORF2 polypeptide. It is further understood that such sequences may be a part of larger fragments or truncated forms.

A further preferred PCV3 ORF2 polypeptide provided herein is encoded by the nucleotide sequence of SEQ ID NO: 1. However, it is understood by those of skill in the art that this sequence could vary by as much as 6-20% in sequence homology and still retain the antigenic characteristics that render it useful in immunogenic compositions. In some forms, a truncated or substituted form, or fragment of this PVC3 ORF2 polypeptide is used as the antigenic component in the composition. Preferably, such truncated or substituted forms, or fragments will comprise at least 18 contiguous nucleotides from the full-length ORF2 nucleotide sequence. More preferably, the truncated or substituted forms, or fragments, will have at least 30, more preferably at least 45, and still more preferably at least 57 contiguous nucleotides of the full-length ORF2 nucleotide sequence, e.g. SEQ ID NO: 1.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5 or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, the immunogenic composition as used herein also refers to a composition that comprises PCV3 ORF2 protein, wherein said PCV3 ORF2 protein is anyone of those, described above.

According to a further aspect, PCV3 ORF2 protein is provided in the immunological composition at an antigen inclusion level effective for inducing the desired immune response, namely reducing the incidence of, lessening the severity of, or preventing one or more clinical signs resulting from PCV3 infection. Preferably, the PCV3 ORF2 protein inclusion level is at least 0.2 µg antigen/ml of the final immunogenic composition (g/ml), more preferably from about 0.2 to about 400 µg/ml, still more preferably from about 0.3 to about 200 µg/ml, even more preferably from about 0.35 to about 100 µg/ml, still more preferably from about 0.4 to about 50 µg/ml, still more preferably from about 0.45 to about 30 µg/ml, still more preferably from about 0.6 to about g/ml, even more preferably from about 0.75 to about 8 µg/ml, even more preferably from about 1.0 to about 6 µg/ml, still more preferably from about 1.3 to about 3.0 µg/ml, even more preferably from about 1.4 to about 2.5 µg/ml, even more preferably from about 1.5 to about 2.0 g/ml, and most preferably about 1.6 µg/ml.

According to a further aspect, the ORF2 antigen inclusion level is at least 0.2 µg PCV3 ORF2 protein as described above per dose of the final antigenic composition (g/dose), more preferably from about 0.2 to about 400 µg/dose, still more preferably from about 0.3 to about 200 µg/dose, even more preferably from about 0.35 to about 100 µg/dose, still more preferably from about 0.4 to about 50 µg/dose, still more preferably from about 0.45 to about 30 µg/dose, still more preferably from about 0.6 to about 15 µg/dose, even more preferably from about 0.75 to about 8 µg/dose, even more preferably from about 1.0 to about 6 µg/dose, still more preferably from about 1.3 to about 3.0 µg/dose, even more preferably from about 1.4 to about 2.5 µg/dose, even more preferably from about 1.5 to about 2.0 µg/dose, and most preferably about 1.6 µg/dose. In an embodiment, ORF2 antigen (e.g., PCV3 ORF2 protein) may be present in a dose of the final composition in a range from about 1.3 to about 3 ug. For example, the final antigenic composition may include about 1.6 ug of PCV3 ORF2 protein in a 1 mL dose.

The PCV3 ORF2 polypeptide used in the immunogenic composition in accordance with the present disclosure can be derived in any fashion including isolation and purification of PCV3 ORF2, standard protein synthesis, and recombinant methodology. Preferred methods for obtaining PCV3 ORF2 polypeptide are provided in U.S. patent application Ser. No. 11/034,797, the teachings and content of which are hereby incorporated by reference. Briefly, susceptible cells are infected with a recombinant viral vector containing PCV3 ORF2 DNA coding sequences, PCV3 ORF2 polypeptide is expressed by the recombinant virus, and the expressed PCV3 ORF2 polypeptide is recovered from the supernate by filtration and inactivated by any conventional method, preferably using binary ethylenimine, which is then neutralized to stop the inactivation process.

The immunogenic composition as used herein also refers to a composition that comprises i) any of the PCV3 ORF2 protein described above, preferably in concentrations described above, and ii) at least a portion of the viral vector expressing said PCV3 ORF2 protein, preferably of a recombinant baculovirus. Moreover, the immunogenic composition can comprise i) any of the PCV3 ORF2 proteins described above, preferably in concentrations described above, ii) at least a portion of the viral vector expressing said PCV3 ORF2 protein, preferably of a recombinant baculovirus, and iii) a portion of the cell culture supernatant.

The immunogenic composition as used herein also refers to a composition that comprises i) any of the PCV3 ORF2 proteins described above, preferably in concentrations described above, ii) at least a portion of the viral vector expressing said PCV3 ORF2 protein, preferably of a recombinant baculovirus, and iii) a portion of the cell culture; wherein about 90% of the components may have a size smaller than 1 m.

The immunogenic composition as used herein also refers to a composition that comprises i) any of the PCV3 ORF2 proteins described above, preferably in concentrations described above, ii) at least a portion of the viral vector expressing said PCV3 ORF2 protein, iii) a portion of the cell culture, iv) and inactivating agent to inactivate the recombinant viral vector preferably BEI, wherein about 90% of the components i) to iii) may have a size smaller than 1 m. Preferably, BEI is present in concentrations effective to inactivate the baculovirus. Effective concentrations are described above.

The immunogenic composition as used herein also refers to a composition that comprises i) any of the PCV3 ORF2 proteins described above, preferably in concentrations described above, ii) at least a portion of the viral vector expressing said PCV3 ORF2 protein, iii) a portion of the cell culture, iv) an inactivating agent to inactivate the recombinant viral vector preferably BEI, and v) an neutralization agent to stop the inactivation mediated by the inactivating agent, wherein about 90% of the components i) to iii) may have a size smaller than 1 m. Preferably, if the inactivating agent is BEI, said composition comprises sodium thiosulfate in equivalent amounts to BEI.

The polypeptide is incorporated into a composition that can be administered to an animal susceptible to PCV3 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV3 ORF2 protein as provided herewith, preferably in concentrations described above, which is mixed with an adjuvant, preferably Carbopol®, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminum hydroxide and aluminum phosphate, saponins e.g., Quil-A®, QS-21® STIMULON (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic® products, especially L121. See Hunter et al., The Theory and Practical Application of Adjuvants (Ed.Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid, which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol®; (BF Goodrich, Ohio, USA) are particularly appropriate. They are cross-linked with an allyl sucrose or with allyl pentaerythritol. Among them, there may be mentioned Carbopol® 974P, 934P and 971P. Most preferred is the use of Carbopol®, in particular the use of Carbopol® 971P, preferably in amounts of about 500 µg to about 5 mg per dose, even more preferred in an amount of about 750 g to about 2.5 mg per dose and most preferred in an amount of about 1 mg per dose. In particular, a dose of the final composition may include Carbopol® or Carbopol® 971 in a range from about 750 µg to about 2.5 mg Carbopol®. For example, in some embodiments a dose of the final composition may include about 1 mg of Carbopol® 971.

Further suitable adjuvants include, but are not limited to, the RIBI® adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, MONTANIDE™ IMS 1314, or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV3 ORF2 protein recovered from the supernate of in vitro cultured cells, wherein said cells were infected with a recombinant viral vector containing PCV3 ORF2 DNA and expressing PCV3 ORF2 protein, and wherein said cell culture was treated with about 2 to about 8 mM BEI, preferably with about 5 mM BEI to inactivate the viral vector, and an equivalent concentration of a neutralization agent, preferably sodium thiosulfate solution in a final concentration of about 2 to about 8 mM, preferably of about 5 mM.

The present disclosure also relates to an immunogenic composition that comprises i) any of the PCV3 ORF2 proteins described above, preferably in concentrations described above, ii) at least a portion of the viral vector expressing said PCV3 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol® 971 in amounts described above; wherein about 90% of the components i) to iii) have a size smaller than 1 μm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

In an embodiment, the immunogenic composition may refer to a composition that includes in a one ml dose i) at least some PCV3 ORF2 protein, ii) baculovirus expressing said PCV3 ORF2 protein iii) cell culture, iv) an inactivating agent (e.g, BEI) having a concentration in a range from about 2 to about 8 mM, v) a neutralization agent (e.g., sodium thiosulfate) in equivalent amounts to the inactivating agent; and vi) a predetermined amount of adjuvant (e.g., Carbopol® 971), and vii) phosphate salt in a physiologically acceptable concentration. In some embodiments, components may be selected such that 90% of the combination of components that includes the i. PCV3 ORF2 protein, ii. baculovirus that expresses the protein and iii. cell culture have a size smaller than 1 m. Further, in some embodiments one or more components of the immunogenic composition may be selected such that the immunogenic composition has a pH in a range from about 6.5 to about 7.5. Selection of the components and/or determinations with respect to amounts and/or concentrations may relate to various factors that affect stability of the immunogenic composition, ease of manufacturing, availability of materials, age, size, and/or condition of animals to be treated and/or results desired.

For example, the immunogenic composition as used herein also refers to a composition that comprises per one ml i) at least 1.6 μg of PCV3 ORF2 protein described above, ii) at least a portion of baculovirus expressing said PCV3 ORF2 protein iii) a portion of the cell culture, iv) about 2 to 8 mM BEI, v) sodium thiosulfate in equivalent amounts to BEI; and vi) about 1 mg Carbopol® 971, and vii) phosphate salt in a physiologically acceptable concentration; wherein about 90% of the components i) to iii) may have a size smaller than 1 m and the pH of said immunogenic composition is adjusted to about 6.5 to 7.5.

The immunogenic compositions can further include one or more other immunomodulatory agents such as, e.g., interleukins, interferons, or other cytokines (such as, but not limited to, IL-1, IL-2, IL-7, IFN-alpha, IFN-beta, IFN-gamma, etc.). The immunogenic compositions can also include Gentamicin and Merthiolate. While the amounts and concentrations of adjuvants and additives useful in the context of the present disclosure can readily be determined by the skilled artisan, the present disclosure contemplates compositions comprising from about 50 μg to about 2000 μg of adjuvant. In some embodiments, it may be preferable to use adjuvants in an amount of about 250 μg of adjuvant per one milliliter dose of the vaccine composition. In some embodiments, an immunogenic composition may include antibiotics at a concentration in a range from about 1 μg/mL to about 60 µg/mL. For example, an immunogenic composition may include less than about 30 µg/ml of antibiotics.

The immunogenic composition as used herein also refers to a composition that comprises i) any of the PCV3 ORF2 proteins described above, preferably in concentrations described above, ii) at least a portion of the viral vector expressing said PCV3 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol® 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 µm.

The composition according to the disclosure may be applied intradermally, intratracheally, or intravaginally. The composition preferably may be applied intramuscularly or intranasally, most preferably intramuscularlly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, orogastric or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the disclosure may be administered once or several times, also intermittently, for instance on a daily basis for several days, weeks or months and in different dosages. A single dose as well as multiple doses are contemplated. Also contemplated are combination vaccines in with other antigens of porcine pathogens. Preferred combination compositions contain PCV3 ORF2 protein and a PPV, a PRRSV antigen, a *M. hyopneumoniae* antigen (supernatant or bacterin), or a PRRSV antigen and a *M. hyopneumoniae* antigen (supernatant or bacterin) or any combination of the foregoing with a PCV2 ORF2 protein.

In some embodiments, a dosing regimen may be developed to deliver effective amounts of PCV3 ORF2 to induce a desired effect, such as an immune response in an animal and/or their progeny. Determinations with respect to dosing regimens may be related to the desired results, components selected for use in the immunogenic composition, administration route, such as parenteral and/or subcutaneous administration, number or doses delivered, for example, a single administration or multiple doses, and/or the specific properties of the animal or animal population to be treated, for example, the age, size, and/or condition of animals. Condition of animals may refer to, for example, health status, pregnancy status, size, etc. Thus, sows and piglets may require different effective doses.

As stated above, treatment methods may be different based on the outcome desired. For example, a sow may be treated to inhibit and/or prevent conditions related to porcine *circovirus* or a sow may be treated to inhibit and/or prevent the negative effects of infection with porcine *circovirus* in her piglets.

A dosing regimen may include one or more doses of an immunogenic composition that includes a predetermined amount of PCV3 ORF2 protein. For example, the dosing regimen may include doses in a range from about 2 micrograms to about 400 micrograms of the PCV3 ORF2 protein. In an embodiment, a dosing regimen of a particular immunogenic composition may include greater than about two micrograms of PCV3 ORF2 protein. In some instances, each dose of a particular immunogenic composition many include PCV3 ORF2 protein in an amount greater than about 4 micrograms. Some dosing regimen embodiments for an immunogenic composition may include immunogenic compositions at doses of at least about 8 micrograms of PCV3 ORF2 protein. For example, some dosing regimens of the immunogenic composition as disclosed herein may be structured such that at least one dose includes greater than about 16 micrograms of the desired PCV3 ORF2 protein.

In an embodiment, a dosing regimen may be selected based on the desired expression of a specific PCV3 ORF2 protein within an animal. For example, given an immunogenic composition that includes an appropriate vector and/or expression system for pigs, it may be desired that the vector delivered in the immunogenic composition is capable of delivering PCV3 ORF2 protein in amount that is in a range from about 2 micrograms to about 400 micrograms in vivo. In an embodiment, a dosing regimen of a particular immunogenic composition is structured to deliver an amount of PCV3 ORF2 protein greater than about two micrograms to an animal. In some instances, a dosing regimen for a particular immunogenic composition is structured to deliver an amount of PCV3 ORF2 protein greater than about 4 micrograms to an animal. Some dosing regimen embodiments for an immunogenic composition are structured to deliver an amount of PCV3 ORF2 protein greater than about 8 micrograms to an animal. For example, some dosing regimens of the immunogenic composition as disclosed herein may be structured such that greater than about 16 micrograms of the desired PCV3 ORF2 protein may be delivered to an animal.

Dosing regimens may also include guidance on administration routes and/or times. For example, it may be desirable to deliver a dose of an immunogenic composition to a piglet at a specific age, in particular, at about 1 week, 2 weeks or 3 weeks of age depending on the immunogenic compositions and desired results. In some instances, piglets may be administered immunogenic compositions at an age in a range from about 7 days to about 28 days. In a dosing regimen embodiment, pigs may be administered the immunogenic composition at an age in a range from about 14 days to about 26 days. For example, an administration window for piglets may be selected in range from an age of about 16 days to about 26 days. Some dosing regimen embodiments may include administering the immunogenic composition to a piglet at an age in a range from about 18 days to about 24 days.

An immunogenic composition may include recombinant PCV3 ORF2 protein. In particular, an immunogenic composition may include recombinant PCV3 ORF2 protein expressed from baculoviruses.

Further, in some instances, the immunogenic composition that includes recombinant PCV3 ORF2 protein may be administered in combination with one or more doses of additional antigens, for example, antigens from PCV2 ORF2, PPV, PRRSV, and/or *M. hyopneumoniae* ("M. Hyo"). The PRRSV antigen may be an attenuated live vaccine. The M. Hyo. antigen may be a bacterin, a supernatant, or a combination of bacterin and supernatant.

Multiple doses of immunogenic compositions may be administered in a dosing regimen. For example, a dosing regimen may be made of a dose of immunogenic composition that includes recombinant PCV3 ORF2 protein and a dose of an immunogenic composition that includes a recombinant PCV2 ORF2 protein. In an instance, the doses may include approximately equivalent amounts of recombinant PCV3 ORF2 protein and PCV2 ORF2 protein. An embodiment of the dosing regimen may include doses of immunogenic compositions that include recombinant PCV3 ORF2 protein and recombinant PCV2 ORF2, both of which may be expressed using baculoviruses systems expression systems.

An embodiment of a recombinant PCV3 ORF2 immunogenic composition may include additional antigens, for example antigens such as recombinant proteins from PCV3 ORF2, as well as an attenuated live PRRSV and/or a bacterin, a supernatant, or a combination of bacterin and supernatant of M. Hyo. Some embodiments of an immunogenic composition may include baculovirus expressed recombinant proteins from PCV3 ORF2 and PCV2 ORF2, as well as antigens of PRRSV (e.g., attenuated live vaccine) and/or of M. Hyo (e.g., a bacterin and/or a supernatant). Further, in some instances, an immunogenic composition may include PCV3 ORF2 protein in combination with PCV2 ORF2 protein, an attenuated live PRRSV, and/or an M. Hyo bacterin and/or a supernatant.

Immunogenic compositions may include recombinant PCV3 ORF2 protein and recombinant PCV2 ORF2 protein. In an instance, the doses may include approximately equivalent amounts of recombinant PCV3 ORF2 protein and PCV2 ORF2 protein. An embodiment of the dosing regimen may include doses of immunogenic compositions that include recombinant PCV3 ORF2 protein and recombinant PCV2 ORF2, both of which may be expressed using baculovirus expression systems.

Some embodiments of an immunogenic composition may include baculovirus expressed recombinant proteins from PCV3 ORF2, as well as PRRSV and/or M. Hyo antigens. Further, baculovirus expressed recombinant proteins from PCV3 ORF2 and PCV2 ORF2 may be combined with antigens of PRRSV and/or M. Hyo to form an inmmunogenic composition. As disclosed above the additional antigens may include an attenuated live PRRSV and/or an M Hyo bacterin and/or a supernatant.

For example, an immunogenic composition may comprise recombinant PCV3 ORF2 protein and recombinant PCV2 ORF2 protein. In some instances, an immunogenic composition includes approximately equivalent amounts of recombinant PCV3 ORF2 protein and PCV2 ORF2 protein. Some embodiments of an immunogenic composition may include a combination of baculovirus expressed recombinant proteins from PCV3 ORF2 and PCV2 ORF2, as well as PRRSV and/or M. Hyo.

Dosing regimens may be used to improve the economics of swine husbandry. For example, immunogenic compositions, such as vaccines may be administered to sows and/or piglets in an effort to protect sows, piglets, or both.

In particular, vaccination of sows prior to gestation may reduce the number of mummified, stillborn and/or weak piglets at farrowing if the sows are challenged by an exposure to PCV3. Generally, PCV3 is believed to be a reproductive disease. Further, use of an inactivated baculovirus-expressed PCV3 ORF2 vaccine may reduce and/or inhibit virus replication in sows. This reduction in replication may reduce the number of mummies at farrowing for the vaccinated sows at about a rate of 4%. Such a reduction may have a significant economic impact for swine producers.

It is further claimed that, the vaccine is able to protect bred gilts and sows when challenged with PCV3 in all or two or at least one trimester during the 114 days of gestation.

It is also claimed that the vaccine is able to significantly reduce the incidence of mummies, stillborns and fetus in vaccinated gilts and sows vaccinated when challenged with PCV3 in all or two or at least one trimester during the 114 days of gestation.

A dosing regimen may include vaccinating young sows (i.e., less than or equal to 5 months of age) with at least one dose of an immunogenic composition as described herein prior to breeding. The dose of the immunogenic composition as described herein may be administered intramuscularly as a one (1) mL dose prior to breeding. In some embodiments, one or more doses of vaccine may be given to sows. For example, a first vaccine may be given and followed by a booster vaccine 21 days later and prior to breeding. In some embodiments, sows may be bred in a range from 14 days to 21 days after the booster vaccination. This time frame may allow sows to mount an immune response. Utilizing such a dosing regimen may reduce and/or inhibit the number of mummies at farrowing.

Further, use of a dosing regimen that includes administering a 1 ml dose of an immunogenic composition than includes PCV3 antigen (i.e., recombinant PCV3 ORF2) may reduce, lessen and/or inhibit lymphadenopathy, lymphoid depletion and/or multinucleated/giant histiocytes in pigs infected with PCV3.

In some embodiments, a dosing regimen for vaccinating piglets at about 3 weeks of age using a baculovirus expressed PCV3 ORF2 vaccine may reduce viral load if the piglets are subsequently challenged by PCV3. For example, an amount of replicating virus in tissues of vaccinated piglets may be reduced relative to unvaccinated piglets. Further, vaccinating piglets with a PCV3 ORF2 vaccine may reduce mortality, clinical signs, gross lesions, and/or histologic lesions in vaccinated piglets relative to unvaccinated piglets that are subsequently exposed to PCV3.

The term "immune stimulant" or "immunostimulant" as used herein, means any agent or composition that can trigger the immune response, preferably without initiating or increasing a specific immune response, for example the immune response against a specific pathogen. It is further instructed to administer the immune stimulant in a suitable dose. Advantageously, the immune stimulant is Keyhole Limpet Hemacyanin (KLH) and/or incomplete Freunds adjuvant (IFA). As used herein, the role of the immune stimulant is not of an adjuvant, but as a challenge enhancer. Advantageously, KLH is emulsified in IFA containing 1 mg KLH/mL may be administered intramuscularly two days before and two days after challenge.

According to a further consideration, a porcine *circovirus* type 3 (PCV3) antigenic protein is provided, wherein said protein is a functional antigenic variant of PCV3 ORF2 protein, and wherein said protein is in particular also termed "the protein of the further consideration" hereinafter.

Preferably, the protein of the further consideration is a functional antigenic variant of the PCV3 ORF2 protein encoded by SEQ ID No. 1.

In one peferred aspect, the protein of the further consideration comprises substitutions and/or extensions of PCV3 ORF2.

In another preferred aspect, the protein of the further consideration is a functional antigenic variant of the protein encoded by SEQ ID No. 1 and/or the functional antigenic variant is capable of a higher yield of virus-like particles (VLPs) than the protein encoded by SEQ ID No. 1.

Preferably, said functional antigenic variant is capable of a higher yield of VLPs than the protein encoded by SEQ ID No. 1 as determinable by Western blot analysis.

According to one preferred aspect, said functional antigenic variant has fewer positive charged amino acid residues than the protein encoded by SEQ ID No. 1.

According to another preferred aspect, said functional antigenic variant has one or more substitutions in the FG loop of the protein encoded by SEQ ID No. 1, and wherein preferably those substitutions comprise substitutions of one or more of the S residue and/or the K residues and/or the H residue of the motif SKKKH (SEQ ID NO: 14) of the FG loop of the protein encoded by SEQ ID No. 1.

According to yet another preferred aspect, said functional antigenic variant has one or more substitutions in the FG loop of the protein encoded by SEQ ID No. 1, wherein those substitutions comprise substitutions of one or more of the S residue and/or the K residues of the motif SKKKH (SEQ ID NO: 14) of the FG loop of the protein encoded by SEQ ID No. 1.

According to yet a further preferred aspect, said functional antigenic variant has one or more substitutions in the FG loop of the protein encoded by SEQ ID No. 1, wherein those substitutions comprise substitutions of the S residue or H residue and all of the K residues of the motif SKKKH (SEQ ID NO: 14) of the FG loop of the protein encoded by SEQ ID No. 1.

In still another preferred aspect, said functional antigenic variant has one or more substitutions in the FG loop of the protein encoded by SEQ ID No. 1, wherein those substitutions comprise a substitution of at least S and/or H and any K of the motif SKKKH (SEQ ID NO: 14) of the FG loop of the protein encoded by SEQ ID No. 1 with Q or P or F or S.

In still a further preferred aspect. said functional antigenic variant has one or more substitutions in the FG loop of the protein encoded by SEQ ID No. 1, wherein those substitutions comprise substitution of the motif SKKK (SEQ ID NO: 11) within the motif SKKKH (SEQ ID NO: 14) of the FG loop of the protein encoded by SEQ ID No. 1 with QPFS (SEQ ID NO: 12) or substitution of the motif KKKH (SEQ ID NO: 15) within the motif SKKKH (SEQ ID NO: 14) of the FG loop of the protein encoded by SEQ ID No. 1 with QPFS (SEO ID NO: 12).

In yet another further preferred aspect, said functional antigenic variant is encodable by all or part of SEQ ID No. 1, 2, 5, 6 or 7.

In still a further preferred aspect, said functional antigenic variant is encoded by all or part of SEQ ID No. 1, 2, 5, 6 or 7.

According to a particularly preferred aspect, said functional antigenic variant has a C terminal end that extends beyond the terminal SVL sequence of the protein encoded by SEQ ID No. 1, preferably wherein said extension is all or includes a sequence from a circoviridae virus, and preferably wherein at least a part of said extension replaces the terminal SVL sequence of the protein encoded by SEQ ID No. 1.

According to another preferred aspect, said functional antigenic variant has a C terminal end that extends beyond the terminal SVL sequence of the protein encoded by SEQ ID No. 1; and wherein said extension is from 1 to 100 amino acids long.

According to a further preferred aspect, said functional antigenic variant has a C terminal end that extends beyond the terminal SVL sequence of the protein encoded by SEQ ID No. 1; and wherein said extension is from 1 to 50 amino acids long.

According to yet a another preferred aspect, said functional antigenic variant has a C terminal end that extends beyond the terminal SVL sequence of the protein encoded by SEQ ID No. 1; and wherein said extension is from 1 to 30 amino acids long.

In one particularly preferred aspect, said functional antigenic variant has a C terminal end that extends beyond the terminal SVL sequence of the protein encoded by SEQ ID No. 1.

Preferably, said extension is from 1 to 30 amino acids long and/or said extension comprises all of the sequence VKININLTPPVATSRVPSRALPLRFGCGHR (SEQ ID NO: 16).

In a further preferred aspect, said functional antigenic variant is encodable by all or part of SEQ ID No. 1, 2, 5, 6 or 7.

In a preferred aspect, said variant protein comprises or consists of an amino acid sequence having a sequence identity and/or sequence homology of at least about 80% or at least about 85% or at least about 86% or at least about 87% or at least about at least 88% or at least about 89%, e.g., in a range from about 83% to about 89%, such as 84% or 85% or 86% or 87% or 88% or 89% sequence identity and/or sequence homology, with the sequence of SEQ ID NO: 3, 4, 8, 9 or 10, and/or wherein the protein is a recombinant protein, and wherein said protein has one or more substitutions in the FG loop.

In a preferred aspect, said variant protein comprises or consists of an amino acid sequence having a sequence identity and/or sequence homology of at least about 80% or at least about 85% or at least about 86% or at least about 87% or at least about at least 88% or at least about 89%, e.g., in a range from about 83% to about 89%, such as 84% or 85% or 86% or 87% or 88% or 89% sequence identity and/or sequence homology, with the sequence of SEQ ID NO: 3, 4, 8, 9 or 10, and/or wherein the protein is a recombinant protein, and wherein said protein has a C terminal end that extends beyond the terminal SVL sequence of the protein encoded by SEQ ID No. 1.

In a preferred aspect, said variant protein comprises an FG loop having one or more substitutions in the FG loop and further comprises a C terminal end that extends beyond the terminal SVL sequence of the protein encoded by SEQ ID No. 1, wherein the sequence of the variant protein comprises or consists of an amino acid sequence having sequence identity and/or sequence homology of at least about 80% or at least about 85% or at least about 86% or at least about 87% or at least about at least 88% or at least about 89%, e.g., in a range from about 83% to about 89%, such as 84% or 85% or 86% or 87% or 88% or 89% sequence identity and/or sequence homology, with the sequence of SEQ ID NO: 3, 4, 8, 9 or 10, and/or wherein the protein is a recombinant protein.

In another preferred aspect, the protein of the further consideration is a recombinant protein having been prepared by recombinant DNA techniques.

In still another preferred aspect, the protein of the further consideration is a baculovirus expressed protein.

Preferably, said PCV3 is any phylogenetic clade of PCV3 or combination of clades Preferably, said PCV3 is selected from the group consisting of PCV3a and PCV3b.

In particular, said PCV3 is preferably selected from the group consisting PCV3al, PCV3b1 and PCV3b2.

The PCV3 may also be selected from PCV3c (BMC Vet Res. 2019 Jul. 15;15(1):244. doi: 10.1186/s12917-019-1977-7).

More particular, said PCV3 ORF2 is preferably from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4).

In a preferred aspect, said PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO: 1.

In another preferred aspect, said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:6.

In yet another preferred aspect, said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:7.

In yet a further preferred aspect, said PCV3 ORF2 protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein.

In still another preferred aspect, said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein.

In still another preferred aspect, said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has one or more substitutions in the FG loop.

In a preferred aspect, said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein.

In another preferred aspect, said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has a C terminal end that extends beyond the terminal SVL sequence of the protein encoded by SEQ ID No. 1.

According to a preferred aspect, said protein is a recombinant protein from expression thereof by an expression vector, comprising a polynucleotide sequence that encodes the protein.

According to a preferred aspect, said protein is a recombinant protein from expression thereof by a baculovirus expression vector, comprising a polynucleotide sequence that encodes the protein.

In another preferred aspect, a nucleotide sequence is provided, wherein the nucleotide sequence encodes the protein of the further consideration, and wherein said nucleotide is also termed "the nucleotide sequence of the further consideration" hereinafter.

In a further preferred aspect, a vector is provided, wherein the vector comprises the nucleotide sequence of the further consideration, and wherein said vector is also termed "the vector of the further consideration" hereinafter.

Also, recombinant vector is provided, wherein the recombinant vector comprises the nucleotide sequence of the further consideration.

Further, an expression host is provided, wherein the expression host is transformed or transfected with the nucleotide sequence of the further consideration and wherein said expression host is also termed "the expression host of the further consideration" hereinafter.

Also, a baculovirus expression host is provided, wherein the baculovirus expression host is transformed or transfected with the nucleotide sequence of the further consideration, and wherein said baculovirus expression host is also termed "the baculovirus expression host of the further consideration" hereinafter.

Further, a method of preparing the protein of the further consideration is provided comprising expressing a nucleotide sequence of the further consideration.

Also, a method of preparing the protein of the further consideration is provided, wherein the method comprises expressing a vector of the further consideration.

Further, a method of preparing the protein of the further consideration is provided, wherein the method comprises expressing a recombinant vector of the further consideration.

Also, a method of preparing the protein of the further consideration is provided, wherein the method comprises culturing the expression host of the further consideration to cause expression of the protein.

Further, a method of preparing the protein of the further consideration is provided, wherein the method comprises transfecting an expression host with the nucleotide sequence of the further consideration or the vector according of the further consideration, and culturing the expression host to cause expression of the protein.

Also, a method of preparing the protein of the further consideration is provided, wherein the method comprises culturing the baculovirus expression host of the further consideration to cause expression of the protein.

Also, a method of preparing the protein of the further consideration is provided, wherein the method comprises transfecting a baculovirus expression host with the nucleotide sequence of the further consideration or the vector according of the further, and culturing the baculovirus expression host to cause expression of the protein.

Preferably, in any of the above methods of preparing the protein of the further consideration an inactivating agent is used when sufficient levels of expressed protein have been achieved and wherein the inactivating agent is preferably binary ethyleneimine (BEI) is used when sufficient levels of expressed protein have been achieved.

Preferably, any of the above methods of preparing the protein of the further consideration comprises transfecting a baculovirus expression host with the nucleotide sequence of vector and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein.

Preferably, any of the above methods of preparing the protein of the further consideration comprises transfecting a baculovirus expression host with the nucleotide sequence of vector and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 μm.

Preferably, any of the above methods of preparing the protein of the further consideration comprises transfecting a baculovirus expression host with the nucleotide sequence of vector and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 m and the pH of said composition is adjusted to about 6.5 to 7.5.

Preferably, any of the above methods of preparing the protein of the further consideration comprises producing the protein by a baculovirus expression system in cultured insect cells.

Preferably, any of the above methods of preparing the protein of the further consideration comprises producing the protein by a baculovirus expression system in cultured insect cells; and wherein the method includes the step of inactivating the baculovirus.

Preferably, any of the above methods of preparing the protein of the further consideration comprises producing the protein by a baculovirus expression system in cultured insect cells; and wherein the method includes the step of inactivating the baculovirus; and wherein inactivating step comprises heat treatment or use of a virus inactivating agent.

Preferably, any of the above methods of preparing the protein of the further consideration comprises producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound.

Preferably, any of the above methods of preparing the protein of the further consideration comprises producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound; wherein the aziridine compound comprises BEI.

Further, a protein is provided, wherein said protein is obtainable by any of the above methods of preparing the protein of the further consideration.

Also, a composition is provided comprising a protein obtainable by any of the above methods of preparing the protein of the further consideration, and wherein the composition preferably comprises a carrier, diluent or excipient. Further, a composition is provided obtainable by any of the above methods of preparing the protein of the further consideration, and wherein the composition preferably comprises a carrier, diluent or excipient.

In particular, any of said compositions is also termed "the composition of the further consideration" hereinafter.

In the composition of the further consideration the protein is preferably present in an amount of 0.2 to about 400 μg/ml, or 2 to about 400 μg/ml, or 4 to about 400 μg/ml, or 8 to about 400 μg/ml, or about 0.3 to about 200 μg/ml, or 2 to about 200 μg/ml, or 4 to about 200 μg/ml, or 8 to about 200 μg/ml, or about 0.35 to about 100 μg/ml, or 2 to about 100 μg/ml, or 4 to about 100 μg/ml, or 8 to about 100 μg/ml, or about 0.4 to about 50 μg/ml, or about 0.45 to about 30 μg/ml, or about 0.6 to about 15 μg/ml, or about 0.75 to about 8 μg/ml, or about 1.0 to about 6 μg/ml, or about 1.3 to about 3.0 μg/ml, or about 1.4 to about 2.5 μg/ml, or about 1.5 to about 2.0 μg/ml, or about 1.6 μg/ml.

Preferably, the composition of the further consideration comprises any one or more of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, and/or an immunomodulatory agent.

Preferably, a composition of the further consideration is provided, wherein the carrier, diluent or excipient is any one or more of an adjuvant, immunomodulatory agent, cell culture supernatant, viral or expression vector or any combination thereof.

Preferably, a composition of the further consideration is provided, wherein the carrier, diluent or excipient comprises an adjuvant.

Preferably, a composition of the further consideration is provided, wherein the carrier, diluent or excipient comprises an adjuvant; wherein the adjuvant comprises one or more of a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A@; QS-21@ STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from E. coli (recombinant or otherwise); cholera toxin; MONTANIDE™ IMS 1314, or muramyl dipeptide.

Preferably, a composition of the further consideration is provided, wherein the carrier, diluent or excipient comprises an adjuvant; wherein the adjuvant comprises Carbopol® or Carbopol® 971.

Preferably, a composition of the further consideration is provided, wherein the carrier, diluent or excipient comprises an adjuvant; wherein the adjuvant is present in an amount from about 50 µg to about 2000 of the composition; or wherein adjuvant is present in an amount about 250 µg/ml dose of the composition, or wherein the adjuvant is present in an amount of about 100 g to about 10 mg of the composition; or wherein the adjuvant is present in an amount of about 500 µg to about 5 mg of the composition; the adjuvant is present in an amount of about 750 µg to about 2.5 mg of the composition; or the adjuvant is present in an amount of about 1 mg of the composition.

Preferably, a composition of the further consideration is provided, wherein the composition comprises an immunomodulatory agent.

Preferably, a composition of the further consideration is provided, wherein the composition comprises an immunomodulatory agent; and wherein the immunomodulatory agent is any one or more of interleukin(s), interferon(s), or other cytokine(s).

Preferably, a composition of the further consideration is provided, wherein the composition comprises an antibiotic (s).

Preferably, a composition of the further consideration is provided, wherein the composition comprises an antibiotic (s); wherein the antibiotic(s) comprise Gentamicin.

Preferably, a composition of the further consideration is provided, wherein the composition comprises an antibiotic (s); and wherein the composition comprises from about 1 µg/ml to about 60 µg/ml of antibiotic(s).

Preferably, a composition of the further consideration is provided, wherein the composition comprises an antibiotic (s); and wherein the composition comprises from about 1 µg/ml to less than about 30 µg/ml of antibiotic(s).

Preferably, a composition of the further consideration is provided, wherein the composition comprises an additional antigen.

Preferably, a composition of the further consideration is provided, wherein the composition comprises an additional antigen; wherein said additional antigen is not a PCV3 ORF2 antigen.

Preferably, a composition of the further consideration is provided, wherein the composition comprises an additional antigen; wherein said additional antigen is not a PCV3 antigen.

Preferably, a composition of the further consideration is provided, wherein the composition comprises an additional antigen of an additional porcine pathogen.

Preferably, a composition of the further consideration is provided, wherein the composition further comprises an antigen of an additional porcine pathogen, wherein said pathogen is any one or more of PCV2, PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen.

Preferably, a composition of the further consideration is provided, wherein the composition further comprises an antigen of an additional porcine pathogen, wherein said composition further comprises one or more of an antigen of PCV2, an antigen of a PRRSV and an antigen of a PPV.

Preferably, a composition of the further consideration is provided, wherein the composition further comprises an antigen of PCV2.

Preferably, a composition of the further consideration is provided, wherein the composition further comprises an antigen of PCV2; wherein PCV2 antigen is PCV2 ORF2 protein.

Preferably, a composition of the further consideration is provided, wherein the composition further comprises an antigen of PCV2; wherein PCV2 antigen is recombinant PCV2 ORF2 protein.

Preferably, a composition of the further consideration is provided, wherein the composition further comprises an antigen of PCV2; wherein PCV2 antigen is recombinant baculovirus expressed PCV2 ORF2 protein.

Preferably, a composition of the further consideration is provided, wherein the composition is in a dosage form.

Preferably, a composition of the further consideration is provided, wherein the composition is formulated and/or packaged for a single dose or one shot administration.

Preferably, a composition of the further consideration is provided, wherein the composition is formulated and/or packaged for a multi-dose regimen.

Preferably, a composition of the further consideration is provided, wherein the composition is formulated and/or packaged for a two-dose regimen.

Preferably, a composition of the further consideration is provided, wherein the composition is in a dosage form; and wherein said dosage form is delivered from a container containing a larger amount of said composition and wherein a dosage form of said composition is capable of being delivered from said container.

Preferably, a composition of the further consideration is provided, wherein the composition is in a dosage form; and wherein said dosage form is delivered from a container containing a larger amount of said composition and wherein a dosage form of said composition is capable of being delivered from said container; and wherein said container contains at least 10 doses of said composition.

Preferably, a composition of the further consideration is provided, wherein the composition is in a dosage form; and wherein said dosage form is delivered from a container containing a larger amount of said composition and wherein a dosage form of said composition is capable of being delivered from said container; and wherein said container contains at least 50 doses of said composition.

Preferably, a composition of the further consideration is provided, wherein the composition is in a dosage form; and wherein said dosage form is delivered from a container containing a larger amount of said composition and wherein a dosage form of said composition is capable of being delivered from said container; and wherein said container contains at least 100 doses of said composition.

Preferably, a composition of the further consideration is provided, wherein the composition is in a dosage form; and wherein said dosage form is delivered from a container containing a larger amount of said composition and wherein a dosage form of said composition is capable of being delivered from said container; and wherein said container contains at least 200 doses of said composition.

Preferably, a composition of the further consideration is provided, wherein the composition is in a dosage form; and wherein said dosage form is delivered from a container containing a larger amount of said composition and wherein a dosage form of said composition is capable of being delivered from said container; and wherein said container contains at least 250 doses of said composition.

Preferably, a composition of the further consideration is provided, wherein the composition comprises an antigen of PCV2; wherein PCV2 antigen is recombinant baculovirus expressed PCV2 ORF2 protein; and wherein either the protein or combined total amount of the PCV3 ORF protein and PCV2 ORF protein are present in an amount of about 0.2 to about 400 ag/dose, or 2 to about 400 µg/dose, or 4 to about 400 µg/dose, or 8 to about 400 µg/dose, or about 0.3 to about 200 µg/dose, or 2 to about 200 µg/dose, or 4 to about 200 µg/dose, or 8 to about 200 µg/dose, or about 0.35 to about 100 µg/dose, or 2 to about 100 µg/dose, or 4 to about 100 µg/dose, or 8 to about 100 µg/dose, or about 0.4 to about 50 µg/dose, or about 0.45 to about 30 µg/dose, or about 0.6 to about 15 µg/dose, or about 0.75 to about 8 µg/dose, or about 1.0 to about 6 µg/dose, or about 1.3 to about 3.0 µg/dose, or about 1.4 to about 2.5 µg/dose, or about 1.5 to about 2.0 µg/dose, or about 1.6 µg/dose.

Preferably, a composition of the further consideration is provided, wherein the composition comprises a salt.

Preferably, a composition of the further consideration is provided, wherein the composition comprises an inactivated viral vector and/or cell culture supernate.

Preferably, a composition of the further consideration is provided, wherein the composition comprises an inactivated viral vector and cell culture supernate.

Preferably, a composition of the further consideration is provided, wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.

Preferably, a composition of the further consideration is provided, wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration; and wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.

Preferably, a composition of the further consideration is provided, wherein the composition is an immunogenic composition comprising a protein of the further consideration and a carrier, diluent or excipient.

Preferably, a composition of the further consideration is provided, wherein the composition is an immunogenic composition comprising a protein of the further consideration and a carrier, diluent or excipient; and an additional antigen as mentioned above.

Also, a process of making the composition of the further consideration is provided, wherein the protein of the further consideration is admixed with the carrier, diluent or excipient.

Further, a process of making the composition of the further consideration is provided, wherein the protein of the further consideration is admixed with the carrier, diluent or excipient; and the additional antigen.

Moreover, a protein of the further consideration is provided for use as a medicament.

Also, the protein of the further consideration or the composition of the further consideration is provided for use as a vaccine.

Also, the protein of the further consideration or the composition of the further consideration is provided for use in a method for eliciting an immune response or an immunological response or a protective immune or immunological response against PCV3 in an animal.

Also, the protein of the further consideration or the composition of the further consideration is provided for use in a method for eliciting an immune response or an immunological response or a protective immune or immunological response against PCV3 in swine.

Also, the protein of the further consideration or the composition of the further consideration is provided for use in a method for eliciting an immune response or an immunological response or a protective immune or immunological response against PCV3 in pigs.

Also, the protein of the further consideration or the composition of the further consideration is provided for use in a method for eliciting an immune response or an immunological response or a protective immune or immunological response against PCV3 in piglets.

Also, the protein of the further consideration or the composition of the further consideration is provided for use in a method for eliciting an immune response or an immunological response or a protective immune or immunological response against PCV3 in piglets; wherein the piglets are to be suckled by sows to which the protein of the further consideration or a composition of the further consideration has been administered.

Also, the protein of the further consideration or the composition of the further consideration is provided for use in a method for eliciting an immune response or an immunological response or a protective immune or immunological response against PCV3 in sows.

Also, the protein of the further consideration or the composition of the further consideration is provided for use in a method for eliciting an immune response or an immunological response or a protective immune or immunological response against PCV3 in pregnant sows, gilts or prebreeding gilts.

Also, the protein of the further consideration or the composition of the further consideration is provided for use in inducing an immune response against PCV3 in animals.

Also, the protein of the further consideration or the composition of the further consideration is provided for use in inducing an immune response against PCV3 in swine.

Also, the protein of the further consideration or the composition of the further consideration is provided for use in inducing an immune response against PCV3 in pigs.

Also, the protein of the further consideration or the composition of the further consideration is provided for use in inducing an immune response against PCV3 in piglets.

Also, the protein of the further consideration or the composition of the further consideration is provided for use in inducing an immune response against PCV3 in piglets; wherein the piglets are to be suckled by sows to which the protein of the further consideration or a composition of the further consideration has been administered.

Also, the protein of the further consideration or the composition of the further consideration is provided for use in inducing an immune response against PCV3 in sows.

Also, the protein of the further consideration or the composition of the further consideration is provided for use in inducing an immune response against PCV3 in pregnant sows, gilts or pre-breeding gilts.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal; wherein said animal is swine.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal; wherein said animal is a pig.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal; wherein said animal is a piglet.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal; wherein said animal is a piglet; and wherein the piglet is to be suckled by a sow to which the protein of the further consideration or the composition of the further consideration has been administered.

Also, the protein of the further consideration or the composition of the further consideration is provided for use in a method of reducing or preventing the clinical signs or disease caused by an infection with PCV3 in an animal or for use in a method of treating or preventing an infection with PCV3 in an animal; wherein said animal is a sow.

Also, the protein of the further consideration or the composition of the further consideration is provided for use in a method of reducing or preventing the clinical signs or clinical symptoms or disease caused by an infection with PCV3 in an animal or for use in a method of treating or preventing an infection with PCV3 in an animal; wherein said animal is a pregnant sow, gilt or pre-breeding gilt.

Also, the protein of the further consideration or the composition of the further consideration is provided for use in immunizing an animal against PCV3.

Also, the protein of the further consideration or the composition of the further consideration is provided for use in immunizing an animal against PCV3; wherein said animal is swine.

Also, the protein of the further consideration or the composition of the further consideration is provided for use in immunizing an animal against PCV3; wherein said animal is a pig.

Also, the protein of the further consideration or the composition of the further consideration is provided for use in immunizing an animal against PCV3; wherein said animal is a piglet.

Also, the protein of the further consideration or the composition of the further consideration is provided for use in immunizing an animal against PCV3; wherein said animal is a piglet; and wherein the piglet is to be suckled by a sow to which the protein of the further consideration or the composition of the further consideration has been administered.

Also, the protein of the further consideration or the composition of the further consideration is provided for use in immunizing an animal against PCV3; wherein said animal is a sow.

Also, the protein of the further consideration or the composition of the further consideration is provided for use in immunizing an animal against PCV3; wherein said animal is a pregnant sow, gilt or pre-breeding gilt.

Also, the protein of the further consideration or the composition of the further consideration is provided for use in a method of reducing or eliminating or abrogating PCV3 viral expression in an animal.

Also, the protein of the further consideration or the composition of the further consideration is provided for use in a method of reducing or eliminating or abrogating PCV3 viral expression in an animal; wherein said animal is swine.

Also, the protein of the further consideration or the composition of the further consideration is provided for use in a method of reducing or eliminating or abrogating PCV3 viral expression in an animal; wherein said animal is a pig.

Also, the protein of the further consideration or the composition of the further consideration is provided for use in a method of reducing or eliminating or abrogating PCV3 viral expression in an animal; wherein said animal is a piglet.

Also, the protein of the further consideration or the composition of the further consideration is provided for use in a method of reducing or eliminating or abrogating PCV3 viral expression in an animal; wherein said animal is a piglet; and wherein the piglet is to be suckled by a sow to which the protein of the further consideration or the composition of the further consideration has been administered.

Also, the protein of the further consideration or the composition of the further consideration is provided for use in a method of reducing or eliminating or abrogating PCV3 viral expression in an animal; wherein said animal is a sow.

Also, the protein of the further consideration or the composition of the further consideration is provided for use in a method of reducing or eliminating or abrogating PCV3 viral expression in an animal; wherein said animal is a pregnant sow, gilt or pre-breeding gilt.

Also, the protein of the further consideration or the composition of the further consideration is provided for use in inducing the production of antibodies specific for PCV3 in an animal.

Also, the protein of the further consideration or the composition of the further consideration is provided for use in inducing the production of antibodies specific for PCV3 in an animal; wherein said animal is swine.

Also, the protein of the further consideration or the composition of the further consideration is provided for use in inducing the production of antibodies specific for PCV3 in an animal; wherein said animal is a pig.

Also, the protein of the further consideration or the composition of the further consideration is provided for use in inducing the production of antibodies specific for PCV3 in an animal; wherein said animal is a piglet.

Also, the protein of the further consideration or the composition of the further consideration is provided for use in inducing the production of antibodies specific for PCV3 in an animal; wherein said animal is a piglet; and wherein the piglet is to be suckled by a sow to which the protein of the further consideration or the composition of the further consideration has been administered.

Also, the protein of the further consideration or the composition of the further consideration is provided for use in inducing the production of antibodies specific for PCV3 in an animal; wherein said animal is a sow.

Also, the protein of the further consideration or the composition of the further consideration is provided for use in inducing the production of antibodies specific for PCV3 in an animal; wherein said animal is a pregnant sow, gilt or pre-breeding gilt.

Preferably, said protein of the further consideration or the composition of the further consideration is administered intramuscularly or intradermally to said animal.

Preferably, said protein of the further consideration or the composition of the further consideration is administered to said animal in conjunction with another antigen, preferably wherein the other pathogen is an antigen to a porcine pathogen.

Preferably, said protein of the further consideration or the composition of the further consideration is administered to said animal in conjunction with another antigen; wherein said other antigen is not a PCV3 ORF2 antigen, preferably wherein the other pathogen is an antigen to a porcine pathogen.

Preferably, said protein of the further consideration or the composition of the further consideration is administered to said animal in conjunction with another antigen; wherein said other antigen is not a PCV3 antigen, preferably wherein the other pathogen is an antigen to a porcine pathogen.

Also, the protein of the further consideration or the composition of the further consideration is provided for any of the above uses, wherein said animal is a sow pregnant with a piglet.

Also, the protein of the further consideration or the composition of the further consideration is provided for any of the above uses, wherein said animal is a sow pregnant with a piglet; and wherein the piglet is to be suckled by a sow to which the protein of the further consideration or the composition according to a further consideration has been administered.

Also, the protein of the further consideration or the composition of the further consideration is provided for any of the above uses, wherein said animal is a sow; and wherein said protein of the further consideration or said composition of the further consideration is administered twice to said sow.

Preferably said animal is a sow; and wherein said protein of the further consideration or said composition of the further consideration is only administered twice to said sow.

Also, the protein of the further consideration or the composition of the further consideration is provided for any of the above uses wherein said animal is a piglet; and wherein the protein of the further consideration or the composition of the further consideration is administered once to said piglet.

Also, the protein of the further consideration or the composition of the further consideration is provided for any of the above uses wherein said animal is a piglet; and wherein the protein of the further consideration or a composition of the further consideration is only administered once to said piglet.

Also, the protein of the further consideration or the composition of the further consideration is provided for any of the above uses wherein said animal is a sow; and wherein the protein of the further consideration or a composition of the further consideration is administered twice to said sow; and wherein said use does not include the administration of any other PCV3 antigen to said animal before or during the administration of said protein of the further consideration or composition of the further consideration.

Also, the protein of the further consideration or the composition of the further consideration is provided for any of the above uses wherein said animal is a sow; and wherein the protein of the further consideration or the composition of the further consideration is administered twice to said sow; and wherein said use does not include the administration of any other PCV3 antigen to said animal before or during the administration of said protein of the further consideration or the composition of the further consideration.

Also, the protein of the further consideration or the composition of the further consideration is provided for any of the above uses wherein said animal is a sow; and wherein the protein of the further consideration or the composition of the further consideration is administered only twice to said sow; and wherein said use does not include the administration of any other PCV3 antigen to said animal before or during the administration of said protein of the further consideration or the composition of the further consideration.

Also, the protein of the further consideration or the composition of the further consideration is provided for any of the above uses wherein said animal is a piglet; and wherein the protein of the further consideration or the composition of the further consideration is administered once to said piglet; and wherein said use does not include the administration of any other PCV3 antigen to said animal before or during the administration of said protein of the further consideration or the composition of the further consideration.

Also, the protein of the further consideration or the composition of the further consideration is provided for any of the above uses wherein said animal is a piglet; and wherein the protein of the further consideration or the composition of the further consideration is administered once to said piglet; and wherein said use does not include the administration of any other PCV3 antigen to said animal before or during the administration of said protein of the further consideration or the composition of the further consideration.

Also, the protein of the further consideration or the composition of the further consideration is provided for any of the above uses wherein said animal is a piglet; is administered only once to said piglet; and wherein said use does not include the administration of any other PCV3 antigen to said animal before or during the administration of said protein of the further consideration or the composition of the further consideration.

Also, the protein of the further consideration or the composition of the further consideration is provided for any of the above uses wherein the administration to the animal in the use consists of a single, one shot administration or a single, one dose administration of said protein of the further consideration or the composition of the further consideration.

Also, the protein of the further consideration or the composition of the further consideration is provided for any of the above uses wherein the administration to the animal in the use consists of a multi-shot or multi-dose regimen of said protein of the further consideration or the composition of the further consideration.

Also, the protein of the further consideration or the composition of the further consideration is provided for any of the above uses wherein the administration to the animal in the use consists of a double shot administration; or a dual dose administration of said protein of the further consideration or the composition of the further consideration.

Also, the protein of the further consideration or the composition of the further consideration is provided for any of the above uses wherein the administration to the animal occurs within at least 1 or 2 or 3 weeks of exposure to virulent Porcine *Circovirus*.

Also, the protein of the further consideration or the composition of the further consideration is provided wherein the animal is a piglet not older than 15 weeks of age, or not older than 6 weeks of age, or not older than 3 weeks of age, or not older than 2 weeks of age, or not older than 1 week of age.

Also, the protein of the further consideration or the composition of the further consideration is provided for any of the above uses wherein said protein of the further consideration is for any of the above uses.

Also, the protein of the further consideration or the composition of the further consideration is provided for any of the above uses wherein said protein of the further consideration is for the use of two or more uses mentioned above.

Also, the protein of the further consideration or the composition of the further consideration is provided for any of the above uses wherein said composition of the further consideration is for any of the above uses.

Also, the protein of the further consideration or the composition of the further consideration is provided for any of the above uses wherein a second antigen is administered to the animal before administration of the protein of the further consideration or the composition of the further consideration.

Also, the protein of the further consideration or the composition of the further consideration is provided for any of the above uses wherein a second antigen is administered to the animal at the same time as administration of the protein of the further consideration or a composition of the further consideration.

Also, the protein of the further consideration or the composition of the further consideration is provided for any of the above uses wherein a second antigen is administered to the animal at the same time and in the same composition as administration of the protein of the further consideration or the composition of the further consideration.

Also, the protein of the further consideration or the composition of the further consideration is provided for any of the above uses wherein a second antigen is administered to the animal at the same time and in a different composition as administration of the protein of the further consideration or the composition of the further consideration.

Also, the protein of the further consideration or the composition of the further consideration is provided for any of the above uses wherein a second antigen is administered to the animal after the administration of the protein of the further consideration or a composition of the further consideration.

Also, the protein of the further consideration or the composition of the further consideration is provided for use in the vaccination of a pig to lessen the severity of clinical signs or clinical symptoms resulting from PCV3 infection in the pig, wherein the protein is in an immunogenic composition that is administered in one dose to the pig.

Also, the protein of the further consideration or the composition of the further consideration is provided for use in the vaccination of a pig to lessen the severity of clinical signs or clinical symptoms resulting from PCV3 infection in the pig, wherein the protein is in an immunogenic composition that is administered in only one dose to the pig.

Also, the protein of the further consideration or the composition of the further consideration is provided for use in the vaccination of a pig to lessen the severity of clinical signs or clinical symptoms resulting from PCV3 infection in the pig, wherein the protein is in an immunogenic composition that is administered in two doses to the pig.

Also, the protein of the further consideration or the composition of the further consideration is provided for use in the vaccination of a pig to lessen the severity of clinical signs or clinical symptoms resulting from PCV3 infection in the pig, wherein the protein is in an immunogenic composition that is administered in only two doses to the pig.

Also, the protein of the further consideration or the composition of the further consideration is provided for use as the single PCV3 antigen for vaccination of a pig to lessen the severity of clinical signs or clinical symptoms resulting from PCV3 infection in the pig, wherein the protein is in an immunogenic composition that is administered in one dose to the pig.

Also, the protein of the further consideration or the composition of the further consideration is provided for use as the single PCV3 antigen for vaccination of a pig to lessen the severity of clinical signs or clinical symptoms resulting from PCV3 infection in the pig, wherein the protein is in an immunogenic composition that is administered in only one dose to the pig.

Also, the protein of the further consideration or the composition of the further consideration is provided for use as the single PCV3 antigen for vaccination of a pig to lessen the severity of clinical signs or clinical symptoms resulting from PCV3 infection in the pig, wherein the protein is in an immunogenic composition that is administered in two doses to the pig.

Also, the protein of the further consideration or the composition of the further consideration is provided for use as the single PCV3 antigen for vaccination of a pig to lessen the severity of clinical signs or clinical symptoms resulting from PCV3 infection in the pig, wherein the protein is in an immunogenic composition that is administered in only two doses to the pig.

Also, the protein of the further consideration or the composition of the further consideration is provided for lessening the severity of clinical signs or clinical symptoms resulting from PCV3 infection in a pig;

wherein one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein of the further consideration is the antigenic component in the one dose of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

Also provided herein is an immunogenic composition of the further consideration for lessening the severity of clinical signs or clinical symptoms resulting from PCV3 infection in a pig;

wherein only one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein of the further consideration is the antigenic component in the one dose of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

Also, the protein of the further consideration or the composition of the further consideration is provided for lessening the severity of clinical signs or clinical symptoms resulting from PCV3 infection in a pig;

wherein two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessens the severity of clinical signs or clinical symptoms resulting from PCV3 infection in the pig;

wherein the protein of the further consideration is the antigenic component in the two doses of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

Also, an immunogenic composition of the further consideration is provided for lessening the severity of clinical signs or clinical symptoms resulting from PCV3 infection in a pig;

wherein only two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessens the severity of clinical signs or clinical symptoms resulting from PCV3 infection in the pig;

wherein the protein of the further consideration is the antigenic component in the two doses of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

Preferably, in any of the above-mentioned uses, said clinical signs or symptoms are selected from the group consisting of reduction of average daily weight gain and mortality.

Preferably, in any of the above-mentioned uses, said clinical signs or symptoms are selected from the group consisting of gross lesions, histological lesions, replication of PCV3 in a tissue, and PCV3 viremia.

Preferably, in any of the above-mentioned uses, said clinical signs or symptoms are selected from the group consisting of development or production of a mummified, stillborn and/or weak fetus.

Preferably, in any of the above-mentioned uses, said clinical signs or symptoms is or include expelling of a mummified, stillborn and/or weak fetus.

The present invention will now be described by way of the following sets of clauses. For ease of reference, these sets of clauses have been labelled Clause Set A, Clause Set B etc. The disclosure in each set of clauses is equally applicable to the present invention. Likewise the disclosure in each set of clauses is equally applicable to every other set of clauses:

Clause Set A:

Clause Set A—The present invention will now be described by way of the following set of numbered clauses (Clause Set A). The disclosure in this set of clauses is equally applicable to the present invention. Likewise the disclosure in this set of clauses is equally applicable to each of the other set of clauses.

1. A composition comprising:
porcine *circovirus* type 3 (PCV3) ORF2 protein; and
a veterinary-acceptable carrier comprising a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral or expression vector, and an immunomodulatory agent or any combination thereof.

2. The composition of clause 1, wherein the veterinary-acceptable carrier comprises an adjuvant, immunomodulatory agent, cell culture supernatant, viral or expression vector or any combination thereof.

3. The composition of clause 1, wherein the veterinary-acceptable carrier comprises an adjuvant.

4. The composition of any of clauses 1-3, wherein the PCV3 ORF2 is from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4).

5. The composition of any of clauses 1-3, wherein the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 sequence identity or sequence homology with SEQ ID NO:1.

6. The composition of any of clauses 1-5, wherein the PCV3 ORF2 protein is a recombinant PCV3 ORF2 protein from expression thereof by an expression vector, comprising a polynucleotide sequence that encodes the PCV3 ORF2 protein.

7. The composition of clause 6, wherein the expression vector is a baculovirus.

8. The composition of any one of clauses 1-7, further comprising a PCV2 ORF2 protein.

9. The composition of clause 8, wherein the PCV2 ORF2 protein is from expression by an expression vector, comprising a polynucleotide sequence that encodes the PCV2 ORF2 protein.

10. The composition of clause 9, wherein the expression vector is a baculovirus.

11. The composition of any one of clauses 1-10, further comprising an additional antigen of an additional porcine pathogen.

12. The composition of clause 11, wherein the additional antigen of an additional porcine pathogen comprises a PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, or a *Pasteurella multocida* antigen.

13. The composition of any of clauses 1-12, wherein the PCV3 ORF2 protein is present in an amount of 0.2 to about 400 µg/ml, or about 0.3 to about 200 µg/ml, or about 0.35 to about 100 µg/ml, or about 0.4 to about 50 µg/ml, or about 0.45 to about 30 µg/ml, or about 0.6 to about 15 µg/ml, or about 0.75 to about 8 µg/ml, or about 1.0 to about 6 µg/ml, or about 1.3 to about 3.0 µg/ml, or about 1.4 to about 2.5 µg/ml, or about 1.5 to about 2.0 µg/ml, or about 1.6 µg/ml.

14. The composition of any of clauses 1-12, wherein the PCV3 ORF2 protein or total PCV2 and PCV3 ORF2 proteins are present in an amount of about 0.2 to about 400 µg/dose, or about 0.3 to about 200 µg/dose, or about 0.35 to about 100 µg/dose, or about 0.4 to about 50 µg/dose, or about 0.45 to about 30 µg/dose, or about 0.6 to about 15 µg/dose, or about 0.75 to about 8 µg/dose, or about 1.0 to about 6 µg/dose, or about 1.3 to about 3.0 µg/dose, or about 1.4 to about 2.5 µg/dose, or about 1.5 to about 2.0 µg/dose, or about 1.6 µg/dose.

15. The composition of any one of clauses 1-14, wherein the adjuvant comprises aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, a Carbopol®; Carbopol® 974P; Carbopol® 934P; Carbopol® 971P; a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; RIBI® adjuvant system; Block copolymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

16. The composition of any one of clauses 1-15, comprising from about 50 µg to about 2000 µg of adjuvant; or wherein adjuvant present in an amount about 250 µg/ml dose of the composition, or wherein the adjuvant is present in an amount of about 100 µg to about 10 mg per dose; or wherein the adjuvant is present in an amount of about 500 µg to about 5 mg per dose; the adjuvant is present in an amount of about 750 µg to about 2.5 mg per dose; or the adjuvant is present in an amount of about 1 mg per dose.

17. The composition of any one of clauses 1-16, wherein immunomodulatory agent comprises interleukin(s), interferon(s), or other cytokine(s), or keyhole limpet hemocyanin (KLH), or KLH emulsified with incomplete Freund's adjuvant (KLH/ICFA).

18. The composition of any one of clauses 1-17, wherein comprising from about 1 ug/ml to about 60 µg/ml of antibiotic(s), or less than about 30 µg/ml of antibiotic(s).

19. The composition of any one of clauses 1-18, wherein the antibiotic(s) comprise Gentamicin.

20. The composition of any one of clauses 1-19, comprising (i) PCV3 ORF2 protein, (ii) at least a portion of baculovirus that expressed said PCV3 ORF2 protein, (iii) a portion of cell culture of cells that were infected or transfected with recombinant baculovirus that expressed said PCV3 ORF2 protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.

21. The composition of clause 20, wherein about 90% of the components (i) to (iii) have a size smaller than 1 m and the pH of said composition is adjusted to about 6.5 to 7.5

22. The composition of clauses 20 or 21 wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.

23. The composition of any one of clauses 1-22, formulated and/or packaged for a single dose or one shot administration, and not a multi-dose regimen.

24. A method for eliciting an immune response or an immunological response or a protective immune or immunological response against (i) PCV3 and/or (ii) PCV2 and PCV3 and/or (iii) PCV3 and another porcine pathogen and/or (iv) PCV3, PCV2 and another porcine pathogen, comprising administering to an animal a composition as defined in any of clauses 1-23.

25. The method of clause 25 wherein the animal is a porcine.

26. The method of clause 25, wherein the porcine is a pig or piglet.

27. The method of clause 26, wherein the pig or piglet is not older than 15 weeks of age, or not older than 6 weeks of age, or not older than 3 weeks of age, or not older than 2 weeks of age, or not older than 1 week of age.

28. The method of clause 26, wherein the administration occurs within at least 1 or 2 or 3 weeks of exposure to virulent Porcine *Circovirus*.

29. The method of any one of clauses 24-28, wherein the administration comprises a single, one shot administration; or a single, one dose administration; and not a multi-shot or multi-dose regimen.

30. Use of a composition of any one of clauses 1-23 in a method of any one of clauses 24-29; or use of a PCV3 ORF2 protein, alone or in combination, of any one of the compositions of clauses 1-23, for use in the preparation of a composition for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen, or for use in a method for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen.

31. A method for preparing a composition as defined in any one of clauses 1-23, comprising producing the PCV3 ORF2 protein by a baculovirus expression system in cultured insect cells.

32. The method of clause 31, including inactivating the baculovirus.

33. The method of clause 32, wherein the inactivating comprises heat treatment or use of a virus inactivating agent.

34. The method of clause 25, wherein the virus inactivating agent comprises an aziridine compound.

35. The method of clause 26, wherein the aziridine compound comprises BEI.

36. A recombinant vector comprising a polynucleotide sequence that encodes a polypeptide sequence that encodes a PCV3 ORF2 protein.

37. The recombinant vector of clause 36, wherein the PCV3 ORF2 is from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4).

38. The recombinant vector of clause 36, wherein the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity or sequence homology with SEQ ID NO: 1.

39. The recombinant vector of any of clauses 36-38, wherein the recombinant vector is a baculovirus.

40. The recombinant vector of clause 39, wherein the recombinant vector comprises at least 90% or at least 91%, or at least 92%, or at least 93%, or at least 94%, or at least 95%, or at least 96%, or at least 97%, or at least 98%, or at least 99%, or 100% sequence identity or sequence homology with SEQ ID NO:2.

CLAUSE SET B:

Clause Set B—The present invention will now be described by way of the following set of numbered clauses (Clause Set B). The disclosure in this set of clauses is equally applicable to the present invention. Likewise the disclosure in this set of clauses is equally applicable to each of the other set of clauses.

1. A composition comprising a porcine *circovirus* type 3 (PCV3) ORF2 protein, preferably an antigenic PCV3 ORF2 protein (a PCV3 ORF2 antigen).

2. The composition of clause 1, further comprising a veterinary-acceptable carrier selected from the group consisting of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, an immunomodulatory agent, and/or any combination thereof.

3. A composition, in particular the composition of clause 1 or 2, comprising: porcine *circovirus* type 3 (PCV3) ORF2 protein; and a veterinary-acceptable carrier comprising a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral or expression vector, an immunomodulatory agent and/or any combination thereof.

4. The composition of any one of clauses 1 to 3, wherein the veterinary-acceptable carrier comprises an adjuvant, immunomodulatory agent, cell culture supernatant, viral or expression vector or any combination thereof.

5. The composition of any one of clauses 1 to 4, wherein the veterinary-acceptable carrier comprises an adjuvant.

6. The composition of any of clauses 1 to 5, wherein the PCV3 is selected from the group consisting of PCV3a and PCV3b.

7. The composition of any of clauses 1 to 6, wherein the PCV3 is any phylogenetic clade of PCV3 or selected from the group consisting PCV3al, PCV3b1, PCV3b2 and PCV3c.

8. The composition of any of clauses 1 to 7, wherein the PCV3 ORF2 is from group a1, b1 or b2.

9. The composition of any of clauses 1 to 8, wherein the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:1.

10. The composition of any of clauses 1-9, wherein the PCV3 ORF2 protein comprises or consists of an amino acid sequence having at least 90% sequence identity with the sequence of SEQ ID NO: 4.

11. The composition of any of clauses 1 to 10, wherein the PCV3 ORF2 protein is a recombinant PCV3 ORF2 protein.

12. The composition of any of clauses 1 to 11, wherein the PCV3 ORF2 protein is a recombinant PCV3 ORF2 protein from expression thereof by an expression vector, comprising a polynucleotide sequence that encodes the PCV3 ORF2 protein.

13. The composition of clause 12, wherein the expression vector is a baculovirus.

14. The composition of any of clauses 1 to 13, wherein the PCV3 ORF2 protein is a recombinant baculovirus expressed PCV3 ORF2.

15. The composition of any one of clauses 1 to 14, further comprising a PCV2 ORF2 protein, preferably an antigenic PCV2 ORF2 protein (a PCV2 ORF2 antigen).

16. The composition of clause 15, wherein the PCV2 ORF2 protein is from expression by an expression vector, comprising a polynucleotide sequence that encodes the PCV2 ORF2 protein.

17. The composition of clause 16, wherein the expression vector is a baculovirus.

18. The composition of any one of clauses 1 to 17, further comprising an additional antigen of an additional porcine pathogen.

19. The composition of clause 18, wherein the additional antigen of an additional porcine pathogen comprises a PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen, or a combination thereof.

20. The composition of any of clauses 1 to 19, wherein the PCV3 ORF2 protein is present in an amount of 0.2 to about 400 µg/ml, or about 0.3 to about 200 µg/ml, or about 0.35 to about 100 µg/ml, or about 0.4 to about 50 µg/ml, or about 0.45 to about 30 µg/ml, or about 0.6 to about 15 µg/ml, or about 0.75 to about 8 µg/ml, or about 1.0 to about 6 µg/ml, or about 1.3 to about 3.0 µg/ml, or about 1.4 to about 2.5 µg/ml, or about 1.5 to about 2.0 µg/ml, or about 1.6 µg/ml.

21. The composition of any of clauses 1 to 20, wherein the PCV3 ORF2 protein or total PCV2 and PCV3 ORF2 proteins are present in an amount of about 0.2 to about 400 µg/dose, or about 0.3 to about 200 µg/dose, or about 0.35 to about 100 µg/dose, or about 0.4 to about 50 µg/dose, or about 0.45 to about 30 µg/dose, or about 0.6 to about 15 ag/dose, or about 0.75 to about 8 ag/dose, or about 1.0 to about 6 µg/dose, or about 1.3 to about 3.0 µg/dose, or about 1.4 to about 2.5 µg/dose, or about 1.5 to about 2.0 µg/dose, or about 1.6 µg/dose.

22. The composition of any one of clauses 2 to 21, wherein the adjuvant comprises a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

23. The composition of any one of clauses 2 to 22, comprising from about 50 µg to about 2000 µg of adjuvant; or wherein adjuvant present in an amount about 250 µg/ml dose of the composition, or wherein the adjuvant is present in an amount of about 100 µg to about 10 mg per dose; or wherein the adjuvant is present in an amount of about 500 µg to about 5 mg per dose; the adjuvant is present in an amount of about 750 µg to about 2.5 mg per dose; or the adjuvant is present in an amount of about 1 mg per dose.

24. The composition of any one of clauses 2 to 23, wherein immunomodulatory agent comprises interleukin(s), interferon(s), or other cytokine(s).

25. The composition of any one of clauses 1 to 24, wherein said composition comprises from about 1 ug/ml to about 60 µg/ml of antibiotic(s), or less than about 30 µg/ml of antibiotic(s).

26. The composition of any one of clauses 1 to 25, wherein the antibiotic(s) comprise Gentamicin.

27. The composition of any one of clauses 1 to 26, comprising (i) PCV3 ORF2 protein, (ii) at least a portion of baculovirus that expressed said PCV3 ORF2 protein, (iii) a portion of cell culture of cells that were infected or transfected with recombinant baculovirus that expressed said PCV3 ORF2 protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.

28. The composition of clause 27, wherein about 90% of the components (i) to (iii) have a size smaller than 1 m and the pH of said composition is adjusted to about 6.5 to 7.5.

29. The composition of clauses 27 or 28 wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.

30. The composition of any one of clauses 1 to 29, wherein said composition is formulated and/or packaged for a single dose or one shot administration of the composition, and not a multi-dose regimen; or wherein said composition is formulated and/or packaged for a multi-dose regimen of the composition.

31. The composition of any one of clauses 1 to 30, wherein the composition is an immunogenic composition.

32. The composition of any one of clauses 1 to 31 for use as a medicament.
33. The composition of any one of clauses 1 to 31 for use as a vaccine.
34. The composition of any one of clauses 1 to 31 for use in a method for eliciting an immune response or an immunological response or a protective immune or immunological response against (i) PCV3 and/or (ii) PCV2 and PCV3 and/or (iii) PCV3 and another porcine pathogen and/or (iv) PCV3, PCV2 and another porcine pathogen.
35. The composition of any one of clauses 1 to 31 for use in a method of reducing or preventing the clinical signs or disease caused by an infection with PCV3 in an animal or for use in a method of treating or preventing an infection with PCV3 in an animal, and wherein said animal is preferably a pig.
36. The composition of any one of clauses 1 to 31 for use in a method for inducing an immune response against PCV3 in a pig, in particular in a preferably pregnant sow.
37. The composition of any one of clauses 1 to 31 for use in a method of reducing or preventing the clinical signs or disease caused by an infection with a PCV3 in a piglet, wherein the piglet is to be suckled by a sow to which the composition has been administered.
38. The composition for use according to clause 37, wherein said sow to which the composition has been administered is a sow to which the immunogenic composition has been administered while said sow has been pregnant, in particular with said piglet, or a pre-breeding gilt.
39. The composition for use according to any one of clauses 32 to 38, wherein said composition is to be administered intramuscularly or intradermally.
40. The composition for use according to any one of clauses 36 to 39, wherein said composition is to be administered intramuscularly or intradermally to said sow.
41. A method for eliciting an immune response or an immunological response or a protective immune or immunological response against (i) PCV3 and/or (ii) PCV2 and PCV3 and/or (iii) PCV3 and another porcine pathogen and/or (iv) PCV3, PCV2 and another porcine pathogen, comprising administering to an animal a composition as claused in any of clauses 1 to 31.
42. The method of clause 41 wherein the animal is a porcine.
43. The method of clause 42, wherein the porcine is a pig or piglet.
44. The method of clause 42 or 43, wherein the porcine is a sow.
45. A method of immunizing a subject comprising administering to the subject a composition according to any one of clauses 1 to 31.
46. A method of immunizing swine against a clinical disease caused by at least one pathogen in said animal, said method comprising the step of administering to the animal the composition according to any one of clauses 1 to 31, wherein said immunogenic composition fails to cause clinical signs of infection but is capable of inducing an immune response that immunizes the animal against pathogenic forms of said at least one pathogen.
47. The method of clause 46, wherein said at least one pathogen is PCV3.
48. A method for inducing the production of antibodies specific for PCV3 in a sow, wherein said method comprises administering the composition according to any one of clauses 1 to 31 to said sow.
49. A method of reducing or preventing the clinical signs or clinical symptoms caused by an infection with a PCV3 in a piglet, wherein said method comprises administering the composition according to any one of clauses 1 to 31 to a sow, and allowing said piglet to be suckled by said sow.
50. The method of clause 49, wherein said sow is a sow being pregnant, in particular with said piglet, or a pre-breeding gilt.
51. The method of clause 49 or 50, comprising the steps of administering the composition according to any one of clauses 1 to 31 to a sow being pregnant with said piglet, allowing said sow to give birth to said piglet, and allowing said piglet to be suckled by said sow.
52. A method of reducing the clinical signs and/or clinical symptoms caused by an infection with a PEDV in a piglet, wherein the piglet is to be suckled by a sow to which the composition of any one of clauses 1 to 31 has been administered.
53. The method of any one of clauses 45 to 52, wherein said immunogenic composition or said vaccine or pharmaceutical composition is administered intramuscularly or intradermally to said sow.
54. The method of any one of clauses 45 to 53, wherein said immunogenic composition or said vaccine or pharmaceutical composition is administered twice to said sow.
55. The method of any one of clauses 45 to 54, wherein said immunogenic composition or said vaccine or pharmaceutical composition is administered twice mucosally, preferably twice intranasally, to said sow.
56. The composition for use according to any one of clauses 32-40 or the method of any one of clauses 41 to 55, wherein said clinical signs are selected from the group consisting of reduction of average daily weight gain and mortality.
57. The composition for use according to any one of clauses 32-40 or the method of any one of clauses 41 to 55, wherein the clinical signs are selected from the group consisting of expelling of a mummified, stillborn and/or weak fetus.
58. The composition for use according to any one of clauses 32 to 40 or the method of any one of clauses 41 to 55, wherein the clinical symptoms are selected from the group consisting of, gross lesions, histologic lesions, replication of PCV3 in a tissue, and PCV3 viremia.
59. The composition for use according to any one of clauses 32 to 40 or the method of any one of clauses 41 to 55, wherein the clinical symptoms are selected from the group consisting of development or production of a mummified, stillborn and/or weak fetus.
60. The composition for use according to any one of clauses 32 to 40 or the method of any one of clauses 41 to 55, wherein the pig or piglet is not older than 15 weeks of age, or not older than 6 weeks of age, or not older than 3 weeks of age, or not older than 2 weeks of age, or not older than 1 week of age.
61. The method of clause 60, wherein the administration occurs within at least 1 or 2 or 3 weeks of exposure to virulent Porcine *Circovirus*.
62. The composition for use according to any one of clauses 32 to 41 or the method of any one of clauses 42 to 55, wherein the administration comprises a single, one shot administration; or a single, one dose administration of the composition; and not a multi-shot or multi-dose regimen; or wherein the administration consists of a single, one shot administration; or a single, one dose administration; and not a multi-shot or multi-dose regimen; or wherein the administration comprises a multi-shot or multi-dose regimen of the composition; or wherein the administration comprises a two-shot or two-dose regimen of the composition or wherein the administration consists of a two-shot or two-dose regimen of the composition.

63. Use of a composition of any one of clauses 1 to 31 in a method of any one of clauses 42-55; or use of a PCV3 ORF2 protein, alone or in combination, of any one of the compositions of clauses 1 to 31, for use in the preparation of a composition for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen, or for use in a method for inducing an immunological or immune response or a protective immune or immunological response against (i) PCV3 and/or (ii) PCV2 and PCV3 and/or (iii) PCV3 and another porcine pathogen and/or (iv) PCV3, PCV2 and another porcine pathogen.

64. A method for preparing a composition as claused in any one of clauses 1 to 31, comprising producing the PCV3 ORF2 protein by a baculovirus expression system in cultured insect cells.

65. The method of clause 64, including inactivating the baculovirus.

66. The method of clause 65, wherein the inactivating comprises heat treatment or use of a virus inactivating agent.

67. The method of clause 66, wherein the virus inactivating agent comprises an aziridine compound.

68. The method of clause 67, wherein the aziridine compound comprises BEI.

69. A recombinant vector comprising a polynucleotide sequence that encodes a polypeptide sequence that encodes a PCV3 ORF2 protein.

70. The recombinant vector of clause 69, wherein the PCV3 ORF2 is from group a1, b1 or b2.

71. A composition comprising a (i) porcine *circovirus* type 3 (PCV3) ORF2 protein, a parvovirus (PPV) protein and optionally a PRRSV (porcine respiratory and reproductive syndrome virus) protein and (ii) a veterinary-acceptable carrier selected from the group consisting of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, an immunomodulatory agent, and/or any combination thereof.

72. The composition of clause 71, wherein the veterinary-acceptable carrier comprises an adjuvant, immunomodulatory agent, cell culture supernatant, viral or expression vector or any combination thereof.

73. The composition of clause 71 or 72, wherein the PPV protein is a PPV VP2 capsid protein.

74. The composition of any one of clauses 71 to 73, wherein the PRRSV protein is a PRRSV ORF4, ORF5, ORF6, or ORF7.

75. The composition of clause 73 or 74, wherein the PPV protein and/or the PRRSV protein is expressed in a vector.

76. The composition of any one of clauses 71 to 75 wherein the composition is an immunogenic composition administered in two doses to a porcine.

77. The composition of clause 76, wherein the porcine is a gilt or a sow.

78. The composition of clause 76 or 77, wherein the administrating is before mating/semination, before pregnancy, during pregnancy or during lactation.

79. The composition of any one of clauses 76-78, wherein the immunogenic composition comprises between 0.1 µg and 150 µg, preferably between 0.25 µg and 75 µg, more preferably between 0.5 µg and 37.5 µg, even more preferably between 0.5 µg and 15 µg, most preferably between 0.5 µg and 6 µg of the PCV3, PPV and/or PRRSV antigen.

80. The composition of any one of clauses 76-79, wherein the immunogenic composition is administered intramuscularly.

81. A method for eliciting an immune response or an immunological response or a protective immune or immunological response against porcine *circovirus* 3 (PCV3) comprising parenterally or subcutaneously administering to a porcine of a single shot, single administration or single dose (i) at least 2 µg to about 400 µg of a PCV3 ORF2 recombinant protein expressed by a baculovirus system and (ii) a veterinary-acceptable carrier comprising a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral or expression vector, an immunomodulatory agent and/or any combination thereof.

82. The method of clause 81, wherein the porcine is a piglet, pig or a sow, or a pre-breeding gilt.

83. The method of clause 81 or clause 82, wherein the porcine is about 1 week or 2 weeks or 3 weeks of age or 7-28 or 7-22 or 14-22 or 16-22 or 21+/−5 days of age.

84. The method of any one of clauses 81 to 83, wherein the veterinary-acceptable carrier comprises an adjuvant, immunomodulatory agent, cell culture supernatant, viral or expression vector or any combination thereof.

85. The method of any one of clauses 81 to 84, wherein the PCV3 ORF2 is any phylogenetic clade of PCV3 or from group PCV3a, PCV3a1, PCV3b, PCV3b1, or PCV3b.

86. The method of any one of clauses 81 to 85, wherein the PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:1, SEQ ID NO: 6 or SEQ ID NO: 7.

87. The method of any one of clauses 81 to 86, wherein the single shot, single administration or single dose further comprises a PCV2 ORF2 protein or an additional antigen of an additional porcine pathogen.

88. The method of clause 87, wherein the additional antigen of an additional porcine pathogen comprises a PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen, or a combination thereof.

89. The method of any one of clauses 81 to 88, wherein the adjuvant comprises a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

90. The method of any one of clauses 81 to 89, wherein the PCV3 ORF2 protein is present in an amount of 0.2 to about 400 μg/ml, or about 0.3 to about 200 μg/ml, or about 0.35 to about 100 g/ml, or about 0.4 to about 50 μg/ml, or about 0.45 to about 30 μg/ml, or about 0.6 to about 15 g/ml, or about 0.75 to about 8 μg/ml, or about 1.0 to about 6 μg/ml, or about 1.3 to about 3.0 g/ml, or about 1.4 to about 2.5 μg/ml, or about 1.5 to about 2.0 μg/ml, or about 1.6 μg/ml.

91. The method of clause 87, wherein the PCV3 ORF2 protein or total PCV2 and PCV3 ORF2 proteins are present in an amount of about 0.2 to about 400 μg/dose, or about 0.3 to about 200 μg/dose, or about 0.35 to about 100 μg/dose, or about 0.4 to about 50 μg/dose, or about 0.45 to about 30 μg/dose, or about 0.6 to about 15 μg/dose, or about 0.75 to about 8 μg/dose, or about 1.0 to about 6 μg/dose, or about 1.3 to about 3.0 μg/dose, or about 1.4 to about 2.5 μg/dose, or about 1.5 to about 2.0 μg/dose, or about 1.6 μg/dose.

92. The method of any one of clauses 81 to 91, comprising from about 50 μg to about 2000 μg of adjuvant; or wherein adjuvant present in an amount about 250 μg/ml dose of the composition, or wherein the adjuvant is present in an amount of about 100 μg to about 10 mg per dose; or wherein the adjuvant is present in an amount of about 500 μg to about 5 mg per dose; the adjuvant is present in an amount of about 750 μg to about 2.5 mg per dose; or the adjuvant is present in an amount of about 1 mg per dose.

93. The method of any one of clauses 82 to 92, wherein the immunomodulatory agent comprises an interleukin, an interferon or other cytokine.

94. The method of any one of clauses 81 to 93, wherein the single shot, single administration or single dose further comprises from about 1 ug/ml to about 60 μg/ml of antibiotic(s), or less than about 30 μg/ml of an antibiotic.

95. The method of clause 84, wherein the antibiotic comprises Gentamicin.

96. The method of any one of clauses 81 to 95, wherein the single shot, single administration or single dose comprises (i) PCV3 ORF2 protein, (ii) at least a portion of baculovirus that expressed said PCV3 ORF2 protein, (iii) a portion of cell culture of cells that were infected or transfected with recombinant baculovirus that expressed said PCV3 ORF2 protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.

97. The method of clause 96, wherein about 90% of the components (i) to (iii) have a size smaller than 1 m and the pH of said composition is adjusted to about 6.5 to 7.5.

98. The method of clause 96 or 97, wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.

99. The method of any one of clauses 81 to 98, wherein the method further comprises reducing or preventing clinical signs or disease caused by a PCV3 or porcine epidemic diarrhea virus (PEDV) infection in a pregnant sow or a piglet.

100. The method of clause 99, wherein the reducing or preventing clinical signs or disease in the piglet comprises the piglet suckling a sow administered with the single shot, single administration or single dose.

101. The method of clause 99, wherein the reducing or preventing clinical signs or disease in the piglet comprises administering the single shot, single administration or single dose to the pregnant sow.

102. The method of clause 101, further comprising the piglet suckling the sow after the sow has given birth to the piglet.

103. The method of any one of clauses 99 to 102, wherein the clinical sign is reduction of average daily weight gain, mortality, development, production or expelling of a mummified, stillborn and/or weak fetus, a gross lesion, a histologic lesion, replication of PCV3 in a tissue or PCV3 viremia.

104. The method of any one of clauses 81 to 103, wherein the parenterally or subcutaneously administering is intramuscular or intradermal.

105. A non-naturally occurring PCV3 ORF2protein comprising an engineered FG loop, wherein the FG loop comprises three or fewer positively charged amino acids.

106. The PCV3 ORF2 protein of clause 105, wherein the FG loop comprises two positively charged amino acids.

107. The PCV3 ORF2 protein of clause 105, wherein the FG loop comprises one positively charged amino acid.

108. The PCV3 ORF2 protein of clause 105, wherein the FG loop lacks positively charged amino acids.

109. The PCV3 ORF2 protein of clause 105, wherein the FG loop lacks arginine and lysine residues.

110. The PCV3 ORF2 protein of clause 105, wherein the FG loop lacks arginine, lysine, and histidine residues.

111. The PCV3 ORF2 protein of clause 105, wherein the FG loop comprises QPFSYH (SEQ ID NO: 17), LSRGF (SEQ ID NO: 18), or MASGF (SEQ ID NO: 19).

112. A non-naturally occurring PCV3 ORF2protein comprising an engineered C-terminal extension.

113. The PCV3 ORF2 protein of clause 112, wherein the C-terminal extension comprises from about 1 to about 10, from about 5 to about 20, or from about 10 to about 30 amino acids.

114. The PCV3 ORF2 protein of clause 112, wherein the C-terminal extension comprises from about 1 to about 10, or from about 5 to about 20, or from about 10 to 30 amino acids, about 50 to about 200 amino acids, about 60 to about 190 amino acids, about 70 to about 180 amino acids, about 80 to about 170 amino acids, about 90 to about 160 amino acids or about 100 to about 150 amino acids.

115. The PCV3 ORF2 protein of clause 112, wherein the C-terminal extension comprises C-terminal amino acids from a different capsid protein.

116. The PCV3 ORF2 protein of clause 115, wherein the C-terminal extension comprises C-terminal amino acids from a PCV2 capsid, as BFDV capsid, or a CaCV capsid.

117. The PCV3 ORF2 protein of clause 112, wherein the C-terminal extension comprises EFNLKDPPLN (SEQ ID NO: 20), PK, or QFAPNNPSTEFDYETGRQL (SEQ ID NO: 21).

118. A method of making a self-assembling PCV3 ORF2 capsid protein, which comprises substituting one or more arginine, lysine, or histidine amino acids in the FG loop with non-positively charged amino acids.

119. A method of enhancing self-assembly of a PCV3 ORF2 capsid protein, which comprises adding or inserting amino acid residues at the C-terminal of the protein.

120. The method of clause 118, which comprises adding or inserting from 1 to 10, or from about 5 to about 20, or from about 10 to about 30 amino acids, about 50 to about 200 amino acids, about 60 to about 190 amino acids, about 70 to about 180 amino acids, about 80 to about 170 amino acids, about 90 to about 160 amino acids or about 100 to about 150 amino acids.

121. The method of clause 119, which comprises adding or inserting amino acids from a different capsid protein.

122. The method of clause 121, wherein the added or inserted amino acids are from a PCV2 capsid, as BFDV capsid, or a CaCV capsid.

123. The method of clause 121, wherein the added or inserted amino acids comprise EFNLKDPPLN (SEQ ID NO: 20), PK, or QFAPNNPSTEFDYETGRQL (SEQ ID NO: 21).

124. A composition comprising the PCV protein of any one of clauses 105 to 117 or the protein produced by the method of any one of clauses 118 to 123 in an amount to elicit an immune response or a protective immune response against PCV3 and/or clinical symptoms thereof, from a single administration and a veterinary-acceptable carrier comprising a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral or expression vector, an immunomodulatory agent and/or any combination thereof.

125. The composition of clause 124, wherein the PCV3 ORF2 protein is encoded by SEQ ID NO: 6 or SEQ ID NO: 7.

126. The composition of clause 124 or 125, wherein the veterinary-acceptable carrier comprises an adjuvant, immunomodulatory agent, cell culture supernatant, viral or expression vector or any combination thereof.

127. The composition of any one of clauses 124 to 126 further comprising a PCV2 ORF2 protein, preferably an antigenic PCV2 ORF2 protein (a PCV2 ORF2 antigen), or an additional antigen of an additional porcine pathogen.

128. The composition of clause 127, wherein the additional antigen of an additional porcine pathogen comprises a PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen, or a combination thereof.

129. The composition of any one of clauses 124 to 128, wherein the adjuvant comprises a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

130. The composition of any one of clauses 124 to 129, wherein the PCV3 ORF2 protein is present in an amount of 0.2 to about 400 μg/ml, or about 0.3 to about 200 μg/ml, or about 0.35 to about 100 μg/ml, or about 0.4 to about 50 μg/ml, or about 0.45 to about 30 μg/ml, or about 0.6 to about 15 μg/ml, or about 0.75 to about 8 μg/ml, or about 1.0 to about 6 μg/ml, or about 1.3 to about 3.0 μg/ml, or about 1.4 to about 2.5 μg/ml, or about 1.5 to about 2.0 μg/ml, or about 1.6 μg/ml.

131. The composition of any one of clauses 124 to 130, wherein the PCV3 ORF2 protein or total PCV2 and PCV3 ORF2 proteins are present in an amount of about 0.2 to about 400 μg/dose, or about 0.3 to about 200 μg/dose, or about 0.35 to about 100 μg/dose, or about 0.4 to about 50 μg/dose, or about 0.45 to about 30 μg/dose, or about 0.6 to about 15 μg/dose, or about 0.75 to about 8 μg/dose, or about 1.0 to about 6 μg/dose, or about 1.3 to about 3.0 μg/dose, or about 1.4 to about 2.5 μg/dose, or about 1.5 to about 2.0 μg/dose, or about 1.6 μg/dose.

132. The composition of any one of clauses 124 to 131, comprising from about 50 μg to about 2000 μg of adjuvant; or wherein adjuvant present in an amount about 250 μg/ml dose of the composition, or wherein the adjuvant is present in an amount of about 100 μg to about 10 mg per dose; or wherein the adjuvant is present in an amount of about 500 μg to about 5 mg per dose; the adjuvant is present in an amount of about 750 μg to about 2.5 mg per dose; or the adjuvant is present in an amount of about 1 mg per dose.

133. The composition of any one of clauses 125 to 132, wherein the immunomodulatory agent comprises an interleukin, an interferon or other cytokine.

134. A vector containing and expressing the PCV protein of any one of clauses 105 to 117 or the protein produced by the method of any one of clauses 118 to 123.
135. The vector of clause 134 wherein the PCV protein is expressed by SEQ ID NO: 6 or SEQ ID NO: 7.
136. The vector of clause 134 or 135, wherein the vector is a baculovirus.
137. A method of preparing the composition of any one of clauses 125 to 133, comprising producing the PCV3 ORF2 protein by a baculovirus expression system in cultured insect cells.
138. The method of clause 137 further comprising inactivating the baculovirus.
139. The method of clause 138, wherein the inactivating comprises heat treatment or use of a virus inactivating agent.
140. The method of clause 139, wherein the virus inactivating agent comprises an aziridine compound.
141. The method of clause 140, wherein the aziridine compound comprises BEI.

Clause Set C:

Clause Set C—The present invention will now be described by way of the following set of numbered clauses (Clause Set C). The disclosure in this set of clauses is equally applicable to the present invention. Likewise the disclosure in this set of clauses is equally applicable to each of the other set of clauses.
1. A porcine *circovirus* type 3 (PCV3) antigenic protein, wherein said protein is PCV3 ORF2 protein or a functional antigenic variant thereof.
2. A protein according to clause 1 wherein said PCV3 ORF2 protein is a protein encoded by SEQ ID No. 1.
3. A protein according to clause 1 or clause 2 wherein said protein is a functional antigenic variant of PCV3 ORF2.
4. A protein according to any one of the preceding clauses wherein said protein is a functional antigenic variant of the protein encoded by SEQ ID No. 1.
5. A protein according to any one of the preceding clauses wherein said functional antigenic variant is capable of a higher yield of virus-like particles (VLPs) than the protein encoded by SEQ ID No. 1.
6. A protein according to any one of the preceding clauses wherein said functional antigenic variant is capable of a higher yield of VLPs than the protein encoded by SEQ ID No. 1 as determinable by Western blot analysis.
7. A protein according to any one of the preceding clauses wherein said functional antigenic variant has fewer positive charged amino acid residues than the protein encoded by SEQ ID No. 1.
8. A protein according to any one of the preceding clauses wherein said functional antigenic variant has one or more substitutions in the FG loop of the protein encoded by SEQ ID No. 1.
9. A protein according to any one of the preceding clauses wherein said functional antigenic variant has one or more substitutions in the FG loop of the protein encoded by SEQ ID No. 1, wherein those substitutions comprise substitutions of one or more of the S residue and/or the K residues and/or the H residue of the motif SKKKH (SEQ ID NO: 14) of the FG loop of the protein encoded by SEQ ID No. 1.
10. A protein according to any one of the preceding clauses wherein said functional antigenic variant has one or more substitutions in the FG loop of the protein encoded by SEQ ID No. 1, wherein those substitutions comprise substitutions of one or more of the S residue and/or the K residues of the motif SKKKH (SEQ ID NO: 14) of the FG loop of the protein encoded by SEQ ID No. 1.
11. A protein according to any one of the preceding clauses wherein said functional antigenic variant has one or more substitutions in the FG loop of the protein encoded by SEQ ID No. 1, wherein those substitutions comprise substitutions of the S residue or H residue and all of the K residues of the motif SKKKH (SEQ ID NO: 14) of the FG loop of the protein encoded by SEQ ID No. 1.
12. A protein according to any one of the preceding clauses wherein said functional antigenic variant has one or more substitutions in the FG loop of the protein encoded by SEQ ID No. 1, wherein those substitutions comprise a substitution of at least S and/or H and any K of the motif SKKKH (SEQ ID NO: 14) of the FG loop of the protein encoded by SEQ ID No. 1 with Q or P or F or S.
13. A protein according to any one of the preceding clauses wherein said functional antigenic variant has one or more substitutions in the FG loop of the protein encoded by SEQ ID No. 1, wherein those substitutions comprise substitution of the motif SKKK (SEQ ID NO: 11) within the motif SKKKH (SEQ ID NO: 14) of the FG loop of the protein encoded by SEQ ID No. 1 with QPFS (SEQ ID NO: 12) or substitution of the motif KKKH (SEQ ID NO: 15) within the motif SKKKH (SEQ ID NO: 14) of the FG loop of the protein encoded by SEQ ID No. 1 with QPFS (SEQ ID NO: 12).
14. A protein according to any one of the preceding clauses wherein said functional antigenic variant is encodable by all or part of SEQ ID Nos. 1, 2, 5, 6 or 7.
15. A protein according to any one of the preceding clauses wherein said functional antigenic variant is encoded by all or part of SEQ ID No. 1, 2, 5, 6 or 7.
16. A protein according to any one of the preceding clauses wherein said functional antigenic variant has a C terminal end extends beyond the terminal SVL sequence of the protein encoded by SEQ ID No. 1, preferably wherein said extension is all or includes a sequence from a circoviridae virus, and preferably wherein at least a part of said extension replaces the terminal SVL sequence of the protein encoded by SEQ ID No. 1.
17. A protein according to any one of the preceding clauses wherein said functional antigenic variant has a C terminal end that extends beyond the terminal SVL sequence of the protein encoded by SEQ ID No. 1; and wherein said extension is from 1 to 100 amino acids long.
18. A protein according to any one of the preceding clauses wherein said functional antigenic variant has a C terminal end that extends beyond the terminal SVL sequence of the protein encoded by SEQ ID No. 1; and wherein said extension is from 1 to 50 amino acids long.
19. A protein according to any one of the preceding clauses wherein said functional antigenic variant has a C terminal end that extends beyond the terminal SVL sequence of the protein encoded by SEQ ID No. 1; and wherein said extension is from 1 to 30 amino acids long.
20. A protein according to any one of the preceding clauses wherein said functional antigenic variant has a C terminal end that extends beyond the terminal SVL sequence of the protein encoded by SEQ ID No. 1; wherein said extension is from 1 to 30 amino acids long; and wherein said extension comprises all of part of the sequence VKININLTPPVATSRVPSRALPLRFGCGHR (SEQ ID NO: 16).
21. A protein according to any one of the preceding clauses wherein said functional antigenic variant has a C terminal end that extends beyond the terminal SVL sequence of the protein encoded by SEQ ID No. 1; wherein said extension is from 1 to 30 amino acids long; and wherein said extension comprises all of the sequence VKININLTPP-VATSRVPSRALPLRFGCGHR (SEQ ID NO: 16).

22. A protein according to any one of the preceding clauses wherein said functional antigenic variant is encodable by all or part of SEQ ID No. 1, 2, 5, 6 or 7.

23. A protein according to any one of the preceding clauses wherein said functional antigenic variant is encoded by all or part of SEQ ID No. 1, 2, 5, 6 or 7.

24. A protein according to any one of the preceding clauses wherein said protein is recombinant protein having been prepared by recombinant DNA techniques.

25. A protein according to any one of the preceding clauses wherein said protein is baculovirus expressed protein.

26. A protein according to any one of the preceding clauses wherein said PCV3 is selected from the group consisting of PCV3a and PCV3b.

27. A protein according to any one of the preceding clauses wherein said PCV3 is any phylogenetic clade of PCV3 or selected from the group consisting PCV3a1, PCV3b1, PCV3b2 and PCV3c.

28. A protein according to any one of the preceding clauses wherein said PCV3 ORF2 is from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4).

29. A protein according to any one of the preceding clauses wherein said PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:1.

30. A protein according to any one of the preceding clauses wherein said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:6.

31. A protein according to any one of the preceding clauses wherein said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:7.

32. A protein according to any one of the preceding clauses wherein said PCV3 ORF2 protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein. 33 A protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein; or a protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has one or more substitutions in the FG loop.

34. A protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein; or a protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has a C terminal end that extends beyond the terminal SVL sequence of the protein encoded by SEQ ID No. 1.

35. A protein according to any one of the preceding clauses wherein said protein is a recombinant protein from expression thereof by an expression vector, comprising a polynucleotide sequence that encodes the protein.

36. A protein according to any one of the preceding clauses wherein said protein is a recombinant protein from expression thereof by a baculovirus expression vector, comprising a polynucleotide sequence that encodes the protein.

37. A nucleotide sequence encoding the protein according to any of the preceding clauses.

38. A vector comprising the nucleotide sequence of any of the preceding clauses.

39. A recombinant vector comprising the nucleotide sequence of any of the preceding clauses.

40. An expression host transformed or transfected with the nucleotide sequence of any of the preceding clauses.

41. A baculovirus expression host transformed or transfected with the nucleotide sequence of any of the preceding clauses.

42. A method of preparing a protein according to any one of the preceding clauses comprising expressing a nucleotide sequence according to any of the preceding clauses.

43. A method of preparing a protein according to any one of the preceding clauses comprising expressing a vector according to any of the preceding clauses.

44. A method of preparing a protein according to any one of the preceding clauses comprising expressing a recombinant vector according to any of the preceding clauses.

45. A method of preparing a protein according to any one of the preceding clauses comprising culturing the expression host according to any of the preceding clauses to cause expression of the protein.

46. A method of preparing a protein according to any one of the preceding clauses comprising transfecting an expression host with the nucleotide sequence of vector according to any one of the preceding clauses and culturing the expression host to cause expression of the protein.

47. A method of preparing a protein according to any one of the preceding clauses comprising culturing the baculovirus expression host according to any of the preceding clauses to cause expression of the protein.

48. A method of preparing a protein according to any one of the preceding clauses comprising transfecting a baculovirus expression host with the nucleotide sequence of vector according to any one of the preceding clauses and culturing the baculovirus expression host to cause expression of the protein.

49. A method according to any one of the preceding clauses wherein an inactivating agent is used when sufficient levels of expressed protein have been achieved.

50. A method according to any one of the preceding clauses wherein an inactivating agent comprising binary ethyleneimine (BEI) is used when sufficient levels of expressed protein have been achieved.

51. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein.

52. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 μm.

53. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 μm and the pH of said composition is adjusted to about 6.5 to 7.5.

54. A method of preparing a protein according to any one of the preceding clauses comprising producing the protein by a baculovirus expression system in cultured insect cells.

55. A method of preparing a protein according to any one of the preceding clauses comprising producing the protein by a baculovirus expression system in cultured insect cells; and wherein the method includes the step of inactivating the baculovirus.

56. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent.

57. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound.

58. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound; wherein the aziridine compound comprises BEI.

59. A protein obtainable by the method according to any one of the preceding clauses.

60. A composition comprising the protein obtainable by the method according to any one of the preceding clauses.

61. A composition obtainable by the method according to any one of the preceding clauses.

62. A composition comprising a protein according to any one of the preceding clauses and a carrier, diluent or excipient.

63. A composition comprising a protein according to any one of the preceding clauses and a veterinary-acceptable carrier, diluent or excipient.

64. A composition according to any one of the preceding clauses wherein the protein is present in an amount of 0.2 to about 400 μg/ml, or 2 to about 400 μg/ml, or 4 to about 400 μg/ml, or 8 to about 400 μg/ml, or about 0.3 to about 200 μg/ml, or 2 to about 200 μg/ml, or 4 to about 200 μg/ml, or 8 to about 200 μg/ml, or about 0.35 to about 100 μg/ml, or 2 to about 100 μg/ml, or 4 to about 100 μg/ml, or 8 to about 100 μg/ml, or about 0.4 to about 50 μg/ml, or about 0.45 to about 30 μg/ml, or about 0.6 to about 15 μg/ml, or about 0.75 to about 8 μg/ml, or about 1.0 to about 6 μg/ml, or about 1.3 to about 3.0 μg/ml, or about 1.4 to about 2.5 μg/ml, or about 1.5 to about 2.0 μg/ml, or about 1.6 μg/ml.

65. A composition comprising a protein according to any one of the preceding clauses wherein the composition comprises any one or more of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, and/or an immunomodulatory agent.

66. A composition according to any one of the preceding clauses wherein the carrier, diluent or excipient is any one or more of an adjuvant, immunomodulatory agent, cell culture supernatant, viral or expression vector or any combination thereof.

67. A composition according to any one of the preceding clauses wherein the carrier, diluent or excipient comprises an adjuvant.

68. A composition according to any one of the preceding clauses wherein the carrier, diluent or excipient comprises an adjuvant; wherein the adjuvant comprises one or more of a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

69. A composition according to any one of the preceding clauses wherein the carrier, diluent or excipient comprises an adjuvant; wherein the adjuvant comprises Carbopol® or Carbopol® 971.

70. A composition according to any one of the preceding clauses wherein the carrier, diluent or excipient comprises an adjuvant; wherein the adjuvant is present in an amount from about 50 µg to about 2000 of the composition; or wherein adjuvant is present in an amount about 250 µg/ml dose of the composition, or wherein the adjuvant is present in an amount of about 100 µg to about 10 mg of the composition; or wherein the adjuvant is present in an amount of about 500 µg to about 5 mg of the composition; the adjuvant is present in an amount of about 750 µg to about 2.5 mg of the composition; or the adjuvant is present in an amount of about 1 mg of the composition.

71. A composition according to any one of the preceding clauses wherein the composition comprises an immunomodulatory agent.

72. A composition according to any one of the preceding clauses wherein the composition comprises an immunomodulatory agent; and wherein the immunomodulatory agent is any one or more of interleukin(s), interferon(s), or other cytokine(s).

73. A composition according to any one of the preceding clauses wherein the composition comprises an antibiotic(s).

74. A composition according to any one of the preceding clauses wherein the composition comprises an antibiotic(s); wherein the antibiotic(s) comprise Gentamicin.

75. A composition according to any one of the preceding clauses wherein the composition comprises an antibiotic(s); and wherein the composition comprises from about 1 µg/ml to about 60 µg/ml of antibiotic(s).

76. A composition according to any one of the preceding clauses wherein the composition comprises an antibiotic(s); and wherein the composition comprises from about 1 Ug/ml to less than about 30 µg/ml of antibiotic(s).

77. A composition according to any one of the preceding clauses wherein the composition comprises an additional antigen.

78. A composition according to any one of the preceding clauses wherein the composition comprises an additional antigen; wherein said additional antigen is not a PCV3 ORF2 antigen.

79. A composition according to any one of the preceding clauses wherein the composition comprises an additional antigen; wherein said additional antigen is not a PCV3 antigen.

80. A composition according to any one of the preceding clauses wherein the composition comprises an additional antigen of an additional porcine pathogen.

81. A composition according to any one of the preceding clauses wherein the composition further comprises an antigen of an additional porcine pathogen, wherein said pathogen is any one or more of PCV2, PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen.

82. A composition according to any one of the preceding clauses wherein the composition further comprises an antigen of an additional porcine pathogen, wherein said composition further comprises one or more of an antigen of PCV2, an antigen of a PRRSV and an antigen of a PPV.

83. A composition according to any one of the preceding clauses wherein the composition further comprises an antigen of PCV2.

84. A composition according to any one of the preceding clauses wherein the composition further comprises an antigen of PCV2; wherein PCV2 antigen is PCV2 ORF2 protein.

85. A composition according to any one of the preceding clauses wherein the composition further comprises an antigen of PCV2; wherein PCV2 antigen is recombinant PCV2 ORF2 protein.

86. A composition according to any one of the preceding clauses wherein the composition further comprises an antigen of PCV2; wherein PCV2 antigen is recombinant baculovirus expressed PCV2 ORF2 protein.

87. A composition according to any one of the preceding clauses wherein the composition is in a dosage form.

88. A composition according to any one of the preceding clauses wherein the composition is formulated and/or packaged for a single dose or one shot administration.

89. A composition according to any one of the preceding clauses wherein the composition is formulated and/or packaged for a multi-dose regimen.

90. A composition according to any one of the preceding clauses wherein the composition is formulated and/or packaged for a two-dose regimen.

91. A composition according to any one of the preceding clauses wherein the composition is in a dosage form; and wherein said dosage form is delivered from a container containing a larger amount of said composition and wherein a dosage form of said composition is capable of being delivered from said container.

92. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 10 doses of said composition.

93. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 50 doses of said composition.

94. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 100 doses of said composition.

95. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 200 doses of said composition.

96. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 250 doses of said composition.

97. A composition according to any one of the preceding clauses wherein the composition comprises an antigen of PCV2; wherein PCV2 antigen is recombinant baculovirus expressed PCV2 ORF2 protein; and wherein either the protein or combined total amount of the PCV3 ORF2 protein and PCV2 ORF protein are present in an amount of about 0.2 to about 400 µg/dose, or 2 to about 400 µg/dose, or 4 to about 400 µg/dose, or 8 to about 400 µg/dose, or about 0.3 to about 200 µg/dose, or 2 to about 200 µg/dose, or 4 to about 200 µg/dose, or 8 to about 200 µg/dose, or about 0.35 to about 100 µg/dose, or 2 to about 100 ag/dose, or 4 to about 100 µg/dose, or 8 to about 100 µg/dose, or about 0.4 to about 50 ag/dose, or about 0.45 to about 30 ag/dose, or about 0.6 to about 15 ag/dose, or about 0.75 to about 8 ag/dose, or about 1.0 to about 6 ag/dose, or about 1.3 to about 3.0 ag/dose, or about 1.4 to about 2.5 ag/dose, or about 1.5 to about 2.0 ag/dose, or about 1.6 ag/dose.

98. A composition according to any one of the preceding clauses wherein the composition comprises a salt.

99. A composition according to any one of the preceding clauses wherein the composition comprises an inactivated viral vector and/or cell culture supernate.

100. A composition according to any one of the preceding clauses wherein the composition comprises an inactivated viral vector and cell culture supernate.

101. A composition according to any one of the preceding clauses wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.

102. A composition according to any one of the preceding clauses wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration; and wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.

103. A composition according to any one of the preceding clauses wherein the composition is an immunogenic composition comprising a protein according to any one of the preceding clauses and a carrier, diluent or excipient.

104. A composition according to any one of the preceding clauses wherein the composition is an immunogenic composition comprising a protein according to any one of the preceding clauses and a carrier, diluent or excipient; and an additional antigen according to any one of the preceding clauses.

105. A process of making the composition according to any one of the preceding clauses wherein the protein according to any one of the preceding clauses is admixed with the carrier, diluent or excipient.

106. A process of making the composition according to any one of the preceding clauses wherein the protein according to any one of the preceding clauses is admixed with the carrier, diluent or excipient; and the additional antigen.

107. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use as a medicament.

108. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use as a vaccine.

109. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in an animal.

110. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in swine.

111. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immuno- 112. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in piglets.

113. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in piglets; wherein the piglets are to be suckled by sows to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

114. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in sows.

115. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method for eliciting an immune response or an immunological response or a protective immune or immunological response against PCV3 in pregnant sows, gilts or pre-breeding gilts.

116. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in animals.

117. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in swine.

118. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in pigs.

119. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in piglets.

120. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in piglets; wherein the piglets are to be suckled by sows to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

121. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in sows.

122. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing an immune response against PCV3 in pregnant sows, gilts or pre-breeding gilts.

123. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal.

124. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is swine.

125. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a pig.

126. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a piglet.

127. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a piglet; and wherein the piglet is to be suckled by a sow to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

128. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or disease caused by an infection with PCV3 in an animal or for use in a method of treating or preventing an infection with PCV3 in an animal; wherein said animal is a sow.

129. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a pregnant sow, gilt or pre-breeding gilt.

130. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3.

131. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is swine.

132. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is a pig.

133. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is a piglet.

134. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is a piglet; and wherein the piglet is to be suckled by a sow to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

135. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is a sow.

136. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in immunizing an animal against PCV3; wherein said animal is a pregnant sow, gilt or pre-breeding gilt.

137. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal.

138. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is swine.

139. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is a pig.

140. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is a piglet.

141. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is a piglet; and wherein the piglet is to be suckled by a sow to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

141. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is a sow.

142. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in a method of reducing or eliminating or abrogating PCV3 viral expression in an animal; wherein said animal is a pregnant sow, gilt or pre-breeding gilt.

143. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal.

144. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is swine.

145. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is a pig.

146. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is a piglet.

147. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is a piglet; and wherein the piglet is to be suckled by a sow to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

148. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is a sow.

149. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for use in inducing the production of antibodies specific for PCV3 in an animal; wherein said animal is a pregnant sow, gilt or pre-breeding gilt.

150. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered intramuscularly or intradermally to said animal.

151. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered to said animal in conjunction with another antigen, preferably wherein the other pathogen is an antigen to a porcine pathogen.

152. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered to said animal in conjunction with another antigen; wherein said other antigen is not a PCV3 ORF2 antigen, preferably wherein the other pathogen is an antigen to a porcine pathogen.

153. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered to said animal in conjunction with another antigen; wherein said other antigen is not a PCV3 antigen, preferably wherein the other pathogen is an antigen to a porcine pathogen.

154. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow pregnant with a piglet.

155. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow pregnant with a piglet; and wherein the piglet is to be suckled by a sow to which the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses has been administered.

156. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow; and wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered twice to said sow.

157. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow; and wherein said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is only administered twice to said sow.

158. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a piglet; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered once to said piglet.

159. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a piglet; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is only administered once to said piglet.

160. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered twice to said sow; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

161. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered twice to said sow; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

162. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a sow; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered only twice to said sow; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

163. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a piglet; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered once to said piglet; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

164. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a piglet; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered once to said piglet; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

165. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said animal is a piglet; and wherein the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses is administered only once to said piglet; and wherein said use does not include the administration of any other PCV3 antigen to said animal before or during the administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

166. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein the administration to the animal in the use consists of a single, one shot administration or a single, one dose administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

167. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein the administration to the animal in the use consists of a multi-shot or multi-dose regimen of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

168. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein the administration to the animal in the use consists of a double shot administration; or a dual dose administration of said protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

169. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein the administration to the animal occurs within at least 1 or 2 or 3 weeks of exposure to virulent Porcine *Circovirus*.

170. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein the animal is a piglet not older than 15 weeks of age, or not older than 6 weeks of age, or not older than 3 weeks of age, or not older than 2 weeks of age, or not older than 1 week of age.

171. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses or said composition according to any one of the preceding clauses is for the use of any one of the preceding clauses.

172. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said protein according to any one of the preceding clauses is for the use of any one of the preceding clauses.

173. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein said composition according to any one of the preceding clauses is for the use of any one of the preceding clauses.

174. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein a second antigen is administered to the animal before administration of the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

175. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein a second antigen is administered to the animal at the same time as administration of the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

176. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein a second antigen is administered to the animal at the same time and in the same composition as administration of the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

177. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein a second antigen is administered to the animal at the same time and in a different composition as administration of the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

178. A protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses for the use according to any one of the preceding clauses wherein a second antigen is administered to the animal after the administration of the protein according to any one of the preceding clauses, or a nucleotide sequence according to any one of the preceding clauses, or an expression vector according to any one of the preceding clauses, or an expression host according to any one of the preceding clauses, or a composition according to any one of the preceding clauses.

179. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in one dose to the pig.

180. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in only one dose to the pig.

181. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in two doses to the pig.

182. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in only two doses to the pig.

183. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in one dose to the pig.

184. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in only one dose to the pig.

185. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in two doses to the pig.

186. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in only two doses to the pig.

187. An immunogenic composition according to any one of the preceding clauses for lessening the severity of clinical signs or clinical symptoms resulting from PCV3 infection in a pig;

wherein one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein according to any one of the preceding clauses is the antigenic component in the one dose of the immunogenic composition in the vaccination method that lessens the severity of clinical signs or clinical symptoms resulting from PCV3 infection in the pig; preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

188. An immunogenic composition according to any one of the preceding clauses for lessening the severity of clinical signs or clinical symptoms resulting from PCV3 infection in a pig;

wherein only one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein according to any one of the preceding clauses is the antigenic component in the one dose of the immunogenic composition in the vaccination method that lessens the severity of clinical signs or clinical symptoms resulting from PCV3 infection in the pig; preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

189. An immunogenic composition according to any one of the preceding clauses for lessening the severity of clinical signs or clinical symptoms resulting from PCV3 infection in a pig; wherein two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessens the severity of clinical signs or clinical symptoms resulting from PCV3 infection in the pig;

wherein the protein according to any one of the preceding clauses is the antigenic component in the two doses of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

190. An immunogenic composition according to any one of the preceding clauses for lessening the severity of clinical signs or clinical symptoms resulting from PCV3 infection in a pig;
wherein only two doses of the immunogenic composition is administered to the pig in a vaccination method to lessen the severity of clinical signs or clinical symptoms resulting from PCV3 infection in the pig;
wherein the administration of the two doses of the immunogenic composition to the pig in the vaccination method lessens the severity of clinical signs or clinical symptoms resulting from PCV3 infection in the pig;
wherein the protein according to any one of the preceding clauses is the antigenic component in the two doses of the immunogenic composition in the vaccination method that lessens the severity of clinical signs or clinical symptoms resulting from PCV3 infection in the pig;
preferably wherein the protein is in an amount of at least 2 µg in the one dose of the immunogenic composition;
wherein the protein is the antigenic component in the vaccination method that lessens the severity of clinical signs or clinical symptoms resulting from PCV3 infection in the pig.

191. The use according to any one of the preceding clauses wherein said clinical signs or symptoms are selected from the group consisting of reduction of average daily weight gain and mortality.

192. The use according to any one of the preceding clauses wherein said clinical signs or symptoms are selected from the group consisting of gross lesions, histological lesions, replication of PCV3 in a tissue, and PCV3 viremia.

193. The use according to any one of the preceding clauses wherein said clinical signs or symptoms are selected from the group consisting of development or production of a mummified fetus.

194. The use according to any one of the preceding clauses wherein said clinical signs or symptoms is or include expelling of a mummified, stillborn and/or weak fetus.

Clause Set D:

Clause Set D—The present invention will now be described by way of the following set of numbered clauses (Clause Set D). The disclosure in this set of clauses is equally applicable to the present invention. Likewise the disclosure in this set of clauses is equally applicable to each of the other set of clauses.

1. A porcine *circovirus* type 3 (PCV3) antigenic protein wherein said protein is a functional antigenic variant of PCV3 ORF2 protein.

2. A protein according to clause 1 wherein said PCV3 ORF2 protein is a protein encoded by SEQ ID No. 1.

3. A protein according to clause 1 or clause 2 wherein said protein comprises substitutions and/or extensions of PCV3 ORF2.

4. A protein according to any one of the preceding clauses wherein said protein is a functional antigenic variant of the protein encoded by SEQ ID No. 1.

5. A protein according to any one of the preceding clauses wherein said functional antigenic variant is capable of a higher yield of virus-like particles (VLPs) than the protein encoded by SEQ ID No. 1.

6. A protein according to any one of the preceding clauses wherein said functional antigenic variant is capable of a higher yield of VLPs than the protein encoded by SEQ ID No. 1 as determinable by Western blot analysis.

7. A protein according to any one of the preceding clauses wherein said functional antigenic variant has fewer positive charged amino acid residues than the protein encoded by SEQ ID No. 1.

8. A protein according to any one of the preceding clauses wherein said functional antigenic variant has one or more substitutions in the FG loop of the protein encoded by SEQ ID No. 1.

9. A protein according to any one of the preceding clauses wherein said functional antigenic variant has one or more substitutions in the FG loop of the protein encoded by SEQ ID No. 1, wherein those substitutions comprise substitutions of one or more of the S residue and/or the K residues and/or the H residue of the motif SKKKH (SEQ ID NO: 14) of the FG loop of the protein encoded by SEQ ID No. 1.

10. A protein according to any one of the preceding clauses wherein said functional antigenic variant has one or more substitutions in the FG loop of the protein encoded by SEQ ID No. 1, wherein those substitutions comprise substitutions of one or more of the S residue and/or the K residues of the motif SKKKH (SEQ ID NO: 14) of the FG loop of the protein encoded by SEQ ID No. 1.

11. A protein according to any one of the preceding clauses wherein said functional antigenic variant has one or more substitutions in the FG loop of the protein encoded by SEQ ID No. 1, wherein those substitutions comprise substitutions of the S residue or H residue and all of the K residues of the motif SKKKH (SEQ ID NO: 14) of the FG loop of the protein encoded by SEQ ID No. 1.

12. A protein according to any one of the preceding clauses wherein said functional antigenic variant has one or more substitutions in the FG loop of the protein encoded by SEQ ID No. 1, wherein those substitutions comprise a substitution of at least S and/or H and any K of the motif SKKKH (SEQ ID NO: 14) of the FG loop of the protein encoded by SEQ ID No. 1 with Q or P or F or S.

13. A protein according to any one of the preceding clauses wherein said functional antigenic variant has one or more substitutions in the FG loop of the protein encoded by SEQ ID No. 1, wherein those substitutions comprise substitution of the motif SKKK (SEQ ID NO: 11) within the motif SKKKH (SEQ ID NO: 14) of the FG loop of the protein encoded by SEQ ID No. 1 with QPFS (SEQ ID NO: 12) or substitution of the motif KKKH (SEQ ID NO: 15) within the motif SKKKH (SEQ ID NO: 14) of the FG loop of the protein encoded by SEQ ID No. 1 with QPFS (SEQ ID NO: 12).

14. A protein according to any one of the preceding clauses wherein said functional antigenic variant is encodable by all or part of SEQ ID No. 1, 2, 5, 6 or 7.

15. A protein according to any one of the preceding clauses wherein said functional antigenic variant is encoded by all or part of SEQ ID No. 1, 2, 5, 6 or 7.

16. A protein according to any one of the preceding clauses wherein said functional antigenic variant has a C terminal end that extends beyond the terminal SVL sequence of the protein encoded by SEQ ID No. 1, preferably wherein said extension is all or includes a sequence from a circoviridae virus, and preferably wherein at least a part of said extension replaces the terminal SVL sequence of the protein encoded by SEQ ID No. 1.

17. A protein according to any one of the preceding clauses wherein said functional antigenic variant has a C terminal end that extends beyond the terminal SVL sequence of the protein encoded by SEQ ID No. 1; and wherein said extension is from 1 to 100 amino acids long.

18. A protein according to any one of the preceding clauses wherein said functional antigenic variant has a C terminal end that extends beyond the terminal SVL sequence of the protein encoded by SEQ ID No. 1; and wherein said extension is from 1 to 50 amino acids long.

19. A protein according to any one of the preceding clauses wherein said functional antigenic variant has a C terminal end that extends beyond the terminal SVL sequence of the protein encoded by SEQ ID No. 1; and wherein said extension is from 1 to 30 amino acids long.

20. A protein according to any one of the preceding clauses wherein said functional antigenic variant has a C terminal end that extends beyond the terminal SVL sequence of the protein encoded by SEQ ID No. 1; wherein said extension is from 1 to 30 amino acids long; and wherein said extension comprises all of part of the sequence VKININLTPP-VATSRVPSRALPLRFGCGHR (SEQ ID NO: 16).

21. A protein according to any one of the preceding clauses wherein said functional antigenic variant has a C terminal end that extends beyond the terminal SVL sequence of the protein encoded by SEQ ID No. 1; wherein said extension is from 1 to 30 amino acids long; and wherein said extension comprises all of the sequence VKININLTPP-VATSRVPSRALPLRFGCGHR (SEQ ID NO: 16).

22. A protein according to any one of the preceding clauses wherein said functional antigenic variant is encodable by all or part of SEQ ID No. 1, 2, 5, 6 or 7.

23. A protein according to any one of the preceding clauses wherein said functional antigenic variant is encoded by all or part of SEQ ID No. 1, 2, 5, 6 or 7.

24. A protein according to any one of the preceding clauses wherein said protein is recombinant protein having been prepared by recombinant DNA techniques.

25. A protein according to any one of the preceding clauses wherein said protein is baculovirus expressed protein.

26. A protein according to any one of the preceding clauses wherein said PCV3 is selected from the group consisting of PCV3a and PCV3b.

27. A protein according to any one of the preceding clauses wherein said PCV3 is any phylogenetic clade of PCV3 or selected from the group consisting PCV3a1, PCV3b1, PCV3b2 and PCV3c.

28. A protein according to any one of the preceding clauses wherein said PCV3 ORF2 is from group a1, b1 or b2 (using the subtyping designation of Fux et al., "Full genome characterization of porcine *circovirus* type 3 isolates reveals the existence of two distinct groups of virus strains," Virology Journal (2018) 15:25, DOI 10.1186/s12985-018-0929-3 (incorporated herein by reference); see, e.g., Table 4).

29. A protein according to any one of the preceding clauses wherein said PCV3 ORF2 protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:1.

30. A protein according to any one of the preceding clauses wherein said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:6.

31. A protein according to any one of the preceding clauses wherein said variant protein comprises or consists of an amino acid sequence encoded by a polynucleotide sequence having at least 90%, or at least 91%, or at least 92%, or at least 93%, or at least 94%, or at least 95%, or at least 96%, or at least 97%, or at least 98%, or at least 99%, or 100% sequence identity with SEQ ID NO:1 or sequence homology with SEQ ID NO:7.

32. A protein according to any one of the preceding clauses wherein said PCV3 ORF2 protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein.

33. A protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein; or a protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has one or more substitutions in the FG loop.

34. A protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10 and/or wherein the protein is a recombinant protein; or a protein according to any one of the preceding clauses wherein said variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10, and/or wherein the protein is a recombinant protein, and wherein said protein has a C terminal end that extends beyond the terminal SVL sequence of the protein encoded by SEQ ID No. 1.

35. A protein according to any one of the preceding clauses wherein said protein is a recombinant protein from expression thereof by an expression vector, comprising a polynucleotide sequence that encodes the protein.

36. A protein according to any one of the preceding clauses wherein said protein is a recombinant protein from expression thereof by a baculovirus expression vector, comprising a polynucleotide sequence that encodes the protein.

37. A nucleotide sequence encoding the protein according to any of the preceding clauses.

38. A vector comprising the nucleotide sequence of any of the preceding clauses.

39. A recombinant vector comprising the nucleotide sequence of any of the preceding clauses.

40. An expression host transformed or transfected with the nucleotide sequence of any of the preceding clauses.

41. A baculovirus expression host transformed or transfected with the nucleotide sequence of any of the preceding clauses.
42. A method of preparing a protein according to any one of the preceding clauses comprising expressing a nucleotide sequence according to any of the preceding clauses.
43. A method of preparing a protein according to any one of the preceding clauses comprising expressing a vector according to any of the preceding clauses.
44. A method of preparing a protein according to any one of the preceding clauses comprising expressing a recombinant vector according to any of the preceding clauses.
45. A method of preparing a protein according to any one of the preceding clauses comprising culturing the expression host according to any of the preceding clauses to cause expression of the protein.
46. A method of preparing a protein according to any one of the preceding clauses comprising transfecting an expression host with the nucleotide sequence of vector according to any one of the preceding clauses and culturing the expression host to cause expression of the protein.
47. A method of preparing a protein according to any one of the preceding clauses comprising culturing the baculovirus expression host according to any of the preceding clauses to cause expression of the protein.
48. A method of preparing a protein according to any one of the preceding clauses comprising transfecting a baculovirus expression host with the nucleotide sequence of vector according to any one of the preceding clauses and culturing the baculovirus expression host to cause expression of the protein.
49. A method according to any one of the preceding clauses wherein an inactivating agent is used when sufficient levels of expressed protein have been achieved.
50. A method according to any one of the preceding clauses wherein an inactivating agent comprising binary ethyleneimine (BEI) is used when sufficient levels of expressed protein have been achieved.
51. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein.
52. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 m.
53. A method of preparing a protein according to any one of the preceding clauses comprising transfecting a baculovirus expression host with the nucleotide sequence of vector according to any one of the preceding clauses and culturing the baculovirus expression host in a medium to cause expression of the protein; wherein the medium post expression of the protein comprises (i) said protein, (ii) at least a portion of baculovirus that expressed said protein, (iii) a portion of cell culture of cells that were infected or transfected with recombinant baculovirus that expressed said protein; and wherein about 90% of the components (i) to (iii) have a size smaller than 1 m and the pH of said composition is adjusted to about 6.5 to 7.5.
54. A method of preparing a protein according to any one of the preceding clauses comprising producing the protein by a baculovirus expression system in cultured insect cells.
55. A method of preparing a protein according to any one of the preceding clauses comprising producing the protein by a baculovirus expression system in cultured insect cells; and wherein the method includes the step of inactivating the baculovirus.
56. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent.
57. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound.
58. A method of preparing a protein according to any one of the preceding clauses comprising producing the protein by a baculovirus expression system in cultured insect cells; and wherein the method includes the step of inactivating the baculovirus; and wherein inactivating step comprises heat treatment or use of a virus inactivating agent; and wherein the virus inactivating agent comprises an aziridine compound; wherein the aziridine compound comprises BEI.
59. A protein obtainable by the method according to any one of the preceding clauses.
60. A composition comprising the protein obtainable by the method according to any one of the preceding clauses.
61. A composition obtainable by the method according to any one of the preceding clauses.
62. A composition comprising a protein according to any one of the preceding clauses and a carrier, diluent or excipient.
63. A composition comprising a protein according to any one of the preceding clauses and a veterinary-acceptable carrier, diluent or excipient.
64. A composition according to any one of the preceding clauses wherein the protein is present in an amount of 0.2 to about 400 µg/ml, or 2 to about 400 µg/ml, or 4 to about 400 µg/ml, or 8 to about 400 µg/ml, or about 0.3 to about 200 µg/ml, or 2 to about 200 µg/ml, or 4 to about 200 µg/ml, or 8 to about 200 µg/ml, or about 0.35 to about 100 µg/ml, or 2 to about 100 µg/ml, or 4 to about 100 µg/ml, or 8 to about 100 µg/ml, or about 0.4 to about 50 µg/ml, or about 0.45 to about 30 µg/ml, or about 0.6 to about 15 µg/ml, or about 0.75 to about 8 µg/ml, or about 1.0 to about 6 µg/ml, or about 1.3 to about 3.0 µg/ml, or about 1.4 to about 2.5 µg/ml, or about 1.5 to about 2.0 µg/ml, or about 1.6 µg/ml.
65. A composition comprising a protein according to any one of the preceding clauses wherein the composition comprises any one or more of a solvent, a dispersion media, a coating, a stabilizing agent, a diluent, a preservative, an anti-microbial agent, an antifungal agent, an isotonic agent, an adsorption delaying agent, an adjuvant, cell culture supernatant, a stabilizing agent, a viral vector, an expression vector, and/or an immunomodulatory agent.

66. A composition according to any one of the preceding clauses wherein the carrier, diluent or excipient is any one or more of an adjuvant, immunomodulatory agent, cell culture supernatant, viral or expression vector or any combination thereof.

67. A composition according to any one of the preceding clauses wherein the carrier, diluent or excipient comprises an adjuvant.

68. A composition according to any one of the preceding clauses wherein the carrier, diluent or excipient comprises an adjuvant; wherein the adjuvant comprises one or more of a polymer of acrylic or methacrylic acid; copolymer of maleic anhydride and alkenyl derivative; a polymer of acrylic or methacrylic acid which is cross-linked; a polymer of acrylic or methacrylic acid which is cross-linked with a polyalkenyl ether of sugar or polyalcohol; a carbomer; an acrylic polymer cross-linked with a polyhydroxylated compound having at least 3 and not more than 8 hydroxyl groups with hydrogen atoms of at least three hydroxyls optionally or being replaced by unsaturated aliphatic radicals having at least 2 carbon atoms with said radicals containing from 2 to 4 carbon atoms such as vinyls, allyls and other ethylenically unsaturated groups and the unsaturated radicals may themselves contain other substituents, such as methyl; a Carbopol®; Carbopol® 974P; Carbopol® 934P; Carbopol® 971P; aluminum hydroxide; aluminum phosphate; a saponin; Quil-A®; QS-21® STIMULON; GPI-0100; a water-in-oil emulsion; an oil-in-water emulsion; a water-in-oil-in-water emulsion; an emulsion based on light liquid paraffin oil or European Pharmacopea type adjuvant; an isoprenoid oil; squalane; squalene oil resulting from oligomerization of alkenes or isobutene or decene; (an) ester(s) of acid(s) or of alcohol(s) containing a linear alkyl group; plant oil(s); ethyl oleate; propylene glycol di-(caprylate/caprate); glyceryl tri-(caprylate/caprate); propylene glycol dioleate; (an) ester(s) of branched fatty acid(s) or alcohol(s); isostearic acid ester(s); nonionic surfactant(s); (an) ester(s) of sorbitan or of mannide or of glycol or of polyglycerol or of propylene glycol or of oleic, or isostearic acid or of ricinoleic acid or of hydroxystearic acid, optionally ethoxylated, anhydromannitol oleate; polyoxypropylene-polyoxyethylene copolymer blocks, a Pluronic® product, RIBI® adjuvant system; Block co-polymer; SAF-M; monophosphoryl lipid A; Avridine lipid-amine adjuvant; heat-labile enterotoxin from *E. coli* (recombinant or otherwise); cholera toxin; MONTANIDE™ IMS 1314, or muramyl dipeptide.

69. A composition according to any one of the preceding clauses wherein the carrier, diluent or excipient comprises an adjuvant; wherein the adjuvant comprises Carbopol® or Carbopol® 971.

70. A composition according to any one of the preceding clauses wherein the carrier, diluent or excipient comprises an adjuvant; wherein the adjuvant is present in an amount from about 50 µg to about 2000 of the composition; or wherein adjuvant is present in an amount about 250 µg/ml dose of the composition, or wherein the adjuvant is present in an amount of about 100 µg to about
10 mg of the composition; or wherein the adjuvant is present in an amount of about 500 µg to about 5 mg of the composition; the adjuvant is present in an amount of about 750 µg to about 2.5 mg of the composition; or the adjuvant is present in an amount of about 1 mg of the composition.

71. A composition according to any one of the preceding clauses wherein the composition comprises an immunomodulatory agent.

72. A composition according to any one of the preceding clauses wherein the composition comprises an immunomodulatory agent; and wherein the immunomodulatory agent is any one or more of interleukin(s), interferon(s), or other cytokine(s).

73. A composition according to any one of the preceding clauses wherein the composition comprises an antibiotic(s).

74. A composition according to any one of the preceding clauses wherein the composition comprises an antibiotic(s); wherein the antibiotic(s) comprise Gentamicin.

75. A composition according to any one of the preceding clauses wherein the composition comprises an antibiotic(s); and wherein the composition comprises from about 1 µg/ml to about 60 µg/ml of antibiotic(s).

76. A composition according to any one of the preceding clauses wherein the composition comprises an antibiotic(s); and wherein the composition comprises from about 1 µg/ml to less than about 30 µg/ml of antibiotic(s).

77. A composition according to any one of the preceding clauses wherein the composition comprises an additional antigen.

78. A composition according to any one of the preceding clauses wherein the composition comprises an additional antigen; wherein said additional antigen is not a PCV3 ORF2 antigen.

79. A composition according to any one of the preceding clauses wherein the composition comprises an additional antigen; wherein said additional antigen is not a PCV3 antigen.

80. A composition according to any one of the preceding clauses wherein the composition comprises an additional antigen of an additional porcine pathogen.

81. A composition according to any one of the preceding clauses wherein the composition further comprises an antigen of an additional porcine pathogen, wherein said pathogen is any one or more of PCV2, PRRSV (porcine respiratory and reproductive syndrome virus) antigen, a *Mycoplasma hyopneumoniae* bacterin antigen, a *Mycoplasma hyopneumoniae* supernatant antigen, an Aujeszky's disease or pseudorabies antigen, a swine influenza antigen, a swine fever antigen (classical or African or combination thereof), an *Actinobacillus pleuropneumoniae* antigen, an *Escherichia coli* antigen, a porcine parvovirus (PPV) antigen or a *Pasteurella multocida* antigen.

82. A composition according to any one of the preceding clauses wherein the composition further comprises an antigen of an additional porcine pathogen, wherein said composition further comprises one or more of an antigen of PCV2, an antigen of a PRRSV and an antigen of a PPV.

83. A composition according to any one of the preceding clauses wherein the composition further comprises an antigen of PCV2.

84. A composition according to any one of the preceding clauses wherein the composition further comprises an antigen of PCV2; wherein PCV2 antigen is PCV2 ORF2 protein.

85. A composition according to any one of the preceding clauses wherein the composition further comprises an antigen of PCV2; wherein PCV2 antigen is recombinant PCV2 ORF2 protein.

86. A composition according to any one of the preceding clauses wherein the composition further comprises an antigen of PCV2; wherein PCV2 antigen is recombinant baculovirus expressed PCV2 ORF2 protein.

87. A composition according to any one of the preceding clauses wherein the composition is in a dosage form.
88. A composition according to any one of the preceding clauses wherein the composition is formulated and/or packaged for a single dose or one shot administration.
89. A composition according to any one of the preceding clauses wherein the composition is formulated and/or packaged for a multi-dose regimen.
90. A composition according to any one of the preceding clauses wherein the composition is formulated and/or packaged for a two-dose regimen.
91. A composition according to any one of the preceding clauses wherein the composition is in a dosage form; and wherein said dosage form is delivered from a container containing a larger amount of said composition and wherein a dosage form of said composition is capable of being delivered from said container.
92. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 10 doses of said composition.
93. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 50 doses of said composition.
94. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 100 doses of said composition.
95. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 200 doses of said composition.
96. A composition according to any one of the preceding clauses wherein the composition is in a dosage form; and wherein said dosage form is delivered from a container containing a larger amount of said composition and wherein a dosage form of said composition is capable of being delivered from said container; and wherein said container contains at least 250 doses of said composition.
97. A composition according to any one of the preceding clauses wherein the composition comprises an antigen of PCV2; wherein PCV2 antigen is recombinant baculovirus expressed PCV2 ORF2 protein; and wherein either the protein or combined total amount of the PCV3 ORF2 protein and PCV2 ORF protein are present in an amount of about 0.2 to about 400 µg/dose, or 2 to about 400 µg/dose, or 4 to about 400 µg/dose, or 8 to about 400 µg/dose, or about 0.3 to about 200 µg/dose, or 2 to about 200 µg/dose, or 4 to about 200 µg/dose, or 8 to about 200 µg/dose, or about 0.35 to about 100 µg/dose, or 2 to about 100 ag/dose, or 4 to about 100 µg/dose, or 8 to about 100 µg/dose, or about 0.4 to about 50 ag/dose, or about 0.45 to about 30 ag/dose, or about 0.6 to about 15 µg/dose, or about 0.75 to about 8 µg/dose, or about 1.0 to about 6 µg/dose, or about 1.3 to about 3.0 µg/dose, or about 1.4 to about 2.5 µg/dose, or about 1.5 to about 2.0 µg/dose, or about 1.6 µg/dose.
98. A composition according to any one of the preceding clauses wherein the composition comprises a salt.
99. A composition according to any one of the preceding clauses wherein the composition comprises an inactivated viral vector and/or cell culture supernate.
100. A composition according to any one of the preceding clauses wherein the composition comprises an inactivated viral vector and cell culture supernate.
101. A composition according to any one of the preceding clauses wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration.
102. A composition according to any one of the preceding clauses wherein the composition comprises (i) the protein, (ii) at least a portion of baculovirus that expressed said protein, (iii) a portion of cell culture of cells that were infected or transfected with recombinant baculovirus that expressed said protein, (iv) inactivating agent or inactivating agent comprising binary ethyleneimine (BEI), (v) sodium thiosulfate or sodium thiosulfate in equivalent amounts to inactivating agent or BEI; (vi) adjuvant or adjuvant comprising Carbopol® or Carbopol® 971, and (vii) phosphate salt in a physiologically acceptable concentration; and wherein the BEI is from the cell culture having been treated with about 2 to 8 or about 5 mM BEI to inactivate the baculovirus and/or the composition contains about 2 to 8 or about 5 mM BEI and/or the composition contains about 1 mg of the Carbopol® or Carbopol® 971.
103. A composition according to any one of the preceding clauses wherein the composition is an immunogenic composition comprising a protein according to any one of the preceding clauses and a carrier, diluent or excipient.
104. A composition according to any one of the preceding clauses wherein the composition is an immunogenic composition comprising a protein according to any one of the preceding clauses and a carrier, diluent or excipient; and an additional antigen according to any one of the preceding clauses.
105. A process of making the composition according to any one of the preceding clauses wherein the protein according to any one of the preceding clauses is admixed with the carrier, diluent or excipient.
106. A process of making the composition according to any one of the preceding clauses wherein the protein according to any one of the preceding clauses is admixed with the carrier, diluent or excipient; and the additional antigen.
107. A protein according to any one of the preceding clauses or a composition according to any one of the preceding clauses for use as a medicament.
108. A protein according to any one of the preceding clauses or a composition according to any one of the preceding clauses for use as a vaccine.
109. A protein according to any one of the preceding clauses or a composition according to any one of the preceding clauses for use in a method for eliciting an immune response or an immunological response or a protective immune or immunological response against PCV3 in an animal.

110. A protein according to any one of the preceding clauses or a composition according to any one of the preceding clauses for use in a method for eliciting an immune response or an immunological response or a protective immune or immunological response against PCV3 in swine.

111. A protein according to any one of the preceding clauses or a composition according to any one of the preceding clauses for use in a method for eliciting an immune response or an immunological response or a protective immune or immunological response against PCV3 in pigs.

112. A protein according to any one of the preceding clauses or a composition according to any one of the preceding clauses for use in a method for eliciting an immune response or an immunological response or a protective immune or immunological response against PCV3 in piglets.

113. A protein according to any one of the preceding clauses or a composition according to any one of the preceding clauses for use in a method for eliciting an immune response or an immunological response or a protective immune or immunological response against PCV3 in piglets; wherein the piglets are to be suckled by sows to which the protein according to any one of the preceding clauses or a composition according to any one of the preceding clauses has been administered.

114. A protein according to any one of the preceding clauses or a composition according to any one of the preceding clauses for use in a method for eliciting an immune response or an immunological response or a protective immune or immunological response against PCV3 in sows.

115. A protein according to any one of the preceding clauses or a composition according to any one of the preceding clauses for use in a method for eliciting an immune response or an immunological response or a protective immune or immunological response against PCV3 in pregnant sows, gilts or pre-breeding gilts.

116. A protein according to any one of the preceding clauses or a composition according to any one of the preceding clauses for use in inducing an immune response against PCV3 in animals.

117. A protein according to any one of the preceding clauses or a composition according to any one of the preceding clauses for use in inducing an immune response against PCV3 in swine.

118. A protein according to any one of the preceding clauses or a composition according to any one of the preceding clauses for use in inducing an immune response against PCV3 in pigs.

119. A protein according to any one of the preceding clauses or a composition according to any one of the preceding clauses for use in inducing an immune response against PCV3 in piglets.

120. A protein according to any one of the preceding clauses or a composition according to any one of the preceding clauses for use in inducing an immune response against PCV3 in piglets; wherein the piglets are to be suckled by sows to which the protein according to any one of the preceding clauses or a composition according to any one of the preceding clauses has been administered.

121. A protein according to any one of the preceding clauses or a composition according to any one of the preceding clauses for use in inducing an immune response against PCV3 in sows.

122. A protein according to any one of the preceding clauses or a composition according to any one of the preceding clauses for use in inducing an immune response against PCV3 in pregnant sows, gilts or pre-breeding gilts.

123. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal.

124. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is swine.

125. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a pig.

126. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a piglet.

127. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a piglet; and wherein the piglet is to be suckled by a sow to which the protein according to any one of the preceding clauses or a composition according to any one of the preceding clauses has been administered.

128. A protein according to any one of the preceding clauses or a composition according to any one of the preceding clauses for use in a method of reducing or preventing the clinical signs or disease caused by an infection with PCV3 in an animal or for use in a method of treating or preventing an infection with PCV3 in an animal; wherein said animal is a sow.

129. A protein according to any one of the preceding clauses or a composition according to any one of the preceding clauses for use in a method of reducing or preventing the clinical signs or clinical symptoms or disease caused by an infection with PCV3 in an animal or for use in a method of treating or preventing an infection with PCV3 in an animal; wherein said animal is a pregnant sow, gilt or pre-breeding gilt.

130. A protein according to any one of the preceding clauses or a composition according to any one of the preceding clauses for use in immunizing an animal against PCV3.

131. A protein according to any one of the preceding clauses or a composition according to any one of the preceding clauses for use in immunizing an animal against PCV3; wherein said animal is swine.

132. A protein according to any one of the preceding clauses or a composition according to any one of the preceding clauses for use in immunizing an animal against PCV3; wherein said animal is a pig.

133. A protein according to any one of the preceding clauses or a composition according to any one of the preceding clauses for use in immunizing an animal against PCV3; wherein said animal is a piglet.

134. A protein according to any one of the preceding clauses or a composition according to any one of the preceding clauses for use in immunizing an animal against PCV3; wherein said animal is a piglet; and wherein the piglet is to be suckled by a sow to which the protein according to any one of the preceding clauses or a composition according to any one of the preceding clauses has been administered.

135. A protein according to any one of the preceding clauses or a composition according to any one of the preceding clauses for use in immunizing an animal against PCV3; wherein said animal is a sow.

136. A protein according to any one of the preceding clauses or a composition according to any one of the preceding clauses for use in immunizing an animal against PCV3; wherein said animal is a pregnant sow, gilt or pre-breeding gilt.

137. A protein according to any one of the preceding clauses or a composition according to any one of the preceding clauses for use in a method of reducing or eliminating or abrogating PCV3 viral expression in an animal.

138. A protein according to any one of the preceding clauses or a composition according to any one of the preceding clauses for use in a method of reducing or eliminating or abrogating PCV3 viral expression in an animal; wherein said animal is swine.

139. A protein according to any one of the preceding clauses or a composition according to any one of the preceding clauses for use in a method of reducing or eliminating or abrogating PCV3 viral expression in an animal; wherein said animal is a pig.

140. A protein according to any one of the preceding clauses or a composition according to any one of the preceding clauses for use in a method of reducing or eliminating or abrogating PCV3 viral expression in an animal; wherein said animal is a piglet.

141. A protein according to any one of the preceding clauses or a composition according to any one of the preceding clauses for use in a method of reducing or eliminating or abrogating PCV3 viral expression in an animal; wherein said animal is a piglet; and wherein the piglet is to be suckled by a sow to which the protein according to any one of the preceding clauses or a composition according to any one of the preceding clauses has been administered.

141. A protein according to any one of the preceding clauses or a composition according to any one of the preceding clauses for use in a method of reducing or eliminating or abrogating PCV3 viral expression in an animal; wherein said animal is a sow.

142. A protein according to any one of the preceding clauses or a composition according to any one of the preceding clauses for use in a method of reducing or eliminating or abrogating PCV3 viral expression in an animal; wherein said animal is a pregnant sow, gilt or pre-breeding gilt.

143. A protein according to any one of the preceding clauses or a composition according to any one of the preceding clauses for use in inducing the production of antibodies specific for PCV3 in an animal.

144. A protein according to any one of the preceding clauses or a composition according to any one of the preceding clauses for use in inducing the production of antibodies specific for PCV3 in an animal; wherein said animal is swine.

145. A protein according to any one of the preceding clauses or a composition according to any one of the preceding clauses for use in inducing the production of antibodies specific for PCV3 in an animal; wherein said animal is a pig.

146. A protein according to any one of the preceding clauses or a composition according to any one of the preceding clauses for use in inducing the production of antibodies specific for PCV3 in an animal; wherein said animal is a piglet.

147. A protein according to any one of the preceding clauses or a composition according to any one of the preceding clauses for use in inducing the production of antibodies specific for PCV3 in an animal; wherein said animal is a piglet; and wherein the piglet is to be suckled by a sow to which the protein according to any one of the preceding clauses or a composition according to any one of the preceding clauses has been administered.

148. A protein according to any one of the preceding clauses or a composition according to any one of the preceding clauses for use in inducing the production of antibodies specific for PCV3 in an animal; wherein said animal is a sow.

149. A protein according to any one of the preceding clauses or a composition according to any one of the preceding clauses for use in inducing the production of antibodies specific for PCV3 in an animal; wherein said animal is a pregnant sow, gilt or pre-breeding gilt.

150. A protein according to any one of the preceding clauses or a composition according to any one of the preceding clauses for the use according to any one of the preceding clauses wherein said protein according to any one of the preceding clauses or a composition according to any one of the preceding clauses is administered intramuscularly or intradermally to said animal.

151. A protein according to any one of the preceding clauses or a composition according to any one of the preceding clauses for the use according to any one of the preceding clauses wherein said protein according to any one of the preceding clauses or a composition according to any one of the preceding clauses is administered to said animal in conjunction with another antigen, preferably wherein the other pathogen is an antigen to a porcine pathogen.

152. A protein according to any one of the preceding clauses or a composition according to any one of the preceding clauses for the use according to any one of the preceding clauses wherein said protein according to any one of the preceding clauses or a composition according to any one of the preceding clauses is administered to said animal in conjunction with another antigen; wherein said other antigen is not a PCV3 ORF2 antigen, preferably wherein the other pathogen is an antigen to a porcine pathogen.

153. A protein according to any one of the preceding clauses or a composition according to any one of the preceding clauses for the use according to any one of the preceding clauses wherein said protein according to any one of the preceding clauses or a composition according to any one of the preceding clauses is administered to said animal in conjunction with another antigen; wherein said other antigen is not a PCV3 antigen, preferably wherein the other pathogen is an antigen to a porcine pathogen.

154. A protein according to any one of the preceding clauses or a composition according to any one of the preceding clauses for the use according to any one of the preceding clauses wherein said animal is a sow pregnant with a piglet.

155. A protein according to any one of the preceding clauses or a composition according to any one of the preceding clauses for the use according to any one of the preceding clauses wherein said animal is a sow pregnant with a piglet; and wherein the piglet is to be suckled by a sow to which the protein according to any one of the preceding clauses or a composition according to any one of the preceding clauses has been administered.

156. A protein according to any one of the preceding clauses or a composition according to any one of the preceding clauses for the use according to any one of the preceding clauses wherein said animal is a sow; and wherein said protein according to any one of the preceding clauses or a composition according to any one of the preceding clauses is administered twice to said sow.

157. A protein according to any one of the preceding clauses or a composition according to any one of the preceding clauses wherein said animal is a sow; and wherein said protein according to any one of the preceding clauses or a composition according to any one of the preceding clauses is only administered twice to said sow.

158. A protein according to any one of the preceding clauses or a composition according to any one of the preceding clauses for the use according to any one of the preceding clauses wherein said animal is a piglet; and wherein the protein according to any one of the preceding clauses or a composition according to any one of the preceding clauses is administered once to said piglet.

159. A protein according to any one of the preceding clauses or a composition according to any one of the preceding clauses for the use according to any one of the preceding clauses wherein said animal is a piglet; and wherein the protein according to any one of the preceding clauses or a composition according to any one of the preceding clauses is only administered once to said piglet.

160. A protein according to any one of the preceding clauses or a composition according to any one of the preceding clauses for the use according to any one of the preceding clauses wherein said animal is a sow; and wherein the protein according to any one of the preceding clauses or a composition according to any one of the preceding clauses is administered twice to said sow; and wherein said use does not include the administration of any other PCV3 antigen to said animal before or during the administration of said protein according to any one of the preceding clauses or a composition according to any one of the preceding clauses.

161. A protein according to any one of the preceding clauses or a composition according to any one of the preceding clauses for the use according to any one of the preceding clauses wherein said animal is a sow; and wherein the protein according to any one of the preceding clauses or a composition according to any one of the preceding clauses is administered twice to said sow; and wherein said use does not include the administration of any other PCV3 antigen to said animal before or during the administration of said protein according to any one of the preceding clauses or a composition according to any one of the preceding clauses.

162. A protein according to any one of the preceding clauses or a composition according to any one of the preceding clauses for the use according to any one of the preceding clauses wherein said animal is a sow; and wherein the protein according to any one of the preceding clauses or a composition according to any one of the preceding clauses is administered only twice to said sow; and wherein said use does not include the administration of any other PCV3 antigen to said animal before or during the administration of said protein according to any one of the preceding clauses or a composition according to any one of the preceding clauses.

163. A protein according to any one of the preceding clauses or a composition according to any one of the preceding clauses for the use according to any one of the preceding clauses wherein said animal is a piglet; and wherein the protein according to any one of the preceding clauses or a composition according to any one of the preceding clauses is administered once to said piglet; and wherein said use does not include the administration of any other PCV3 antigen to said animal before or during the administration of said protein according to any one of the preceding clauses or a composition according to any one of the preceding clauses.

164. A protein according to any one of the preceding clauses or a composition according to any one of the preceding clauses for the use according to any one of the preceding clauses wherein said animal is a piglet; and wherein the protein according to any one of the preceding clauses or a composition according to any one of the preceding clauses is administered once to said piglet; and wherein said use does not include the administration of any other PCV3 antigen to said animal before or during the administration of said protein according to any one of the preceding clauses or a composition according to any one of the preceding clauses.

165. A protein according to any one of the preceding clauses or a composition according to any one of the preceding clauses for the use according to any one of the preceding clauses wherein said animal is a piglet; and wherein the protein according to any one of the preceding clauses or a composition according to any one of the preceding clauses is administered only once to said piglet; and wherein said use does not include the administration of any other PCV3 antigen to said animal before or during the administration of said protein according to any one of the preceding clauses or a composition according to any one of the preceding clauses.

166. A protein according to any one of the preceding clauses or a composition according to any one of the preceding clauses for the use according to any one of the preceding clauses wherein the administration to the animal in the use consists of a single, one shot administration or a single, one dose administration of said protein according to any one of the preceding clauses or a composition according to any one of the preceding clauses.

167. A protein according to any one of the preceding clauses or a composition according to any one of the preceding clauses for the use according to any one of the preceding clauses wherein the administration to the animal in the use consists of a multi-shot or multi-dose regimen of said protein according to any one of the preceding clauses or a composition according to any one of the preceding clauses.

168. A protein according to any one of the preceding clauses or a composition according to any one of the preceding clauses for the use according to any one of the preceding clauses wherein the administration to the animal in the use consists of a double shot administration; or a dual dose administration of said protein according to any one of the preceding clauses or a composition according to any one of the preceding clauses.

169. A protein according to any one of the preceding clauses or a composition according to any one of the preceding clauses for the use according to any one of the preceding clauses wherein the administration to the animal occurs within at least 1 or 2 or 3 weeks of exposure to virulent Porcine *Circovirus*.

170. A protein according to any one of the preceding clauses or a composition according to any one of the preceding clauses wherein the animal is a piglet not older than 15 weeks of age, or not older than 6 weeks of age, or not older than 3 weeks of age, or not older than 2 weeks of age, or not older than 1 week of age.

171. A protein according to any one of the preceding clauses or a composition according to any one of the preceding clauses for the use according to any one of the preceding clauses wherein said protein according to any one of the preceding clauses is for the use of any one of the preceding clauses.

172. A protein according to any one of the preceding clauses or a composition according to any one of the preceding clauses for the use according to any one of the preceding clauses wherein said protein according to any one of the preceding clauses is for the use of two or more uses of the preceding clauses.

173. A protein according to any one of the preceding clauses or a composition according to any one of the preceding clauses for the use according to any one of the preceding clauses wherein said composition according to any one of the preceding clauses is for the use of any one of the preceding clauses.

174. A protein according to any one of the preceding clauses or a composition according to any one of the preceding clauses for the use according to any one of the preceding clauses wherein a second antigen is administered to the animal before administration of the protein according to any one of the preceding clauses or a composition according to any one of the preceding clauses.

175. A protein according to any one of the preceding clauses or a composition according to any one of the preceding clauses for the use according to any one of the preceding clauses wherein a second antigen is administered to the animal at the same time as administration of the protein according to any one of the preceding clauses or a composition according to any one of the preceding clauses.

176. A protein according to any one of the preceding clauses or a composition according to any one of the preceding clauses for the use according to any one of the preceding clauses wherein a second antigen is administered to the animal at the same time and in the same composition as administration of the protein according to any one of the preceding clauses or a composition according to any one of the preceding clauses.

177. A protein according to any one of the preceding clauses or a composition according to any one of the preceding clauses for the use according to any one of the preceding clauses wherein a second antigen is administered to the animal at the same time and in a different composition as administration of the protein according to any one of the preceding clauses or a composition according to any one of the preceding clauses.

178. A protein according to any one of the preceding clauses or a composition according to any one of the preceding clauses for the use according to any one of the preceding clauses wherein a second antigen is administered to the animal after the administration of the protein according to any one of the preceding clauses or a composition according to any one of the preceding clauses.

179. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in one dose to the pig.

180. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in only one dose to the pig.

181. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in two doses to the pig.

182. A protein according to any one of the preceding clauses as the single PCV3 antigen for use in the vaccination of a pig to lessen the severity of clinical signs or clinical symptoms resulting from PCV3 infection in the pig, wherein the protein is in an immunogenic composition that is administered in only two doses to the pig.

183. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in one dose to the pig.

184. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in only one dose to the pig.

185. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in two doses to the pig.

186. A protein according to any one of the preceding clauses for use as the single PCV3 antigen for vaccination of a pig to lessen the severity of clinical signs or clinical symptoms resulting from PCV3 infection in the pig, wherein the protein is in an immunogenic composition that is administered in only two doses to the pig.

187. An immunogenic composition according to any one of the preceding clauses for lessening the severity of clinical signs or clinical symptoms resulting from PCV3 infection in a pig; wherein one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein according to any one of the preceding clauses is the antigenic component in the one dose of the immunogenic composition in the vaccination method that lessens the severity of clinical signs or clinical symptoms resulting from PCV3 infection in the pig;

preferably wherein the protein is in an amount of at least 2 µg in the one dose of the immunogenic composition;

wherein the protein is the antigenic component in the vaccination method that lessens the severity of clinical signs or clinical symptoms resulting from PCV3 infection in the pig.

188. An immunogenic composition according to any one of the preceding clauses for lessening the severity of clinical signs or clinical symptoms resulting from PCV3 infection in a pig;

wherein only one dose of the immunogenic composition is administered to the pig in a vaccination method to lessen the severity of clinical signs or clinical symptoms resulting from PCV3 infection in the pig;

wherein the administration of the one dose of the immunogenic composition to the pig in the vaccination method lessens the severity of clinical signs or clinical symptoms resulting from PCV3 infection in the pig;

wherein the protein according to any one of the preceding clauses is the antigenic component in the one dose of the immunogenic composition in the vaccination method that lessens the severity of clinical signs or clinical symptoms resulting from PCV3 infection in the pig;

preferably wherein the protein is in an amount of at least 2 μg in the one dose of the immunogenic composition;

wherein the protein is the antigenic component in the vaccination method that lessens the severity of clinical signs or clinical symptoms resulting from PCV3 infection in the pig.

189. An immunogenic composition according to any one of the preceding clauses for lessening the severity of clinical signs or clinical symptoms resulting from PCV3 infection in a pig; wherein two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessens the severity of clinical signs or clinical symptoms resulting from PCV3 infection in the pig;

wherein the protein according to any one of the preceding clauses is the antigenic component in the two doses of the immunogenic composition in the vaccination method that lessens the severity of clinical signs or clinical symptoms resulting from PCV3 infection in the pig;

preferably wherein the protein is in an amount of at least 2 μg in the one dose of the immunogenic composition;

wherein the protein is the antigenic component in the vaccination method that lessens the severity of clinical signs or clinical symptoms resulting from PCV3 infection in the pig.

190. An immunogenic composition according to any one of the preceding clauses for lessening the severity of clinical signs or clinical symptoms resulting from PCV3 infection in a pig;

wherein only two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessens the severity of clinical signs or clinical symptoms resulting from PCV3 infection in the pig;

wherein the protein according to any one of the preceding clauses is the antigenic component in the two doses of the immunogenic composition in the vaccination method that lessens the severity of clinical signs or clinical symptoms resulting from PCV3 infection in the pig;

preferably wherein the protein is in an amount of at least 2 μg in the one dose of the immunogenic composition;

wherein the protein is the antigenic component in the vaccination method that lessens the severity of clinical signs or clinical symptoms resulting from PCV3 infection in the pig.

191. The use according to any one of the preceding clauses wherein said clinical signs or symptoms are selected from the group consisting of reduction of average daily weight gain and mortality.

192. The use according to any one of the preceding clauses wherein said clinical signs or symptoms are selected from the group consisting of gross lesions, histological lesions, replication of PCV3 in a tissue, and PCV3 viremia.

193. The use according to any one of the preceding clauses wherein said clinical signs or symptoms are selected from the group consisting of development or production of a mummified, stillborn and/or weak fetus.

194. The use according to any one of the preceding clauses wherein said clinical signs or symptoms is or include expelling of a mummified, stillborn and/or weak fetus.

Clause Set E—The present invention will now be described by way of the following set of numbered clauses (Clause Set E). The disclosure in this set of clauses is equally applicable to the present invention. Likewise the disclosure in this set of clauses is equally applicable to each of the other set of clauses.

1. A porcine *circovirus* type 3 (PCV3) antigenic protein wherein said protein is a functional antigenic variant of PCV3 ORF2 protein.

2. A protein according to clause 1 wherein said PCV3 ORF2 protein is a protein encoded by SEQ ID No. 1.

3. A protein according to clause 1 or clause 2 wherein said protein comprises substitutions and/or extensions of PCV3 ORF2.

4. A protein according to any one of the preceding clauses wherein said functional antigenic variant is capable of a higher yield of virus-like particles (VLPs) than the protein encoded by SEQ ID No. 1.

5. A protein according to any one of the preceding clauses wherein said functional antigenic variant has one or more substitutions in the FG loop of the protein encoded by SEQ ID No. 1.

6. A protein according to any one of the preceding clauses wherein said functional antigenic variant has one or more substitutions in the FG loop of the protein encoded by SEQ ID No. 1, wherein those substitutions comprise substitutions of one or more of the S residue and/or the K residues and/or the H residue of the motif SKKKH (SEQ ID NO: 14) of the FG loop of the protein encoded by SEQ ID No. 1.

7. A protein according to any one of the preceding clauses wherein said functional antigenic variant has a C terminal end that extends beyond the terminal SVL sequence of the protein encoded by SEQ ID No. 1.

8. A protein according to any one of the preceding clauses wherein said functional antigenic variant has a C terminal end that extends beyond the terminal SVL sequence of the protein encoded by SEQ ID No. 1; wherein said extension is from 1 to 30 amino acids long; and wherein said extension comprises all of part of the sequence VKININLTPPVATSRVPSRALPLRFGCGHR (SEQ ID NO: 16).

9. A protein according to any one of the preceding clauses wherein said functional antigenic variant is encodable by all or part of SEQ ID No. 1, 2, 5, 6 or 7.

10. A protein according to any one of the preceding clauses wherein said functional antigenic variant protein comprises or consists of an amino acid sequence having at least 90%, or at least 91%, or at least 92%, or at least 93%, or at least 94%, or at least 95%, or at least 96%, or at least 97%, or at least 98%, or at least 99%, or 100% sequence identity with the sequence of SEQ ID NO: 3, 4, 8, 9 or 10.

11. A nucleotide sequence encoding the protein according to any of the preceding clauses.

12. A baculovirus expression host transformed or transfected with the nucleotide sequence of clause 11.

13. A method of preparing a protein according to any one of clauses 1 to 10 comprising culturing the baculovirus expression host of claim 12 to cause expression of the protein.

14. A composition comprising a protein according to any one of clauses 1 to 10 and a carrier, diluent or excipient.

15. A composition according to clause 14 wherein the composition comprises an immunomodulatory agent.

16. A protein according to any one of clauses 1 to 10 or a composition according to any one of clauses 14 to 15 for use as a vaccine.

17. A protein according to any one of clauses 1 to 10 or a composition according to any one of clauses 14 to 15 for use in a method for eliciting an immune response or an immunological response or a protective immune or immunological response against PCV3 in swine.

18. A protein according to any one of clauses 1 to 10 or a composition according to any one of clauses 14 to 15 for use in a method of treating or preventing an infection with PCV3 in an animal; wherein said animal is swine.

19. A protein according to any one of the preceding clauses or a composition according to any one of the preceding clauses for use in immunizing an animal against PCV3; wherein said animal is swine.

20. A protein according to any one of the preceding clauses or a composition according to any one of the preceding clauses for use in a method of reducing or eliminating or abrogating PCV3 viral expression in an animal; wherein said animal is swine.

21. A protein according to any one of the preceding clauses or a composition according to any one of the preceding clauses for use in inducing the production of antibodies specific for PCV3 in an animal.

22. A protein according to any one of clauses 1 to 10 or a composition according to any one of clauses 14 to 15 for use in a method of reducing or preventing the clinical signs or clinical symptoms or disease caused by an infection with PCV3 in an animal; wherein said animal is swine.

23. The protein or composition for the use according to clause 22 wherein said clinical signs or symptoms are selected from the group consisting of reduction of average daily weight gain, mortality, gross lesions, histological lesions, replication of PCV3 in a tissue, PCV3 viremia, development or production of a mummified, stillborn and/or weak fetus, expelling of a mummified, stillborn and/or weak fetus.

24. The protein or composition for the use according to any one of clauses 16 to 23 wherein the administration to the animal in the use consists of a single, one shot administration or a single, one dose administration of said protein or said composition.

25. The protein or composition for the use according to any one of clauses 16 to 23 wherein the administration to the animal in the use consists of a double shot administration; or a dual dose administration of said protein or said composition according to any one of the preceding clauses.

26. The protein or composition for the use according to any one of clauses 16 to 25 wherein said protein or said composition is administered intramuscularly or intradermally to said animal.

27. A porcine *circovirus* type 3 (PCV3) antigenic protein for use as the single PCV3 antigen for use in the vaccination of a swine and/or to lessen the severity of clinical signs or clinical symptoms resulting from PCV3 infection in a swine, wherein the protein is in an immunogenic composition that is administered in only one dose to the swine; wherein said antigenic protein is PCV3 ORF2 protein or a functional antigenic variant thereof, preferably wherein said functional antigenic variant thereof is a protein according to any one of clauses 1 to 10; preferably wherein said swine is a piglet, preferably wherein said piglet is not older than 15 weeks of age.

28. A porcine *circovirus* type 3 (PCV3) antigenic protein for use as the single PCV3 antigen for use in the vaccination of a swine and/or to lessen the severity of clinical signs or clinical symptoms resulting from PCV3 infection in a swine, wherein the protein is in an immunogenic composition that is administered in only two doses to the swine; wherein said antigenic protein is PCV3 ORF2 protein or a functional antigenic variant thereof, preferably wherein said functional antigenic variant thereof is a protein according to any one of clauses 1 to 10; preferably wherein said swine is a sow or a pre-breeding gilt.

29. An immunogenic composition for lessening the severity of clinical signs or clinical symptoms resulting from PCV3 infection in a pig;
  wherein only one dose of the immunogenic composition is administered to the pig in a vaccination method to lessen the severity of clinical signs or clinical symptoms resulting from PCV3 infection in the pig;
  wherein the administration of the one dose of the immunogenic composition to the pig in the vaccination method lessens the severity of clinical signs or clinical symptoms resulting from PCV3 infection in the pig;
  wherein a protein is the antigenic component in the one dose of the immunogenic composition in the vaccination method that lessens the severity of clinical signs or clinical symptoms resulting from PCV3 infection in the pig;
  wherein the protein is the antigenic component in the vaccination method that lessens the severity of clinical signs or clinical symptoms resulting from PCV3 infection in the pig;
  wherein said protein is a porcine *circovirus* type 3 (PCV3) antigenic protein;
  wherein said antigenic protein is PCV3 ORF2 protein or a functional antigenic variant thereof;
  preferably wherein said functional antigenic variant thereof is a protein according to any one of clauses 1 to 10.

30. An immunogenic composition for lessening the severity of clinical signs or clinical symptoms resulting from PCV3 infection in a pig;
  wherein only one dose of the immunogenic composition is administered to the pig in a vaccination method to lessen the severity of clinical signs or clinical symptoms resulting from PCV3 infection in the pig;
  wherein the administration of the one dose of the immunogenic composition to the pig in the vaccination method lessens the severity of clinical signs or clinical symptoms resulting from PCV3 infection in the pig;
  wherein a protein is the antigenic component in the one dose of the immunogenic composition in the vaccination method that lessens the severity of clinical signs or clinical symptoms resulting from PCV3 infection in the pig;
  wherein the protein is the antigenic component in the vaccination method that lessens the severity of clinical signs or clinical symptoms resulting from PCV3 infection in the pig;
  wherein the pig is a piglet, preferably wherein said piglet is not older than 15 weeks of age wherein said protein is a porcine *circovirus* type 3 (PCV3) antigenic protein;
  wherein said antigenic protein is PCV3 ORF2 protein or a functional antigenic variant thereof;
  preferably wherein said functional antigenic variant thereof is a protein according to any one of clauses 1 to 10.

31. An immunogenic composition for lessening the severity of clinical signs or clinical symptoms resulting from PCV3 infection in a pig;
  wherein only two doses of the immunogenic composition are administered to the pig in a vaccination method to lessen the severity of clinical signs or clinical symptoms resulting from PCV3 infection in the pig;

wherein the administration of the two doses of the immunogenic composition to the pig in the vaccination method lessen the severity of clinical signs or clinical symptoms resulting from PCV3 infection in the pig;

wherein a protein is the antigenic component in the two doses of the immunogenic composition in the vaccination method that lessens the severity of clinical signs or clinical symptoms resulting from PCV3 infection in the pig;

wherein the protein is the antigenic component in the vaccination method that lessens the severity of clinical signs or clinical symptoms resulting from PCV3 infection in the pig; wherein said protein is a porcine *circovirus* type 3 (PCV3) antigenic protein;

wherein said antigenic protein is PCV3 ORF2 protein or a functional antigenic variant thereof;

preferably wherein said functional antigenic variant thereof is a protein according to any one of clauses 1 to 10.

32. An immunogenic composition for lessening the severity of clinical signs or clinical symptoms resulting from PCV3 infection in a pig;

wherein only two doses of the immunogenic composition is administered to the pig in a vaccination method to lessen the severity of clinical signs or clinical symptoms resulting from PCV3 infection in the pig;

wherein the administration of the two doses of the immunogenic composition to the pig in the vaccination method lessen the severity of clinical signs or clinical symptoms resulting from PCV3 infection in the pig;

wherein a protein is the antigenic component in the two doses of the immunogenic composition in the vaccination method that lessens the severity of clinical signs or clinical symptoms resulting from PCV3 infection in the pig;

wherein the protein is the antigenic component in the vaccination method that lessens the severity of clinical signs or clinical symptoms resulting from PCV3 infection in the pig; wherein the pig is a sow or a pre-breeding gilt;

wherein said protein is a porcine *circovirus* type 3 (PCV3) antigenic protein;

wherein said antigenic protein is PCV3 ORF2 protein or a functional antigenic variant thereof;

preferably wherein said functional antigenic variant thereof is a protein according to any one of clauses 1 to 10.

33. The immunogenic composition for the use according to any one of clauses 29-32 wherein said clinical signs or symptoms are selected from the group consisting of reduction of average daily weight gain, mortality, gross lesions, histological lesions, replication of PCV3 in a tissue, PCV3 viremia, development or production of a mummified, stillborn and/or weak fetus, expelling of a mummified, stillborn and/or weak fetus.

34. The immunogenic composition for the use according to any one of clauses 29-33 wherein said protein or said composition is administered intramuscularly or intradermally to said animal.

In a practice of any of the embodiments of the invention, the PCV3 proteins of the invention discussed throughout this disclosure, the invention comprehends nucleic acid molecules encoding the PCV3 proteins of the invention, vectors, such as baculovirus vectors (see EP 2 460 821 A2, incorporated herein by reference, along with the documents cited therein as the methods and materials therein for expressing PCV2 ORF2 capsid protein via a baculovirus expression system can be employed in the practice of the present invention to express PCV3 ORF2 capsid protein, including such a PCV3 ORF2 wild type or mutant capsid protein as herein disclosed, as well as one or more proteins of one or more porcine pathogens if desired, to include such in a composition of the invention), containing such nucleic acid molecules, and methods for producing or expressing such mutated PCV3 proteins of the invention, such as by infecting or transfecting relevant cells with the vector (e.g., if the vector be baculovirus, a relevant cell can be an insect or Sf cell or Sf+cell; see EP 2 460 821 A2, incorporated herein by reference, along with the documents cited therein). It is advantageous to recover or isolate the protein after expression or production, e.g., separating solids and retaining liquid or supernatant that contains soluble protein (e.g., VLPs) and filtering the supernant. The supernatant containing the soluble protein (e.g., VLPs) is inactivated, advantageously with BEI, such as about 2 to 8 or about 5 mM BEI to inactivate the baculovirus. An adjuvant, advantageously about 1 mg or about 20% v/v of the Carbopol® or Carbopol® 971, is also added to the composition. A dosage of about 2, 4, 8 or 16 μg of the composition in a dosage of about 1 ml or about 2 ml in a single dose or a multiple dose is administered to a pig or piglet not older than 15 weeks of age, or not older than 6 weeks of age, or not older than 3 weeks of age, or not older than 2 weeks of age, or not older than 1 week of age.

The present disclosure will be further illustrated in the following Examples, which are given for illustration purposes only and are not intended to limit the disclosure in any way. Molecular cloning techniques (such as, but not limited to, construction of DNA inserts, plasmids and recombinant viral or plant vectors) were carried out using the standard molecular biology techniques described by J. Sambrook et. al. (Molecular Cloning: A Laboratory Manual, 2nd Edition, Cold Spring Harbor Laboratory, Cold Spring Harbor, N.Y., 1989), and in U.S. Pat. No. 8,865,183, the disclosure of which is incorporated by reference.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

In the Examples presented herein, the primary data have been included in addition to the summary tables that analyse that primary data. As with any field trials, the results are not exactly the same with each animal and, in addition, there can be one or more anomalous results. However, it is to be understood that the summary tables present the analysis of the primary data. The analysis results show that the present invention is effective.

Example 1

Identifying and Cloning PCV3 ORF2, and Production and Purification of BaculoG/PCV3 ORF2

The PCV3 ORF2 coding sequence (SEQ ID NO:1) was cloned by PCR from a synthetic gene containing the KT869077 ORF2 sequence (see Fan et al., "Complete Genome Sequence of a Novel Porcine *Circovirus* Type 3 Strain, PCV3/CN/Hubei-618/2016, Isolated from China, Genome Announc 2017 Apr. 5(15) e00100-17, Apr. 13. doi: 10.1128/genomeA.00100-17, incorporated herein reference;

see also SEQ ID NO: 4; U.S. Pat. No. 10,450,351, also incorporated herein by reference) and ligated into baculovirus transfer plasmid pVL1393 (Invitrogen) utilizing 5' BamHI and 3' NotI restriction sites. The BamHI/NotI restriction fragment also contained a Kozak consensus sequence (GCCACC) directly between the 5' BamHI site and the PCV3 ORF2 start codon. Recombinant baculovirus containing the PCV3 ORF2 coding sequence under the control of the polyhedron promoter was generated by co-transfection of Sf9 insect cells (*Spodoptera frugiperda*) with linearized baculovirus DNA and transfer plasmid pVL1393-PCV3 ORF2. The resulting recombinant baculovirus, BaculoG/PCV3 ORF2, was amplified on Sf9 insect cells and subsequently purified by limiting dilution cloning. Mention is also made as to employing the method of EP 2 460 821 A2, incorporated herein by reference, along with the documents cited therein, with the coding sequence being for a PCV3 ORF2 protein as herein disclosed (including that the foregoing methods are employed for preparing any mutant or variant or modified PCV3 ORF2 protein, especially SEQ ID NO: 3, 4, 8, 9 or 10).

The PCV3 ORF2 coding sequence (SEQ ID NO:1) was cloned by PCR from a synthetic gene containing the KT869077 ORF2 sequence and ligated into baculovirus transfer plasmid pVL1393 utilizing 5' BamHI and 3' NotI restriction sites. The BamHI/NotI restriction fragment also contained a Kozak consensus sequence (GCCACC) directly between the 5' BamHI site and the PCV3 ORF2 start codon. Recombinant baculovirus containing the PCV3 ORF2 coding sequence under the control of the polyhedron promoter was generated by co-transfection of Sf9 insect cells (*Spodoptera frugiperda*) with linearized baculovirus DNA and transfer plasmid pVL1393-PCV3 ORF2. The resulting recombinant baculovirus, BaculoG/PCV3 ORF2, was amplified on Sf9 insect cells and subsequently purified by limiting dilution cloning.

Examples 1A, 1B, 1C

Identifying and Cloning PCV3 ORF2 and Mutants or Variants Thereof (FG Loop Mutations, FG Loop Mutations and Extended or Added to C-Terminus), Production and Purification of BaculoG/PCV3 ORF2 and Mutants or Variants Thereof (FG Loop Mutations, FG Loop Mutations and Extended or Added to C-Terminus), and Uses Thereof Example 1A: The nucleic acid molecule encoding the PCV3 ORF2 protein of SEQ ID NO: 4 was cloned into a vector, a baculovirus vector (see Example 1, see also EP 2 460 821 A2, incorporated herein by reference, along with the documents cited therein as the methods and materials therein for expressing PCV2 ORF2 capsid protein via a baculovirus expression system) (when desired to include such in a composition of the invention, one or more proteins of one or more porcine pathogens may be also expressed using a vector system such as a baculovirus system, or can be inactivated pathogen such as inactivated virus, e.g., PRRSV or bacterin or supernatant of bacteria culture). Cells are infected or transfected with the vector, the baculovirus vector (See Example 1, Example 2, see EP 2 460 821 A2, incorporated herein by reference, along with the documents cited therein; SF+ (*Spodoptera frugiperda*) cells infected or transfected at an approximate MOI of 0.076 with a recombinant baculovirus containing the coding for Porcine *Circovirus* 3 ORF2 gene 2 under control of the baculovirus polyhedrin promoter). After expression or production of protein, the protein is recovered or isolated, e.g., separating solids and retaining liquid or supernatant that contains soluble protein (e.g., VLPs) and filtering the supernatant. The supernatant containing the soluble protein (e.g., VLPs) is inactivated, advantageously with BEI, such as about 2 to 8 or about 5 mM BEI to inactivate the baculovirus. An adjuvant, advantageously about 1 mg or about 20% v/v of the Carbopol® or Carbopol® 971, is also added to make the composition. (See, e.g., Example 2, flask is incubated at 28° C.±2° C. with constant agitation at approximately 100 rpm for seven days. Cells and media are aseptically transferred to 2×1 L centrifuge bottles and cells are pelleted at 15,000×g for 20 minutes at 4° C. The resulting supernatant is 0.2 m filtered and stored at 4° C.; inactivated Baculovirus PCV3 ORF2 Antigen, 800 mL; Carbopol® 971P (0.5% stock solution) Adjuvant, 200 mL; total 1000 mL or 1 L).

A single dosage (i.e., one shot or single administration) of the composition containing either 2 μg, 4 μg, 8 μg or 16 μg of PCV3 ORF2 Antigen in a 1 ml or about 2 ml total volume is administered to groups of pigs (e.g., 6 pigs per group). A group of pigs or piglets is not older than 15 weeks of age. A group of pigs or piglets is not older than 6 weeks of age. A group of pigs or piglets is not older than 3 weeks of age. A group of pigs or piglets is not older than 2 weeks of age. A group of pigs or piglets is not older than 1 week of age. A group of pigs is sows, pre-insemination. Administration, e.g., as to timing, of single doseage is one of the below-mentioned administrations of the multiple dose regimen discussed immediately below. From the single administration, each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

A multiple dosage regimen, i.e., two shots or two single administrations (e.g., a prime and a boost), spaced apart by at least a week of the composition containing either 2 μg, 4 μg, 8 μg or 16 μg of PCV3 ORF2 Antigen in a 1 ml or about 2 ml total volume is administered to groups of pigs (e.g., 6 pigs per group). A group of pigs or piglets is not older than 15 weeks of age (first administration at 2 or 3 weeks of age and second administration at 3 or 4 weeks of age). A group of pigs or piglets is not older than 6 weeks of age (first administration at 2 or 3 weeks of age and second administration at 3, 4 or 5 weeks of age). A group of pigs or piglets is not older than 3 weeks of age (first administration between 7 and 14 days of age, second administration between 14 and 21 days of age). A group of pigs or piglets is not older than 2 weeks of age (first administration at 1 week of age and second administration at 2 weeks of age). A group of pigs or piglets is not older than 1 week of age (administrations at days 3 or 4 and 7). A group of pigs is sows, pre-insemination (first administration between 4 and 6 weeks pre-insemination and second administration between 2 and 4 weeks pre-insemination). From the multiple administration, each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

Example 1B: The nucleic acid molecule encoding the PCV3 ORF2 protein of SEQ ID NO: 8 (4 mutations in FG Loop; FG Loop of PCV3 ORF2 protein replaced with that of PCV2 (SKKK (SEQ ID NO: 11)>QPFS (SEQ ID NO: 12)) was cloned into a vector, a baculovirus vector (see Example 1, see also EP 2 460 821 A2, incorporated herein by reference, along with the documents cited therein as the methods and materials therein for expressing mutated PCV2

ORF2 capsid protein via a baculovirus expression system) (when desired to include such in a composition of the invention, one or more proteins of one or more porcine pathogens may be also expressed using a vector system such as a baculovirus system, or can be inactivated pathogen such as inactivated virus, e.g., PRRSV or bacterin or supernatant of bacteria culture). Cells are infected or transfected with the vector, the baculovirus vector (See Example 1, Example 2, see EP 2 460 821 A2, incorporated herein by reference, along with the documents cited therein; SF+(*Spodoptera frugiperda*) cells infected or transfected at an approximate MOI of 0.076 with a recombinant baculovirus containing the coding for mutated Porcine *Circovirus* 3 ORF2 gene 2 under control of the baculovirus polyhedrin promoter).

After expression or production of mutated protein, the mutated protein is recovered or isolated, e.g., separating solids and retaining liquid or supernatant that contains soluble mutated protein (e.g., VLPs) and filtering the supernant. The supernatant containing the soluble mutated protein (e.g., VLPs) is inactivated, advantageously with BEI, such as about 2 to 8 or about 5 mM BEI to inactivate the baculovirus. An adjuvant, advantageously about 1 mg or about 20% v/v of the Carbopol® or Carbopol® 971, is also added to make the composition. (See, e.g., Example 2, flask is incubated at 28° C.±2° C. with constant agitation at approximately 100 rpm for seven days. Cells and media are aseptically transferred to 2×1 L centrifuge bottles and cells are pelleted at 15,000×g for 20 minutes at 4° C. The resulting supernatant is 0.2 m filtered and stored at 4° C.; inactivated Baculovirus mutated PCV3 ORF2 Antigen, 800 mL; Carbopol® 971P (0.5% stock solution) Adjuvant, 200 mL; total 1000 mL or 1 L). The amount of VLP (soluble mutated PCV3 ORF2 protein) obtained with the mutant is greater than the amount of VLP obtained from native sequence of SEQ ID NO: 4.

A single dosage (i.e., one shot or single administration) of the composition containing either 2 µg, 4 µg, 8 µg or 16 µg of mutated PCV3 ORF2 Antigen in a 1 ml or about 2 ml total volume is administered to groups of pigs (e.g., 6 pigs per group). A group of pigs or piglets is not older than 15 weeks of age. A group of pigs or piglets is not older than 6 weeks of age. A group of pigs or piglets is not older than 3 weeks of age. A group of pigs or piglets is not older than 2 weeks of age. A group of pigs or piglets is not older than 1 week of age. A group of pigs is sows, pre-insemination. Administration, e.g., as to timing, of single doseage is one of the below-mentioned administrations of the multiple dose regimen discussed immediately below. From the single administration, each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

A multiple dosage regimen, i.e., two shots or two single administrations (e.g., a prime and a boost), spaced apart by at least a week of the composition containing either 2 µg, 4 µg, 8 µg or 16 µg of mutated PCV3 ORF2 Antigen in a 1 ml or about 2 ml total volume is administered to groups of pigs (e.g., 6 pigs per group). A group of pigs or piglets is not older than 15 weeks of age (first administration at 2 or 3 weeks of age and second administration at 3 or 4 weeks of age). A group of pigs or piglets is not older than 6 weeks of age (first administration at 2 or 3 weeks of age and second administration at 3, 4 or 5 weeks of age). A group of pigs or piglets is not older than 3 weeks of age (first administration between 7 and 14 days of age, second administration between 14 and 21 days of age). A group of pigs or piglets is not older than 2 weeks of age (first administration at 1 week of age and second administration at 2 weeks of age). A group of pigs or piglets is not older than 1 week of age (administrations at days 3 or 4 and 7). A group of pigs is sows, pre-insemination (first administration between 4 and 6 weeks pre-insemination and second administration between 2 and 4 weeks pre-insemination). From the multiple administration, each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

Example 1C: The nucleic acid molecules encoding (a) the mutated PCV3 ORF2 protein having 4 mutations in FG Loop; FG Loop of PCV3 ORF2 protein replaced with that of PCV2 (SKKK (SEQ ID NO: 11)>QPFS (SEQ ID NO: 12)) and 30 amino acid extension of C-terminus by removal of stop codon in natural PCV3 ORF2 coding sequence-term extended by removal of stop codon, i.e., after "SVL" at natural PCV3 ORF2 protein C-terminus, the addition of: VKININLTPPVATSRVPSRALPLRFGCGHR (SEQ ID NO: 16), see SEQ ID NO: 8 and 9; and (b) the mutated PCV3 ORF2 protein having 30 amino acid extension of C-terminus by removal of stop codon in natural PCV3 ORF2 coding sequence-term extended by removal of stop codon, i.e., after "SVL" at natural PCV3 ORF2 protein C-terminus, the addition of: VKININLTPP-VATSRVPSRALPLRFGCGHR (SEQ ID NO: 16), see SEQ ID NO:9, each was cloned into a vector, a baculovirus vector (see Example 1, see also EP 2 460 821 A2, incorporated herein by reference, along with the documents cited therein as the methods and materials therein for expressing mutated PCV2 ORF2 capsid proteins via a baculovirus expression system) (when desired to include such in a composition of the invention, one or more proteins of one or more porcine pathogens may be also expressed using a vector system such as a baculovirus system, or can be inactivated pathogen such as inactivated virus, e.g., PRRSV or bacterin or supernatant of bacteria culture). Cells are infected or transfected with the vectors encoding (a) or (b), the baculovirus vectors encoding (a) or (b) (See Example 1, Example 2, see EP 2 460 821 A2, incorporated herein by reference, along with the documents cited therein; SF+(*Spodoptera frugiperda*) cells infected or transfected at an approximate MOI of 0.076 with a recombinant baculovirus containing the coding for mutated Porcine *Circovirus* 3 ORF2 gene 2 under control of the baculovirus polyhedrin promoter).

After expression or production of mutated proteins (a) or (b), the mutated proteins each is recovered or isolated, e.g., separating solids and retaining liquid or supernatant that contains soluble mutated protein (e.g., VLPs) and filtering the supernant. The supernatant containing the soluble mutated protein (e.g., VLPs) is inactivated, advantageously with BEI, such as about 2 to 8 or about 5 mM BEI to inactivate the baculovirus. An adjuvant, advantageously about 1 mg or about 20% v/v of the Carbopol® or Carbopol® 971, is also added to make the composition. (See, e.g., Example 2, flask is incubated at 28° C.±2° C. with constant agitation at approximately 100 rpm for seven days. Cells and media are aseptically transferred to 2×1 L centrifuge bottles and cells are pelleted at 15,000×g for 20 minutes at 4° C. The resulting supernatant is 0.2 m filtered and stored at 4° C.; inactivated Baculovirus mutated PCV3 ORF2 Antigen, 800 mL; Carbopol® 971P (0.5% stock solution) Adjuvant, 200 mL; total 1000 mL or 1 L). The amount of VLP (soluble mutated PCV3 ORF2 proteins) obtained with each mutant is greater than the amount of VLP obtained from native sequence of SEQ ID NO: 4. The amount of VLP (soluble mutated PCV3 ORF2 protein) obtained with the mutant having both the FG Loop mutation and the extension (mutant (b) can be greater than the amount of VLP obtained from the FG Loop mutant or variant alone or the extension alone.

A single dosage (i.e., one shot or single administration) of the composition containing either 2 μg, 4 μg, 8 μg or 16 μg of either mutated PCV3 ORF2 Antigen (a) or (b) in a 1 ml or about 2 ml total volume is administered to groups of pigs (e.g., 6 pigs per group). A group of pigs or piglets is not older than 15 weeks of age. A group of pigs or piglets is not older than 6 weeks of age. A group of pigs or piglets is not older than 3 weeks of age. A group of pigs or piglets is not older than 2 weeks of age. A group of pigs or piglets is not older than 1 week of age. A group of pigs is sows, pre-insemination. Administration, e.g., as to timing, of single dosage is one of the below-mentioned administrations of the multiple dose regimen discussed immediately below. From the single administration of each of (a) or (b) in the dosages, each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

A multiple dosage regimen, i.e., two shots or two single administrations (e.g., a prime and a boost; or same mutant, i.e., prime and boost are either with both (a) or both (b), and prime and boost are in same dosage amount), spaced apart by at least a week of the composition containing either 2 μg, 4 μg, 8 μg or 16 μg of mutated PCV3 ORF2 Antigen (a) or (b) in a 1 ml or about 2 ml total volume is administered to groups of pigs (e.g., 6 pigs per group). A group of pigs or piglets is not older than 15 weeks of age (first administration at 2 or 3 weeks of age and second administration at 3 or 4 weeks of age). A group of pigs or piglets is not older than 6 weeks of age (first administration at 2 or 3 weeks of age and second administration at 3, 4 or 5 weeks of age). A group of pigs or piglets is not older than 3 weeks of age (first administration between 7 and 14 days of age, second administration between 14 and 21 days of age). A group of pigs or piglets is not older than 2 weeks of age (first administration at 1 week of age and second administration at 2 weeks of age). A group of pigs or piglets is not older than 1 week of age (administrations at days 3 or 4 and 7). A group of pigs is sows, pre-insemination (first administration between 4 and 6 weeks pre-insemination and second administration between 2 and 4 weeks pre-insemination). From the multiple administration or either (a) or (b), each of the groups of pigs demonstrates immunity, e.g., a protective immunity, against PCV3 and/or clinical signs or symptoms thereof, and/or reduction or lessening or prevention of PCV3 infection or incidence thereof and/or of clinical signs or symptoms thereof.

Example 2

Production of BaculoG/PCV3 ORF2 Antigen for the Study

A 1 L lot of antigen was produced in a 3 L spinner flask by infecting SF+(*Spodoptera frugiperda*) cells at an approximate MOI of 0.076 with a recombinant baculovirus containing the Porcine *Circovirus* 3 ORF2 gene 2 under control of the baculovirus polyhedrin promoter (BaculoG/PCV3 ORF2 Clone 4B4-2E12 Pre-MSV p8). The flask was incubated at 28° C.±2° C. with constant agitation at approximately 100 rpm for seven days. Cells and media were aseptically transferred to 2×1 L centrifuge bottles and cells were pelleted at 15,000×g for 20 minutes at 4° C. The resulting supernatant was 0.2 m filtered and stored at 4° C.

TABLE 1

Formulation of PCV3 ORF2 inactivated baculovirus vaccine

| Component | Purpose | Volume |
| --- | --- | --- |
| Inactivated Baculovirus PCV3 ORF2 | Antigen | 800 mL |
| Carbopol 971P (0.5% stock solution) | Adjuvant | 200 mL |

Example 3

Efficacy Evaluation of Prototype Vaccines for Porcine *Circovirus* Type 3 (PCV3) in Caesarian-Derived Colostrum-Deprived Pigs The objectives of the Example are to: evaluate the efficacy of prototype PCV3 vaccines in caesarian-derived colostrum-deprived (CDCD) pigs, develop a challenge model for PCV3 in CDCD pigs including defining primary and secondary outcome variables, confirm infectivity of infectious molecular clones.

This study was designed to evaluate the use of whole virus and PCR positive tissue homogenate (both provided by Iowa State University Veterinary Diagnostic Laboratory (ISU VDL)) as potential challenge materials for future studies. In addition, the rescue of a PCV3 infectious clone in pigs would provide an additional option for future challenge model studies and was therefore incorporated into the study design. As prototype vaccines were available, they were included to provide a stronger evaluation of the challenge model.

TABLE 2

Study design

| Group | N | Room* | Vaccination (D0; at 3 weeks of age) | Challenge (D21; at 6 weeks of age) | Necropsy (D49; at 10 weeks of age) | Necropsy (D63; at 12 weeks of age) |
| --- | --- | --- | --- | --- | --- | --- |
|  | 8 | A | BaculoG/PCV3 - ISA | Whole virus + KLH | All remaining animals euthanized; tissue collection | Not applicable |
|  | 8 |  | BaculoG/PCV3 - Carbopol |  |  |  |
|  | 8 |  | Placebo |  |  |  |
|  | 12 | B | BaculoG/PCV3 - Carbopol | PCR + tissue homogenate + KLH | 8 animals euthanized; tissue collection | 4 animals euthanized; tissue collection |
|  | 12 |  | Placebo |  |  |  |

TABLE 2-continued

| | | | Study design | | |
|---|---|---|---|---|---|
| | 6 | C | Nous | Placebo challenge controls (whole virus media) | 3 animals euthanized; tissue collection | 3 animals euthanized; tissue collection |

| Group | N | Room | Challenge (at D14; at 5 wks) | Necropsy |
|---|---|---|---|---|
| | 2 | D | Infectious clone - BIAH re-circularized genome | All animals euthanized at D28 or D42 |
| | 2 | | Infectious clone - ISU re-circularized genome | |
| | 2 | | Infectious clone - ISU dimerized genome in plasmid | |

A total of 54 pigs were used. The animals were randomized into five treatment groups (n=8-12/group) and one strict control group (n=6). Animals were housed in three rooms. At 7 days of age, pigs were vaccinated with PCV2. On D0, at three weeks of age, pigs were vaccinated with either a vectored construct expressing PCV3 ORF2 adjuvanted with ISA 207VG, a vectored construct expressing PCV3 ORF2 adjuvanted with Carbopol®, or a placebo (matched control for vectored construct). Pigs were moved at approximately five weeks of age. On D21, at six weeks of age, pigs were challenged with either whole virus or tissue homogenate. An immunostimulant (TFA/KLH) was administered in addition to the challenge material. As used herein, the role of the immune stimulant was not of an adjuvant, but as a challenge enhancer. Rectal temperatures, body weight, serum, whole blood, nasal swabs, and fecal swabs were collected periodically throughout the study. Samples were tested jointly. Animals were euthanized at either D49 or D63 as described in Table 2. Multiple fresh and fixed tissues were collected and evaluated.

For the investigation with infectious clone constructs, a total of 6 pigs were used. The animals were randomized into three groups (n=2/group) and housed in a single room. At D14 when animals were approximately 5 weeks of age, they were inoculated with one of three infectious clone constructs. Inoculation was done intrahepatically (ultrasound-guided). In addition, animals in Group 9 were inoculated intramuscularly. Rectal temperatures, body weight, serum, nasal, and fecal samples were collected periodically throughout the study. Samples were tested by qPCR to determine whether clones were able to replicate. Animals were euthanized on D49. Multiple fresh and fixed tissues were collected only from animals that were viremic and were transferred for evaluation.

A schedule of events for the study is shown in Table 3.

TABLE 3

| Study Day | Study Event |
|---|---|
| D −22 | Collection of cord blood |
| D −14 | Vaccination of animals for PCV2 at 7 days of age |
| D 0 | Vaccination of animals in groups 1-6 (3 weeks of age) |
| | Blood collection (Note: no fecal swabs, nasal swabs, temperatures or weight data collected) |
| D 12 | Transport of animals |
| D 14 | Challenge of animals in groups 7-9 (5 weeks of age) |
| D 19 | Administration KLH/ICFA to animals in groups 1-6 |

TABLE 3-continued

| Study Day | Study Event |
|---|---|
| D 21 | Challenge of animals in groups 1-5 (6 weeks of age) |
| D 23 | Administration KLH/ICFA to animals in groups 1-6 |
| D 49 | Necropsy selected animals in groups 4-6; all animals in group 1-3, 7-9 |
| D 63 | Necropsy of remaining animals in groups 4-6 |
| D 21 through D 12 | General health observations on all animals |
| D 13-D 63 | Clinical observations on all available animals |
| D 13, 15, 16, 19, 21, 23, 28 | Rectal temperature from groups 7-9 Blood collection, fecal swabs, nasal swabs in animal from groups 7-9 |
| D 13, 21, 22, 23, 26, 28, 35, 42, 49 | Rectal temperature from groups 1-5 Blood collection, fecal swabs, nasal swabs in animals from groups 1-5 |
| D 13, 15, 16, 19, 21, 22, 23, 26, 28, 35, 42, 49 | Rectal temperature from group 6 Blood collection, fecal swabs, nasal swabs in animals from group 6 |
| D 13, 21, 28, 35, 42, 49 | Body weights (all available animals) |

An experimental vaccine (BaculoG/PCV ORF2) was compared with a placebo-matched control. Treatments are outline in Table 4.

TABLE 4

| Group | Treatment |
|---|---|
| 1 | BaculoG/PVC3 ORF2, P9; live, adjuvanted with 50% ISA 207VG; L#3624-171 |
| 2 & 4 | BaculoG/PVC3 ORF2, P9; live, adjuvanted with 20% carbopol; L#3624-172A |
| 3 & 5 | BaculoG/no insert control; P4; live, adjuvanted with 20% carbopol; L#3624-172B |
| 6 | No treatment |
| 7 | Infectious clone - BIAH re-circularized genome; Lot#3718-050 |
| 8 | Infectious clone - ISU dimerized genome in plasmid |
| 9 | Infectious clone - ISU rescued virus |

The vaccines were administered on D0 intramuscularly into the right side of the neck (2 mL), midway between the base of the ear and point of the shoulder, using appropriately-sized sterile needles and syringes. Commercial PCV2 vaccine (Circoflex, serial #3091134A) was administered to all animals per manufacturer's instructions.

Whole virus challenge: Challenge material was stored at −70° C.±10° C. until use. Immediately prior to challenge, material was thawed at 37° C. and used undiluted. Dosage was 2 mL total (1 mL IN/1 mL IM). On D21, each pig received 1 mL of viral harvest intranasally and 1 mL intramuscularly. Administration of challenge material intramuscularly was done by injecting the viral harvest into the left side of the neck, midway between the base of the ear and point of the shoulder, using appropriately-sized sterile needles and syringes. Administration of the challenge material intranasally was done by attaching a nasal tip atomizer to a 5cc luer lock syringe. Duration of challenge was 28 days. Routine culture of the material was done on blood agar plates at 37° C. anaerobically and aerobically for 48 hrs. No growth was observed and the test was considered satisfactory. The material was tested by PCR for the presence of *mycoplasma*; no contamination was identified. The PCV3 qPCR result was: 6.6 log 10 genomic copies/mL (Cq=23.58). Deep sequencing was completed on the samples (MiSeq_127) using both DNA and RNA processing. Sequencing did not result in recovery of PCV3.

Challenge by PCV3 PCR positive tissue homogenate. Challenge material was stored at −70° C.±10° C. until use. Immediately prior to challenge, material was thawed at 37° C. and used undiluted. Dosage was 2 mL total (1 mL IN/1 mL IM). On D21, each pig received 1 mL of viral harvest intranasally and 1 mL intramuscularly. Administration of challenge material intramuscularly was done by injecting the viral harvest into the left side of the neck, midway between the base of the ear and point of the shoulder, using appropriately-sized sterile needles and syringes. Administration of the challenge material intranasally was done by attaching a nasal tip atomizer to a 5cc luer lock syringe. Duration of challenge was 28 days. Routine culture of the material was done on blood agar plates at 37° C. anaerobically and aerobically for 48 hrs. No growth was observed and the test was considered satisfactory. The material was tested by PCR for the presence of *mycoplasma*; no contamination was identified. The PCV3 qPCR result was: 9.1 log 10 genomic copies/mL (Cq=14.82). Deep sequencing was completed on the samples (MiSeq_127) using both DNA and RNA processing. Sequencing resulted in recovery of the full PCV3 genome (99% nt to PCV3 GB MG564174.1).

Table 5 describes the immunostimulant given to the animals.

TABLE 5

| Generic Name: | Keyhole limpet hemocyanin emulsified in incomplete Freund's adjuvant (KLH/ICFA) |
|---|---|
| Formulations (per dose): | BIVI-R&D formulated KLH/ICFA to contain the equivalent of 1 mg KLH/1 mL adjuvanted with 1 mL of ICFA. |
| Manufacturer: | BI AH USA - Ames, IA |
| Lot Number: | 3519-049 |
| Expiration Date: | N/A |
| Storage: | Stored at 2-8° C. prior to use. |
| Presentation: | 52 mL - in 60 mL plastic bottle |
| Testing: | KLG/ICFA was tested for sterility |
| Applied Dose: | 2.0 mL in the right ham muscle on D 19 and 2.0 mL in the left ham muscle on D 23. Treatments were administered by a Dose Administrator, a person not responsible for collecting data for this study. KLH administration was documented on the Product Dosing Record. |

On D14, pigs in Groups 7 and 8 were infected via ultrasound guided injection into the liver only –lymph nodes were not inoculated. For challenge, 1 mL of material was drawn up into a tuberculin syringe and attached to a sterile 22 g×1.5 inch needle. The needle was directed into three different areas within the liver. Approximately 300 µl was administered into each location. Pigs in Group 9 were administered inoculum as described above. In addition, they were intramuscularly injected with a total of 3 mL of material; 1.5 mL of material in the musculature of the right neck and 1.5 mL of material into the musculature of the left neck. Following challenge, pigs were administered 0.5 mL of Baytril into the musculature of the right neck. Group 7 (pigs 1 and 2) were administered material with a re-circularized genome. Group 8 (pigs 3 and 4) were administered a dimerized plasmid. Group 9 (pigs 5 and 6) were administered a transfection cell culture harvest. Table 6 shows the inclusion/exclusion criteria used in the study.

TABLE 6

| Specifications | Requirements |
|---|---|
| Species & Breed: | Porcine, CDCD |
| Age: | Pigs were 21 days of age at D 0 |
| Weight Range: | No specified weight range was required |
| Source & Ownership: | Source: Struve Labs International; 1603 Enterprise St., Manning Iowa 51455 Ownership: Boehringer Ingelheim Animal Health USA, Inc. |
| Number: | 60 |
| Identification: | Ear tag (uniquely numbered) |
| Physiological status: | All pigs were vaccinated for PCV2 prior to shipment to AMVC. All piglets were healthy at the time of vaccination as determined by observation by the Study Investigator. |
| Serological status: | Not specified. |
| Additional inclusion requirements: | Serum samples collected on D 0 and D 13 were tested for the presence of PCV3 and PCV2 DNA by qPCR. No PCV3 or PCV2 DNA was detected at either time-point |
| Exclusion: | A total of 60 animals were transferred and there were no mortalities following transfer. All animals were included in the study. |
| Post-inclusion removal: | No animals were removed following inclusion into the study. |

The pig was the experimental unit. The randomization of pigs to pen and treatment was conducted by a statistician or designee. Prior to the start of the study, the available pigs, litter information, and housing facility set-up were used to assign treatments randomly within litter. A total of four litters ranging from 12 to 14 pigs were included for Groups 1-6. A total of two litters with three pigs were included for Groups 7-9. Personnel involved with collecting data or performing laboratory assays were blinded to the allocation of pigs to groups throughout the study. Treatments were administered by an individual not involved with data collection. The use of animals in this study was approved. Adequate floor and feeder space was provided in accordance with acceptable animal husbandry practices. Pigs were observed daily to ensure access to an adequate supply of feed and water and to determine the animals' general health. The animals were under veterinary supervision upon arrival at the facility until the end of the study. No treatments were administered to animals throughout the duration of the study. Throughout the study pigs were feed the following medicated feeds: UltraCare 100 Medicated (Lot #7Nov.03); UltraCare 240 Medicated (Lot #8 Jun.25); UltraCare 500 Medicated (Lot #8 Aug.30); or Lean Metrics CEPS Medicated (Lot #08Nov.14). Animals were disposed of via rendering following the conclusion of the study with the exception of animal #13 which was incinerated on D46.

All pigs were observed daily for general health from D1 through D12. No abnormalities were noted. Beginning on D13 and continuing through the end of the study, all pigs were observed daily for the presence of clinical signs as described in Table 7.

TABLE 7

| Score | Respiratory Signs | Neurological Signs | Body Condition | Diarrhea |
|---|---|---|---|---|
| 0 | Normal | Normal | Normal | Normal |
| 1 | Mild = mild increase in respiratory rate | Depressed = depressed to lethargic, requires physical stimulation to provoke locomotion | Mild = depressed appetite but still eating, slightly thin compared to pen mates | Mild = slightly loose stool observed from pig |
| 2 | Moderate = notable increase in respiratory rate | Ataxic = unable to coordinate muscle activity, spastic movements involving head, limbs, and/or trunk | Moderate = not eating, ribs and backbone obviously pronounced | Moderate = runny, loose stool observed; obvious staining of the perianal region |
| 3 | Severe = thumping | Tremors = involuntary repetitive muscle movements | Severe = emaciated | Severe = very watery stool observed |
| 4 | | Recumbent = laying down, unable to raise when provoked with physical stimulus | | |
| 5 | | Seizures = bilateral tonic or clonic contraction of muscles resulting in partial or complete unconsciousness | | |

On the days of temperature collection, the body temperature of each animal was collected using a microchip (Destron Fearing LifeChip® with bio-Thermo Technology) and an Allflex thermometer (Model number RS420-45, serial no. C088 26001). Data was recorded in ° F. For statistical analysis, data was baseline corrected. Pyrexia was defined as a temperature greater than 104° F. On the days of body weight collection, weights were recorded in kilograms using a calibrated scale.

On blood collection dates, venous whole blood was collected via the anterior vena cava from each pig using an appropriately sized sterile Vaccutainer® needle, a Vaccutainer® needle holder, and serum separator tubes (SST). The blood was hand delivered and serum was decanted into two screw-cap cryogenic vials and one 5 mL Falcon tube labeled with at least study number, day of study, and animal ID. Serum samples in cryogenic vials were stored at −70° C.±10° C. and tracked via Freezerworks electronic management system. Serum was tested by qPCR for the presence of PCV3. The 5 mL Falcon tubes were transferred for ELISA testing.

Swab samples were collected from pigs. A separate, sterile, swab (Fisher catalog no. 23-400-111 or similar) was used to obtain a fecal sample from the rectum of the animal or a nasal sample from one nostril. Upon sampling, each swab was placed in a tube containing 1.0 mL of minimal essential media (SAFC cat #62892-1000M3056). Tubes of media were prepared and were stored at 4° C. prior to use. Following use, tubes were labeled with a minimum of animal id, study number and date. Tubes were stored at −70° C.±10° C. and delivered on the day of collection and were processed using routine methods. Processed materials were stored in vials labeled with at least study number, day of study, and animal ID. Samples were stored at −70° C.±10° C. and tracked via Freezerworks electronic management system. Samples were tested by qPCR.

Animals in Groups 7-9 were necropsied on D49. Animals in Groups 1-6 were euthanized at either D49 or D63. At the time of necropsy, macroscopic lesions were recorded on the Necropsy Report Record. The study investigator or designee collected formalin-fixed tissue samples of cerebrum (½ of the organ), cerebellum (½ of organ), brainstem (½ of organ), lung (1 section of accessory lobe or area with lesion), heart (2 sections), kidney (1 section), liver (1 section), spleen (1 section), tonsil (½ organ), small intestine (3 sections), colon (2 sections), and lymph nodes (superficial inguinal, tracheobronchial, iliac, mesenteric, gastrohepatic, and iliocecal). All fixed tissues were placed into one container containing 10% buffered formalin solution such that there was a 1:10 ratio of fixed tissue to formalin. For each pig, a replicate sample of sections listed above was collected into the following whirl pack bags; 1—cerebrum, cerebellum, brainstem; 2—lung, heart, kidney, liver, spleen, 3—lymph nodes and tonsil, 4—small intestine and colon. Bags containing fresh tissues and the jar of fixed tissues were labeled with at least study number, day of study, and animal ID. All fresh tissues were transferred on either D49 or D63. Note, no tissues were collected from animals 1 and 2 (Group 7); 4 (Group 8); or 5 and 6 (Group 9) as viremia was not detected by qPCR.

Terminal blood was collected from the following animals at D63: 57 and 55 (Group 6); 53, 50, 46, and 44 (Group 5); 41, 37, 35, and 33 (Group 4). The pigs were deeply anesthetized prior to blood collection. Blood was collected into SST tubes and delivered on the day of collection. The serum was separated from the clot by centrifugation and decanted into 50 mL centrifuge tubes labeled with at least study number, day of study, and animal ID. Serum samples were tracked via FreezerWorks electronic management system. One half of the serum collected from each animal was transferred.

Statistical analysis of data was conducted using SAS version 9.2 or higher (SAS, Cary, N.C./USA, SAS Institute, Inc.). Data listings and summary statistics by treatment group were generated for all variables, as appropriate. Viremia data from Groups 1-5 was dichotomized to a binary outcome (present/absent) for each animal and median PCR values by group and day were plotted. The proportion of affected animals was analyzed with a Fisher's Exact comparison between treatment groups; p-values less than 0.01 were considered significant. Fecal and nasal shedding data from Groups 1-5 was dichotomized to a binary outcome (present/absent) for each animal and median PCR values by group and day were plotted. The proportion of affected animals was analyzed with a Fisher's Exact comparison between treatment groups; p-values less than 0.01 were considered significant. The proportion of affected animals for Groups 4 and 5 by day was analyzed with a Wilcoxon test. Rectal temperatures and body weights were analyzed using a mixed model with baseline adjustment. Least-square means by group and day are reported. Group comparisons by day were analyzed; p-values less than 0.01 were considered significant.

There were three amendments to the protocol. First, due to the small size of the pigs, the protocol for inoculation of the infectious clone material was modified. Second, additional bleed dates were added for pigs in Groups 7, 8, 9 based on PCR results. Dates added included: D36, D42, and D49. In addition, the necropsy date was performed on D49 instead of on D42. Third, it was recommended by the Study Investigator that weight and temperature should not be collected on D0 and blood not be collected on D7 due to the additional stress it would place on the animal.

TABLE 8

| | | Viremia detected (ever) | | | |
|---|---|---|---|---|---|
| Group | Treatment | No | Yes | Total | % positive |
| 1 | BaculoPCV3/ISA - WV | 7 | 1 | 8 | 12.5% |
| 2 | BaculoPCV3/Carb - WV | 8 | 0 | 8 | 0.0% |
| 3 | Placebo/Carb - WV | 0 | 8 | 8 | 100.0% |
| 4 | BaculoPCV3/Carb - TH | 5 | 7 | 12 | 58.3% |
| 5 | Placebo/Carb - TH | 0 | 12 | 12 | 100.0% |
| 6 | Strict control | 6 | 0 | 6 | 0.0% |

As only two animals per group were included in the infectious clone portion of the study, raw data by animal and day is presented Table 9. PCV3 DNA was detected in both animals in Groups 7 and 8, but in only one animal from Group 9. Only one animal (#3; Group 8) developed viremia for consecutive weeks. Interestingly, viremia did not begin until D28.

TABLE 9

Log10 PCV3 DNA genomic copies/ML by animal and day

| Group | Treatment | Animal | D13 | D15 | D16 | D19 | D21 | D23 | D28 | D35 | D42 | D49 |
|---|---|---|---|---|---|---|---|---|---|---|---|---|
| 7 | IC - BI AH USA re-circularized genome | 1 | 0.00 | 3.37 | 0.00 | 0.00 | 0.00 | 0.00 | 0.00 | 0.00 | 0.00 | 0.00 |
| | | 2 | 0.00 | 3.84 | 2.58 | 0.00 | 0.00 | 0.00 | 0.00 | 0.00 | 0.00 | 0.00 |
| 8 | IC - ISU VDL dimerized genome | 3 | 0.00 | 2.87 | 0.00 | 0.00 | 0.00 | 0.00 | 3.88 | 6.03 | 6.51 | 5.93 |
| | | 4 | 0.00 | 3.41 | 0.00 | 0.00 | 0.00 | 0.00 | 0.00 | 0.00 | 0.00 | 0.00 |
| 9 | IC - ISU VDL transfection harvest | 5 | 0.00 | 2.81 | 0.00 | 0.00 | 0.00 | 0.00 | 0.00 | 0.00 | 0.00 | 0.00 |
| | | 6 | 0.00 | 0.00 | 0.00 | 0.00 | 0.00 | 0.00 | 0.00 | 0.00 | 0.00 | 0.00 |

Viremia was not detected in any of the six strict control animals throughout the study (Group 6). Frequency distributions of viremia by group are presented in Table 8 below. Group median log 10 PCV3 DNA genomic copies/mL by day for Groups 1-5 are presented in FIG. 4.

In non-vaccinated pigs, exposure to the whole virus (WV) challenge material resulted in viremia in 100% of animals (Groups 3). Viremia in these animals was first observed between D28 and D42 and was present in all animals at the time of off-test (D49). In contrast, viremia was prevented in 94% (15/16) of vaccinated animals exposed to the whole virus challenge (p<0.001). The one vaccinated animal observed with viremia (#14) was in Group 1 and had detectable viremia at D49 only.

In non-vaccinated pigs, exposure to the tissue homogenate (TH) challenge material resulted in viremia in 100% of animals (Group 5). Viremia in these animals was first observed on D22 (in all animals) and was present in all animals at the time of off-test (D49). The four animals (#53, 50, 46, and 44) which were held for an additional two weeks had detectable levels of viremia at the time of necropsy on D63. In contrast, viremia was prevented in 42% (5/12) of vaccinated animals exposed to the tissue homogenate challenge (p=0.0373). Of the seven vaccinated animals that became viremic, only one animal (#40) had viremia from D22 through D49. Viremia occurred between D35 and D49 in the remaining six vaccinated animals. Table 8 shows the frequency of PCV3 DNA detection in serum by treatment group.

No clinical signs were observed in any animal following vaccination through D12 (day of transport). Throughout the study, only two animals (#13, Group 1; #59, Group 6) had ongoing abnormalities. Three additional animals were observed to have sporadic abnormalities.

Animal #13 (Group 1) was observed to have pronounced ribs and backbone and was not eating (body condition score of 2) shortly after arrival on D13 and 14. On D23, the animal was uncoordinated following bleeding. On D28, the animal was noted to have a lame left rear leg. The animal was found dead on D46. Macroscopic examination at the time of death revealed fibrinous pleuritis with multifocal areas of atelectasis in the cranial ventral lung lobes and fibrinous pericarditis. Based on the gross lesions, death was secondary to a systemic bacterial infection. The death was likely unrelated to vaccination or challenge as PCV3 DNA was not detected in serum from this animal at any point during the study.

Animal #59 (Group 6) was observed to be lame on the right rear leg from D32 through 43 and was noted to have stiff rear legs from D44 through 49. As this animal was in the strict control group, the clinical signs were unrelated to vaccination or challenge. Three additional animals were observed to have sporadic clinical signs. Animal #14 (Group 1) was observed to have pronounced ribs and backbone and was not eating (body condition score of 2) shortly after arrival at AMVC on D13. In addition, the animal was noted to have a rough hair coat on D16 and 17. As clinical signs started prior to challenge and were not present until 13 days following vaccination, the signs are thought to be associated with movement of the CDCD animal at a young age not vaccination or challenge. Animal #11 (Group 1) was observed to have depression/lethargy (neurology score of 1) on D19. As this animal did not have evidence of viremia throughout the study, it is unlikely that the clinical signs were associated with challenge. Animal #5 (Group 9) was observed to be slightly thin compared to pen mates with a mild decrease in appetite (body condition score of 1) on D19. As transient viremia was detected in this animal on D15, the clinical sign may have been associated with infection. However, the clinical signs were not consistent with a previous publication [25] and were transient.

Figure 5:
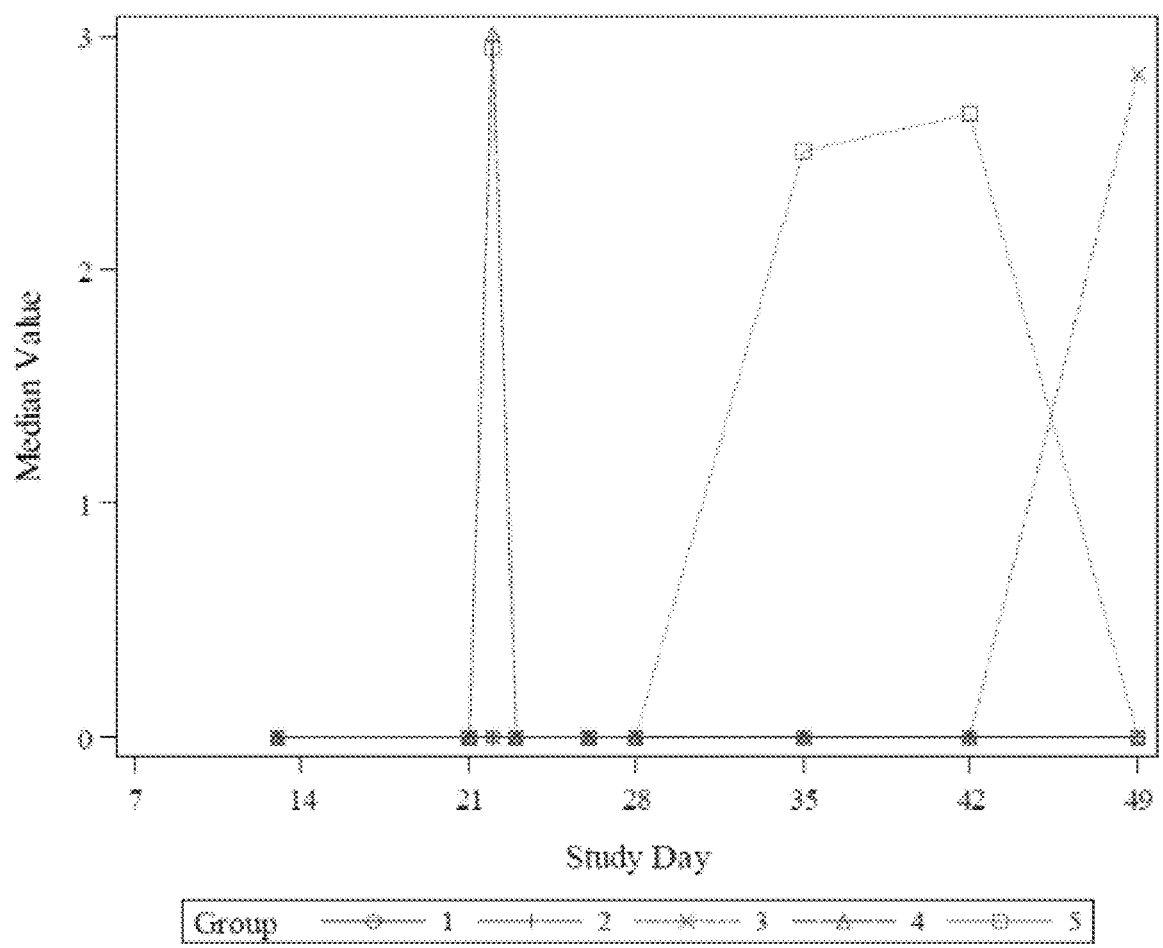
FIG. 5 shows group median log 10 PCV3 DNA genomic copies/mL by study day in fecal samples; Groups 1-5.

Fecal shedding was not detected in any of the six strict control animals throughout the study (Group 6). Frequency distributions of fecal shedding by group are presented in Table 10. Group median log 10 PCV3 DNA genomic copies/mL in fecal samples by day for Groups 1-5 are presented in FIG. 5.

TABLE 10

Frequency of PCV3 DNA detection by group in fecal samples

| Group | Treatment | Fecal shedding detected (ever) | | Total | % positive |
|---|---|---|---|---|---|
| | | No | Yes | | |
| 1 | BaculoPCV3/ISA - WV | 7 | 1 | 8 | 12.5% |
| 2 | BaculoPCV3/Carb - WV | 5 | 3 | 8 | 37.5% |
| 3 | Placebo/Carb - WV | 1 | 7 | 8 | 57.5% |
| 4 | BaculoPCV3/Carb - TH | 1 | 11 | 12 | 91.7% |
| 5 | Placebo/Carb - TH | 0 | 12 | 12 | 100.0% |
| 6 | Strict control | 6 | 0 | 6 | 0.0% |

In non-vaccinated pigs, exposure to the whole virus challenge material resulted in shredding in 88% of animals (Group 3). Fecal shedding in these animals was first observed between D35 and D49. In contrast, fecal shedding was prevented in 75% (12/16) of vaccinated animals exposed to the whole virus challenge (p=0.0101 (Group 1 vs 3); p=0.1189 (Group 2 vs 3)). Overall, shedding in the vaccinated animals was sporadic and appeared inconsistent with a true infection.

In non-vaccinated pigs, exposure to the tissue homogenate challenge material resulted in fecal shedding in 100% of animals (Group 5). Fecal shedding in these animals was biphasic with multiple animals have detectable amounts of PCV3 in the feces on D22 and again on D35-49. Fecal shedding was observed in 92% of vaccinated animals. However, unlike non-vaccinated animals, shedding was most prevalent on D22 and D23 without a second peak.

PCV3 DNA was not detected in any of the fecal samples collected from animals in Groups 7-9.

Figure 6:
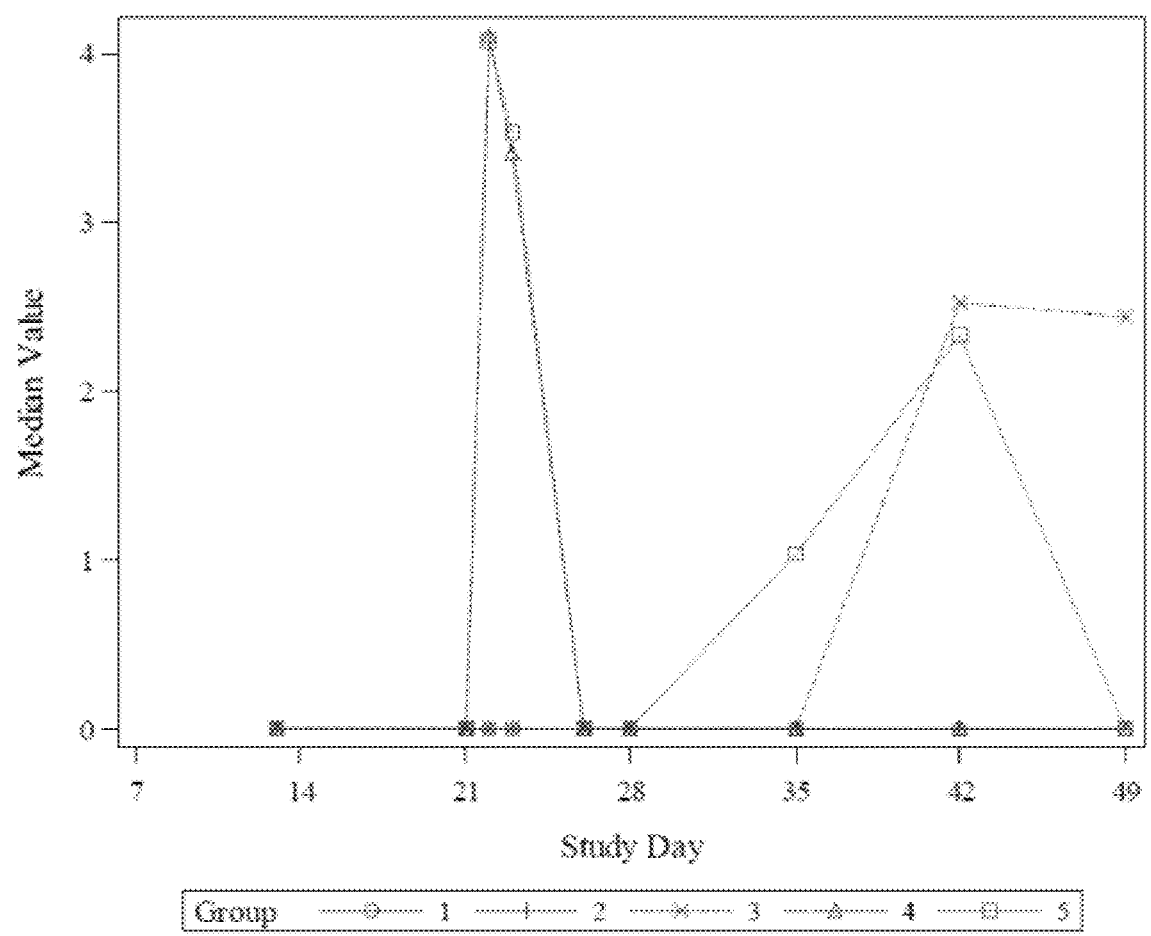
FIG. 6 shows group median log 10 PCV3 DNA genomic copies/mL by study day in nasal samples; Groups 1-5.

Nasal shedding was not detected in any of the strict control animals throughout the study (Group 6) with the exception of animal #59. As PCV3 DNA was only detected on D15 and all other samples (serum, fecal) were negative, this is likely a false positive. Group median log 10 PCV3 DNA genomic copies/mL in fecal samples by day for Groups 1-5 are presented in FIG. 6. (*Nasal detection in animal #59 is thought to be a false positive.)

In non-vaccinated pigs, exposure to the whole virus challenge material resulted in nasal shedding in 88% of animals (Group 3). Nasal shedding in these animals was first observed between D35 and D49. In contrast, nasal shedding was prevented in 94% (15/16) of vaccinated animals exposed to the whole virus challenge (p=0.0014 (Group 1 vs 3); p=0.0101 (Group 2 vs 3)). The one vaccinated animal (#19, Group 2) considered positive had PCV2 detection on D49 only.

In non-vaccinated pigs, exposure to the tissue homogenate challenge material resulted in nasal shedding in 100% of animals (Group 5). Nasal shedding in these animals was biphasic with multiple animals having detectable amounts of PCV3 in the nares on D22 and again on D35-49. Nasal shedding was observed in 100% of vaccinated animals. However, unlike non-vaccinated animals, nasal shedding was present in the majority of animals on D22 and 23 without a second peak. Sporadic shedding was seen in only two animals after D28.

Only two animals per group were included in the infectious clone portion of the study, the raw data by animal and day is presented in Table 11. PCV3 DNA was detected 5/6 animals the day after inoculation (D15) and in all animals regardless of the inoculum between D16-21. Only one animal (#4; Group 8) had detectable PCV3 DNA in nasal swabs after D21.

TABLE 11

Log10 PCV3 DNA genomic copies/mL in nasal swabs by animal and day for Groups 7-9

| Group | Treatment | Animal | D13 | D15 | D16 | D19 | D21 | D23 | D28 |
|---|---|---|---|---|---|---|---|---|---|
| 7 | IC - BI AH USA re-circularized genome | 1 | 0.00 | 5.66 | 4.29 | 3.95 | 3.22 | 0.00 | 0.00 |
| | | 2 | 0.00 | 4.82 | 5.18 | 4.18 | 3.77 | 0.00 | 0.00 |
| 8 | IC - ISU VDL dimerized genome | 3 | 0.00 | 3.56 | 4.65 | 3.01 | 2.44 | 0.00 | 0.00 |
| | | 4 | 0.00 | 4.70 | 3.58 | 3.73 | 2.34 | 0.00 | 2.23 |
| 9 | IC - ISU VDL transfection harvest | 5 | 0.00 | 2.82 | 3.48 | 3.27 | 2.55 | 0.00 | 0.00 |
| | | 6 | 0.00 | 0.00 | 3.91 | 3.33 | 3.58 | 0.00 | 0.00 |

Figure 7:
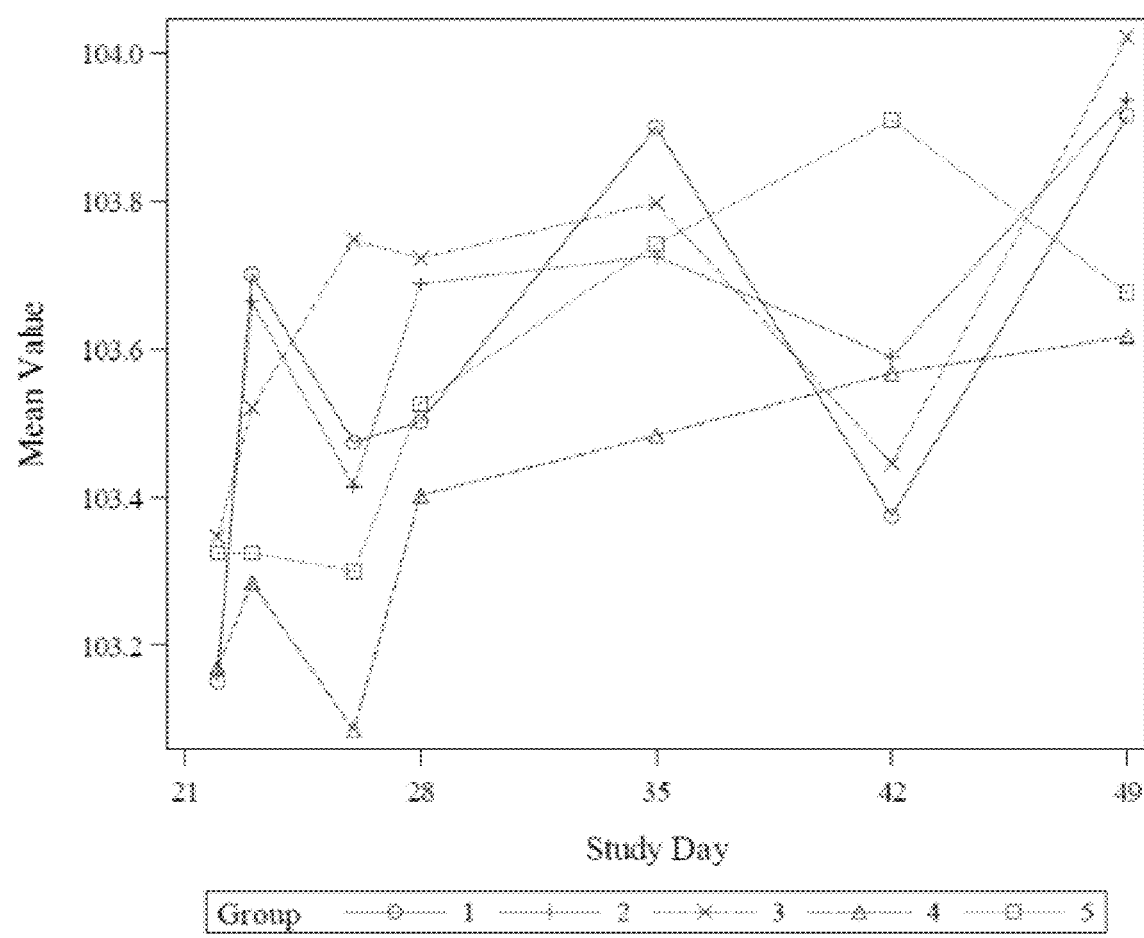
FIG. 7 shows baseline adjusted, least square group mean rectal temperatures (° F.) by study day.
Figure 8:
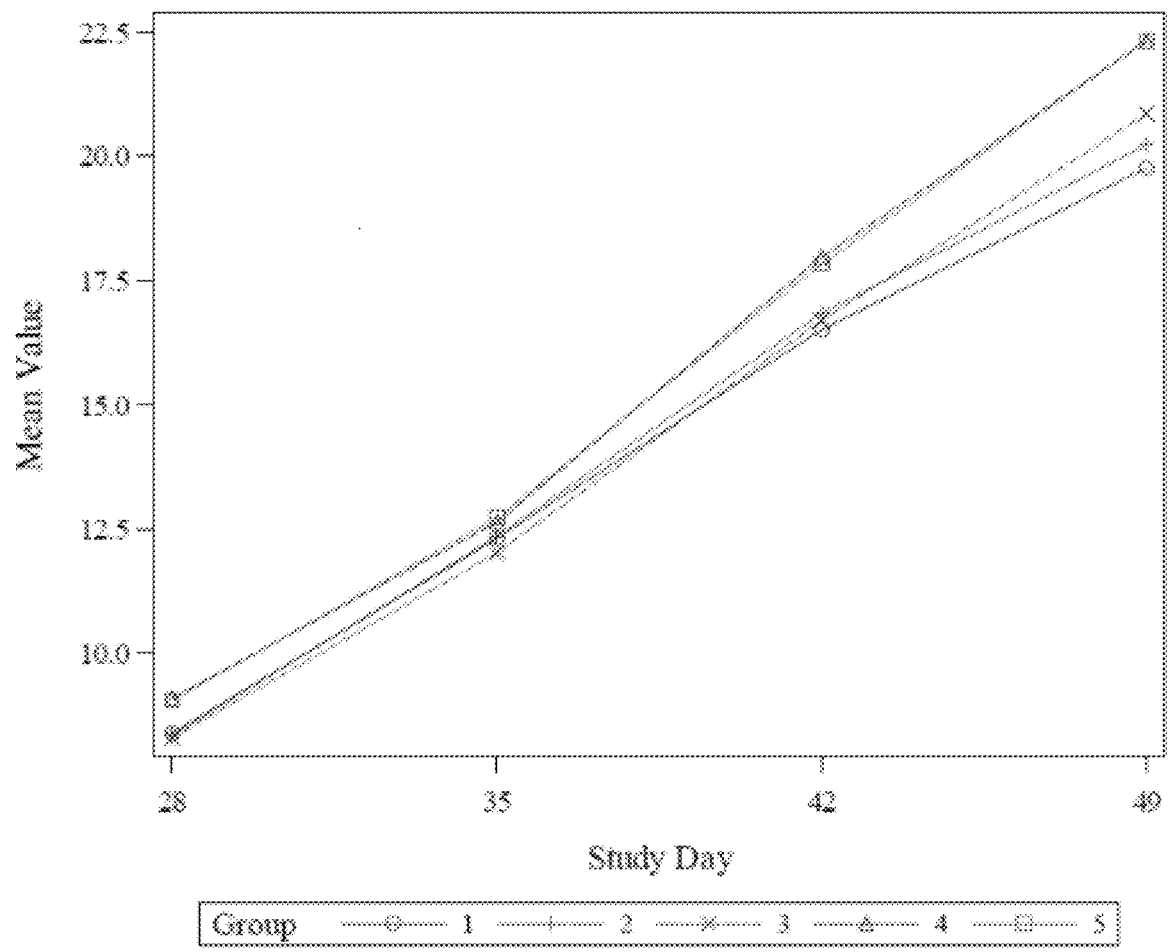
FIG. 8 shows baseline -adjusted, group least square means daily weight (kg) by day; Groups 1-5.
Figure 9:
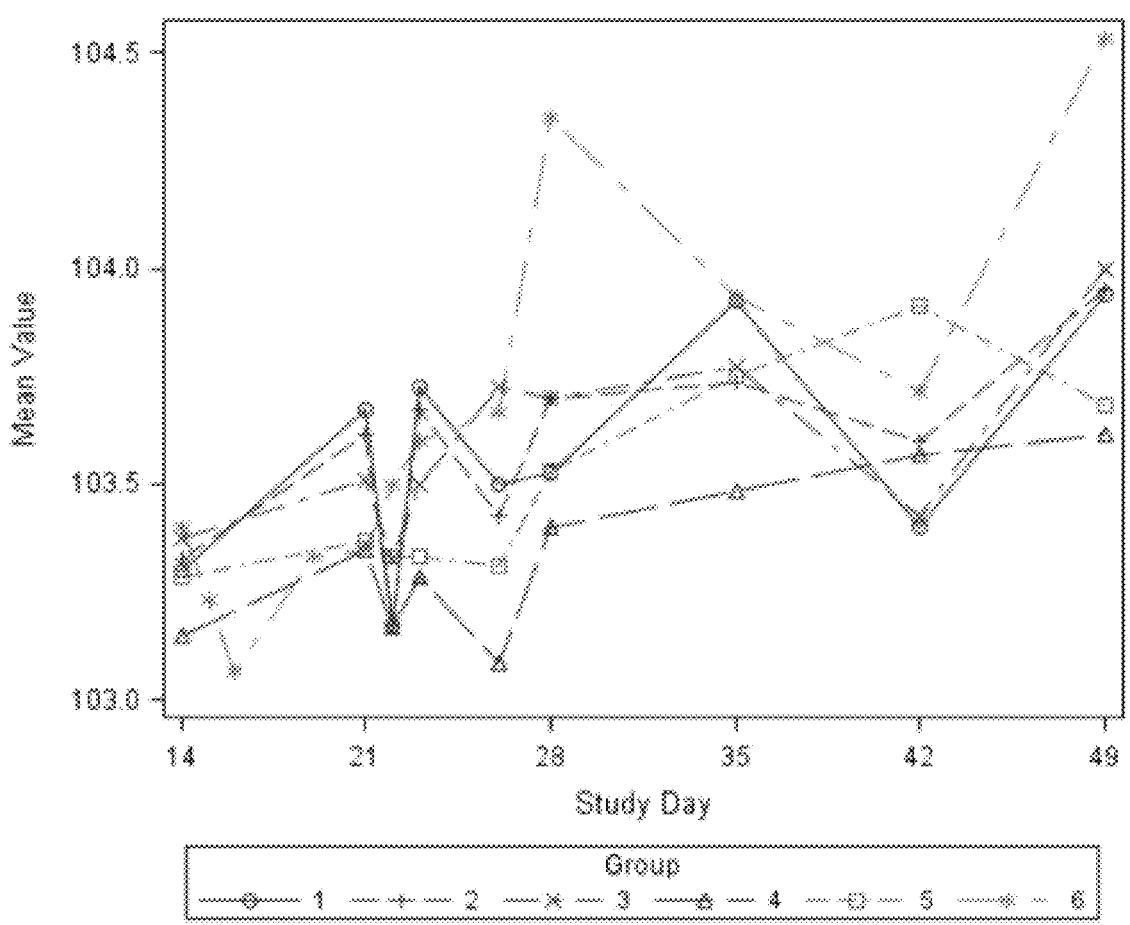
FIG. 9 shows group mean body temperatures (° F.) by day.

Baseline adjusted, least square group mean rectal temperatures (° F.) by study day are presented in FIG. 7. Data for Group 6 is not included in the figure as the analysis was model-based and animals in Group 6 were housed in a separate room. Raw data and descriptive statistics by group and day can be found in the statistical report associated with this study. No differences were observed between Groups 1-3 regardless of the vaccination status. Vaccinated animals challenged with the tissue homogenate (Group 4) had significantly lower temperatures in comparison to non-vaccinated challenged animals (Group 5) during the challenge period (p=0.0021).

No animal was considered pyrexic (had a temperature greater than 104° F.) throughout the study.

Baseline-adjusted, group least square means weights (kg) are presented for Groups 1-5 in FIG. 7. Raw data and descriptive statistics for all groups can be found in the statistical report associated with this study. No differences were observed between groups regardless of the challenge material or vaccination status (p>0.1).

The first objective of this study was to develop a challenge model for PCV3 in CDCD pigs and define the primary and secondary outcome variables. Two challenge materials, tissue homogenate and a whole virus were evaluated. As 100% of animals exposed to the tissue homogenate became viremic within 24 hours of challenge and had detectable nasal and fecal shedding, the material was considered highly infectious. The development of PCV3 viremia and shedding by fecal and nasal routes did not appear to require a co-infection as other pathogens, including PRRSV, PCV2 and PPV, were not detected by routine culture, deep sequencing, and specific PCR assays conducted on the original tissues.

The whole virus material resulted in viremia in 100% and nasal and fecal shedding in 88% of animals and is therefore considered infectious. However, viremia occurred 14 days following challenge; considerably slower in comparison to the tissue homogenate. The hypothesis is that the delay is related to the viral load of the challenge material. Specifically, the Cq values of the tissue homogenate and the whole virus were 14.82 and 23.58, respectively, suggesting that the tissue homogenate contained a higher amount of PCV3 DNA in comparison to the whole virus.

As original PCV3 case reports in the field were of reproductive failure and PDNS in sows [3], it was hypothesized that infection of CDCD pigs may result in PDNS. However, there was no outward evidence of PDNS (or other clinical disease) or pyrexia following exposure to either of the challenge materials. Because the tissue homogenate contained a high amount of virus and the onset of viremia was within 24 hours, it is unlikely that infection of CDCD pigs with PCV3 alone will result in PDNS. Therefore, based on the currently available data, viremia appears to be the most suitable primary parameter for use in future studies using the CDCD pig model. Also, fecal and nasal shedding were each reduced and could be used as secondary parameters. Biologically significant differences were not observed in body temperatures or weights; these parameters are not likely useful for future studies. As other parameters (serology, histopathology) were not evaluated at the time of the report generation, these may provide additional parameters.

The first objective of the study incorporated the initial evaluation of a vaccine prototype using two different adjuvants. This study provides preliminary data that one intramuscular dose of a baculovirus-expressed PCV3 ORF2 antigen administered to three week old pigs prevented viremia, nasal shedding, and fecal shedding following challenge with whole virus. Little to no shedding or viremia was detected in the animals of Groups 1 and 2, therefore, a strong conclusion to the preference of one adjuvant over the other cannot be made. The data from Group 3 and 4 suggest that the efficacy of the vaccine is reduced when the challenge material contains higher amounts of PCV3 DNA. Therefore, establishing a challenge dose which results in infection but will not overwhelm vaccination can be useful for future efficacy studies.

In order to evaluate the efficacy of PCV3 vaccination in a singular co-infection model, the CDCD pigs were vaccinated at seven days of age against PCV2. Based on the differences in capsid amino acid structure (26% amino acid identity in the cap gene between the two viruses [2]) it was hypothesized that there would be no cross-protection. Based on the results of this study, PCV2 vaccination did not appear to prevent PCV3 viremia, therefore, it is unlikely that PCV2 vaccination had any role in the lack of clinical disease.

The second objective of this study was to confirm the infectivity of infectious molecular clones generated by an external collaborator and an internal molecular clone generated by the vaccine design group. Interestingly, intrahepatic inoculation of the CDCD pigs with the infectious clone materials resulted in detectable nasal shedding for seven days following challenge. It is hypothesized that a transient viremia led to distribution of the virus to the nasal epithelium where replication occurred. Further studies and evaluation of nasal tissue with an antigen specific reagent will be needed to confirm this hypothesis. It is unknown why viremia was detected again in animal #3 on D28 through 49. Perhaps if larger numbers of animals had been used, detection of viremia would have occurred in a larger percentage of animals. While the development of viremia for multiple weeks suggests that animal #3 truly became infected, the infection was subclinical. This result does not agree with a recent publication [25] in which infection of conventional four week old pigs with a PCV3 infectious clone resulted in PDNS.

One intramuscular dose of a baculovirus-expressed PCV3 ORF2 antigen administered to three week old pigs prevented viremia, nasal shedding, and fecal shedding following challenge with tissue homogenate challenge material, which was considered infectious. In research studies or reasonable expectation of efficacy studies, viremia can be used as a primary parameter for vaccination evaluation. For future pivotal studies associated with a fully licensed product, a different primary parameter (detection of PCV3 antigen within tissues or clinical disease) would be required. Inoculation of CDCD pigs with infectious clone material resulted in viremia in one animal and nasal shedding in multiple animals. However, no clinical signs were observed.

Example 4

Vaccine Administered to Group 1

The vaccine designated as "Porcine *Circovirus* Vaccine, Type 3, Modified Live Baculovirus Vector" was by the following procedure. A 1 L lot of antigen was produced in a 3 L spinner flask by infecting SF+(*Spodoptera frugiperda*) cells at an approximate MOI of 0.076 with a recombinant baculovirus containing the Porcine *Circovirus* 3 ORF2 gene under control of the baculovirus polyhedrin promoter. The flask was incubated at 28° C.+2° C. with constant agitation at approximately 100 rpm for seven days. Cells and media were aseptically transferred to 2×1 L centrifuge bottles and cells were pelleted at 15,000×g for 20 minutes at 4° C. The resulting supernatant was 0.2 m filtered and stored at 4° C. The material was formulated with 50% ISA207 VG as shown Table 12. The vaccine satisfactorily completed sterility testing post-dispensation into final containers. Mouse safety was not conducted prior to putting the material into swine.

TABLE 12

| Vaccine formulation - ISA207 VG adjuvant | | | | |
|---|---|---|---|---|
| Component | Purpose | Lot no. | Weight | Concentration |
| BaculoG/PCV3 ORF2 | Antigen | 3624-144 | 101.07 g | 50% |
| ISA2017 VG | Adjuvant | 15060911879 | 101.07 g | 50% |

Example 5

Vaccine Administered to Groups 2 and 4

Vaccine administered to Groups 2 and 4: Methods of Production—The vaccine designated as "Porcine *Circovirus* Vaccine, Type 3, Modified Live Baculovirus Vector" was produced by the method described as above for Group 1. Supernatant was formulated with 20% Carbopol® as shown in Table 13. The vaccine satisfactorily completed sterility testing post-dispensation into final containers. Mouse safety was not conducted prior to putting the material into swine.

TABLE 13

Vaccine formulation - Carbopol adjuvant

| Component | Purpose | Lot no. | Volume |
|---|---|---|---|
| BaculoG/PCV3 ORF2 | Antigen | 3624-144 | 80 mL |
| Carbopol | Adjuvant | A80371 | 20 mL |

Example 6

Vaccine Administered to Groups 3 and 5

The vaccine designated as "Modified Live Baculovirus Vector" is a product-matched placebo. It was prepared by the following procedure. A 0.5 L lot of antigen was produced in a 1 L spinner flask by infecting SF+(*Spodoptera frugiperda*) cells at an approximate MOI of 0.1 with a recombinant baculovirus containing no insert. The flask was incubated at 28° C.+2° C. with constant agitation at approximately 100 rpm for four days. Cells and media were aseptically transferred to a 1 L centrifuge bottle and cells were pelleted at 10,000×g for 20 minutes at 4° C. The resulting supernatant was 0.2 μm filtered and stored at 4° C. The material was formulated with 20% Carbopol® as shown in Table 14. The vaccine satisfactorily completed sterility testing post-dispensation into final containers. Mouse Safety was not conducted prior to putting the material into swine.

TABLE 14

Placebo formulation - Carbopol adjuvant

| Component | Purpose | Lot no. | Volume |
|---|---|---|---|
| BaculoG/No Insert control | Antigen | 3624-153 | 60 mL |
| Carbopol | Adjuvant | A80371 | 15 mL |

FIG. 10 shows sequence information on the PCV3 PCR positive tissue homogenate used for challenge material.

The pCR-BluntII-TOPO-PCV3 infectious clone plasmid was created from a 2,000 base pair PCV3 genome (KT869077) gBlock ordered from Integrated DNA Technologies (IDT). The gBlock was ligated into the pCR-BluntII-TOPO vector and transformed into Stbl2 *E. coli*. The infectious clone plasmid was amplified and purified from a 1 L expansion of Stbl2 *E. coli* using a Qiagen CompactPrep Maxi-DNA Purification kit following the manufacturer's recommended procedure. The pCR-BluntII-TOPO-PCV3 Clone 3624-046.06 Lot #3718-038 was diluted in sterile PBS pH7.4 Life Technologies Gibco Cat #10010-023 Lot #1967438 for a final concentration of 400 μg/mL of plasmid in a total of 4 mL. The diluted plasmid was aliquoted into a sterile vaccine bottle and stored at −20° C.

Example 7

Development of a PCV3 Challenge Model

PCV3 is an emerging disease in the global swine population and due to its potential correlation with clinical disease it has led to interest in the development of PCV3 vaccines. To evaluate prototype vaccines, the development of a challenge model was necessary.

As depicted in the following Tables and FIGS., Example 7 reflects studies conducted to develop a challenge model for PCV3 in pigs. In particular, caesarian derived, colostrum deprived ("CDCD") pigs were used.

Studies were designed to evaluate the use of whole virus and PCR positive tissue homogenate as potential challenge materials for future studies. In addition, the rescue of a PCV3 infectious clone in pigs provided an additional option for future challenge model studies and was therefore incorporated into the study design.

Any prototype vaccines available during the course of experiments were included to provide a stronger evaluation of the challenge model.

PCV3 was isolated from clinical material. Virus isolation was confirmed by real-time qPCR transmission electron microscopy and immunofluorescence assay using suitable antibodies. The isolated viral harvest was shown to be free of other viruses including PCV1, PCV2, PRRSV, SIV, swine coronaviruses. Virus harvest provided was a pure culture. Purity was confirmed using Next Generation Sequencing.

The entire PCV3 genome was cloned into a suitable plasmid vector by full synthetic synthesis of the whole PCV3.

The genomic sequence was confirmed and the genome was cut out of the plasmid enzymatic digestion. The genome was then religated to generate a closed covalent circular PCV3 genome.

The circularized PCV3 genome was transfected into suitable cell lines to rescue infectious virus. The rescued virus and/or circularized genome was inoculated into swine. Circularized genome was delivered into the liver and inguinal lymph node guided by ultrasound.

In a second iteration, plasmids were generated that contained two copies of the PCV3 genome. Sufficient quantities of purified plasmid containing the dimeric PCV3 were made for use in challenge model development and pathogenicity/virulence studies.

Clinical material, including tissue and fluids, containing high titer PCV3 as determined by qPCR were generated. The clinical material was shown to be free of other swine viruses including PCV1, PCV2, PRRSV, SIV, and/or swine coronaviruses.

Clinical material was used to develop a PCV3 challenge model and for pathogenicity/virulence studies. Animal studies were conducted to evaluate pathogenicity and spread of the virus using various routes of inoculation. Specifically, in addition to other routes being evaluated, PCV3 viral harvest and/or high titer tissue homogenate was inoculated into one horn of the uterus of sows at 40 days of gestation. PCV3 spread to the fetus in the inoculated horn and the non-inoculated uterine horn was evaluated. Development of mummies as a result of PCV3 infection was evaluated.

The challenge model was used to form the basis for evaluation of vaccine candidates.

Samples from PCV3 studies were tested, including pre-screen PCRs and serology, PCRs for the challenge model and infectious clones, serology for vaccine studies.

Limit of detection, sensitivity and specificity of assays were conducted.

Vaccine candidates were evaluated in different adjuvant combinations. Vaccine candidates included, for example, baculovirus expressed PCV3 ORF2 and PCV3 genome expressed in plasmid (nucleic acid vaccine). Serology was conducted for the vaccine study.

Table 15 relates to product dosing and how the animals were housed. In particular, Table 15 shows animals evaluated by groups. In particular, the litter, specific animal, whether they were vaccinated, the room they were in and the tub they were in were identified.

TABLE 15

| Group | Litter | Animal | Vaccinated 0 = no, 1 = yes | Room | Tub |
|---|---|---|---|---|---|
| 1 | 3 | 7 | 1 | A | 1 |
|  |  | 8 | 1 | A | 1 |
|  | 4 | 9 | 1 | A | 2 |
|  |  | 10 | 1 | A | 2 |
|  | 6 | 11 | 1 | A | 4 |
|  |  | 12 | 1 | A | 3 |
|  | 10 | 13 | 1 | A | 5 |
|  |  | 14 | 1 | A | 4 |
| 2 | 3 | 15 | 1 | A | 1 |
|  |  | 16 | 1 | A | 1 |
|  | 4 | 17 | 1 | A | 3 |
|  |  | 18 | 1 | A | 2 |
|  | 6 | 19 | 1 | A | 3 |
|  |  | 20 | 1 | A | 4 |
|  | 10 | 21 | 1 | A | 4 |
|  |  | 22 | 1 | A | 5 |
| 3 | 3 | 23 | 1 | A | 1 |
|  |  | 24 | 1 | A | 2 |
|  | 4 | 25 | 1 | A | 3 |
|  |  | 26 | 1 | A | 2 |
|  | 6 | 27 | 1 | A | 4 |
|  |  | 28 | 1 | A | 3 |
| 3 | 10 | 29 | 1 | A | 5 |
|  |  | 30 | 1 | A | 5 |
| 4 | 3 | 31 | 1 | B | 4 |
|  |  | 32 | 1 | B | 3 |
|  |  | 33 | 1 | B | 5 |

TABLE 15-continued

| Group | Litter | Animal | Vaccinated 0 = no, 1 = yes | Room | Tub |
|---|---|---|---|---|---|
|  | 4 | 34 | 1 | B | 3 |
|  |  | 35 | 1 | B | 5 |
|  |  | 36 | 1 | B | 2 |
|  | 6 | 37 | 1 | B | 4 |
|  |  | 38 | 1 | B | 2 |
|  |  | 39 | 1 | B | 2 |
|  | 10 | 40 | 1 | B | 1 |
|  |  | 41 | 1 | B | 4 |
|  |  | 42 | 1 | B | 1 |
| 5 | 3 | 43 | 1 | B | 3 |
|  |  | 44 | 1 | B | 5 |
|  |  | 45 | 1 | B | 4 |
|  | 4 | 46 | 1 | B | 5 |
|  |  | 47 | 1 | B | 3 |
|  |  | 48 | 1 | B | 3 |
|  | 6 | 49 | 1 | B | 2 |
|  |  | 50 | 1 | B | 5 |
|  |  | 51 | 1 | B | 2 |
| 5 | 10 | 52 | 1 | B | 1 |
|  |  | 53 | 1 | B | 4 |
|  |  | 54 | 1 | B | 1 |
| 6 | 3 | 55 | 0 | C | 2 |
|  |  | 56 | 0 | C | 1 |
|  | 4 | 57 | 0 | C | 2 |
|  |  | 58 | 0 | C | 1 |
|  | 6 | 59 | 0 | C | 1 |
|  |  | 60 | 0 | C | 2 |
| 7 | 5 | 1 | 0 | D | 1 |
|  | 9 | 2 | 0 | D | 1 |
| 8 | 5 | 3 | 0 | D | 2 |
|  | 9 | 4 | 0 | D | 2 |
| 9 | 5 | 5 | 0 | D | 3 |
|  | 9 | 6 | 0 | D | 3 |

The following data relate to viremia data in animal subjects and the analysis thereof.

As is shown in Table 16, viremia values measured using qPCR Serum and shown in log genomic copies/mL are depicted by group for animals on a selection of study days.

TABLE 16

| Group | Animal | 0 | 13 | 15 | 16 | 19 | 21 | 22 | 23 | 26 | 28 | 35 | 42 | 49 |
|---|---|---|---|---|---|---|---|---|---|---|---|---|---|---|
| 1 | 7 | 0.00 | 0.00 | — | — | — | 0.00 | 0.00 | 0.00 | 0.00 | 0.00 | 0.00 | 0.00 | 0.00 |
|  | 8 | 0.00 | 0.00 | — | — | — | 0.00 | 0.00 | 0.00 | 0.00 | 0.00 | 0.00 | 0.00 | 0.00 |
|  | 9 | 0.00 | 0.00 | — | — | — | 0.00 | 0.00 | 0.00 | 0.00 | 0.00 | 0.00 | 0.00 | 0.00 |
|  | 10 | 0.00 | 0.00 | — | — | — | 0.00 | 0.00 | 0.00 | 0.00 | 0.00 | 0.00 | 0.00 | 0.00 |
|  | 11 | 0.00 | 0.00 | — | — | — | 0.00 | 0.00 | 0.00 | 0.00 | 0.00 | 0.00 | 0.00 | 0.00 |
|  | 12 | 0.00 | 0.00 | — | — | — | 0.00 | 0.00 | 0.00 | 0.00 | 0.00 | 0.00 | 0.00 | 0.00 |
|  | 13 | 0.00 | 0.00 | — | — | — | 0.00 | 0.00 | 0.00 | 0.00 | 0.00 | 0.00 | 0.00 | — |
|  | 14 | 0.00 | 0.00 | — | — | — | 0.00 | 0.00 | 0.00 | 0.00 | 0.00 | 0.00 | 0.00 | 4.05 |
| 2 | 15 | 0.00 | 0.00 | — | — | — | 0.00 | 0.00 | 0.00 | 0.00 | 0.00 | 0.00 | 0.00 | 0.00 |
|  | 16 | 0.00 | 0.00 | — | — | — | 0.00 | 0.00 | 0.00 | 0.00 | 0.00 | 0.00 | 0.00 | 0.00 |
|  | 17 | 0.00 | 0.00 | — | — | — | 0.00 | 0.00 | 0.00 | 0.00 | 0.00 | 0.00 | 0.00 | 0.00 |
|  | 18 | 0.00 | 0.00 | — | — | — | 0.00 | 0.00 | 0.00 | 0.00 | 0.00 | 0.00 | 0.00 | 0.00 |
|  | 19 | 0.00 | 0.00 | — | — | — | 0.00 | 0.00 | 0.00 | 0.00 | 0.00 | 0.00 | 0.00 | 0.00 |
|  | 20 | 0.00 | 0.00 | — | — | — | 0.00 | 0.00 | 0.00 | 0.00 | 0.00 | 0.00 | 0.00 | 0.00 |
|  | 21 | 0.00 | 0.00 | — | — | — | 0.00 | 0.00 | 0.00 | 0.00 | 0.00 | 0.00 | 0.00 | 0.00 |
|  | 22 | 0.00 | 0.00 | — | — | — | 0.00 | 0.00 | 0.00 | 0.00 | 0.00 | 0.00 | 0.00 | 0.00 |
| 3 | 23 | 0.00 | 0.00 | — | — | — | 0.00 | 0.00 | 0.00 | 0.00 | 0.00 | 0.00 | 5.76 | 5.70 |
|  | 24 | 0.00 | 0.00 | — | — | — | 0.00 | 0.00 | 0.00 | 0.00 | 0.00 | 5.05 | 0.00 | 6.25 |
|  | 25 | 0.00 | 0.00 | — | — | — | 0.00 | 0.00 | 0.00 | 0.00 | 4.24 | 6.02 | 6.47 | 6.37 |
|  | 26 | 0.00 | 0.00 | — | — | — | 0.00 | 0.00 | 0.00 | 0.00 | 0.00 | 3.78 | 6.71 | 5.72 |
|  | 27 | 0.00 | 0.00 | — | — | — | 0.00 | 0.00 | 0.00 | 0.00 | 0.00 | 5.39 | 6.03 | 5.72 |
|  | 28 | 0.00 | 0.00 | — | — | — | 0.00 | 0.00 | 0.00 | 0.00 | 0.00 | 5.29 | 7.04 | 6.93 |
|  | 29 | 0.00 | 0.00 | — | — | — | 0.00 | 0.00 | 0.00 | 0.00 | 0.00 | 4.71 | 6.86 | 6.22 |
|  | 30 | 0.00 | 0.00 | — | — | — | 0.00 | 0.00 | 0.00 | 0.00 | 0.00 | 4.64 | 6.50 | 5.80 |
| 4 | 31 | 0.00 | 0.00 | — | — | — | 0.00 | 0.00 | 0.00 | 0.00 | 0.00 | 0.00 | 0.00 | 0.00 |
|  | 32 | 0.00 | 0.00 | — | — | — | 0.00 | 0.00 | 0.00 | 0.00 | 0.00 | 0.00 | 0.00 | 0.00 |
|  | 33 | 0.00 | 0.00 | — | — | — | 0.00 | 0.00 | 0.00 | 0.00 | 0.00 | 0.00 | 0.00 | 0.00 |

TABLE 16-continued

| Group | Animal | \multicolumn{13}{c}{Study Day} |
|---|---|---|---|---|---|---|---|---|---|---|---|---|---|---|
| | | 0 | 13 | 15 | 16 | 19 | 21 | 22 | 23 | 26 | 28 | 35 | 42 | 49 |
| | 34 | 0.00 | 0.00 | — | — | — | 0.00 | 0.00 | 0.00 | 0.00 | 0.00 | 2.52 | 3.57 | 5.02 |
| | 35 | 0.00 | 0.00 | — | — | — | 0.00 | 0.00 | 0.00 | 0.00 | 0.00 | 0.00 | 0.00 | 3.44 |
| | 36 | 0.00 | 0.00 | — | — | — | 0.00 | 3.41 | 0.00 | 0.00 | 0.00 | 2.37 | 0.00 | 3.41 |
| | 37 | 0.00 | 0.00 | — | — | — | 0.00 | 0.00 | 0.00 | 0.00 | 0.00 | 0.00 | 0.00 | 0.00 |
| | 38 | 0.00 | 0.00 | — | — | — | 0.00 | 0.00 | 0.00 | 0.00 | 0.00 | 3.04 | 3.81 | 4.52 |
| | 39 | 0.00 | 0.00 | — | — | — | 0.00 | 0.00 | 0.00 | 0.00 | 0.00 | 0.00 | 3.67 | 3.55 |
| | 40 | 0.00 | 0.00 | — | — | — | 0.00 | 4.81 | 3.64 | 3.34 | 4.42 | 5.62 | 6.51 | 6.76 |
| | 41 | 0.00 | 0.00 | — | — | — | 0.00 | 0.00 | 0.00 | 0.00 | 0.00 | 0.00 | 0.00 | 0.00 |
| | 42 | 0.00 | 0.00 | — | — | — | 0.00 | 0.00 | 0.00 | 0.00 | 0.00 | 0.00 | 0.00 | 3.38 |
| 5 | 43 | 0.00 | 0.00 | — | — | — | 0.00 | 4.53 | 3.82 | 3.19 | 4.61 | 4.60 | 5.00 | 5.67 |
| | 44 | 0.00 | 0.00 | — | — | — | 0.00 | 4.50 | 3.16 | 3.03 | 4.91 | 5.40 | 6.09 | 5.86 |
| | 45 | 0.00 | 0.00 | — | — | — | 0.00 | 4.04 | 3.20 | 3.34 | 4.31 | 5.29 | 5.54 | 6.10 |
| | 46 | 0.00 | 0.00 | — | — | — | 0.00 | 3.94 | 2.64 | 0.00 | 3.92 | 4.91 | 5.16 | 6.01 |
| | 47 | 0.00 | 0.00 | — | — | — | 0.00 | 4.07 | 3.32 | 2.92 | 4.32 | 5.47 | 5.64 | 5.71 |
| | 48 | 0.00 | 0.00 | — | — | — | 0.00 | 4.48 | 3.09 | 2.73 | 4.79 | 5.88 | 5.77 | 6.15 |
| | 49 | 0.00 | 0.00 | — | — | — | 0.00 | 4.31 | 0.00 | 3.05 | 5.73 | 4.85 | 5.65 | 5.30 |
| | 50 | 0.00 | 0.00 | — | — | — | 0.00 | 4.77 | 3.59 | 3.21 | 5.42 | 6.62 | 6.35 | 5.66 |
| | 51 | 0.00 | 0.00 | — | — | — | 0.00 | 4.95 | 3.56 | 3.19 | 5.63 | 4.95 | 5.65 | 5.36 |
| | 52 | 0.00 | 0.00 | — | — | — | 0.00 | 4.73 | 3.47 | 3.21 | 4.52 | 5.79 | 5.89 | 5.60 |
| | 53 | 0.00 | 0.00 | — | — | — | 0.00 | 4.48 | 3.17 | 3.16 | 4.33 | 4.89 | 5.89 | 6.12 |
| | 54 | 0.00 | 0.00 | — | — | — | 0.00 | 4.62 | 3.63 | 2.78 | 4.63 | 5.88 | 6.10 | 5.72 |
| 6 | 55 | 0.00 | 0.00 | 0.00 | 0.00 | 0.00 | 0.00 | 0.00 | 0.00 | 0.00 | 0.00 | 0.00 | 0.00 | 0.00 |
| | 56 | 0.00 | 0.00 | 0.00 | 0.00 | 0.00 | 0.00 | 0.00 | 0.00 | 0.00 | 0.00 | 0.00 | 0.00 | 0.00 |
| | 57 | 0.00 | 0.00 | 0.00 | 0.00 | 0.00 | 0.00 | 0.00 | 0.00 | 0.00 | 0.00 | 0.00 | 0.00 | 0.00 |
| | 58 | 0.00 | 0.00 | 0.00 | 0.00 | 0.00 | 0.00 | 0.00 | 0.00 | 0.00 | 0.00 | 0.00 | 0.00 | 0.00 |
| | 59 | 0.00 | 0.00 | 0.00 | 0.00 | 0.00 | 0.00 | 0.00 | 0.00 | 0.00 | 0.00 | 0.00 | 0.00 | 0.00 |
| | 60 | 0.00 | 0.00 | 0.00 | 0.00 | 0.00 | 0.00 | 0.00 | 0.00 | 0.00 | 0.00 | 0.00 | 0.00 | 0.00 |
| 7 | 1 | 0.00 | 0.00 | 3.37 | 0.00 | 0.00 | 0.00 | — | 0.00 | — | 0.00 | 0.00 | 0.00 | 0.00 |
| | 2 | 0.00 | 0.00 | 3.84 | 2.58 | 0.00 | 0.00 | — | 0.00 | — | 0.00 | 0.00 | 0.00 | 0.00 |
| 8 | 3 | 0.00 | 0.00 | 2.87 | 0.00 | 0.00 | 0.00 | — | 0.00 | — | 3.88 | 6.03 | 6.51 | 5.93 |
| | 4 | 0.00 | 0.00 | 3.41 | 0.00 | 0.00 | 0.00 | — | 0.00 | — | 0.00 | 0.00 | 0.00 | 0.00 |
| 9 | 5 | 0.00 | 0.00 | 2.81 | 0.00 | 0.00 | 0.00 | — | 0.00 | — | 0.00 | 0.00 | 0.00 | 0.00 |
| | 6 | 0.00 | 0.00 | 0.00 | 0.00 | 0.00 | 0.00 | — | 0.00 | — | 0.00 | 0.00 | 0.00 | 0.00 |

Figure 11:
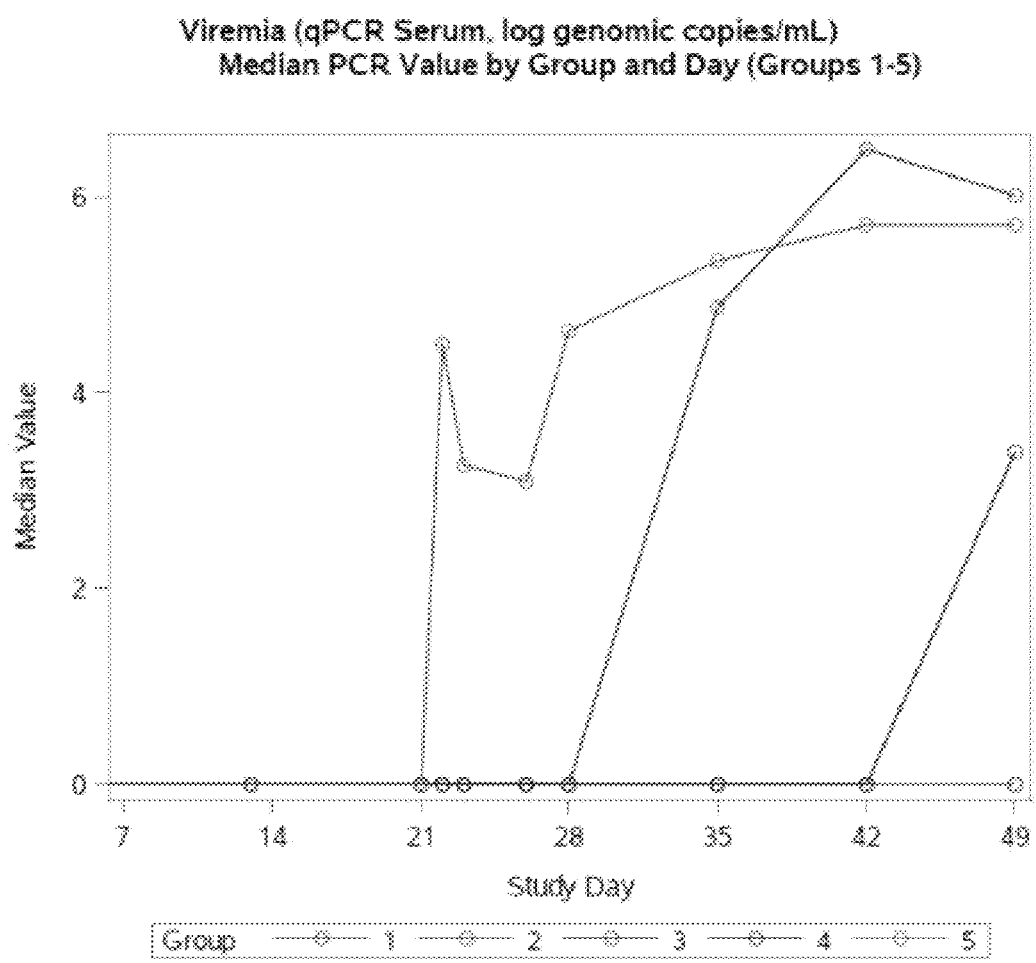
FIG. 11 shows the median PCR value for Groups 1-5 from seven to forty-nine days.

FIG. 11 shows the median PCR value for Groups 1-5 from seven to forty-nine days.

Figure 12:
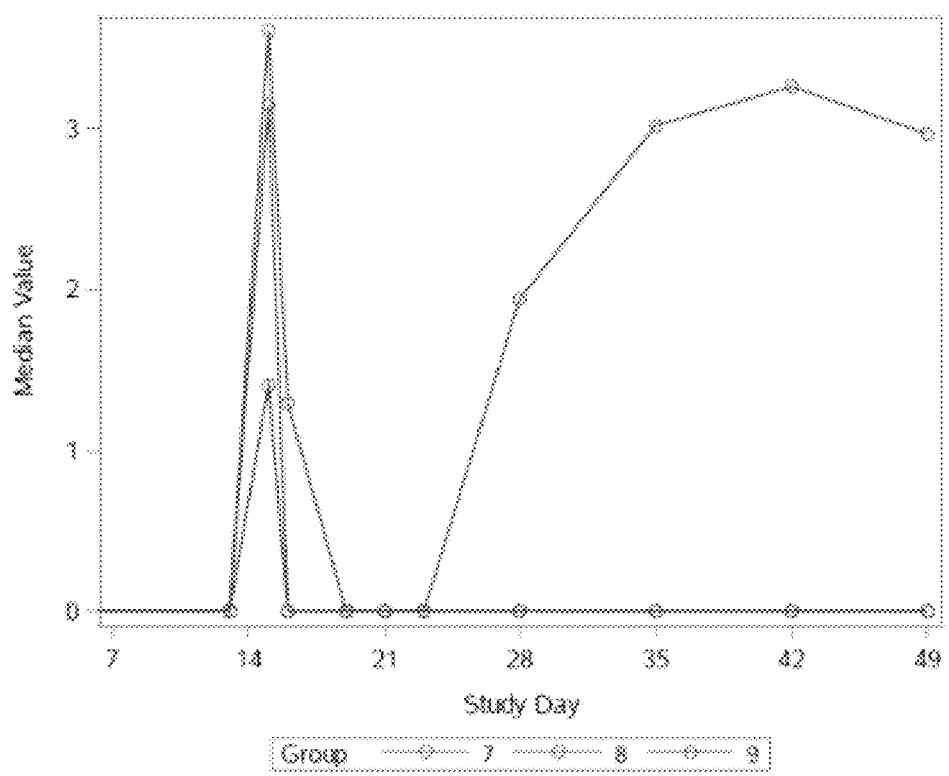
FIG. 12 shows the median PCR value for Groups 7-9 from seven to forty-nine.

FIG. 12 shows the median PCR value for Groups 7-9 from seven to forty-nine.

Table 18 depicts results of viremia determinations for groups 1-5.

TABLE 18

Viremia (qPCR Serum, log genomic copies/mL: Viremia Results by Group
Frequency Row Pct
Table of grp by viremia

| | \multicolumn{2}{c}{viremia} | |
|---|---|---|---|
| | No | Yes | Total |
| 1 | 7<br>87.50 | 1<br>12.50 | 8 |
| 2 | 8<br>100.00 | 0<br>0.00 | 8 |
| 3 | 0<br>0.00 | 8<br>100.00 | 8 |
| 4 | 5<br>41.67 | 7<br>58.33 | 12 |
| 5 | 0<br>0.00 | 12<br>100.00 | 12 |
| Total | 20 | 28 | 48 |

A comparison of the P-values for the data of Table 18 is shown in Table 19.

TABLE 19

Viremia (qPCR Serum, log genomic copies/mL)
Group Comparison P-values

| Group Comparison | P-value |
|---|---|
| 1 vs 3 | 0.0014 |
| 2 vs 3 | 0.0002 |
| 4 vs 5 | 0.0373 |

The following data relate to fecal shedding data measured using qPCR fecal (i.e., log genomic copies/mL) in animal subjects and the analysis thereof.

As is shown in Table 20, fecal shedding values measured using qPCR Fecal and shown in log genomic copies/mL are depicted by group for animals on a selection of study days.

TABLE 20

| Group | Animal | \multicolumn{12}{c}{Study Day} |
| | | 13 | 15 | 16 | 19 | 21 | 22 | 23 | 26 | 28 | 35 | 42 | 49 |
|---|---|---|---|---|---|---|---|---|---|---|---|---|---|
| 1 | 7 | 0.00 | — | — | — | 0.00 | 0.00 | 0.00 | 0.00 | 0.00 | 2.88 | 0.00 | 0.00 |
|  | 8 | 0.00 | — | — | — | 0.00 | 0.00 | 0.00 | 0.00 | 0.00 | 0.00 | 0.00 | 0.00 |
|  | 9 | 0.00 | — | — | — | 0.00 | 0.00 | 0.00 | 0.00 | 0.00 | 0.00 | 0.00 | 0.00 |
|  | 10 | 0.00 | — | — | — | 0.00 | 0.00 | 0.00 | 0.00 | 0.00 | 0.00 | 0.00 | 0.00 |
|  | 11 | 0.00 | — | — | — | 0.00 | 0.00 | 0.00 | 0.00 | 0.00 | 0.00 | 0.00 | 0.00 |
|  | 12 | 0.00 | — | — | — | 0.00 | 0.00 | 0.00 | 0.00 | 0.00 | 0.00 | 0.00 | 0.00 |
|  | 13 | 0.00 | — | — | — | 0.00 | 0.00 | 0.00 | 0.00 | 0.00 | 0.00 | 0.00 | — |
|  | 14 | 0.00 | — | — | — | 0.00 | 0.00 | 0.00 | 0.00 | 0.00 | 0.00 | 0.00 | 0.00 |
| 2 | 15 | 0.00 | — | — | — | 0.00 | 0.00 | 0.00 | 0.00 | 0.00 | 0.00 | 0.00 | 0.00 |
|  | 16 | 0.00 | — | — | — | 0.00 | 0.00 | 0.00 | 0.00 | 0.00 | 0.00 | 0.00 | 0.00 |
|  | 17 | 0.00 | — | — | — | 0.00 | 0.00 | 0.00 | 0.00 | 0.00 | 3.60 | 0.00 | 0.00 |
|  | 18 | 0.00 | — | — | — | 0.00 | 0.00 | 0.00 | 3.99 | 0.00 | 3.42 | 0.00 | 0.00 |
|  | 19 | 0.00 | — | — | — | 0.00 | 0.00 | 0.00 | 0.00 | 0.00 | 0.00 | 2.63 | 0.00 |
|  | 20 | 0.00 | — | — | — | 0.00 | 0.00 | 0.00 | 0.00 | 0.00 | 0.00 | 0.00 | 0.00 |
|  | 21 | 0.00 | — | — | — | 0.00 | 0.00 | 0.00 | 0.00 | 0.00 | 0.00 | 0.00 | 0.00 |
|  | 22 | 0.00 | — | — | — | 0.00 | 0.00 | 0.00 | 0.00 | 0.00 | 0.00 | 0.00 | 0.00 |
| 3 | 23 | 0.00 | — | — | — | 0.00 | 0.00 | 0.00 | 0.00 | 0.00 | 0.00 | 0.00 | 0.00 |
|  | 24 | 0.00 | — | — | — | 0.00 | 0.00 | 0.00 | 0.00 | 0.00 | 0.00 | 0.00 | 2.90 |
|  | 25 | 0.00 | — | — | — | 0.00 | 0.00 | 0.00 | 0.00 | 0.00 | 3.46 | 4.11 | 4.32 |
|  | 26 | 0.00 | — | — | — | 0.00 | 0.00 | 0.00 | 0.00 | 0.00 | 0.00 | 0.00 | 2.31 |
|  | 27 | 0.00 | — | — | — | 0.00 | 0.00 | 0.00 | 0.00 | 0.00 | 2.53 | 0.00 | 0.00 |
|  | 28 | 0.00 | — | — | — | 0.00 | 0.00 | 0.00 | 0.00 | 0.00 | 0.00 | 3.59 | 4.13 |
|  | 29 | 0.00 | — | — | — | 0.00 | 0.00 | 0.00 | 0.00 | 0.00 | 0.00 | 3.17 | 3.46 |
|  | 30 | 0.00 | — | — | — | 0.00 | 0.00 | 0.00 | 0.00 | 0.00 | 0.00 | 0.00 | 2.79 |
| 4 | 31 | 0.00 | — | — | — | 0.00 | 2.95 | 3.05 | 0.00 | 0.00 | 0.00 | 0.00 | 0.00 |
|  | 32 | 0.00 | — | — | — | 0.00 | 3.33 | 3.09 | 0.00 | 0.00 | 0.00 | 0.00 | 0.00 |
|  | 33 | 0.00 | — | — | — | 0.00 | 2.52 | 0.00 | 0.00 | 0.00 | 0.00 | 0.00 | 0.00 |
|  | 34 | 0.00 | — | — | — | 0.00 | 2.44 | 0.00 | 0.00 | 0.00 | 0.00 | 0.00 | 0.00 |
|  | 35 | 0.00 | — | — | — | 0.00 | 2.48 | 0.00 | 0.00 | 0.00 | 0.00 | 0.00 | 0.00 |
|  | 36 | 0.00 | — | — | — | 0.00 | 3.06 | 0.00 | 0.00 | 0.00 | 0.00 | 0.00 | 0.00 |
|  | 37 | 0.00 | — | — | — | 0.00 | 0.00 | 0.00 | 0.00 | 0.00 | 0.00 | 0.00 | 0.00 |
|  | 38 | 0.00 | — | — | — | 0.00 | 3.37 | 2.90 | 0.00 | 0.00 | 0.00 | 0.00 | 0.00 |
|  | 39 | 0.00 | — | — | — | 0.00 | 3.45 | 2.92 | 0.00 | 0.00 | 0.00 | 0.00 | 0.00 |
|  | 40 | 0.00 | — | — | — | 0.00 | 3.55 | 3.49 | 0.00 | 0.00 | 2.75 | 2.54 | 2.62 |
|  | 41 | 0.00 | — | — | — | 0.00 | 3.30 | 0.00 | 0.00 | 0.00 | 0.00 | 0.00 | 0.00 |
|  | 42 | 0.00 | — | — | — | 0.00 | 2.67 | 0.00 | 0.00 | 0.00 | 0.00 | 0.00 | 0.00 |
| 5 | 43 | 0.00 | — | — | — | 0.00 | 3.24 | 0.00 | 0.00 | 0.00 | 0.00 | 0.00 | 0.00 |
|  | 44 | 0.00 | — | — | — | 0.00 | 0.00 | 3.37 | 0.00 | 0.00 | 0.00 | 0.00 | 2.74 |
|  | 45 | 0.00 | — | — | — | 0.00 | 0.00 | 0.00 | 0.00 | 0.00 | 0.00 | 2.68 | 2.36 |
|  | 46 | 0.00 | — | — | — | 0.00 | 2.96 | 0.00 | 0.00 | 0.00 | 0.00 | 0.00 | 0.00 |
|  | 47 | 0.00 | — | — | — | 0.00 | 2.94 | 0.00 | 0.00 | 0.00 | 2.49 | 3.37 | 2.55 |
|  | 48 | 0.00 | — | — | — | 0.00 | 2.05 | 0.00 | 0.00 | 0.00 | 3.61 | 0.00 | 0.00 |
|  | 49 | 0.00 | — | — | — | 0.00 | 0.00 | 0.00 | 0.00 | 0.00 | 2.67 | 4.39 | 0.00 |
|  | 50 | 0.00 | — | — | — | 0.00 | 0.00 | 0.00 | 0.00 | 0.00 | 4.22 | 3.27 | 2.47 |
|  | 51 | 0.00 | — | — | — | 0.00 | 3.37 | 0.00 | 0.00 | 0.00 | 2.53 | 2.70 | 0.00 |
|  | 52 | 0.00 | — | — | — | 0.00 | 3.29 | 0.00 | 0.00 | 0.00 | 3.02 | 2.66 | 0.00 |
|  | 53 | 0.00 | — | — | — | 0.00 | 3.28 | 0.00 | 0.00 | 0.00 | 0.00 | 0.00 | 0.00 |
|  | 54 | 0.00 | — | — | — | 0.00 | 3.26 | 0.00 | 0.00 | 0.00 | 2.97 | 2.71 | 0.00 |
| 6 | 55 | 0.00 | 0.00 | 0.00 | 0.00 | 0.00 | 0.00 | 0.00 | 0.00 | 0.00 | 0.00 | 0.00 | 0.00 |
|  | 56 | 0.00 | 0.00 | 0.00 | 0.00 | 0.00 | 0.00 | 0.00 | 0.00 | 0.00 | 0.00 | 0.00 | 0.00 |
|  | 57 | 0.00 | 0.00 | 0.00 | 0.00 | 0.00 | 0.00 | 0.00 | 0.00 | 0.00 | 0.00 | 0.00 | 0.00 |
|  | 58 | 0.00 | 0.00 | 0.00 | 0.00 | 0.00 | 0.00 | 0.00 | 0.00 | 0.00 | 0.00 | 0.00 | 0.00 |
|  | 59 | 0.00 | 0.00 | 0.00 | 0.00 | 0.00 | 0.00 | 0.00 | 0.00 | 0.00 | 0.00 | 0.00 | 0.00 |
|  | 60 | 0.00 | 0.00 | 0.00 | 0.00 | 0.00 | 0.00 | 0.00 | 0.00 | 0.00 | 0.00 | 0.00 | 0.00 |
| 7 | 1 | 0.00 | 0.00 | 0.00 | 0.00 | 0.00 | — | 0.00 | — | 0.00 | — | — | — |
|  | 2 | 0.00 | 0.00 | 0.00 | 0.00 | 0.00 | — | 0.00 | — | 0.00 | — | — | — |
| 8 | 3 | 0.00 | 0.00 | 0.00 | 0.00 | 0.00 | — | 0.00 | — | 0.00 | — | — | — |
|  | 4 | 0.00 | 0.00 | 0.00 | 0.00 | 0.00 | — | 0.00 | — | 0.00 | — | — | — |
| 9 | 5 | 0.00 | 0.00 | 0.00 | 0.00 | 0.00 | — | 0.00 | — | 0.00 | — | — | — |
|  | 6 | 0.00 | 0.00 | 0.00 | 0.00 | 0.00 | — | 0.00 | — | 0.00 | — | — | — |

Figure 13:
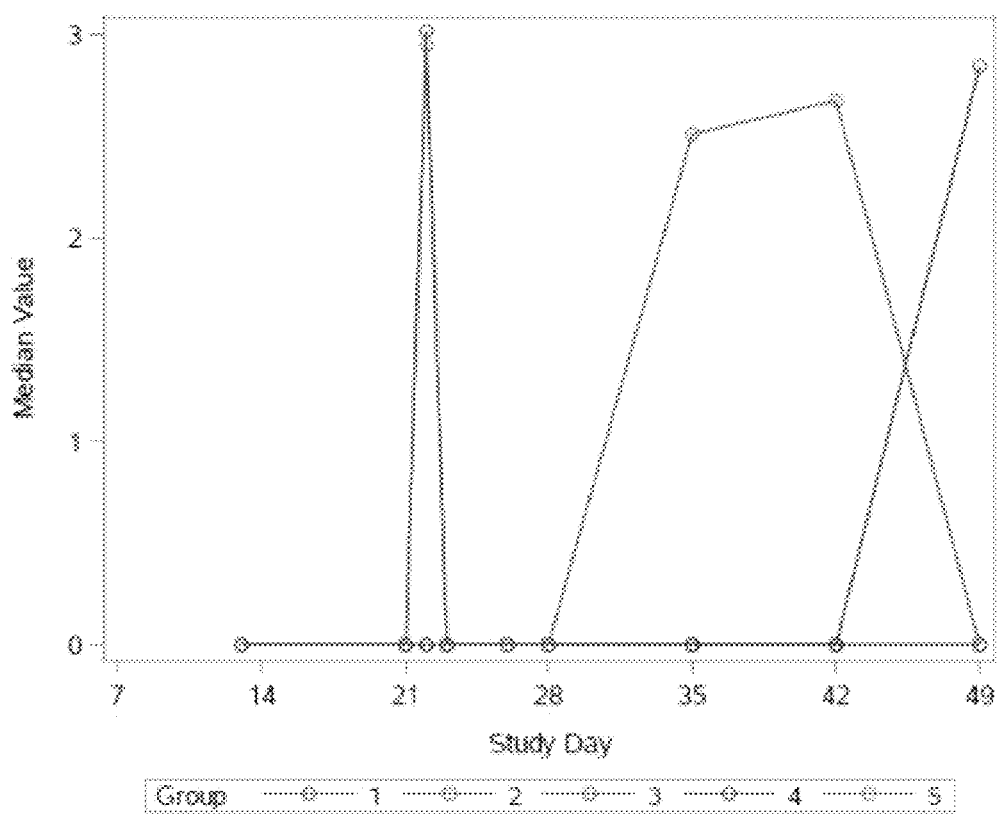
FIG. 13 shows the median PCR values for fecal shedding for Groups 1-5 from seven to forty-nine days.

FIG. 13 shows the median PCR values for fecal shedding for Groups 1-5 from seven to forty-nine days.

Table 22 depicts results for fecal shedding determinations for groups 1-5.

TABLE 22

Table of grp by shedding

| grp(Group) | shedding No | shedding Yes | Total |
|---|---|---|---|
| 1 | 7<br>87.50 | 1<br>12.50 | 8 |
| 2 | 5<br>62.50 | 3<br>37.50 | 8 |
| 3 | 1<br>12.50 | 7<br>87.50 | 8 |
| 4 | 1<br>8.33 | 11<br>91.67 | 12 |
| 5 | 0<br>0.00 | 12<br>100.00 | 12 |
| Total | 14 | 34 | 48 |

Frequency Row Pct

A comparison of the P-values for the data of Table 22 (fecal shedding determinations) is shown in Table 23.

TABLE 23

| Group Comparison | P-value |
|---|---|
| 1 vs 3 | 0.0101 |
| 2 vs 3 | 0.1169 |
| 4 vs 5 | 1.0000 |

A direct comparison of the P-values (i.e., Wilcoxon Test) for Group 4 and 5 is shown in Table 24.

TABLE 24

| Day | P-value |
|---|---|
| 22 | 0.239 |
| 23 | 0.131 |
| 26 | 1.000 |
| 28 | 1.000 |
| 35 | 0.014 |
| 42 | 0.005 |
| 49 | 0.261 |

The following data relate to nasal shedding data measured using qPCR Nasal (i.e., log genomic copies/mL) in animal subjects and the analysis thereof.

As is shown in Table 25, nasal shedding values measured using qPCR Nasal and shown in log genomic copies/mL are depicted by group for animals on a selection of study days.

TABLE 25

| Group | Animal | 13 | 15 | 16 | 19 | 21 | 22 | 23 | 26 | 28 | 35 | 42 | 49 |
|---|---|---|---|---|---|---|---|---|---|---|---|---|---|
| 1 | 7 | 0.00 | — | — | — | 0.00 | 0.00 | 0.00 | 0.00 | 0.00 | 0.00 | 0.00 | 0.00 |
|  | 8 | 0.00 | — | — | — | 0.00 | 0.00 | 0.00 | 0.00 | 0.00 | 0.00 | 0.00 | 0.00 |
|  | 9 | 0.00 | — | — | — | 0.00 | 0.00 | 0.00 | 0.00 | 0.00 | 0.00 | 0.00 | 0.00 |
|  | 10 | 0.00 | — | — | — | 0.00 | 0.00 | 0.00 | 0.00 | 0.00 | 0.00 | 0.00 | 0.00 |
|  | 11 | 0.00 | — | — | — | 0.00 | 0.00 | 0.00 | 0.00 | 0.00 | 0.00 | 0.00 | 0.00 |
|  | 12 | 0.00 | — | — | — | 0.00 | 0.00 | 0.00 | 0.00 | 0.00 | 0.00 | 0.00 | 0.00 |
|  | 13 | 0.00 | — | — | — | 0.00 | 0.00 | 0.00 | 0.00 | 0.00 | 0.00 | 0.00 | — |
|  | 14 | 0.00 | — | — | — | 0.00 | 0.00 | 0.00 | 0.00 | 0.00 | 0.00 | 0.00 | 0.00 |
| 2 | 15 | 0.00 | — | — | — | 0.00 | 0.00 | 0.00 | 0.00 | 0.00 | 0.00 | 0.00 | 0.00 |
|  | 16 | 0.00 | — | — | — | 0.00 | 0.00 | 0.00 | 0.00 | 0.00 | 0.00 | 0.00 | 0.00 |
|  | 17 | 0.00 | — | — | — | 0.00 | 0.00 | 0.00 | 0.00 | 0.00 | 0.00 | 0.00 | 0.00 |
|  | 18 | 0.00 | — | — | — | 0.00 | 0.00 | 0.00 | 0.00 | 0.00 | 0.00 | 0.00 | 0.00 |
|  | 19 | 0.00 | — | — | — | 0.00 | 0.00 | 0.00 | 0.00 | 0.00 | 0.00 | 0.00 | 2.56 |
|  | 20 | 0.00 | — | — | — | 0.00 | 0.00 | 0.00 | 0.00 | 0.00 | 0.00 | 0.00 | 0.00 |
|  | 21 | 0.00 | — | — | — | 0.00 | 0.00 | 0.00 | 0.00 | 0.00 | 0.00 | 0.00 | 0.00 |
|  | 22 | 0.00 | — | — | — | 0.00 | 0.00 | 0.00 | 0.00 | 0.00 | 0.00 | 0.00 | 0.00 |
| 3 | 23 | 0.00 | — | — | — | 0.00 | 0.00 | 0.00 | 0.00 | 0.00 | 0.00 | 0.00 | 0.00 |
|  | 24 | 0.00 | — | — | — | 0.00 | 0.00 | 0.00 | 0.00 | 0.00 | 0.00 | 0.00 | 1.95 |
|  | 25 | 0.00 | — | — | — | 0.00 | 0.00 | 0.00 | 0.00 | 0.00 | 2.24 | 2.72 | 1.95 |
|  | 26 | 0.00 | — | — | — | 0.00 | 0.00 | 0.00 | 0.00 | 0.00 | 0.00 | 2.60 | 3.59 |
|  | 27 | 0.00 | — | — | — | 0.00 | 0.00 | 0.00 | 0.00 | 0.00 | 0.00 | 2.25 | 1.97 |
|  | 28 | 0.00 | — | — | — | 0.00 | 0.00 | 0.00 | 0.00 | 0.00 | 2.43 | 3.50 | 3.20 |
|  | 29 | 0.00 | — | — | — | 0.00 | 0.00 | 0.00 | 0.00 | 0.00 | 0.00 | 2.67 | 3.85 |
|  | 30 | 0.00 | — | — | — | 0.00 | 0.00 | 0.00 | 0.00 | 0.00 | 0.00 | 2.45 | 2.91 |
| 4 | 31 | 0.00 | — | — | — | 0.00 | 4.11 | 0.00 | 0.00 | 0.00 | 0.00 | 0.00 | 0.00 |
|  | 32 | 0.00 | — | — | — | 0.00 | 4.70 | 3.66 | 0.00 | 0.00 | 0.00 | 0.00 | 0.00 |
|  | 33 | 0.00 | — | — | — | 0.00 | 4.05 | 0.00 | 0.00 | 0.00 | 0.00 | 0.00 | 0.00 |
|  | 34 | 0.00 | — | — | — | 0.00 | 4.07 | 0.00 | 0.00 | 0.00 | 0.00 | 0.00 | 0.00 |
|  | 35 | 0.00 | — | — | — | 0.00 | 4.97 | 0.00 | 0.00 | 0.00 | 0.00 | 0.00 | 0.00 |
|  | 36 | 0.00 | — | — | — | 0.00 | 3.68 | 3.50 | 0.00 | 0.00 | 0.00 | 0.00 | 0.00 |
|  | 37 | 0.00 | — | — | — | 0.00 | 3.96 | 3.78 | 0.00 | 0.00 | 0.00 | 0.00 | 0.00 |
|  | 38 | 0.00 | — | — | — | 0.00 | 4.48 | 0.00 | 0.00 | 0.00 | 0.00 | 0.00 | 0.00 |
|  | 39 | 0.00 | — | — | — | 0.00 | 4.28 | 3.76 | 0.00 | 0.00 | 0.00 | 0.00 | 0.00 |
|  | 40 | 0.00 | — | — | — | 0.00 | 4.10 | 3.85 | 0.00 | 0.00 | 0.00 | 2.33 | 2.01 |
|  | 41 | 0.00 | — | — | — | 0.00 | 4.86 | 3.80 | 0.00 | 2.91 | 0.00 | 0.00 | 0.00 |
|  | 42 | 0.00 | — | — | — | 0.00 | 0.00 | 3.33 | 0.00 | 0.00 | 0.00 | 0.00 | 0.00 |
| 5 | 43 | 0.00 | — | — | — | 0.00 | 0.00 | 4.30 | 0.00 | 0.00 | 0.00 | 0.00 | 0.00 |
|  | 44 | 0.00 | — | — | — | 0.00 | 4.03 | 0.00 | 0.00 | 0.00 | 2.07 | 0.00 | 2.08 |
|  | 45 | 0.00 | — | — | — | 0.00 | 4.01 | 3.62 | 0.00 | 0.00 | 0.00 | 2.60 | 0.00 |
|  | 46 | 0.00 | — | — | — | 0.00 | 4.05 | 3.43 | 0.00 | 0.00 | 0.00 | 0.00 | 0.00 |
|  | 47 | 0.00 | — | — | — | 0.00 | 4.11 | 0.00 | 0.00 | 0.00 | 0.00 | 3.13 | 2.10 |
|  | 48 | 0.00 | — | — | — | 0.00 | 4.74 | 3.68 | 0.00 | 0.00 | 2.83 | 2.37 | 0.00 |

TABLE 25-continued

| | | Study Day | | | | | | | | | | | |
|---|---|---|---|---|---|---|---|---|---|---|---|---|---|
| Group | Animal | 13 | 15 | 16 | 19 | 21 | 22 | 23 | 26 | 28 | 35 | 42 | 49 |
| | 49 | 0.00 | — | — | — | 0.00 | 3.92 | 0.00 | 0.00 | 0.00 | 2.44 | 0.00 | 0.00 |
| | 50 | 0.00 | — | — | — | 0.00 | 4.80 | 3.43 | 0.00 | 0.00 | 3.11 | 2.29 | 2.17 |
| | 51 | 0.00 | — | — | — | 0.00 | 5.08 | 3.58 | 0.00 | 0.00 | 2.26 | 2.71 | 0.00 |
| | 52 | 0.00 | — | — | — | 0.00 | 4.47 | 3.56 | 0.00 | 0.00 | 2.50 | 2.70 | 0.00 |
| | 53 | 0.00 | — | — | — | 0.00 | 4.64 | 3.97 | 0.00 | 0.00 | 0.00 | 2.25 | 0.00 |
| | 54 | 0.00 | — | — | — | 0.00 | 3.48 | 3.50 | 0.00 | 0.00 | 0.00 | 3.55 | 0.00 |
| 6 | 55 | 0.00 | 0.00 | 0.00 | 0.00 | 0.00 | 0.00 | 0.00 | 0.00 | 0.00 | 0.00 | 0.00 | 0.00 |
| | 56 | 0.00 | 0.00 | 0.00 | 0.00 | 0.00 | 0.00 | 0.00 | 0.00 | 0.00 | 0.00 | 0.00 | 0.00 |
| | 57 | 0.00 | 0.00 | 0.00 | 0.00 | 0.00 | 0.00 | 0.00 | 0.00 | 0.00 | 0.00 | 0.00 | 0.00 |
| | 58 | 0.00 | 0.00 | 0.00 | 0.00 | 0.00 | 0.00 | 0.00 | 0.00 | 0.00 | 0.00 | 0.00 | 0.00 |
| | 59 | 0.00 | 3.06 | 0.00 | 0.00 | 0.00 | 0.00 | 0.00 | 0.00 | 0.00 | 0.00 | 0.00 | 0.00 |
| | 60 | 0.00 | 0.00 | 0.00 | 0.00 | 0.00 | 0.00 | 0.00 | 0.00 | 0.00 | 0.00 | 0.00 | 0.00 |
| 7 | 1 | 0.00 | 5.66 | 4.29 | 3.95 | 3.22 | — | 0.00 | — | 0.00 | — | — | — |
| | 2 | 0.00 | 4.82 | 5.18 | 4.18 | 3.77 | — | 0.00 | — | 0.00 | — | — | — |
| 8 | 3 | 0.00 | 3.56 | 4.55 | 3.11 | 2.44 | — | 0.00 | — | 0.00 | — | — | — |
| | 4 | 0.00 | 4.70 | 3.58 | 3.73 | 2.34 | — | 0.00 | — | 2.23 | — | — | — |
| 9 | 5 | 0.00 | 2.82 | 3.48 | 3.27 | 2.55 | — | 0.00 | — | 0.00 | — | — | — |
| | 6 | 0.00 | 0.00 | 3.91 | 3.33 | 3.58 | — | 0.00 | — | 0.00 | — | — | — |

Figure 14:
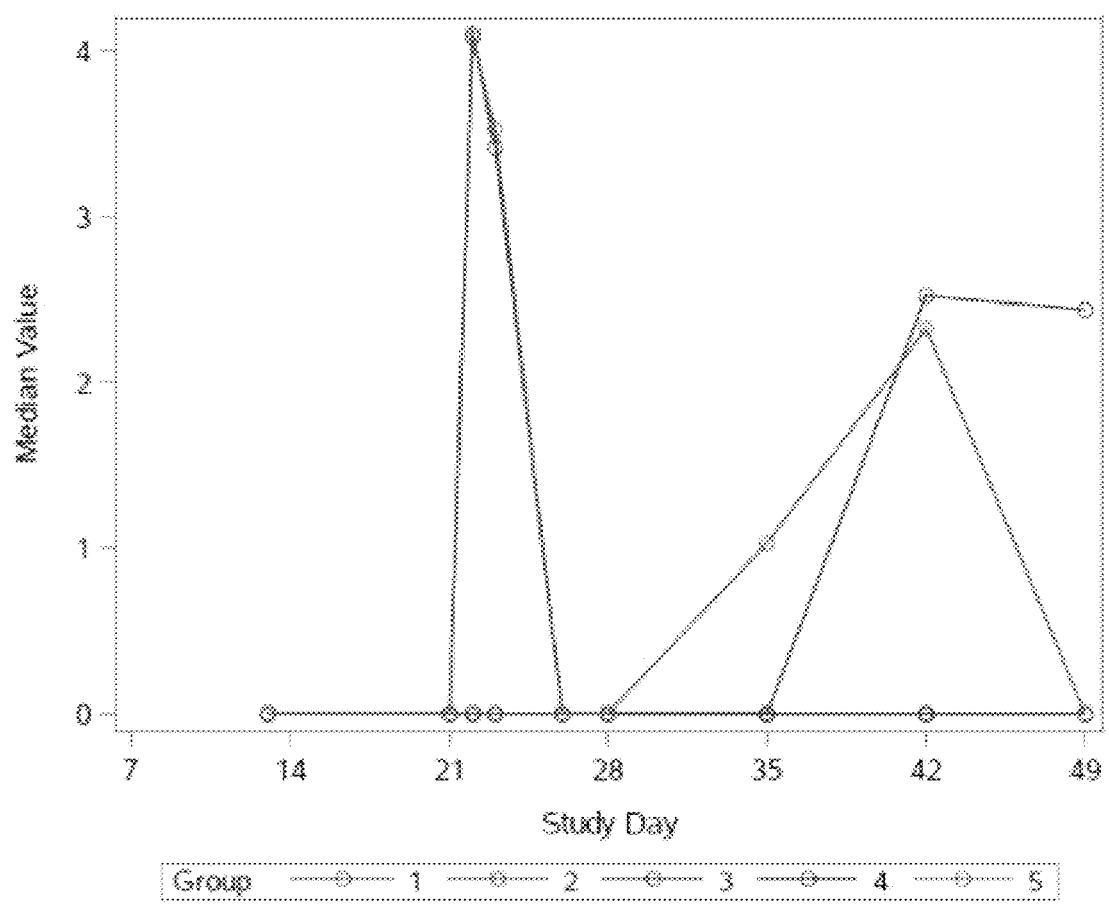
FIG. 14 shows the median PCR values for nasal shedding for Groups 1-5 from seven to forty-nine days.

FIG. 14 shows the median PCR values for nasal shedding for Groups 1-5 from seven to forty-nine days.

Table 27 depicts results for nasal shedding determinations for groups 1-5.

TABLE 27

Table of grp by shedding

| | shedding | | |
|---|---|---|---|
| grp(Group) | No | Yes | Total |
| 1 | 8 | 0 | 8 |
| | 100.00 | 0.00 | |
| 2 | 7 | 1 | 8 |
| | 87.50 | 12.50 | |
| 3 | 1 | 7 | 8 |
| | 12.50 | 87.50 | |
| 4 | 0 | 12 | 12 |
| | 0.00 | 100.00 | |
| 5 | 0 | 12 | 12 |
| | 0.00 | 100.00 | |
| Total | 16 | 32 | 48 |

Frequency Row Pct

A comparison of the P-values for the data of Table 27 (nasal shedding determinations) is shown in Table 28.

TABLE 28

| Group Comparison | P-value |
|---|---|
| 1 vs 3 | 0.0014 |
| 2 vs 3 | 0.0101 |
| 4 vs 5 | 1.0000 |

A direct comparison of the P-values (i.e., Wilcoxon Test) for Group 4 and 5 is shown in Table 29.

TABLE 29

| Day | P-value |
|---|---|
| 22 | 0.812 |
| 23 | 0.760 |
| 26 | 1.000 |
| 28 | 1.000 |
| 35 | 0.014 |
| 42 | 0.003 |
| 49 | 0.217 |

The following data relate to rectal temperature (° F.) data measured in animal subjects and the analysis thereof.

As is shown in Table 30, rectal temperature values measured in Fahrenheit are depicted by group for animals on a number of study days.

TABLE 30

| | | Study Day | | | | | | | | | | | |
|---|---|---|---|---|---|---|---|---|---|---|---|---|---|
| Group | Animal | 14 | 15 | 16 | 19 | 21 | 22 | 23 | 26 | 28 | 38 | 42 | 49 |
| 1 | 7 | 102.5 | — | — | — | 103.9 | 103.0 | 104.0 | 103.4 | 103.2 | 104.0 | 103.4 | 104.2 |
| | 8 | 104.6 | — | — | — | 103.9 | 104.0 | 104.0 | 103.8 | 104.0 | 101.6 | 103.6 | 104.6 |
| | 9 | 102.8 | — | — | — | 103.4 | 103.2 | 104.5 | 103.2 | 103.8 | 104.4 | 103.4 | 104.4 |
| | 10 | 104.0 | — | — | — | 103.9 | 103.4 | 104.0 | 104.2 | 103.2 | 103.4 | 103.4 | 104.0 |
| | 11 | 103.0 | — | — | — | 103.9 | 103.4 | 103.8 | 103.8 | 103.8 | 104.2 | 104.0 | 103.6 |
| | 12 | 103.2 | — | — | — | 103.4 | 103.0 | 103.4 | 102.8 | 103.4 | 103.4 | 102.8 | 103.0 |
| | 13 | 102.6 | — | — | — | 103.6 | 102.8 | 102.8 | 103.8 | 103.4 | 103.2 | 103.6 | — |
| | 14 | 103.6 | — | — | — | 103.4 | 102.6 | 103.8 | 103.4 | 103.6 | 104.2 | 103.2 | 103.8 |
| 2 | 15 | 103.2 | — | — | — | 103.4 | 103.6 | 104.0 | 103.6 | 104.0 | 104.0 | 103.6 | 104.0 |
| | 16 | 103.0 | — | — | — | 103.4 | 102.6 | 103.2 | 103.0 | 103.0 | 103.4 | 102.6 | 103.6 |
| | 17 | 103.6 | — | — | — | 102.7 | 103.0 | 103.8 | 102.8 | 103.6 | 103.4 | 103.2 | 104.0 |
| | 18 | 103.4 | — | — | — | 103.9 | 103.6 | 103.8 | 103.2 | 104.4 | 104.0 | 103.4 | 103.8 |
| | 19 | 104.0 | — | — | — | 103.6 | 103.4 | 103.8 | 104.2 | 104.0 | 104.0 | 104.2 | 104.6 |
| | 20 | 103.2 | — | — | — | 103.9 | 103.2 | 104.0 | 103.6 | 103.4 | 103.4 | 104.0 | 104.2 |
| | 21 | 103.2 | — | — | — | 104.1 | 103.0 | 104.0 | 103.6 | 104.0 | 104.1 | 104.2 | 103.8 |
| | 22 | 103.0 | — | — | — | 103.9 | 103.0 | 102.8 | 103.4 | 103.2 | 103.6 | 103.6 | 103.6 |

TABLE 30-continued

| Group | Animal | Study Day | | | | | | | | | | | |
|---|---|---|---|---|---|---|---|---|---|---|---|---|---|
| | | 14 | 15 | 16 | 19 | 21 | 22 | 23 | 26 | 28 | 38 | 42 | 49 |
| 3 | 23 | 104.0 | — | — | — | 104.3 | 103.6 | 103.6 | 103.6 | 103.8 | 104.4 | 103.6 | 104.8 |
| | 24 | 103.4 | — | — | — | 103.9 | 103.2 | 103.6 | 104.2 | 103.8 | 103.8 | 103.8 | 104.0 |
| | 25 | 103.2 | — | — | — | 103.4 | 103.2 | 103.2 | 103.8 | 103.6 | 103.4 | 103.2 | 104.0 |
| | 26 | 103.2 | — | — | — | 103.2 | 103.2 | 103.4 | 103.4 | 103.4 | 103.4 | 103.6 | 104.0 |
| | 27 | 103.2 | — | — | — | 103.0 | 103.2 | 103.5 | 103.4 | 103.0 | 103.6 | 103.6 | 103.8 |
| | 28 | 103.2 | — | — | — | 103.0 | 103.4 | 103.5 | 104.4 | 104.0 | 104.2 | 103.2 | 104.4 |
| | 29 | 103.6 | — | — | — | 104.1 | 103.2 | 103.8 | 103.8 | 103.6 | 103.8 | 103.2 | 103.0 |
| | 30 | 103.2 | — | — | — | 103.2 | 103.6 | 103.2 | 103.2 | 103.6 | 103.6 | 103.4 | 103.6 |
| 4 | 31 | 102.4 | — | — | — | 103.2 | 102.6 | 103.4 | 102.6 | 103.4 | 103.4 | 103.6 | 103.6 |
| | 32 | 103.4 | — | — | — | 103.6 | 103.4 | 103.4 | 103.0 | 103.4 | 103.8 | 103.2 | 104.2 |
| | 33 | 103.0 | — | — | — | 103.2 | 103.4 | 103.4 | 103.4 | 103.5 | 104.2 | 103.8 | 104.0 |
| | 34 | 103.6 | — | — | — | 103.4 | 103.2 | 103.4 | 103.2 | 103.2 | 102.8 | 103.6 | 103.2 |
| | 35 | 102.4 | — | — | — | 103.6 | 103.4 | 103.2 | 103.4 | 103.8 | 103.0 | 103.4 | 103.2 |
| | 36 | 102.6 | — | — | — | 103.6 | 103.4 | 103.6 | 102.4 | 103.4 | 103.6 | 103.2 | 103.8 |
| | 37 | 103.4 | — | — | — | 103.6 | 103.2 | 103.0 | 103.4 | 103.4 | 103.6 | 103.8 | 103.4 |
| | 38 | 103.6 | — | — | — | 103.9 | 103.8 | 103.8 | 103.8 | 103.8 | 103.8 | 103.2 | 103.8 |
| | 39 | 104.4 | — | — | — | 103.4 | 103.4 | 103.2 | 103.4 | 103.4 | 103.8 | 104.0 | 103.8 |
| | 40 | 103.0 | — | — | — | 102.3 | 102.2 | 102.6 | 102.2 | 103.2 | 103.2 | 103.4 | 103.4 |
| | 41 | 102.6 | — | — | — | 103.0 | 103.0 | 103.0 | 103.2 | 103.8 | 103.4 | 103.8 | 104.0 |
| | 42 | 103.2 | — | — | — | 103.4 | 103.0 | 103.4 | 103.2 | 103.8 | 103.2 | 103.8 | 103.4 |
| 5 | 43 | 103.6 | — | — | — | 103.4 | 102.8 | 103.2 | 103.4 | 103.4 | 103.4 | 103.8 | 104.0 |
| | 44 | 103.0 | — | — | — | 103.0 | 103.2 | 103.0 | 103.2 | 102.8 | 103.4 | 103.8 | 103.6 |
| | 45 | 103.2 | — | — | — | 103.6 | 103.8 | 103.4 | 103.6 | 103.4 | 103.8 | 103.8 | 104.0 |
| | 46 | 104.0 | — | — | — | 103.2 | 103.6 | 103.4 | 103.8 | 103.6 | 103.8 | 104.2 | 104.4 |
| | 47 | 103.2 | — | — | — | 103.2 | 103.4 | 103.2 | 103.4 | 103.0 | 103.8 | 103.8 | 103.2 |
| | 48 | 103.0 | — | — | — | 103.6 | 102.6 | 103.6 | 103.0 | 103.2 | 103.8 | 104.2 | 103.2 |
| | 49 | 103.0 | — | — | — | 103.6 | 103.2 | 103.8 | 103.6 | 103.4 | 103.8 | 104.2 | 103.8 |
| | 50 | 102.6 | — | — | — | 103.6 | 104.0 | 103.6 | 103.1 | 104.0 | 104.4 | 104.4 | 104.4 |
| | 51 | 104.0 | — | — | — | 103.4 | 104.0 | 103.2 | 103.4 | 104.0 | 104.0 | 104.0 | 102.6 |
| | 52 | 104.2 | — | — | — | 103.0 | 102.6 | 103.0 | 103.0 | 103.0 | 103.2 | 104.2 | 103.0 |
| | 53 | 102.5 | — | — | — | 103.5 | 103.4 | 103.4 | 103.4 | 102.6 | 103.8 | 103.8 | 104.2 |
| | 54 | 103.0 | — | — | — | 103.2 | 103.0 | 103.2 | 104.0 | 103.8 | 103.8 | 102.0 | 102.8 |
| 6 | 55 | 102.2 | 103.0 | 102.5 | 102.2 | 103.6 | 103.4 | 103.4 | 103.0 | 104.3 | 103.6 | 103.4 | 104.1 |
| | 56 | 104.3 | 103.2 | 103.4 | 103.6 | 103.4 | 103.8 | 103.6 | 103.9 | 103.9 | 103.9 | 103.6 | 104.5 |
| | 57 | 103.6 | 103.5 | 103.0 | 103.2 | 103.4 | 103.0 | 103.2 | 104.1 | 104.5 | 103.4 | 103.4 | 105.0 |
| | 58 | 103.4 | 103.0 | 102.5 | 103.4 | 103.8 | 103.9 | 103.9 | 103.9 | 104.9 | 104.1 | 103.0 | 103.9 |
| | 59 | 103.4 | 103.6 | 103.4 | 103.8 | 103.4 | 103.6 | 104.1 | 104.1 | 104.8 | 104.5 | 104.3 | 104.5 |
| | 60 | 103.2 | 103.0 | 103.6 | 103.0 | 102.7 | 103.2 | 103.4 | 103.0 | 104.1 | 104.1 | 102.6 | 103.2 |
| 7 | 1 | 102.8 | 102.8 | 102.2 | 102.8 | 103.2 | — | 103.0 | — | 103.2 | — | — | — |
| | 2 | 103.4 | 103.6 | 103.2 | 102.4 | 103.4 | — | 102.8 | — | 103.4 | — | — | — |
| 8 | 3 | 102.6 | 103.6 | 103.2 | 103.4 | 102.8 | — | 103.0 | — | 103.4 | — | — | — |
| | 4 | 102.5 | 102.0 | 102.6 | 102.6 | 102.5 | — | 102.2 | — | 102.8 | — | — | — |
| 9 | 5 | 101.8 | 102.8 | 102.8 | 102.8 | 102.6 | — | 103.0 | — | 102.6 | — | — | — |
| | 6 | 103.0 | 103.2 | 103.8 | 102.6 | 103.2 | — | 102.8 | — | 102.6 | — | — | — |

Figure 15:
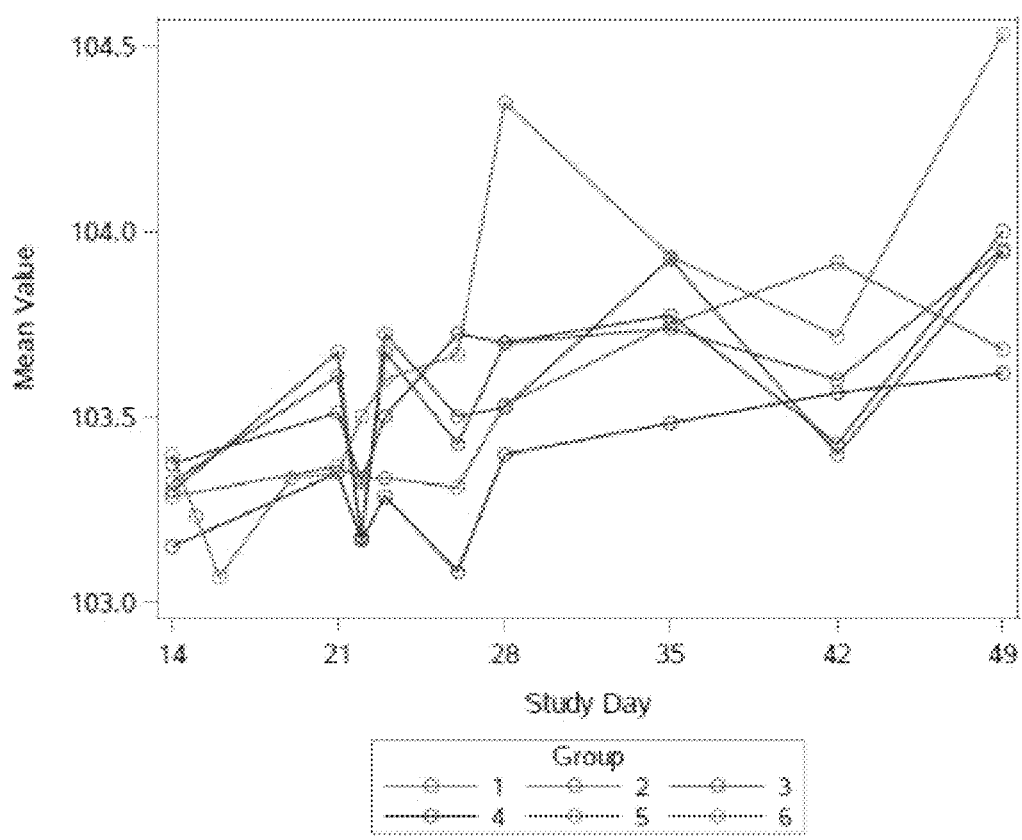
FIG. 15 depicts the arithmetic mean rectal temperature value for Groups 1-6 from fourteen to forty-nine days of the evaluation.

FIG. 15 depicts the arithmetic mean rectal temperature value for Groups 1-6 from fourteen to forty-nine days of the evaluation.

Figure 16:
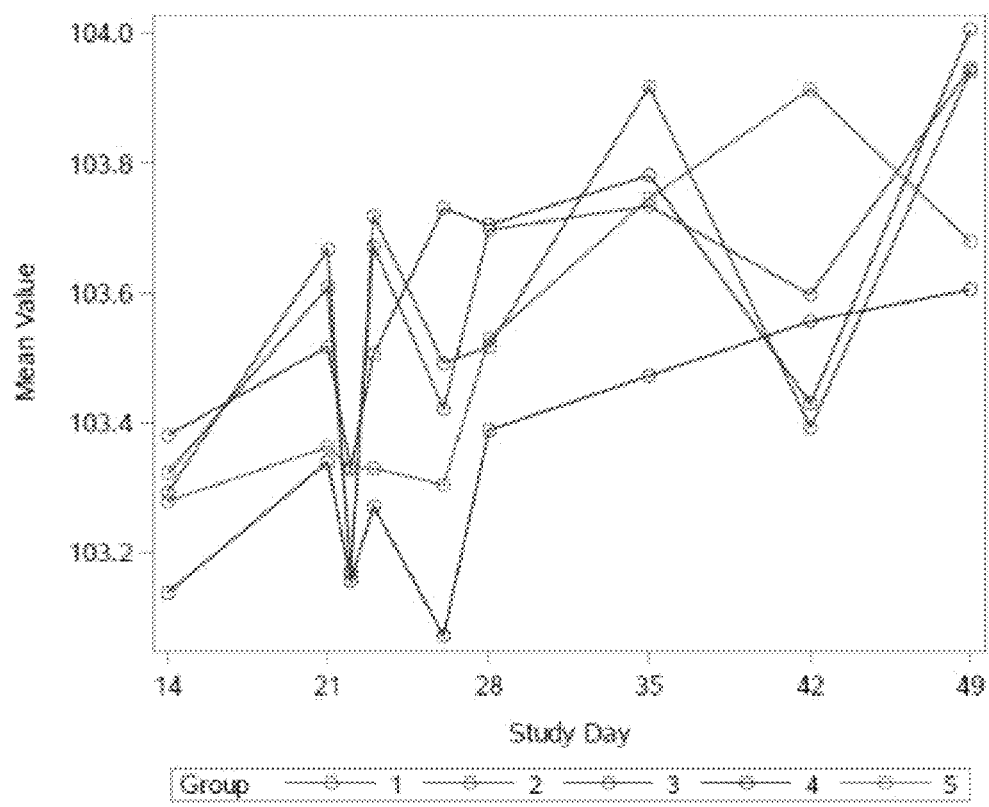
FIG. 16 depicts the least-squares mean temperature values by group and day for groups 1-5.

FIG. 16 depicts the least-squares mean temperature values by group and day for groups 1-5.

Table 53 shows a comparison of the P-values for the data relating to rectal temperature.

TABLE 53

| Rectal Temperature (F.) Group Comparison P-values | | | |
|---|---|---|---|
| Group Comparison | Day | estimate | P-value |
| 1 vs 2 | 14 | −0.03 | 0.8834 |
| | 21 | 0.06 | 0.7691 |
| | 22 | −0.00 | 0.9848 |
| | 23 | 0.05 | 0.8173 |
| | 26 | 0.07 | 0.7218 |
| | 28 | −0.18 | 0.3716 |
| | 35 | 0.18 | 0.3587 |
| | 42 | −0.20 | 0.3087 |
| | 49 | −0.01 | 0.9734 |
| 1 vs 3 | 14 | −0.09 | 0.6635 |
| | 21 | 0.15 | 0.4525 |
| | 22 | −0.10 | 0.4133 |
| | 23 | 0.21 | 0.2990 |
| | 26 | −0.24 | 0.2370 |
| | 28 | −0.19 | 0.3504 |
| | 35 | 0.14 | 0.4909 |
| | 42 | −0.04 | 0.8530 |
| | 49 | −0.06 | 0.7581 |
| 4 vs 5 | 14 | −0.14 | 0.3519 |
| | 21 | −0.02 | 0.8736 |
| | 22 | −0.17 | 0.2499 |
| | 23 | −0.06 | 0.7041 |
| | 26 | −0.23 | 0.1249 |
| | 28 | −0.14 | 0.3519 |
| | 35 | −0.27 | 0.0707 |
| | 42 | −0.36 | 0.0188 |
| | 49 | −0.07 | 0.6240 |

Figure 17:
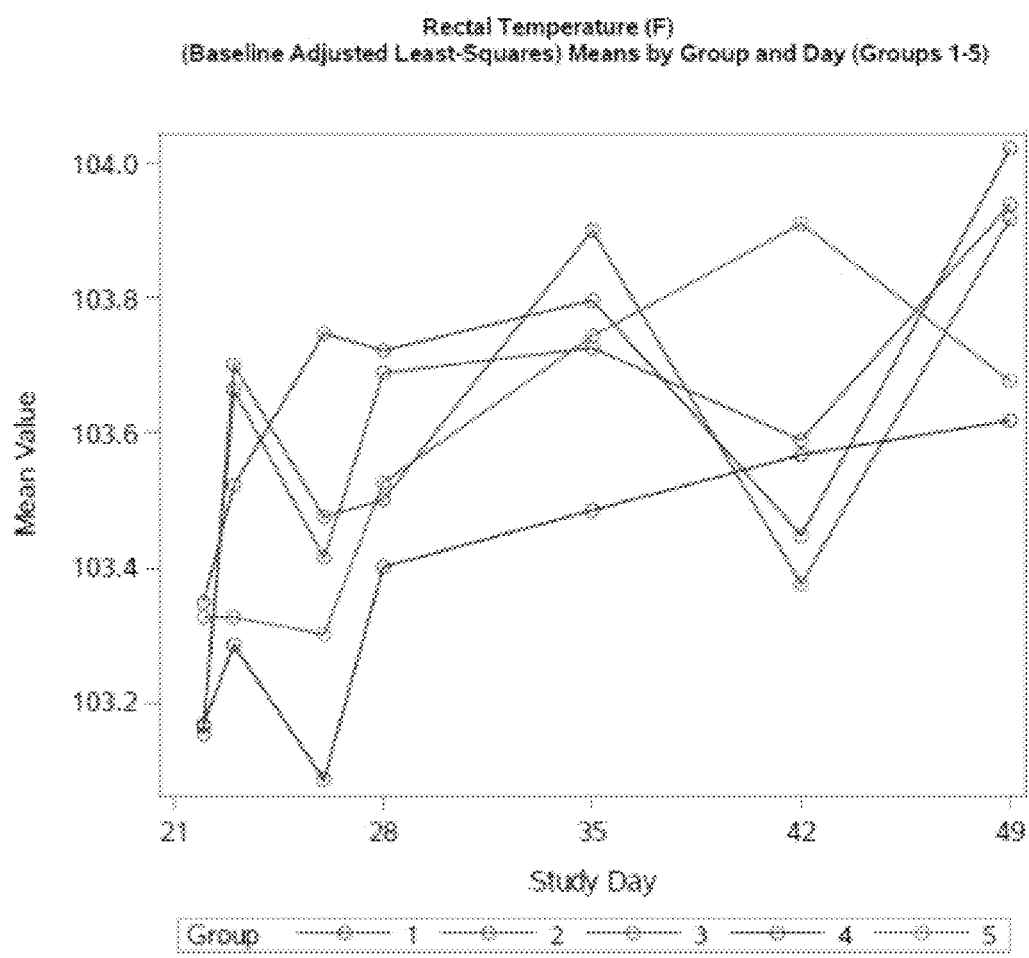
FIG. 17 is a line chart illustrating the mean rectal temperatures of animals (Baseline Adjusted Least-Squares) by Group and Day for Groups 1-5.
Figure 18:
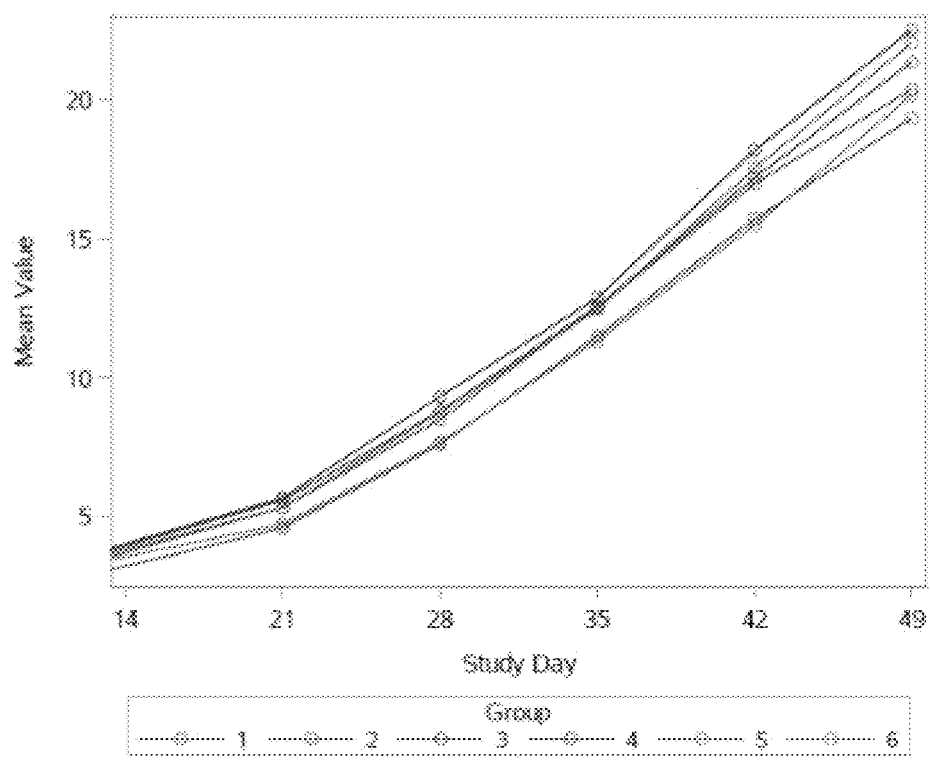
FIG. 18 shows the arithmetic mean body weight values for Groups 1-6 from fourteen to forty-nine days.

FIG. 17 is a line chart illustrating the mean rectal temperatures of animals (Baseline Adjusted Least-Squares) by Group and Day for Groups 1-5.

Table 73 shows a comparison of P-values for the various groups (1-5).

TABLE 73

Rectal Temperature (F.)
(Baseline Adjusted) Group Comparison P-values

| Group Comparison | Day | estimate | P-value |
|---|---|---|---|
| 1 vs 2 | 22 | −0.01 | 0.9355 |
|  | 23 | 0.04 | 0.8392 |
|  | 26 | 0.06 | 0.7705 |
|  | 28 | −0.19 | 0.2529 |
|  | 35 | 0.17 | 0.3463 |
|  | 42 | −0.21 | 0.2804 |
|  | 49 | −0.02 | 0.9129 |
| 1 vs 3 | 22 | −0.20 | 0.2341 |
|  | 23 | 0.18 | 0.3264 |
|  | 26 | −0.27 | 0.2030 |
|  | 28 | −0.22 | 0.1819 |
|  | 35 | 0.10 | 0.5758 |
|  | 42 | −0.07 | 0.7193 |
|  | 49 | −0.10 | 0.5977 |
| 4 vs 5 | 22 | −0.16 | 0.2454 |
|  | 23 | −0.04 | 0.6069 |
|  | 26 | −0.22 | 0.0906 |
|  | 28 | −0.13 | 0.3229 |
|  | 35 | −0.26 | 0.0479 |
|  | 42 | −0.34 | 0.0171 |
|  | 49 | −0.06 | 0.7374 |

The following data relate to body weight (kg) data measured in animal subjects and the analysis thereof.

As is shown in Table 74, body weight values measured in kilograms are depicted by group for animals on a selection of study day

TABLE 74

Body Weight (Kg) Data Listing

| Group | Animal | 13 | 21 | 28 | 35 | 42 | 49 |
|---|---|---|---|---|---|---|---|
| 1 | 7 | 2.9 | 4.8 | 8.0 | 11.8 | 16.3 | 20.1 |
|  | 8 | 3.7 | 5.6 | 8.8 | 12.7 | 17.4 | 21.8 |
|  | 9 | 3.6 | 5.6 | 8.6 | 12.0 | 15.4 | 18.8 |
|  | 10 | 3.0 | 4.7 | 8.3 | 12.2 | 15.9 | 18.5 |
|  | 11 | 3.0 | 4.4 | 8.0 | 12.1 | 16.7 | 19.2 |
|  | 12 | 3.2 | 4.7 | 7.9 | 12.2 | 16.3 | 20.1 |
|  | 13 | 2.2 | 3.4 | 5.2 | 9.4 | 13.0 |  |
|  | 14 | 2.4 | 3.7 | 6.0 | 9.6 | 14.7 | 17.1 |
| 2 | 15 | 3.3 | 5.0 | 8.3 | 12.3 | 17.4 | 20.7 |
|  | 16 | 4.7 | 7.3 | 11.9 | 17.3 | 22.9 | 27.6 |
|  | 17 | 2.5 | 3.8 | 6.3 | 8.9 | 13.2 | 15.6 |
|  | 18 | 3.4 | 5.2 | 8.0 | 11.5 | 15.9 | 19.7 |
|  | 19 | 2.9 | 4.1 | 6.5 | 9.4 | 12.7 | 16.0 |
|  | 20 | 4.8 | 7.4 | 11.7 | 16.5 | 21.6 | 26.3 |
|  | 21 | 3.4 | 5.6 | 9.1 | 14.0 | 17.7 | 19.9 |
|  | 22 | 2.9 | 4.2 | 6.3 | 10.3 | 14.6 | 17.4 |
| 3 | 23 | 3.6 | 5.8 | 8.7 | 11.9 | 16.7 | 20.7 |
|  | 24 | 3.0 | 4.5 | 7.2 | 11.2 | 15.4 | 20.1 |
|  | 25 | 3.3 | 5.4 | 8.9 | 12.8 | 17.1 | 20.6 |
|  | 26 | 4.7 | 7.5 | 10.5 | 13.1 | 18.0 | 23.4 |
|  | 27 | 3.9 | 5.7 | 8.7 | 12.7 | 16.9 | 20.8 |
|  | 28 | 3.8 | 5.1 | 8.0 | 11.9 | 16.2 | 19.5 |
|  | 29 | 3.7 | 6.0 | 10.1 | 14.0 | 19.4 | 23.2 |
|  | 30 | 3.6 | 4.8 | 8.4 | 12.9 | 18.1 | 22.8 |
| 4 | 31 | 3.2 | 4.8 | 8.1 | 12.1 | 17.0 | 21.7 |
|  | 32 | 3.3 | 5.1 | 8.3 | 11.4 | 16.3 | 20.5 |
|  | 33 | 4.0 | 5.7 | 9.4 | 12.7 | 17.7 | 22.1 |
|  | 34 | 3.1 | 5.1 | 8.5 | 11.3 | 15.9 | 19.9 |
|  | 35 | 3.8 | 5.8 | 10.2 | 13.9 | 18.6 | 21.9 |
|  | 36 | 4.8 | 7.2 | 12.0 | 15.0 | 20.9 | 25.5 |
|  | 37 | 3.9 | 5.8 | 9.5 | 12.6 | 17.3 | 21.6 |
|  | 38 | 4.2 | 6.2 | 9.8 | 14.3 | 19.8 | 25.0 |

TABLE 74-continued

Body Weight (Kg) Data Listing

| Group | Animal | 13 | 21 | 28 | 35 | 42 | 49 |
|---|---|---|---|---|---|---|---|
|  | 39 | 3.7 | 5.6 | 8.8 | 12.3 | 17.2 | 21.6 |
|  | 40 | 3.5 | 5.0 | 8.4 | 11.8 | 17.8 | 22.6 |
|  | 41 | 3.8 | 5.5 | 7.9 | 12.2 | 18.0 | 22.6 |
|  | 42 | 3.9 | 6.4 | 10.9 | 15.2 | 21.9 | 25.5 |
| 5 | 43 | 3.6 | 5.4 | 8.6 | 11.3 | 16.5 | 21.1 |
|  | 44 | 2.7 | 4.2 | 7.4 | 11.3 | 15.5 | 19.6 |
|  | 45 | 3.0 | 4.5 | 7.8 | 12.0 | 16.6 | 20.3 |
|  | 46 | 4.7 | 6.8 | 10.8 | 15.0 | 20.1 | 24.4 |
|  | 47 | 4.4 | 5.7 | 8.9 | 12.2 | 17.2 | 21.2 |
|  | 48 | 4.4 | 6.6 | 10.9 | 14.7 | 20.8 | 24.9 |
|  | 49 | 4.2 | 6.1 | 9.8 | 13.4 | 18.9 | 23.7 |
|  | 50 | 4.4 | 6.1 | 9.9 | 14.1 | 19.2 | 24.0 |
|  | 51 | 2.4 | 4.0 | 6.8 | 10.1 | 14.8 | 19.0 |
|  | 52 | 2.8 | 4.6 | 7.3 | 10.9 | 15.5 | 20.7 |
|  | 53 | 2.6 | 4.3 | 7.7 | 11.2 | 16.1 | 20.6 |
|  | 54 | 4.1 | 5.8 | 9.4 | 13.5 | 19.7 | 25.3 |
| 6 | 55 | 3.1 | 4.1 | 6.2 | 10.0 | 15.0 | 20.1 |
|  | 56 | 2.8 | 4.2 | 7.7 | 11.6 | 16.0 | 22.2 |
|  | 57 | 3.7 | 4.8 | 8.0 | 12.0 | 16.5 | 18.1 |
|  | 58 | 4.0 | 5.4 | 8.0 | 11.7 | 15.1 | 19.1 |
|  | 59 | 3.6 | 5.8 | 10.0 | 12.3 | 15.4 | 21.8 |
|  | 60 | 3.3 | 4.0 | 6.2 | 10.5 | 15.1 | 19.7 |
| 7 | 1 | 4.0 | 5.7 | 9.5 | 15.0 | 18.7 | 24.8 |
|  | 2 | 4.4 | 6.4 | 10.6 | 16.4 | 21.4 | 27.0 |
| 8 | 3 | 4.9 | 8.0 | 12.3 | 17.8 | 21.8 | 25.5 |
|  | 4 | 3.9 | 6.2 | 9.7 | 15.4 | 19.6 | 24.5 |
| 9 | 5 | 3.0 | 3.9 | 6.3 | 10.6 | 13.5 | 16.9 |
|  | 6 | 2.9 | 2.7 | 6.6 | 10.7 | 13.9 | 16.6 |

Figure 19:
FIG. 19 is a line graph showing the body weight (Least-Squares) means by Group and Day for Groups 1-5.

FIG. 19 is a line graph showing the body weight (Least-Squares( means by Group and Day for Groups 1-5.

Table 96 is a group comparison P-values for body weight.

TABLE 96

Body Weight (Kg)
Group Comparison P-values

| Group Comparison | Day | estimate | P-value |
|---|---|---|---|
| 1 vs 2 | 13 | −0.49 | 0.1409 |
|  | 21 | −0.71 | 0.1971 |
|  | 28 | −0.91 | 0.2752 |
|  | 35 | −1.03 | 0.3117 |
|  | 42 | −1.29 | 0.2718 |
|  | 49 | −1.48 | 0.2998 |
| 1 vs 3 | 13 | −0.70 | 0.0353 |
|  | 21 | −0.99 | 0.0747 |
|  | 28 | −1.21 | 0.1478 |
|  | 35 | −1.06 | 0.2944 |
|  | 42 | −1.51 | 0.1972 |
|  | 49 | −2.47 | 0.0853 |
| 4 vs 5 | 13 | 0.16 | 0.5802 |
|  | 21 | 0.33 | 0.3429 |
|  | 28 | 0.54 | 0.3284 |
|  | 35 | 0.42 | 0.4901 |
|  | 42 | 0.62 | 0.4249 |
|  | 49 | 0.47 | 0.5637 |

Figure 20:
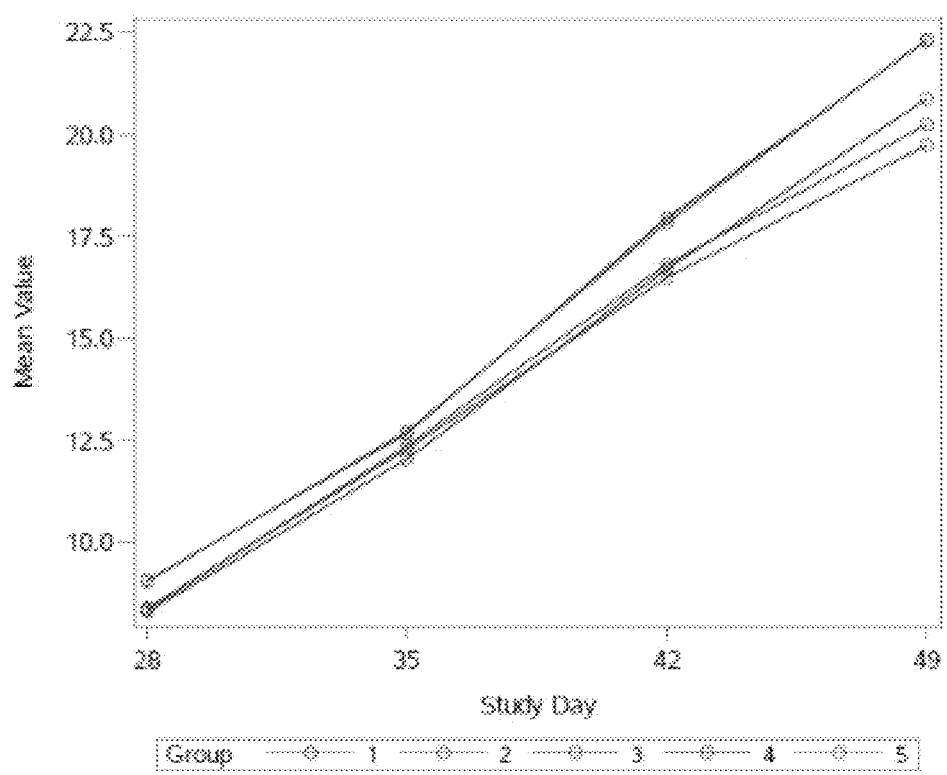
FIG. 20 is a line graph depicting data for Least-Squares Means for body weight (Baseline Adjusted) by Group and day.
Figure 24:
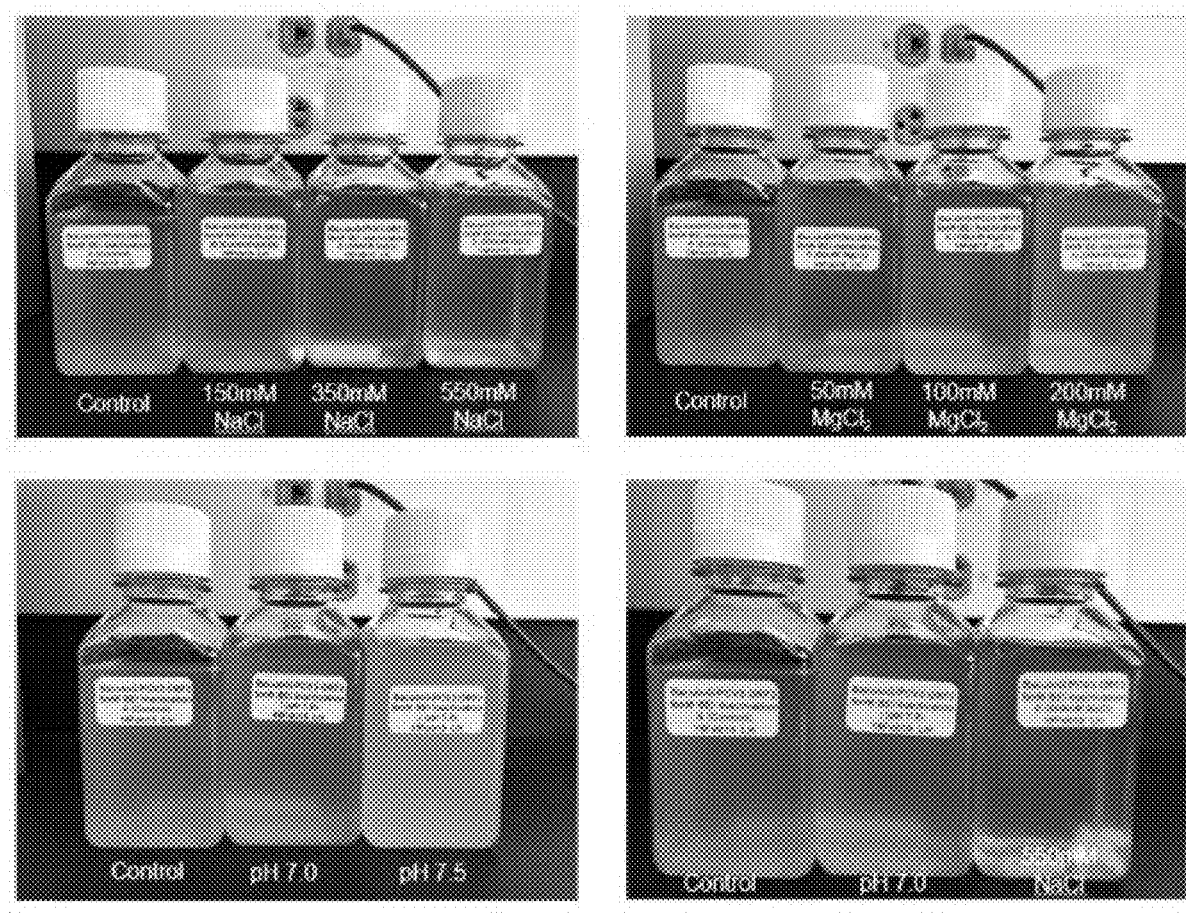
FIG. 24 shows images of inactivations at 72 hours.
Figure 25:
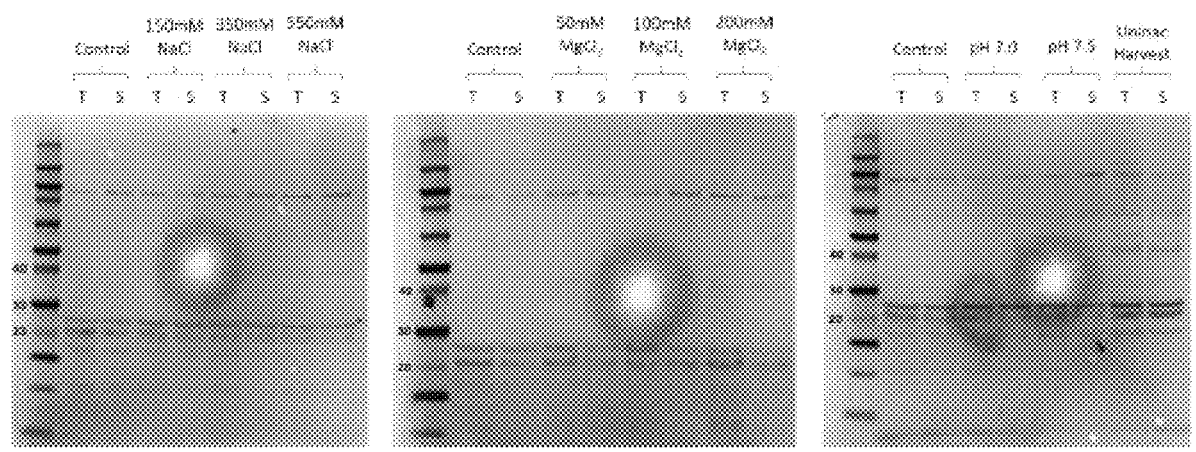
FIG. 25 shows western comparison of inactivation conditions for BaculoG/PCV3 ORF2 antigen—post inactivation.
Figure 26:
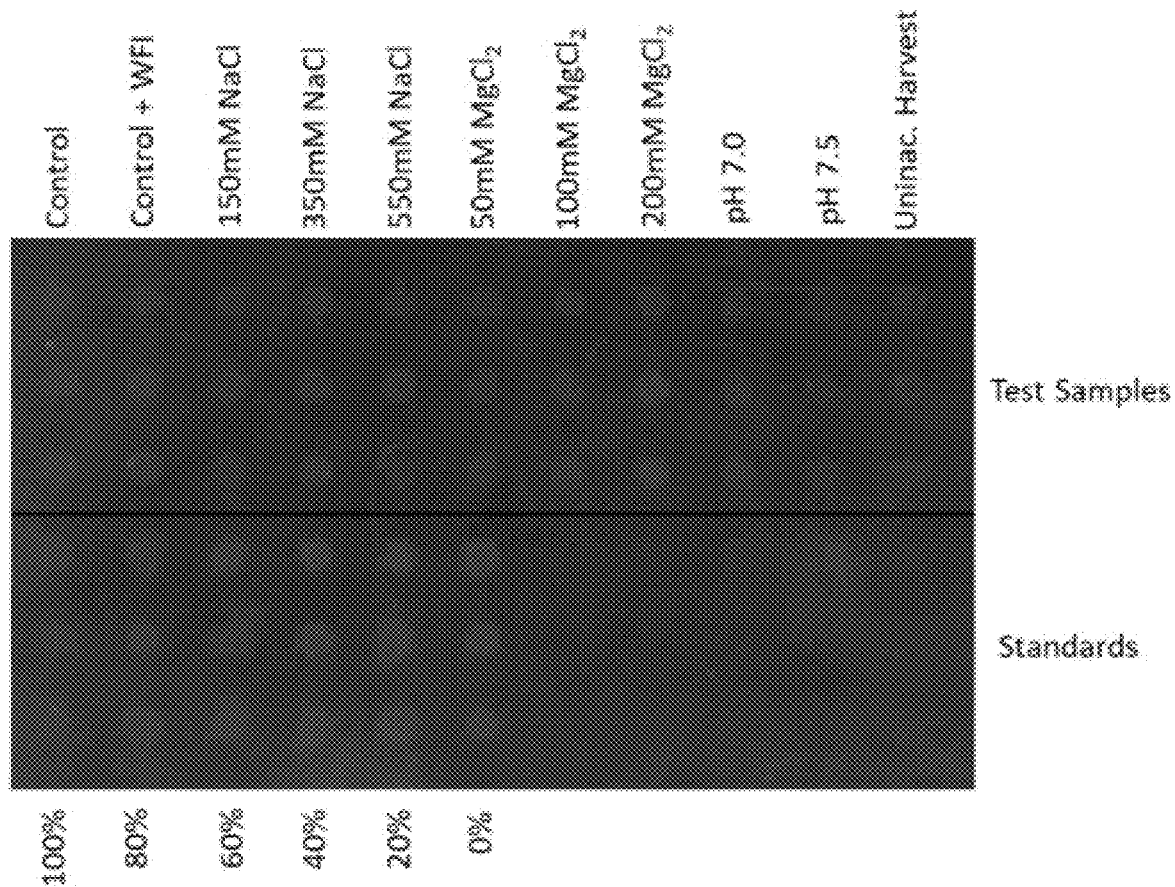
FIG. 26 shows a PCV3 ORF2 fluorescent dot blot.

FIG. 20 is a line graph depicting data for Least-Squares Means for body weight (Baseline Adjusted) by Group and day.

Table 119 is a table of the Comparison P-values for the various groups (1-5) baseline adjusted body weights.

TABLE 119

| Body Weight (Kg) (Baseline Adjusted) Group Comparison P-values | | | |
|---|---|---|---|
| Group Comparison | Day | estimate | P-value |
| 1 vs 2 | 28 | 0.04 | 0.8895 |
| | 35 | −0.07 | 0.8912 |
| | 42 | −0.34 | 0.6344 |
| | 49 | −0.49 | 0.5923 |
| 1 vs 3 | 28 | 0.10 | 0.7072 |
| | 35 | 0.25 | 0.6418 |
| | 42 | −0.20 | 0.7836 |
| | 49 | −1.11 | 0.2258 |
| 4 vs 5 | 28 | 0.05 | 0.7993 |
| | 35 | −0.07 | 0.8086 |
| | 42 | 0.13 | 0.7314 |
| | 49 | −0.02 | 0.9671 |

Example 8

PCV3 Bioprocess

Infection was accomplished via a baculovirus seed, BaculoG/PCV3 ORF2 Pre-MSV. The target MOI was 0.1 and the final calculated MOI was 0.1.

Infection parameters are shown in Table 120.1D 44TM

TABLE 120

| Parameter | Details |
|---|---|
| Vessel size/ configuration | 10 L Sartorius Biostat B glass-jacketed vessel<br>Ring sparger<br>2 × 45° pitched-blade impeller with negative slope mounted approximately one inch to seven inches from the bottom of the agitator shaft |
| Working volume | 8 L |
| Media | Ex-Cell 420 Serum-Free Medium |
| Cells and target CPD | SF+ Cells @ 1 × $10^6$ cells/mL |
| Temperature | 27° C. |
| Gas/DO control | Sparge $O_2$ at 0.3 slpm with duty cycle controlled DO controller |
| pH control | Monitor only |
| Agitation | 100 rpm |

Bioreactor fluids were harvested aseptically into a 10 L biotainer, dispensed into 8×1 L centrifuge bottles, and centrifuged at 10,000×g for 20 min at 4° C. The clarified fluids were aseptically collected into a 10 L biotainer and filtered through 0.8/0.2 mm filter into a new 10 L biotainer and the final filtered harvest was stored at 4° C.

Ten different inactivation conditions were investigated at 5 mM binary ethyleneimine (BEI) at 37° C. for 72 hours as shown in Table 121. Samples were taken to monitor pH (Table 122) and PCV3 ORF2 solubility.

FIG. 24 shows images of inactivations at 72 hours.

TABLE 122

| Group | Treatment | Day 0 pH | Day 3 pH |
|---|---|---|---|
| A | Control | 5.89 | 6.09 |
| B | Control + WFI | 5.97 | 6.05 |
| C | 150 mM NaCl | 5.82 | 6.11 |
| D | 350 mM NaCl | 5.82 | 6.07 |
| E | 550 mM NaCl | 5.74 | 6.07 |
| F | 50 mM $MgCl_2$ | 5.66 | 5.91 |
| G | 100 mM $MgCl_2$ | 5.60 | 5.80 |
| H | 200 mM $MgCl_2$ | 5.46 | 5.62 |
| I | pH 7.0 | 7.00 | 6.99 |
| J | pH 7.5 | 7.42 | 7.36 |

FIG. 25 shows a western comparison of inactivation conditions for BaculoG/PCV3 ORF2 Antigen—Post Inactivation.

FIG. 26 shows a PCV3 ORF2 Fluorescent Dot Blot.

From this study, a low level of PCV3 ORF2 produced from the bioreactor that are similar to runs in spinners and infection kinetics suggest slight under seeding. There was minimal loss of PCV3 ORF2 from bioreactor harvest after inactivation as each of the conditions had minimal impact on soluble ORF2 although $MgCl_2$ at 200 mM may have had more of an effect on the observed PCV ORF2 loss. There was no loss of PCV3 ORF2 in harvest fluids stored at 4° C. for 9 days.

Example 9

Vaccination of Caesarian-Derived Colostrum-Deprived Pigs with an Inactivated Baculovirus-Expressed PCV3 ORF2 Vaccine This study evaluated an experimental inactivated baculovirus-expressed PCV3 ORF2 vaccine when administered to 3-week-old pigs. The randomized, blinded, vaccination-challenge study was conducted using 50 Caesarean-derived, colostrum-deprived ("CDCD") pigs that were 22 days of age on DO. Pigs were blocked by litter and randomized to treatment group with littermates housed in the same pen. On D0, pigs received either control product of product-matched placebo or experimental vaccine intramuscularly. Pigs were observed daily for general health, and blood was collected to evaluate seroconversion. All pigs were challenged 14 days post-vaccination with tissue homogenate (which tested positive for PCV3 by PCR) and were necropsied four weeks later. Clinical observations were conducted daily post-challenge until study off-test (D42), and blood was collected weekly to evaluate viremia (PCV3 by PCR). At necropsy, internal organs were evaluated for gross lesions, and tissues were collected for histopathologic assessment. The histology slides were stained, evaluated by RNAScope, and scored.

TABLE 121

| | Control | Control + WFI | 250 mM NaCl | 350 mM NaCl | 550 mM NaCl | 50 mM $MgCl_2$ | 100 mM $MgCl_2$ | 200 mM $MgCl_2$ | pH 7.0 | pH 7.5 |
|---|---|---|---|---|---|---|---|---|---|---|
| Baculovirus Harvest (mL) | 220 | 220 | 220 | 220 | 220 | 220 | 220 | 220 | 220 | 220 |
| 7M $MgCl_2$ (mL) | 0 | 0 | 0 | 0 | 0 | 6.3 | 12.5 | 25 | 0 | 0 |
| 5M NaCl (mL) | 0 | 0 | 7.5 | 17.5 | 27.5 | 0 | 0 | 0 | 0 | 0 |
| 1M Tris HCl, pH 7.5 (mL) | 0 | 0 | 0 | 0 | 0 | 0 | 0 | 0 | 11.3 | 25 |
| WFI (mL) | 0 | 30 | 22.5 | 12.5 | 2.5 | 23.7 | 17.5 | 5 | 18.7 | 5 |
| Total Volume (mL) | 220 | 250 | 250 | 250 | 250 | 250 | 250 | 250 | 250 | 250 |

Throughout the study, any personnel involved in collecting data or performing laboratory assays did not know the allocation of treatment to pigs. Treatments were administered by the Study Investigator, who was not involved with any data collection.

The use of 20 animals in the control and vaccine groups, respectively, is consistent with prior vaccination-challenge licensing studies for porcine *circovirus*. Extra animals were included to account for natural attrition of CDCD pigs prior to challenge.

Pigs were blocked by litter and randomly assigned to treatment making the individual pig the experimental unit.

All randomizations were conducted using SAS version 9.4. Litters of six (7 litters) or eight (1 litter) pigs were utilized. For randomization to treatment group, a random variate was generated for each pig using the RANUNI function in SAS. Pig IDs were then sorted based on litter and variate values. Within each litter, the three (or four for the litter with 8 pigs) animals with the smallest variate values were assigned to T01, and the remainder assigned to T02. During the vaccination phase, pigs were housed by litter to the degree possible, with three or four pigs per brooder using brooders in three rooms. During the challenge phase, with the exception of the litter with 8 pigs, pigs were housed by litter, one litter per pen, in one of two rooms. The litter with 8 littermates was housed in two pens with 6 and 2 littermates, respectively, in a pen. For the challenge housing, litters were randomized to room and pen within room by generating a random variate for each litter, sorting by variate value, and aligning the sorted order to room-pen combinations.

Vaccination phase: Twenty-five Caesarian-derived colostrum-deprived (CDCD) pigs at approximately 3 weeks of age were vaccinated with either baculovirus expressed PCV3 ORF2 vaccine or a placebo matched control vaccine. The virus titer was determined to be $6.76 \times 10^6$ TCID$_{50}$/mL. The inactivated antigen was formulated with 20% Carbopol® and dispensed into final containers. The placebo used as a negative control was prepared in the same manner with inactivated antigen from a negative control baculovirus. The vaccine or placebo was administered intramuscularly to each animal. Cord blood was collected from all pigs at delivery (C-section; Day-22). Serum was separated and tested for PCV3 DNA and PCV2 DNA by PCR. All samples were negative for both PCV3 and PCV2. On D-2, all pigs were bled for serum collection and then vaccinated with PCV2 Ingelvac CircoFLEX®. All serum samples were negative by PCR for both PCV3 and PCV2 and seronegative for *M. hyopneumoniae* and Porcine Reproductive and Respiratory Syndrome Virus.

Challenge phase: All animals were challenged with PCV3 positive tissue homogenate (1 mL intranasally and 1 mL intramuscularly) at 14 days post vaccination. Keyhole limpet hemocyanin (KLH) emulsified in incomplete Freund's adjuvant (ICFA) containing 1 mg KLH/mL was administered intramuscularly two days before and two days after challenge (Table 123). The tissue homogenate used for challenge was screened for extraneous agents by qPCR and deep sequencing. Animals were euthanized at day 42. At necropsy, a number of tissues were collected. These included brain, heart, kidney, lung, spleen, large intestine, tonsil, tracheobronchial lymph node (TBLN), mesenteric lymph node (MLN), and external iliac lymph node (ILN).

TABLE 123

Study Design

| Group | N | Vaccination | KLH/ICFA | Challenge | KLH/ICFA | Necropsy |
|---|---|---|---|---|---|---|
| Placebo | 25 | D 0 | D 12 | D 14 | D 16 | D 42 |
| Vaccine | 25 | 2 mL IM (right neck) | 2 mL IM | 1 mL IN/1 mL IM | 2 mL IM | |

Table 124 describes the tissue homogenate used to challenge the animals to PCV3.

TABLE 124

| | |
|---|---|
| Description | PCV3 pluck tissue homogenate; Lot # 3743-105, Ct = 9.5 |
| Formulation | Frozen tissue ground using sterile mortar and pestle, suspended in MEM, and spun at 1000 g for 15 min. Supernatant filtered through 0.2 µm filter and stored at −70° C. ± 10° C. until use. One day prior to challenge, material was thawed at 37° C., bottled into sterile vaccine-type bottles and capped. |
| Dosage and challenge procedure | 1 mL intranasally by attaching a nasal tip atomizer to a 5 cc luer lock syringe and applying the full 1-mL dose into one nostril. 1 mL intramuscularly in the left neck muscle neck midway between the base of the ear and point of the shoulder using appropriate-sized sterile syringes and sterile needles. |
| Testing | Routine culture of the material was conducted on blood agar plates at 37° C. anaerobically and aerobically for 48 hours; no growth was observed and the test was considered satisfactory. The material was tested by PCR for the presence of mycoplasma and PCV2; no contamination was identified. The PCV3 qPCR result was 9.1 log$_{10}$ genomic copies/mL (Cq = 14.82). Deep sequencing was completed on the samples (MiSeq_127 9 Oct. 2018) using both DNA and RNA processing; sequencing resulted in recovery of the full PCV3 genome (99% nt to PCV3 GB MG564174.1). |

Table 125 provides information regarding the pigs used in the study.

TABLE 125

| Specifications | Requirements |
|---|---|
| Species & breed | Porcine, commercial mixed breed |
| Age & sex | Pigs were 22 days of age at D 0 (born by caesarian section), both females and males |

TABLE 125-continued

| Specifications | Requirements |
| --- | --- |
| Weight range | Typical weight for CDCD pigs of this age |
| Source & ownership | CDCD pigs were derived and raised at Struve Labs International; 1603 Enterprise St., Manning, Iowa 51455 |
| Number | 50 (seven litters of 6 pigs, one litter of 8 pigs) |
| Identification | Ear tag (uniquely numbered) |
| Conditioning | A venous blood sample was collected from all pigs at delivery (cord blood at C-section; D-22). Serum was shipped on ice or frozen immediately and tested for PCV3 DNA and PCV2 DNA by PCR at ISU-VDL to establish sero-status for all available pigs. All samples were negative for both PCV3 and PCV2. On D-2, all pigs were bled for serum collection and then vaccinated with PCV2 Ingelvac CircoFLEX ®. Serum was shipped on ice or frozen to BI AH USA-Ames immediately and tested for PCV3 DNA and PCV2 DNA by PCR at ISU-VDL. All samples were negative by PCR for both |

TABLE 125-continued

| Specifications | Requirements |
| --- | --- |
| | PCV3 and PCV2. Retention samples of D-2 sera (except pig #18 and #45 because of a lack of sera) were submitted to ISU-VDL to confirm seronegative status for *M. hyopneumoniae* (S/P ratio <0.3), and PRRSV (S/P ratio <0.4). All samples were negative. |
| Veterinary care and treatment | Pigs received a medicated feed ration. On D 8, pigs received a label dose of Excede ® prior to shipment to VRI. Because of suspected bacterial sepsis, all remaining pigs received Baytril (lot #AHO2X32, exp November 2021) on D 30 in the left neck via label directions. |

All 50 pigs met requirements outlined above, and the Study Investigator conducted a Health Examination on D-2 to ensure only healthy animals were included in the study.

After the start of the study, pigs were to be removed only in the case of injury, illness, or death that would interfere with the outcome of the study. Two pigs were removed during the vaccination phase, and five pigs were removed during the challenge phase.

Pig #5 (vaccinated group) was observed with lack of appetite and depressed on D6; the pig was euthanized and removed from the study on D6. Necropsy revealed icteric skin, subcutis fascia, and fibrin on liver and spleen with a mottled liver surface, and a collapsed left apical lung lobe. The carcass was disposed by composting.

Pig #4 (vaccinated group) was euthanized and removed from the study prior to challenge on D14 because of poor body condition and lameness in both rear legs. No gross lesions were observed at necropsy. The carcass was disposed by incineration.

Figure 27:
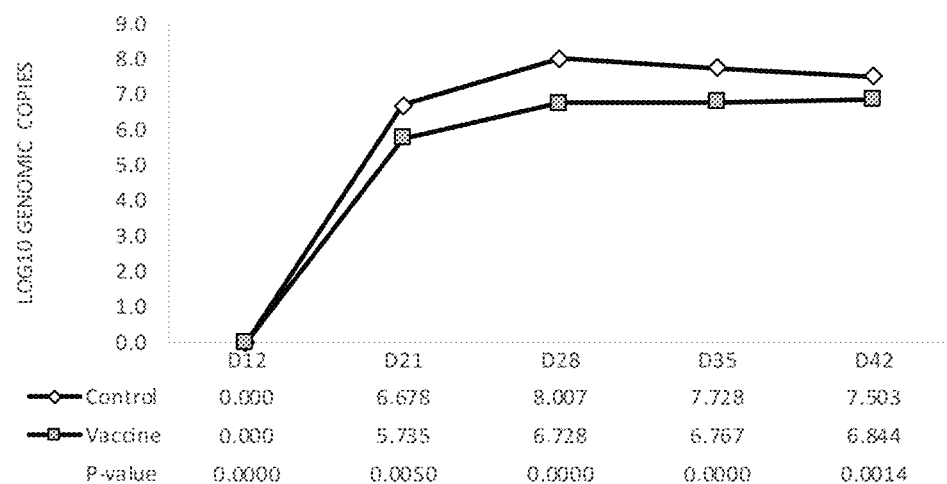
FIG. 27 shows a plot of observed viremia in the sample population of pigs post-challenge based on the log 10 genomic copies/mL. All control pigs were viremic as determined by PCR at each sampling point during the challenge phase, and the viral load at each sampling point during the challenge phase was significantly reduced by vaccination ($P \leq 0.0050$).

Viremia: Viremia was defined as PCV3 positive results by PCR (cycle threshold (Ct) value <37, genomic equivalence 4.697 logs for this study). Post-challenge viremia in vaccinates and control animals was evaluated at by qPCR. All control pigs were viremic at each sampling point during the challenge phase (Table 126). Three vaccinated pigs had positive results on D7 with Ct-values of 35.6 to 36.7 (with ≥37 being the cut-off for negative), which most likely indicated a false positive result considering all vaccinated pigs were negative at D12, pre-challenge. Following challenge, two vaccinated pigs did not become viremic. While up to 91% of the vaccinated pigs did become viremic, the load of virus (genomic copies) in the blood was significantly reduced by approximately a log in the vaccinates at each post-challenge time point ($P \leq 0.0050$) compared to the controls (FIG. 27).

TABLE 126

Frequency and percent of PCV3 viremic pigs by treatment and day

| | Study Day (vaccination on D 0, PCV3 challenge on D 14) | | | | | | |
| --- | --- | --- | --- | --- | --- | --- | --- |
| Group | D-2 | D 7 | D 12 | D 21 | D 28 | D 35 | D 42 |
| Control | 0/25 (0%) | 0/25 (0%) | 0/25 (0%) | 25/25 (100%) | 25/25 (100%) | 25/25 (100%) | 23/23 (100%) |
| Vaccine | 0/25 (0%) | 3/13 (13%) | 0/24 (0%) | 8/23 (35%) | 20/22 (91%) | 18/20 (90%) | 18/20 (90%) |

General health observations: All pigs were observed daily for general health from D-2 until D14 with an additional observation between 2 and 4 hours post-vaccination. No clinical signs were seen after vaccination until D6 when pig #5 (vaccinated group) was observed with loss of appetite and depression prior to being removed from the study for humane reasons. On D8, pigs #12 (vaccinated group), #15 (placebo group), #36 (vaccinated group), and #38 (placebo group) were observed with hernias. On D9, pig #4 (vaccinated group) was found stuck in between the feeder and wall prior to being transported to VRI; at VRI the pig was found to be lame with a swollen right rear leg which progressed to bilateral rear leg lameness on D11 before being removed from the study prior to challenge on D14.

Post-challenge mortality: Pigs that died or were euthanized post-challenge prior to off-test on D42, were necropsied. Two control pigs (placebo group) and three vaccinated pigs (vaccinated group) died or were euthanized during the challenge phase. Pig #7 (vaccinated group) was found dead on D26. Necropsy observations were congested meningeal vessels and enlarged ILN. Pig #2 (vaccinated group) was found dead on D30. Necropsy observations included chronic-active fibrosing and fibrinous pericarditis and cranial ventral pneumonia. Pig #19 (vaccinated group) was found dead on D31. The pig was observed as small with no gross necropsy lesions suggesting failure to thrive. Pig #49 (placebo group) was found dead on D35 with no previous clinical signs and with gross lesions of pulmonary congestion of the kidney with scant amounts of white exudate. Pig #15 (placebo group) was euthanized for humane reasons on D40. The pig was found comatose and paddling. Necropsy revealed moderate hydrocephalus and diffuse congestion of meningeal vessels. Previously the pig was ataxic for 7 days and depressed for the four preceding days. Additionally, the pig had severe respiratory signs (thumping) on D35 and reduced body condition for the 10 days prior to euthanasia.

Beginning 2 to 4 hours post-challenge and then daily during the challenge phase, all pigs were observed once daily for PCV3-associated clinical signs as described in Table 127.

TABLE 127

| Score | Neurological Signs | Body Condition | Diarrhea | Respiratory Signs | Dermatitis |
|---|---|---|---|---|---|
| 0 None | Normal | Normal | Normal | Normal | Normal |
| 1 Mild | Depressed = depressed to lethargic, requires physical stimulation to provoke locomotion | depressed appetite but still eating, slightly thin compared to pen mates | slightly loose stool observed from pig | mild increase in respiratory rate | Red-purple blotches on the skin most obvious on the hind legs |
| 2 Moderate | Ataxic = unable to coordinate muscle activity, spastic movements involving head, limbs, and/or trunk | not eating, ribs and backbone obviously pronounced | runny, loose stool observed; obvious staining of the perianal region | notable increase in respiratory rate | Slightly raised red-purple blotches on the skin, on the hind legs, perineum, or abdomen |
| 3 Severe | Tremors = involuntary repetitive muscle movements | emaciated | very watery stool observed | thumping | Red-purple blotches covering most of the body |
| 4 Severe | Recumbent = laying down, unable to raise when provoked with physical stimulus | | | | |
| 5 Severe | Seizures = bilateral tonic or clonic contraction of muscles resulting in partial or complete unconsciousness | | | | |

Clinical signs occurred between D21 and D40 with the majority being mild depression (neurologic) and mild increase in respiratory rate (Table 128). Diarrhea and dermatitis were not observed during the challenge phase.

TABLE 128

| | Control | | | | | | | | | Vaccine | | | | | |
|---|---|---|---|---|---|---|---|---|---|---|---|---|---|---|---|
| | | Neurological | | | | Respiratory | | BC | Any | | Neurological | | | Respi- | Any |
| | | | ata | | | | | | | | | ata | rec | ratory | |
| Day | n | dep | xic | recum | mild | mod | thump | mild | Sign | n | dep | xic | um | mild | Sign |
| D 21 | 25 | • | • | • | • | • | • | • | • | 23 | 4% | • | • | 4% | 9% |
| D 22 | 25 | • | • | • | • | • | • | • | • | 23 | 4% | • | • | 4% | 9% |
| D 23 | 25 | • | • | • | • | • | • | • | • | 23 | 4% | • | • | 4% | 9% |
| D 24 | 25 | • | • | • | 4% | • | • | 4% | 8% | 23 | 4% | • | • | 9% | 9% |
| D 25 | 25 | • | • | • | 4% | • | • | 4% | 8% | 23 | 9% | • | • | 13% | 17% |
| D 26 | 25 | • | • | • | 4% | • | • | 4% | 8% | 22 | 5% | • | • | 9% | 9% |
| D 27 | 25 | • | • | • | 20% | • | • | 4% | 24% | 22 | 5% | • | • | 23% | 23% |
| D 28 | 25 | 4% | • | • | 16% | • | • | • | 20% | 22 | 5% | • | • | 23% | 23% |
| D 29 | 25 | 16% | 4% | • | 16% | • | • | • | 28% | 22 | 5% | • | 5% | 23% | 27% |
| D 30 | 25 | 8% | 4% | • | 12% | • | • | 4% | 24% | 22 | 9% | • | 5% | 14% | 27% |
| D 31 | 25 | 12% | • | • | 8% | • | • | 4% | 20% | 21 | 5% | • | 5% | 19% | 29% |
| D 32 | 25 | 4% | • | • | • | • | • | 4% | 4% | 20 | 5% | • | • | 10% | 15% |
| D 33 | 25 | • | 4% | • | • | • | • | 4% | 4% | 20 | • | 5% | • | 10% | 15% |
| D 34 | 25 | • | 4% | • | • | • | • | 4% | 4% | 20 | • | 5% | • | • | 5% |
| D 35 | 24 | • | • | • | 4% | 8% | 4% | • | 17% | 20 | • | • | • | • | • |
| D 36 | 24 | • | 4% | • | 17% | 8% | • | 8% | 25% | 20 | 5% | • | • | 5% | 10% |
| D 37 | 24 | • | 4% | • | 17% | 4% | • | 4% | 21% | 20 | 5% | • | • | 5% | 10% |
| D 38 | 24 | • | 4% | • | 21% | • | • | 4% | 25% | 20 | • | • | • | 5% | 5% |
| D 39 | 24 | • | 4% | • | 8% | • | • | 4% | 13% | 20 | • | • | • | 5% | 5% |
| D 40 | 24 | • | • | 4% | • | • | • | 4% | 4% | 20 | • | • | • | 5% | 5% |
| D 41 | 23 | • | • | • | • | • | • | • | • | 20 | • | • | • | • | • |
| D 42 | 23 | • | • | • | • | • | • | • | • | 20 | • | • | • | • | • |

TABLE 128-continued

| | | Control | | | | | | | | Vaccine | | | | | |
|---|---|---|---|---|---|---|---|---|---|---|---|---|---|---|---|
| | | Neurological | | | Respiratory | | BC | Any | | Neurological | | | Respiratory | | Any |
| Day | n | dep | ataxic | recum | mild | mod | thump | mild | Sign | n | dep | ataxic | recum | mild | Sign |
| Pigs in Each Category | 5 | 2 | 1 | 14 | 4 | 1 | 3 | 14/25 (56%) | • | 4 | 1 | 2 | 11 | 11/23 (48%) |

Diarrhea and dermatitis were not seen during the study.
Only pigs with an observation are shown:
BC = Body Condition,
dep = depressed,
recum = recumbent,
mod = moderate,
thump = thumping Body weights: All pigs were weighed prior to vaccination, prior to challenge, one week following challenge, and prior to necropsy. Least squares means body weight for the vaccine group was numerically (not significantly) heavier at each time point (Table 129).

TABLE 129

| Group | D-2 | D 12 | D 21 | D 42 |
|---|---|---|---|---|
| Control | 4.04 kg | 7.13 kg | 13.20 kg | 39.11 kg |
| Vaccine | 4.06 kg | 7.40 kg | 13.78 kg | 40.70 kg |

Figure 28:
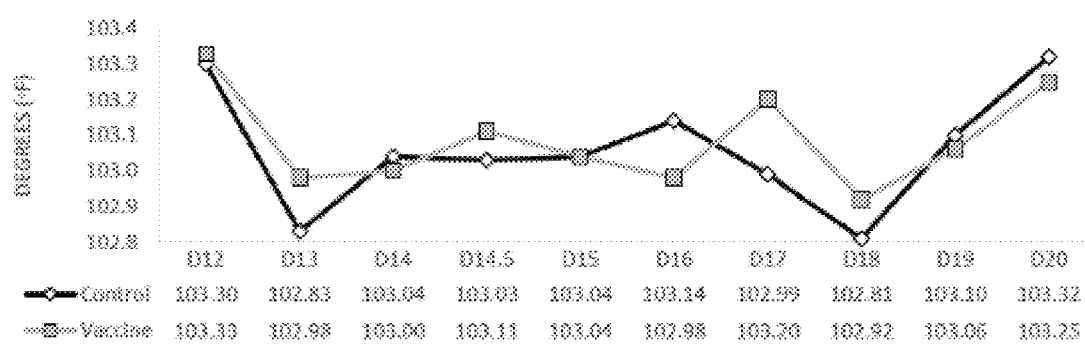
FIG. 28 shows a plot of the measured mean rectal temperatures (° F.) pre-challenge (D12, D13, D14) and post-challenge (D14.5-D20).
Figure 29:
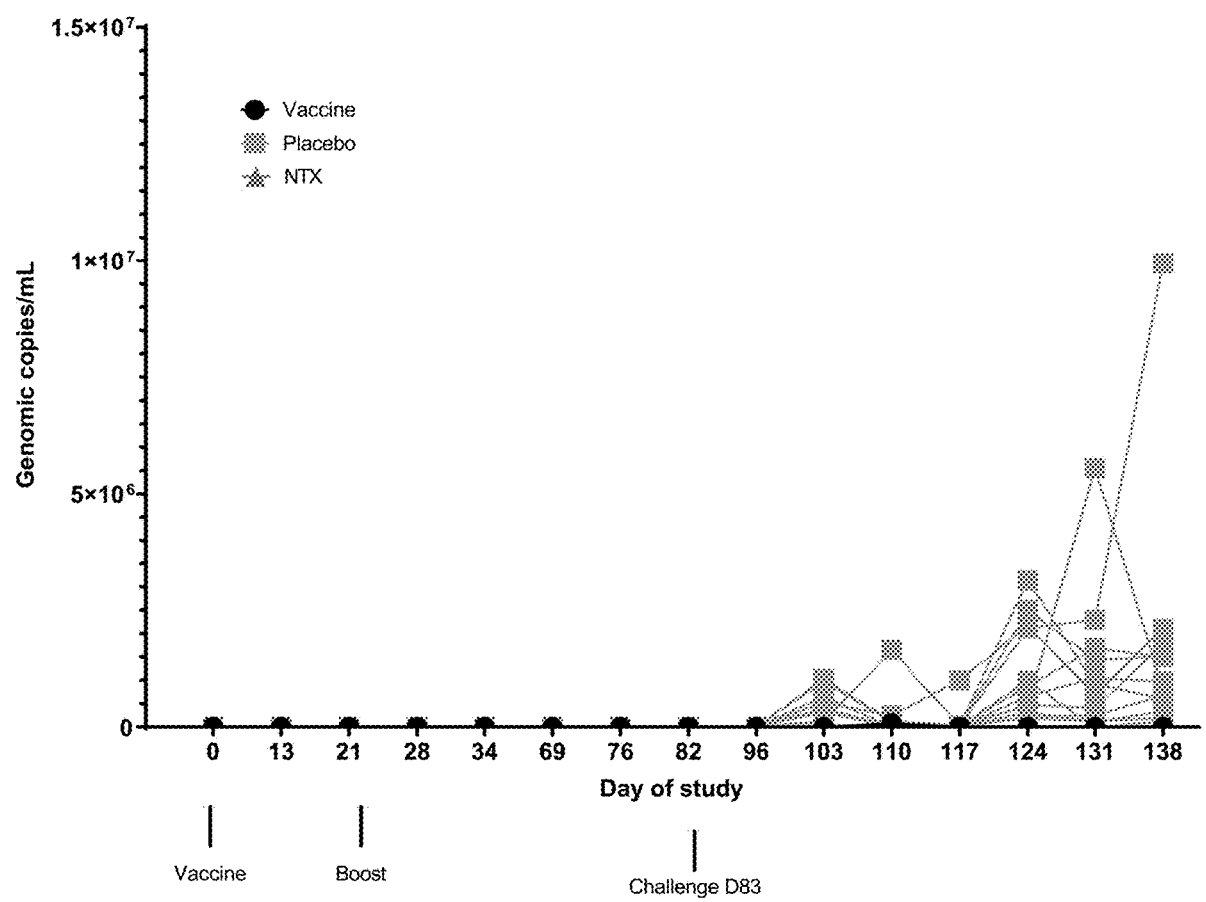
FIG. 29 shows a plot of the observed viremia in gilts challenged at D83 (40 days into gestation). Numbers indicate genomic copies/mL. The Y-axis is shown on a linear scale to accurately represent values at zero. Arrows indicate administration of primary vaccine, booster and challenge.

Body temperatures: Body temperatures were measured by self-calibrating rectal thermometer at and by intradermal microchips. Temperatures were measured three times prior to challenge to establish a baseline, then 2 to 4 hours post-challenge, and once daily until D20. Mean temperatures for treatment groups were within 1° F. on each of the days of collection (FIG. 28).

Gross lesion evaluation: Post-challenge, all pigs were necropsied at time of death or at scheduled off-test (D42). The Study Investigator performed a post-mortem assessment of all major organ systems. Specific pathological descriptions were included for the lymph nodes (tracheobronchial, external inguinal, mesenteric), kidney, heart, and lungs (Table 130).

Very few lesions were observed upon necropsy. No lesions were seen in the heart, kidney, or skin (dermatitis). Multifocal congestion of the lung was seen in three vaccinated pigs, one of which was a mortality. Comments confirmed the lesions as minimal (1%). The balance of lesions were enlarged lymph nodes, 10/25 control pigs and 14/23 vaccinated pigs.

Tissue collection & histologic scoring: At necropsy, the Study Investigator collected brain (cerebellum), heart (affected area, otherwise cross-section of the right and left ventricles), kidney (cross-section), lung (affected area, otherwise accessory lobe), spleen (cross-section), large intestine, small intestine, tonsil, tracheobronchial lymph node (TBLN), mesenteric lymph node (MLN), and inguinal lymph node (ILN). All tissues from a pig were saved in containers filled with a sufficient amount of 10% buffered formalin solution. After 24 hours in 10% buffered formalin solution, tissues were transferred to 70° ethanol and submitted for histologic slide preparation at ISU VDL. Tissue samples were processed for routine hematoxylin and eosin (H&E) staining. Each H&E slide was scored as lesions present or not. If abnormalities were noted, a brief description of the morphological diagnosis was provided along with a severity score according to Table 131.

TABLE 130

| Score | Lymph nodes | Lungs | Dermatitis | Kidney | Heart |
|---|---|---|---|---|---|
| 0 None | normal | normal | normal | normal | normal |
| 1 Mild | Enlarged, but less than 2 times greater than normal | Interstitial pneumonia | Red-purple blotches on the skin most obvious on the hind legs | Enlarged | Enlarged |
| 2 Moderate | Enlarged 2-5x normal | Multifocal areas of consolidation | Slightly raised red-purple blotches on the skin, on the hind legs and perineum or the abdomen | Multifocal white or red pinpoint lesions with or without enlargement | Multifocal pale (necrotic) or red (hemorrhagic) areas present |
| 3 Severe | Enlarged, greater than 5 x normal | Diffuse consolidation with interstitial pneumonia | Red-purple blotches covering most of the body | | |

TABLE 131

| Tissue | Severity Score | | |
|---|---|---|---|
| | None (0) | Mild (1) | Moderate (2) |
| Lymph Nodes | Normal - No significant histological lesions | Lymphadenitis, granulomatous, diffuse, chronic with <5 multi-nucleated giant cell and intralesional lipid vacuoles | Meningoencephaliti s, lymphoplasmacytic, multifocal, subacute, mild perivasculitis with >6 lymphoplasmacytic foci and/or perivascular aggregates |
| Cerebrum & Cerebellum | Normal - No significant histological lesions | Meningoencephalitis, lymphoplasmacytic, multifocal, subacute, minimal perivasculitis with <5 lymphoplasmacytic foci and/or perivascular aggregates | Lymphadenitis, granulomatous, diffuse, chronic, severe with >6 multinucleated giant cells |
| Tonsil | Normal - No significant histological lesions | Tonsillitis, granulomatous, diffuse, chronic, moderate with <5 multinucleated giant cells | Lymphadenitis, granulomatous, diffuse, chronic, severe with >6 multinucleated giant cells |
| Heart | Normal - No significant histological lesions | Myocarditis, lymphoplasmacytic, multifocal, subacute, minimal perivasculitis with <5 lymphoplasmacytic foci and/or perivascular aggregates | Myocarditis, lymphoplasmacytic, multifocal, subacute, mild perivasculitis with >6 lymphoplasmacytic foci and/or perivascular aggregates |
| Dermis | Normal - No significant histological lesions | Interstitial pneumonia, lymphoplasmacytic, multifocal, subacute, minimal perivasculitis with <5 lymphoplasmacytic foci and/or perivascular aggregates | Interstitial pneumonia, lympho-plasmacytic, multifocal, subacute, mild perivasculitis with >6 lympho-plasmacytic foci and/or perivascular aggregates |
| Liver | Normal - No significant histological lesions | Hepatitis, lymphoplasmacytic, multifocal, subacute, minimal perivasculitis with <5 lympho-plasmacytic foci and/or perivascular aggregates | Hepatitis, lymphoplasmacytic, multifocal, subacute, mild perivasculitis with >6 lymphoplasmacytic foci and/or perivascular aggregates |
| Spleen | Normal - No significant histological lesions | Splenitis, lymphoplasmacytic, multifocal, subacute, minimal perivasculitis with < 5 lymphoplasmacytic foci and/or perivascular aggregates | Splenitis, lymphoplasmacytic, multifocal, subacute, mild perivasculitis with >6 lymphoplasmacytic foci and/or perivascular aggregates |
| Kidney | Normal - No significant histological lesions | Interstitial nephritis, lymphoplasmacytic, multifocal, subacute, minimal perivasculitis with <5 lymphoplasmacytic foci and/or perivascular aggregates | Interstitial nephritis, lymphoplasmacytic, multifocal, subacute, mild perivasculitis with >6 lymphoplasmacytic foci and/or perivascular aggregates |
| Small Intestine | Normal - No significant histological lesions | Intestinal serositis, lymphoplasmacytic, multifocal, subacute, minimal perivasculitis with <5 lymphoplasmacytic foci and/or perivascular aggregates | Intestinal serositis, lymphoplasmacytic, multifocal, subacute, mild perivasculitis with >6 lymphoplasmacytic foci and/or perivascular aggregates |
| Large Intestine | Normal - No significant histological lesions | Intestinal serositis, lymphoplasmacytic, multifocal, subacute, minimal perivasculitis with <5 lymphoplasmacytic foci and/or perivascular aggregates | Intestinal serositis, lymphoplasmacytic, multifocal, subacute, mild perivasculitis with >6 lymphoplasmacytic foci and/or perivascular aggregates |

No histologic lesions were observed in the tonsil, TBLN, MLN, or spleen of any pig. Most all pigs had at least mild histologic lesions of the ILN (Table 132).

Overall, histologic lesions of the brain (Table 133), kidney (Table 134), heart (Table 135), and lungs (Table 136) were generally mild with only 2/25 control pigs having histologic lesions of the intestines, one small intestine (Table 137) and one large intestine (Table 138). Two pigs with histologic lesions of the brain were found dead during the study with gross lesions of meningitis (#15 [placebo group] purulent and lymphocytic meningoencephalitis and #7 [vaccinated group] bacterial chronic active meningitis). Four pigs in the placebo group and two pigs in the vaccinated group had lesions in two tissues.

Overall, 9200 of controls had histologic lesions, and 87% of vaccinated pigs had histologic lesions (Table 139).

TABLE 132

Frequency of inguinal lymph node histologic lesion severity

| Group | normal | mild | moderate | severe |
|---|---|---|---|---|
| Control | 4/25 (16%) | 12/25 (48%) | 8/25 (32%) | 1/25 (4%) |
| Vaccine | 5/23 (22%) | 13/23 (57%) | 4/23 (17%) | 1/23 (4%) |

TABLE 133

Frequency of brain histologic lesion severity

| Group | normal | mild |
|---|---|---|
| Control | 24/25 (96%) | 1/25 (4%) |
| Vaccine | 22/23 (96%) | 1/23 (4%) |

TABLE 134

Frequency of kidney histologic lesion severity

| Group | normal | mild | moderate |
|---|---|---|---|
| Control | 22/25 (88%) | 3/25 (12%) | • |
| Vaccine | 19/23 (83%) | 3/23 (13%) | 1/23 (4%) |

TABLE 135

Frequency of heart histologic lesion severity

| Group | normal | mild |
|---|---|---|
| Control | 20/25 (80%) | 5/25 (20%) |
| Vaccine | 20/23 (87%) | 3/23 (13%) |

TABLE 136

Frequency of lung histologic lesion severity

| Group | normal | mild |
|---|---|---|
| Control | 24/25 (96%) | 1/25 (4%) |
| Vaccine | 21/23 (91%) | 2/23 (9%) |

TABLE 137

Frequency of large intestine histologic lesion severity

| Group | normal | mild |
|---|---|---|
| Control | 24/25 (96%) | 1/25 (4%) |
| Vaccine | 23/23 (100%) | 0/23 (0%) |

TABLE 138

Frequency of small intestine histologic lesion severity

| Group | normal | mild |
|---|---|---|
| Control | 24/25 (96%) | 1/25 (4%) |
| Vaccine | 21/21 (100%) | 0/21 (0%) |

TABLE 139

Frequency of histologic lesions by group

| Group | If Ever |
|---|---|
| Control | 23/25 (92%) |
| Vaccine | 20/23 (87%) |

Virus replication in tissues of vaccinates and placebo animals post challenge was evaluated using RNAScope. RNAscope allows specific tagging and visualization of viral mRNA. RNAscope detects replicating virus in a tissue as opposed to immunohistochemistry or PCR, which identifies genetic material of a virus whether regardless of whether the virus is live or dead. Tissues were fixed and permeabilized to allow for target probe access sites of viral replication within the cells. A pair of PCV3 RNA specific oligonucleotide probes were then hybridized so as to sit within close proximity of each other on the PCV3 target RNA. The detection of mRNA means the PCV3 virus is replicating and not simply detecting PCV3 genetic material. This was followed by the hybridization of a signal amplification molecule (SAM) that recognizes the pair of specific oligonucleotide probes. In non-specific reactions, the two probes would not sit next to each other preventing their hybridization with the SAM. The SAMs themselves are conjugated to an enzyme. As in in situ hybridization assays, the signals are detected using a chromogenic substrate followed by bright-field microscopic examination of slides. Slides for PCV3 RNAscope assay were stained, read, and scored according to Table 140.

TABLE 140

RNAScope scoring scale

| Score | Description |
|---|---|
| 0 = normal | zero cells with PCV3 staining |
| 1 = mild | <10% of cells with PCV3 staining |
| 2 = moderate | 10-50% of cells with PCV3 staining |
| 3 = severe | >50% of cells with PCV3 staining |

No evidence of PCV3 replication was observed in any sections of cerebrum/cerebellum of any pig. Nearly all of the control pigs had at least mild PCV3 RNAScope staining in the kidney (Table 141), heart (Table 142), large intestine (Table 143), and small intestine (Table 144) while only one vaccinated pig had mild staining of each of the four tissues, and three other pigs had mild staining of the kidney.

All control pigs had mild to moderate staining of the spleen (Table 145) and mild to severe staining of the ILN (Table 146) and lung (Table 147). In contrast, six vaccinated pigs had no RNAscope staining in any tissue (including that of three pigs that died in the challenge phase). Looking at maximum RNAscope staining by pig, 48% of controls had a score of severe and the other 52% were moderate, compared to only 9% of vaccinated pigs having a severe score and 17% with a moderate score. All control pigs had at least one tissue with replicating PCV3 virus while 71% of vaccinated pigs had at least one tissue with replicating PCV3 virus (Table 148). A significant result of the study is the difference between control and vaccine when evaluating tissues using RNAScope (Table 149). RNAscope detects replicating virus in a tissue as opposed to immunohistochemistry or PCR, which identifies genetic material of a virus whether it is live or dead. Strikingly, all control pigs had mild to moderate staining of the spleen and mild to severe staining of the ILN and lung. In contrast, six vaccinated pigs had no RNAscope staining in any tissue. All tissues from vaccinated animals demonstrated significant prevention of infection.

TABLE 141

Frequency of kidney RNAScope Scores

| Group | normal | mild |
|---|---|---|
| Control | 2/25 (8%) | 23/25 (92%) |
| Vaccine | 19/23 (83%) | 4/23 (17%) |

TABLE 142

Frequency of heart RNAScope Scores

| Group | normal | mild | moderate |
|---|---|---|---|
| Control | 4/25 (16%) | 20/25 (80%) | 1/25 (4%) |
| Vaccine | 22/23 (96%) | 1/23 (4%) | • |

TABLE 143

Frequency of large intestinal RNAScope Scores

| Group | normal | mild |
|---|---|---|
| Control | 4/25 (16%) | 21/25 (84%) |
| Vaccine | 22/23 (96%) | 1/23 (4%) |

TABLE 144

Frequency of small intestinal RNAScope Scores

| Group | normal | mild |
|---|---|---|
| Central | 9/25 (36%) | 16/25 (64%) |
| Vaccine | 20/21 (95%) | 1/21 (5%) |

TABLE 145

Frequency of spleen RNAScope Scores

| Group | normal | mild | moderate | severe |
|---|---|---|---|---|
| Control | • | 13/25 (52%) | 12/25 (48%) | • |
| Vaccine | 9/23 (39%) | 13/23 (57%) | • | 1/23 (4%) |

TABLE 146

Frequency of inguinal lymph node RNAScope Scores

| Group | normal | mild | moderate | severe |
|---|---|---|---|---|
| Control | • | 2/24 (8%) | 16/24 (67%) | 6/24 (25%) |
| Vaccine | 9/23 (39%) | 8/23 (35%) | 6/23 (26%) | • |

TABLE 147

Frequency of lung RNAScope Scores

| Group | normal | mild | moderate | severe |
|---|---|---|---|---|
| Contral | • | 4/25 (16%) | 11/25 (44%) | 10/25 (40%) |
| Vaccine | 13/23 (57%) | 5/23 (22%) | 3/23 (13%) | 2/23 (9%) |

TABLE 148

Frequency of RNAScope Scores

| Group | If Ever |
|---|---|
| Control | 25/25 (100%) |
| Vaccine | 17/23 (71%) |

TABLE 149

Statistical comparisons of RNAScope tissue results

| Tissue | Mitigated Fraction (lower bound, upper bound) | Proportion Positive Control | Proportion Positive Vaccine | Prevented Fraction (upper & lower confidence interval) | Fisher's Exact Test P-Value |
|---|---|---|---|---|---|
| ILN | 0.771 (0.667, 0.879) | 1.000 | 0.609 | 0.397 (0.156, 0.569) | 0.0006 |
| Spleen | 0.616 (0.417, 0.803) | 1.000 | 0.609 | 0.395 (0.156, 0.566) | 0.0005 |
| Lung | 0.712 (0.556, 0.857) | 1.000 | 0.435 | 0.571 (0.310, 0.734) | 0.0000 |
| Kidney | • | 0.920 | 0.174 | 0.802 (0.524, 0.918) | 0.0000 |
| Heart | • | 0.840 | 0.043 | 0.941 (0.632, 0.990) | 0.0000 |
| large Intestine | • | 0.840 | 0.043 | 0.940 (0.638, 0.990) | 0.0000 |
| Small Intestine | • | 0.640 | 0.048 | 0.889 (0.449, 0.978) | 0.0000 |
| All Tissues | 0.781 (0.623, 0.943) | 1.000 | 0.739 | 0.269 (0.059, 0.432) | 0.0082 |

The study was valid based on the control pigs remaining seronegative for PCV3 through the vaccination period. Clinical disease was demonstrated with clinical signs of depression (neurologic) and increase in respiratory rate between 7 and 26 days post-challenge, mortality, weight gain, viremia, gross lesions, microscopic lesions, and RNA-Scope results.

Statistical analysis of data was conducted using SAS version 9.4 (SAS, Cary, North Carolina/USA, SAS Institute, Inc.). Data listings and summary statistics by treatment group were generated for all variables, as appropriate.

For necropsy, histopathologic, clinical observations, pyrexia and PCV3 RNA Scope assessments, methods for data analysis varied depending on the distribution of the data for the variable under assessment. In general, data were analyzed using methods described below for the Prevented Fraction (PF) and Fisher's Exact Test, and/or Mitigated Fraction (MF). For some variables, nearly all/all responses were in one category and thus no analysis was conducted. Mortality was analyzed similarly, with the exception that no MF analysis was conducted. For clinical observations, a case definition of two or more days with abnormal clinical observations was used to identify affected animals. Additionally, number and duration of abnormal clinical observations were evaluated utilizing the MF method. For pyrexis, animals with temperature values of 1 degree or greater above the baseline were identified as pyrexic for an individual day.

Data analyzed using the PF and Fisher's Exact methods, if not already dichotomous were dichotomized to a binary outcome (e.g. normal/abnormal) for each animal. Binary data was summarized by group via frequency distributions. In addition, for binary data, the relative risk (RR) was estimated and a 95% confidence interval (CI) calculated using the Cochran-Mantel-Haenszel method in SAS procedure PROC FREQ. The RR and associated CI were then translated to the PF scale (1-RR) for presentation. For the PROC FREQ analysis, stratification based on litter was utilized. Statistical significance was concluded if the 95% CI for the RR does not include 0. The MF method utilized a stratified bootstrap approach with the Highest Density Interval utilized to construct a 95% confidence interval for the MF based on the bootstrap distribution. Stratification was based on litter. Statistical significance was concluded if 0 was not in the confidence interval.

Viremia data were analyzed using a Generalized Friedman test (blocking on litter) to compare the group viremia distributions (quantitative) at each time point post-challenge. P-values smaller than 0.05 are considered statistically significant.

Pre-vaccination (Day −2) weight was analyzed using a linear mixed model with group (fixed effect), litter (random effect) and residual. Least-squares means were estimated and group comparisons were evaluated via P-values. Ninety-five percent Confidence Intervals were constructed as appropriate. Challenge Phase weights (Days 12, 21, 42) were analyzed using a linear mixed model with group, day and group by day interactions (fixed effects), challenge room and pen within challenge room (random effects) and an unstructured covariance representing the repeated measures on the animal level. Least-squares means were estimated and group comparisons were evaluated via P-values by study day. Average Daily Weight Gain was estimated and evaluated using a linear contrast of the fixed effect terms. Ninety-five percent Confidence Intervals were constructed as appropriate. P-values smaller than 0.05 are considered statistically significant.

The experimental inactivated baculovirus-expressed PCV3 ORF2 vaccine significantly prevented replicating virus being found in ILN, spleen, and lung, and significantly mitigated the severity of the amount of replicating PCV3 virus found in all tissues. The vaccine also numerically reduced mortality, clinical signs, gross lesions, and histologic lesions, in addition to a numerical increase in body weights following the challenge phase. These data demonstrates a clinically-relevant disease, correlating the clinical picture with evidence of replicating PCV3 virus in the tissues by RNAscope evaluation.

Two control pigs died during the challenge phase; no tentative diagnosis was suggested at necropsy of either pig. ILN, spleen and lung tissues from both pigs had moderate or severe evidence of the presence of PCV3, and kidney, heart, large intestine, and small intestine had PCV3 RNAscope scores of 1. In contrast, the three vaccinated pigs that died post-challenge had tentative diagnoses of bacterial septicemia or failure to thrive, which is common with young CDCD pigs. This diagnosis is supported by RNAscope results that were negative for all tissues, so the vaccinated pigs that died post-challenge are not considered mortalities due to PCV3.

Evaluating clinical signs, 14/25 (56%) control pigs had a clinical observation post-challenge compared to 11/23 (48%) vaccinated pigs. The limited occurrence of clinical signs is consistent with expectations from a laboratory evaluation of *circovirus*. Clinical observations during this study are similar to what are historically seen with the laboratory challenge model for PCV2.

This same trend was observed with body weights; least squares mean body weights were 0.92 kg heavier for vaccinates than controls at off-test, indicating better overall health (hydration and appetite). While up to 91% of the vaccinated pigs did become viremic, the load of virus (genomic copies) in the blood was significantly reduced by approximately a log in the vaccinates at each post-challenge time point ($P<0.0050$; FIG. 28) when compared to controls. Few lesions were seen during gross evaluation at off-test and during histologic examination. The majority of the macroscopic lesions were enlarged lymph nodes (10/25 control pigs and 14/23 vaccinated pigs), and the majority of the microscopic lesions were mild lesions of the ILN.

RNAScope detects replicating virus in a tissue as opposed to immunohistochemistry or PCR which identifies genetic material of a virus whether it is replicating or dead. Strikingly, all control pigs had mild to moderate staining of the spleen and mild to severe staining of the ILN and lung. In contrast, six vaccinated pigs had no RNAScope staining in any tissue. All tissues from vaccinated animals demonstrated significant prevention of infection (by both prevented fraction and hypothesis testing analyses), and the ILN, spleen, and lung also demonstrated a reduction in severity by mitigated fraction.

Serology results were negative for all samples on all days. This may be due to the short window between vaccination and challenge.

The experimental inactivated baculovirus-expressed PCV3 ORF2 vaccine significantly prevented replicating virus being found in ILN, spleen, and lung, and significantly mitigated the severity of the amount of replicating PCV3 virus found in all tissues. The vaccine also numerically reduced mortality, clinical signs, gross lesions, and histologic lesions, in addition to a numerical increase in body weights following the challenge phase. This data demonstrates a clinically-relevant disease correlating the clinical picture with RNAscope evaluation and scoring. Taken altogether, the experimental baculovirus-expressed killed PCV3 ORF2 vaccine was shown to be efficacious against PCV3.

Example 10

Reproductive Study of PCV3 in Farrowing Sow

Vaccination phase: Forty-six pre-breeding gilt (≥5 months of age) were used in this study. All dams were screened to be free of viremia prior to vaccination by qPCR for the following agents: PCV3, PCV2, atypical porcine pestivirus (APPV), transmissible gastroenteritis virus (TGEV), porcine reproductive and respiratory syndrome virus (PRRSV) and porcine parvovirus (PPV). Animals were also shown to be seronegative for Influenza A and *M. hyopneumoniae*.

Gilts were divided into three treatment groups for this study: r=non-exposure and non-challenge to PCV3 (NTX), receipt of a placebo with challenge to PCV3, and vaccination with the PCV3 ORF2 vaccine with challenge to PCV3. Gilts were vaccinated on D0 and D21 based on their treatment groups (2 mL intramuscularly in the right neck). Gilts in the NTX treatment group were administered the placebo vaccine and housed separately from the gilts of the other treatment groups. Estrus synchronization was done by administration of MATRI™ (altrenogest) in their feed from day 17 to day 30. On day 30, P.G. 600© (serum gonadotropin [PMSG] and chorionic gonadotropin) was administered to all gilts. Animal were evaluated for estrus and bred between day 35-42. Thirty-six sows were confirmed pregnant on D77 (D35 of gestation) and used in this study (Table 150).

TABLE 150

Treatment groups and study design

| Treatment group | Treatment | n | Challenge | Farrowing | Necropsy |
|---|---|---|---|---|---|
| NTX | Placebo | 2 | None | D147-D159 litter data & necropsy/ tissue/blood collection | D168-D180 (21 days Post farrowing) litter data & necropsy/ tissue/blood collection |
| Placebo | | 12 | D83 (~40 days of gestation) PCV3 tissue homogenate 2 mL each IM and IN | | |
| Vaccine | Vaccine | 19 | | | |

Challenge phase: All animals in the placebo and vaccine treatment groups were challenged with PCV3 positive tissue homogenate 40 days into gestation. The PCV3 tissue homogenate was administered 2 mL each intramuscularly and intranasally to each animal. Keyhole limpet hemocyanin (KLH) emulsified in incomplete Freund's adjuvant (JCFA) containing 1 mg KLH/mL was administered two days before and two days after challenge. The tissue homogenate used for challenge was screened for extraneous agents by qPCR and deep sequencing.

Viremia: Serum was collected from sows throughout the study and was evaluated for viremia by qPCR (see Table 151 and FIG. 28). The bolded numbers in the top row of Table 151 indicate the respective day of the study. The unbolded numbers in Table 151 correspond to the measured number of genomic copies of PCV3/mL.

TABLE 1

Viremia of gilts challenged at D83 (40 days into gestation)

| Sow | Group | 0 | 13 | 21 | 28 | 34 | 69 | 76 | 82 | 96 | 103 | 110 | 117 | 124 | 131 | 138 |
|---|---|---|---|---|---|---|---|---|---|---|---|---|---|---|---|---|
| 104 | Vaccine | 0 | 0 | 0 | 0 | 0 | 0 | 0 | 0 | 0 | 0 | 0 | 0 | 0 | 0 | 0 |
| 108 | | 0 | 0 | 0 | 0 | 0 | 0 | 0 | 0 | 0 | 0 | 0 | 0 | 0 | 0 | 0 |
| 114 | | 0 | 0 | 0 | 0 | 0 | 0 | 0 | 0 | 0 | 0 | 0 | 0 | 0 | 0 | 0 |
| 116 | | 0 | 0 | 0 | 0 | 0 | 0 | 0 | 0 | 0 | 0 | 0 | 0 | 0 | 0 | 0 |
| 118 | | 0 | 0 | 0 | 0 | 0 | 0 | 0 | 0 | 0 | 0 | 0 | 0 | 0 | 0 | 0 |
| 120 | | 0 | 0 | 0 | 0 | 0 | 0 | 0 | 0 | 0 | 0 | 0 | 0 | 0 | 0 | 0 |
| 127 | | 0 | 0 | 0 | 0 | 0 | 0 | 0 | 0 | 0 | 0 | 0 | 0 | 0 | 0 | 0 |
| 132 | | 0 | 0 | 0 | 0 | 0 | 0 | 0 | 0 | 0 | 0 | 0 | 0 | 0 | 0 | 0 |
| 135 | | 0 | 0 | 0 | 0 | 0 | 0 | 0 | 0 | 0 | 0 | 0 | 0 | 0 | 0 | 0 |
| 136 | | 0 | 0 | 0 | 0 | 0 | 0 | 0 | 0 | 0 | 0 | 0 | 0 | 0 | 0 | 0 |
| 139 | | 0 | 0 | 0 | 0 | 0 | 0 | 0 | 0 | 0 | 0 | 0 | 0 | 0 | 0 | 0 |
| 142 | | 0 | 0 | 0 | 0 | 0 | 0 | 0 | 0 | 0 | 0 | 0 | 0 | 0 | 0 | 0 |
| 147 | | 0 | 0 | 0 | 0 | 0 | 0 | 0 | 0 | 0 | 0 | 35006 | 0 | 0 | 0 | 0 |
| 148 | | 0 | 0 | 0 | 0 | 0 | 0 | 0 | 0 | 0 | 0 | 0 | 0 | 0 | 0 | 0 |
| 152 | | 0 | 0 | 0 | 0 | 0 | 0 | 0 | 0 | 0 | 0 | 32676 | 0 | 0 | 0 | 0 |
| 153 | | 0 | 0 | 0 | 0 | 0 | 0 | 0 | 0 | 0 | 0 | 0 | 0 | 0 | 0 | 0 |
| 154 | | 0 | 0 | 0 | 0 | 0 | 0 | 0 | 0 | 0 | 0 | 0 | 0 | 0 | 0 | 0 |
| 158 | | 0 | 0 | 0 | 0 | 0 | 0 | 0 | 0 | 0 | 0 | 78456 | 0 | 0 | 0 | 0 |
| 159 | | 0 | 0 | 0 | 0 | 0 | 0 | 0 | 0 | 0 | 0 | 0 | 0 | 0 | 0 | 0 |
| 101 | NTX | 0 | 0 | 0 | 0 | 0 | 0 | 0 | 0 | 0 | 0 | 0 | 0 | 0 | 0 | 0 |
| 150 | | 0 | 0 | 0 | 0 | 0 | 0 | 0 | 0 | 0 | 0 | 37613 | 0 | 0 | 0 | 0 |
| 4 | Placebo | 0 | 0 | 0 | 0 | 0 | 0 | 0 | 0 | 0 | 125239 | 1648655 | 5091 | 461578 | 5554067 | 793015 |
| 103 | | 0 | 0 | 0 | 0 | 0 | 0 | 0 | 0 | 3893 | 1019339 | 133891 | 7911 | 651478 | 1046103 | 969657 |
| 125 | | 0 | 0 | 0 | 0 | 0 | 0 | 0 | 0 | 5278 | 518944 | 243141 | 1004485 | 2180344 | 690203 | 2100557 |
| 131 | | 0 | 0 | 0 | 0 | 0 | 0 | 0 | 0 | 17824 | 953267 | 121375 | 28287 | 2497839 | 1440941 | 1499740 |
| 137 | | 0 | 0 | 0 | 0 | 0 | 0 | 0 | 0 | 4778 | 45726 | 21069 | 2087 | 214688 | 249939 | 673275 |
| 138 | | 0 | 0 | 0 | 0 | 0 | 0 | 0 | 0 | 0 | 2940 | 6278 | 24441 | 990226 | 0 | 118748 |
| 144 | | 0 | 0 | 0 | 0 | 0 | 0 | 0 | 0 | 6545 | 320446 | 0 | 25158 | 469376 | 412792 | 1793810 |
| 149 | | 0 | 0 | 0 | 0 | 0 | 0 | 0 | 0 | 5025 | 647548 | 0 | 20126 | 2106547 | 2294852 | 9940749 |
| 151 | | 0 | 0 | 0 | 0 | 0 | 0 | 0 | 0 | 1535 | 3077 | 0 | 19658 | 3143481 | 913922 | 604511 |
| 155 | | 0 | 0 | 0 | 0 | 0 | 0 | 0 | 0 | 1717 | 0 | 0 | 34934 | 189094 | 119791 | 190931 |
| 156 | | 0 | 0 | 0 | 0 | 0 | 0 | 0 | 0 | 0 | 11605 | 19861 | 1331 | 314544 | 105099 | 336322 |
| 157 | | 0 | 0 | 0 | 0 | 0 | 0 | 0 | 0 | 2711 | 395432 | 20268 | 29523 | 868779 | 1688576 | 1485114 |

Three pigs in the vaccine group showed viremia at D110. The absence of viremia on D103 and D1 17 may indicate that this reading was either a false positive or a vaccine effect towards suppressing virus replication. Similarly, one of the two non-challenged NTX sows showed viremia at D110. The NTX animals were housed separately and the absence of viremia on D103 and D 117 may indicate that these readings could be false positives. All of the placebo sows showed viremia after challenge and continued to have viremia until the day of farrow. Overall, the viremia data from sows indicates that the vaccine is able to abrogate virus replication in the sows.

Figure 30:
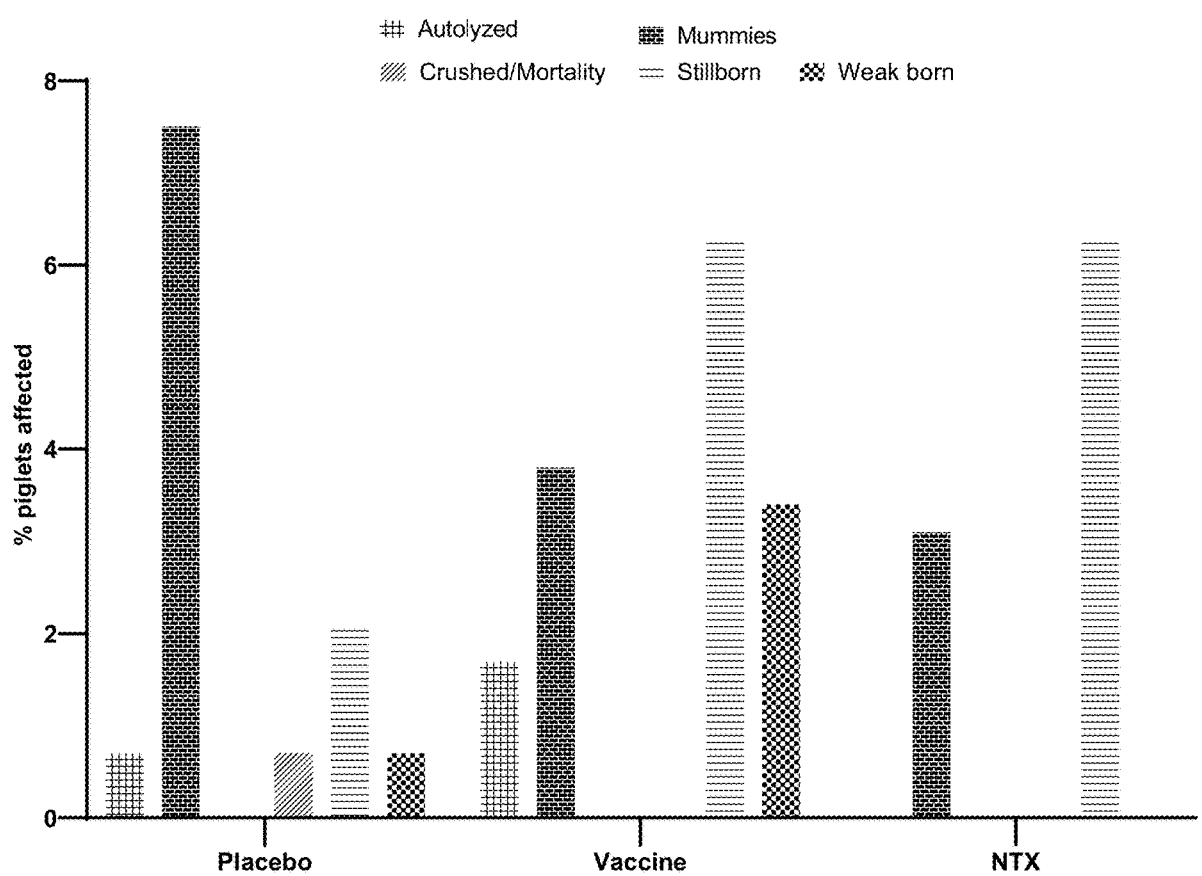
FIG. 30 shows a bar graph indicating the percent of affected piglets based on the observed number of autolyzed, crushed, mummified born piglets from farrowing sow of each treatment group.

Clinical signs: All gilts were taken to farrowing. At farrow, the piglets were scored as healthy, mummies, weak-born, stillborn and autolysed. Any mortality arising from being crushed in the first three days after farrowing were also recorded. The percentage of affected mummies is shown in FIG. 30. One sow each in vaccine and placebo groups did not farrow.

According to FIG. 30, there is a clear reduction in the number of mummies in the vaccine group in comparison to the placebo group. One of the two sows in the NTX group had a single mummy and both sows had one stillborn piglet.

PCV3 is widely believed to be a reproductive disease. In the reproductive study, sows were vaccinated, boosted, and bred to evaluate the effect of a PCV3 challenge. The experimental inactivated baculovirus-expressed PCV3 ORF2 vaccine appears to almost completely abrogate virus replication in sows. Moreover, at farrow, vaccinated sows had just under 4% reduction in the number of mummies. This reduction could have a significant economic impact for swine producers.

Example 11

Figure 31B:
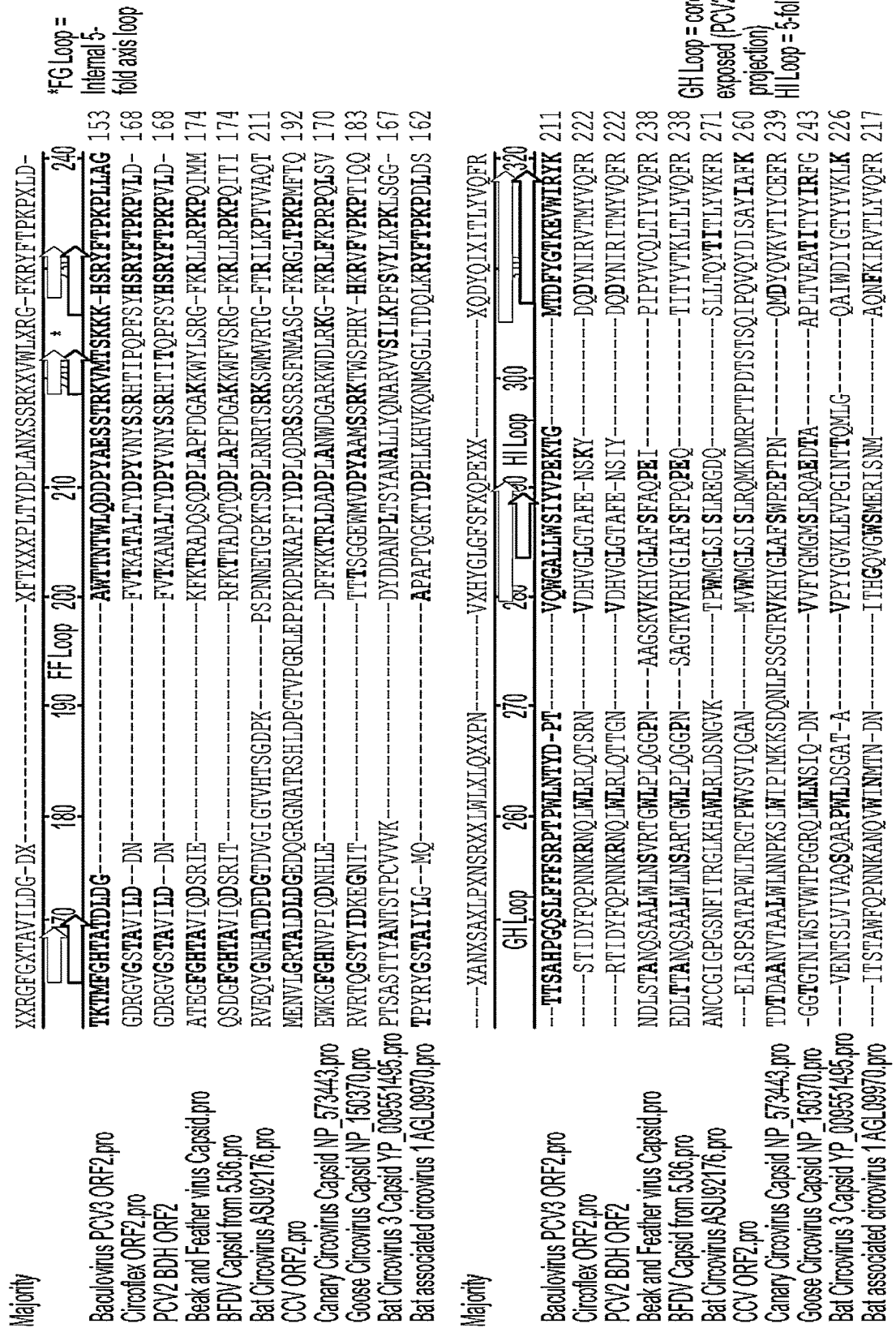
Figure 32:
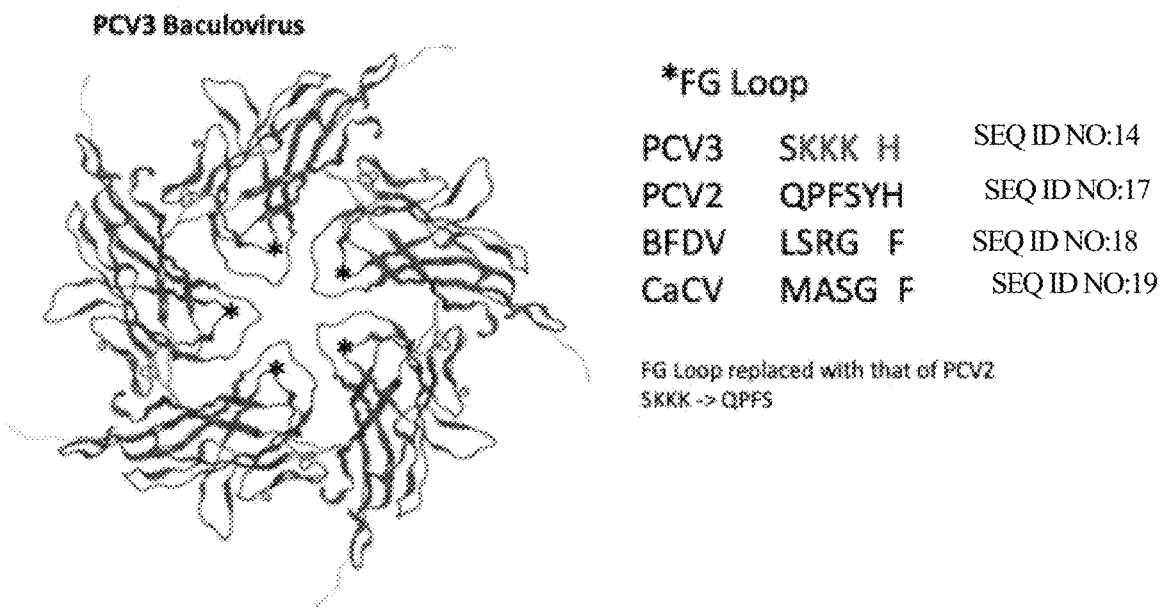
FIG. 32 shows the structure of the PCV3 ORF2 mutant in the FG loop having mutations in the lysines and histidines.

Preparation of PCV3 ORF2 Mutant in the FG Loop for Enhanced Virus-Like Particle Assembly A number of *Circovirus* capsid sequences were aligned with Porcine *circovirus* type 3 (PCV3) capsid and two sequences for which structural data was available, Porcine *circovirus* type 2 (PCV2) capsid and Beak and feather disease virus (BFDV) capsid. Evaluation of the alignments with the structural data revealed that, despite the divergence of the capsid amino acid sequences between PCV2 and BFDV, the solved structures were very similar. This suggests that the structures of *circovirus* capsids may be similar despite their sequence divergence (FIGS. 31 and 32).

Additionally, the PCV3 capsid was the only aligned *circovirus* sequence that contained large amounts of positive charge in the FG loop which sits at the 5-fold interface of the PCV3 capsid. The large amount of positive charge in this region may result in repulsive forces without the presence of nucleic acid, as would be expected of virus-like particles (VLPs). Therefore, the lysines and histidine in this loop were mutated to the amino acids from PCV2 capsid (FIG. 32). This sequence was called PCV3 ORF2 FG (SEQ ID NO: 6).

The sequence was synthesized at Genscript and is cloned for recombinant baculoviruses for evaluation of PCV3 ORF2 expresssion and assembly into VLPs.

Example 12

Figure 33:
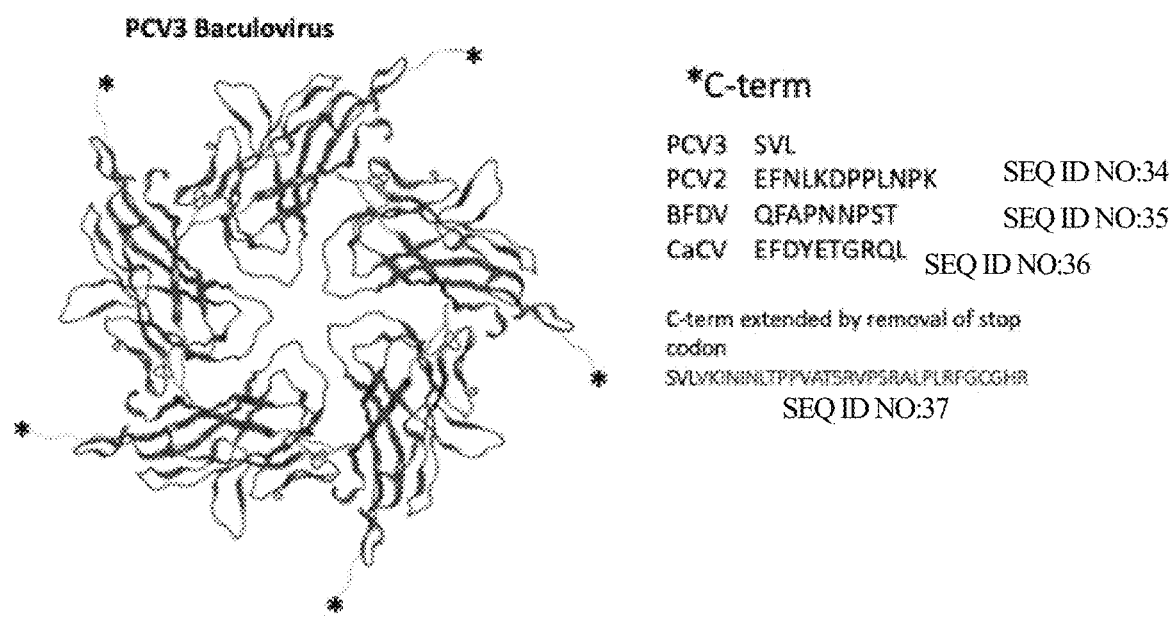
FIG. 33 shows the structure of the PCV3 ORF2 mutant wherein the native stop codon for the PCV3 capsid protein was mutated and the C-terminus was extended to the next stop codon.

Preparation of PCV3 ORF2 Mutant in the Native Stop Codon and Extension of the C-Terminus for Enhanced VLP Assembly Evaluation of the alignments with the structural data described in Example 13 further disclosed that the PCV3 capsid had the shortest C-terminus sequence of any of the *circovirus* capsid sequences aligned. The C-terminus of PCV2 and BFDV capsid proteins project out away from the capsid. The short hydrophobic nature of the PCV3 capsid C-terminus would lead to the C-terminus being buried in the capsid and could lead to VLP instability without the presence of nucleic acid. Therefore, the native stop codon for the PCV3 capsid protein was mutated and the C-terminus was extended to the next stop codon in the virus sequence (FIG. 33). This sequence was called PCV3 ORF2 PC (SEQ ID NO: 7).

The sequence was synthesized at Genscript and is cloned for recombinant baculoviruses for evaluation of PCV3 ORF2 expresssion and assembly into VLPs.

Example 13

Challenge Data from the Mutated PCV3 ORF2 Candidates in CDCD Pigs

Vaccination phase: Twenty-five Caesarian-derived colostrum-deprived (CDCD) pigs at approximately 3 weeks of age are vaccinated with either the enhanced expression baculovirus PCV3 ORF2 vaccine or a placebo matched control vaccine. Cord blood is collected from all pigs at delivery (C-section; D-22). Serum is separated and tested for PCV3 DNA and PCV2 DNA by PCR. On D-2, all pigs are bled for serum collection and then vaccinated with PCV2 Ingelvac CircoFLEX©.

Challenge phase: All animals are challenged with PCV3 positive tissue homogenate at
14 days post vaccination. Keyhole limpet hemocyanin (KLH) emulsified in incomplete Freund's adjuvant (ICFA) containing 1 mg KLH/1 mL is administered two days before and two days after challenge (Table 152). The tissue homogenate used for challenge is screened for extraneous agents by qPCR and deep sequencing. Animals are euthanized at day 42. At necropsy, a number of tissues including brain, heart, kidney, lung, spleen, large intestine, tonsil, tracheobronchial lymph node (TBLN), mesenteric lymph node (MLN), and external iliac lymph node (ILN) are collected.

TABLE 152

| | | Study design | | | | |
|---|---|---|---|---|---|---|
| Group | N | Vaccination | KLH/ICFA | Challenge | KLH/ICFA | Necropsy |
| Placebo | 25 | D 0 | D 12 | D 14 | D 16 | D 42 |
| Vaccine | 25 | 2 mL IM (right neck) | 2 mL IM | 1 mL IN/1 mL IM | 2 mL IM | |

Laboratory Phase

Viremia: Post-challenge viremia in vaccinates and control animals is evaluated by qPCR. Following challenge, all control pigs are viremic. The viremia load (genomic copies/mL) is completely abrogated in the vaccinates.

Clinical signs: Virus replication in tissues of vaccinates and placebo animals post challenge is evaluated using RNAScope. RNAScope is a recently available technology that allows us to specifically tag and visualize viral mRNA. RNAScope detects replicating virus in a tissue as opposed to immunohistochemistry or PCR which identifies genetic material of a virus whether it is live or dead. Tissues are fixed and permeabilized to allow for target probe access sites of viral replication within the cells. A pair of PCV3 RNA specific oligonucleotide probes are then hybridized so as to sit within close proximity of each other on the PCV3 target RNA. (The detection of messenger RNA means the PCV3 virus is replicating, not just detection of PCV3 genetic material.) This is followed by the hybridization of a signal amplification molecule (SAM) that recognizes the pair of specific oligonucleotide probes. In non-specific reactions, the two probes do not sit next to each other preventing their hybridization with the SAM. The SAMs themselves are conjugated to an enzyme. As in in situ hybridization assays, the signals are detected using a chromogenic substrate followed by bright-field microscopic examination of slides. Slides for PCV3 RNAscope assay are stained and stained slides are read and scored (Table 153).

TABLE 153

RNAScope scoring scale

| Score | Description |
| --- | --- |
| 0 = normal | zero cells with PCV3 staining |
| 1 = mild | <10% of cells with PCV3 staining |
| 2 = moderate | 10-50% of cells with PCV3 staining |
| 3 = severe | >50% of cells with PCV3 staining |

No evidence of PCV3 replication is observed in any sections of cerebrum/cerebellum of any pig. Nearly all of the control pigs have at least mild PCV3 RNAscope staining in the kidney, heart, large intestine, and small intestine. Barring one pig, none of the other vaccinated pigs show any staining in the tissues evaluated.

The experimental inactivated enhanced expression baculovirus PCV3 ORF2 vaccine significantly prevents virus replication in ILN, spleen, and lung, and significantly mitigated the severity of the amount of replicating PCV3 virus found in all tissues. The vaccine also numerically reduces mortality, clinical signs, gross lesions, and histologic lesions, in addition to a numerical increase in body weights following the challenge phase. Taken altogether, the experimental enhanced expression baculovirus PCV3 ORF2 is shown to be efficacious against PCV3.

Example 14

Challenge Data from the Mutated PCV3 ORF2 Candidates in Reproductive Model

Vaccination Phase: Forty-six pre-breeding gilt (>5 months of age) are used in this study. All dams are screened at the Iowa State University Veterinary Diagnostic Laboratory (ISU-VDL) to be free of viremia prior to vaccination by qPCR for the following agents: PCV3, PCV2, atypical porcine pestivirus (APPV), transmissible gastroenteritis virus (TGEV), porcine reproductive and respiratory syndrome virus (PRRSV) and porcine parvovirus (PPV). Animals are also shown to be Seronegative for Influenza A and *M. hyopneumoniae* as confirmed by ISU-VDL.

Gilts are vaccinated on DO and D21 based on their treatment groups. The NTX gilts are administered with the placebo vaccine. Estrus synchronization is done by administration of MATRI™ (altrenogest) in their feed from day 17 to day 30. On day 30, P.G. 600 is administered to all gilts. Animals are evaluated for estrus and bred between day 35-42. Thirty-six sows are confirmed pregnant on D77 (D35 of gestation) and used in this study (Table 154).

TABLE 154

Study design showing treatment groups

| Treatment group | Treatment | n | Challenge | Farrowing | Necropsy |
|---|---|---|---|---|---|
| NTX | Placebo | 5 | None | D147-D159 litter data & necropsy/ tissue/blood collection | D168-D180 (21 days Post farrowing) litter data & necropsy/ tissue/blood collection |
| Placebo | | 15 | D83 (~40 days of gestation) PCV3 tissue homogenate 2 mL each IM and IN | | |
| Vaccine | Vaccine | 16 | | | |

Challenge phase: All animals are challenged with PCV3 positive tissue homogenate 40 days into gestation. Keyhole limpet hemocyanin (KLH) emulsified in incomplete Freund's adjuvant (ICFA) containing 1 mg KLH/1 mL is administered two days before and two days after challenge. The tissue homogenate used for challenge was screened for extraneous agents by qPCR and deep sequencing.

Laboratory Phase

Viremia: Serum is collected from sows throughout the study and is evaluated for viremia by qPCR.

None of the vaccinated gilts show viremia on any data point samples post challenge. All NTX and Placebo gilts show viremia starting on week post challenge and continuing to show viremia for 3-5 weeks post challenge. Overall, the viremia data from sows indicates that the vaccine is able to abrogate virus replication in the sows.

Clinical signs: All gilts are taken to farrowing. At farrow, the piglets are scored as healthy, mummies, weak-born, stillborn and autolysed. Any mortality arising from being crushed in the first three days after farrowing are also recorded.

There is a clear and significant reduction in the total number of mummies in the vaccine group in comparison to the placebo group. A similar reduction in stillborn and weak born piglets is observed in the vaccine group as compared to the placebo and NTX group. Additionally, RNAScope data from the tissues indicate a significant reduction to complete abrogation of viral replication in tissues of vaccinated sows and piglets when compared to tissue from NTX and Placebo groups.

PCV3 is widely believed to be a reproductive disease. In the reproductive model, sows are vaccinated, boosted, and bred to evaluate the effect of a PCV3 challenge. Vaccinates (sows and piglets at thereof) also show a reduction or elimination of virus replication in examined tissues. The experimental inactivated enhanced expression baculovirus PCV3 ORF2 vaccine appears to almost completely abrogate virus replication in sows. Moreover, at farrow, vaccinated sows had a significant reduction in the number of mummies. This reduction could have a significant economic impact for swine producers.

PCV3 in Combination with PPV

Reference is made to WO2018/083156, the disclosure of which is incorporated by reference.

The objective of this study is to evaluate the onset of immunity for the herein disclosed PCV3 vaccine (investigational vaccine product 1 (termed "IVP1" in the following)) when used in association with a subunit porcine parvovirus vaccine as described in the Examples, in particular produced according to Examples 1 and 2, of WO2018/083156 (termed "IVP2" in the following), and wherein this mixture of IVP1 and IVP2 is also named "IVP2/IVP1" hereinafter.

This study includes 60 cesarean-derived, colostrum deprived (CDCD) pigs that are seronegative for PCV3 and PPV, of which 30 are vaccinated with the mixture IVP2/IVP1 and 30 (the control group) receive a sterile diluent (water for injection) at 3 weeks of age (i.e., on study day 0 (DO)), followed by a virulent challenge of PCV3 on D14.

Vaccination with IVP2/IVP1 results in a significant increase in pigs positive for PCV3 serology, viremia and RNAscope. By D42, all pigs of the IVP2/IVP1 group are serologically positive for PVC3, while in the control group significantly less pigs are positive.

Upon assessment of the primary outcome parameters, the vaccination with IVP2/IVP1 significantly reduces and/or abrogates viremia in vaccinates. Furthermore, the overall level of the histologic lesions as determined by H&E staining is more severe in the control group with significantly more pigs having moderate to severe scores in at least one category of lesion evaluation, whereas a considerable less number of the vaccinated pigs have a moderate lesion score, with none being severe. More importantly, on a histological level as determined by virus specific RNAScope staining, the vaccine is able to prevent or reduce viral replication in tissues including but not limited to heart, kidney, lung, intestine and neural tissue.

In conclusion, IVP1 used in association with IVP2 provides efficacious active immunization of 3 week old CDCD pigs when challenged with virulent PCV3 on day 14 post vaccination.

Example 16

PCV3 in Combination with PPV and PRRSV

Reference is made to WO2018/083156 and WO2012/110489, the disclosure of which is incorporated by reference.

The objective of this vaccination-challenge study is to provide data on the associated use of the herein disclosed PCV3 vaccine and the above described (in Example 15, with reference to WO2018/083156) parvovirus subunit vaccine IVP2 (IVP1/IVP2 as described above) with a PRRS MLV vaccine (said PRRS MLV deposited with European Collection of Cell Cultures (ECACC) under the Accession Number ECACC 1 1012502) described in the Examples of WO2012/110489 (termed "IVP3", and the mixture is termed "IVP1/IVP2/IVP3" in the following) in 5- to 6-month-old gilts.

Twenty-seven gilts originate from a herd previously tested negative for PCV3 with no prior PCV3 history of disease or vaccination. Gilts are randomized into 3 treatment groups of n=9 receiving vaccination on DO and boostered on D21: T1 Negative Control, T2 IVP1/IVP2/IVP3, T3 non-treated control gilts (NTX) with each group housed separately.

Gilts are vaccinated, bred and become pregnant. At approximately 40 days of gestation (dG), all gilts are inoculated with the PCV3 challenge strain (as herein described). Gilts are bled weekly except during synchronization and breeding (D35-D70), and sera are tested.

Gilts are allowed to farrow and the litters are examined for mummies, stillborn and weak born piglets. Overall, vaccinated gilts and sows show none to a significantly lesser number of mummies, stillborn and weak born litters when compared to controls or NTX groups When examined for viremia, contrary to control groups, T2 gilts show complete abrogation of viremia post challenge. In conclusion, the combination vaccine IVP1/IVP2/IVP3 is efficacious in preventing viremia and PCV3 infection of fetuses at 40dG.

Histologically, T2 gilts are able to prevent viral replication in key tissues post-challenge. Significant virus relication and thereby clinical manifestation of PCV3 is observed in control gilts/sows and litters. This is visualized by using H&E staining and virus RNAScope assay that detects replication virual mRNA in cells and tissues. In conclusion, the combination vaccine IVP1/IVP2/IVP3 is efficacious in preventing clinical signs PCV3 infection of gilts, sows and fetuses at 40dG.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of preventing PCV3 viremia in a piglet, wherein the method comprises administering a composition to a pig, wherein the pig is a pregnant gilt or sow; and wherein the pregnant gilt or sow gives birth to the piglet;

and wherein the composition comprises a PCV3 ORF2 protein, wherein the PCV3 ORF2 protein comprises an amino acid sequence having at least 97% sequence identity with SEQ ID NO:4; and wherein the PCV3 ORF2 protein is a recombinant baculovirus expressed PCV3 ORF2 protein.

2. The method of claim 1 wherein the sow suckles the piglet.

3. A method of administering the composition of claim 1 to the pig comprising a multi-shot or multi-dose regimen; or wherein the administration comprises a two-shot or two-dose regimen of the composition.

4. A method of preventing PCV3 viremia in a piglet, wherein the method comprises administering a composition to a pig, wherein the pig is a gilt or sow before pregnancy with the piglet, wherein the gilt or sow becomes pregnant with the piglet, and wherein the pregnant gilt or sow gives birth to the piglet;

and wherein the composition comprises a PCV3 ORF2 protein, wherein the PCV3 ORF2 protein comprises an amino acid sequence having at least 97% sequence identity with SEQ ID NO:4; and wherein the PCV3 ORF2 protein is a recombinant baculovirus expressed PCV3 ORF2 protein.

5. The method of claim 4, wherein the administration to the pig is before mating/insemination of the pig.

6. The method of claim 4, wherein the sow suckles the piglet.

7. A method of administering the composition of claim 4 to the pig comprising a multi-shot or multi-dose regimen; or wherein the administration comprises a two-shot or two-dose regimen of the composition.

* * * * *

SEQUENCE LISTING

```
<160> NUMBER OF SEQ ID NOS: 37

<210> SEQ ID NO 1
<211> LENGTH: 645
<212> TYPE: DNA
<213> ORGANISM: Porcine circovirus 3

<400> SEQUENCE: 1
atgagacaca gagctatatt cagaagaaga ccccgcccaa ggagacgacg acgccacaga      60
aggcgctatg ccagaagacg actattcatt aggaggccca cagctggcac atactacaca     120
aagaaatact ccacaatgaa cgtcatatcc gttggaaccc ctcagaataa caagccctgg     180
cacgccaacc acttcattac ccgcctaaac gaatgggaaa ctgcaattac ctttgaatat     240
tataagatac taaaaatgaa agttacactc agccctgtaa tttctccggc tcagcaaaca     300
aaaactatgt tcgggcacac agccatagat ctagacggcg cctggaccac aaacacttgg     360
ctccaagacg acccttatgc ggaaagttcc actcgtaaag ttatgacttc taaaaaaaaa     420
```

| | |
|---|---|
| cacagccgtt acttcacccc caaaccactt ctggcgggaa ctaccagcgc tcacccagga | 480 |
| caaagcctct tcttttttctc cagacccacc ccatggctca acacatatga ccccaccgtt | 540 |
| caatggggag cactgctttg gagcatttat gtcccggaaa aaactggaat gacagacttc | 600 |
| tacggcacca agaagtttg gattcgttac aagtccgttc tctga | 645 |

<210> SEQ ID NO 2
<211> LENGTH: 134448
<212> TYPE: DNA
<213> ORGANISM: Porcine circovirus 3

<400> SEQUENCE: 2

| | |
|---|---|
| gaattctacc cgtaaagcga gtttagtttt gaaaaacaaa tgacatcatt tgtataatga | 60 |
| catcatcccc tgattgtgtt ttacaagtag aattctatcc gtaaagcgag ttcagttttg | 120 |
| aaaacaaatg agtcatacct aaacacgtta ataatcttct gatatcagct tatgactcaa | 180 |
| gttatgagcc gtgtgcaaaa catgagataa gtttatgaca tcatccactg atcgtgcgtt | 240 |
| acaagtagaa ttctactcgt aaagccagtt cggttatgag ccgtgtgcaa acatgacat | 300 |
| cagcttatga ctcatacttg attgtgtttt acgcgtagaa ttctactcgt aaagcgagtt | 360 |
| cggttatgag ccgtgtgcaa acatgacat cagcttatga gtcataatta atcgtgcgtt | 420 |
| acaagtagaa ttctactcgt aaagcgagtt gaaggatcat atttagttgc gtttatgaga | 480 |
| taagattgaa agcacgtgta aatgttttcc cgcgcgttgg cacaactatt tacaatgcgg | 540 |
| ccaagttata aaagattcta atctgatatg ttttaaaaca cctttgcggc ccgagttgtt | 600 |
| tgcgtacgtg actagcgaag aagatgtgtg gaccgcagaa cagatagtaa aacaaaaccc | 660 |
| tagtattgga gcaataatcg atttaaccaa cacgtctaaa tattatgatg gtgtgcattt | 720 |
| tttgcgggcg ggcctgttat acaaaaaaat tcaagtacct ggccagactt tgccgcctga | 780 |
| aagcatagtt caagaattta ttgacacggt aaaagaattt acagaaaagt gtcccggcat | 840 |
| gttggtgggc gtgcactgca cacacggtat taatcgcacc ggttacatgg tgtgcagata | 900 |
| tttaatgcac accctgggta ttgcgccgca ggaagccata gatagattcg aaaaagccag | 960 |
| aggtcacaaa attgaaagac aaaattacgt tcaagattta ttaatttaat taatattatt | 1020 |
| tgcattcttt aacaaatact ttatcctatt ttcaaattgt tgcgcttctt ccagcgaacc | 1080 |
| aaaactatgc ttcgcttgct ccgtttagct tgtagccgat cagtggcgtt gttccaatcg | 1140 |
| acggtaggat taggccggat attccacc acaatgttgg caacgttgat gttacgttta | 1200 |
| tgcttttggt tttccacgta cgtcttttgg ccggtaatag ccgtaaacgt agtgccgtcg | 1260 |
| cgcgtcacgc acaacaccgg atgtttgcgc ttgtccgcgg ggtattgaac cgcgcgatcc | 1320 |
| gacaaatcca ccactttggc aactaaatcg gtgacctgcg cgtctttttt ctgcattatt | 1380 |
| tcgtctttct tttgcatggt ttcctggaag ccggtgtaca tgcggtttag atcagtcatg | 1440 |
| acgcgcgtga cctgcaaatc tttggcctcg atctgcttgt ccttgatggc aacgatgcgt | 1500 |
| tcaataaact cttgtttttt aacaagttcc tcggttttt gcgccaccac cgcttgcagc | 1560 |
| gcgtttgtgt gctcggtgaa tgtcgcaatc agcttagtca ccaactgttt gctctcctcc | 1620 |
| tcccgttgtt tgatcgcggg atcgtacttg ccggtgcaga gcacttgagg aattacttct | 1680 |
| tctaaaagcc attcttgtaa ttctatggcg taaggcaatt tggacttcat aatcagctga | 1740 |
| atcacgccgg atttagtaat gagcactgta tgcggctgca aatacagcgg gtcgccctt | 1800 |
| ttcacgacgc tgttagaggt agggccccca ttttggatgg tctgctcaaa taacgatttg | 1860 |

```
tatttattgt ctacatgaac acgtatagct ttatcacaaa ctgtatattt taaactgtta    1920
gcgacgtcct tggccacgaa ccggacctgt tggtcgcgct ctagcacgta ccgcaggttg    1980
aacgtatctt ctccaaattt aaattctcca attttaacgc gagccatttt gatacacgtg    2040
tgtcgatttt gcaacaacta ttgttttta acgcaaacta aacttattgt ggtaagcaat     2100
aattaaatat gggggaacat gcgccgctac aacactcgtc gttatgaacg cagacggcgc    2160
cggtctcggc gcaagcggct aaaacgtgtt gcgcgttcaa cgcggcaaac atcgcaaaag    2220
ccaatagtac agttttgatt tgcatattaa cggcgatttt ttaaattatc ttatttaata    2280
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tggggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat taaatagctt gcgacgcaac    2880
gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt ttcgtgtgcc aagtgtgaaa accgatgttt    3540
aatcaaggct ctgacgcatt tctacaacca cgactccaag tgtgtgggtg aagtcatgca    3600
tcttttaatc aaatcccaag atgtgtataa accaccaaac tgccaaaaaa tgaaaactgt    3660
cgacaagctc tgtccgtttg ctggcaactg caagggtctc aatcctattt gtaattattg    3720
aataataaaa caattataaa tgtcaaattt gttttttatt aacgatacaa accaaacgca    3780
acaagaacat ttgtagtatt atctataatt gaaaacgcgt agttataatc gctgaggtaa    3840
tatttaaaat cattttcaaa tgattcacag ttaatttgcg acaatataat tttatttca    3900
cataaactag acgccttgtc gtcttcttct tcgtattcct tctcttttc attttctcc     3960
tcataaaaat taacatagtt attatcgtat ccatatatgt atctatcgta tagagtaaat    4020
tttttgttgt cataaatata tatgtctttt ttaatggggt gtatagtacc gctgcgcata    4080
gttttctgt aatttacaac agtgctattt tctggtagtt cttcggagtg tgttgcttta     4140
attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
```

```
taactttcca aaatgttgta cgaaccgtta aacaaaaaca gttcacctcc ctttctata    4320 ctattgtctg cgagcagttg tttgttgtta aaaataacag ccattgtaat gagacgcaca   4380
aactaatatc acaaactgga aatgtctatc aatatatagt tgctgatatc atggagataa   4440
ttaaaatgat aaccatctcg caaataaata agtattttac tgttttcgta acagttttgt   4500
aataaaaaaa cctataaata ttccggatta ttcataccgt cccaccatcg ggcgcggatc   4560
cgccaccatg agacacagag ctatattcag aagaagaccc cgcccaagga gacgacgacg   4620
ccacagaagg cgctatgcca gaagacgact attcattagg aggcccacag ctggcacata   4680
ctacacaaag aaatactcca caatgaacgt catatccgtt ggaacccctc agaataacaa   4740
gccctggcac gccaaccact tcattacccg cctaaacgaa tgggaaactg caattacctt   4800
tgaatattat aagatactaa aaatgaaagt tacactcagc cctgtaattt ctccggctca   4860
gcaaacaaaa actatgttcg ggcacacagc catagatcta gacggcgcct ggaccacaaa   4920
cacttggctc caagacgacc cttatgcgga aagttccact cgtaaagtta tgacttctaa   4980
aaaaaaacac agccgttact tcaccccccaa accacttctg gcgggaacta ccagcgctca   5040
cccaggacaa agcctcttct ttttctccag acccaccca tggctcaaca catatgaccc    5100
caccgttcaa tggggagcac tgctttggag catttatgtc ccggaaaaaa ctggaatgac   5160
agacttctac ggcaccaaag aagtttggat tcgttacaag tccgttctct gagcggccgc   5220
tgcagatctg atcctttcct gggacccggc aagaaccaaa aactcactct cttcaaggaa   5280
atccgtaatg ttaaacccga cacgatgaag cttgtcgttg gatggaaagg aaaagagttc   5340
tacagggaaa cttggacccg cttcatggaa gacagcttcc ccattgttaa cgaccaagaa   5400
gtgatggatg ttttccttgt tgtcaacatg cgtcccacta gacccaaccg ttgttacaaa   5460
ttcctggccc aacacgctct gcgttgcgac cccgactatg tacctcatga cgtgattagg   5520
atcgtcgagc cttcatgggt gggcagcaac aacgagtacc gcatcagcct ggctaagaag   5580
ggcggcggct gcccaataat gaaccttcac tctgagtaca ccaactcgtt cgaacagttc   5640
atcgatcgtg tcatctggga gaacttctac aagcccatcg tttacatcgg taccgactct   5700
gctgaagagg aggaaattct ccttgaagtt tccctggtgt tcaaagtaaa ggagtttgca   5760
ccagacgcac ctctgttcac tggtccggcg tattaaaaca cgatacattg ttattagtac   5820
atttattaag cgctagattc tgtgcgttgt tgatttacag acaattgttg tacgtatttt   5880
aataattcat taaatttata atctttaggg tggtatgtta gagcgaaaat caaatgattt   5940
tcagcgtctt tatatctgaa tttaaatatt aaatcctcaa tagatttgta aaataggttt   6000
cgattagttt caaacaaggg ttgttttttcc gaaccgatgg ctggactatc taatggattt   6060
tcgctcaacg ccacaaaact tgccaaatct tgtagcagca atctagcttt gtcgatattc   6120
gtttgtgttt tgttttgtaa taaaggttcg acgtcgttca aatattatg cgcttttgta   6180 tttctttcat cactgtcgtt agtgtacaat tgactgacg taaacacgtt aaataaagct   6240
tggacatatt taacatcggg cgtgttagct ttattaggcc gattatcgtc gtcgtcccaa   6300
ccctcgtcgt tagaagttgc ttccgaagac gattttgcca tagccacacg acgcctatta   6360
attgtgtcgg ctaacacgtc cgcgatcaaa tttgtagttg agcttttgg aattatttct   6420 gattgcgggc gttttgggc gggtttcaat ctaactgtgc ccgattttaa ttcagacaac   6480
acgttagaaa gcgatggtgc aggcggtggt aacatttcag acggcaaatc tactaatggc   6540
ggcggtggtg gagctgatga taaatctacc atcggtggag gcgcaggcgg ggctggcggc   6600
```

```
ggaggcggag gcggaggtgg tggcggtgat gcagacggcg gtttaggctc aaatgtctct   6660
ttaggcaaca cagtcggcac ctcaactatt gtactggttt cgggcgccgt ttttggtttg   6720
accggtctga gacgagtgcg attttttttcg tttctaatag cttccaacaa ttgttgtctg   6780
tcgtctaaag gtgcagcggg ttgaggttcc gtcggcattg gtggagcggg cggcaattca   6840
gacatcgatg gtggtggtgg tggtggaggc gctggaatgt taggcacggg agaaggtggt   6900
ggcggcggtg ccgccggtat aatttgttct ggtttagttt gttcgcgcac gattgtgggc   6960
accggcgcag gcgccgctgg ctgcacaacg gaaggtcgtc tgcttcgagg cagcgcttgg   7020
ggtggtggca attcaatatt ataattggaa tacaaatcgt aaaaatctgc tataagcatt   7080
gtaatttcgc tatcgtttac cgtgccgata tttaacaacc gctcaatgta agcaattgta   7140
ttgtaaagag attgtctcaa gctcggatcc cgcacgccga taacaagcct tttcattttt   7200
actacagcat tgtagtggcg agacacttcg ctgtcgtcga cgtacatgta tgctttgttg   7260
tcaaaaacgt cgttgcaag ctttaaaata tttaaaagaa catctctgtt cagcaccact   7320
gtgttgtcgt aaatgttgtt tttgataatt tgcgcttccg cagtatcgac acgttcaaaa   7380
aattgatgcg catcaatttt gttgttccta ttattgaata aataagattg tacagattca   7440
tatctacgat tcgtcatggc caccacaaat gctacgctgc aaacgctggt acaatttttac   7500
gaaaactgca aaaacgtcaa aactcggtat aaaataatca acgggcgctt tggcaaaata   7560
tctattttat cgcacaagcc cactagcaaa ttgtatttgc agaaaacaat ttcggcgcac   7620
aattttaacg ctgacgaaat aaaagttcac cagttaatga gcgaccaccc aaattttata   7680
aaaatctatt ttaatcacgg ttccatcaac aaccaagtga tcgtgatgga ctacattgac   7740
tgtcccgatt tatttgaaac actacaaatt aaaggcgagc tttcgtacca acttgttagc   7800
aatattatta gacagctgtg tgaagcgctc aacgatttgc acaagcacaa tttcatacac   7860
aacgacataa aactcgaaaa tgtcttatat ttcgaagcac ttgatcgcgt gtatgtttgc   7920
gattacggat tgtgcaaaca cgaaaactca cttagcgtgc acgacggcac gttggagtat   7980
tttagtccgg aaaaaattcg acaccacaac tatgcacgtt cgtttgactg gtacgccgtc   8040
ggcgtgttaa catacaagtt gctaaccggc ggccgcacac catttgaaaa aagcgaagac   8100
gaaatgttgg acttgaatag catgaagcgt cgtcagcaat acaatgacat ggcgtttta   8160
aaacacgttc gtaacgttaa cgctcgtgac tttgtgtact gcctaacaag atacaacata   8220
gattgtagac tcacaaatta caaacaaatt ataaaacatg agttttgtc gtaaaaatgc   8280
cacttgtttt acgagtagaa ttctacgtgt aacacacgat ctaaaagatg atgtcatttt   8340
ttatcaatga ctcatttgtt ttaaaacaga cttgttttac gagtagaatt ctacgtgtaa   8400
agcatgatcg tgagtggtgt taataaaatc ataaaaatta ttgtaaatgt ttattattta   8460
aaaacgattc aaatatataa taaaaacaat ctacatctat ttcttcacaa tccataacac   8520
acaacaggtc catcaatgag ttttttgtctt tatccgacat actatgtgca tgtaacaaat   8580
caaatacatc ttttaaattt ttatacacat ctttacattg tctaccaaaa tctttaataa   8640
ccctataaca aggaaaagac ttttcttctt gcgtggtttt gccgcgcaga tattgaaata   8700
aaatgtgcat gcacgacaac ttgtgtttac taaaatgctc cttgcctata ccgcaaaacc   8760
ggccatacat ttcggcgatt acacgcggac aattgtacga ttcgtctacg tgtaaacgat   8820
catcataatc actcttgcgc aaacgaataa atttttcac cgcttccgac aaacgaggca   8880
ccaattcggc gggcacgctt cgatacatta ttctgtgcac ataagttacc acacaaaatt   8940
tattgtacca ccatccgaca acgtcgttat tagggttgaa cacgttggcg atgcgcagca   9000
```

```
gtttcccgtt tctcatgaaa tattcaaagc ggcccaaaat aatttgcaag caatccaaca    9060
tgtcttgaga aatttctcgt tcaaaattgt tcaaagagaa tatctgccat ccgttttgaa    9120
cgcgcacgct gacgggaacc accgcatcga tttgctccaa cacttcacgg acgttatcgt    9180
cgatgcccat cgtttcgctg gtgctgaacc aatgggaaag gctcttgatg gaatcgcccg    9240
cgtctatcat cttgaccgct tcgtcaaagg tgcaactgcc gctcttcaaa cgccgcatag    9300
cggtcacgtc ccgctctatg cacgacatac cgtttacgta cgattctgat aggtattcct    9360
gaactatacg gtaatggtga tacgactcgc catacacgtc gtgcacctca ttgtatttag    9420
cataataatt gtaaattatt aactttgcag cgagagacat gttgtcagta aagcggtgct    9480
aggctcaata atactgatgt acaggcacgc gtgctattta tatataattt cgcaaggagg    9540
ggagctgtta tcggttgcta ttattaaaga atggccgtct gttttatca caagcttggc    9600
agcctcaacc atgaagcgtc gtcattgtaa attaaattct ctgcctcaag aattatttga    9660
caagattgtc gagtatttat ctttatctga ttactgcaat ttggtgcttg tctgtaaaag    9720
accttctagt aaatataacg tgatatttga tagtactaat caccaacatt tgaaaggcgt    9780
gtacaaaaag acagacgtgc aaataacaag ctacaacgaa tacatcaact gtatttgcaa    9840
cgaactgaga caagacgaat tctatgccaa atcatcatgg attgcgagta tttgcggtca    9900
ccagagagcg acaatttta gtgtaacaaa taaacaagta gaaatgaaat atcatttgta    9960
taatatagca attgtggaaa gtgaagattg caacggattt tacccatttg agccaacgcg   10020
cgattgttta atatgcaaac aaaaaaacca atgtcctcgt aattcattta ttgtttcgtt   10080
gtgtaaatat ttagaaaaac aaaatgtaca atcaaacttt atatattatt tatacgaaat   10140
aaatacataa taataactat tatacatgtt tttattttac aatacttcct gtataacctc   10200
tctaactaca ttaggagtac aatccacgtc aattacacgt ttagctattt ttctaatttt   10260
gtaatgttta tcgtagagtt tttcgttaat acattgaata gccaacaagg gatttgggtg   10320
cacaccgtca tagagtactt ccatgtcgtc ttcaaagcgc attttcgct tgcgaaaatg    10380
ccgctcttgg cccaaaacaa aagcgagttt gatgcggtcg tcgatgcgtt ccgaaaatac   10440
ggccaaatgc tggtgtttgg tgatgtcgcg cggaaacgtc accgtgccat ttttgctttc   10500
cgccacgacg gcggttttca atttttcggc cgactgcagc atgttaagtt tggcgtcgag   10560
ttcgtgcaaa cgcaattcaa actgctcaaa cctgttgccc acctcgttct tgaacgtctc   10620
gtgggtgacc ataaattttt cgctgtttgc attcagtttc tttacatgtt ttaaaacaga   10680
ttcaatcttg tcgcgcaaat catcacgctc gccttcagtt tgaatgtgca gcaacgcgtt   10740
gcttttgttg gcaaaattta accgcatcaa aatttccaac aacccgtgct tggtcgcgaa   10800
caatgcgccc aacgagttga gatcgcgttt ggatctctgt ttgtgaaaaa caatttcgtt   10860
taaatggtaa acttgatcgc cgtcccaatt gcaatcaagt atgtcgtcgt gcgcaatttc   10920
aagacctttg caaaaatcta tcacattgta gcattttgcg ttcgtgtcgc tgtgcacgta   10980
tctgtacttg aaactgtgcg tgttgcattt gaatgagtcc catttaacga tgtgcgacca   11040
ttgttgggcg tttatgtggt acttttgta gtcgtctgca ttgaaccgat cttcggcggc   11100
gatggcgtcg ttgtcgttgt caccggacca catccaccag ttccataacc aggatagcat   11160
tgctttagct tgtctagcaa ttcctttgtt atacaacgag aaaatttcgt tcccttataa   11220
ttatagctgt acggtgcgcg tatttgtttg ttaacgttac aaaaaatatc cctgtccacg   11280
tccggccaat actgcaacgt gagcgcgtcc aagtttgaat cttgcatatg cggaacgtac   11340
```

```
aaacgtacgg cctctctcac acaatgcgca aaactgcccg gctgaatgta atcactgtcc    11400
aactttgcag gtttctcgaa agccttgtac cgatgcacgc gaacattttg agcggacgtg    11460
attttaaact tgtcggtgaa ttttaaccac aaatgaaatc cacggttgcc ggtatacatg    11520
actcttgaca cgttctcttc cgtgtaaaac aacagaaacg ccgtggcgcc aatgtaaatt    11580
ttcagcatta aatcgtgttc gtcaacataa tttttgtaat cggcgtctac gacccattcc    11640
ctgccgccgc cgtcgtccaa cggtttgacg tgcacgtcgg acactttgtt ttgcacaata    11700
taactataca attgtgcgga ggtatcaaaa tatctgtcgg cgtgaatcca gcgcgcgttg    11760
accgtcatga acgcgtactt gcggctgtcg ttgtacgcaa tggcgtccca catcatgtcg    11820
acgcgcttct gcgtataatt gcacactaac atgttgccct ttgaacttga cctcgattgt    11880
gttaattttt ggctataaaa aggtcaccct ttaaaatttg ttacataatc aaattaccag    11940
tacagttatt cggtttgaag caaaatgact attctctgct ggcttgcact gctgtctacg    12000
cttactgctg taaatgcggc caatatattg gccgtgtttc ctacgccagc ttacagccac    12060
catatagtgt acaaagtgta tattgaagcc cttgccgaaa aatgtcacaa cgttacggtc    12120
gtcaagccca aactgtttgc gtattcaact aaaacttatt gcggtaatat cacggaaatt    12180
aatgccgaca tgtctgttga gcaatacaaa aaactagtgg cgaattcggc aatgtttaga    12240
aagcgcggag tggtgtccga tacagacacg gtaaccgccg ctaactacct aggcttgatt    12300
gaaatgttca aagaccagtt tgacaatatc aacgtgcgca atctcattgc caacaaccag    12360
acgtttgatt tagtcgtcgt ggaagcgttt gccgattatg cgttggtgtt tggtcacttg    12420
tacgatccgg cgcccgtaat tcaaatcgcg cctggctacg gttggcgga aaactttgac    12480 acggtcggcg ccgtggcgcg gcaccccgtc caccatccta acatttggcg cagcaatttc    12540
gacgacacgt aggcaaacgt gatgacggaa atgcgtttgt ataagaatt taaaattttg    12600 gccaacatgt ccaacgcgtt gctcaaacaa cagtttggac ccaacacacc gacaattgaa    12660
aaactacgca acaaggtgca attgcttttg ctaaacctgc atcccatatt tgacaacaac    12720
cgacccgtgc cgcccagcgt gcagtatctt ggcggaggaa tccatcttgt aaagagcgcg    12780
ccgttgacca aattaagtcc ggtcatcaac gcgcaaatga acaagtcaaa aagcggaacg    12840
atttacgtaa gttttgggtc gagcattgac accaaatcgt ttgcaaacga gtttctttac    12900
atgttaatca atacgttcaa aacgttggat aattacacca tattatggaa aattgacgac    12960
gaagtagtaa aaaacataac gttgcccgcc aacgtaatca cgcaaaattg gtttaatcaa    13020
cgcgccgtgc tgcgtcataa aaaaatggcg gcgtttatta cgcaaggcgg actacaatcg    13080
agcgacgagg ccttggaagc cgggatacccc atggtgtgtc tgcccatgat gggcgaccag    13140
ttttaccatg cgcacaaatt acagcaactc ggcgtagccc gcgccttgga cactgttacc    13200
gtttccagcg atcaactact agtggcgata aacgacgtgt tgtttaacgc gcctacctac    13260
aaaaaacaca tggccgagtt atatgcgctc atcaatcatg ataaagcaac gtttccgcct    13320
ctagataaag ccatcaaatt cacagaacgc gtaattcgat atagacatga catcagtcgt    13380
caattgtatt cattaaaaac aacagctgcc aatgtaccgt attcaaatta ctacatgtat    13440
aaatctgtgt tttctattgt aatgaatcac ttaacacact tttaattacg tcaataaatg    13500
ttattcacca ttatttacct ggtttttttg agagggcctt tgtgcgactg cgcacttcca    13560
gcctttataa acgctcacca accaaagcag gtcattattg tgccaggacg ttcaaaggcg    13620
aaacatcgaa atggagtctg ttcaaacgcg cttatgtgcc agtagcaatc aatttgctcc    13680
gttcaaaaag cgccagcttg ccgtgccggt cggttctgtg aacagtttga cacacaccat    13740
```

```
cacctccacc accgtcacca gcgtgattcc aaaaaattat caagaaaaac gtcagaaaat   13800
atgccacata atatcttcgt tgcgtaacac gcacttgaat ttcaataaga tacagtctgt   13860
acataaaaag aaactgcggc atttgcaaaa tttgctaaga aaaagaacg aaattattgc    13920
cgagttggtt agaaaacttg aaagtgcaca gaagaagaca acgcacagaa atattagtaa   13980
accagctcat tggaaatact ttggagtagt cagatgtgac aacacaattc gcacaattat   14040
tggcaacgaa aagtttgtaa ggagacgttt ggccgagctg tgcacattgt acaacgccga   14100
gtacgtgttt tgccaagcac gcgccgatgg agacaaagat cgacaggcac tagcgagtct   14160
gctgacggcg gcgtttggtt cgcgagtcat agtttatgaa aatagtcgcc ggttcgagtt   14220
tataaatccg gacgagattg ctagtggtaa acgtttaata attaaacatt gcaagatga    14280
atctcaaagt gatattaacg cctattaatt tgaaaggtga ggaagagccc aattgcgttg   14340
agcgcattac cataatgcca tgtattttaa tagatactga gatctgttta aatgtcagat   14400
gccgttctcc ttttgccaaa ttcaaagtat tgattattgt agatggcttt gatagcgctt   14460
atattcaggc tacctttgt agcattagcg atagtgtaac aattgttaac aaatctaacg    14520
aaaagcatgt aacgtttgac gggtttgtaa ggccggacga tgaaggtaca acaatgcctt   14580
atgtcattgg accattatat tctgtcgacg ctgctgtcgc cgaccgtaaa gtgaaggacg   14640
tggtggattc aattcaaaac caacagacaa tgttaaaagt atttattaac gaggctaatg   14700
tgtataacaa atggaatatg cttaaaggtt taatttataa taataacaat gaatctgttt   14760
tagtaaaata atgtagtaaa atttataaag gtagataaaa attataatat taataaaaaa   14820
aataatgtta ctaaatgggt tcctgcgtta aattatttta cgggtagaca gctattaact   14880
atttatttta tttttaaatt taaataaatg tattgttaga aaattgtgtt gttttattag   14940
tataacgaaa aaatacatga cataaaccgc ttccaatttt ggtcacacaa actcttgtgt   15000
ggatagttta cgtaatgagt taaataggcg ggcagttgtc cgctaaacgt gtcggtggtc   15060
aagtagatgt gcattaattt acgacaaccc aaagcggggc cgcttatgtc aagtattttt   15120
ttcacaaaat tggtaatggt ttcgttttgt tccttgtaca aacacatgtc ggtgtgatcg   15180
ttgacgcacg agttgtacga ttccgccggc aggttggcaa acaagcgctt gagatgcttg   15240
agtctgcgtt caattttata atcaaacttg ttggtgaaaa tgtctttcag caagcacatt   15300
aactggtcgt tcaaaacgcg ctgcaacgac gacaccaaca catgatattc gtttccaaaa   15360
agcgaaaaat ttttgatgca gcggtccgcg ttgaagggtc gtttcataat gcgcacgttg   15420
acaaaaaaca cgttgaaaga cagcggggct gtggttattt taacgccgtt gtcggtatac   15480
tcgtcgacgc cgtctgcgct tgttatgtca atttgtagcg caaatctaac caaatcaaac   15540
tcatcgttgt actgtgtctt tatgcatttt atatggcggt ttaagtgcaa gttgatttgg   15600
ccgtttaatc tataggctcc gttttgataa catttcagca ctaccaacgg atccgacatg   15660
taaacttgac gcgttagcac gtccaattca gcgtaatgtt ggtcgacgca ttttgtaaa    15720
ttagtttgca ggttgcaaaa cattttgcg caaaagccgt aatagtcaaa atctatgcat    15780
tttaatgcgc ttctgtcgtc gtcaatatgg catgtcacgg ctgcgcctcc agttaacacg   15840
aataaaccgc cgttttcgca aactacggct tcgaacaat ctttgataaa tgccaacttt    15900
gctttagcca caattttatc gcgcaggcga tcttcaatat cctttgtcgt aatataaggt   15960
aggacgccaa gatttagttg attcaacaaa cgttccataa tgaatagcgg cgacgcaaca   16020
cgactacact gttcaaatgc gcacgcaaaa caaacccttg caactttatt tgccaatcgt   16080
```

```
aatcacagta gttttacga gtacgccatc gcgtttgtaa gcacattgct tttaaaaat    16140
aatttaaatt taatgaccgc gtgcaatttg atcaactcgt tgatcaactt tgaactcaac    16200
atgtttggta aaagtttatt gctaaatgga tttgttaatt tctgcattgc taacagcgac    16260
ggggttacga ttcaacataa aatgttaacc aacgtgttaa gttttttgtt ggaaaaatat    16320
tattaaaaat aaataaataa acttgttcag ttctaattat tgttttattt tttataaaat    16380
aatacaattt tatttataca ttaatacttt ggtatttatt aatacaatta tttacaatac    16440
tttatttaca ctataatact ttatttacat tagtactaaa ttaatactaa attacgctaa    16500
tactaaatta atactttata taatcaaaaa taatacttta tataatactt tctaatcatc    16560
ataaacgggt aatagttttt tctcttgaaa tttacgctgc aactcttcgc taaaacacat    16620
gggcggtgga gtgggagcgg gtggagtagg agtccttacg ggtttgatgg gcgacagttc    16680
tctggacttg cggaacagct tgggcgaaag cgtcggcgtg cgccgactaa tgatttcttc    16740
atccggcaac ggaggctcgc acattgtgca cgcgtccggt gaggtacaca aactttctt    16800
gggcacgctg tacaccggct tgggcacgct atatgtgttg ccaaaataga actcgttgtg    16860
gttgccgaac ggagacgatg ggtgtgaaga cggcgatggc tgtgaagaca agtccgaagg    16920
cgcgataaaa gatgaaagtg tttctgaaac cgaagtggtg gtagaagtgg tagaaggcgg    16980
gtgcgttacg gcaaccacgc tgctgctatt tctgccttcg gagaccactt ccagcaatct    17040
agagttactc tctcgttctt cgcggcgata gtcaatgtcg caataatgtt cataagatgc    17100
cttttcggct tcggcgcgcc ttttcatgta tatgttgtga cgcatctcct ttaactgcac    17160
gtacaaattc cagcattgca cagccagtat cgtaagcacg cccattatga ttacgggata    17220
attttgatta aacacggtcg gctcgtgatc gcttacaatc gctcggcaca tgatgcattt    17280
tttgtaaatg ttcacataca cacagttttg gctcaaggtt tcggtatttg cgtagtcaat    17340
ttccagatac acgatagagt tccagcacat tgattccaaa tcgtagtgac gatataaaac    17400
atctagcgcc ggtagatgac catttttgaa cacgtagatt tgaaacgcgg caaacagcat    17460
ccaacacagc ccagtgatca cgtttaccat aatacacgtg atagcgacgt aaaagttttc    17520
tttcgcattg aaatttacat ttgtgtttga agagctgctg cgattttttcg tccacacgat    17580
aatcttccat ataaaataaa acatgtaaaa taatatccac atgccgaacg ccagcattat    17640
cggtatagat agattgataa ccgattgctt tccttcaatt tccagcaaaa acgcgtatct    17700
gctgtctatc actcccatta tagataacac aaacactatc agatatgcta ataataatga    17760
ggcattaagc ccgaattgta aaactgcagt gatttttattt aacattttga atatttaatt    17820
caacaactaa gtaatggcaa tatgtatcga gtactgatcg tgttttttcct gttcgtgttt    17880
ctttatatag tgtaccagcc cttttatcag gcatacttgc atatcggaca tgcccaacaa    17940
gattacaatg acacgttgga cgataggatg gattacattg aatccgtaat gcgtagaagg    18000
cactacgtgc cgattgaagc gttgcccgca atcaggtttg atactaatct cggcacgttg    18060
gccggtgaca cgattaaatg catgtcggtg cctttgtttg ttagtgacat tgacctgccg    18120
atgtttgatt gtagtcagat atgcgataac ccgtctgcgg cgtatttctt tgtcaacgaa    18180
acggatgtgt ttgtggtcaa cggccacaga ctgacggtgg gcggatactg ctccactaat    18240
agtttgcccc gcaactgtaa tcgcgagacg agcgtcattt taatgagtct caatcagtgg    18300
acgtgcatag ccgaggaccc gcgttactat gcgggcacag ataacatgac gcaactcgca    18360
ggcagacaac acttttgaccg cattatgccc ggacagagtg ataggaacgt cctgtttgac    18420
cgattactag gccgagaggt gaacgtgacc actaacacgt ttcgccgcag ctgggacgag    18480
```

```
ttgctggagg acggcactag gcggttcgaa atgcgctgca acgcccgaga taacaacaat    18540
aatctcatgt ttgttaatcc gcttaatccc ctcgagtgtc tcccgaacgt gtgcactaac    18600
gttagcaacg tgcacaccag tgttagaccc gtatttgaaa cgggagagtg tgactgcggc    18660
gacgaagcgg tcacgcgtgt tacgcacatt gtgccggggg acaggacctc tatgtgtgcc    18720
agcattatag atggcctgga taaaagtacg gcatcatata gatatcgcgt agagtgcgtt    18780
aatctgtaca cctctattct aaattattct aataacaaat tgttatgtcc cagtgacact    18840
tttgatagta acacggacgc agcttttgcc tttgaagtgc ccggctccta ccctttatcg    18900
cgcaacggca tcaacgagcc aacttatcgc ttttatcttg ataccagatc tcgagttaat    18960
tacaatgacg tcagagggca gttatcttaa ttgtgataac acaaacaata agtcatttaa    19020
atgttacgtc agtagttagt atataagccg tacatgttgg cttgcaaatt cagtcaatat    19080
caggctttta tcatggacgg tgtaaagctg ctagggacgt gcgcgctaat aattttgtta    19140
tcgacgacga gtacagttgt cgggcgtgac cgtatcacgt ttacgccgat agaagatagc    19200
gcaggcctca tgtttgaacg catgtacggc ttgcgacatc atacagacga cagatttgtg    19260
tttgtgaaaa aattcaattt tgtttcggtg ctgcaagagc tcaataatat caaatctaaa    19320
attgaattat atgaagcgca agtttcaact tgcacaaacg tcagacaaat aaaacagaac    19380
agatcgagta tcatcaaagc tcgcattgaa aatcagctgc agttttttgac gcaactaaac    19440
aaaaatctca tcacatactc tgtggaaagc agcattttaa gcaacgacgt gctggacaac    19500
atcgatctgg aatatgacga cagcggtgag tttgacgttt acgacgaata cgaacagcct    19560
tcgcattgga gcaacatgac tgtatccgac gcgcaagctt tgctccgaaa cccgcccaaa    19620
gacagagtaa tgttttttgga catggttacc accagcgacg tgagcagcaa atacgaagaa    19680
tacataaact gcattgtgag caaccgtacc gttgaaaacg agtgcatgtt tttagccaac    19740
atgatgaacg tgctcaacga caaattggac gacgcagcag cttttggccaa gatgctggag    19800
cgaatagtaa aacaaacgcg aaagaacaaa ctcaacatct ccaacacggt tatagacgac    19860
gacacgctgc taacggaaat gaaaaaatta acacaaactt tatacaacca aaaccgcgtg    19920
tgggtagtgg attttaacaa ggacatgaat agttatttcg atttgtcgca agcgtataaa    19980
ttgcatttat atgttgattt aaacacggtc attatgttta ttaccatgcc attgttaaaa    20040
tccaccgccg tttcgtttaa tttgtatcgc gtcatgacgg tgccttttttg caggggcaaa    20100
atgtgtctgc ttatcatttc gggcaatgaa tactttggga ttacagacag caaaaactat    20160
tatgtgcccg tatctgataa ctttagacaa gattgccaag agtttacggg ctacaatgag    20220
ttttttgtgtc ccgaaactga gccgattgcc actatgaact cgaaagtgtg cgagattgaa    20280
atgtttatgg gtcgatatag cgacgacgtg gacaacatgt gcgacattag ggtggccaat    20340
tataatccca aaaagctta cgtgaacact ttaatagact accgaaaatg gttgtacatt    20400
tttccaaaca cgaccgtgtc cgtccactat tattgtcacg acgcgcttgt agaagttgat    20460
acaaaagttt cgcccggcgt tggtgttatg ttttcgacta tggcgcaaac gtgttcgatt    20520
agaataacgt atgatgtgac cataactgta gattcgcgat tttatgtcag ccattcaact    20580
acatactggc ctaaaaagaa atttaatttt aacaactaca tcgaccaaat gttgcttgaa    20640
aaagcgacca ccagttttat accgactgtt gacaattttta cccggcccgt tttattgcaa    20700
cttcctcata aatttcacat taaagattac acatcgacgc cccatcattt tttccatcag    20760
tctaaaattt acaccaacag cgcggcgccc gacgaagact cgcaagacga cagtaatacc    20820
```

```
accgtggtaa ttatcgctat tgtcgctgca atgatcctat tctgtggatt attgttattt   20880
ttgttttgct gtataaaaaa acggtgtcat caatcaaata acgtggttgt gcaatacaaa   20940
aataacaatg aatttgtcac aatttgcaat aatttagaag acaatcgagc atacattaat   21000
ttacctaatg aatacgatag cgatgatatg ccaaaaccat tgtacccttt acttggcttt   21060
aatgatgatt tgttaaaaga tgataaacct gtgttgtacc ctatgattat agaaagaata   21120
aaataaaaca tgtataattg aaataaatat attatttaat aaaatgtttt ttatttatat   21180
actattttct attacatatt ccaatgcaca caaatgttta atggctatca gttttaattt   21240
tactaattcg tctaaacaaa aattattcac ttgctgtttt tcatccattt gacatatggc   21300
gtttataaat aattcgctgt gttttatgaa cgaatcgtaa accgctgcct gggccttcag   21360
cacggtcggc gcattgtatt tttgggtaaa gtacgcaata ttttagtca aacacagaga     21420 ttttaaatct ttttcattta tatccaagtc ggaacaatcg tatacaaaat ctagcttttc   21480
actttcgggc gcgcccagat actggttac gagttcgagc tgctccactt ggcctttgat    21540
atcggccgct atgcacaaca ttttgtcgat tgcagtttca ttgttttaa cataataatt    21600 tttaactttt ttattttgca atttaatcaa actatttaaa ttcgcttgac ctttcttaca   21660
aagcgcagtt aatatgcaag acattttgac ttataataaa aaacaaaact tttatatatt   21720
catttattgt tcaataataa caaatattcc aggcttaaaa gctaacgaat agggcttttc   21780
ggtaattttc ttattattca tgtccgtcat ctgcatctct ttgccgtact tgacgccgtc   21840
aatggtgccc atcatgtaca ttttaatctc ctccgaaggt ccgtctattt tgtccatttc   21900
gaacaatcta tcaaaatctt caacgctcat tctctgcata tcaagaggaa cgtttctgat   21960
ctttccggtg gcgtaaattg atccgttgtt gtcacggttg attatgtaaa accgacgaat   22020
caacatgtcg cgctcgctag ttttgttctt atccggcaaa tgaatgcaca cgtttggttc   22080
catcttcaaa ggaaaatcgc tttgcaagtg ttttgcaaa atgttgccaa atatattgtt    22140
gtgtttgtga atgtctccgt attgaatgct aaaaaactgg ccaaagttgc ttttggcacg   22200
ttttatggtt ccaaagtcgg aaaaccaaaa tccgcagggc ttgccctgca ctcttggacc   22260
gatggtgtac gtagtcttgc cgttggccgg ctccaacacc acgatatttt tatcgggctc   22320
gggatacaac ttgtcttccc attcgtgcaa actgttcaaa ttagacagtc gacaaaattc   22380
gtttttcaaa aatctgcctt cgaaacaact acaattcagt attgaaaagt tgcctcgttt   22440
cacattaatc gccatctgct cctgccacaa catcttcgtc aactcgtgtg gctccaattg   22500 aatgacgac ggcgtaaaat agcacattac gcccgtttcg tcgtgtttca cgttaaaagc    22560
gccgctgttg tacggcacca gctgctggtc ctcaccacct tccgatcttt cccgcttcgg   22620
ctggttgtcg tcgctgctcg aatatccatc gccaatcttg cgtttagttg ccatgctacc   22680
gacgtgcgct gtctgctgtg gttcaagtct aattgaagtg tttcacagaa tataagatat   22740
ataataaata tggacgactc tgttgccagc atgtgcgtag acaacgcgtt tgcgtacact   22800
actgacgatt tattgaaaaa tattccttt agtcattcca aatgcgcccc tttcaagcta    22860
caaaattaca ccgttttgaa gcggttgagc aacgggttta tcgacaagta tgtggacgtg   22920
tgctctatca gcgagttgca aaagtttaat tttaagatag atcggctaac caactacata   22980
tcaaacattt tcgagtacga gtttgtagtt ttagaacacg atttgtccac agtgcacgtc   23040
attaacgccg aaacaaaaac caaactgggc catataaacg tgtcgctaaa ccaaaacgac   23100
gcaaacgtgc tcattttgac cgtaactta acgagctaaa atgaacgagg acacgccccc    23160
gttttatttt atcagcgtgt gtgacaactt tcgcgacaac accgccgaac acgtattcga   23220
```

```
catgttaata gaaagacata gttcgtttga aaattatccc attgaaaaca cggcgtttat   23280
taacagcttg atcgttaacg ggtttaaata caatcaagtt gacgatcacg ttgtgtgcga   23340
gtattgcgaa gcagaaataa aaaattggtc cgaagacgag tgtattgaat atgcacacgt   23400
aaccttgtcg ccgtattgcg cgtatgctaa caagatcgcc gagcgtgaat cgtttggcga   23460
caacattacc atcaacgctg tactagtgaa agaaggcaaa cccaagtgtg tgtacagatg   23520
catgtccaat ttacagtcgc gtatggatac gtttgttaac ttttggcctg ccgcattgcg   23580
tgacatgatt acaaacattg cggaagcggg actttttttac acgggtcgcg gagacgaaac   23640
tgtgtgtttc ttttgcgact gttgcgtacg tgattggcat actaatgaag acacctggca   23700
gcgacacgcc gccgaaaacc cgcaatgtta ttttgtattg tcggtgaaag gtaaagaatt   23760
ttgtcaaaac tcaattactg tcactcacgt tgataaacgt gacgacgaca atttaaacga   23820
aaacgccgac gacattgagg aaaaatatga atgcaaagtc tgtctcgaac gccaacgcga   23880
cgccgtgctt atgccgtgtc ggcattttttg cgtttgcgtt cagtgttatt ttggattaga   23940
tcaaaagtgt ccgacgtgtc gtcaggacgt caccgatttt ataaaatat ttgtggtgta    24000 ataaaatggt gttcaacgtg tactacaacg gctattatgt ggaaaaaaaa ttctccaagg   24060
agtttttaat tcatattgcg cctgatttga aaaacagcgt cgactggaac ggcagcacgc   24120
gcaaacagct gcgcgttcta gacaagcgcg cctacaggca ggtgttgcac tgcaacggca   24180
gatactactg gcccgatggc acaaagtttg tctctcatcc gtacaacaaa tctattcgca   24240
cgcacagcgc aacagtcaaa cggaccgaca gctcgcatcg attaaaaagc cacgtggtcg   24300
acaaacgacc gcgccgctct ttagattctc ctcgcttgga cggatatgtt ttggcatcgt   24360
cgcccatacc acacagcgac tggaatgaag aactaaagct gtacgcccag agccacggct   24420
acgacgacta cgacgacaat ttagaagatg gcgaaatcga cgaacgtgac tctttaaaaa   24480
gtttaaataa tcatctagac gacttgaatg tattagaaaa acaataaaac atgtattaaa   24540
aataataata ataaaactat attttgtaat atataatgta ttttatttaa aaattgtcta   24600
ttccgtagtt gagaaagttt tgtcttgact tcataactct cttctccata ttctgcagct   24660
cgtttacgtt ttttgtgacg cttttaattt tctcaaaatg ctggctgtca atagttattt   24720
tttgcttttg tctattaatt tcttccaatt gagattttaa atctcgctga gattgagatg   24780
cgttgtaatt ccttgagaac atcttgagaa acatacaga tgaggtaaaa cagcatcttt     24840
tatccaaatt aggagttaat tattattcat ttgtatcgcg accatttgct cgtacacatc   24900
ttccataaaa tggttatttt tattgcgata agtgttggca ttgacatttt gcaaatgtcg   24960
taggttaaag gggcaaatgg gctgcgtggc cgataaaaga ttccagttca acaatccctc   25020
ttcgcccccg tttaacttga aaatggcgct acacgtttct acgctatcgt gttcctgttg   25080
agtggcgcac ggttcgacca gtatcatctt gtgatatgcg gttttgacat tcatgtgcaa   25140
cggaataact tgcgggtcat cgcattcgtc ggaattaagc tttaaatggc gtccgtatgc   25200
tttccaaagt ttttcgtcgt cgaaccgcgg cactgcttgc aagtcgacgc ggggaaacgg   25260
cgctctgtac aaaacgccta aattcaaaaa ctgattgcat tgttcagct ctgtccaatc    25320 gacgcgattt ttgtaatttt gaaacagcat caggttgaac gccgcgctgg cgcgcacgtt   25380
tgtaatcact gtgtaattga tcagcttgtg ccaatactgg gcattgaaat tttcttcaaa   25440
ctcatttcta aactctggat gcgcaaacat gtgtctaatg tagtacgcgg gcggggcgtt   25500
gaacgcagtc catttgtcaa tacacttcca gtctgaatgt aacgtgttca ccaaaccggg   25560
```

```
atattcgtca aacacgagca tgtgatccga ccacggtatg ctgtgggcga tcaatttag      25620
ttcttgcacg cggccttcgc gtaagcaata caaaatgagc gcgtcgctga tcttgacaca    25680
gtcttgcatg tacgcggaca aattaacgtt ttccatacag ctcacattgt ttattagcgc    25740
cgtgttcaag tgtttgtatt tggacacata atcgtagttg atgtactgtt taatgggttc    25800
ttgaaaccat tctttagta gtatgtgact ggccactatg cgtttccaat ttaatttgtg    25860
tgcgtatttt tgctgcaccg acaacgagag gttattgtaa tttttggata tttcttccat    25920
gtccaacaag tccccaaacg cgagtataaa atcttgcgtc aaaattttt gctcagacac     25980
caacgaccag atcaaatgtg atttaaacct gttggcgatt gttatcgaca acggcgaaat    26040
tgaaataatt ttccaatcca acttgttgcg aaacacgtga ataaaatcga cgcgtccgta    26100
acattcgcgc gatatgcgct tccaaaacgt gtcatcttgc aaattaagca aatagacacg    26160
attgttggga gatttgacgg ccaattcaat tattttttata tattcttttt gctttaaagc   26220
gcgttgtagc acttgggttg gagccatgtc gactgaagct ccacgctgtt tgaagcaagg    26280
tgaccgtttt ggtcggcatg ttcaaacgtc gattacatgt ttgctttgca tcaaaatggc    26340
gtaattaatt aagaaacaac atgaaagcca tctgcatcat tagcggcgat gttcatggaa    26400
aaatttattt tcaacaagaa tcagcgaatc aaccgcttaa aattagcggc tatttgttaa    26460
atttgcctcg aggtttgcac ggctttcacg tgcacgaata tggcgacacg agcaacggtt    26520
gcacgtcggc cggtgagcac tttaatccca ccaatgagga ccacggcgct cccgatgctg    26580
aaattaggca tgttggcgac ttgggcaaca taaaatcggc tggctacaat tcactgaccg    26640
aagtaaacat gatggacaac gttatgtctc tatatggccc gcataatatt atcggaagaa    26700
gtttggtcgt gcacacggac aaagacgatt tgggccttac cgatcatccg ttgagcaaaa    26760
caaccggcaa ttctggcggc cgtttgggat gcggaataat tgccatatgt aaatgatgtc    26820
atcgttctaa ctcgctttac gagtagaatt ctacgtgtaa aacataatca agagatgatg    26880
tcatttgttt ttcaaaactg aactcaagaa atgatgtcat tgttttca aaactgaact     26940
ggctttacga gtagaattct acttgtaacg catgatcaag ggatgatgtc atttgttttt    27000
caaaaccgaa ctcgctttac gagtagaatt ctacttgtaa aacataatcg aaagatgatg    27060
tcatttgttt tttaaaattg aactggcttt acgagtagaa ttctacttgt aaaacacaat    27120
cgagagatga tgtcatattt tgcacacggc tctaattaaa ctcgctttac gagtaaaatt    27180
ctacttgtaa cgcatgatca agggatgatg tattggatga gtcatttgtt tttcaaaact    27240
aaactcgctt tacgagtaga attctacttg taacgcacga tcaagggatg atgtcattta    27300
tttgtgcaaa gctgatgtca tcttttgcac acgattataa acactaatca aataatgact    27360
catttgtttt caaactgaa ctcgctttac gagtagaatt ctacttgtaa aacacaatca    27420
agggatgatg tcattataca atgatgtcat tgtttttca aaactaaact cgctttacga    27480
gtagaattct acgtgtaaaa cacaatcaag ggatgatgtc atttactaaa ataaataat     27540
tatttaaata aaaatgtttt tattgtaaaa tacacattga ttacacgtga catttacgat    27600
ggcgaacaat aatttcactt tttatattag gacacgacgt gtatatagga aagcttaagc    27660
gtttcaataa agccatggcg tacacgctaa gcttgcccag cttgcggctc tttgaaatct    27720
gtagttttcg gggagtaccg tcgttcttca gtgccacata cgtcaacttg cgatcgtaca    27780
ctttataata cgtgttgtag ttattttttt ccagaaattc cctcataaag caatccttgg    27840
ataaagtttt tgatccgtac agttggccac accggtccat gcacaggtac acacacgtga    27900
tggcgttttg aatgacgatg cgatttctgt caacggcaac gcgcttgaat atggtgtcga    27960
```

```
cgttgtccga ttcaatggtt ccgtaaacag ctccgtctgg atttactgcc aaaaactgcc    28020
ggttaataaa cagctggccg ggaatagacg tgcccgtgat gtgtgtcagc agagctgagc    28080
agtcagccat agaggctaga gctacaagtg ccagcaagcg atacatgatg aactttaatt    28140
ccccacagca aactggcgct tttatataaa aatttgggcc attttttggcg attagataat    28200 ttttgaagat tagataatat tgagattagt taataatttg tgtgattaga taacttttta    28260
gggtattgcg cattataaat caaggtcgag ttgtataaac tgctctggcg tgtaaaactg    28320
cagacttaag ttttttgcaa acactcggtc tgaatcgcta aaatctttct gaccggtggt    28380
tagattaatt cggccagccg cgtcgcccac ataaaaagat tgttccttgt caatatgcgt    28440
aaactgtttg gccatctcgc gccacattcc cgtgtcgggc tttcgatgct catccttgtt    28500
gggcgacaca taaaacgata tgggcacgcc agtagctttt ttaatattct ctaatttata    28560
taataaatcg ctcgctttga ttttgccgga acctaaatgg gcttggttcg taaaaacaac    28620
taaatcgtag cctaattcgt acaaacgctt tagcttgtgt gcgcacggaa ggagctgcca    28680
gtcgtctggg ttttttggaa atttggaccg tgtctttgag ctaattagcg tgccgtccaa    28740
atcaaaagcc gcaattttgg ttcttttagc gccgtcatga accgcgtacg catacaaatc    28800
gggctgctgt aacgtccaca tggtgaatgc atcttactca aagtccatca attcgtacgc    28860
gtttgtgtcc aggtcgggcg ttgaaaaatt gtagcttgcc attagatcgg atagcgattc    28920
aaattttgta agcgtttgta gcgcacgttt ggcatcttgt ttaaaattac acgacgacag    28980
acagtaaaaa tattcctcga taagcatgac tacacccata tcactgttta agtgctcgac    29040
gtagttgttg catgttatgt cgcgtgtgcc gcgatacgcg tgatttcggt gaaaatcaca    29100
ccacaaccag tcggcgtgcg tgtaacaaag tcgacagcga aacaatttat cgttttccaa    29160
aaaatttaaa tactcgacag ttttgcagct tagattccgc gtttgattca ccttaaaatc    29220
gtcgtcagcc tctataatct cgggcaacag cttgccttgt tgcccatcg tatcgatcac    29280 ctcccccaag tggcccggtg ttatattaag tcgtttaaaa tcatttattg cttcctgcac    29340
gtcggcctgg taattttga ccacgggcgt ggaaatcaat tgccgttgaa gggaaataat    29400
tcgtggtgtg ggtatcggcc gcctgttgca caattccacc agcggtggag gcaagggcgc    29460
attcacagca accgttgtca tttataagta atagtgtaaa aatgcaaata ttcatcaaaa    29520
cattgacggg caaaaccatt accgccgaaa cggaacccgc agagacggtg gccgatctta    29580
agcaaaaaat tgccgataaa gaaggtgtgc ccgtagatca acaaagactt atctttgcgg    29640
gcaaacaact ggaagattcc aaaactatgg ccgattacaa tattcagaag gaatctactc    29700
ttcacatggt gttacgatta cgaggagggt attaataata acaataataa aaaccattaa    29760
atatacataa aagttttta tttaatctga catatttgta tcttgtgtat tatcgctaac    29820
cattaaaagt gctggagcca cagtgttgcg gcgagtcttt atagaagatc gttgtttggc    29880
tggaactgag cttttccttt tcctgctgcc gctaatggga gtgggcacgt actctgtagt    29940
agacggtgca acgggcaact tgagcgctac cgtcttaaat ttggccatac ttttagtgat    30000
gaaatcgcgc gttaacactt cgtcgtaaat gttacttagc agaggcgcaa cattgtgatt    30060
aaatgtctcg tttaacaagc tgtaaaactc cgaataaagc ttatcgcgca tttcgcagct    30120
ctccttcaat tctgccaaat ttgcgttggt aagcaccaca gtctgtcttt ttttgctcgc    30180
tggaattgct gcgttctcgc ttgaagacga cgatgtcgat cggtcggcca tttttttgcc    30240
cagcttttca gtgtgatcaa aaatgaacac aaaatctgcc aattcgggct tgttttcac    30300
```

```
caaatcccac atggccgggc tactaggcca ctcgggctgc ttgatcttag tgtaccaact    30360
gttaaacaaa atgtatttat tgttgttaat cactttcttc ttgcgtttgg acattttgcg    30420
ttcgtcttgc atgacaggca ccacgttaag gatatagtta atgttctttc tttccaagaa    30480
atttacaata acggccagct ggtccatgtt ggatttgttg taagagctcg attccagttt    30540
attcaacagc ttttcatttt tgcacacggc cgcagtctcc ggagattgtt gctccggcac    30600
gtttaccatg tttgcttctt gtaaaccttt gaaacaaccc gtttgtattc ttgatgatat    30660 attttttttaa tgcccaacaa cctggcaatt cgtttgtgat gaagacacac cttacgcttc    30720
gaacatttgt cggtgattac tgtgaaatgg cctaaattag ctcttatata ttctttttata    30780 cgctcaaacg acacgatgtc caacatgtgc gcgcagacgt tttctgtgtt catcgtgtgc    30840
ttgagcgtgt tgatggcttc cctgaacagc gcttgtattt cgctgcgagt caagcagtcc    30900
gaatcacacc cgcctaagtg cgtgcaattt ttgggggggca tcgttgtcta tcttttttcag    30960 agtggcgtag aaaaagtcct gcaattgcct attatcaaaa cgcgccttga cgctgcgcac    31020
aaaatcaaaa aattcaatgt aattgctgta atcgtacgtg atcagttgtt tgtcgttcat    31080
ataattaaag tatttgttga gcggcacgat ggccaggctg cgcgctatttt cgcaattgaa    31140 gcgtcgcggt tttaacatta tacgtagtc attgccaaac gtgcccggca acaacttcac    31200
ggtgtacgtg ttgggtttgg cgttcacgtt aatcaagttg ccgcgcacga cgcctacgta    31260
tatcaaatac ttgtaggtga cgccgtcatc tttccattgt aacgtaaatg gcaacttgta    31320
gatgaacgcg ctgtcaaaaa accggccagt ttcttccaca aactcgcgca cggctgtctc    31380
gtaaactttt gcgtcgcaac aatcgcgatg acctcgtggt atggaaattt tttctaaaaa    31440
agtgtcgttc atgtcggcgg cgggcgcgtt cgcgctccgg tacgcgcgac gggcacacag    31500
caggacagcc ttgtccggct cgattatcat aaacaatcct gcagcgtttc gcattttaca    31560
tatttgacac ttaaaaaatt gcgcacacga gcaccatcgt ttgataccta attgcaacta    31620
tttacaattt atcagtttac gttgaacccg ttttaatttt ttagatccgt ccttgttcag    31680
ttgcaagttg actaaatgac aaaattttc ggttctgcaa aaccgcccttt gtctgttcca    31740 cccgttgtat ttgaaaaaac ttttttttcac gcggcgacaa ctgcttgtat aatattgccc    31800
aatgtaaaca tgcaaaattt tgttactctc gtcaaaacag cggttggcgt tccattccat    31860
aattttttta ttatttatca acgatggcca ttgtaaattg tcgtcattta tacgcatcat    31920
atgatttaac aaaagctttt cgtatagcgg aacttcaatt cccttggaac attttttcaaa    31980 cgataattta atttgtttct cggttggcag catttcatgc ttgattaaca atcgcctgac    32040
ttttatagcc acgtttatgt ctttgcacag caaatgtggg ttgtcgacaa tgtaatagtg    32100
caaagcattt gttacggcaa atgcgtagtt tgatttgacg acgccctttt tcttgacggg    32160
cattgcggct tttaaaatta cttgcaagca ttgtacgaat acctctttgt gtttaaacaa    32220
taatatggac aaacatcggc gaaacaattt gtaataatta tgaaatccca aattgcaggt    32280
tttaaacttc tttgttactt gttttataat aaataaaatt tgctgaccca tgtctgcgcc    32340
cacaacttta attaaccatt tgtgcgcata ttgattgtct cgttgttccc aaccggaaaa    32400
ttgattgatc tcgagccacc ggcattggtc gtttgatacc gtcgttaacg ccgacgctcc    32460
tgcctgtttg attacgggtt ctaaaagacg aaacagcagc gtaaatttgt ttttgcgtcg    32520
gtagtatttt ggcaggcaat aatcaaaaaa atccgtaagc aattctctgc atctattaat    32580
attcgttgcg tacgaatcga gttttttcaaa aattactttg tttgtatgaa ataacgtttt    32640
gggcttctca caataataat cttcgttgta gaacagaaac ggtttgcgag aattggcacg    32700
```

```
tttgtccatg attggctcag tgtaacgatt gattcaaatc aaaattgaca acacgtttgc   32760
cgtaatgtgc accggttcgc acacgtttgc cgcgtatgta atccatgttt atttcgctgt   32820
cgcaattgat tacacgattg tgttgggcgg cgcgttttat tgaatttagg cgacgcgtcg   32880
acaactccaa aggattgtaa agcgcagatt tttccagagt aaacgagttt aagtggccac   32940
cgttgaacca ttccagagcc acgattgtgt acagcaaaaa gaatatttct ttgtcgacgt   33000
tttcaaacgc aaacttgttt tttaggcaat agtagtaaaa ttttaacgaa ttgtataaat   33060
aaaacataaa attgccattt ttaaagtaaa attctacatc cgtgacgaac aaaaggttta   33120
ctattttgtt ctccaacaag tgtgccaatt ttcttaagta caccattgaa tttttgtcgt   33180
cgtccatctc gatcaacaac acgtacggcg ttttggaatt taaaattatt ctaaaatttt   33240
cctgttgcaa cgattccaca gcgtccgacc aatatgacgc tgccacctct agacagatgt   33300
atttcttgga aaacacgtgt cgtttgataa cctcgctgat ggacgtgatc gattgtaaat   33360
acttttcaaa cgtcgcgtct tcccaaccac gcaccgacac gggcgctgtc gtgtcgggct   33420
gatgtttgaa atccaaacca ctctgaatta acttggttgt gattcgtatg ctcaactgtt   33480
gacccaacgt gtagtgatct tcgtaggcgc gctcccacat cacgttacac acaaatttga   33540
cgagatcatc aacgtctttc tgttgcaaaa ttcgccgcaa acgcgccaca tcgcccttgt   33600
accaccgatc tcggcacaca agctgtagca tttttaaatc gtgatcgctc aagctattaa   33660
ttctggttag atttatatag tcgtcaatat cctcgggcgt ggtttgcgtc atgtctgtaa   33720
aacgtgcaaa atcaaacatt tttatgttgt agtcgaatct aacaaatcca tcggcgttca   33780
cttgcacttc gcgctttaca aaacgaggta gcgtgtaatc gaacccgttt aaatagattg   33840
cgtacaaaac cagcacttca tcttccagtt tgcacgcttg cggcaaaaat tgtgtggtgt   33900
gctccaaccg ggtgacaaac atgactatgg aaaataacgc ggaattcaac agacgactag   33960
agtacgtggg cacgatcgcc acaatgatga aacgaacatt gaacgtttta cgacagcagg   34020
gctattgcac gcaacaggat gcggattctt tgtgcgtgtc agacgacacg gcggcctggt   34080
tatgcggccg tttgccgacc tgcaattttg tatcgttccg cgtgcacatc gaccagtttg   34140
agcatccaaa tccggcgttg gaatatttta aatttgaaga agtctggcg caacgccaac   34200 acgtgggccc gcgttacacg tacatgaatt acacgctttt taaaaacgtc gtggccctca   34260
aattggtcgt gtacacgcgc acgctacaag ctaacatgta cgcggacggg ttgccgtatt   34320
ttgtgcaaaa ttttcagaa acaagctaca aacatgttcg tgtgtatgtt agaaaacttg   34380
gtgcgataca agtagcgaca ttatcagttt acgaacaaat tattgaagat acaataaatg   34440
aactcgtcgt caatcacgtt gattagataa tgtccgtgtt aaatgtgata tcttagatta   34500
cgagcgcgca ataaccatag tttaatcgaa gagaatagcc gtcgccacaa tggataatta   34560
caaattgcaa ttgcaagaat ttttgacca agcgcccgac aacgacgatc ccaactttga   34620
acatcaaacg cccaatctat tggcgcatca gaaaaaggc atacagtgga tgattaacag   34680
agaaaaaaac ggccggccca acggcggcgt gcttgccgac gacatgggac tcggcaaaac   34740
gctctctgtg ctaatgttaa tcgcaaaaaa caactctcta caattgaaaa ctctaatagt   34800
gtgtcctttg tctttaatca atcattgggt aaccgaaaac aagaagcata atttaaattt   34860
taacatttta agtattaca atctttgga tgccgacacg tttgagcatt accacattgt   34920
ggtgaccacg tacgacgttt tattggcaca tttcaaattg atcaaacaaa ataaacagtc   34980
aagtctgttt tcaacccgct ggcatcgagt tgttctagat gaagcgcata ttatcaaaaa   35040
```

```
ctgcaagacg ggcgtgcaca acgccgcgtg cgctttgacc gcaacaaacc gatggtgcat   35100
taccggcaca ccgatccaca acaagcattg ggacatgtac tcgatgatta attttttgca   35160
atgtcgtcct tttaacaatc aagagtgtg gaaaatgtta aataaaaaca acgactctac    35220
aaatcgcata aaaagtatta ttaaaaaaat tgttttaaaa cgcgacaaat ctgaaatttc   35280
ttctaacatt cctaaacaca cggttgagta tgtacatgtt aattttaatg aagaagaaaa   35340
aacgttgtac gataaattaa agtgtgaatc ggaagaggcg tatgtgaagg ctgtggcagc   35400
gcgtgaaaac gaaaacgcac taagccgatt gcagcaaatg cagcacgtgt tatggctaat   35460
actgaaattg aggcaaatct gctgccaccc gtatttggcc atgcacggta aaaatatttt   35520
ggaaacaaac gactgtttta aaatggatta tatgagcagc aagtgcaaac gagtgctcga   35580
cttggtagac gacattttga acacaagcaa cgacaagata atattggttt cgcaatgggt   35640
ggaatattta aaaatatttg aaaacttttt taaacaaaaa aacattgcta cgttaatgta   35700
cacgggccaa ttaaaagtgg aagacaggat tttggccgag acgacattca atgatgctgc   35760
caatactcaa catcgaattt tgctgctttc cattaagtgc ggcggcgtcg ggttaaactt   35820
aataggcgga aaccacattg taatgttgga gcctcattgg aacccgcaaa ttgaattgca   35880
ggcgcaagac cgaatcagtc gtatgggaca acaaaaaaac acgtacgtgt acaagatgct   35940
aaatgtggaa gacaacagca tcgaaaaata cattaaacaa cgccaagaca aaaagattgc   36000
gtttgtcaac acggtctttg aagagactct gctcaattac gaagacatta aaaaatttt   36060 caacttgtag ctggtaagtc gtcatgaaca cccgatatgc tacttgctat gtttgcgacg   36120
agttggtgta cttgtttaag aaaacgttta gtaacatgtc cccttcggcc gctgcgtttt   36180
accaacggcg catggccatt gttaaaaacg gtatcgtgct gtgcccacgt tgttcgtcgg   36240
aactaaaaat tggcaacggc gtttcgattc caatttaccc ccaccgcgct caacaacatg   36300
cacgacggtc gcgttaagac gcaagcgctt cgagttttgg cccgctcgct acctccgctg   36360
tacgactcga ccgtcgatcg acacggctgc aaggtgttca cggtgcggcg ctacaacaga   36420
cgcgtaatcg actttgcggg cattcgcaac aaaacgctgg aaatcattaa aacggataga   36480
aacttgccgc tcaacacaga atgcaatgtg aaagttgtcg acagtgcatg catgcgttgc   36540
agaaaaagtt tcgcagttta ccccgccgtt acctatctgc attgcggaca ttcgtgtctg   36600
tgcaccgact gcgacgaaac ggtaaacgtg gacaacacgt gtcctaaatg taaaagcggc   36660
attagatata aattaaaata caaaactttg taacatgttg ccctacgaaa tggtgattgc   36720
cgtgttggtt tacttgtcgc cggcgcagat tctaaattta aaccttcctt ttgcatacca   36780
aaaaagtgtg ctgtttgcca gcaactctgc aaaagttaac gaacgcatca ggcggcgagc   36840
gcgtgacgac aacgacgacg acccctattt ttactacaaa cagttcataa agattaattt   36900
tttaactaaa aaataataa atgtttataa taaaactgaa aagtgtatta gagcgacgtt    36960
tgatggtcgg tatgtggtta cacgcgacgt tttaatgtgc tttgtaaaca agagttatat   37020
gaagcaattg ctgcgcgagg ttgacactcg cattacacta cagcaacttg ttaaaatgta   37080
tagtccagaa tttggttttt atgtaaatag caaaattatg tttgtgttaa ctgaatcggt   37140
gttggcgtct atttgtttaa aacactcgtt cggcaaatgc gagtggttgg acaaaaatat   37200
aaaaactgtg tgtttacaat taagaaaaat ttgtattaat aataagcaac attcgacatg   37260
tctatcgtat tgattattgt catagttgta atatttttaa tatgtttttt gtacctatca   37320
aatagcaata ataaaaatga tgccaataaa acaatgctt ttattgatct caatcccttg    37380
ccgctcaatg ctacaaccgc tactactacc actgccgttg ctaccaccac taccaacaac   37440
```

```
aacaacagca tagtggcctt tcggcaaaac aacattcaag aactacaaaa ctttgaacga    37500
tggttcaaaa ataatctctc atattcgttt agccaaaaag ctgaaaaggt ggtaaatccc    37560
aatagaaatt ggaacgacaa cacggtattt gacaatttga gtccgtggac aagcgttccg    37620
gactttggta ccgtgtgcca cacgctcata gggtattgcg tacgctacaa caacaccagc    37680
gacacgttat accagaaccc tgaattggct tacaatctca ttaacgggct gcgcatcatt    37740
tgcagcaaac tgcccgatcc gccgccgcac caacaagcgc cctggggccc ggtcgccgat    37800
tggtaccatt tcacaatcac aatgcccgag gtgtttatga acattaccat tgtgctaaac    37860
gaaacgcagc attacgacga agctgcgtcc ctcacgcgtt actggctcgg cttgtatctg    37920
cccacggccg tcaactcgat gggctggcac cggacggcag gcaactcaat gcgcatgggt    37980
gtgccctaca cgtacagtca aatgttgcgc ggatattcat tggcgcaaat taggcaagag    38040
cagggaatac aagaaatcct aaacacgatc gcgtttccgt acgtgactca aggcaacggc    38100
ttgcacgtcg attcgatata catcgatcac attgacgtgc gcgcttacgg ctatttgata    38160
aattcatact ttacgtttgc ctattacacg tactattttg gagacgaggt aatcaacacg    38220
gtgggtttga cgagagccat cgaaaacgtg ggcagtcccg agggagttgt ggtgccaggc    38280
gtcatgtctc gaaacggcac gttgtactcc aacgtgatag gcaactttat tacgtatccg    38340
ttggccgtcc attcggccga ttactccaaa gtgttgacca aactttcaaa acatattac     38400 ggttcggttg tgggcgtaac gaataggttg gcttactacg aatccgatcc cacaaacaac    38460
attcaagcgc ccctgtggac catggcgcgg cgcatttgga atcggcgcgg cagaattatc    38520
aactataatg ccaacacggt gtcgtttgag tcgggtatta ttttgcaaag tttgaacgga    38580
atcatgcgca tcccgtcggg caccacgtcc acgcagtcgt tcagaccgac cattggccaa    38640
acggctatag ccaaaaccga cacggccggc gccattttgg tgtacgccaa gtttgcggaa    38700
atgaacaatt tgcaatttaa atcgtgcacg ttgttctacg atcacggcat gttccagcta    38760
tattacaaca ttggcgtgga accaaactcg ctcaacaaca caaacgggcg ggtgattgtg    38820
ctaagcagag acacgtcggt caacaccaac gatttgtcat ttgaagcgca aagaattaac    38880
aacaacaact cgtcggaagg caccacgttc aacggtgtgg tctgtcatcg cgttcctatc    38940
acaaacatca acgtgccttc tctgaccgtt cgaagtccca attctagcgt cgaactagtc    39000
gagcagataa ttagttttca aacaatgtac acggccacgg cttcggcctg ttacaaatta    39060
aacgtcgaag gtcattcgga ttccctgaga gcttttagag ttaattccga cgaaaacatt    39120
tatgtaaacg tgggcaacgg cgttaaagcc ctgtttaatt atccctgggt aatggtcaaa    39180
gaaaataaca aagtgtcttt catgtcggct aacgaagaca ctactatacc atttagcgtt    39240
ataatgaatt ccttcaccct tatcggcgaa ccagctttgc aatactctcc atcaaattgc    39300
tttgtgtatg gaaacggttt caaattgaac aacagcacgt ttgatttaca atttatttt     39360 gaaattgtgt aattatattt agggagaatg tgatattcaa aagactgact gttaacacaa    39420
aagactgata ttgttgttgt tacaaaatag ataataaaac aaaaaataaa ttaaatatta    39480
tttatttatt aaactgttta attttaatgc taacgcgtac aaatcacgct gttccgacgt    39540
ggacatggaa ttgcgcagaa aagtcttgat agtgtcgatt tcttcgccgt catccacttc    39600
catatatttg attcttcct cgatttgcat ttccaagttt gcgtattctt gcaaataata    39660
atctagtcgt gggcgaccct cgccaatttt aaataataca ttatccgaca ccaaatgcca    39720
gcgagtgact gtgcgctcca tcatcctggc acttttaat gtgaatatta aaggttgtt     39780
```

```
gcatatatat cgttaaacgt ttatgtttac tttcacgtta gctcgtttca ttgatgtaaa    39840
catttagttt tataacagcg tcggtaattt tattttttaa agtaaacaga ccaaaatcaa    39900
aggtgtcttc gacaggtacg attattttcc cattgacact gttttcgtgc acagatataa    39960
ttttatcacc gtttattatt ttgcccaaac acacgtactc gtttcttctc aagccaacta    40020
tttctaaaca attcactttt ctattatcgt gtacgcaatt aaaagtaaac gaagcgctac    40080
aattgtcgta ttctattaca attctgcggc atttataaaa tttattaatg ttgacgcaaa    40140
ttccatgcag cgcatccatt tcgtactgca aatgcggcgc aattaaaaaa tttcctcgtc    40200
gttgttaaca atcttgggcg ctaaaaagca cgccaacacg cccacgtctt taatgcaata    40260
ttccaatttg aacggcagtt cctcggacat gtatattgtc acggtgggcg ccaaaggagc    40320
ggctttagca aaatgacaca agtaatcgcc cgcaaaagtg tgcgttacgg tttgctttgc    40380
tttgagaacg gaaaagtttt cgttgtccgc gctcatctgc acgtccgccg agccaatgtc    40440
gccatttgct ctaaactgca gacccttctt ggaacacgac acaataatat cgtggtcgaa    40500
ttgcgtcatg tctttgcaca cctgcgcaaa ctcgacgctc gacatgtgga cgacgcaatc    40560
gtaatcgcta tccggaattc ccaaatgttc cacgtcgatg cacatcaact tgagcgtgta    40620
cgtgcagatt ctattgtcgt tgttaacac gaacgccatc acatcgccct gatcttccgc    40680
tttcatcagt acagagctgc gctcgttaac gcatttgaca attttactta aactgtttat    40740
ggacacgttg agcggcacgt tgcggtcaca tctatatttt ttgaaaccct cggcgtgtag    40800
ttgcaacgac acgagcgcga catgcgaggt gtccataacc tgcatgctta cgcctcgatt    40860
atcacaatca aaagtagcgt gcggcagcag atccttaaaa gtttccacca gcctcttcaa    40920
aactgcgccg gttttaaatt ccgcttcgaa catttttagc agtgattcta attgcagctg    40980
ctctttgata caactaattt tacgacgacg atgcgagctt ttattcaacc gagcgtgcat    41040
gtttgcaatc gtgcaagcgt tatcaatttt tcattatcgt attgttgcac atcaacaggc    41100
tggacaccac gttgaactcg ccgcagtttt gcggcaagtt ggacccgccg cgcatccaat    41160
gcaaactttc cgacattctg ttgcctacga acgattgatt ctttgtccat tgatcgaagc    41220
gagtgccttc gacttttcg tgtccagtgt ggcttgtttt aataaattct ttgaaaatat    41280
tgtcgggtgt attattaaat agcatgtatg gtatgttgaa gatgggataa cgcttggcgt    41340
gcgggtcgtc atgatttcca ccgcgcacca catatttgcg ctcaattta tcaaaattgg    41400 actggcgaga caaaaacgag acgggcgaca ggcatatttg ggcgtgcgta ccatcttcgg    41460
ccatccactc ggtcaggtct tcgctgcggt taaacacacc tttctgaccg tgaatgccac    41520 atattttat tccttccaaa tcgttggtgg acgtgactat gactatttta agcataacgt    41580
tgtcgccgtt aaccaccatg ctggcgtcga gtttttcaat ttttttgattt ttaatttgtc    41640 taaagtaaac gtacactttg taaacgttaa aattgccgtt ggtgcacgtt tcaattttgt    41700
accgtcggcc gtcgtacacc caattaatct ttgcgttgct caccaacaca ccggccatgt    41760
acagcacaag tccgtcgtct agcgcaacgt aattttttgtc gctactattc gtaaacttta    41820
ctaaacacga ctgcttgggg ccgaccacaa gcttgcccctt caatttgttc actttgttgt    41880
tgtataaaca aatgggcagc gcaatgtgcg gaatgtacgg atcttcggcg gtcatgagtt    41940
tattgtctcg caccaacgtc cacaatttaa acattttatt gttgagcaaa atggacttgt    42000
ttaccgccac agagtagcca tttggtaaac ccgatacgca attttcctct ttgtactcaa    42060
acacgggcat ggcattcttt agattggtta gggacacaat caatttgggt acgggcgtgg    42120
tatgaaataa atgtataaaa ttacgataat aatactgctc caacttggac atgagcgatt    42180
```

```
tgacgtcatc gtttctacg atcgtacact gaataatggg attatagtat atagaatgtt    42240
tatagtggta ttcgtagggt gtcaacaata cgttaatgtc ggcttcgttg ttcacccgca    42300
actttttttt gatgcatatc attccttcgt gatgattaac gtaaagtatt ctgtctgtaa    42360
tcttcaattc gatgggcgcc atgtttcttt tcatagtgta cacgataaac gacgtgtttg    42420
atttaaaca ttttaaattt gtgggtctat cattaaacgc gatcagcaac gagtcgtctt    42480
gaacgtcgtt gaggtcgtcc acgaacgcga ccagattgtg ttttagcaaa tattgaaatt    42540
tttgcgcaac catttcgtag tccacgttgg gcaaacatgc gttgcggcaa aggaaaaact    42600
ttttgcccgc cacggtcatt tcgccgtgaa aaaaactgcc aataaatttc acaaaatcct    42660
tttttgctt caacattttc tggcgcatgc tgtcgttggt gattcgcgcc acctcgttgc    42720
cgacgcgata ttttaacacg ggcaacgaaa tttcaatatt gttattgctg ctgttgtcct    42780
gttgattggg aaagactttg cgttgcttgc taaaagtttt cgatacgcaa tatatgagac    42840
gcccgttgac tatacaatcg acaatctttt tcgactcttt gttgtacaag acgctttgaa    42900
ttttacgacg cttgttcgcc accgtgtacg cgtcgtcgtc ggccgtcttg tcgagaactc    42960
gttgatagtt ttgcaaaatt gtcgaagtta ataacagttc tatcaaatag gcgtgcttgt    43020
atacaatttt gttggccaaa ctgtctatag aatagtttat gtcgtgattc ataataattt    43080
ttatgtgttc cacgagttgt tgcttgtgaa gcgtgttgta ttcgaagaga aaatcgagcg    43140
gtttccattt gccgctgttg gccagatatg tttccagcac agaatttaaa tcttccgtca    43200
ctacgtaatc gctagcgtac acgtctcgag caaacaggac gtcgtcttgt ttgtcgtaaa    43260
ctagttggat tgcgcgattg atgtgcttct cttgatccac gttgccgtac aaaaacatgc    43320
gtttgcaatg tttggcgtat agcttgtcgt agaaattgtg caccaaaacg ttgttgttca    43380
tcattatgtt gggaaaactc aaaaatctgc cgtccagcat aaaagttccg ttaatattgt    43440
tgtttgcgtc gacatcgtcc gtttctctaa attgcttgtc taagcgcgtg ccgaatataa    43500
cgggcacaca tttatgcatt acgcaactga gctgttcatt aagagcgcaa cacaaataag    43560
acttgcgttc ttgaatagcg caaaaaagca tacgttcatt gctgtttgta gcgcaatcaa    43620
aagtatattt taatttgtat ttatttttcaa ttctatcgta caactcgttg aaatcttgaa    43680
ccacgtccgt catcgtgaag cgattactgc gcactaatta tgtctaaacg tgttcgtgaa    43740
cggtcggttg tttcggatga aacggccaaa cgcattcgac aaaacgaaca ctgtcatgcc    43800
aaaaatgaat ctttttttggg gttttgcaac ttggaagaaa ttgattatta tcaatgttta    43860
aaaatgcaat acgttccgga ccaaaagttt gacaacgatt ttattttaac agtgtacaga    43920
atggccaacg tggtgacgaa acaagttaga ccgtataaca gtatcgacga aaagcaccat    43980
tacaacacgg tgcgtaacgt gttgattta ataaaaatg cgcgtttagt gcttagtaat    44040
agtgtcaaaa agcaatacta tgacgatgtg ttaaaattga aaaaaatac agacttggaa    44100
tcgtacgatc cattgattac ggtcttttta caaattggcg aatctgtaaa tgaagaaata    44160
caaaaactca gaaaagcttt ggtcaatttt tttactaata acccgacaa gtcggatata    44220
aacaacccag atgtagtttc gtatcaattt attttggca gagtacaaaa attgtataac    44280
agggcaatta aacaaaaaac taaaactata attgtaaaac gtcctacaac tatgaacaga    44340
attcaaatag attggaaaac tctttccgaa gacgaacaaa aaatgactag acaagaaatt    44400
gccgaaaaaa ttgtaaagcc ttgttttgag caatttggca ctatattaca catatacgta    44460
tgtcctttaa aacacaaccg aattattgtc gagtatgcaa actcagagtc ggtacaaaaa    44520
```

```
gccatgactg taaatgacga cactcgattt acagttacag agttttccgt ggttcagtac    44580
tacaacgtgg ccaaaacaga aatggtgaac cagcgaattg acataataag caaggacatt    44640
gaggatttaa gaaacgcttt aaaatcttac acataaatta aaatatcgaa caaaggaaaa    44700
aaacaattgt aacaaaaata atttacatta aaatttacaa gttttttcct agtgtcgtac    44760
ttttttacaa tgcgtctgtt gtccgtcgag cattgcaaac atattgtgga cggcgcaaaa    44820
tagcaaacaa aaggcacgtc cgcgctctcc cacgctattc taaaacgatg aatccatatt    44880
aatttttcat tgtcgccaaa cgtcgctccg ctggcctcct tccaataaca aatactcaga    44940
aacacaaaca tgtacaattg ctgtcgcggc gttaattgtc gctgttttc caaatagtct    45000 attatgggaa acaaacactt gtcacaacac aaatactcgt taattgtcac aaccgacaag    45060
cacatttggc aaaatgcgtc gcaattttg tacggacgag attctatgcg aagttcgttg    45120
tccatgacgt cttgggtcca cttttcaac aagacacttt tatatttgtg atttgtacaa    45180
ctttggtacg tgttagagtg ttttgataa gctttgataa gtttaaaact gttggagtaa    45240
ggccacgtca ttatgttctg cacctttgt ttaaaagaca gaaattacta tatgttcaaa    45300
ctatttaaag attattggcc aacgtgcacg acagaatgcc agatatgtct tgagaaaatt    45360
gacgataacg ggggcatagt ggcaatgccc gacactggca tgttaaactt ggaaaagatg    45420
tttcacgaac aatgtattca gcgttggcgt cgcgaacata ctcgagatcc ctttaatcgt    45480
gttataaaat attattttaa ctttcccca aaaacactag aggagtgcaa cgtgatgctt    45540
cgagaaacta aagggtttat aggcgatcac gaaattgatc gcgtttacaa acgcgtttat    45600
caacgcgtta cacaggaaga cgccctggac attgaactcg atttaggca ttttttttaaa    45660 atgcaatcat gacgaacgta tggttcgcga cggacgtcaa cctgatcaat tgtgtactga    45720
aagataattt attttgtata gataataatt acattatttt aaatgtgttc gaccaagaaa    45780
ccgatcaagt tagacctctg tgcctcggtg aaattaacgc ccttcaaacc gatgcggccg    45840
cccaagccga tgcaatgctg gatacatcct cgacgagcga attgcaaagt aacgcgtcca    45900
cgtaacaatt attcagatcc cgataacgaa aacgacatgt tgcacatgac cgtgttaaac    45960
agcgtgtttt tgaacgagca cgcgaaattg tattatcggc acttgttgcg caacgatcaa    46020
gccgaggcga gaaaaacaat tctcaacgcc gacagcgtgt acgagtgcat gttaattaga    46080
ccaattcgta cggaacattt tagaagcgtc gacgaggctg gcgaacacaa catgagcgtt    46140
ttaaagatca tcatcgatgc ggtcatcaag tacattggca aactggccga cgacgagtac    46200
attttgatag cggaccgcat gtatgtcgat ttaatctatt ccgaatttag ggccattatt    46260
ttgcctcaaa gcgcgtacat tatcaaagga gattacgcag aaagcgatag tgaaagcggg    46320
caaagtgtcg acgtttgtaa tgaactcgaa tatccttgga aattaattac ggcgaacaat    46380
tgtattgttt ctacggacga gtcacgtcag tcgcaataca tttatcgcac ttttcttttg    46440
tacaatacag tcttgaccgc aattcttaaa caaacaatc cattcgacgt aattgccgaa    46500
aatacttcta tttcaattat agtcaggaat ttgggcagct gtccaaacaa taaagatcgg    46560
gtaaagtgct gcgatcttaa ttacggcggc gtcccgccgg gacatgtcat gtgcccgccg    46620
cgtgagatca ccaaaaaagt ttttcattac gcaaagtggg ttcgaaatcc caacaagtac    46680
aaacgataca gcgagttaat cgcgcgccaa tcagaaaccg gcggcggatc tgcgagttta    46740
cgcgaaaacg taaacaacca gctacacgct cgagatgtgt ctcaattaca tttattggat    46800
tgggaaaact ttatgggtga attcagcagt tattttggtc tgcacgcaca caacgtgtag    46860
catcgccagt atttaacagc tgacctattt gttaaacaag cattcttatc tcaataattg    46920
```

```
gtccgacgtg gtgacaattg tatccacaat catgaaaaaa gtagcgcttg gaaaaattat   46980
cgaaaacaca gtagaaagca aatataaaag caacagtgtg tcgtcgtcat tgtcaacggg   47040
cgccagtgca aaattgagtt taagcgaata ttacaaaact tttgaagcaa ataaagtggg   47100
ccagcacact acgtacgacg tggtcggcaa gcgagattac acgaaatttg acaaattggt   47160
gaaaaaatat tgacatgctg cgatcaatca tgcgacgttt caagagtaca acaatctca    47220 gcaaaaaacc ctccgattat tatgtagtgt tatgtccaaa gtgttatttt gtgacgtcgg   47280
ccgaagtgag cgtggctgaa tacatagaaa tgcataaaaa ttttaacacg aaattcgccg   47340
atcggtgccc taacgatttt attgtgacca actctaaaag ttggaataat catgaaaatt   47400
gttctgccct attttaccct ctgtgttaat aaagtttgtt gtttgtattt tgtggtttta   47460
tttatttacg ctagatattg ggtttaaggt tcttagaaat agagttgtat tttccctacc   47520
aaaagggatt tgagcttcat ataaatacaa ttttcgctcg acaagcggtt tatttcactc   47580
ggaggtatta tatcaggcag tcgaacgtgc gcgatgaaac atcccgttta cgctagatat   47640
ttggagtttg atgatgtagt gttagatttg actagtttaa tattttttaga gtttgataac   47700 gctcaaaatg aagagtacat tatttttatg aatgtaaaaa aggcgtttta caaaaacttt   47760
cacattactt gtgatttgtc gcttgaaacg ctgaccgtgt tggtgtacga aaaagctcgc   47820
ctaattgtga aacaaatgga gtttgagcag ccgccaaact tgttaatttt tatcagtttc   47880
aacgcgaccg acaacgacaa ctccatgata atagacttgt gttccgacgc gcgcataatc   47940
gtggccaaga agctgacgcc cgacgaaacg tatcatcagc gcgtgtccgg atttttggat   48000
tttcaaaaac gtaactgcat acctcggccc ccaatcgagt cggacccaaa agtgcgagac   48060
gccttggatc gtgaactaga aataaaacta tacaagtaga aaaaaattaa tttattaata   48120
gttgtaataa ttatcttcgt cctcatcttc gctggtgtca taatgcggtg gtgtgtttgt   48180
gttttgtttt aatcgtttgc gcgtcgacac cacttcgccg ataggaaatt ttttggattt   48240
cgcattaaat gcccgcttag cgacgcgccg tttacgacta ctaaacatgt tgacgcgctc   48300
gtcgtcttca gtgtcataat ccgtgctagt gttttcgttg ttattttcta tgagacgatc   48360
gtttgattta gttttcgtag aattgtccgc gttatcgtcg ctttcgtcga tgtcgtccct   48420
aactatctcg taggcggctt tgcgcggaat ccaagaattt tgcaatgtat ctattttaac   48480
gtacttttct tcgagcgctt ttctagcttt atgcatagca atgtcttcgt cgccgccgtt   48540
cattttatga tactttgtaa acgtctcgac gaataacttt ttggcgcgag gaggcatttt   48600
ttcattgtat aacatatcgg gaatttgata cattgtaatt agaattaagc aagttcgtct   48660
tcggttgtac tgtattcggt ttctgtatct gtagtggaat cctctgtact agtagtagtg   48720
tcgctattgt tggcgtcagg ccttggctgc catttaccgt ctatcaacat gtattttttc   48780
ctaacagcac aacatgctag cttggtagct atctgtgtcg acttatattt ttgtaaacta   48840
cgatcgtaga atttttcaaa tatcctctta ccgttatagg gaaggttttg ataatattta   48900
ggcaacatat caataaaaga caatataaaa actttgtgtt tgtgttttat ttatcacata   48960
aaatggacgt ctggcaagaa tcacaaccaa tattagtgtt ttttttctta cattacgaga   49020
ttcaacttga tactaaaatt aattattaat taaattaaat taaattttga agcatttttt   49080
cgctatcgtt ttcagactca aaattatcga cgctatcgct atgaaaagcg taatatttgt   49140
tggctttgag atattctata ttttgctcat ttttaacaat aaacacgcga ctcttttcgt   49200
cgcgtctcac cataacaccg tttttacaaa tggaaatgta tttgtaaaac ggcaacagag   49260
```

```
cgtcgcgagt ttttttaagt aacagctttt gctccgctgt ggcggccaca aatattttta    49320
cgggcccgtc gtaattaatg tttaaattaa aattttttaag tcgacgctcg cgcgacttgg   49380
tttgccattc tttagcgcgc gtcgcgtcac acagcttggc cacaatgtgg tttttgtcaa    49440
acgaagattc tatgacgtgt ttaaagttta ggtcgagtaa agcgcaaatc ttttttaaat    49500
aatagtttct aattttttta ttattcagcc tgctgtcgtg aataccgtat atctcaacgc    49560
tgtctgtgag attgtcgtat tctagccttt ttagttttc gctcatcgac ttgatattgt     49620
ccgacacatt ttcgtcgatt tgcgttttga tcaacgactt gagcagagac acgttaatca    49680
actgttcaaa ttgatccata ttaactatat caacccgatg cgtatatggt gcgtaaaata    49740
tatttttaa ccctcttata ctttgcactc tgcgttaata cgcgttcgtg tacagacgta     49800
atcatgtttt ctttttggga taaaactcct actgagtttg acctcatatt agaccctcac    49860
aagttgcaaa acgtggcatt ttttaccaat gaagaattta aagttatttt aaaaaatttc    49920
atcacagatt taaagaagaa ccaaaaatta aattatttca acagtttaat cgaccaatta    49980
atcaacgtgt acacagacgc gtcggtgaaa aacacgcagc ccgacgtgtt ggctaaaatt    50040
atcaaatcaa cttgtgttat agtcacagat ttgccgtcca acgtgtttct caaaaagttg    50100
aagaccaaca agtttacaga cactattaat tatttaattt tgccccactt tattttgtgg    50160
gatcacaatt ttgttatatt tttaaacaaa gctttcaatt ctaaacatga aaacaatctg    50220
gttgacattt cgggcgctct gcagaaaatc aaacttacac acggtgtcat caaagatcag    50280
ttgcagagca aaaacgggta cgcggtccaa tacttgtact cgacgtttct caacacggcc    50340
tcgttctacg ccaacgtgca atgtttaaat ggtgtcaacg aaattatgcc gccgcggagc    50400
agcgtaaagc gctattatgg acgtgatgtg gacaacgtgc gtgcatggac cacgcgtcat    50460
cccaacatta gccagctgag tacgcaagtc tcggacgtcc acattaacga gtcatctacc    50520
gactggaatg taaaagtggg tctgggaata tttcccggcg ctaacacaga ctgcgacggt    50580
gacaaaaaaa ttattacatt tttacccaaa cctaattccc taatcgactc ggaatgcctt    50640
ttgtacggcg accctcggtt taatttcatt tgctttgaca aaaccgtttt gtcgtttgtg    50700
tcacaacaaa tttattattt gtacaaaaat attgacgcaa tggaggcgtt gtttaaatct    50760
acaccattgg tttacgcgct gtggcaaaaa cataaacatg agcagtttgc acagaggcta    50820
gagatgttgt tgcgtgattt ttgcttaatt gccagttcaa acgctagtta tttacttttt    50880
aaacagctta cacagctcat agctaacgaa gaaatggtgt gcggagatga agaaatattc    50940
aatttaggcg gccaatttgt agacatgatt aaaagcggtg ctaaaggcag tcaaaatctg    51000
attaaaagca cgcaacaata ccgacagact ttaaatacag atattgaaac tgtgtcttca    51060
cgagccacca ccagttttaaa tagttacata tcttctcaca ataaggtaaa agtgtgtggc    51120
gccgacatat atcataacac ggttgtgtta cagagcgtgt ttattaaaaa taactatgtt    51180
tgttacaaaa acgacgaacg tacaatcatg aatatttgcg ctttgccctc tgagtttctg    51240
tttccagaac atttgctcga catgttcatt gaatgataat ataaatagag cgcatttgat    51300
tgcatgcaat cagtgtttta ttaattttag agcaacatgt acgataaatt tatgatctat    51360
cttcacttga atgggctgca cggagaagca aaatactaca aatatttaat gtctcaaatg    51420
gattttgaaa atcaagtagc cgatgaaatc aagcggtttt gtgaaactcg tctgaaaccg    51480
gcaatcagtt gcaacacttt aactgcggaa agtctcaata cgctcgtaga cagcgtagtc    51540
tgcaaaaatg gactgttaaa tccttacgcc aaagaagtac agtttgcttt gcaatatctt    51600
tttgacgatg acgaaatatc caaacgagat caagatggct ttaaactatt tttattacat    51660
```

```
aattatgaca ggtgtgaaaa tatggaagaa tattttttaa ttaacaattt tagcatagca   51720
gactacgaat ttgaagacat gtttgaaatt gttcgtattg attgtagaga tctgttatta   51780
cttcttgcta aatataatat gtaattaaaa ttttgtttgt tttattaaaa tcctggatta   51840
aaaaatgacg aataatttga tttgcgtgca cgccaacaag attcttcgtc attatgatca   51900
atgcgtgcat caagtttatg cttttgtaat tggcttctga ccactttagc catttgagcg   51960
tatctgcatt cgtcgtctag agtttcaaac accagatcgg cgcaattata aaatccttca   52020
cccacgggat ctatgcgctg ccaacgcaca tacattacaa attgatttga cctgtacggt   52080
attactacgg gtatagaata gactagactg ttgtcacata atgaatcgcc cggatttgga   52140
attaaatttg aatcgttacc acctatgtat tctaattcgt tccaagttat tggattgcga   52200
cgatcccagt ttgatttagt aataaacact tcaaaataac tgggctcgtg tatggctgtt   52260
ggacaaaaat gaacattcat ctgataaacc ggttgatagc gatttaaata tagcgtattt   52320
ggcctccagt tgttaaaagg ttcgtccatt ccgcttttat caccaaacac agaattgcga   52380
tcgtttgaac cggcaccgca aagtgtgtgc ggcacaaccc tttgttcgat taggtcaaaa   52440
tcgtcataat taggaccggc cacagccgcg tattccatat actgttgaaa catgtattgc   52500
gctgtggaag cggccgcccc ggattctaaa tcgagagctc gatatttata atagactgat   52560
ttgtaagcat tgcggcacgc ggcgtcggga atgttatcgc cattgtcggg ccaataaaag   52620
tttccatctt taaaacattt atattgacgg gccgtcggca cggacaaata gccgtgagag   52680
cgcactgccg gcgcgtgaat cgcagcaaac aatgcaatta ataatgcaat cattatgatt   52740
atacttatag aacactaatc ggaataataa ccgctgtcgt aatcttggtc aaaaacgtta   52800
tgttgaaaca taataacacc ttacagtaac atacaataaa acaacatagt atcgtatata   52860
attataaact ttatttttc atttataca aacaaaattt atacgtattg ttagcacatt   52920
gagtgtcatt ttcgctgtct gaactatcac aatcatcgtc atcatcatca tcattgtcat   52980
cgtcgtcgtc acgtttgcgt ttgacactgc atttttttg gttaattttc actaacactg   53040
gttcttttcg atcgtacaat tgattctgca tgtacttttg catgatcgcg gtaaaacact   53100
ttgcaatttt atcctttgt tcgtcgccaa atatttccag caactcgttc ataaatgtgc   53160
acaaaatgcc catgtgtttt atccagctga ttcgcatttt cactggatcg aacaaacgca   53220 agggggtacgc ttttctgtt accttgcctt cgatgtctat caaaaggtac gggatacgat   53280
ctccgttgcc gggcacaaaa tccgtgcctt tgttaaccaa aatttctcta caatgcctag   53340
ccaccgtaat cacgcgtctt ttgggtgacg gaccctcatt atcgtcagtt gatttgcgtt   53400
ttttgcccgg gttatcgtta taggtcatac taaagctgta gtcggtcaac gattttgatt   53460
tggcaaactc atcatagtat tcataaaaac tagtctgtaa actttgcaaa catttgtcca   53520
tgtccaaatg acgcaatatt tgttccactg ccgtcctaaa cgcgattctc ataaaaacgg   53580
gcatatcctt tttaactaac caacccttgt atacgatttt attctcactg ttgagatagc   53640
aatatttttt ctttttaat agtattaaaa cttttcattaa attttcaaat gccattttgt   53700
aaccgtccgt gaatgagtta ttaacgcgtg tctcaacatg tgtgcatatt tgttttaatg   53760
tgtcggtttc gttggatatt tcgttatagt taaatgtggg caaacaaat gtagaatctg   53820 tgtcgccgta cacaacttta aaagtgatgc tgcccagatt gaattttct aaaatctcag   53880 ggtcgttgct caaccttca atcagagaaa tggccagccg caactgattg cgaccaactc   53940
tagtgatgta gtttgcaagc actttgtaaa aaatgccata ataaccgtat atgctattgg   54000
```

```
cggtgcgctt cacggaattt tgtttttgat cgtacagatc gtacaagaat gccgattcgc    54060
tttgattgtc gcgattcttt ttaaatttgc acctttcgct taacaatttt aatagcaatt    54120
taacaactat tgcacgcgaa ttgtggttca aatacacgtt gccgtcttcg cataaaatta    54180
aattggacaa acaagcacaa atggctatca ttatagtcaa gtacaaagaa ttaaaatcga    54240
gagaaaacgc gttcttgtaa atgcctgcac gaggttttaa cactttgccg cctttgtact    54300
tgaccgtttg attggcgggt cccaaattga tggcatcttt aggtatgttt ttagaggta    54360 tcaattttct tttgagatta gaaatacccg ctgcggcttt gtcggctttg aattggcccg    54420
atattattga cagatcgttt ttgttaaaaa aatacgggtc aggctcctct ttgccggtgc    54480
tctcgttaat gcgcgtgttt gtgatggctg cgtaaaagca cgccacgcta atcaaatgcg    54540
aaatattaca tatcacgtcg tctgtacaca acgatgcaa tatacattgc gaatatacag    54600
aatcggccat tttcaatttg acaaacaatt ttatcggcaa catgcaatcc tgcacgttgt    54660
acttggcaat cacgtccagc cgtcgagtgt tgtacatctt gaccatttcg gtccaaggca    54720
aatcgatttt gttttcaccc aaatagtaac tactgattgt gttcaattga agttttcaa    54780 ctttatgctg attagaatcg ctgctgaaaa atttatacaa atcaatgtga atgtaatagt    54840
taaaataata cgtgtccact ttgttgccca acttgtttat aaacagcttt gtcgtcggcg    54900
ccgcagccgg caaatcgtaa cgctttaata gcattttggt tttattcaat cgtccaagta    54960 tatgggcag atcaaatacg tctccgttaa atccaaaat cacatcggga tttgtaattt     55020
ttatcatgtc aaaaaacgct gtaatcatgt cgatttcatt ttgaaacatg accacatacg    55080
tgtcatcgtc ataggtctct ggaatctggg tcggcagctt gtgatacata aaacaaaatt    55140
ttgcatactc gtcgtttttg tacaccacaa atcctataga cattatgcaa tcaaccgatg    55200
ctttcgacat gttgtggccg tccgaatgag tctcaatgtc atagcacgac aaaacgggca    55260
tgatgccgct ggttaaagtc atttcatcga ccaactcaaa gtcttcatta aaatgttgca    55320
aattaaacat gcgcgtcgtc gatccaccga catagttatt ttggcagcgt gtgtttct    55380 tgaatcgcat ataggcgcct tccacaaacg gcgtttgcat gtgtacgcga ttaacgttgt    55440
gaagaaactt gtccaaacac gccgcgttgt ccgatggcgc tgctttgttt ctttcgtatt    55500
taatcacgtt tatcttgttc aaataatttc cttccacgcc cggcgccaca aacgtggtgt    55560
agctgatgca cttgttgcgg caagacggaa atatgtgctt gtcgtagcat tgttgtaag    55620 aatacaaatt tagttttact ttaaagtaaa actgcagcac tcgttctttg atatttgtat    55680
tacaaaatgc aaacaagcaa ccttgttttt catcgtaatg caaacgaatg atacgaaacg    55740
tatcggctga agtaatattg aattctcctg gttttgcata ttctgcaaag cgcgttttga    55800
gttcattgta aggatatatt ttcattttta aatatgcagc gatggccaa atatggaggc    55860 acagacgtca acacgcgcac tgtacacgat ttgttaaaca ccataaacac catgagtgct    55920
cgaatcaaaa ctctggagcg gtatgagcac gctttgcgag agattcacaa agtcgttgta    55980
attttgaaac cgtccgcgaa cacacatagc tttgaacccg acgctctgcc ggcgttgatt    56040
atgcaatttt tatcggattt cgccggccga gatatcaaca cgttgacgca caacatcaac    56100
tacaagtacg attacaatta tccgccggcg cccgtgcccg cgatgcaacc accgccaccg    56160
cctcctcaac cccccgcgcc acctcaacca ccgtattaca acaattatcc gtattatccg    56220
ccgtatccgt tttcgacacc gccgccaaca cagccgccag aatcgaacgt cgcgggcgtc    56280
ggcggctcgc aaagtttgaa tcaaatcacg ttgactaacg aggaggagtc tgaactggcg    56340 gcttttattta aaaacatgca aacgaacatg acttgggaac ttgttcaaaa tttcgttgaa    56400
```

```
gtgttaatca ggatcgtacg cgtgcacgta gtaaacaacg tgaccatgat taacgttata    56460
tcgtctataa cttccgttcg aacattaatt gattacaatt ttacagaatt tattagatgc    56520
gtataccaaa aaacaaacat acgttttgca atagatcagt atctgtgcac taacatagtt    56580
acgtttatag atttttttac tagagtcttt tatttggtga tgcgaacaaa ttttcagttc    56640
accacttttg accaattgac ccaatactct aacgaactt  acacaagaat tcaaacgagc    56700
atacttcaaa gcgcggctcc tctttctcct ccgaccgtgg aaacggtcaa cagcgatatc    56760
gtcatttcaa atttgcaaga acaattaaaa agagaacgcg ctttgatgca acaaatcagc    56820
gagcaacata gaattgcaaa cgaaagagtg gaaactctgc aatcgcaata cgacgagttg    56880
gatttaaagt ataagagat  atttgaagac aaaagtgaat tcgcacaaca aaaaagtgaa    56940
aacgtgcgaa aaattaaaca attagagaga tccaacaaag aactcaacga caccgtacag    57000
aaattgagag atgaaaatgc cgaaagattg tctgaaatac aattgcaaaa aggcgatttg    57060
gacgaatata aaaacatgaa tcgccagttg aacgaggaca tttataaact caaaagaaga    57120
atagaatcga catttgataa agattacgtc gaaaccttga acgataaaat tgaatcgttg    57180
gaaaagcaat tggatgataa acaaaattta aaccgggaac taagaagcag catttcaaaa    57240
atagacgaaa ctacacagag gtacaaactt gacgccaaag atattatgga actcaaacag    57300
tcggtatcga ttaagatca  agaaattgcc atgaaaaacg ctcaatattt agaattgagt    57360
gctatatatc aacaaactgt aaatgaatta actgcaacta aaaatgaatt gtctcaagtc    57420
gcgacaacca atcaaagttt atttgcagaa aatgaagaat ctaaagtgct tttagaaggc    57480
acgttggcgt ttatagatag cttttatcaa ataattatgc agattgaaaa acctgattac    57540
gtgccgattt ctaaaccaca gcttacagca caagaaagta tatatcaaac ggattatatc    57600
aaagattggt tgcaaaaatt gaggtctaaa ctgtcaaacg ccgacgttgc caatttgcaa    57660
tcagtttccg aattgagtga tttaaaaagt caaataattt ctattgtacc acgaaatatt    57720
gtaaatcgaa ttttaaaaga aaattataaa gtaaaagtag aaaatgtcaa tgcagaatta    57780
ctggaaagtg ttgctgtcac aagtgctgta agcgctttag tacagcaata tgaacgatca    57840
gaaaagcaaa acgttaaact tagacaagaa ttcgaaataa aattaaacga tttacaaaga    57900
ttattggagc aaaatcagac tgattttgag tcaatatcag agtttatctc acgagatccg    57960
gctttcaaca gaaatttaaa tgacgagcga ttccaaaact tgaggcaaca atacgacgaa    58020
atgtctagta aatattcagc cttggaaacg actaaaatta agagatgga  gtctattgca    58080 gatcaggctg tcaaatctga aatgagtaaa ttaaacacac aactagatga attaaactct    58140
ttatttgtta aatataatcg taaagctcaa gacatatttg agtggaaaac tagcatgctt    58200
aaaaggtacg aaacgttggc gcgaacaaca gcggccagcg ttcaaccaaa cgtcgaatag    58260
aattacaaaa atttatattc attttcatct tcgtcatact tcaacagtcc caacacgttc    58320
atgttgtgat tctcgccgtt ttcgacagtt acgtaaatag ttactttgat taaattatct    58380
tccagcagca ttgagatttg attgaaatcc gcacatagct tttgtagcga atccgcttct    58440 tttttttat  ttgtgttgac gtagaaaaca gatttgttcc atttgcccaa gtcggaagag    58500
gtagaacagt catccgaatc ggcaatgttc aactcgtcgc ttttaaactg cacaataaac    58560
ttgttatcgc ccatgtcatt ttcttccaat tcgcttttta acacatttac attgtacgaa    58620
gcaacgtgtt tgttcgatcg actaatgttg atctttgcgt ttgtgcaatt ttgcaaattt    58680
gaatatgctt cgctttcttt agcctcgcac aattcgatgc gcgtagagtt gaccacgttc    58740
```

```
caattcatgt acacgtttga tccattaaaa atttgttgac actttatact gtaaatggta    58800
aagatttggt tttcattgtc ttttaaatat ttaaacacct cattgatgtc gtcagacccc    58860
tttatattgt tcttgaatag atttattagt gttttcgcat tgacagaaca ttccacttga    58920
accacgtcgg gatcgtcgtt gagattttg tacacaacct caaaaacaac tttgtacaaa    58980
ccgctgttga ttttcttgta gataaatttg tactttacaa taatattgac gccatcttca    59040
ttttcaaaat gtttgttagt caaatagtcg ctcatggggg ttgcagtttc aatttccatt    59100
tcacattctt tgtattcgtt gatctgaatc atttgactaa actttgtttt cacataattt    59160
aaactaatgt catagcactt gccttcttcc atgtctttga aagattgcga atcgccgtag    59220
tattcttgaa ttttgttgtc ggacattatt cgaaaagtgt aatggtattc attatcgata    59280
ctcaacgtca ttttgctcat caatttacca ctaatccttt tgtaattttc tctaatcttc    59340
ttggggctac tggccatagc catgcgtttt ataagcggct caccgctact ttctccagac    59400
aaagatcttt tggtcgccat attgctgttg tcgatatgtg ggaatctatc cgatggcaaa    59460
tactgaatgg cgacgaaatc gaagtgtcgc cagagcaccg ttcgttagcg tggagggagt    59520
tgattataaa cgtggccagc aacacgccgc tcgacaacac gttcagaaca atgtttcaaa    59580
aagccgattt tgaaaatttc gactacaaca cgccgattgt gtacaattta aaaacaaaaa    59640
ctttaacaat gtacaacgag agaataagag cggctctgaa cagacccgtc cgatttaacg    59700
atcaaacggt caatgttaat attgcgtacg tatttttgtt cttttatttgt atagttttgc    59760 tgagcgtgtt ggccgtcttt ttcgacacaa acattgcgac cgacacgaag agtaaaaatg    59820
ttgcagcaaa aattaaataa actcaaagat ggtttgaaca cgttcagcag caagtcggtg    59880
gtttgcgctc gctcaaaatt atttgacaaa cgcccaacgc gcagacctag atgttggcga    59940
aaactatcag agatcgacaa aaagtttcac gtttgccgac acgttgacac gttttttggat    60000 ttgtgcggcg gaccgggcga gttgccaac tataccatgt cgttgaaccc gctttgcaaa    60060
gcgtatggcg tcacgttgac aaacaactcg gtgtgcgtgt acaaaccgac agtgcgcaaa    60120
cgcaaaaatt tcacaaccat tacggggccc gacaagtcag gcgacgtgtt tgataaaaat    60180
gttgtatttg agattagcat caagtgtggc aacgcgtgcg atctggtgtt ggcagatggc    60240
tcggttgacg ttaatggacg cgaaaacgaa caagaacgtc tcaactttga tttgatcatg    60300
tgcgagacgc agctaatttt aatttgcctg cgtcccggcg gcaattgcgt tttaaaagtt    60360
ttcgacgcgt ttgaacacga aacgatccaa atgctaaaca agtttgttaa ccatttcgaa    60420
aaatgggttt tatacaaacc gccttcttct cggcctgcca attccgaacg ctatttaatt    60480
tgtttcaata aattagttag accgtattgt aacaattatg tcaacgagtt ggaaaaacag    60540
tttgaaaaat attatcgcat acaattaaaa aacttaaaca agttgataaa cttgttgaaa    60600 ataacgtg tgtataaaaa gccagcggct tcaaatcagg catcattcaa catggattcg    60660
ctagccaatt tgtgcttgaa aaccctgcct tacaagtttg agccgcctaa gttttttacga    60720 acaaatatt gcgacgcatg tcgctacaga ttttttaccaa aattttctga tgaaaaattt    60780
tgtggacaat gcatatgcaa catatgcaac aatccaaaaa atatagattg tccatcatca    60840
tatatatcga aaattaaacc gaagaaagaa acaaagaaa tatatattac cagcaacaag    60900
tttaataaaa cgtgcaaaaa cgaatgtaat caacaatcaa accggagatg tttaatttcc    60960
tattttacaa atgaaagttg taaagagctc aattgttgtt ggtttaataa aaactgttac    61020
atgtgtttgg aatataaaaa gaatttatac aatgtaaatt tgtatacgat tgatggtcat    61080
tgtccttcgt ttaaagccgt tgttttttca tgtataaaaa gaatcaaaac gtgccaagtt    61140
```

```
tgcaatcaac ctttattgaa aatgtacaaa gagaagcaag aagagcgttt gaagatgcag    61200
tcgctgtacg caacgttggc cgatgtagat ttaaaaatat tagacattta cgatgtcgac    61260
aattattcta gaaaatgat attgtgtgct caatgtcata tatttgcacg ctgttttgt      61320 accaatacca tgcaatgttt ttgtcctcga cagggttata agtgtgaatg tatatgccga    61380
cgatctaaat attttaaaaa taatgtattg tgtgttaaaa gtaaagcggc ttgttttaat    61440
aaaatgaaaa taaaacgtgt tccaaaatgg aagcatagtg tagattatac tttcaaaagt    61500
atatacaagt taataaatgt ttaattttaa ggatattgtt atggaataaa ctataaaatg    61560
aatttgatgc aatttaattt tttgatactt tccacagacg gtagattcag aacgatggca    61620
aacatgtcgc tagacaatga gtacaaactt gaattggcca aaacgggggct gttttctcac   61680 aataacctga ttaaatgtat aggctgtcgc acgattttgg acaagattaa cgccaagcaa    61740
attaaacgac acacgtattc gaattattgc atatcgtcaa ccaacgcgtt gatgttcaat    61800
gaatcgatga gaaaaaaatc atttacgagt tttaaaagct ctcggcgtca gtttgcatca    61860
caatccgtgg tcgttgacat gttggctcgt cgcggcttct attattttgg caaagccggc    61920
catttgcgtt gttccggatg ccatatagtt tttaaatata aaagcgtaga cgacgcccaa    61980
cgccggcaca aacaaaattg caagtttctc aacgcaatag aagactattc cgtcaatgaa    62040
caatttggca aactcgatgt tgcggaaaaa gaaatactgg ctgccgattt gattcctccg    62100
cggctaagcg ttaaaccttc ggcgccgccc gccgaaccgc taactcaaca ggtctccgaa    62160
tgcaagtttt gttttgatag agaaaaatcg gtgtgtttca tgccgtgccg tcacctggct    62220
gtgtgcacgg aatgttcgcg tcggtgcaag cgttgttgtg tgtgcaacgc aaaaattatg    62280
cagcgcatcg aaacattacc tcagtaaaca ttgcaaacga ctacgacatt ctttaaaaat    62340
aagctatata taaatattgc attgtatgac aaaaaaatta ttaacctact gcaaagtaaa    62400
acttgtaaaa ggcttttcaa aaaaatttgc gagtttattt tgtcgctgcg tcgtgtcgca    62460
tctaagcgac gaagacgaca gcgacggtga tcgctattat cagtataata acaattgtaa    62520
tttcatatac ataaatattg taaaataaaa gacatattat tgtacataat gtttttattgt   62580 aattaaatta atacaccaat ttaaacacat gttgatgttg ttgtgaataa ttttaaatt      62640 tttactttt tcgtcaaaca ctatggcgtt gctttcgatt agtttttcg ttagcatttc       62700 atctaaaaaa tcaaactgtt tgcccggcgc gtttagggat tctatggtgt agtcgggcgt    62760
gtcgctgttt agatattggt ccacttcgcg cattatgtcc aagacgttgt tctgcaaatg    62820
aatgagcttt gtcaccacgt ccacggacgt gttcatgttt cttttttgaa aactaaattg    62880
caacaattgt acgtgtccac tatacaattc ggcttaatat actcgtcggc gcaatcgtat    62940
ttgcaatcca atttcgtgtt caacaaattg gtgatgatat ctttgaacgt gcacgttttc    63000
aatttgtcct tatcggccaa cgcaagtttc aattcgctct gtaaagtttc taaaattttg    63060
tctttattgt tgtcaaattc gtgcgtgttg cgttccaacc acaatttgaa cggctcgtcg    63120
acaaaaatgc tgcgcaacac ctcgtacaac tgtctgccta acgtgtacac ttgctcgtat    63180
tctttcatgc tgacctcttt gctaacgtac attactaaaa aatctacaag tattttcaaa   63240
catttgtaat aggcgacgta ttttgattta agttttaaac cgtccaccgt gtattcgtcc    63300
acgttcgcat cgaccacttt tcgattatta tcgccgcttg ttgccggcgc gtcggcctgt   63360
tcggttttaa ctatatccgg ttcaatattt aaagttttcaa aagatttaat ggcattcata    63420
aaatcatctt tttgctttgg cgtggtcaat ggtaaatcta tcgaggagtt gtcgtccgtg   63480
```

```
tgctcttcgg gcacgctgtt cagacgtaac gtaatctttt tgggatcgtc ttcatcgggt   63540
atcaaatcgg ctttaatttt attagaattg agcaacgaca tggtggtcgc ttgtaaattt   63600
aataaattaa ttaaagactg aaattgtata ttgcacaaat ttattttcat ttttattgat   63660
cttactatta atacgctggc agttggtatg cttcatccat ttttgtgact agaaaatttg   63720
ctaaaaaact gagctcgtcc tgtgttaaaa cgttgtcgtc cacgaatcta tgcaatgtaa   63780
atgttacact gacattgttt aacaatgcat gtattaaaaa atcaacctgt cgcctactga   63840
gtttattaga agagtcgacc gtttctacta gtttgtagat tttgttattt tcaatttcat   63900
tgtttaaaaa catgttaact actcgtttga gtttaagcga aaaatccttg tccggataga   63960
cttgttcgca cagccaattg ctaagagtgg ttttgaccac ggacaccttg gtggtgaacg   64020
tcgtcgattt gaccagttcg gtgaaaaagt ttttcattaa attggacatt ttaacaaaca   64080
cttatcaatc tattgagctg gtattttgt ttagaatcgc atcaagcgct tgctcgatct   64140
ccaatttttt tcggacgctc ttagctttat gactcggtat gtcttctacg gtagactcgg   64200
tgttcttact tataatggcc gggctgacga taataaacac gagaaacaat atgagcagat   64260
acaaaaagat gctgttttcc ttttgtcat acactaggct aaatatggcc agtgcgccca   64320
acaacaaata taaattcatt tttattccct tactctattc gttgcgatag tacaacaacg   64380
attctcccga cgaaccggac gaattgcgat tatgctgcgc gtcgtcgtcg tcgttgttgt   64440
tctcctcttc gctgctcgtt tcgtctaaac ctatattgta tttgttcaag taatgtttgg   64500
tgcttgcgga ggattcgtgg ttcattaatt tggccacttt ttgtaaaggc acgccgctat   64560
tgtataggtt actgctcaaa taatgtctta tcatgttgct gcgcggccgt tccatctcga   64620
cgcccgactc ttcaaggagt cgcctgaaat ctttgaaggg cgtcgaggtg ttttagata   64680 tttgcaaaat ggtcgggttt cgtgaataaa tctcgcgtgc caattccaac ggtttcattt   64740
tgatgttgtt gagtgtgtta ttacgactgc gttttcgctt taaattaatc gtgtcgctgt   64800
gcagttttcc tcttttaatt agcacgttga gatcgtccac gctgagttgg cgcgcttcgt   64860
tgattcgcat acccgtccct aacatgatgc aaaacactat cgcgcccta attagaccgc   64920 ggtcgtgaac ataatcgctg ttgagcattt taattttatc attaataaaa tttaatatgg   64980
tatctattac gttttaagc attaaattct tttccttttc cctgatattt ttgagctcct   65040
tgtcgcgcgg cagcataacc atgcggggaa ttttgtattc gggcaagttc atcatgttgg   65100
tgtaaaagtt tatagtcaac tgtagtgttt cttggtgac cgagcgaagt tcgagcatgc   65160
gcctgcacag ttcttgggga tcaatgagaa gtgtttggtt ttctatcgag tcaaactcct   65220
tgtccaacga gtacgacatg tcttccaggt gaacatcgtc taccgagcag tacacaattt   65280
taatgaatcg agacttgtaa ctttttaaag tggtgggcgc aaacggtttg gggaacatgt   65340
acttgctcca cagactgttg ttttcacct cgtcgggcgt gcatcgttgc cgatcggtgg   65400
ccaaatcgaa cacggactcg aaccggggag cggattgaat tttattttc caagaattaa   65460 aattgttttc gttgcgaaca ttaaaaccgt tcattgtggt taatcaaatt tattaaaaac   65520
aaaaggagaa tcggtgtcaa tactatccga atattgttgt tgttctctta atattacgaa   65580
ataatatatt acatcagca gtaagaataa agctataaaa gcgactacac taattaaaat   65640
tataattccc gccgacacgt tgctcgtcgt gttgtcatag cccaccatgt cgtttattgg   65700 catttttgtga acgggctcgc taaattgttg cggttcgctg gcagtatcgt cgttgagcgc   65760
caatttcaac gggatgtatt ccacctttc gtggttgccc aaccgatagt agggcacgtc   65820
caaattcatg tttacaactt atttgctaac aggaatttat gcaacaaaag tggtttggct   65880
```

```
ttgatgagac gcaatttgaa atacttgctg catttacgct taagattgta ttccatgcgg    65940
gcggcggtct tgtagtcgta cgcgctcgcg ctgtgataca cgagccgtaa attggttgcg    66000
ttgcgcaaac acttggcgcc ttgtttgttc gaatgctgtt ttatgcgtct gttaagattg    66060
ctcgtgatgc ccgtgtacaa ttttccattg tcttgccgca gaatgtacac gcaccacacc    66120
ttgttggtgt acagagtcgt cgccatgatt atgcagtgcg ccctttcgtg ttcggccgag    66180
tggcgttagg cgcagccgcg gcaataatcg cgttggcgtc cttgttgtaa tttatttgtt    66240
gaaaaataaa acgtcttaga gtttcgtttt ggaacgccaa ttcggtcaag ctctcctggc    66300
aagcgctttt ggtcaaatga gcggccggcg aattgaccgc gttggcggcc gacgttaaga    66360
aggtggcgtt ctggaacatg ctgggctgct tgccggctcg cgtcgccagc tcggccatgt    66420
aattgaatat gttggcagac gcagatagcg gcgccaaaaa cgcaacgttc tcttttaaac    66480
tcatgactcg cgccctgttt ttttcgttca gcacgtagtg gtagtaatcg ccgccgccgg    66540
caaacagatc gtcaatcacg gcgttgatca gatcgttgat catgttgatg tgcggaaagc    66600
gacgcgactc gactgcgctc tgtatgtttg gcggcagagt ggcgtgcttg agcaacagag    66660
tcatgtaatt gttggccagc tgctgattga aaggtaacgg aatgggaatg ttgcacgtca    66720
ccgcttccgc caccatgtac tggacggcca gactgagttg tttggcggcc tcggccaaag    66780 cgtcttttgcc caacatatca gcgccaccgt tgtaaaactt ttgcgcgtac gccggcagcg    66840
aatttagcac aaacgatggc tgaaatatat ttgaatcgct cgacagggac tcggccgcgt    66900
tgctctgtcc caactctttt tgcaaccgaa tcaggtggcg tatcatggtt tcctccgatt    66960
caaaccgctt taccacgttt acgctgattg ggttcgtgtc gatgcacatg tcacgaatag    67020
tgtttataaa aagaatcatg agaggactaa gttctgacat gtcattgcac ctgtaatatc    67080
taataatctt ttgaacaaaa tccacacatt tgttgtacca aatagattca ccggcgtcga    67140
gcgtcggttc tttgctcttg ttgtacggtg caatcgctac cgagtttgtg ctgttgctgc    67200
ggctcgtgta atccatcctg ttgtcgcgcg tggcgacggt cgtaggcacc gtcgccggcg    67260
gcacgtaccc gggcgcgttg taagtttgcg cgctggtgaa tatggccgtt gccggattag    67320
agggatacct cagcggcgga ggggtgttgt aataaaaatt gccacgttca tctgtcatac    67380
tttttatttg tactcttatg attacaaaac tcaatatacg gattacttat aatatagttg    67440
ttgtgacaaa aaagcgataa taaaattaac aaaattatca acaagttaat catggaaaat    67500
ttttcaacgt tgaataacaa caacaaaatg gcgcaggtca acagcaccgt ttgaaaactg    67560
acgcgccgac acaaaatgct ttcgcaattt ctaaaagcca cattaaacga attttcacct    67620
ttgatataat cacgcagttc ttttttacaa cattcgtcgc acaaaattaa cacctttata    67680
atgaggccgt cggtgtgtat cgtttgaaat gtccgcggtt gactgcctgg atgaaattca    67740
aacgagtacc cagtggacac gtgtatctgt gcaaataat gggctaatat cgaggcgccc    67800 gttttttaa cctttacttt tgatatttta ataacattaa tgttgttatt tgcgtaatca    67860
gagtttttat tgtggtgatc atcgtacaaa taatgaagca acagttcact atcgtattta    67920
atcttgttta gcgttgtcaa gttttgtttt cttaggcgtt ggagcgtctc cgtcgtcgat    67980
attttcttcg aaatcgagtc caacaacgtc ggcgtttcct tcttgctcat cgatagcggc    68040
ggcggaggcg gcctctccgt cgtcgtcatt ctcggtttct acagtgcgtt tgggcgacga    68100
cgtgtgtaca gcacgtccg tcttactatt atcggaccgc caaattttg tttgaaataa    68160 catttggccc ttgttcaact ttatttcggc gcagttaaac attattgcat taagatcata    68220
```

```
ttcgccgttt tgcaccaaat tgcacaaaac accatagttg ccgcacgaca ctgtagaata    68280 ggcgttttg  tacaacaatc tgagttgcgg cgagctagcc accttgataa tatgggcgcc    68340 aacgcccgt  ttttttaagt aatattcgtc ttcaattata aaatctagta cgttttcatc    68400
ttcactgttg atttgggcgt tcacgatgat gtctggcgta atgttgctca tgcttgccat    68460
ttttcttata atagcgttta ctttaatgta tttggcaatt tattttgaat ttgacgaaac    68520
gactttcacc aagcggctcc aagtgatgac tgaatatgtg aagcgcacca acgcagacga    68580
acccacaccc gacgtaatag gctacgtgtc ggatattatg caaaacactt atattgtaac    68640
gtggttcaac accgtcgacc tttccaccta tcacgaaagc gtgcatgatg accggattga    68700 aattttgat  ttcttaaatc aaaaatttca acctgttgat cgaatcgtac acgatcgcgt    68760
tagagcaaat gatgaaaatc ccaacgagtt tattttgagc ggcgacaagg ccgacgtgac    68820
catgaaatgc cccgcatatt ttaactttga ttacgcacaa ctaaaatgtg ttcccgtgcc    68880
gccgtgcgac aacaagtctg ccggtcttta tcccatggac gagcgtttgc tggacacgtt    68940
ggtgttgaac caacacttgg acaaagatta ttctaccaac gcgcacttgt atcatcccac    69000
gttctatctt aggtgttttg caaacggagc gcacgcagtc gaagaatgtc cagataatta    69060
cacgtttgac gcggaaaccg gccagtgtaa agttaacgaa ttgtgtgaaa acaggccaga    69120
cggctatata ctatcatact ttccctccaa tttgctcgtc aaccagttta tgcagtgcgt    69180
aaatgggcgc cacgtggtgg gcgaatgccc cgcgaataaa atatttgatc gcaacttaat    69240
gtcgtgcgtg gaagcgcatc cgtgcgcgtt taacggcgcc ggacacacgt acataacggc    69300
cgatatcggc gacacgcaat atttcaaatg tttgaataat aacgagtcac aactgataac    69360
gtgcatcaac cggatcagaa actctgacaa ccagtacgag tgttccggcg actccagatg    69420
catagattta cccaacggta cgggccaaca tgtattcaaa cacgttgacg acgatatttc    69480
gtacaacagt ggccaattgg tgtgcgataa ttttgaagtt atttccgaca tcgaatgtga    69540
tcaatcaaac gtgtttgaaa acgcgttgtt tatggacaaa tttagattaa acatgcaatt    69600
cccaactgag gtgtttgacg gcaccgcgtg cgtgccagcc accgcggaca atgtcaactt    69660
tttacgttcc acgtttgcca ttgaaaatat tccaaaccat tatggcatcg acatgcaaac    69720
ctccatgttg ggcacgaccg aaatggttaa acagttggtt tccaaagatt tgtcgttaaa    69780
caacgacgcc atctttgctc aatggctttt gtatgcgaga gacaaagacg ccatcgggct    69840
taacccgttc accggcgagc ctatcgactg ttttggagac aacttgtacg atgtgtttga    69900
cgctagacgc gcaaacattt gtaacgattc gggaacgagc gttttaaaaa cgctcaattt    69960
tggcgatggc gagttttaa  acgtattgag cagcacgctg accggaaaag atgaggatta    70020
tcgccaattt tgtgctatat cctacgaaaa cggccaaaaa atcgtagaaa cgaacatttt    70080
tcagcgacgt atattgacaa atatactaca gtcggacgtt tgtgccgacc tatatactac    70140
actttaccaa aaatatacta cactaaactc taaatatact acaactccac ttcaatataa    70200
ccacactctc gtaaaacggc ccaaaaatat cgaaatatat ggggcaaata cacgtttaaa    70260
aaacgctacg attccaaaaa acgctgcaac tattccgccc gtgtttaatc cctttgaaaa    70320
ccagccaaat aacaggcaaa acgattctat tctaccgctg tttaacccct tcaaacgac   70380 cgacgccgta tggtacagcg aaccaggtgg cgacgacgac cattgggtag tggcgccgcc    70440
aaccgcacca cctccaccgc ccgagccaga accagagcca gaaccgagc  cagaacccga    70500 gccagagtta ccgtcaccgc taatattaga caacaaagat ttatttttatt catgccacta    70560 ctcggttccg tttttcaagc taaccagttg tcatgcggaa aatgacgtca ttattgatgc    70620
```

```
tttaaacgag ttacgcaaca acgttaaagt ggacgctgat tgcgaattgg ccaaagacct    70680
atcgcacgtt ttgaacgcgt acgcttatgt gggcaatggg attggttgta gatccgcgta    70740
cgacggagat gcgatagtgg taaaaaaaga agccgtgcct agtcacgtgt acgccaacct    70800
gaacacgcaa tccaacgacg gcgtcaaata caaccgttgg ttgcacgtca aaaacggcca    70860
atacatggcg tgtcccgaag aattgtacga taacaacgaa tttaaatgta acatagaatc    70920
ggataaatta tactatttgg ataatttaca agaagattcc attgtataaa cattttatgt    70980
cgaaaacaaa tgacatcatt ccggatcatg atttacgcgt agaattctac ttgtaaagca    71040
agttaaaata agccgtgtgc aaaaatgaca tcagacaaat gacatcatct acctatcatg    71100
atcatgttaa taatcatgtt ttaaaatgac atcagcttat gactaataat tgatcgtgcg    71160
ttacaagtag aattctactc gtaaagcgag tttagttttg aaaaacaaat gagtcatcat    71220
taaacatgtt aataatcgtg tataaaggat gacatcatcc actaatcgtg cgttacaagt    71280
agaattctac tcgtaaagcg agttcggttt tgaaaaacaa atgacatcat ttcttgattg    71340
tgttttacac gtagaattct actcgtaaag tatgttcagt ttaaaaaaca aatgacatca    71400
ttttacagat gacatcattt cttgattatg ttttacaagt agaattctac tcgtaaagca    71460
agtttagttt taaaaaacaa atgacatcat ctcttgatta tgttttacaa gtagaattct    71520
actcgtaaag cgagtttagt tttgaaaaac aaatgacatc atctcttgat tatgttttac    71580
aagtagaatt ctactcgtaa agcgagttta gttttcaaaa acaaatgaca tcatcccttg    71640
atcatgcgtt acaagtagaa ttctactcgt aaagcgagtt gaattttgat tacaaatatt    71700
ttgtttatga tagcaagtat aaataaccga acaaagttaa attttttttca tttacttgtc    71760 accatgtttc gaatatacccc taataacaca actgtgcccg ttgtttagt gggtgacatt    71820 attcaagttc gttataaaga tgtatcacat attcgctttt tgtcagatta tttatctttg    71880
atgcctaacg ttgcgattgt aaacgaatat ggacctaaca accagttagt aataaaacgc    71940
aaaaacaaat cgctgaaaag cttgcaagat ttgtgtctgg acaaaatagc cgtttcgctc    72000
aagaaacctt ttcgtcagtt aaaatcgtta aatgctgttt gtttgatgcg agacattata    72060
ttttcgctgg gtttaccaat tatttttaat ccggcttttgc tacaaagaaa agtgccgcag    72120
cgcagcgtgg gatatttcat gaattcaaaa ttggaaaggt ttgccaattg tgatcggggt    72180
catgtcgttg aagagaaaca attgcagagt aatttgtata tagattattt ttgtatgatt    72240
tgtggtttaa atgtttttaa aataaaagaa taacaattta cacattgttt tattacatgg    72300
ataatgttgt ttgtttgaca ttaaaggtta tcatggtgca atgattaata ataaaacaat    72360
attatgacat tattttcctg ttatttttaca atataaaatc acaccaattg tgcaaagttt    72420
tattatttgt ttgtcgacgg tcgaggggtc agcggcgtgt gcaacaataa aaaacatgaa    72480
gctgttaaca attttgattt tatttttattc atttttttatg aatttgcaag cgctaccaga    72540
ttaccatcaa gcaaataggt gtgtgttgct gggaactcgc attggatgga acgatgacaa    72600
tagccaagat cccaacgtat attggaaatg gtgttaaata aaagtgaata tatttttttat    72660 aaaatttttt atttaaaatt ccaagtaatc cctgcaaaca ttaaacactg taggtatttt    72720
taaatcttgc cacatgcgaa caacgcacgg cctgtcgtcg aacaccgcta ttacattata    72780
ttttcctctg atatagttgt taaacaattt taattttaat aaataatctt tacaagtatc    72840
gtctgaaggc ctcataaaca atttatatga tttaatatca aaatacttttt caatccagtt    72900 tcgagtgggc tgttcacaaa ttacgcttct cccgctcata aacacgataa ttgcgtcgtg    72960
```

```
gcaatttgcc aaatacttaa cgcaagtaat aacgtctaag cgggcttcat cttgagcaac    73020
tctattatca aaatcataaa acgatctatt tgtgggcaaa gctactgtac cgtctaaatc    73080
acataataca gcgcgggaa atttgtcgcc gacaggaacg taatattcga aattatttac    73140
ctttagaaac ttttatatt gcttttaat agtttctgga tttaatggaa atttatcaga    73200
gcgtttataa ttgcgttcaa gagccgtttc caaagaaacg tccatcaaac gcgttaaaaa    73260
atggtaatta tgcgttgcgg ccattttttg ccacatgtcc accgattgag tgttcaaatt    73320
agtgtcgctg acaaccacgt tggcaccaca ttttgcggct tttaaaaact gttcaatgca    73380
cattttggta atttgttctt ctttagtttg tctacatttc cgcgattggt tatagaaagc    73440
gttcagtttt gtataatcgc cgtttaaaaa caacttaacg cgcacgtcgt ctctgttgat    73500
ttctgtatag cctttaaac ttttggcata cgtgcttttg cccgaacccg aaatgcctat    73560
caacaccaac aattgttttg aagaaggcaa tttaattgtt ggagcaagtt tattatttaa    73620
tgcctgctta gtcgatacaa attttataat attttgatc atttaatttt tttcaggctc    73680
ggttaatttt aaaaattcgc tctccacatc gatcgtttgt gctttacgac atctgtacgc    73740
taaacatttc cacggcaaag tttgcaccag ttcgttgaaa cgctgttgat tcaaagtcaa    73800
acccgacacc ataatattta ttgtagactc gttggtgaac gtgtttctag catcaacgta    73860
cggtttaatg acacttttta aatgcgggaa aagagctaga aagtcatcgt gttcgccatt    73920
tataacaagc tgcgccaatt tagtaggatt ttcagcacgg ctctgatttt tgtgcatgtt    73980
caaatacacg tcgcttttaa tcttgcatag tggcgcgttg ttttatcgt aaactacaaa    74040 tccttcttcc aaattttca actgggccgc gtgttcgaca cattcttgca cagacgtaaa    74100
ctcgtaacat ttggggtatt tgcaaaacgg caaattggaa cagtaaaaat aatcgcccgt    74160
ttcgttgttt ctgcttgcca ataccacaa cgttggctgt tcatcgtaaa cggttacaat    74220
tctgttgtgt ttgcttgtta actcaaacat gtgagtcgac gcgcagtcta atattcgtt    74280 acacaacgct tgaaattgat tgtgggcctc gtcaagttga agagcttgca aaactaaacg    74340
tttaaacgtc acgtctgaca cgcaaaggtt ttctgcaaaa gcacttcctc gggtgctggc    74400
atgccattcg ccgttgtact tgtagatttt aattaaactt ccgtcgattt tttcgtaaaa    74460
cttaaaattc tccttcgatt ggaacagttt gtgatgagca tcttcgccgc cgatattttg    74520
tagcaattct tgaaaattaa agaaacgatc gaaagaacgc gacacaacgg cgtacgtgcg    74580
gctgttaaga attaaaccgc gacattccac gaccacagga tgatctcgat cgcgttcaaa    74640
cgattcgtaa ttaagaacca tcaaatcgtg ttccggtataa ttttaattt tgactttaaa    74700 cttgtcacaa agatttttca ctccgccgtt tgcaagtaga cgcgaaacgt gcaacatgat    74760
tgctgtttaa taatgcatac caatgctaaa ctgtctatta tataaagtgc agtgataact    74820
ttgttatcaa cgcgttcgat gccgacatat ataaacgcaa tgtaacagtt tttgctagta    74880
ccatcgcata caacattatg aatacaaggg gttgtgttaa taataataaa atgatatttta   74940 tgaatgcttt gggcttgcaa cctcaaagta aattgaaaat tattgcacat aaaatactag    75000
aaaaatgtaa acgtgacgcg tacacgcgtt tcaagggcgt aaaggcgatc aagaatgaac    75060
taaaaacata caatcttacg ttgcaacaat acaacgaggc gctcaatcag tgcgctttaa    75120
acgatagccg atggcgcgac acaaataatt ggcatcacga tattgaagaa ggtgtgaaaa    75180
taaacaagag acatatatat agagttaatt ttaattctaa aacccaagaa attgaagaat    75240 attattcacat taaagtagaa tgttatgtaa acagttaatt aatctacatt tattgtaaca    75300
tttgtggtaa tagtggcgtt ggttatacat ttatatgatt gtaatgttgt gtactcgttt    75360
```

```
tgtaataaat ttttgtgttt aatcaattca atatttttat ttgataaaac cttattttcg   75420
ctactcaatt tggcgttttt agacgcaagt tttgcgtaat cgtcattgag cgattttagc   75480 gcctttcag ttgtaattcg tttcagttgc aattctttaa aagatttatg catgttgttg   75540
tagtcgcttt taattttgtc taacttttct tgcatagaaa cgcttgtttg ttgtaatttg   75600
tctaaatcta attgttgttt aatgttgagc tgcgtttgtt cggcaatgtc tacctgtagt   75660 tttttagta tcgcttgtgc ttcagacagc atagtgtcgt cggcatttgc gttgttgtct   75720
tctgcgtcgt ccaacagact tttttcaaac aacacactgg ccaaagaggc cgcatcaaaa   75780
ttagcgttta ttttattcca ttgtgcgaca ctcgacgcgc tgcatttaat cacatccaca   75840
acgtttcggt ttacgctgta aacgttgaaa tgcaaacttt caaccctaca caagggacat   75900
ggtacttttt ttcgttttct aatcttgcgt atacacattg agcataattg atgtttgcac   75960
gtgtctagtt ctaatacggg tattatagtc aatctgtcta ttggttgcag aaaataattt   76020
ttaatttctg caaccgaaaa acaaatgttg cattgcaatt taacaaactc cattttaga    76080 cggctattcc tccacctgct tcgcctgcaa caccaggcgc aggacctgcc actgcgccgc   76140
cgcccagagt agcgttagga tttgctcttg gtataaagtc gttgcgcaaa aagttgttt    76200 ctgaattgat tatttggtat cccaaaaaca gcggaacgta cgtcgggtat tcttcgtatc   76260
cgctaagcgt tctgtccagc tcacgtgtgt cgccttcaaa tttcaaaacg tttctaattt   76320
gcaaacgatt gggttgactt ctcataatgt cactgcttct tatcgggttg tacaactcgg   76380
ggccgtcggg cacagacgcg accagacccg tttcgtcaat tatacacgtg gcgcaatttc   76440
taaacctcaa ttcctccgtg tcgatttgca agtactcggg cgctactgcg cgtcgaatca   76500
aattttgcaa aaatccactg taattgttaa ataattgatc gccagcaccg cctcgaagcg   76560
ctcgggcgtt ggtcacgtca aagaaacgca attcgtctcg cgacacccgc gaacaaaacg   76620
tgttcgggtt tgtggtgtcc agaatgcttt ttgtagttgc gtaaacgctg tgtataacgc   76680
gttgcgtgtt gcttgtgaaa ccttcggtat attttagatt gtcgcatata gtgttaactg   76740
cgttttcgtt gttatatatc aaatgaaaga ttagctgttc ggcttgcatc atactgttta   76800
gattaaacac gtcttggtaa ttggttgcgc ttggaattaa aattcgcttg atacctcttt   76860
ctttatttcc aactaaatgc ctagcgatcg tcattttgaa ttgattgtcg tcttcgtcga   76920
aaatgggcaa aaccattttt gacattttaa aacgttttat gaggtggttg ttgcaaataa   76980
accatccatc gtcatgatac gcgtcgggcg aacacggcga tttgtatgtt atgcacgcgt   77040
cgaacgacac gatggacgcg aaaatgcagc gattaactct catttgtcgc ggcgccatac   77100
ccacgggcac tagcgccata ttgttgccgt tataaatatg gactacggcg attttgtgat   77160
tgagaaagaa atctcttatt caataaattt tagccaagat ttgttgtata aaattttaaa   77220
ttcttatatt gttcctaatt attcgctggc acaacaatat ttcgatttgt acgacgaaaa   77280
cggctttcgc actcgtatac ctattcagag cgcttgcaat aacataatat caagcgtgaa   77340
aaagactaat tccaaacaca aaaaatttgt ttattggcct aaagatacca acgcgttggt   77400
gccgttggtg tggagagaaa gcaaagaaat caaactgcct tacaagactc tttcgcacaa   77460
cttgagtaaa ataattaaag tgtacgttta ccaacacgat aaaattgaaa tcaaatttga   77520
acatgtatat ttttcgaaaa gtgacattga tctatttgat tccacgatgg cgaacaagat   77580
atccaaactg ctgactttgt tggaaaatgg ggacgcttca gagacgctgc aaaactcgca   77640
agtgggcagc gatgaaattt tggcccgcat acgtctcgaa tatgaatttg acgacgacgc   77700
```

```
gcccgacgac gcgcagctaa acgtgatgtg caacataatt gcggacatgg aagcgttaac    77760
cgacgcgcaa aacatatcac cgttcgtgcc gttgaccacg ttgattgaca agatggcccc    77820
tcgaaaattt gaacgggaac aaaaaatagt gtacggcgac gacgcgttcg acaacgcgtc    77880
cgtaaaaaaa tgggcgctca aattggacgg tatgcggggc agaggtctgt ttatgcgcaa    77940
tttttgcatt attcaaaccg acgatatgca attctacaaa accaaatgg ccaatctgtt    78000 tgcgctaaac aacattgtgg cctttcaatg cgaggttatg gacaaacaaa agatttacat    78060
tacagatttg ctgcaagtgt ttaaatacaa atacaacaat cgaacacagt acgaatgcgg    78120
cgtgaacgcg tcatacgcta tagatccggt gacggccatc gaatgtataa actacatgaa    78180
caacaacgtg caaagcgtca cgttgaccga cacttgcccc gcaattgaat tacgtttca    78240 gcaatttttt gatccaccgc tacagcagag caattacatg accgtgtccg tggacgggta    78300
tgtcgtgctc gacaccgagt tgagatacgt caaatataaa tggatgccaa caaccgagtt    78360
agagtatgac gccgtgaata agtcgtttaa cacactcaat gggccattga acggtctcat    78420
gattttaacc gacttgccgg agttactgca cgaaaacatt tacgaatgtg taatcacgga    78480
cacgacaata aacgtgttga acatcgtcg cgaccgaatc gtgccaaatt aaagcacgtt    78540
aagcggatac aacgggcagt ccgagctgtt aaagtcaata caaccatcgt taacaaacga    78600
atacgcattg ttgtgacagc tgaggatata aaaaggaata gagaagtaat tgcaatgaaa    78660
tatcccgtta caattccacg gcacagcgta tgttgctcga gttctatcag ttgcacacaa    78720
cggcctaaga aaatttatta atgcttcatt tgtatctata ttagaaggat aatacatagg    78780
ttcgcccaaa ggactgggag aaggcggcgg cgaaggtgta ggtgtaggag aataggaga    78840 aggcggcggc gaaggtgtag gtgttggagg aataggagaa ggcggcggcg aaggtgtagg    78900
tgtaggagga ataggagaag gtggaggtgt aggtgtaggt gttggaggta taggtgttgg    78960
aggaggtgta ggtgtaggtg ttggaggtat aggtgttgga ggaggtgtag gcgaaggtgg    79020
agaaggtgta ggagtaggtg gaggtgtagg taacggtaca attggtggag atgtaggtgg    79080
tggtacaatt ggtggatttg gatacaattc ctgaatgtcg tctaatattt ttaaagttaa    79140
taaaattatt ataaataaat ttaatattat tattattatt attatcacaa taatgtacca    79200
catgttgctt aaatataaaa attaaacaaa gaatgttgta ttattgcaaa tttaacaatt    79260
ttttgtattc tccccatgtc atgcgttcgt aatgagcggg cggttttta tttctttgta    79320 tccacttgta atcgttaatg tggttgtgaa aagtcatact gacgtaggcc attaaatttt    79380
tcatgagcat attatttgac acaactgcaa catctgcgcc tgccgtttct tgctggtacg    79440
aatcgacaaa cgtaatgtct gtgccgtatt tttctttgtc aagtgcaatt tctataagct    79500
caatgtggta aatgatgaaa cctttgacgt tcatataatg atcgcggcac atggcgcact    79560
gtagtatgaa aaatacgttg taaaatagca ccttcattgt tttcaactgc tgcatgacaa    79620
aatctaaact gcttttgtct cgcgtataca ccatatcgtc gatgatgaga ctgagaaagt    79680
gcatggtgtc ccatatggta gtaaacgtgt aagtaaaact cttgggctgg cacgaacgca    79740
aattgagttc tgtggttttg tccataaatt ctatgcgaaa ctgttgcaag tccatgtcgg    79800
gggatgcgtt aatggcccat tcgatcaact gctgcacctc gtacttttga atgtctttgt    79860
atttcatcaa acacgcaaaa tggtataagt aagttgcttg cgaagacaac agtttggtga    79920
ggtgcgtcga tttagaggct cgcaaaaggt ctatgagacg aaacgaatac aacagatagc    79980
tgtctttgta acgagaaaaa agcggcgtca gcggtatcat ggcgactagc aaaacgatcg    80040
tgctgtactt gtgtcaggcg ccggccacag cgtcgttgta cgttagcgca gacacggacg    80100
```

```
ccgacgagcc tattatttat ttcgaaaata ttacagaatg tcttacggac gaccaatgcg  80160
acaagtttac ttattttgct gaactcaaac aggagcaagc cttatttatg aaaaaagtat  80220
acaaacactt ggtgcttaaa aacgagggtg cttttaacaa acaccacgta ttgttcgatg  80280
caatgattat gtataagaca tatgtgcatt tggtcgacga gtctgcgttc ggaagcaacg  80340
ttatcaacta ttgcgaacag tttatcacgg ccattttga aatttttacg ctcagcagta  80400
aaatcgtcgt ggccgtgccc gtcaattggg aaaacgataa tttaagtgta cttttgaaac  80460
atttgcacaa cctaaatctc attggaattg aaattgtaaa ttaaaacaaa tcatgtgggg  80520
aatcgtgtta cttatcgttt tgctcatact gttttatctt tattggacga atgcattaaa  80580
tttcaattcc ttaaccgagt cgtcgcccag tttagggcag agcagcgact cggtggaatt  80640
agacgagaac aaacaattaa acgtaaagct gaataacggc cgggtggcca acttgcgcat  80700
cgcacacggc gataataaat tgagccaagt gtatattgcc gaaaaaccgc tatctataga  80760
cgacatagtc aaagagggct ccaacaaggt gggcactaac agcgttttc tgggcaccgt  80820 atacgactat ggaatcaaat caccaaacgc ggccagcaca tctagtaatg taaccatgac  80880
gcgcggcgcc gcaaactttg atatcaagga attcaagtcc atgtttatcg tattcaaggg  80940
tgtgacgccc actaaaactg tagaggacaa tggcatgttg cgattcgaag tcgacaacat  81000
gattgtgtgt ttgatcgacc ccaacacggc gccgctgtcc gaacgagagg tgcgcgaatt  81060
gcgcaaatct aattgcactt ggtgtacac aagaaacgcg gcagctcagc aagttttatt  81120
ggaaaataac tttaccgtca ttaatgctga acaaaccgcc tatctcaaaa actataaatc  81180
atacagagaa atgaattaat aaaacaaaaa gtctatttat ataatatatt atttattaac  81240
atacaaaatt tggtacacta gtgttcaaat cgtttctgtt caacgccatt gtcatgttat  81300
aaaacacatt tgtagtttta ttgtaattat ttttaaattt attttaatt tgctgtaata  81360 aaacttgttc attaaataca aaagactttg aactacttgc gtttatattc tttttataat  81420
tgtactgaac aaacgagggg tgcaaaaagt ttttcaaatg ctgcacggca ataccctatca  81480 tctcctccat tttgtcctct cctattgtaa tagtggcact gcgcaccgtt ttaatgttta  81540
gaatgtaaat gagcgcatac agcggactat tgttggtgct caagcacatt aggttgtgct  81600
tatgcatagg gtcgttgctc agcagcgttt tgtatactac aaagcccgtt ttggggtcgc  81660
gtctgtacat tagtacgtgc gacaaaaaca aacgcaccgg cgtcacaagc gactcgtaat  81720
acatgctttc tatcggaaac tgtttggact tgatgtgttc gtacacggag ccggcaaact  81780
tgacgctgtc tacaaactta tggttcgtgt aaacaatcaa aaatctgtct tgtacaccgt  81840
cgtcataatc gtccacgtac agcggcttgt tgttaacaat taacattttg tagttggctt  81900
catactttag cagcccttgg tattttctgc tcttggaatc gctcttgctc gaatcggcat  81960
gcttcttaaa gtacgactcg ctgcattgtt tcaactcgtt gatagtgtac aactgcgagt  82020
tgagtttgct cacttccttg tcgctcgttt ccttgttgga ctctccgctg tggttgtcat  82080
cgtcaaactt gtgcatcaac accaaatagt ccaacagctc aaaaaacgac gacttgcccg  82140
aacccggttc gccgggcatg taaatagcct tctttccgta atctacggga atggccaaac  82200
tagcggcgaa atgcatcaac ataatcgcgt tcgcgtgatt aaaattggtg aagcgtttaa  82260
agtacaaata gccttcgaca atcttttca ataattgta cgagtactcc ttcaagtcca  82320
ctttggacat gatgatgcgc atgtagaatc gagtcagcca gtgggcaaa tcgtccgtgc  82380 tgcgcgccaa tatgattttg tcccaccaca cattgtactt cttcaagatc attaacgcgt  82440
```

```
cggcgtggtg cgtgtaaaat ttggaaatgt tatccgattc ttcaaactga acatcgggtt    82500
cacgtgcaac atcatcgcgc aattcggtta aaaacaaacg tttatcatta aacttgtcca    82560
tcaacatgtc gacatattcg attttgtgaa ttgttcgata caagtactga ataattttgt    82620
tgtgttcttt ggaaaaaaac tctccgtgtt ggttaacaaa ttcgctgttc gtgcgaatca    82680
acgtggtcga cacgtacgtt ttgttagtaa aaattagcat ccaaatcaat tcgctcaatt    82740
ctgcatcgtt accgaacatg tccgccatca agcagacttt tagcgctttt ctattgatct    82800
ttatttcctt gtagcatttg catttgggtc gagatcccga taccgttgac cgacacggtt    82860
tgcattttag gttgtgcaac atgtcggaaa ccctgttctt gtttacgtac agagcgagcg    82920
taatcagatt ttcatcgtcc aaattccaca atcgcgaaa caggttgttt aacgcgactc    82980
gcatatcggc ttggcatgtg ttgcaattgc ccatgtagtt aactatggcc gtgttagttt    83040
ttagcatttt tacatctcgg cacattttgg cgatgtgata agttctataa atgctgagct    83100
cgtcggcgct agtagatagc atgtaattaa acgcgtcctc gggcaaatac ttttcgtcgg    83160
tgggcttctt gaatgtctgc ggcaacgtgg tgcccaacaa aaatgacag ctcgaatgaa    83220 agctgttggt gaacacgttg tacacaccgt gcgttgtcaa gtacaagtat ttccaattgt    83280
taaattttat gttgctcaac ttgtaacaat tgcttttggt caatttgaat aggtcatcct    83340
ctttctttac aatttgataa tgtttgccgt tgaaaaccaa attgactccg gtcactacgt    83400
tttccaattt tctaaagaat cctttacaca caatgtcagg cggcaagttt agcgccatca    83460
cattctcgta cgtgtacgcc cacaattcat cgtgatccaa aatttcgttt ttagccgact    83520
gagtcaaata tatcatgtag tgtatgccaa aataatagcc caacgatacg cacaatttgg    83580
tatcgtcaaa gtcaaaccaa tgattgcagg ccctattaaa cactattttc tcttgttttt    83640
tgtaaggctc acatcgcttc aaagcttcat tcaaagcttc tttgtcgcag gcaaataatg    83700
attcacacaa aagttccaaa aacagtttga tgtcggtttc tctgtacgag aaattttcgt    83760
tcttggtcaa tatcttccac agtacataga ttaaaaaatc aaaatttta aatttgcttt    83820 tttcaaagta ttgttgtaga aggtttggat cgttggctcg ttcgtgggtc gccaaaactt    83880
taaccatgtt ctcgtgaatt gctataagcc ccaaattgat ttgcgtttga atgtagtctg    83940
cattttcgct gctcgccgat ataatgggta cgatgcgcgg ttttctggaa cgcgtgtcgc    84000
tcaagtccac gtcgtttttg tcaaaattgt tgttctcgaa cactctgagg cttttgaggt    84060
tgacgttgac gatatgcttg tacttgggca ccgtaatgca ttcctccaaa ttaatgtcgt    84120
ccctaatgta attgaaaaaa ttttatccg aattgaccag ctcgccatta actttgcacg    84180
tggccacagt gccgtcggcc attttgagta aaacaagtc ttcgtgagaa tcgtcaaact    84240
tggtttttcc atttacaaac agcgtttgcg gcggatcgtg attcgtgcgc aggctgagct    84300
cgacgttgag aaaacattta gggtcaaaca caaacaaatc cacagggcct agttttttgt    84360
tgtgtatgat tggtatcgtg ggttcgatga caattccaaa ttttatattt aaaaacagct    84420
gccatccgtt aaaagagaaa gcttgctttt tgggccagtt gggccaataa tagtaatcgc    84480
ccgcttgcac gcatttgtta atgtatccag ggtcggtgct cttgaaaaaa tcttcaaaat    84540
taatatactt ttgtatgatg tcatagtgct tcttcaaaat gaaaggtttt acaaaaatgc    84600
aaaaatcgtt actttccaac acccagtcgt ggccgtctaa tgtttgagct gcgtgtttct    84660
ctgcaggttc ttcggtgtct tcgcaagatg cgcccatgtc gtgtttcgcg cacggaccgt    84720
taaagttgtt tctaattgtg tttaagaact gttgaaagtt gttgacgtac tcaaacaatc    84780
tacgtgttcc tgttcgcgtg tttctaatga ttaaatgatt tgcatcttgc aagttgttaa    84840
```

```
tctcgtacgt tttgtcttga ggcacgtttt tcaaaaaaaa ttgtaaaatg ttgtcaatca    84900
tgttggctat cgtgtttgta cttttcgtgt taatttattt aataatttcg atcaaaaatc    84960
accatccatt cttacataga atagaaacgc taatacaaga tttcaacaac acattgttgt    85020
ttggcgcgta tgtacagatt tacgatttaa gcacgcccgc ccgcaccgaa cgattgttta    85080
ttattgcgcc cgaaaatgtg gtgttgtata attttaacaa aacgctctat tattacttgg    85140
actcggcgaa cgtgttttgt cccaacgagt ttagcgtgac cacgttcacg caatccacta    85200
ttaaaacgat caacgagacg ggaatatatg ccaccgcatg cacgccggtc agcagcttga    85260
cgctaattga acattttgca acattaaaaa ataacgtgcc cgatcacacg ctcgttctcg    85320
atgtggtcga ccaacagatt cagttttcaa tactcgacat tatcaattat ttgatttaca    85380
atggctacgt ggatttgttg gccgaataac gcgtatatag acgcttgtac gttcatcgta    85440
gtaatcattt taatacattt gattgaacta acatacatc tgcaatgggt gaaagagtca    85500
ctaaattttg caatggaaaa cggcgataaa gaagacagcg acaatgaata gagtttatat    85560
ttttatttaa taaaatattg ttcgtaatcc ataatgtttt gtattatttc attgtgataa    85620
tgttcccaat cttgcacggg ggtggggcat cgtttgactt tgacgtagaa atcgtacgcg    85680
tagttattag ttggcagatc gtcgacaagt gtgatcgact tgaaaaagtt tacatttta    85740
tcgctcaaat atttaattac aatttttggc gatttgggta tattgttgtc ggatcgatga    85800
ttgtgaatgt caaaaacaaa tttatttca atgaaacgct tttttaaatt gtaatctaca    85860
atagcgttgt gtgaattttg aactaaatca gagcgttctt cttgaacggt ggaaccttcg    85920
ctgataatga tatcaaaata gccttccaaa tcgacgtctc gcatcgagtg tgctacatga    85980
tctctactgc catacgacca caagactaaa acgcaaccca tctcgtgcaa ctcctgcaag    86040
ctgtcataca caaacggatc tcgaatctca acttgctcct cttcggttat gagagtgctg    86100
tccaaatcaa acacgaccac gtgcggaaat ccccacgtca aagattcgct tttgagagag    86160
accactttgt agtgtggcaa tagaaaccat tctttaagaa acgaatacat tggcggtttg    86220
ttgctaagca cgcacatgtg gcccaacact ggcgttttga atgcgcgttt aatattgtgc    86280
ctgatgtcgc gcatgtcgtc ggcgggcgct ttgaatattt gcatacagta attgtaattg    86340
ttttctatga tcttgcacag ctgcgggtcg ttgcaaaatt gaaatattac atattcaaaa    86400
aatttatact tttcaaagcc aaggtatttg aggtcggcgt actcgcttaa aacgagaaca    86460
tgtcgtttga tgatggcgtc gttaaggcgc aaacagatcc atttgctttg aagcgaggag    86520
gccataatgt acaaaaatgg accagttacg cctttattaa actgtttaaa gagtttcgta    86580
taaacaaaaa ctactctaaa ctaatagatt tcttaacaga aaattttccc aacaacgtca    86640
aaaacaaaac gttcaactt tcgtctaccg gccatctgtt tcactcgttg cacgcgtacg    86700
tgcccagcgt cagtgatttg gtgaaagagc gcaaacaaat tcgattgcag acagaatatt    86760
tggcaaagct gttcaacaac acaataaacg atttcaaact gtacactgag ctgtacgagt    86820
ttatcgaacg gaccgaaggc gtcgattgct gttgtccgtg ccagctattg cacaagagtc    86880
tactcaacac caaaaattac gtggaaaact taaattgcaa actgtttgac ataaagccgc    86940
ccaaatttaa aaaaaaacct tttgacaaca ttctttacaa gtattcccta aattacaaaa    87000
gtttgttgtt gaaaaataag gaaaaacata ccagcactgg gtgtacacgc aaaaagaaaa    87060
tcaaacacag gcaaatattg aatgataaag ttatttattt acaaaacagt aataaaaata    87120
aactatttga gcttagcggg cttagtttaa aatcttgcag acatgatttt gtaacagtcg    87180
```

```
aaagccaaac gagggcaggc gacgaaatcg cttcgttcat tcgctactgt cggctgtgtg    87240
gaatgtctgg ttgttaatag tagcgtgttc tgtaacttcg gcgacctgtc gatgaacggc    87300
tcctggatct tctgtatgtg cggggtctac ccggcggcg tctgtaaccc gagcttctgc     87360
gcctgcgtgt cgaaccatat gtggtaccgg ttgaagaacg gcgacggcga cgataaacca    87420
tgtttaaatt gtgtaattta tgtagctgta attttaacct tattaatatt ttttacgctt    87480
tgcattcgac gactgaactc ccaaatatat gtttaactcg tcttggtcgt ttgaatttt     87540 gttgctgtgt ttcctaatat tttccatcac cttaaatatg ttattgtaat cctcaatgtt    87600
gaacttgcaa ttggacacgg catagttttc catagtcgtg taaaacatgg tattggctgc    87660
attgtaatac atccgactga gcgggtacgg atctatgtgt ttgagcagcc tgttcaaaaa    87720
ctctgcatcg tcgcaaaacg gaatttcggt accgctgttg atgtattgtt gcggctgcaa    87780
catttgtatc ttttcgccgc gctcgatcaa caattcttca agagtggtgc gtttgtcgcg    87840
ctgtaaagcc acgttttgta acagcactat tttcgcatat ctcataatcg gactgttgaa    87900
acagcgtgca aacgacgacc gcataatatc gacggtcgtc aagtcgattg tggtcgaagg    87960
catctccaac agagatcgca cggcgtccaa cagcgtgtcc gtttgaacct gcgtcatttg    88020
cggtctgcac gtgtagtcgt caaacgtggt ttcgagcagt ttgaacaacg aatgatactt    88080
ttccgatcgc agcaaaaata tcatggtcat gaccacgtcg ctgattttgt attctgtaga    88140
actggtgctg ttcaacgaat agtgatggat tagtttgcga gcagcatttc tgtatcggcg    88200
catgttgatc aactcttcgg aaggctgcgc gggcgcggcg gcgttggctc gcgcaaacaa    88260
atttattacg ggacgcggcg taggctgcgc ggacgctggc gcggcgacga cgtccgcgtt    88320
tcccgccgcg tactgagacg ctatggcagc gttgttattt aaaattgtgt tttgcgattt    88380
gcgagccacg tgcatcataa aatttatcaa cacgtcggtg ttcaactgca cgctttgatg    88440
ttcgtcgcag agcaaaggaa atagctgggg ccatatcgcc aattgcatag gctcgtctat    88500
ttttaaccgc aatttgttta tttccaaata caacgcgata gcgctcatcg tgaccgacga    88560
cgcacactta ctctgtaact atcacttgga tcgtgttgtc gtaaacgctt cccaaaaagt    88620
ctaacacgtt gaccgtttcg attctattca acttaattgt ggacgcgttg gcttgcatcg    88680
gttccaacag actgcgcgct ccgacagatt gagtagacaa aattttaaa ctttccgtct     88740 tattgggcgt aatgtcgttg attaacaacg acgcagccgt ttgagaggcc gcagtgttga    88800
tggtttgcaa catgtcgacg gccgccattt gcgtttgcgc cgaaggtctt gctggcggcc    88860
tgttgcggcg gtttcttcgt gcttgcgaca tgttgtcgtc agtgtccata tcggtatcat    88920
ttattgaagc aatcatggtt gagttcgata agcagagata tttcgttgtc caattggtac    88980
ttggtaatga tgtgccttat aaatgtttcg ggcacaatca tttctgtcat tagcacgtta    89040
caaatatcta ttttgatcaa tttcaattta tgaattaaca gattaatgtt ttcgtccgag    89100
tacttgctca tgatgaaacg acaaacgttg cggagttcca actccgctac cggatacgct    89160
ttgttgggca aactctctaa atagtgtctc aaataaaagc cgatcaatac ggtggacgct    89220 atttgttaa ccttttcat tttagtattg cggcccattt ctatcatgaa gttttaaac      89280 ggtagcaaca gcctgtctcc gttagcaaca gtggagcagc cgttgcattg cgcgctcaaa    89340
atactcaaca cgcgctcgtg atcttcttgg cgcaatccga cggttgcttt tttgcattct    89400
ttgacaaatg gcacgcacat gtcgcgtttc gtgtacaaag aatacgcttt gtcgcaaatc    89460
aagttataga aaaattgcac aaatatctgc gtaatcaagt tgtttcgtt aataatgtca     89520 ctttcgtttt tgtaatcggt tcgaagcaac acgtacaaca tcagaggcat gccgaacatg    89580
```

```
ggtcttaaaa aaatgtccca accattttgc aagcccgcgt cgagggtgct cagcgaggac    89640
gccaagtatt tgcatttgca ctcaaaacat tgaattttgt ttgcgggctt gcacgactga    89700
cacatgatcg catccacgtc gggtgccggc gtcggattgt aatattttg caagtattgc     89760 ataatggtcc taaaatgggg tacctgtttg ataaactcg cgcgcaaaaa tatcgaaaaa     89820 atgttttta cattgtgtat gttgtctgtg ttgttggctt gattctcaaa actactcttt     89880
atggaaacaa tacatttgtt aaattctgtg aaaaaagtaa gacctttact gtccacgatc    89940
aagctttggt tgaaatattt tgaaaataaa aaacacaacg aatcgatttc atcttgtaac    90000
aattgcgctt caaaacacac gttttcaaag cggtcgtaaa tgttaaacct taaactgtat    90060
tgtaatctgt aagcgcacat ggtgcattcg atataacctt ataatatgaa cgattccaat   90120
tctctgttga ttacgcgttt ggcagcgcaa atactgtcca gaaacatgca aacggtggat    90180
gtgattgttg acgacaaaac gctcagtttg aagaaaaaaa tagacacgtt gaccagcatg    90240
gtgttggctg taaatagccc gccgcaatcg ccgccgcggg taacatccag cgacctggcc    90300
gcatcgatca ttaaaaataa cagcaaaatg gtgggcaacg attttgaaat gcgatacaac    90360
gtgttgcgta tggccgtcgt ttttgttaag cattatccca agtattacaa cgagacgacc    90420
gccggtttag ttgccgaaat agaaagtaat ctgttgcaat atcaaaatta tgtaaaccaa    90480
ggcaattatc agaacattga gggttacgat agtttattaa ataaggcgga agagtgttat    90540
gttaaaattg atagactatt taaagagagc attaaaaaaa tcatggacga cacggaagcg    90600
ttcgaaagag aacaggaagc ggagagattg agggccgaac aaactgccgc aaacgctctt    90660
ctggagaggc gagcgcagac gtccgcagac gatgtcgtta atcgtgccga cgccaatatt    90720
cccacggcat ttagcgatcc gcttccaggc cccagcgcgc gcggtacat gtacgaaagt      90780 tcagagtcgg acacgtacat ggaaaccgcc cgacgtaccg ccgaacatta caccgatcag    90840
gacaaagact acaacgcggc gtacactgcc gacgagtaca attccctggt caagacggtt    90900
cttttgcgtt taatcgaaaa ggcgctggcc actctaaaaa atcggttgca cataacaact    90960
attgatcaat tgaaaaagtt tagagattat ctgaatagcg atgctgatgc tggagaattt    91020
caaatatttt taaaccagga agattgtgtg atactgaaaa atttgtcaaa tttagcgtca    91080 aagttttca acgttcgttg cgtggccgac acgttagagg taatgttgga agcgcttcgc     91140
aataatattg agttggtgca gcctgaaagc gatgccgtac ggcgaatagt cataaaaatg    91200
acgcaagaaa ttaaagattc gagcacgccg ctgtacaaca ttgccatgta caaaagcgat    91260
tatgacgcca taaaaaacaa aaacattaaa accttgttcg acttgtacaa cgacaggctg    91320
ccaatcaatt tcttggacac gtccgcaacc agtccagttc gcaaaacttc cggcaagaga    91380
tctgcggaag acgacttgtt gccgactcgc agcagcaaac gtgccaatag acccgaaatt    91440
aatgtaatat cgtcagaaga cgagcaggaa gatgatgacg ttgaagatgt cgactacgaa    91500
aaagaaagta aacgcagaaa attagaagac gaagattttc tcaaattaaa agcattagaa    91560
tttagcaagg acattgtcaa cgaaaagctt caaaaaatta ttgtggtcac cgacggtatg    91620
aaacggctgt acgaatactg caactgcaaa aattctttag agactttacc gagcgccgct    91680
aactatggca gcttgctcaa aaggctaaac ctgtacaatc tcgatcatat cgaaatgaat    91740
gtaaattttt acgagttgct gtttccattg acactgtaca atgacaatga taacagtgac    91800
aaaacgcttt ctcatcaatt ggtaaattac atattttgg ccagtaacta ttttcaaaac    91860
tgcgctaaaa acttcaacta tatgcgcgaa acttttaacg tgtttggccc gtttaaacaa    91920
```

```
atcgacttta tggtcatgtt tgttataaaa tttaactttt tatgcgacat gcgtaatttt   91980
gccaaattaa tcgacgagct ggtgcccaac aaacagccca acatgagaat tcacagcgtg   92040
ttggtcatgc gggataaaat tgttaaacta gcttttagta atttacaatt caaacctttt   92100
tcaaagaaag acaagtcgcg caacacaaaa catttgcaaa gactaataat gttgatgaac   92160
gcaaactaca atgttatata ataaaaaatt ataaaatatt tttaattttt atttatattc   92220
agtacattta cacatattaa catattgttt atacaaattc ttataatcat tatgatttaa   92280
attgaattgt tgtctaaaca aattaaacac tttattaaac aataaccttt cgttgtaatt   92340
ttttactttg cacatgttat aacaaaaaat taaaattttc atcatgtctg atttgtctat   92400
ggcgtcacag ttgcttttaa tgtaatcgca agttaaccac tcaaaaggac ccttttctat   92460
ttttaatttg tttaaatctt tataatcaga cttcagtttg taaattagat ttccacatcg   92520
aataataaat ccttccagcg ggctttgggg aaacattaaa gacttgaaat ttaacctttc   92580
tacaaaatcg ttgtacaaat atttgtgaca cggaatagta ttaaacccca cgttagtcaa   92640
caactcttgc gcctccacaa agggcacaaa ctccccgccg tataattgaa tttcgtaagc   92700
gtagtatttc aaactctctt tctggtccac gtagttaatt acgttaatgg gtgtcgtttt   92760
tgcgtcgtct ttccaaccca ttaattcgcc gtagacaata aaaccgtcat tgaaccgcgc   92820
ctgaagcgat cgcatgcacg tttctaaatc ttttcgaatg cggtaataat tcataaaatt   92880
gccgtccggt ctgtaagtgt ttcttgaccc gtacgtaatt ttattttggt tgcaaatgat   92940
tctgaaatta caaccgtcca acttttcttg aacaataatt tctttgtcgg ccaacgtacc   93000
ttttttacct tgatctagat gcgacacaga tggataaatt tgatacacaa ttttattctc   93060
atcttcgggc attacgggtc cgcgttcatt taacgcgtac atgacaatgt tgtggcgaat   93120
gtcggtcgcg tccggcggtt ctggcacgtg gtgcagtctg tcctgcaatt gttgcttcca   93180
ttgttgaaaa tattcggtcc attcttgttg atactcgccg cgttgcatga gttttacgta   93240
cagtttaaa agtttgacat tctttacaaa taacgttaga gtttcgtcga ttttgtatcc   93300
tccattattt ttgtttaaat ccaatacatt taaatcgttc actaccagtt gattgttttt   93360
atccatcgta atttttatct catcgcccac gttgaacaac atgtttaaaa ttttggtgga   93420
tttcggcgca cgtttataat ctaaataata ttcaacgtac acgtaattga acatgagctg   93480
caacaatcct ttggcattgt tcaaaatttt gtatctcatc aaagtataaa taattttcac   93540
catcgacacc gtcatcaact tggttacaaa ctcgtacaat tgcaagtttt caataccgta   93600
tttgtcttta aaatcttcac gtttactgaa catgcttaat tcgggagatt ttccagtcaa   93660
aatgccaatt aatcccgtgt acaagtcaac gtatttgaca tcgttgcccg attcatcttt   93720
tgcatgtcga ttttttcaaaa gctctttatt gtcgataaat ttttcaaagg tctctcgatc   93780
acatttagtg taaatatggt agtcagtgtc gctgctttcg accgcgtatc ccttggcatg   93840
gctgcccgta tcaatgcaaa tgtacaccat gttagaatgt gctgcttact gtgcctgtat   93900
caagccttat atacctcaaa atatttcaca tttttgcatc atcgtaaaat atacatgcat   93960
ataattgtgt acaaaatatg actcattaat cgatcgtgcg ttacaagtag aattctactg   94020
gtaaagcaag ttcggttgtg agccgtgtgc aaaacatgac atcataacta atcatgttta   94080
taatcatgtg caaaatatga catcatccga cgattgtgtt ttacaagtag aattctactc   94140
gtaaagcgag tttaaaaatt ttgtgacgtc aatgaaacaa cgtgtaatat tttttacaat   94200
atttaagtga aacattatga cttccaataa ttttgtggat gtggatacgt ttgcaagaca   94260
attgattaca gataaatgta gtgctctaat caaaagtgcg gatctgttgc cggcaaacat   94320
```

```
tttagagatt gtagagaagg ccagagacaa gtattttgag gagccaactc aaaaaaacta   94380
tgaatacatt aaaaaattat ttttacgaac aaaatatatg gacgattcga tagattataa   94440
agattttaac agacgcatcc tattgatagt ttttaaattc gctttaaaca agagcaccaa   94500
ctactttcca tcgtacaaag agatcatcga ggtggccatt aaacgtttaa acaaaattaa   94560
ccccgattta aagagttctc cgcgcgcaat gcttcagcat tacaatgaat gtttggaaaa   94620
tctagacaat ccagtcacgg acgaacatca tttgttaaca tttggaaaag aagttgctac   94680
aaaaatattt atcgaagcgt ttgaatacag ttacaccaac actaatgcca tcagcatgga   94740
caaaacagat gaatttgatt ttattaaacc ggcattgaaa cctttgccag atgcaagacc   94800
gccatcgctt ttggccaacg tgatgaacga acgtaaaaga aaattacaaa acaccaactc   94860
aacggcaaaa tgtttgctac cagcaccacc gccacaattg cgtaaacttg aaaaaaagaa   94920
tcatttattg cctttgtttt ctttgtaatt atattgttgc atttctattt ctaatatcat   94980
agttttctaa taaagtagtt tcatattttt gttttttgtac agtaattgtt tcttggttta   95040
acaagatcac aaccaataac ataaagaata acacaatcat aacaaaaatt aaaaagccgc   95100
atactactag aacaaattct ttaattagcg atcggtttct atttacaaat tggccgagct   95160
gatcgccttc agtcggcgag ttgtgggctt ggatgatgtc gacgatattg ttgccggcgc   95220
gaccgcctgt cgctctcgat ataatgtcgg ccgccgtcgg tttcatgatg tgcttaacta   95280
caaataatag ttgtacttga cgggcgtcac cgtgatgccg ctgctaaaac ctccgtccgt   95340
taagacgcgt tgcgttacaa aattaatgtt tgtccgatta gcgtagtcgg aataatcaaa   95400
cgtgttgggc ggactaaaat cgggcatgtt gatgggcaca atgccgctgg agctgatagc   95460
aatgctgtcg ttcttgcaaa acagccgaat tttttttgtag ggctctgctt tattcggcgc   95520
agacgacacc atctggtcaa agttgttcaa ttttatgatt acgttgggta ccaattgata   95580
ggggaaaatt attttctgga acattttgac aaagtccaca accgtttggc tatagtcggg   95640
aatgccgagc aaagactgcg cctgtttaat gtatttgaga ctggagcggt ttactgtagc   95700
gcaattggat ggcacgtcgc ccttcataag ccggcgcgtt ctctcccaat tcaatttgtt   95760
gtacaaatta tcaatctcct cgtgcggcag attgattaca tagcgcgcgg gctgtttgcg   95820
atattgaaag atgcaaaaaa tgcgtttcaa cgacaatatc ttcaccatgg tggacgtttc   95880
cagattgaaa cataacaaaa agtcattgct ttccaccaat tctttaaaat gagacagcgg   95940
aatttcacaa gcgatcggtc gcaaattgct ttttattgga ggcggaacgc tttgaccgtt   96000
gcggtttttt agtaacgcgc tgcacgcaga ttgcatgtcc gtttcgggat acgtaaactc   96060
gatgggacat ttgggggttttt catggtgaac gatcatagtg ttgcaataaa acaagttgtt   96120
ggtcaggagc acgctaaaaa cacgcgtttc gcccgcaccg atttcggtga tgggtaccaa   96180
cgggttccag tagactatgg tggcggacgc tgttttttttt ggcgatcgac tgtctatgtt   96240
aacatcatgc tcgtgcctgt acactagcac agaattgaat tttggaaatt gttttttgtc   96300
aatgtacaac cggtcgtcgt ctgtgggcac gtacacgatc aagttttcga ttaatttgtt   96360
gcctacgtcg ctttgcggtt ccaccaaatt gtgagggaac gcaaaaaagc gatcgctaat   96420
acaaacttga atctgaaacg ggcactccat cgtgatgtat atgtcttact tcattagact   96480
ttagattatt ttaatttgtg aactcgtacc gtattcaata gggtgtcggg cacgtaattg   96540
taatggtaaa acagatcctg ttgaacacgt gcgttgttca ctacgattga aatgcaaaaa   96600
tacatcaagt acataaacac tatgattaga aaggtagcag acagaaaata tttcatcttt   96660
```

```
aaatcttatg ctagttgaat aaaatacata gtactttat acgtttattt atatttgttt      96720
tctttgttat aaccgtaatt gtaaaacttg tgatcgtgct cgccaggcat aatttctttg      96780
cacatcagct tgcgaatata tgtgacatct tcgtacaccg atttcttgat gttaccatcg      96840
tgaagcgttg tcggcttgag aggtttgcgg tcgttgttgt aaaaattttg caccgaataa      96900
ttatccatag tgcagcacag gcaatgtcac tgatgcatat gctttaattt tttattgcat      96960
tcagttatta tatgatttaa taaacgtaca caatagcacg tttatcggtt aaagataact      97020
ttcaatatat aaaagtgttt gaattgcgag accgtcaaca taacgtttat caacgcgatg      97080
actaaacgac aatttgcttt gctgtttgtg tggcaccacg acaaccaatt tgtttgcaac      97140
acggacgaat acccgttttg gcacaacatt gaataccatg cacggcgcta taaatgcatc      97200
gttttgtact gtgtggaaaa cgacggatcg ctacaactgc ccgtttgcaa aaacataaat      97260
ctcataaatt ataaaaaagc gtatcctcat tattatggaa actgtgttga cagtatagtg      97320
aaacgtgctg gcaaaattga ttatatgaaa gtaactgcaa tgttaaaccc ccacctgttg      97380
gacgtcgcgt acaattattt gctgttgatg gacatggatt gtgtggtgca aagcgtgcaa      97440
tggaaacaat tgtcaaccga cacgtattgt tttgagccgt tttacgactc tcaaattaaa      97500
tggttgtacg cgcccaaaag cggacaaagt tttgatagtt atcttgaaaa ctatgcaact      97560
ctaattcgag tcaaacaagt gcagcaacat cgaaaagaat taatactgca ttgtgtggat      97620
tttcttacaa tgaaagcaaa tgacaatttt atggtgttca aaaattatat taacatgatt      97680 ataaagtgt atttgcaatt ttacaattac agatttccca tcaattttga ggacaacacg      97740
atgaaacctt gtgtaaattt aactttaga cgtggcggca gttggaaaac tcaactgcaa      97800
cccgtatgca attatgttta caaaagtaaa aatatgccaa aatttattaa ataaaacaaa      97860
ttaatttaaa caagcgtttt tattgacaat actcacattt gatattattt ataatcaaga      97920
aatgatgtca tttgtttca aaattgaact ggctttacga gtagaatttt acttgtaaaa      97980
cacaatcaag aaatgatgtc attttgtac gtgattataa acatgtttaa acatggtaca      98040
ttgaacttaa tttttgcaag ttgataaaca tgattaatgt acgactcatt tgtttgtgca      98100
agttgataaa cgtgattaat atatgactca tatgtttgtg caaaaatgat gtcatcgtac      98160
aaactcgctt tacgagtaga attctacttg taacgcatga tcaagggatg atgtcatttg      98220 ttttttaaa attcaactcg ctttacgagt agaattctac ttgtaaaaca caatcgaggg      98280
atgatgtcat ttgtagaatg atgtcatttg tttttcaaaa ccgaactcgc tttacgagta      98340
gaattctact tgtaacgcaa gatcggtgga tgatgtcatt ttaaaaatga tgtcatcgta      98400
caaactcgct ttacgagtag aattctacgt gtaaaacacg attacagcac ttcgtagttg      98460
tatcgaaaat tgttcaatgg ctctttgtta atgtcgtaat tgattaatat gtcgtacaat      98520
ttggcggcgt tgtgtttgca cacgaccgtt tttagttctt gaaacatttt ttcgtgtatg      98580
tttagcatgt tgtatttcag agtgcgatgt gtaatgctgg tgacgagcat caaaatgata      98640
aaatctaaag cggctaattt gtaatcccgt tcatacgctc tgtaatcgcc aacaactctg      98700
tggccagatc tttttagatt ttgacaggcg ttatggtacg aattgataat atttactata      98760
gtttctcttg ttatcggttt gtcgattaaa ctgttaacaa acatcacgtt gcccaagcgc      98820
gacggtttag acaccgactt gttttttgtc tgttcaaatt tgtacaaatt aaaaacgctc      98880
atagactggt cgtcaggcag tgtgtcgtta tacaaacaaa atggtaaaac gtttaattcg      98940
acaaacgacg agcacattaa agtttgttgg ctgttaacgt cctggggatg taaactgtta      99000
ttcataacgt aacacacttc aatgtcggaa tgcttgtttt caaatttgtc cttgtctaca      99060
```

```
gtttcaatgg tgattgagcg aggtttgagt ttattttgta aattcatttg gatattttca   99120
atatggtata ccaccgacac gttgtgagcc agcgatcctt gattggtttt aatcatattc   99180
aaaatattca tgatatggtt gaaaaaagag tctgtcaaaa cgtttgtgtc gttgttaaat   99240
atcgctttcc agggtttact gttgcgtgac tcaacgacgg ccgtgtaaca taacaagcgc   99300
gccagttgca tgtgcgacaa cttaatgtta tcaatgtcgg tgatgtttgg caccagattt   99360
tcattgccgt cttccagtag cgtgctcagt tcggtcgagt agttattcaa cgatcgattg   99420
tgcgattcaa acaagtttac tatcgcaggt tgtacatagt tttttatgtc gtcaaattga   99480
attatatcga tcttgtcctt gttctccagc ataaacgaca aatttttag gtcgaattta    99540 atatttggcg cgttttcgtt ggacttttg taatttaaca acatcgccaa cagtttgtgt    99600
aactcgccgt tagcttgatc tttgctaaac agtttattgg tagcgtaatt cacgttgtcg   99660
ttcaaaaaca gcaactcgtt gatgatcatt ttttgtaaaa gcgcgtactt gctcatgttg   99720
acagaatctc ttacatttca gttgtaaacg cgtctgtaca aattggccat gcgattcgga   99780
atgcacacgg ggatcgtgcg agccagtgcc gtttggcgaa atagcatttt ttcatagccg   99840
ctcgaacaat cgcacgcgtc cggcgaaaat tgcaccgtgt tcaaattcat attcaaccgg   99900
ccgtcgttgc atagataagg cctcggtgtt cccgtatcgt ccaccaagtc tctgtacgtg   99960
ctcacgcatg tttgagacac gacaaaatct ccgccggcgg agaaaacgtg aaccaagccc  100020
agtgcgggat cgcattctat caagtccgga gcctgcgcgt ttaccaaagc gtcggaggcg  100080
ttgcaaaagc catcctggca ggtcaactcg tttgcagcgc tggagatcac gcagttgtct  100140
ctacactgct gatccgtcac gcacggtaac cggttcaatg aacaatctac gcctcgattg  100200
cgctgaaacg taaaatttaa cggcggcgct tccaactcgt taatgtgcat gtatgcatct  100260
tgcaaaataa attttgaac aaatttaaac gtgtacatgt acacgattag tataattacc   100320
agtagaataa gtatttgcca aaagttcaac atgatcgtct taactgagtg tgaaaagcgt  100380
ggtgtgacgc acgaaatgac tggttgcgca aaaaataaac cggggtctat ataactcggc  100440
gtcgaccgcg ttcattttta ccgtcatgca tctgacggct aatgtattgc tcgttcctaa  100500
cgcgctcaaa aagcgggacg tgaaatacat ttataatacc tatttgaaaa attacagtgt  100560
aattgaaggt gtgatgtgtt gcaatggcga ttgtttggcc gtggtggtgt tggaccgaaa  100620
tcagctgcaa aacacggaca tggaagtgtt ggagagttta gaatacacta gtgacaacat  100680
tgaactgtta tgcgaaaaaa tatgtgtgat agttgataat tacgacaagt attaccaaaa  100740
aaattgtgta taaataaaat accaaatttt attatatcat tttgttttat ttaataatta  100800
aagaatacaa cgccacatct attcctagta caacaaataa tttgattatt attttgagt   100860 gcacattaaa aaataacaaa cagtgtaaaa atactacaga ataatacaat acataaatat  100920
tatagtaaat agctgcaatt ttgatagcgt aatttatact ttgatatttt tcaacgtaca  100980
acgttaaatg ttgatacgca ttattcacaa ataacaaaat ttttctaata tgccatttgt  101040
ccgcaattgt ttttgcgata tcaaagcctt tttcaaacaa ttgaaaaatt gcaaacaaaa  101100
ccacgtacat gacgttatac atagtgttaa agttttttaca taacaattct ataatgaaga  101160
aaattgctaa acacggcatg agcgcgcaca taatcgcgtt ggccgcaaat atctcgtacg  101220
tacaaaaata ctcggacatt ctccaataag taaaatgcat tttgctatta tactgttgtt  101280
tcttctagtg attattgcaa tagtgtacac gtatgtagac ttgatagatg tgcaccatga  101340
agaggtgcgt tatcctatta cggttttttga caacacacgc gcgccgctta ttgaaccgcc  101400
```

```
gtccgaaata gtaatcgaag gcaatgcaca cgaatgtcac aaaactttga cgccgtgctt   101460
cacacacggc gattgcgatc tgtgccgcga aggattagcc aactgccagt tgtttgacga   101520
agatacaata gtcaagatgc gtggagatga cggccaagaa cacgagacgc ttattcgagc   101580
gggagaagcg tactgcttgg cttttggatcg agaacgcgcc cgatcgtgta acccaaacac   101640
gggtgtgtgg ttgttggccg aaactgaaac tggtttcgct cttttgtgca actgcttacg   101700
gcccggactt gttacgcagc tcaacatgta cgaagactgc aacgtgcccg tgggctgcgc   101760
gcctcacggc cgtatcgaca atatcaacag cgcttcgatc cggtgcgtgt gcgacgacgg   101820
gtacgtgagc gactataacg ccgacaccga aactccgtat tgccgtccgc gcaccgtgcg   101880
cgacgtaatg tacgacgaga gttttttttcc gcgggcgcca tgcgcagacg gccaagttcg   101940
tctggatcat ccggcgctca atgatttttta ccgcagacac tttagactcg aagacatttg   102000
cgtgatcgac ccttgctcgg tggacccgat tagcgggcaa cgcacatcgg gacgcttatt   102060
tcaccaacca accgtaaatg gtgtgggaat caacggatgc aattgtccgg ccgatgacgg   102120
gttactgccc gtgtttaatc gacacaccgc cgacacgggc atggttagac aaagcgaccg   102180
caccgtcgcg aacgcttgct tgcagccgtt taacgtgcac atgttatcgt tgcgtcatgt   102240
ggattacaaa ttttttctggg gccgcagcga ccacaccgag tttgccgacg cggacatggt   102300
gtttcaagcg aatgtcaacc aactcagtca cgaacggtat cgagcgattt tgtactcgtt   102360
gctcgagtcg cacccggacg taacagaaat cgtaacagtc aacatgggtg tcatgaaaat   102420
ttccgtgtca tacgatacca cattgaaaaa tatactatta ccatcttctg ttttttaggct   102480 atttagattt aaagaaagtg gcactgctca gccggtatgc ttctttccag gcgtaggacg   102540
gtgcataacc gtcaattccg attcgtgcat caggcgacac gctggtggtc aagtgtggac   102600
cgcagaaacg ttcaccaact cgtggtgtgt actgagtcgt gaaggtacgc atataaaagt   102660
ttggagtcgc gcgtcacgat atccacgcgg agacgcgcct gcagcgttaa gattgcgcgg   102720 cttcttttctg aacaacgatc gcgaacgaaa cacaataaga gcggtcacta caggcgacat   102780
gacccaaggg caacaaatag acgcattaac ccaaatactt gaaacttacc ccaactactc   102840
tgtataacaa catgagcatt ttaaaagttg tagaagcgtg cgatttggca cacactttttt   102900 tgaaattggg ttatttatttt agggccaaga cttgtttgga tatcgcttta gataaatttgg   102960 aactattgcg tcgaaaagact aacataaaag aagtggcagt catgttaaac aagaaaacta   103020
cagagtgttt gcaattgaaa cgaaaaatag ataaaaaaat tgcacaacgt gttttaataa   103080
aaatttacac tatcaaatga tgacatcata acgggttcaa tattctgtgt gcaaaaataa   103140
atgacatcat atttcaaact tgttttacgc gtaaaattct actggtaaaa caagtttgag   103200
atatgatgtc atcatcacaa ataatagtat gtaataaaaat aaacatattt gtgtgtaaat   103260
ataatttatt acaaataaat tttacattga atcaatctgt cttcgtgttt gttgtaaggt   103320
cttcgaatct tgtgtttcag cccctcggga tggtcaaaat gcgccgtagt aattgttaat   103380
ggatctttca acgattttttt gcccatggcg agtgtgacaa acgcggccac gacaaacagc   103440
aggataatca gtttcatggt gttctatatt tgacaatata tgggtcgctt ctaaatcacc   103500
ttgtccccaa aagcctctttt tatagttttt tagaacacgt tgtgtattcc aacagtaatt   103560
gttccatctc tttcaacagc cattcagcat ccggtcgttg actgtaatca tgctgaatta   103620
atttacaaac aatttcggtc aatttaggat ggccttggga taaacttgcc ggcatttgct   103680
gtacattgtt tctaaagtta gttagcgtag tttcgcgttc caaagcagtc ttgaagggca   103740
ttatcaattc gaataaaaca atgcccaaac tatacatgtc attttttgggg gtgtacactt   103800
```

```
ttttgatttg ttctggtgca gcgtacaaag ttatattttg agggttgttt ttgataaacg 103860
ttttgtatag actgccaaac atgccgccca catacaaatc aaagtcgggc ccagtcatga 103920
aaatatcttc gggattaata ttgtggtgca cgatatttac ggaatgaatc gctttcacgg 103980
cgctcaccaa atcaacaaac ttgctaatat aaaagccaaa atccgccgga actttaatgt 104040
tggtctttgc aaaagtttgc aaattgcgtt gtttcaaata gtcgctcaac atgtactcgt 104100
ttagaggcga cgcaaaatat atgcggtgct gccgcggatt caaataaacc aattgttcgg 104160
gtttcatggt atacagttaa gtgttaacgc gtcactaaat tcagacacga gcgcacgccc 104220
tatatacata caatttatcg cacaagatgc ttaacgcgat ctgtttataa actaaaacgc 104280
actgcaataa atttagcaa gcatttgtat ttaatcaatc gaaccgtgca ctgatataag 104340
aattaaaaat gggtttgttt gcgtgttgca caaaatacac aaggctgtcg accgacacaa 104400
aaatgaagtt tccctatgtt gcgttgtcgt acatcaacgt gacgctgtgc acctacaccg 104460
ccatgttggt gggatacatg gtaacattca atgactccag cgaattgaaa tatttacaat 104520
actggttgct gttgtcgttt ttgatgtccg tggtgctaaa cgctccgact ctgtggacga 104580
tgctcaaaac cacagaagcc catgaagtaa tttacgaaat gaagctgttc cacgccatgt 104640
actttagtaa cgtgctgttg aattatgtgg tgttttttgga caatcaaatg ggtacaaatt 104700 ttgttttttgt taacaattta attcactgtt gtgtacttttt tatgatattt gttgaattgc 104760
ttatcctgtt gggccacaca atgggcacgt acacggatta tcaatatgtc aaatcgtgtt 104820
atatggttat attgtttgtt tcagttatga gtgttactat tgttatgggt ttagagtgtt 104880
tgaaaacgaa actaattgat aacagtttga tgtttaacgc gtttgtgtgc gctttgtaca 104940
ttgtgattgc aataatgtgg tctttaaaaa ataatttgac tagttattac gtttcaaatt 105000
tacaaagtat tcaagttgtt ccgttttcat acaacgatcc gccgccaccg ttctctaaca 105060
ttgtaatgga tgacataaaa aataaaaaat aattttataaa aatgttttttt attctttcac 105120 aattctgtaa attctaaaca aaaaatataa atacaaactt attatgttgt cgtctaaata 105180
aacatcaatt tgtaaatctg gacacctatt catatcattg atattacagt ctactataca 105240
acaattaaaa ctaaccaaat tatctttaca acaattaaag caattaaaac aatttaaata 105300
atcttcattg tcgtcgtata agtttatttg cactgtagac ggtgttacac agcgatccat 105360
tcgacgttcg tgttcgatca actttctcgc caacttgtac cataaaaatt gtttggacaa 105420
aaagttttcc aacaatggta acggccaatt caacgtgacg atgcgcacgt cctcgggtat 105480
gcatttgtta aaaaacacac agctcgcttt accaaacgaa agcaaaggta ctaaatatgg 105540
cgccattggc tgatttgtta ttccaagata attacaaata aactgatccg tcgtggggtg 105600
ataactggca ggtgtcagct ttaaataatc ttcaacgttg ttgtcgcgca aaagtctgca 105660
ttttacacgc gttgttaatc ccacgacttt tgcatgtaaa atcggatcca aatactgcag 105720
aatcgtgtct ataatttcta atggtaaacg tatgcgtttt gctcgtgggc gctttgtaac 105780
gctcgacatc ctaataacaa ctaacacaaa actaaaatga tactcaatat attgcttttta 105840 cagttcatct ttaggtttaa actgtgcgtt tatcgcgttg agcaagtcgc cgttatcggc 105900
atcaatctcc caagcaaaca ggccgcccaa tttatttcgg tcgacatatt taacttttcc 105960
taacacagag tcgacgctgt caaacgaaat caaatcacct ttacttttat cgaaaacgta 106020
cgacgcttga gcgcgctgt caaacgtgta cacataattg ttgagatctt tttgaatttg 106080
acgataatct acaacaccgt cctcccacgt gcccgacacc ggcccgttgc cagtgccgga 106140
```

-continued

```
aaaatagttg tcattcgtat aatttgttac gccggtccag ccgcggccgt acatggcgac 106200
gcccacaatt attttgttgg gatcgacgcc ttgtttcagt aacgcatcga cagcgtagtg 106260
tgtagtgtat agctcttccg agttccaact tggcgcgtag actgttgttt ggtagcccaa 106320
atccgtgttt gaccaagccc ctttaaaatc gtaactcatg agaaatattt tgcctaatga 106380
cttttgcgct tcggcgtagt ttaccacggc aatcttgtcg taacccgcgc ttatagcgct 106440
tgttaattcg taaaccctgc cggtttgcgc ttcgaggtcg tctagcattg cgcgcagctc 106500
ctccaacaac aaaatgtatg ttttggcgtc acgctccgca tcgcccaacg acgggttagc 106560
ccctttgccg cccggaaact cccaatcgat gtctacaccg tcaaagaatt tccacacttg 106620
cagaaattcc ttaaccgaat ctacaaaaac gtttcttttt tcaacatcgt gcataaaata 106680
aaatgggtct gatagagtcc agcctcctat tgaaggaaga atttttaaat gggggtttgc 106740
taattttgcc gccatcaact gtccaaaatt gcctttatac ggctcgttcc aagcggacac 106800 accttttttgg ggttttttgta cggcggccca cggatcgtga atggcaactt tgaaatcttc 106860
gcgtcccttg cacgatcttt gcaaagattc aaagcttccg ggtatcgttt tgagggcgtc 106920
gtttattcca tcgccgccgc agatgggtat gaaaccatac aacaagtgtg ataaatttgg 106980
caagggaact ttgtctacgg gaaagttgcg cccgtacaca ccccactcaa caaagtacgc 107040
agcgacaatt ttatcctctc tcctgccagg tttgttgttt tccagccatg tgtattcgag 107100
cggtgccaga tggccgccgt cggtgtctgc gactttgacc aacacgggat cgctcacgga 107160
acagccgtcc tcattgcaaa gtttgacacg catgttaaat tgcccgctca caagaacttt 107220
aatggtagcc cttttacttt cggcgtcgcc tttccatacc tgctgctcgt caaacaacac 107280
gtacgctatg tcgccaatgt cgccgttcca gacgttccaa ctgacttgaa cgtcgacttg 107340
ttctttaggc tttattaaat tttcgtaagc ggtggcctcg taatttattt ctacgagcgc 107400
ataattgcga tcggcccaat cgatcaccgg cgtgccggga atcgcgttag aaacggcgac 107460
caaccacaaa acgtttaaca atttgtacaa cattttaatt tatcttaatt ttaagttgta 107520
attattttat gtaaaaaaat gaacaaaatt ttgtttatt tgtttgtgta cggcgttgta 107580
aacagcgcgg cgtacgacct tttgaaagcg cctaattatt ttgaagaatt tgttcatcga 107640
ttcaacaaag attatggtag cgaagttgaa aaattgcgaa gattcaaaat tttccaacac 107700
aatttaaatg aaattattaa taaaaaccaa aacgattcgg ccaaatatga ataaacaaa 107760 ttctcggatt tgtccaaaga cgaaactatc gcaaaataca caggtttgtc tttgcctatt 107820
cagactcaaa attttttgcaa agtaatagtc ctagaccagc caccgggcaa agggccccctt 107880 gaattcgact ggcgtcgtct caacaaagtc actagcgtaa aaaatcaggg catgtgtggc 107940
gcctgctggg cgtttgccac tctggctagt ttggaaagtc aatttgcaat caaacataac 108000
cagttgatta atctgtcgga gcagcaaatg atcgattgtg attttgtcga cgctggctgt 108060
aacggcggct tgttgcacac agcgttcgaa gccatcatta aaatgggcgg cgtacagctg 108120
gaaagcgact atccatacga agcagacaat aacaattgcc ttatgaactc caataagttt 108180
ctagttcaag taaaagattg ttatagatac attaccgtgt acgaggaaaa acttaaagat 108240
ttgttacgcc ttgtcggccc tattcctatg gccatagacg ctgccgacat tgttaactat 108300
aaacagggta ttataaaata ttgtttcaac agcggtctaa accatgcggt tcttttagtg 108360
ggttatggtg ttgaaaacaa cattccatat tggacccttta aaaacacttg gggcacggat 108420
tggggagagg acggattttt cagggtacaa caaaacataa acgcctgtgg tatgagaaac 108480
gaacttgcgt ctactgcagt catttattaa tctcaacaca ctcgctattt ggaacataat 108540
```

```
catatcgtct cagtagctca aggtagagcg tagcgctctg gatcgtatag atcttgctaa   108600
ggttgtgagt tcaagtctcg cctgagatat taaaaaactt tgtaatttta aaaattttat   108660
tttataatat acaattaaaa actatacaat tttttattat tacattaata atgatacaat   108720
ttttattatt acatttaata ttgtctatta cggtttctaa tcatacagta caaaaataaa   108780
atcacaatta atataattac aaagttaact acatgaccaa acatgaacga agtcaattta   108840
gcggccaatt cgccttcagc catggaagtg atgtcgctca gactggtgcc gacgccgcca   108900
aacttggtgt tctccatggt ggttatgagg ttgctttttt gttgggcaat aaacgaccag   108960
ccgctggcat ctttccaact gtcgtgatag gtcgtgttgc cgatggtcgg gatccaaaac   109020
tcgacgtcgt cgtcaattgc tagttccttg tagttgctaa aatctatgca ttgcgacgag   109080
tccgtgttgg ccacccaacg cccttctttg tagatgctgt tgttgtagca attactggtg   109140
tgtgccggcg gattggtgca cggcatcagc aaaaacgtgt cgtccgacaa aaatgttgaa   109200
gaaacagagt tgttcatgag attgccaatc aaacgctcgt ccaccttggc cacggagact   109260
atcaggtcgt gcagcatatt gtttagcttg ttgatgtgcg catgcatcag ctcaatgttc   109320
attttcagca aatcgttttc gtacatcagc tcctcttgaa tatgcatcag gtcgcctttg   109380
gtggcagtgt ctccctctgt gtacttggct ctaacgttgt ggcgccaagt gggcggccgc   109440
ttcttgactc ggtgctcgac tttgcgttta atgcatctgt taaacttgca gttccacgtg   109500
tttttagaaa gatcatatat atcattgtca atcaaacagt gttcgcgtgt caccgactcg   109560
gggttatttt tgtcatcttt aatgagcaga cacgcagctt ttatttggcg cgtggtgaac   109620
gtagacttt gtttgagaat catactcacg ccgtctcgat gaagcacagt gtccacggtc   109680
acgttgatgg ggttgccctc agcgtccaaa atgtatacct ggcactcgtc cgtgtcgtcc   109740
tggcactcga gcctgctgta catttcgaa gtggaaatgc cgcatcgcca cgatttgttg    109800
cacgtgtggt gcgcaaagtg attgttattc tgccgcttca ccaactcttt gcctttgacc   109860
cactggccgc ggccctcgtt gtcgcgaaaa cagtcgtcgc tgtcactgcc caacggtcg    109920
atcagctctt cgcccacctc gcactgctgc ctgatgctcc acataagcaa atcctctttg   109980
cccacattca gcgttttcat ggtttcttcg acgcgtgtgt tgggatccag cgagccgccg   110040
ttgtacgcat acgcctggta gtacccttg tagccgataa tcacgttttc gttgtagtcc    110100
gtctccacga tggtgatttc cacgtccttt tgcagcgttt ccttgggcgg ggtaatgtcc   110160
aagttttaa tcttgtacgg acccgtcttc atttgcgcgt tgcagtgctc cgccgcaaag   110220
gcagaatgcg ccgccgccgc caaaagcaca tataaaacaa tagcgcttac catcttgctt   110280
gtgtgttcct tattgaagcc ttggtgtgac tgatttacta gtagcattga ggcatcttat   110340
atacccgacc gttatctggc ctacgtgaca caaggcacgt tgttagatta ataatcttat   110400
cttttatct taattgataa gattattttt atctggctgt tataaaaacg ggatcatgaa   110460
cacgacgct cagtcgacat cgaacacgcg caacttcatg tactctcccg acagcagtct    110520
ggaggtggtc atcattacca attcggacgg cgatcacgat ggctatctgg aactaaccgc   110580
cgccgccaaa gtcatgtcac ctttttcttag caacggcagt tcggccgtgt ggaccaacgc   110640
ggcgccctcg cacaaattga ttaaaaacaa taaaaattat attcatgtgt ttggtttatt   110700
taaatatctg tcaaattaca atttaaataa taaaaagcgt cctaaagagt attacaccct   110760
taaatcgatt attagcgact tgcttatggg cgctcaaggc aaagtatttg atccgctttg   110820
cgaagtaaaa acgcaactgt gtgcgattca ggagagtctc aacgaggcta tttcgatttt   110880
```

```
gaacgttcat agcaacgatg cggccgccaa cccgcctgcg ccagacatta acaagttgca 110940
agaactgata caagatttgc agtctgaata caataaaaaa attacccttta ccactgatac 111000 aattttggag aatttaaaaa atataaagga tttaatgtgc ctgaataaat aataataagg 111060
gttttgtacg atttcaacaa tgaacttttg ggccacgttt agcatttgtc tggtgggtta 111120
tttggtgtac gcgggacact tgaataacga gctacaagaa ataaaatcaa tattagtggt 111180
catgtacgaa tctatggaaa agcattttttc caatgtggta gacgaaattg attctcttaa 111240
aacggacacg tttatgatgt tgagcaactt gcaaaataac acgattcgaa cgtgggacgc 111300
agttgtaaaa aatggcaaaa aaatatccaa tctcgacgaa aaaattaacg tgttattaac 111360
aaaaaacggg gtagttaaca acgtgctaaa cgttcaataa acgcttatca ctaagttaat 111420
atactaaaaa tcacatagtc actacaatat ttcaaaatat gaagccgacg aataacgtta 111480
tgttcgacga cgcgtcggtc ctttggatcg acacggacta catttatcaa aatttaaaaa 111540
tgcctttgca ggcgtttcaa caacttttgt tcaccattcc atctaaacat agaaaaatga 111600
tcaacgatgc gggcggatcg tgtcataaca cggtcaaata catggtggac atttacgag 111660 cggccgttct ggttttgcga acgccttgct cgttcgccga ccagttgttg agcacattta 111720
ttgcaaacaa ttatttgtgc tacttttacc gtcgtcgccg atcacgatca cgctcacgat 111780
cacgctcgcg atcacgttct cctcattgca gacctcgttc gcgctctcct cattgcagac 111840
ctcgttcgcg atctcggtcc cggtctagat cgcggtcacg ttcatcgtct cccaggcgag 111900
ggcgtcgaca aatattcgac gcgctggaaa agattcgtca tcaaaacgac atgttgatga 111960
gcaacgtcaa ccaaataaat ctcaaccaaa ctaatcaatt tttagaattg tccaacatga 112020
tgacgggcgt gcgcaatcaa aacgtgcagc tcctcgcggc gttggaaacc gctaaagatg 112080
ttattttgac cagattaaac acattgcttg ccgagattac agactcgtta cccgacttga 112140
cgtccatgtt agataaatta gctgaacaat tgttggacgc catcaacacg gtgcagcaaa 112200
cgctgcgcaa cgagttgaac aacaccaact ctatttgac caatttagcg tcaagcgtca 112260
caaacatcaa cggtacgctc aacaatttgc tagccgctat cgaaaactta gtaggcggcg 112320
gcggcggtgg caattttaac gaagccgaca gacaaaaact ggaccctcgtg tacactttgg 112380 ttaacgaaat caaaaatata ctcacgggaa cgctgacaaa aaaataagca tgtccgacaa 112440
aacaccaaca aaaagggtg gcagccatgc catgacgttg cgagagcgcg gcgtaacaaa 112500
acccccaaaa aagtctgaaa agttgcagca atacaagaaa gccatcgctg ccgagcaaac 112560
gctgcgcacc acagcagatg tttcttcttt gcagaacccc ggggagagtg ccgttttttca 112620 agagttggaa agattagaga atgcagttgt agtattagaa aatgaacaaa aacgattgta 112680
tcccatatta gatacgcctc ttgataattt tattgtcgca ttcgtgaatc cgacgtatcc 112740
catggcctat tttgtcaata ccgattacaa attaaaacta gaatgtgcca gaatcagaag 112800
cgatttactt tacaaaaaca aaaacgaagt cgctatcaac aggcctaaga tatcgtcttt 112860
taaattgcaa ttgaacaacg taattttaga cactatagaa actattgaat acgatttaca 112920
aaataaagtt ctcacaatta ctgcacctgt tcaagatcaa gaactaagaa aatccattat 112980 ttatttttaat attttaaata gtgacagttg ggaagtacca agtatatatga aaaaattgtt 113040 tgatgaaatg caattggaac ctcccgtcat tttaccatta ggtctttaga tttggtaagg 113100
ctagcacgtc gacatcatgt ttgcgtcgtt gacctcagag caaaagctgt tattaaaaaa 113160
atataaattt aacaattatg tgaaaacgat cgagttgagt caagcgcagt tggctcattg 113220
gcgttcaaac aaagatattc agccaaaacc ttttggatcgt gcagaaattt tacgtgtcga 113280
```

```
aaaggccacc aggggacaaa gcaaaaatga gctgtggacg ctattgcgtt tggatcgcaa 113340
cacagcgtct gcatcgtcca actcgtccgg caacatgtta caacgaccag cgcttttgtt 113400
tggaaacgcg caagaaagtc acgtcaaaga aaccaacggc atcatgttag accacatgcg 113460
cgaaatcata gaaagtaaaa ttatgagcgc ggtcgttgaa acggttttgg attgcggcat 113520
gttctttagc cccttgggtt tgcacgccgc ttcgcccgat gcgtattttt ctctcgccga 113580
cggaacgtgg atcccagtgg aaataaaatg tccgtacaat taccgagaca cgaccgtgga 113640
gcagatgcgt gtcgagttgg ggaacggcaa tcgcaagtat cgcgtgaaac acaccgcgct 113700
gttggttaac aagaaaggca cgccccagtt cgaaatggtc aaaacggatg cgcattacaa 113760
gcaaatgcaa cggcagatgt atgtgatgaa cgcgcctatg ggcttttacg tggtcaaatt 113820
caaacaaaat ttggtggtgg tttctgtgcc gcgcgacgaa acgttctgca acaaagaact 113880
gtctacggaa acaacgcgt acgtggcgtt tgccgtggaa aactccaact gcgcgcgcta 113940
ccaatgcgcc gacaagcgac ggctttcatt caaaacgcac agctgcaatc acaactatag 114000
tggtcaagaa atcgatgcta tggtcgatcg cggaatatat ttagattatg acatttaaa 114060 atgtgcgtac tgtgattta gctcagacag tcgggaaacg tgcgattctg ttttaaaacg 114120
cgagcacacc aactgcaaaa gttttaactt gaaacataaa aactttgaca atcctacata 114180
ctttgattat gttaaaagat tgcaaagttt gctaaagagt caccacttta gaaacgacgc 114240
taaaacactt gcctattttg gttactattt aactcataca ggaaccctga agacctttg 114300 ctgcggatcg caaaactcgt cgcccaccaa acacgatcat ttaaacgact gtgtatatta 114360
tttggaaata aataaaccct ttatattata tataattctt ttatttatac atttgtttat 114420
acaattttat ttacgacaaa tattgactcg ttgttcagaa agtttaataa gcttgtcaat 114480
ttcttcggct tgcaaagggc tgccaacgcg ttcgttttga atgcgcgtaa tccggtttac 114540
ggtattgttg gcgcgaacaa taaactcctc aactggcaaa ttacaatttt tgtttgcgta 114600
ctcattgtgc actgcggcca ggttttgtag aatgttttcg ggaaaaatgg caattctatt 114660
aaatttgaca tgttttttgat tgtatacata gttttgatat tcttccagcg taggatattt 114720
gtttaaactc ttgacgcatt caatgtacaa tttgtgcagt gacaaaattc tgttaaaatc 114780
caaacgagaa catttctcaa aagttatttc ttgaccgttg aaatgtacac tttgcaattg 114840
tttcaataaa ctgtcgtaaa aagttttttcc ttcttcaagc acaaacgcgg ggcgcatcgt 114900
gttatctaca acgcttatgt acttgtcaaa atcttcaatt atatgataga aatacaaata 114960
tctctccgcg tttatggacg tgtcgtttaa aacatgttcg tcaacaactc cgttatgatt 115020
tactttcaaa aatttcaaat cttgcaaagc gtccgcgttg gtcaacttgt tgataataaa 115080
tttgtctttg cattcaaacg ctctgtttgc aatccactcc acagcgtcca aaacggacat 115140
gcgtttaaac atgttgatac gttttagaca atacgctcgt tttttaccg cctcaacgtt 115200 cacgtccgtg tagtcgcacc attgcaggat ttgcaacatg tcctcggcaa aatgcgcgaa 115260
ctgccgcagc ttttccttc caaaatgttg attgtcgtgt ttaaaaagca acgttgaaat 115320
ttccgagaca taccacaaag ccgtgggcaa tttactttg atcagcggct ccatagccag 115380
gttgctgaac ccgatcatgc attccgtgtt gttaatgcgg taaatgacat agcgtttaaa 115440
gtagtccttt acattatcgt caatgtattc tgcgtcgttt atgtgcttgt acagcaaata 115500
gtacataagg cccgcgttaa acgcgacctt tttagcgtca aaatacgtgc acgccaacac 115560
gtaatcgttg tattcgtcga attgctcgtt gggcactatg gcgcccgtaa aagggcgtct 115620
```

```
gctgcgcggt gacaaacgcg ttccatgctg aatcaactgc ttcaaacttt ccaaattata   115680
acaatattca attgaatttt taatctcttt attttggctc cataaaagag gaaactcgag   115740
tcggctttta aacttggtca aactgccctg aattgtttca aacaagttgt aatgtgttaa   115800
caatatggcc ggcacaccgc tatcgttggc taaaatacaa tcggggaatc gaatattttc   115860
tacgttgctg taatcgtacg cttcgtcgtc gtcgttggca acaacatcgt cggtttcggc   115920
gtccacgctc gctaacttgt tctgatagtg taaattttc attacatcaa aagcgtatga   115980
cttgttgcga ttgtgcaaat aatttatggc cgtgctaatg gtgctgtcga taattttatc   116040
aaaattgaga acatcggcgt tatacaacgt tttataaaat tctgttgact tgaacgtgtt   116100
tacaaactca tttttatttt taatctggtc aaaattcata ctagaattgt tagtttgttt   116160
gatttcgctg aatagccgct ggcggagacg cttcagcttg tccacctcgt ttaacacgtt   116220
ggcgtccgtc ggcatggaat tgataaattt gaaccgaaca aaagacagca gttcatcttt   116280
tttcgatata aaattttcgg ttgtaatgat atcgtagtta aattcttttgg ttaaattgac   116340 ccattcgacc atttcatcgt tgcgataaat cttgcagtcc gagttgttga caaacgccga   116400
ggcaacggac aaatcaatct gttccgtgtt attattgatg gcataaaaca caatgcgttc   116460
gaaactaaac ggttttttcgt ttagcaaatt tttgcaaacg tttgcctcat ttttggaaat   116520
ttggccgtcg gtcaccatgt acaaaagttt caacttgccg tcgagcaagt ttatattctt   116580
gtgaatccac tttatgaatt cgctgggcct ggtgtcagta ccctcgccat tgcggcgcaa   116640
ataacgactc ttgacgtctc cgatttcttt ttggcggcaa taagcactcc aatgcaaata   116700
caaaactttg tcgcaactac tgatgttttc gatttcattc tgaaattgtt ctaaagtttg   116760
taacgcgttc ttgttaaagt aatagtccga gtttgtcgac aaggaatcgt cggtggcgta   116820
cacgtagtag ttaatcatct tgttgattga tatttaattt tggcgacgga ttttatata   116880 cacgagcgga gcggtcacgt tctgtaacat gagtgatcgt gtgtgtgtta tctctggcag   116940
cgcgatagtg gtcgcgaaaa ttacacgcgc gtcgtaacgt gaacgtttat attataaata   117000
ttcaacgttg cttgtattaa gtgagcattt gagctttacc attgcaaaat gtgtgtaatt   117060
tttccggtag aaatcgacgt gtcccagacg attattcgag attgtcaggt ggacaaacaa   117120
accagagagt tggtgtacat taacaagatt atgaacacgc aattgacaaa acccgttctc   117180
atgatgttta acatttcggg tcctatacga agcgttacgc gcaagaacaa caatttgcgc   117240
gacagaataa aatcaaaagt cgatgaacaa tttgatcaac tagaacgcga ttacagcgat   117300
caaatggatg gattccacga tagcatcaag tattttaaag atgaacacta ttcggtaagt   117360
tgccaaaatg gcagcgtgtt gaaaagcaag tttgctaaaa ttttaaagag tcatgattat   117420
accgataaaa agtctattga agcttacgag aaatactgtt tgcccaaatt ggtcgacgaa   117480
cgcaacgact actacgtggc ggtatgcgtg ttgaagccgg gatttgagaa cggcagcaac   117540
caagtgctat ctttcgagta caacccgatt ggtaacaaag ttattgtgcc gtttgctcac   117600
gaaattaacg acacgggact ttacgagtac gacgtcgtag cttacgtgga cagtgtgcag   117660
tttgatggcg aacaatttga agagtttgtg cagagtttaa tattgccgtc gtcgttcaaa   117720
aattcggaaa aggttttata ttacaacgaa gcgtcgaaaa acaaaagcat gatctacaag   117780
gctttagagt ttactacaga atcgagctgg ggcaaatccg aaaagtataa ttggaaaatt   117840
ttttgtaacg gttttatttta tgataaaaaa tcaaaagtgt tgtatgttaa attgcacaat   117900
gtaactagtg cactcaacaa aaatgtaata ttaaacacaa ttaaataaat gttaaaattt   117960
attgcctaat attattttgt cattgcttgt catttattaa tttggatgat gtcatttgtt   118020
```

```
tttaaaattg aactggcttt acgagtagaa ttctacgcgt aaaacacaat caagtatgag  118080
tcataatctg atgtcatgtt ttgtacacgg ctcataaccg aactggcttt acgagtagaa  118140
ttctacttgt aatgcacgat cagtggatga tgtcatttgt ttttcaaatc gagatgatgt  118200
catgttttgc acacggctca taaactcgct ttacgagtag aattctacgt gtaacgcacg  118260
atcgattgat gagtcatttg ttttgcaata tgatatcata caatatgact catttgtttt  118320
tcaaaaccga acttgattta cgggtagaat tctacttgta aagcacaatc aaaaagatga  118380
tgtcatttgt ttttcaaaac tgaactcgct ttacgagtag aattctacgt gtaaaacaca  118440
atcaagaaat gatgtcattt gttataaaaa taaaagctga tgtcatgttt tgcacatggc  118500
tcataactaa actcgcttta cgggtagaat tctacgcgta aaacatgatt gataattaaa  118560
taattcattt gcaagctata cgttaaatca aacggacgtt atggaattgt ataatattaa  118620
atatgcaatt gatccaacaa ataaaattgt aatagagcaa gtcgacaatg tggacgcgtt  118680
tgtgcatatt ttagaaccgg gtcaagaagt gttcgacgaa acgctaagcc agtaccacca  118740
atttcctggc gtcgttagtt cgattatttt cccgcaactc gtgttaaaca caataattag  118800
cgttttgagc gaagacggca gtttgctcac gttgaaactc gaaaacactt gttttaattt  118860
tcacgtgtgc aataaacgct ttgtgtttgg caatttgcca gcggcggtcg tgaataatga  118920
aacgaagcaa aaactgcgca ttggagctcc aattttgcc ggcaaaaagc tggtttcggt  118980
cgtgacggcg tttcatcgtg ttggcgaaaa cgaatggctg ttaccggtga cgggaattcg  119040
agaggcgtcc cagctgtcgg gacatatgaa ggtgctgaac ggcgtccgtg ttgaaaaatg  119100
gcgacccaac atgtccgtct acgggactgt gcaattgccg tacgataaaa ttaaacagca  119160
tgcgctcgag caagaaaata aaacgccaaa cgcgttggag tcttgtgtgc tattttacaa  119220
agattcagaa atacgcatca cttacaacaa gggggactat gaaattatgc atttgaggat  119280
gccgggacct ttaattcaac ccaacacaat atattatagt taaataagaa ttattatcaa  119340
atcatttgta tattaattaa aatactatac tgtaaattac attttattta caatcatgtc  119400
aaagcctaac gttttgacgc aaattttaga cgccgttacg gaaactaaca caaaggttga  119460
cagtgttcaa actcagttaa acgggctgga agaatcattc cagcttttgg acggtttgcc  119520
cgctcaattg accgatctta acactaagat ctcagaaatt caatccatat tgaccggcga  119580
cattgttccg gatcttccag actcactaaa gcctaagctg aaaagccaag cttttgaact  119640
cgattcagac gctcgtcgtg gtaaacgcag ttccaagtaa atgaatcgtt tttaaaataa  119700
caaatcaatt gttttataat attcgtacga ttctttgatt atgtaataaa atgtgatcat  119760
taggaagatt acgaaaaata taaaaatat gagttctgtg tgtataacaa atgctgtaaa  119820
cgccacaatt gtgtttgttg caaataaacc catgattatt tgattaaaat tgttgttttc  119880
tttgttcata gacaatagtg tgttttgcct aaacgtatac tgcataaact ccatgcgagt  119940
gtatagcgag ctagtggcta acgcttgccc caccaaagta gattcgtcaa atcctcaat  120000
ttcatcaccc tcctccaagt ttaacatttg gccgtcggaa ttaacttcta agatgccac  120060
ataatctaat aaatgaaata gagattcaaa cgtggcgtca tcgtccgttt cgaccatttc  120120
cgaaaagaac tcgggcataa actctatgat ttctctggac gtggtgttgt cgaaactctc  120180
aaagtacgca gtcaggaacg tgcgcgacat gtcgtcggga aactcgcgcg gaaacatgtt  120240
gttgtaaccg aacgggtccc atagcgccaa aaccaaatct gccagcgtca atagaatgag  120300
cacgatgccg acaatggagc tggcttggat agcgattcga gttaacgctt tggcagtcac  120360
```

```
ggtcagcgtt ttgatggcga tcacgttgag cgagtgcact aacgcggctt tgtaagtctc 120420
tcccaacatg cgcacggtca cgcgccgagt cgtgctaagc aacatgtgtt tcatggccgg 120480
aatgagagaa gtgttaattt ttttcaacat gcttttaaac ccggacatta gcatatcaaa 120540
gccaatgtcc gtagcaatac cgaaaacgag cgcgtaatct tccaaaaacg atgttataat 120600
tgactccaag tcttggtcgc tgattgaacg gtcgagcgcc tcgaaatgtt cgacacgtgc 120660
acgttcgtta ccgcggtaat tgtatgcgat cggagtttta gtaaagccgg tttcggccgt 120720
gtacgtgatc tggacgggcg acccgttgac gatcatgccc aaatcgttta gtgttggatt 120780
tttgttaaaa agttttttcaa attccaagtc tgtggcgtta tcgcgcacgc tgcgccattg 120840
cgctagtatt gcgttggagt ccacgttggg tcgtggcggt agtatgctgg aaggcgcttt 120900
gtaatcaaaa tcgcgcagtt cgctaaaaat gttgttggcc agcatttga aagtgacaaa 120960
gatcgtgtcg cccagcacga atccgatgag cgattcccac catctaaacg aacaaccgcc 121020
gttgaatagc tctctgccga aacgtcgaca gtaggcttcg ttgaattcgc ctttaaagcg 121080
ttcgggaaac aaggggtcgg gatcgggccg aacgttaaaa gccggacat cgtccacgcc 121140
catgatcgtg tgttcttcgg tgcgcaagta tgggctgtta aagtacattt tggacagcga 121200
gtccactaag atgcatttgt tgtcgagcgt gtatctaaac tcggcagact gaacttgggt 121260
ttcggcgcct tcacgcatgg ccgccgccct gtccaggtgg tagcacgcgg gctgcgcgta 121320
acccacgcta gtctcggagg tctgcgtgta catgaacggc gtcgtgttgg acacgacgcc 121380
ggtttcgtga acggatagc agctcatgct ttcacacccg cgcttgctga agccagttt 121440
gacgccagc gctttgtcgg ccaatttcgg cggcacataa taatcgtcgt cacttgacgc 121500
gggacgcagc gtgtagtcga ttagtatatg cggaaacctg gtgcgccatc tcgaaataaa 121560
ctcgagacga tgcatatgta tggcatacct actggcatta gttaaatcga cggctgttaa 121620
aaccgccatg ttatatagga cttaaaataa acaacaatat ataatgaaat atttattaga 121680
ttatattata gcaatacatt tacatttatt ataacaatac ttttttattta atctgattat 121740
attataacga tacattttta tttagacatt gttatttaca atattaatta acttttttata 121800
cattttaaa tcataatata taatcatttc gttgtgcatt tcaaagcttt tgatagcttc 121860
aaagtaatac atgaatttag agtattcagg aaaatgataa acgttggtaa acccgcattt 121920
ggtacaatat aacacgggat ttttataata cagtttagtt ttttttacaca atttgcaata 121980
gttgttagtt gtaggtttca aaggaaacgt gattgcgccg tccaatacct gggtaaactt 122040
tttgacttta acagtggcaa acacggttcc tttgatacc gaaaatcggt tgtcttgcag 122100
agcggccatc atttcgcttg gctcttgaag tataaaacag ttgacgtcat ccaccacgtc 122160
gggtctggtg cacatgcttc ggtagcgctg caacactata ttggtgtatg tttccctgag 122220
aacgagaccg ccggtggtgc taagatcgat tgtttgaatg cgctcgttgg gctctttgtg 122280
atttcgaatt atgcgccgaa ttatttcaaa cactttgcag ttgtgatcgt caattctcaa 122340
ttcttttaact tccgtcgtgt gctctaaact tacagggaaa atgtattggt aaaaaaaacct 122400
ctctctggct aaatagctga ggtcgaccaa attgatagaa ggatatattt cgtacgaggt 122460
ttttggaacg ttgtgatata gatagcattt ttgacagcag atgtctatgc ggtcaggatc 122520
gtccaacggc ttttcgatgt gaaccacaac atacaaaaac cattcgcgcg tgttgtcttt 122580
gaatctataa ttgcaagtgg tgcatcgcga atcgctcatg tgctccatag tcttcttgta 122640
tttcacaggc ctgcttgcaa atttgcccgt catgcgcata tctttgctgt ttatgtagcc 122700
cataatgtaa ttggtggaaa attttagcgt ggctttcatg atgtcgcgtt ctaaatcgct 122760
```

```
catgaaatgc atacgtagat cgcgctcttg tttgaaatcc agtttgtcgc tgtacgcggg  122820
caaaccttca aacttgttcc caaactcggg cggcacaaaa tatccatctt ttctgttgac  122880
gactggtttt ttacttacaa tgctgctgtg ctccaacggc ttggccggag aggtgcgcgt  122940
aggctgttta ggcggagaga tgcgcgtagg tggtttgatg ttagattttg gcggcggacg  123000
aacaggcgac ggcggcgagt tggcggcagg cgctggcaaa gatttggcac gacccttgcc  123060
cccggtcctt ggcgcgtcaa aaatgttatt ctctcgaaaa aaacggttca ttgtaactgt  123120
tagttagcac tcagaaatca acacgatact gtgcacgttc agccatcgag aggctttata  123180
tatgaaaacc ttatctatag agataagatt gtatatgcgt aggagagcct ggtcacgtag  123240
gcactttgcg cacggcacta gggctgtgga ggggacaggc tatataaagc ccgtttgccc  123300
aactcgtaaa tcagtatcaa ttgtgctccg gcgcacacgc tcgcttgcgc gccgatagt  123360 ataagtaatt gataacgggc aacgcaacat gataagaacc agcagtcacg tgctgaacgt  123420
ccaggaaaat ataatgacgt caaactgtgc gtcatcgcca tattcgtgcg aggcaacgtc  123480
cgcttgcgca gaagctcaac aggtaatgat cgataacttt gttttctttc acatgtacaa  123540
cgccgacata caaattgacg caaagctgca atgcggcgtg cgctcggccg cgtttgcaat  123600
gatcgacgat aaacatttgg aaatgtacaa gcatagaata gagaataaat ttttttatta  123660
ctatgatcaa tgtgccgaca ttgccaaacc cgaccgtctg cccgatgacg acggcgcgtg  123720
ctgtcaccat tttattttg atgcccaacg tattattcaa tgtattaaag agattgaaag  123780
cgcgtacggc gtgcgtgatc gcggcaatgt aatagtgttt tatccgtact tgaaacagtt  123840
gcgagacgcg ttgaagctaa ttaaaaactc ttttgcgtgt tgttttaaaa ttataaattc  123900
tatgcaaatg tacgtgaacg agttaatatc aaattgcctg ttgtttattg aaaagctgga  123960
aactattaat aaaactgtta aagttatgaa tttgtttgta gacaatttgg ttttgtacga  124020
atgcaatgtt tgtaaagaaa tatctacgga tgaaagattt ttaaagccaa agaatgttg  124080 cgaatacgct atatgcaacg cgtgctgcgt taacatgtgg aagacggcca ccacgcacgc  124140
aaaatgtcca gcgtgcagga catcgtataa ataagcacgc aacgcaaaat gagtggtggc  124200
ggcaacttgt tgactctgga aagagatcat tttaaatatt tatttttgac cagctatttt  124260
gatttaaaag ataatgaaca tgttccttca gagcctatgg catttattcg caattacttg  124320
aattgcacgt ttgatttgct agacgatgcc gtgctcatga actatttcaa ttacttgcaa  124380
agcatgcaat tgaaacattt ggtgggcagc acgtcgacaa acattttcaa gtttgtaaag  124440
ccacaattta gatttgtgtg cgatcgcaca actgtggaca ttttagaatt tgacacgcgc  124500
atgtacataa aacccggcac gcccgtgtac gccacgaacc tgttcacgtc caatccccgc  124560
aagatgatgg ctttcctgta cgctgaattt ggcaaggtgt taaaaataa atattcgta  124620 aacatcaaca actacggctg cgtgttggcg ggcagtgccg gtttcttgtt cgacgatgcg  124680
tacgtggatt ggaatggtgt gcgaatgtgt gcggcgccgc gattagataa caacatgcat  124740
ccgttccgac tgtatctact gggcgaggac atggctaagc actttgtcga taataatata  124800
ctaccgccgc acccttctaa cgcaaagact cgcaaaatca acaattcaat gtttatgctg  124860
aaaaactttt acaaaggtct gccgctgttc aaatcaaagt acacggtggt gaacagcact  124920
aaaatcgtga cccgaaaacc caacgatata tttaatgaga tagataaaga attaaatggc  124980
aactgtccgt ttatcaagtt tattcagcgc gactacatat tcgacgccca gtttccgcca  125040
gatttgcttg atttgctaaa cgaatacatg accaaaagct cgatcatgaa aataattacc  125100
```

```
aagtttgtga ttgaagaaaa ccccgctatg agcggtgaaa tgtctcgcga gattattctt    125160
gatcgctact cagtagacaa ttatcgcaag ctgtacataa aaatggaaat aaccaaccag    125220
tttcctgtca tgtacgatca tgaatcgtcg tacatttttg tgagcaaaga cttttttgcaa   125280 ttgaaaggca ctatgaacgc gttctacgcg cccaagcagc gtatattaag tattttggcg    125340
gtgaatcgtt tgtttggcgc cacggaaacg atcgactttc atcccaacct gctcgtgtac    125400
cggcagagtt cgccgccggt ccgtttgacg ggcgacgtgt atgttgttga taagaacgaa    125460 aaagttttt tggtcaaaca cgtgttctca aacacggtgc ctgcatatct tttaataaga    125520
ggtgattacg aaagttcgtc tgacttgaaa tcccttcgcg atttgaatcc gtgggttcag    125580
aacacgcttc tcaaattatt aatccccgac tcggtacaat aatatgattt acactgatcc    125640
cactactggc gctacgacta gcacagacgc gccgtccaca aactatttaa acaggctaac    125700
tccaaacatg ttcttgacca tcttggctgt agtagtaatt attgctttaa taattatatt    125760
tgttcaatct agcagtaatg gaaacagctc ggggggtaat gtacctccaa acgccctggg    125820
gggttttgta aatcctttaa acgctaccat gcgagctaat ccctttatga acacgcctca    125880
aaggcaaatg ttgtagataa gtgtataaaa aatgaaacgt atcaaatgca acaaagttcg    125940
aacggtcacc gagattgtaa acagcgatga aaaaatccaa aagacctacg aattggctga    126000
atttgattta aaaaatctaa gcagtttaga aagctatgaa actctaaaaa ttaaattggc    126060
gctcagcaaa tacatggcta tgctcagcac cctggaaatg actcaaccgc tgttggaaat    126120
atttagaaac aaagcagaca ctcggcagat tgccgccgtg gtgtttagca cattagcttt    126180
tatacacaat agattccatc cccttgttac taatttttact aacaaaatgg agtttgtggt   126240
cactgaaacc aacgacacaa gcattcccgg agaacccatt ttgtttacgg aaaacgaagg    126300
tgtgctgctg tgttccgtgg acagaccgtc tatcgttaaa atgctaagcc gcgagtttga    126360
caccgaggct ttagtaaact ttgaaaacga caactgcaac gtgcggatag ccaagacgtt    126420
tggcgcctct aagcgcaaaa acacgactcg cagcgatgat tacgagtcaa ataaacaacc    126480
caattacgat atggatttga gcgattttag cataactgag gttgaagcca ctcaatattt    126540
aactctgttg ctgaccgtcg aacatgccta tttacattat tatattttta aaaattacgg    126600
ggtgtttgaa tattgcaaat cgctaacgga ccattcgctt tttaccaaca aattgcgatc    126660
gacaatgagc acaaaaacgt ctaatttact gttaagcaaa ttcaaattta ccattgaaga    126720
ttttgacaaa ataaactcaa attctgtaac atcagggttt aatatatata attttaataa    126780
ataattaaat aatatacaat gttttttatta attatatttt taatattaat taaagtatta    126840
atatttaaaa aaatgaatca aattcatcta aagtgtcaca gcgataaaat ttgtcctaaa    126900
gggtattttg gcctcaacgc cgatccctat gattgcacgg cgtattatct gtgtccgcat    126960
aaagtgcaaa tgttttgcga attaaatcac gaatttgact tggactccgc cagctgcaag    127020
cctatcgtgt acgatcacac gggcagcggg tgtacggctc gcatgtatag aaacttgtta    127080
ctatgaagag cgggtttcca gttgcacaac actattatcg atttgcagtt cgggacataa    127140
atgtttaaat atatcgatgt ctttgtgatg cgcgcgacat ttttgtaggt tattgataaa    127200
atgaacggat acgttgcccg acattatcat taaatccttg gctagaatt tgtcgggtcc    127260 attgtccgtg tgcgctagca tgcccgtaac ggacctcgta cttttggctt caaaggtttt    127320
gcgcacagac aaaatgtgcc acacttgcag ctctgcatgt gtgcgcgtta ccacaaatcc    127380
caacggcgca gtgtacttgt tgtatgcaaa taaatctcga taaaggcgcg cgcgcgaat    127440 gcagctgatc acgtacgctc ctcgtgttcc gttcaaggac ggtgttatcg acctcagatt    127500
```

```
aatgtttatc ggccgactgt tttcgtatcc gctcaccaaa cgcgttttg  cattaacatt 127560 gtatgtcggc ggatgttcta tatctaattt gaataaataa acgataaccg cgttggtttt 127620
agagggcata ataaaagaaa tattgttatc gtgttcgcca ttagggcagt ataaattgac 127680
gttcatgttg gatattgttt cagttgcaag ttgacactgg cggcgacaag atcgtgaaca 127740
accaagtgac tatgacgcaa attaatttta acgcgtcgta caccagcgct tcgacgccgt 127800
cccgagcgtc gttcgacaac agctattcag agttttgtga taaacaaccc aacgactatt 127860
taagttatta taaccatccc accccggatg gagccgacac ggtgatatct gacagcgaga 127920
ctgcggcagc ttcaaacttt ttggcaagcg tcaactcgtt aactgataat gatttagtgg 127980
aatgtttgct caagaccact gataatctcg aagaagcagt tagttctgct tattattcgg 128040
aatcccttga gcagcctgtt gtggagcaac catcgcccag ttctgcttat catgcggaat 128100
cttttgagca ttctgctggt gtgaaccaac catcggcaac tggaactaaa cggaagctgg 128160
acgaatactt ggacaattca caaggtgtgg tgggccagtt taacaaaatt aaattgaggc 128220
ctaaatacaa gaaaagcaca attcaaagct gtgcaaccct tgaacagaca attaatcaca 128280
acacgaacat ttgcacggtc gcttcaactc aagaaattac gcattatttt actaatgatt 128340
ttgcgccgta tttaatgcgt ttcgacgaca acgactacaa ttccaacagg ttctccgacc 128400
atatgtccga aactggttat tacatgtttg tggttaaaaa aagtgaagtg aagccgtttg 128460
aaattatatt tgccaagtac gtgagcaatg tggtttacga atatacaaac aattattaca 128520
tggtagataa tcgcgtgttt gtggtaactt ttgataaaat taggtttatg atttcgtaca 128580
atttggttaa agaaaccggc atagaaattc ctcattctca agatgtgtgc aacgacgaga 128640
cggctgcaca aaattgtaaa aaatgccatt tcgtcgatgt gcaccacacg tttaaagctg 128700
ctctgacttc atatttttaat ttagatatgt attacgcgca aaccacatt  gtgactttgt 128760 tacaatcgtt gggcgaaaga aaatgtgggt ttcttttgag caagttgtac gaaatgtatc 128820
aagataaaaa tttatttact ttgcctatta tgcttagtcg taaagagagt aatgaaattg 128880
agactgcatc taataatttc tttgtatcgc cgtatgtgag tcaaatatta agtattcgg  128940 aaagtgtgca gtttcccgac aatcccccaa acaaatatgt ggtggacaat ttaaatttaa 129000
ttgttaacaa aaaagtacg ctcacgtaca aatacagcag cgtcgctaat cttttgttta 129060
ataattataa atatcatgac aatattgcga gtaataataa cgcagaaaat ttaaaaaagg 129120
ttaagaagga ggacggcagc atgcacattg tcgaacagta tttgactcag aatgtagata 129180
atgtaaaggg tcacaatttt atagtattgt ctttcaaaaa cgaggagcga ttgactatag 129240
ctaagaaaaa caaagagttt tattggattt ctggcgaaat taagatgta  gacgttagtc 129300 aagtaattca aaaatataat agatttaagc atcacatgtt tgtaatcggt aaagtgaacc 129360
gaagagagag cactacattg cacaataatt tgttaaaatt gttagcttta atattacagg 129420
gtctggttcc gttgtccgac gctataacgt ttgcggaaca aaaactaaat tgtaaatata 129480
aaaaattcga atttaattaa ttatacatat attttgaatt taattaatta tacatatatt 129540
ttatattatt tttgtctttt attatcgagg ggccgttgtt ggtgtggggt tttgcataga 129600
aataacaatg ggagttggcg acgttgctgc gccaacacca cctcctcctc ctcctttcat 129660
catgtatctg tagataaaat aaaatattaa acctaaaaac aagaccgcgc ctatcaacaa 129720
aatgataggc attaacttgc cgctgacgct gtcactaacg ttggacgatt tgccgactaa 129780
accttcatcg cccagtaacc aatctagacc caagtcgcca actaaatcac caaacgagta 129840
```

```
aggttcgatg cacatgagtg tttggcccgc aggaagatcg ctaatatcta cgtattgagg  129900
cgaatctggg tcggcggacg gatcgctgcc gcgacaaact gttttttcta cttcatagtt  129960
gaatccttgg cacatgttgg ttagttcggg cggattgtta ggcaacaagg ggtcgaatgg  130020
gcaaatggta acatccgact gatttagatt ggggtcttga cgacaagtgc gctgcaataa  130080
caagcaggcc tcggcgattt ctccggcgtc tttaccttgc acataataac ttccgccggt  130140
gttattgatg gcgttgatta tatcttgtac tagtgtggcg gcgctaaaca agaaatagcc  130200
gccggtggcc aagagtatgc ccgttcctcc tacttttaag ctttgcatgt aactatgtag  130260
acggggtttt tgctgcagtg cgttttgaac accttcgggc gtgcgcacgt tggtttccgg  130320
gaagttttgt ttgactgcat tggatcgcgt ctgcttggtg tggtaattaa agtctggcac  130380
gttgtccacg cgccgcaatt ggctcaatga gtttatttga gggtctgaaa tgccctgaaa  130440
tactccgcgt atgttgggga catcattgtt acgagtaatt ctgtttatgt ctgaagtgct  130500
cacaaactgg ttgttagata gttgatagcc cggctgaaat ctgttgtttc caatgttgcg  130560
tacactgggc gcgttgagca catttgtgaa accggcggga gtgcttgtta aaagacgcgt  130620
attatcagta ataaaactgg cctgattagg atacaattta ttgactgcgc gaagatttga  130680
aaaaaaactc attttaaagc aaacttattt aataaatata tcacagtaaa ggttttgcaa  130740
aactgccgtc gtcaatacaa cacggcagcg gcgtcatgtt ggtaaaatct aatcttctcc  130800
ttgctttaga ttctgggcga gaaggcgcat ttgttgtgta agttatttcg acgtctgcat  130860
tatttgttgt gtaaggtatc tcgacgtatg aagcaacttt aacattgtta taatttttt   130920
taaatattga tgcgctccac ggcgcgcgtt gatacggatg atatctctcc attgtatgat  130980
cgctaaattt ataccgtt tcaataaata tgttaaaacc caacatgtta attataatat  131040
tcataatagt ttgtttgttt tcaataatta tttttactgt tttgaaatct aaaagaggtg  131100
acgatgacga atcagacgac gggttcagtt gctataacaa accaattgga gtaaattttc  131160
cgcatcctac tagatgtgac gctttctaca tgtgtgtcgg tttaaatcaa aaattagagt  131220
taatctgccc tgaaggattt gaatttgatc cagatgttaa aaattgtgtt cctatatcag  131280
attatggatg taccgctaac caaaactaaa aataaaataa aatttatata gattaatgaa  131340
ataaaattta tatagattaa taaaataaaa tttatttaat atattatact atttatatta  131400
tttacaacac ttaacgtcta gacataacag tttgtaactt agaaactaaa tcagagttac  131460
tgcgctcaaa ctctgaaaat ttggcttgag actcggccac ctgcttacgc aattgttctt  131520
gcagattatt cacagtcgat tgcaactctt ctgatttctt ggtagattct tgcaagtcat  131580
agtttgcctt ttgtaaatct aattcggcga cagcatgctt gtgtttaagc ataatgtagt  131640
cgctgtttaa catggtcatt ttatgttcaa cttggctggt cttggctcgc agctcggaca  131700
gttcttttg caattgctcc acatagttca agtccgtggt gtgattgttg accgtgttat  131760
tttctaaaag ctcgcgccaa tgctgtttga tggaatcctg gttacgagtg acgttaatgg  131820
gcataaattc tacataccg tgcttattgt acacgcgaca atctgatgaa gtagcgctgc  131880
aaaaacattt gtacacagaa ttgtccataa ttatcttgac ataacacttg aaacacacag  131940
catggttaca atgaatcgaa gtcacaaacg aggaatttac gttttagtg tctttaaaag  132000
tagtaaaaca atattacac gaaacctcta cttcttcttc gggttctgat tgctgctgct  132060
gctgctgctg cggctgcgga gactgcggcg aggcaaacaa atctggcgac tgtggtatta  132120
cgtaattcgg cgaataagat ggactataag tgggagacct tggggcaatc tcattcatca  132180
gctgagcctc aagatctaaa cctcgttgca gagccctctg cgcagctgtc tccgacgcaa  132240
```

```
tgttatcctg gtactgctgg gcagtgatgt cgggaaaccg ttcacgatcc acattttcac   132300
tattaattag tatgacgtca tcctcttgac ttaatagcgg atcgtcattg ctaatgttaa   132360
cctgaccgtg cacgtaatac gtgacaccct gacgatggta ggtgcgcgtc aacggctcgt   132420
tgacgttccc gataatctgc acgttttctt cgctgacacg ctgctcctga cgccgctcct   132480
gacggcgatg gctgcgactg cttgaagacg gctggctgcg actgcttgaa gacggctggg   132540
cttcgggaga tgttgtaaag ttgatgcggc gacggctgag agacagcctg tggcggcggc   132600
tgctgctggg agtggcggcg ttgatttggc gactcatggc tgggctggta ggatactgtt   132660
cactaggctg tgaggcttga actgtgctta cgagtagaac ggcagctgta tttatactgt   132720
ttatcagtac tgcacgactg ataagacaat agtggtgggg gaacttgcca ggcaaaaatg   132780
aacttttttg taatgcaaaa aagttgatag tgtagtagta tattgggagc gtatcgtaca   132840
gtgtagacta ttctaataaa atagtctacg atttgtagag attgtactgt atatggagtg   132900
tcaggcaaaa gtgaactttt ttgcattgca aaaaaattca ttttaaattt atcatatcac   132960
aggctgcagt ttctgttatc tgtcccccac tcaggcgtgc agctataaaa gcaggcactc   133020
accaactcgt aagcacagtt cgttgtgaag tgaacacgga gagcctgcca ataagcaaaa   133080
tgccaaggga caccaacaat cgccaccggt ctacgccata tgaacgtcct acgcttgaag   133140
atctccgcag acagttgcaa gacaatttgg acagcataaa ccccccgagac agaatgcaag   133200 aagaacaaga agaaaacctg cgctatcaag tgcgtagaag gcagcgtcaa aaccagctcc   133260
gctccataca aatggaacag cagcgaatga tggcggaatt aaacaacgag ccggtgatta   133320
attttaaatt tgagtgtagt gtgtgtttag aaacatattc ccaacaatct aacgatactt   133380 gtccttttttt gattccgact acgtgcgacc acggttttttg tttcaaatgc gtcatcaatc   133440
tgcaaagcaa cgcgatgaat attccgcatt ccactgtgtg ctgtccattg tgcaatacccc  133500 aggtaaaaat gtggcgttcc ttaaagccta acgctgttgt gacgtgtaag ttttacaaga   133560
aaactcaaga aagagttccg cccgtgcagc agtataaaaa cattattaaa gtgctacaag   133620
aacggagcgt gattagtgtc gaagacaacg acaataattg tgacataaat atggagaatc   133680
aggcaaagat agctgctttg gaagctgaat tggaagaaga aaaaaatcac agtgatcaag   133740
tagcttctga aaaccgacag ctgatagaag aaaatactcg tctcaatgaa cagattcaag   133800
agttgcagca tcaggtgagg acattggtgc cgcaacgtgg cattacggtt aatcagcaaa   133860
ttggccgtga cgacagtgcg ccagccgagc tgaacgagcg ttttcgctca cttgtctatt   133920
cgactatttc agagctgttt attgaaaatc gcgttcatag tattcaaaat tatgtttatg   133980
ccggaacttc tgctgctagt tcatgtgatg taaatgttac tgttaatttt gggtttgaaa   134040
attaatgtga tatgaaatgt atatataaaa atgatgaat aaataataaa cattttata    134100 cttttatgt ttttttttatt tcatgtgatt aagaaacttt taagatggat agtagtaatt   134160
gtattaaaat agatgtaaaa tacgatatgc cgttacatta tcaatgtgac aataacgcag   134220
ataaagacgt tgtaaatgcg tatgacacta tcgatgttga ccccaacaaa agatttataa   134280
ttaatcataa tcacgaacaa caacaagtca atgaaacaaa taacaagtt gtcgataaaa    134340 cattcataaa tgacacagca acatacaatt cttgcataat aaaaatttaa atgacatcat   134400
atttgagaat aacaaatgac attatccctc gattgtgttt tacaagta               134448
```

<210> SEQ ID NO 3
<211> LENGTH: 296
<212> TYPE: PRT

-continued

<213> ORGANISM: Porcine circovirus 3

<400> SEQUENCE: 3

Val Arg Arg Glu Ser Pro Lys His Arg Trp Cys Phe Thr Ile Asn Asn
1               5                   10                  15

Trp Thr Pro Thr Glu Trp Glu Ser Ile Val Glu Cys Gly Gly Ser Ile
            20                  25                  30

Ala Arg Tyr Leu Ile Ile Gly Lys Glu Val Gly Lys Gly Gly Thr Pro
        35                  40                  45

His Leu Gln Gly Tyr Val Asn Phe Lys Asn Lys Arg Arg Leu Ser Ser
    50                  55                  60

Val Lys Arg Leu Pro Gly Phe Gly Arg Ala His Leu Glu Pro Ala Arg
65                  70                  75                  80

Gly Ser His Lys Glu Ala Ser Glu Tyr Cys Lys Lys Glu Gly Asp Tyr
                85                  90                  95

Leu Glu Ile Gly Glu Asp Ser Ser Gly Thr Arg Ser Asp Leu Gln
            100                 105                 110

Ala Ala Ala Arg Ile Leu Thr Glu Thr Ser Gly Asn Leu Thr Glu Val
        115                 120                 125

Ala Glu Lys Met Pro Ala Val Phe Ile Arg Tyr Gly Arg Gly Leu Arg
    130                 135                 140

Asp Phe Cys Gly Val Met Gly Leu Gly Lys Pro Arg Asp Phe Lys Thr
145                 150                 155                 160

Glu Val Tyr Val Phe Ile Gly Pro Pro Gly Cys Gly Lys Thr Arg Glu
                165                 170                 175

Ala Cys Ala Asp Ala Ala Ala Arg Glu Leu Gln Leu Tyr Phe Lys Pro
            180                 185                 190

Arg Gly Pro Trp Trp Asp Gly Tyr Asn Gly Glu Gly Ala Val Ile Leu
        195                 200                 205

Asp Asp Phe Tyr Gly Trp Val Pro Phe Asp Glu Leu Leu Arg Ile Gly
    210                 215                 220

Asp Arg Tyr Pro Leu Arg Val Pro Val Lys Gly Gly Phe Val Asn Phe
225                 230                 235                 240

Val Ala Lys Val Leu Tyr Ile Thr Ser Asn Val Val Pro Glu Glu Trp
                245                 250                 255

Tyr Ser Ser Glu Asn Ile Arg Gly Lys Leu Glu Ala Leu Phe Arg Arg
            260                 265                 270

Phe Thr Lys Val Val Cys Trp Gly Glu Gly Gly Ile Lys Lys Asp Met
        275                 280                 285

Glu Thr Val Tyr Pro Ile Asn Tyr
    290                 295

<210> SEQ ID NO 4
<211> LENGTH: 214
<212> TYPE: PRT
<213> ORGANISM: Porcine circovirus 3

<400> SEQUENCE: 4

Met Arg His Arg Ala Ile Phe Arg Arg Lys Pro Arg Pro Arg Arg Arg
1               5                   10                  15

Arg Arg His Arg Arg Arg Tyr Val Arg Lys Leu Phe Ile Arg Arg
            20                  25                  30

Pro Thr Ala Gly Thr Tyr Tyr Thr Lys Lys Tyr Ser Thr Met Asn Val
        35                  40                  45

Ile Ser Val Gly Thr Pro Gln Asn Asn Lys Pro Trp His Ala Asn His

```
              50                  55                  60
Phe Ile Thr Arg Leu Asn Glu Trp Glu Thr Ala Ile Ser Phe Glu Tyr
 65                  70                  75                  80

Tyr Lys Ile Leu Lys Met Lys Val Thr Leu Ser Pro Val Ile Ser Pro
                 85                  90                  95

Ala Gln Gln Thr Lys Thr Met Phe Gly His Thr Ala Ile Asp Leu Asp
            100                 105                 110

Gly Ala Trp Thr Thr Asn Thr Trp Leu Gln Asp Asp Pro Tyr Ala Glu
        115                 120                 125

Ser Ser Thr Arg Lys Val Met Thr Ser Lys Lys His Ser Arg Tyr
    130                 135                 140

Phe Thr Pro Lys Pro Ile Leu Ala Gly Thr Thr Ser Ala His Pro Gly
145                 150                 155                 160

Gln Ser Leu Phe Phe Ser Arg Pro Thr Pro Trp Leu Asn Thr Tyr
                165                 170                 175

Asp Pro Thr Val Gln Trp Gly Ala Leu Leu Trp Ser Ile Tyr Val Pro
            180                 185                 190

Glu Lys Thr Gly Met Thr Asp Phe Tyr Gly Thr Lys Glu Val Trp Ile
        195                 200                 205

Arg Tyr Lys Ser Val Leu
    210

<210> SEQ ID NO 5
<211> LENGTH: 2000
<212> TYPE: DNA
<213> ORGANISM: Porcine circovirus 3

<400> SEQUENCE: 5
tagtattacc cggcacctcg gaacccggat ccacggaggt ctgtagggag aaaaagtggt      60
atcccattat ggatgctccg caccgtgtga gtggatatac cgggcagtgg atgatgaagc     120
ggcctcgtgt tttgatgccg caggacgggg actggataac tgagttttg tggtgctacg     180 agtgtcctga agataaggac ttttattgtc atcctattct aggtccggag ggaaagcccg     240
aaacacaggt ggtgttttac gataaacaac tggaccccga ccgagtggga atctattgtg     300
gagtgtggag gcagtatagc gagataacct tattatcggca aagaggttgg aaaaggcggt     360
accccacact tgcaagggta cgtgaatttc aagaacaaaa ggcgactcag ctcggtgaag     420
cgcttacccg gatttggtcg ggcccatctg gagccggcga gggggagcca caagaggcc      480 agcgagtatt gcaagaaaga gggggattac ctcgagattg cgaagattc ctcttcgggt      540 accagatcgg atcttcaagc agcagctcgg attctgacgg agacgtcggg aaatctgact     600
gaagttgcgg agaagatgcc tgcagtattt atacgctatg gcgggggttt gcgtgattt      660 tgcgggggtga tggggttggg taaaccgcgt gatttttaaaa ctgaagtta tgttttatt     720 ggtcctccag gatgcgggaa aacgcgggaa gcttgtgcgg atgcggctgc gcgggaattg     780
cagttgtatt tcaagccacg ggggccttgg tgggatggtt ataatgggga gggtgctgtt     840
attctggatg atttttatgg gtgggttcca tttgatgaat tgctgagaat tggggacagg     900
taccctctga gggttcctgt taagggtggg tttgttaatt ttgtggctaa ggtattatat     960
attactagta atgttgtacc ggaggagtgg tattcctcgg agaatattcg tggaaagttg    1020
gaggccttgt ttaggaggtt cactaaggtt gtttgttggg gggagggggg gataaagaaa    1080
gacatggaga cagtgtatcc aataaactat tgattttatt tgcacttgtg tacaattatt    1140
gcgttggggt ggggggtattt attgggtggg tgggtgggca gcccctagc cacggcttgt    1200
```

```
cgcccccacc gaagcatgtg ggggatgggg tccccacatg cgaggcgtt tacctgtgcc    1260 cgcacccgaa gcgcagcggg agcgcgcgcg aggggacacg gcttgtcgcc accggagggg    1320
tcagatttat atttattatc acttagagaa cggacttgta acgaatccaa acttctttgg    1380
tgccgtagaa gtctgtcatt ccagttttt ccgggacata aatgctccaa agcagtgctc     1440
cccattgaac ggtggggtca tatgtgttga gccatggggt gggtctggag aaaaagaaga    1500
ggctttgtcc tgggtgagcg ctggtagttc ccgccagaat tggtttgggg gtgaagtaac    1560
ggctgtgttt tttttagaa gtcataactt tacgagtgga actttccgca taagggtcgt     1620
cttggagcca agtgtttgtg gtccaggcgc cgtctagatc tatggctgtg tgcccgaaca    1680 tagttttgt ttgctgagct ggagaaatta cagggctgag tgtaacttc atctttagta      1740 tcttataata ttcaaagcta attgcagttt cccattcgtt taggcgggta atgaagtggt    1800
tggcgtgcca gggcttatta ttctgagggg ttccaacgga aatgacgttc atggtggagt    1860
atttctttgt gtagtatgtg ccagctgtgg gcctcctaat gaatagtttt cttctgacat    1920
agcgccttct gtggcgtcgt cgtctccttg ggcggggttt tcttctgaat atagctctgt    1980
gtctcatttt ggtgccgggc                                                2000

<210> SEQ ID NO 6
<211> LENGTH: 645
<212> TYPE: DNA
<213> ORGANISM: Porcine circovirus 3

<400> SEQUENCE: 6
atgcgccacc gtgctatctt caggcgtagg cctaggccca gaaggaggag gagacaccgc      60
cgtcgttacg ctagacgccg tctgttcatc aggagaccaa ccgccggtac ttactacacc     120
aagaagtact ccactatgaa cgtgatcagc gtcggcaccc cacagaacaa caagccttgg     180
cacgctaacc acttcatcac tcgcctgaac gagtgggaaa ctgccatcac cttcgagtac     240
tacaagatcc tgaagatgaa ggtgaccctg tcccctgtca tcagccccgc tcagcagacc     300
aagactatgt tcggccacac tgctatcgac ctggacggag cctggaccac taacacctgg     360
ctgcaggacg acccctacgc cgaatccagc actaggaagg tcatgaccca gccattctct    420
cactcaagat acttcactcc aaagcctctg ctggctggaa ccacttccgc ccaccctgga    480
cagtctctgt tcttcttctc ccgccccacc ccatggctga acacttacga ccctaccgtg    540
cagtggggtg ccctgctgtg gtctatctac gtccccgaga agactggtat gaccgacttc    600
tacggcacca aggaagtgtg gatcaggtac aagtcagtcc tgtga                    645

<210> SEQ ID NO 7
<211> LENGTH: 214
<212> TYPE: PRT
<213> ORGANISM: Porcine circovirus 3

<400> SEQUENCE: 7

Met Arg His Ar

```
Phe Ile Thr Arg Leu Asn Glu Trp Glu Thr Ala Ile Thr Phe Glu Tyr
 65                  70                  75                  80

Tyr Lys Ile Leu Lys Met Lys Val Thr Leu Ser Pro Val Ile Ser Pro
                 85                  90                  95

Ala Gln Gln Thr Lys Thr Met Phe Gly His Thr Ala Ile Asp Leu Asp
            100                 105                 110

Gly Ala Trp Thr Thr Asn Thr Trp Leu Gln Asp Asp Pro Tyr Ala Glu
        115                 120                 125

Ser Ser Thr Arg Lys Val Met Thr Gln Pro Phe Ser His Ser Arg Tyr
    130                 135                 140

Phe Thr Pro Lys Pro Leu Leu Ala Gly Thr Thr Ser Ala His Pro Gly
145                 150                 155                 160

Gln Ser Leu Phe Phe Phe Ser Arg Pro Thr Pro Trp Leu Asn Thr Tyr
                165                 170                 175

Asp Pro Thr Val Gln Trp Gly Ala Leu Leu Trp Ser Ile Tyr Val Pro
            180                 185                 190

Glu Lys Thr Gly Met Thr Asp Phe Tyr Gly Thr Lys Glu Val Trp Ile
        195                 200                 205

Arg Tyr Lys Ser Val Leu
    210

<210> SEQ ID NO 8
<211> LENGTH: 735
<212> TYPE: DNA
<213> ORGANISM: Porcine circovirus 3

<400> SEQUENCE: 8
atgcgccacc gtgctatctt ccgccgtagg ccaaggccta gacgccgtag gagacaccgc      60
cgtcgttacg ctagacgccg tctgttcatc aggagaccta ccgccggaac ttactacacc     120
aagaagtact ctactatgaa cgtgatctca gtcggtaccc tcagaacaa caagccatgg      180 cacgctaacc acttcatcac tcgcctgaac gagtgggaaa ctgccatcac cttcgagtac     240
tacaagatcc tgaagatgaa ggtgaccctg tctccagtca tctcacctgc tcagcagacc     300
aagactatgt tcggtcacac tgctatcgac tggacggcg cctggaccac taacacctgg      360
ctgcaggacg acccctacgc cgaatccagc actaggaagg tcatgacctc caagaagaag     420
cactcaagat acttcactcc caagccactg ctggctggca ccacttctgc cacccagga     480 cagtccctgt tcttcttctc ccgccctacc cctggctga acacttacga ccctactgtg      540
cagtggggcg ccctgctgtg gtccatctac gtccctgaga agactggaat gaccgacttc     600
tacggtacca aggaagtctg gatcaggtac aagagcgtgc tggtcaagat caacatcaac     660
ctgactcctc ccgtggctac ttctcgtgtg ccaagcagag ctctgccact gaggttcggt     720
tgcggccacc gttga                                                     735

<210> SEQ ID NO 9
<211> LENGTH: 244
<212> TYPE: PRT
<213> ORGANISM: Porcine circovirus 3

<400> SEQUENCE: 9

Met Arg His Arg Ala Ile Phe Arg Arg Arg Pro Arg Pro Arg Arg Arg
  1                 5                  10                  15

Arg Arg His Arg Arg Arg Tyr Ala Arg Arg Arg Leu Phe Ile Arg Arg
             20                  25                  30

Pro Thr Ala Gly Thr Tyr Tyr Thr Lys Lys Tyr Ser Thr Met Asn Val
```

```
                35                  40                  45
Ile Ser Val Gly Thr Pro Gln Asn Asn Lys Pro Trp His Ala Asn His
 50                  55                  60

Phe Ile Thr Arg Leu Asn Glu Trp Glu Thr Ala Ile Thr Phe Glu Tyr
 65                  70                  75                  80

Tyr Lys Ile Leu Lys Met Lys Val Thr Leu Ser Pro Val Ile Ser Pro
                 85                  90                  95

Ala Gln Gln Thr Lys Thr Met Phe Gly His Thr Ala Ile Asp Leu Asp
                100                 105                 110

Gly Ala Trp Thr Thr Asn Thr Trp Leu Gln Asp Asp Pro Tyr Ala Glu
                115                 120                 125

Ser Ser Thr Arg Lys Val Met Thr Ser Lys Lys His Ser Arg Tyr
130                 135                 140

Phe Thr Pro Lys Pro Leu Leu Ala Gly Thr Thr Ser Ala His Pro Gly
145                 150                 155                 160

Gln Ser Leu Phe Phe Phe Ser Arg Pro Thr Pro Trp Leu Asn Thr Tyr
                165                 170                 175

Asp Pro Thr Val Gln Trp Gly Ala Leu Leu Trp Ser Ile Tyr Val Pro
                180                 185                 190

Glu Lys Thr Gly Met Thr Asp Phe Tyr Gly Thr Lys Glu Val Trp Ile
                195                 200                 205

Arg Tyr Lys Ser Val Leu Val Lys Ile Asn Ile Asn Leu Thr Pro Pro
210                 215                 220

Val Ala Thr Ser Arg Val Pro Ser Arg Ala Leu Pro Leu Arg Phe Gly
225                 230                 235                 240

Cys Gly His Arg

<210> SEQ ID NO 10
<211> LENGTH: 244
<212> TYPE: PRT
<213> ORGANISM: Porcine circovirus 3

<400> SEQUENCE: 10

Met Arg His Arg Ala Ile Phe Arg Arg Arg Pro Arg Pro

-continued

```
                165                 170                 175
Asp Pro Thr Val Gln Trp Gly Ala Leu Leu Trp Ser Ile Tyr Val Pro
            180                 185                 190

Glu Lys Thr Gly Met Thr Asp Phe Tyr Gly Thr Lys Glu Val Trp Ile
        195                 200                 205

Arg Tyr Lys Ser Val Leu Val Lys Ile Asn Ile Asn Leu Thr Pro Pro
    210                 215                 220

Val Ala Thr Ser Arg Val Pro Ser Arg Ala Leu Pro Leu Arg Phe Gly
225                 230                 235                 240

Cys Gly His Arg

<210> SEQ ID NO 11
<211> LENGTH: 4
<212> TYPE: PRT
<213> ORGANISM: Porcine circovirus 3

<400> SEQUENCE: 11

Ser Lys Lys Lys
1

<210> SEQ ID NO 12
<211> LENGTH: 4
<212> TYPE: PRT
<213> ORGANISM: Porcine circovirus 3

<400> SEQUENCE: 12

Gln Pro Phe Ser
1

<210> SEQ ID NO 13
<211> LENGTH: 12
<212> TYPE: PRT
<213> ORGANISM: Porcine circovirus 2

<400> SEQUENCE: 13

Ser Thr Ile Asp Tyr Phe Gln Pro Asn Asn Lys Arg
1               5                   10

<210> SEQ ID NO 14
<211> LENGTH: 5
<212> TYPE: PRT
<213> ORGANISM: Porcine circovirus 3

<400> SEQUENCE: 14

Ser Lys Lys Lys His
1               5

<210> SEQ ID NO 15
<211> LENGTH: 4
<212> TYPE: PRT
<213> ORGANISM: Porcine circovirus 3

<400> SEQUENCE: 15

Lys Lys Lys His
1

<210> SEQ ID NO 16
<211> LENGTH: 30
<212> TYPE: PRT
<213> ORGANISM: Porcine circovirus 3

<400> SEQUENCE: 16
```

```
Val Lys Ile Asn Ile Asn Leu Thr Pro Pro Val Ala Thr Ser Arg Val
1               5                   10                  15

Pro Ser Arg Ala Leu Pro Leu Arg Phe Gly Cys Gly His Arg
            20                  25                  30

<210> SEQ ID NO 17
<211> LENGTH: 6
<212> TYPE: PRT
<213> ORGANISM: Porcine circovirus 3

<400> SEQUENCE: 17

Gln Pro Phe Ser Tyr His
1               5

<210> SEQ ID NO 18
<211> LENGTH: 5
<212> TYPE: PRT
<213> ORGANISM: Porcine circovirus 3

<400> SEQUENCE: 18

Leu Ser Arg Gly Phe
1               5

<210> SEQ ID NO 19
<211> LENGTH: 5
<212> TYPE: PRT
<213> ORGANISM: Porcine circovirus 3

<400> SEQUENCE: 19

Met Ala Ser Gly Phe
1               5

<210> SEQ ID NO 20
<211> LENGTH: 10
<212> TYPE: PRT
<213> ORGANISM: Porcine circovirus 3

<400> SEQUENCE: 20

Glu Phe Asn Leu Lys Asp Pro Pro Leu Asn
1               5                   10

<210> SEQ ID NO 21
<211> LENGTH: 19
<212> TYPE: PRT
<213> ORGANISM: Porcine circovirus 3

<400> SEQUENCE: 21

Gln Phe Ala Pro Asn Asn Pro Ser Thr Glu Phe Asp Tyr Glu Thr Gly
1               5                   10                  15

Arg Gln Leu

<210> SEQ ID NO 22
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: R, I, Y, A, L, K, or W
<220> FEATURE:
<221> NAME/KEY: MOD_RES
<222> LOCATION: (15)..(15)
<223> OTHER INFORMATION: P, A, T, R, or F
```

-continued

```
<220> FEATURE:
<221> NAME/KEY: MOD_RES
<222> LOCATION: (26)..(26)
<223> OTHER INFORMATION: W, R, A, K or absent
<220> FEATURE:
<221> NAME/KEY: MOD_RES
<222> LOCATION: (32)..(32)
<223> OTHER INFORMATION: F, Y, H, or A
<220> FEATURE:
<221> NAME/KEY: MOD_RES
<222> LOCATION: (36)..(36)
<223> OTHER INFORMATION: P, R, S, N, or Q
<220> FEATURE:
<221> NAME/KEY: MOD_RES
<222> LOCATION: (43)..(43)
<223> OTHER INFORMATION: T, L, V, F, or G
<220> FEATURE:
<221> NAME/KEY: MOD_RES
<222> LOCATION: (46)..(46)
<223> OTHER INFORMATION: Y, S, K, T, R, V, or A
<220> FEATURE:
<221> NAME/KEY: MOD_RES
<222> LOCATION: (54)..(54)
<223> OTHER INFORMATION: V, K, R, N, P, Q, F, or A
<220> FEATURE:
<221> NAME/KEY: MOD_RES
<222> LOCATION: (58)..(58)
<223> OTHER INFORMATION: Q, V, T, G, S, N, or A
<220> FEATURE:
<221> NAME/KEY: MOD_RES
<222> LOCATION: (59)..(59)
<223> OTHER INFORMATION: N, T, R, Q, S, P, K, G, or E
<220> FEATURE:
<221> NAME/KEY: MOD_RES
<222> LOCATION: (69)..(69)
<223> OTHER INFORMATION: I, R, T, N, S, E, or A
<220> FEATURE:
<221> NAME/KEY: MOD_RES
<222> LOCATION: (78)..(78)
<223> OTHER INFORMATION: P, N, A, M, W, Y or absent
<220> FEATURE:
<221> NAME/KEY: MOD_RES
<222> LOCATION: (83)..(83)
<223> OTHER INFORMATION: I, L, S, H, W, Y, K or absent
<220> FEATURE:
<221> NAME/KEY: MOD_RES
<222> LOCATION: (84)..(84)
<223> OTHER INFORMATION: A, S, T, L, R, H or absent
<220> FEATURE:
<221> NAME/KEY: MOD_RES
<222> LOCATION: (85)..(85)
<223> OTHER INFORMATION: I, V, L, P, Y, or S
<220> FEATURE:
<221> NAME/KEY: MOD_RES
<222> LOCATION: (99)..(99)
<223> OTHER INFORMATION: L, F, M, V, A, I
<220> FEATURE:
<221> NAME/KEY: MOD_RES
<222> LOCATION: (102)..(102)
<223> OTHER INFORMATION: V, C, T, I, L, A, R, or K
<220> FEATURE:
<221> NAME/KEY: MOD_RES
<222> LOCATION: (105)..(105)
<223> OTHER INFORMATION: A, I, Y, V, R, S, P, or G
<220> FEATURE:
<221> NAME/KEY: MOD_RES
<222> LOCATION: (108)..(108)
<223> OTHER INFORMATION: T, G, A, Q, R, M, E, or P
<220> FEATURE:
<221> NAME/KEY: MOD_RES
<222> LOCATION: (109)..(109)
<223> OTHER INFORMATION: K, D, T, S, V, E, W, or P
<220> FEATURE:
<221> NAME/KEY: MOD_RES
<222> LOCATION: (114)..(114)
<223> OTHER INFORMATION: H, S, N, R, or T
<220> FEATURE:
<221> NAME/KEY: MOD_RES
<222> LOCATION: (123)..(123)
```

-continued

```
<223> OTHER INFORMATION: N, E, T, V, Q or absent
<220> FEATURE:
<221> NAME/KEY: MOD_RES
<222> LOCATION: (124)..(124)
<223> OTHER INFORMATION: A, F, K, R, P, D, or T
<220> FEATURE:
<221> NAME/KEY: MOD_RES
<222> LOCATION: (127)..(127)
<223> OTHER INFORMATION: T, K, E, N, S, D, or P
<220> FEATURE:
<221> NAME/KEY: MOD_RES
<222> LOCATION: (128)..(128)
<223> OTHER INFORMATION: N, A, R, T, K, or G
<220> FEATURE:
<221> NAME/KEY: MOD_RES
<222> LOCATION: (129)..(129)
<223> OTHER INFORMATION: T, N, A, G, or Q
<220> FEATURE:
<221> NAME/KEY: MOD_RES
<222> LOCATION: (139)..(139)
<223> OTHER INFORMATION: S, Y, F, R, W, M, L, or H
<220> FEATURE:
<221> NAME/KEY: MOD_RES
<222> LOCATION: (144)..(144)
<223> OTHER INFORMATION: V, T, K, S, R, or M
<220> FEATURE:
<221> NAME/KEY: MOD_RES
<222> LOCATION: (148)..(148)
<223> OTHER INFORMATION: K, P, S, R, A, H, or I
<220> FEATURE:
<221> NAME/KEY: MOD_RES
<222> LOCATION: (160)..(160)
<223> OTHER INFORMATION: L, V, Q, M, T, S, or D
<220> FEATURE:
<221> NAME/KEY: MOD_RES
<222> LOCATION: (163)..(163)
<223> OTHER INFORMATION: S, T, G, I, A, V or absent
<220> FEATURE:
<221> NAME/KEY: MOD_RES
<222> LOCATION: (166)..(166)
<223> OTHER INFORMATION: P, I, Q, V, or T
<220> FEATURE:
<221> NAME/KEY: MOD_RES
<222> LOCATION: (169)..(169)
<223> OTHER INFORMATION: S, F, A, N, T, or V
<220> FEATURE:
<221> NAME/KEY: MOD_RES
<222> LOCATION: (172)..(172)
<223> OTHER INFORMATION: F, N, L, T, W, or A
<220> FEATURE:
<221> NAME/KEY: MOD_RES
<222> LOCATION: (176)..(176)
<223> OTHER INFORMATION: P, N, R, K, G, or A
<220> FEATURE:
<221> NAME/KEY: MOD_RES
<222> LOCATION: (177)..(177)
<223> OTHER INFORMATION: T, Q, H, S, or R
<220> FEATURE:
<221> NAME/KEY: MOD_RES
<222> LOCATION: (181)..(181)
<223> OTHER INFORMATION: N, R, P, S, or D
<220> FEATURE:
<221> NAME/KEY: MOD_RES
<222> LOCATION: (184)..(184)
<223> OTHER INFORMATION: D, T, G, S, Q, K, A, or N
<220> FEATURE:
<221> NAME/KEY: MOD_RES
<222> LOCATION: (185)..(185)
<223> OTHER INFORMATION: S, T, G, N, K or absent
<220> FEATURE:
<221> NAME/KEY: MOD_RES
<222> LOCATION: (189)..(189)
<223> OTHER INFORMATION: Q, D, K, R, P, V, or T
<220> FEATURE:
<221> NAME/KEY: MOD_RES
<222> LOCATION: (198)..(198)
<223> OTHER INFORMATION: Y, E, A, P, or R
<220> FEATURE:
<221> NAME/KEY: MOD_RES
```

```
<222> LOCATION: (202)..(202)
<223> OTHER INFORMATION: K, I, Q, D, P, T, or N
<220> FEATURE:
<221> NAME/KEY: MOD_RES
<222> LOCATION: (203)..(203)
<223> OTHER INFORMATION: T, Y, M, N or absent
<220> FEATURE:
<221> NAME/KEY: MOD_RES
<222> LOCATION: (204)..(204)
<223> OTHER INFORMATION: M, D, P, T, S, I, Q, or A
<220> FEATURE:
<221> NAME/KEY: MOD_RES
<222> LOCATION: (210)..(210)
<223> OTHER INFORMATION: T, R, Q, K, D, or Y
<220> FEATURE:
<221> NAME/KEY: MOD_RES
<222> LOCATION: (219)..(219)
<223> OTHER INFORMATION: S, E, or Q
<220> FEATURE:
<221> NAME/KEY: MOD_RES
<222> LOCATION: (223)..(223)
<223> OTHER INFORMATION: K, N, D, E, T, L, I or absent
<220> FEATURE:
<221> NAME/KEY: MOD_RES
<222> LOCATION: (227)..(227)
<223> OTHER INFORMATION: L, T, H, Q, A or absent

<400> SEQUENCE: 22

Met Trp Leu Thr Arg Arg Arg Phe Arg Arg Arg Arg Xaa Xaa Arg
1               5                   10                  15

Arg Arg Arg Arg His Arg Arg Tyr Xaa Arg Arg Arg Arg Xaa
            20                  25                  30

Arg Arg Arg Xaa Thr Asn Gly Ile Phe Asn Xaa Arg Leu Xaa Arg Thr
        35                  40                  45

Phe Gly Phe Thr Trp Xaa Lys Thr Thr Xaa Xaa Thr Leu Ser Trp Asn
50                  55                  60

Ala Asp His Leu Xaa Phe Asn Leu Asp Asp Phe Leu Pro Xaa Gly Pro
65                  70                  75                  80

Gly Ser Xaa Xaa Xaa Pro Phe Glu Tyr Tyr Arg Ile Arg Lys Val Lys
                85                  90                  95

Val Glu Xaa Arg Pro Xaa Asn Pro Xaa Thr Gln Xaa Xaa Arg Gly Phe
            100                 105                 110

Gly Xaa Thr Ala Val Ile Leu Asp Gly Asp Xaa Xaa Phe Thr Xaa Xaa
        115                 120                 125

Xaa Pro Leu Thr Tyr Asp Pro Leu Ala Asn Xaa Ser Ser Arg Lys Xaa
    130                 135                 140

Trp Lys Leu Xaa Arg Gly Phe Lys Arg Tyr Phe Thr Pro Lys Pro Xaa
145                 150                 155                 160

Leu Asp Xaa Ala Asn Xaa Ser Ala Xaa Leu Pro Xaa Asn Ser Arg Xaa
                165                 170                 175

Xaa Leu Trp Leu Xaa Leu Gln Xaa Xaa Pro Asn Val Xaa His Tyr Gly
            180                 185                 190

Leu Gly Phe Ser Phe Xaa Gln Pro Glu Xaa Xaa Xaa Gln Asp Tyr Gln
            195                 200                 205

Ile Xaa Ile Thr Leu Tyr Val Gln Phe Arg Xaa Phe Asn Leu Xaa Asp
    210                 215                 220

Pro Pro Xaa
225

<210> SEQ ID NO 23
<211> LENGTH: 214
<212> TYPE: PRT
<213> ORGANISM: Porcine circovirus 3
```

```
<400> SEQUENCE: 23

Met Arg His Arg Ala Ile Phe Arg Arg Pro Arg Pro Arg Arg Arg
1               5                   10                  15

Arg Arg His Arg Arg Arg Tyr Ala Arg Arg Leu Phe Ile Arg Arg
            20                  25                  30

Pro Thr Ala Gly Thr Tyr Tyr Thr Lys Lys Tyr Ser Thr Met Asn Val
            35                  40                  45

Ile Ser Val Gly Thr Pro Gln Asn Asn Lys Pro Trp His Ala Asn His
        50                  55                  60

Phe Ile Thr Arg Leu Asn Glu Trp Glu Thr Ala Ile Thr Phe Glu Tyr
65                  70                  75                  80

Tyr Lys Ile Leu Lys Met Lys Val Thr Leu Ser Pro Val Ile Ser Pro
                85                  90                  95

Ala Gln Gln Thr Lys Thr Met Phe Gly His Thr Ala Ile Asp Leu Asp
                100                 105                 110

Gly Ala Trp Thr Thr Asn Thr Trp Leu Gln Asp Asp Pro Tyr Ala Glu
            115                 120                 125

Ser Ser Thr Arg Lys Val Met Thr Ser Lys Lys His Ser Arg Tyr
130                 135                 140

Phe Thr Pro Lys Pro Leu Leu Ala Gly Thr Thr Ser Ala His Pro Gly
145                 150                 155                 160

Gln Ser Leu Phe Phe Phe Ser Arg Pro Thr Pro Trp Leu Asn Thr Tyr
                165                 170                 175

Asp Pro Thr Val Gln Trp Gly Ala Leu Leu Trp Ser Ile Tyr Val Pro
            180                 185                 190

Glu Lys Thr Gly Met Thr Asp Phe Tyr Gly Thr Lys Glu Val Trp Ile
            195                 200                 205

Arg Tyr Lys Ser Val Leu
            210

<210> SEQ ID NO 24
<211> LENGTH: 233
<212> TYPE: PRT
<213> ORGANISM: Porcine circovirus 2

<400> SEQUENCE: 24

Met Thr Tyr Pro Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
        130                 135                 140
```

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 25
<211> LENGTH: 234
<212> TYPE: PRT
<213> ORGANISM: Porcine circovirus 2

<400> SEQUENCE: 25

Met Thr Tyr Pro Arg Arg Phe Arg Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Thr Val Arg Thr
50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 26
<211> LENGTH: 247
<212> TYPE: PRT
<213> ORGANISM: Beak and feather disease virus

<400> SEQUENCE: 26

```
Met Trp Gly Thr Ser Asn Cys Pro Cys Ala Ile Phe Gln Ile Arg Arg
1               5                   10                  15

Ile Ala Arg Pro Arg Tyr Arg Arg His Ile Arg Arg Tyr Arg Pro
            20                  25                  30

Arg Arg Thr Tyr Phe Arg Arg Arg Phe Ser Thr Asn Arg Ile Tyr
        35                  40                  45

Thr Leu Arg Leu Lys Arg Gln Phe Lys Phe Glu Ile Arg Lys Gln Thr
50                  55                  60

Thr Gln Pro Gly Asn Leu Ile Trp Asn Ala Asp Tyr Met Thr Phe Thr
65                  70                  75                  80

Leu Glu Asn Phe Leu Thr Asn Thr Pro Asn Pro Ser Ala Leu Asn Phe
                85                  90                  95

Glu Asp Tyr Arg Ile Lys Leu Ala Lys Met Glu Met Lys Pro Thr Trp
            100                 105                 110

Gly His Tyr Ser Ile Ala Thr Glu Gly Phe Gly His Thr Ala Val Ile
            115                 120                 125

Gln Asp Ser Arg Ile Glu Lys Phe Lys Thr Arg Ala Asp Gln Ser Gln
130                 135                 140

Asp Pro Leu Ala Pro Phe Asp Gly Ala Lys Lys Trp Tyr Leu Ser Arg
145                 150                 155                 160

Gly Phe Lys Arg Leu Leu Arg Pro Lys Pro Gln Ile Met Met Asn Asp
                165                 170                 175

Leu Ser Thr Ala Asn Gln Ser Ala Ala Leu Trp Leu Asn Ser Val Arg
            180                 185                 190

Thr Gly Trp Ile Pro Leu Gln Gly Gly Pro Asn Ala Ala Gly Ser Lys
            195                 200                 205

Val Lys His Tyr Gly Leu Ala Phe Ser Phe Ala Gln Pro Glu Ile Pro
        210                 215                 220

Ile Pro Tyr Val Cys Gln Leu Thr Ile Tyr Val Gln Phe Arg Gln Phe
225                 230                 235                 240

Ala Pro Asn Asn Pro Ser Thr
                245

<210> SEQ ID NO 27
<211> LENGTH: 247
<212> TYPE: PRT
<213> ORGANISM: Beak and feather disease virus

<400> SEQUENCE: 27

Met Trp Gly Thr Ser Asn Cys Ala Cys Ala Thr Phe Gln Ile Arg Arg
1               5                   10                  15

Arg Tyr Ala Arg Pro Tyr Arg Arg His Ile Arg Arg Tyr Arg Arg
            20                  25                  30

Arg Arg Arg His Phe Arg Arg Arg Phe Ser Thr Asn Arg Ile Tyr
        35                  40                  45

Thr Leu Arg Leu Thr Arg Gln Phe Gln Phe Lys Ile Asn Lys Gln Thr
50                  55                  60

Thr Ser Val Gly Asn Leu Ile Phe Asn Ala Asp Tyr Ile Thr Phe Ala
65                  70                  75                  80

Leu Asp Asp Phe Leu Gln Ala Val Pro Asn Pro His Thr Leu Asn Phe
                85                  90                  95

Glu Asp Tyr Arg Ile Lys Leu Ala Lys Met Glu Met Arg Pro Thr Gly
            100                 105                 110

Gly His Tyr Thr Val Gln Ser Asp Gly Phe Gly His Thr Ala Val Ile
```

```
            115                 120                 125
Gln Asp Ser Arg Ile Thr Arg Phe Lys Thr Thr Ala Asp Gln Thr Gln
    130                 135                 140

Asp Pro Leu Ala Pro Phe Asp Gly Ala Lys Lys Trp Phe Val Ser Arg
145                 150                 155                 160

Gly Phe Lys Arg Leu Leu Arg Pro Lys Pro Gln Ile Thr Ile Glu Asp
                165                 170                 175

Leu Thr Thr Ala Asn Gln Ser Ala Ala Leu Trp Leu Asn Ser Ala Arg
            180                 185                 190

Thr Gly Trp Ile Pro Leu Gln Gly Gly Pro Asn Ser Ala Gly Thr Lys
        195                 200                 205

Val Arg His Tyr Gly Ile Ala Phe Ser Phe Pro Gln Pro Glu Gln Thr
    210                 215                 220

Ile Thr Tyr Val Thr Lys Leu Thr Leu Tyr Val Gln Phe Arg Gln Phe
225                 230                 235                 240

Ala Pro Asn Asn Pro Ser Thr
                245
```

<210> SEQ ID NO 28
<211> LENGTH: 281
<212> TYPE: PRT
<213> ORGANISM: Unknown
<220> FEATURE:
<223> OTHER INFORMATION: Description of Unknown:
    Bat circovirus sequence

<400> SEQUENCE: 28

```
Met Thr Ala His Ala Gln Gly Gly Gly Ala Arg His Ala Ser Ala Met
1               5                   10                  15

Phe Leu Phe Leu Glu Met Ala Arg Trp His Thr Arg Arg Trp Arg Arg
            20                  25                  30

Ala Thr Leu His Ala Val Ala Arg Ser His Arg Arg Arg Arg His Ala
        35                  40                  45

Met Gly Gly Arg Arg Arg Arg His Arg Arg Ser Thr Tyr Lys Phe
    50                  55                  60

Phe His Val Arg Leu Thr Arg Tyr Tyr Thr Val Leu Trp Pro Lys Ala
65                  70                  75                  80

Thr Thr Pro Ser Asp Asp Thr Glu Thr Thr Tyr Gly Trp Asn Leu Asp
                85                  90                  95

His Val Asn Phe Lys Leu Ser Asp Phe Leu Pro Met Asp Ser Ser Gly
            100                 105                 110

Arg Pro Ser Leu Pro Ala Phe Lys Asp Tyr Asn Ile Thr Lys Ala Val
        115                 120                 125

Val Arg Val Lys Pro Ile Asn Val Pro Val Ser Met Arg Val Glu Gln
    130                 135                 140

Tyr Gly Asn His Ala Thr Asp Phe Asp Gly Thr Asp Val Gly Ile Gly
145                 150                 155                 160

Thr Val His Thr Ser Gly Asp Pro Lys Pro Ser Asn Asn Glu Thr
                165                 170                 175

Gly Pro Lys Thr Ser Asp Pro Leu Arg Asn Arg Thr Ser Arg Lys Ser
            180                 185                 190

Trp Asn Val Arg Thr Gly Phe Thr Arg Ile Leu Lys Pro Thr Val Val
        195                 200                 205

Ala Gln Thr Ala Asn Cys Cys Gly Ile Gly Pro Gly Ser Asn Phe Ile
    210                 215                 220
```

```
Thr Arg Gly Leu Lys His Ala Trp Leu Arg Leu Asp Ser Asn Gly Val
225                 230                 235                 240

Lys Thr Pro Trp Asn Gly Leu Ser Ile Ser Leu Arg Glu Gly Asp Gln
            245                 250                 255

Ser Leu Leu Thr Gln Tyr Thr Ile Thr Leu Tyr Val Lys Phe Arg Glu
        260                 265                 270

Phe Asp Leu Asp Phe Asn Pro His Ala
    275                 280

<210> SEQ ID NO 29
<211> LENGTH: 270
<212> TYPE: PRT
<213> ORGANISM: Canine circovirus

<400> SEQUENCE: 29

Met Arg Val Arg Arg His Ala Arg Ala Ser Arg Arg Ser Tyr Arg Thr
1               5                   10                  15

Arg Pro Leu Asn Arg Tyr Arg Arg Arg Gln Asn Arg Phe Lys Leu
        20                  25                  30

Phe His Leu Arg Leu Arg Arg Thr Leu Thr Ala Asp Trp Pro Thr Ala
        35                  40                  45

Pro Val Lys Pro Thr Asn Asp Pro Gln Thr Glu Thr Pro Leu Leu Trp
50                  55                  60

Asn Phe Asp His Leu Ser Phe Lys Leu Thr Asp Phe Leu Gln Ala Ser
65                  70                  75                  80

His Gly Thr Gly Asp Phe Gln His Leu Pro Pro Phe Arg Phe Tyr Lys
                85                  90                  95

Phe Lys Lys Val Tyr Ile Arg Ala Arg Trp Ile Asn Trp Pro Arg Thr
            100                 105                 110

Leu Met Glu Asn Val Leu Gly Arg Thr Ala Leu Asp Leu Asp Gly Glu
        115                 120                 125

Asp Gln Gly Arg Gly Asn Ala Thr Arg Ser His Leu Asp Pro Gly Thr
    130                 135                 140

Val Pro Gly Arg Leu Glu Pro Pro Lys Asp Pro Asn Lys Ala Pro Phe
145                 150                 155                 160

Ile Tyr Asp Pro Leu Gln Asp Arg Ser Ser Arg Ser Phe Asn Met
                165                 170                 175

Ala Ser Gly Phe Lys Arg Gly Leu Thr Pro Lys Pro Met Phe Thr Gln
            180                 185                 190

Glu Ile Ala Ser Pro Ser Ala Thr Ala Pro Trp Leu Thr Arg Gly Thr
        195                 200                 205

Pro Trp Val Ser Val Ile Gln Gly Ala Asn Met Val Trp Asn Gly Leu
    210                 215                 220

Ser Ile Ser Leu Arg Gln Met Lys Asp Met Arg Pro Thr Thr Pro Asp
225                 230                 235                 240

Thr Ser Thr Ser Gln Ile Pro Gln Val Gln Tyr Asp Ile Ser Ala Tyr
                245                 250                 255

Ile Ala Phe Lys Glu Phe Asp Tyr Glu Thr Gly Arg Gln Leu
            260                 265                 270

<210> SEQ ID NO 30
<211> LENGTH: 250
<212> TYPE: PRT
<213> ORGANISM: Canary circovirus
<220> FEATURE:
<221> NAME/KEY: MOD_RES
<222> LOCATION: (28)..(28)
```

<223> OTHER INFORMATION: Any amino acid

<400> SEQUENCE: 30

Met Trp Leu Thr Phe Asn Gln Val Ala Arg Arg Arg Pro Leu Ala
1               5                   10                  15

Pro Arg Arg Arg Trp Arg Arg Tyr Trp Xaa Arg Arg Arg
            20                  25                  30

Ile Pro Ala Asn Arg Arg Gly His Arg Thr Asn Arg Val Tyr Arg Phe
            35                  40                  45

Arg Phe Val Arg Glu Phe Gly Gln Val Leu Gln Lys Gly Thr Gly Gly
        50                  55                  60

Ser Gln Leu Ser Phe Gly Thr Asp Gly Ile Asn Ile Leu Asp Asp
65                  70                  75                  80

Phe Leu Asp Trp Gly Thr Ile Asn Trp Arg Leu Pro Phe Glu Asp Tyr
                85                  90                  95

Arg Ile Arg Leu Ala Lys Val Glu Met Arg Pro Leu Asn Glu Ser Trp
            100                 105                 110

Glu Glu Trp Lys Gly Phe Gly His Asn Val Pro Ile Gln Asp Asn His
        115                 120                 125

Leu Glu Asp Phe Phe Lys Lys Thr Arg Leu Asp Ala Asp Pro Leu Ala
    130                 135                 140

Asn Trp Asp Gly Ala Arg Lys Trp Asp Leu Arg Lys Gly Phe Lys Arg
145                 150                 155                 160

Leu Phe Lys Pro Arg Pro Gln Leu Ser Val Thr Asp Thr Asp Ala Ala
                165                 170                 175

Asn Val Thr Ala Ala Leu Trp Leu Asn Asn Pro Lys Ser Leu Trp Ile
            180                 185                 190

Pro Ile Met Lys Lys Ser Asp Gln Asn Leu Pro Ser Ser Gly Thr Arg
        195                 200                 205

Val Lys His Tyr Gly Leu Ala Phe Ser Trp Pro Glu Pro Thr Pro Asn
    210                 215                 220

Gln Met Asp Tyr Gln Val Lys Val Thr Ile Tyr Cys Glu Phe Arg Gln
225                 230                 235                 240

Met Asn Leu Thr His Leu Ala Thr Pro Lys
                245                 250

<210> SEQ ID NO 31
<211> LENGTH: 250
<212> TYPE: PRT
<213> ORGANISM: Goose circovirus

<400> SEQUENCE: 31

Met Pro Leu Tyr Arg Ala Arg Pro Arg Ser Leu Tyr Ser Arg Arg
1               5                   10                  15

Arg Ala Thr Asn Arg Arg Arg Tyr Arg Arg Arg Leu His Ile
            20                  25                  30

Gly Arg Ile Arg Ser Lys Tyr Thr Ile Phe Asn Val Lys Gln Thr Gln
        35                  40                  45

Asn Ile Ser Phe Thr Phe Phe Gly Thr Gly Ser Pro Asp Lys Asn Lys
    50                  55                  60

Trp Gln Ala Met Ser Leu Glu Ala Val Gln Ser Ser Gly Thr Ser Pro
65                  70                  75                  80

Lys Pro Gly Ile Asn Leu Arg Phe Ala Val Phe Gly Asp Arg Leu Pro
                85                  90                  95

Gly Thr Gly Asn Gln Tyr His Tyr Pro Phe Asp Tyr Tyr Met Ile Arg

```
                  100                 105                 110
Met Val Lys Val Glu Leu Arg Pro Ala Phe Asn Pro Phe Gln Arg Val
                115                 120                 125

Arg Thr Gln Gly Ser Thr Tyr Ile Asp Lys Glu Gly Asn Ile Thr Thr
            130                 135                 140

Thr Thr Ser Gly Gly Glu Trp Asn Val Asp Pro Tyr Ala Ala Met Ser
145                 150                 155                 160

Ser Arg Lys Thr Trp Ser Pro His Arg Tyr His Lys Arg Val Phe Val
                165                 170                 175

Pro Lys Pro Thr Ile Gln Gln Gly Gly Thr Gly Thr Asn Ile Trp Ser
            180                 185                 190

Thr Trp Tyr Thr Pro Gly Gly Arg Gln Leu Trp Leu Asn Ser Ile Gln
                195                 200                 205

Asp Asn Val Val Phe Tyr Gly Met Gly Met Ser Leu Arg Gln Ala Glu
            210                 215                 220

Asp Thr Ala Ala Pro Leu Thr Val Glu Ala Thr Ile Thr Tyr Tyr Ile
225                 230                 235                 240

Arg Phe Gly Gln Trp Thr Gly Leu Ser Pro
                245                 250

<210> SEQ ID NO 32
<211> LENGTH: 231
<212> TYPE: PRT
<213> ORGANISM: Unknown
<220> FEATURE:
<223> OTHER INFORMATION: Description of Unknown:
      Bat circovirus sequence

<400> SEQUENCE: 32

Met Arg Arg Lys Phe Arg Arg Phe Arg Arg Lys Phe Lys Lys Phe Ser
1               5                   10                  15

Arg Arg Phe Lys Arg His Phe Gly Gly Lys Arg Arg Lys Thr Thr Arg
                20                  25                  30

Gln Val Gln Phe Lys Phe Lys Val Gln Thr Val Pro Tyr Leu Asn Gly
            35                  40                  45

Ser Ile Ala Pro Ser Ser Ile Asn Trp Asn Asn Thr Ser Asn Thr
        50                  55                  60

Ala Ser His Tyr Thr Phe Ala Phe Thr Leu Gly Asp Ile Pro His Tyr
65                  70                  75                  80

Ser Asp Leu Ser Ser Val Phe Asp Ala Ala Lys Leu Ala Ala Val Lys
                85                  90                  95

Leu Lys Phe Val Pro Arg Tyr Thr Met Gly Gln Leu Pro Thr Ser Ala
            100                 105                 110

Ser Thr Thr Tyr Ala Asn Thr Ser Thr Pro Cys Val Val Val Lys Asp
        115                 120                 125

Tyr Asp Asp Ala Asn Pro Leu Thr Ser Tyr Ala Asn Ala Leu Leu Tyr
130                 135                 140

Gln Asn Ala Arg Val Val Ser Ile Leu Lys Pro Phe Ser Val Tyr Leu
145                 150                 155                 160

Lys Pro Lys Leu Ser Gly Gly Val Glu Asn Thr Ser Leu Val Ile Val
                165                 170                 175

Ala Gln Ser Gln Ala Arg Pro Trp Leu Asp Ser Gly Ala Thr Ala Val
            180                 185                 190

Pro Tyr Tyr Gly Val Lys Leu Glu Val Pro Gly Ile Asn Thr Thr Gln
        195                 200                 205
```

```
Met Leu Gly Gln Ala Ile Trp Asp Ile Tyr Gly Thr Tyr Tyr Val Lys
    210                 215                 220

Leu Lys Gln Ile Arg Leu Leu
225                 230

<210> SEQ ID NO 33
<211> LENGTH: 238
<212> TYPE: PRT
<213> ORGANISM: Bat associated circovirus 3

<400> SEQUENCE: 33

Met Pro Ile Arg Arg Ser Arg Tyr Ser Arg Arg Arg Trp Arg
1               5                   10                  15

Arg Asn Thr Arg Arg Arg Val Ala Arg Gly Ala Tyr Arg Trp Arg
            20                  25                  30

Arg Lys Asn Gly Ile Ile Asn Val Arg Leu Ser Ala Thr Lys Asp Trp
        35                  40                  45

Thr Met Ala Ser Thr Thr Ala Glu Gly Tyr Asn Val Ala Arg Leu Glu
    50                  55                  60

Val Asn Leu Arg Gln Phe Met Pro Ala Gly Pro Gly Ser Ala Ile Asn
65                  70                  75                  80

Thr Lys Ser Ile Pro Trp Ala Tyr Tyr Arg Ile Arg Lys Met Lys Phe
                85                  90                  95

Glu Ile Leu Pro Lys Met Ile Pro Ala Gln Thr Pro Tyr Arg Tyr Gly
            100                 105                 110

Ser Thr Ala Ile Tyr Leu Gly Met Gln Ala Pro Ala Pro Thr Gln Gly
        115                 120                 125

Lys Thr Tyr Asp Pro His Leu Lys His Val Lys Gln Asn Met Ser Gly
    130                 135                 140

Leu Ile Thr Asp Gln Leu Lys Arg Tyr Phe Thr Pro Lys Pro Asp Leu
145                 150                 155                 160

Asp Ser Ile Thr Ser Thr Ala Trp Phe Gln Pro Asn Asn Lys Ala Asn
                165                 170                 175

Gln Val Trp Ile Asn Met Thr Asn Asp Asn Ile Thr His Gly Gln Val
            180                 185                 190

Gly Trp Ser Met Glu Arg Ile Ser Asn Met Ala Gln Asn Phe Lys Ile
        195                 200                 205

Arg Val Thr Leu Tyr Val Gln Phe Arg Glu Phe Asn Leu Ile Asp Tyr
    210                 215                 220

Pro Ala Gln Ala Pro Leu Leu Val Asp Glu Glu Pro Ser Glu
225                 230                 235

<210> SEQ ID NO 34
<211> LENGTH: 12
<212> TYPE: PRT
<213> ORGANISM: Porcine circovirus 3

<400> SEQUENCE: 34

Glu Phe Asn Leu Lys Asp Pro Pro Leu Asn Pro Lys
1               5                   10

<210> SEQ ID NO 35
<211> LENGTH: 9
<212> TYPE: PRT
<213> ORGANISM: Porcine circovirus 3

<400> SEQUENCE: 35

Gln Phe Ala Pro Asn Asn Pro Ser Thr
```

-continued

```
1               5

<210> SEQ ID NO 36
<211> LENGTH: 10
<212> TYPE: PRT
<213> ORGANISM: Porcine circovirus 3

<400> SEQUENCE: 36

Glu Phe Asp Tyr Glu Thr Gly Arg Gln Leu
1               5                   10

<210> SEQ ID NO 37
<211> LENGTH: 33
<212> TYPE: PRT
<213> ORGANISM: Porcine circovirus 3

<400> SEQUENCE: 37

Ser Val Leu Val Lys Ile Asn Ile Asn Leu Thr Pro Pro Val Ala Thr
1               5                   10                  15

Ser Arg Val Pro Ser Arg Ala Leu Pro Leu Arg Phe Gly Cys Gly His
            20                  25                  30

Arg
```